United States Patent
Zhang et al.

(10) Patent No.: US 12,037,344 B2
(45) Date of Patent: Jul. 16, 2024

(54) NLRP3 MODULATORS

(71) Applicant: INNATE TUMOR IMMUNITY, INC., Princeton, NJ (US)

(72) Inventors: Yong Zhang, West Windsor, NJ (US); Ashvinikumar V. Gavai, Princeton Junction, NJ (US); Andrew F. Donnell, West Windsor, NJ (US); Shomir Ghosh, Brookline, MA (US); William R. Roush, Jupiter, FL (US); Prasanna Sivaprakasam, Lawrenceville, NJ (US); Steven P. Seitz, Swarthmore, PA (US); Jay A. Markwalder, Lahaska, PA (US)

(73) Assignee: INNATE TUMOR IMMUNITY, INC, Princeton, NJ (US)

( * ) Notice: Subject to any disclaimer, the term of this patent is extended or adjusted under 35 U.S.C. 154(b) by 885 days.

(21) Appl. No.: 17/049,612

(22) PCT Filed: Apr. 24, 2019

(86) PCT No.: PCT/US2019/028823
§ 371 (c)(1),
(2) Date: Oct. 22, 2020

(87) PCT Pub. No.: WO2019/209896
PCT Pub. Date: Oct. 31, 2019

(65) Prior Publication Data
US 2021/0267964 A1    Sep. 2, 2021

Related U.S. Application Data

(60) Provisional application No. 62/825,044, filed on Mar. 28, 2019, provisional application No. 62/764,818, filed on Aug. 16, 2018, provisional application No. 62/662,240, filed on Apr. 25, 2018.

(51) Int. Cl.
| C07D 519/00 | (2006.01) |
| C07D 471/04 | (2006.01) |
| C07D 498/04 | (2006.01) |
| C07D 513/04 | (2006.01) |

(52) U.S. Cl.
CPC ......... *C07D 519/00* (2013.01); *C07D 471/04* (2013.01); *C07D 498/04* (2013.01); *C07D 513/04* (2013.01)

(58) Field of Classification Search
CPC .................................................. C07D 519/00
See application file for complete search history.

(56) References Cited

U.S. PATENT DOCUMENTS

| 7,544,697 | B2 | 6/2009 | Hays et al. |
| 7,879,849 | B2 | 2/2011 | Hays et al. |
| 8,378,102 | B2 | 2/2013 | Lundquist, Jr. et al. |
| 9,145,410 | B2 | 9/2015 | Hays et al. |
| 10,533,005 | B2 | 1/2020 | Glick et al. |
| 10,533,007 | B2 | 1/2020 | Glick et al. |
| 10,556,903 | B2 | 2/2020 | Glick et al. |
| 2006/0100229 | A1 | 5/2006 | Hays et al. |
| 2007/0259907 | A1 | 11/2007 | Prince |
| 2009/0075980 | A1 | 3/2009 | Hays et al. |
| 2011/0212053 | A1 | 9/2011 | Qian et al. |
| 2017/0114137 | A1 | 4/2017 | Li |
| 2020/0129500 | A1 | 4/2020 | O'Malley |
| 2020/0157096 | A1 | 5/2020 | Glick et al. |
| 2020/0157097 | A1 | 5/2020 | Glick et al. |
| 2021/0386070 | A1 | 12/2021 | Arlt et al. |

FOREIGN PATENT DOCUMENTS

| CN | 104418867 A | 3/2015 |
| WO | 200006577 A1 | 2/2000 |
| WO | 2006029223 A2 | 3/2006 |
| WO | 2006093514 A2 | 9/2006 |
| WO | 2009021961 A1 | 2/2009 |
| WO | 2014179664 A2 | 11/2014 |
| WO | 2015/095780 A1 | 6/2015 |
| WO | 2015112900 A1 | 7/2015 |
| WO | 2016004875 A1 | 1/2016 |
| WO | 2016034085 A1 | 3/2016 |
| WO | 2016149201 A2 | 9/2016 |
| WO | 2016199943 A1 | 12/2016 |

(Continued)

OTHER PUBLICATIONS

Deng, et al., "Study on the agonists for the human Toll-like receptor-8 by moleculara modeling", Molecular BioSystems (2014), 10(8), 2202-2214.

Chen, Lih-Chyang et al., "Tumour inflammasome-derived IL-1β recruits neutrophils and improves local recurrence-free survival in EBV-induced nasopharyngeal carcinoma", EMBO Molecular Medicine, vol. 4, pp. 1276-1293 (2012).

(Continued)

*Primary Examiner* — Golam M Shameem
(74) *Attorney, Agent, or Firm* — Jing G. Sun

(57) ABSTRACT

The present invention provides compounds of Formula (I): wherein all of the variables are as defined herein. These compounds are modulators of NLRP3, which may be used as medicaments for the treatment of proliferative disorders, such as cancer in a subject (e.g., a human).

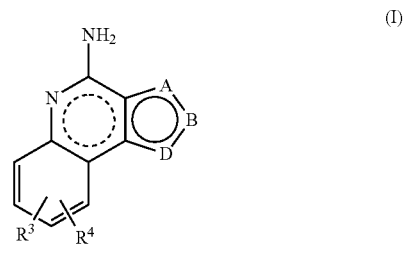

34 Claims, No Drawings

(56) References Cited

FOREIGN PATENT DOCUMENTS

| WO | 2017024465 A1 | 2/2017 |
| WO | 2017025016 A1 | 2/2017 |
| WO | 2017034916 A1 | 3/2017 |
| WO | 2017040670 A1 | 3/2017 |
| WO | 2017101791 A1 | 6/2017 |
| WO | 2017118407 A1 | 7/2017 |
| WO | 2017184735 A1 | 10/2017 |
| WO | 2017184746 A1 | 10/2017 |
| WO | 2018152396 A1 | 8/2018 |

OTHER PUBLICATIONS

Fuertes, Mercedes B. et al., "Type I interferon response and innate immune sensing of cancer", Trends in Immunology, vol. 34(2), pp. 67-73 (2013).

Kokatla et al., "Toll-like receptor-8 agonistic activities in C2, C4, and C8 modified thiazolo[4,5-c]quinolines", Organic & Biomolecular Chemistry, vol. 11(7) p. 1179 (2013).

Lin, Chu et al., "Inflammasomes in Inflammation-Induced Cancer", Frontiers in Immunology, vol. 8, Article 271, pp. 1-22 (2017).

Ma, Zhifeng et al., "Augmentation of Immune Checkpoint Cancer Immunotherapy with IL18" Clinical Cancer Research, vol. 22(12), pp. 2969-2980 (2016).

Oumata et al. "The Toll-Like Receptor Agonist Imiquimod Is Active against Prions" PLOS ONE, vol. 8(8) p. e72112 (2013).

Tse, et al., "IL-18 Inhibits Growth of Murine Orthotopic ProstateCarcinomas via Both Adaptive and Innate Immune Mechanisms" PLOS One, vol. 6(9), pp. 1-12 (2011).

NLRP3 MODULATORS

This application is a 371 of International Application No. PCT/US2019/028823 filed on Apr. 24, 2019, which claims the priority benefit of U.S. Provisional Application 62/662,240, filed Apr. 25, 2018, and 62/764,818 filed Aug. 16, 2018 and 62/825,044 filed Mar. 28, 2019; each of which is incorporated herein by reference in its entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens-sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res.* January 11. (2016) DOI: 10.1158/1078-0432.CCR-15-1655).

SUMMARY

The invention is directed to compounds of Formula (I):

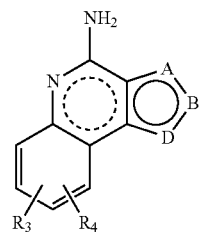

wherein all of the variables are as defined herein below.

Also within the scope of the invention are pharmaceutically acceptable salts, stereoisomers, tautomers, and solvates of the compounds of Formula (I).

The invention is also directed to pharmaceutical compositions comprising one or more compounds of the invention. The invention is also directed to methods of treating cancer using one or more compounds of the invention.

The invention also provides processes and intermediates for making the compounds of Formula (I) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION

Compounds of Invention

In a first aspect, the present invention provides, inter alia, a compound of Formula (I):

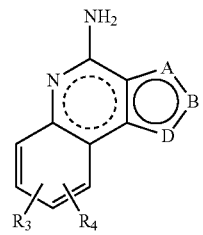

or a stereoisomer, a tautomer or a pharmaceutically acceptable salt thereof, wherein:

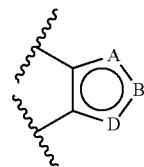

is independently selected from:

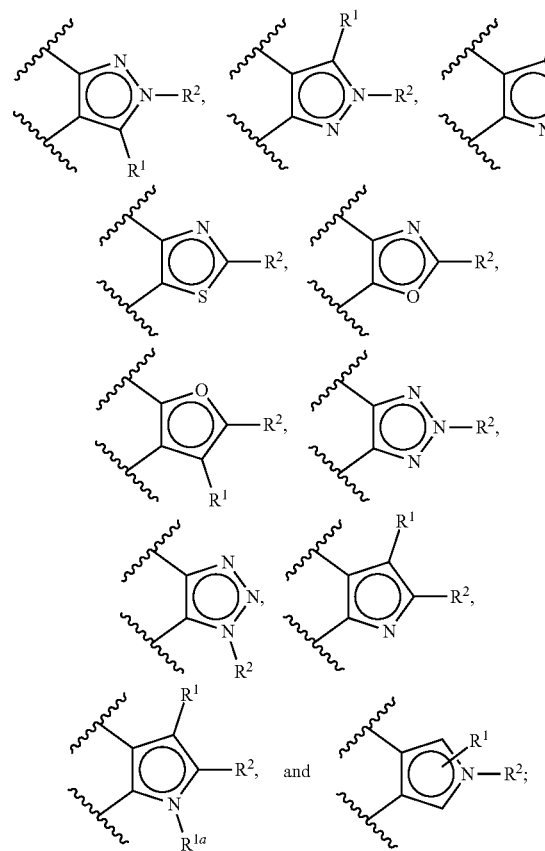

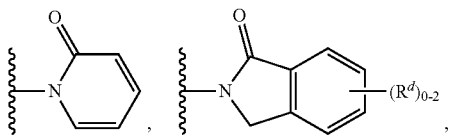

$R^1$ is, at each occurrence, independently:
(i) H;
(ii) halo;
(iii) X—$R^5$, wherein X is $C_{1-6}$ alkylene, and $R^5$ is H, OH, cyano, $C_{1-4}$ alkoxy, $C_{1-4}$ haloalkoxy, —C(O)O$R^a$, —N$R^bR^c$, or —C(O)N$R^bR^k$;
(iv) $C_{1-6}$ alkyl substituted with 1 to 6 F;
(v) $C_{3-6}$ cycloalkyl substituted with 0 to 6 F;
(vi) ($C_{1-3}$ alkylene)-aryl, wherein the aryl is substituted with 0 to 3 $R^d$; or
(vii) ($C_{1-3}$ alkylene)-heteroaryl including from 5 to 6 ring atoms, wherein from 1 to 4 ring atoms are each independently selected from N, N($R^f$), O, and S, wherein the heteroaryl is substituted with 0 to 3 $R^d$;
$R^{1a}$ is independently H, $C_{1-6}$ alkyl substituted with 0 to 6 F, or $C_{3-6}$ cycloalkyl substituted with 0 to 6 F;
$R^2$ is, at each occurrence, independently:
(i) H;
(ii) —Y—$R^6$;
(iii) —C(O)—Y—$R^6$;
wherein:
Y is independently $C_{1-8}$ alkylene substituted with from 0 to 4 $R^e$; and
$R^6$ is, at each occurrence, independently: H, OH, CN, O$R^a$, —C(O)$R^a$, —C(O)O$R^a$, —N$R^bR^c$, —C(O)N$R^bR^k$, —SO$_{1-2}R^h$, or heteroaryl including from 5 to 10 ring atoms, wherein from 1-4 ring atoms are each independently selected from N, N($R^f$), O, and S, wherein the heteroaryl is substituted with from 0 to 3 $R^d$;
(iv) —($Y^1$)$_n$—$Y^2$—($Y^3$)$_p$—$R^7$, wherein:
n is independently 0, 1 or 2;
p is independently 0 or 1;
each of $Y^1$ and $Y^3$ is, independently, $C_{1-3}$ alkylene substituted with from 0 to 2 $R^e$.
$Y^2$ is independently $C_{3-6}$ cycloalkylene substituted with from 0 to 4 $R^g$, or heterocycloalkylene including from 3-8 ring atoms, wherein from 1-2 ring atoms are each independently selected from N, N($R^1$) and O, and wherein the heterocycloalkylene is substituted with from 0 to 4 $R^g$, and
$R^7$ is H, OH, —O$R^a$, —C(O)O$R^a$, —N$R^bR^c$, —C(O)N$R^bR^k$, or heteroaryl including from 5-6 ring atoms, wherein from 1-4 ring atoms are each independently selected from N, N($R^f$), O, and S, and wherein the heteroaryl is substituted with from 0 to 4 $R^g$;
or
(v) —$Z^1$—$Z^2$—$Z^3$—$R^8$, wherein:
$Z^1$ is $C_{1-3}$ alkylene substituted with from 0 to 6 F;
$Z^2$ is —N($R^f$)—, —O—, or —S—;
$Z^3$ is $C_{2-5}$ alkylene substituted with from 0 to 6 F; and
$R^8$ is OH, O$R^a$, —C(O)$R^a$, —C(O)O$R^a$; —N$R^bR^c$, —C(O)N$R^bR^k$, or heteroaryl including from 5-6 ring atoms, wherein from 1-4 ring atoms are each independently selected from N, N($R^f$), O, and S, wherein the heteroaryl is substituted with from 0 to 3 $R^d$;
$R^3$ is independently halo or —($C_{0-3}$ alkylene)-(5-membered heteroaryl) wherein the heteroaryl includes 1 to 4 ring carbon atoms and 1 to 4 ring heteroatoms are each independently selected from: N, N($R^f$), O, and S, and is substituted with from 0 to 3 $R^g$; provided that when $R^3$ is furanyl, $R^2$ is other than $C_{1-4}$ alkyl;
$R^4$ is independently selected from: H, halo, cyano, OH, $C_{1-4}$ alkoxy, $C_{1-4}$ haloalkyl, $C_{1-4}$ haloalkoxy, —C(O)OH, —C(O)O$R^a$, —N$R^jR^k$, —C(O)N$R^bR^k$, —SO$_{1-2}R^h$, and $C_{1-4}$ alkyl substituted with from 0 to 2 $R^e$;
$R^a$ is, at each occurrence, independently:
(i) $C_{1-6}$ alkyl substituted with from 0 to 3 $R^e$;
(ii) —($C_{0-3}$ alkylene)-$C_{3-6}$ cycloalkyl, wherein the cycloalkyl is substituted with from 0 to 4 $R^g$;
(iii) —($C_{0-3}$ alkylene)-heterocyclyl including from 3 to 10 ring atoms, wherein from 1 to 3 ring atoms are each independently selected from N($R^f$), O, and S(O$_{0-2}$, wherein the heterocyclyl is substituted with from 0 to 4 $R^g$;
(iv) —($C_{0-3}$ alkylene)-($C_{6-10}$ aryl), wherein the aryl is substituted with from 0 to 5 $R^d$; or
(v) —($C_{0-3}$ alkylene)-heteroaryl including from 5 to 10 ring atoms, wherein from 1 to 4 ring atoms are each independently selected from N, N($R^f$), O, and S, wherein the heteroaryl is substituted with from 0 to 3 $R^d$;
$R^b$ is, at each occurrence, independently H or $R^a$;
$R^c$ is, at each occurrence, independently selected from: H, —C(O)$R^a$, —C(O)O$R^a$, —C(O)N$R^jR^k$, —S(O)$_{1-2}R^h$, C$_{1-6}$ alkyl substituted with from 0 to 2 R$^e$, —(C$_{0-3}$ alkylene)-(phenyl substituted with from 0 to 4 R$^n$), and —(C$_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 R$^n$;

alternatively, R$^b$ and R$^c$, together with the nitrogen atom to which each is attached form heterocyclyl including from 3 to 10 ring atoms, wherein from 1 to 3 ring atoms are each independently selected from N(R$^f$), O, and S, and wherein the heterocyclyl is substituted with from 0 to 4 R$^g$;

R$^d$ is, at each occurrence, independently selected from: halo, OH, cyano, C$_{2-6}$ alkenyl, C$_{2-6}$ alkynyl, C$_{1-4}$ alkoxy, C$_{1-4}$ haloalkyl, C$_{1-4}$ haloalkoxy, —C(O)(C$_{1-4}$ alkyl), —C(O)OH, —C(O)O(C$_{1-4}$ alkyl), —NR$^j$R$^k$, —N(R$^m$)(C(O)(C$_{1-4}$ alkyl), —N(R$^m$)(C(O)O(C$_{1-4}$ alkyl), —C(O)NR$^j$R$^k$, —S(O)$_{1-2}$R$^h$, —S(O)$_{1-2}$NR$^h$R$^j$, C$_{1-6}$ alkyl substituted with from 0 to 2 R$^e$, and —(C$_{0-3}$ alkylene)-R$^p$;

R$^e$ is, at each occurrence, independently selected from: halo, OH, cyano, C$_{1-4}$ alkoxy, C$_{1-4}$ haloalkyl, C$_{1-4}$ haloalkoxy, —C(O)OR$^a$, —OC(O)R$^h$, —NR$^b$R$^c$, and —CONR$^b$R$^k$;

R$^f$ is, at each occurrence, independently selected from: H, OH, C$_{1-4}$ alkyl, C$_{1-4}$ alkoxy, —C(O)(C$_{1-4}$ alkyl), —C(O)(C$_{1-4}$ haloalkyl), —C(O)O(C$_{1-4}$ alkyl), —C(O)NR$^j$R$^k$, —S(O)$_{1-2}$R$^h$, and —(C$_{0-3}$ alkylene)-phenyl;

R$^g$ is, at each occurrence, independently oxo or R$^d$;

R$^h$ is, at each occurrence, independently selected from C$_{1-6}$ alkyl substituted with 0 to 2 R$^n$, C$_{1-4}$ haloalkyl, and —(C$_{0-3}$ alkylene)-R$^p$;

R$^j$ and R$^m$ are, at each occurrence, independently H or C$_{1-4}$ alkyl;

R$^k$ is, at each occurrence, independently selected from H, C$_{1-4}$ alkyl, and —(C$_{0-2}$ alkylene)-phenyl;

R$^n$ is, at each occurrence, independently selected from: halo, OH, C$_{1-6}$ alkyl, C$_{1-4}$ haloalkyl, C$_{1-4}$ alkoxy, C$_{1-4}$ haloalkoxy, cyano, —C(O)OH, —C(O)O(C$_{1-4}$ alkyl), —NR$^j$R$^k$, and —CONR$^j$R$^k$; and R$^p$ is, at each occurrence, independently selected from: C$_{3-6}$ cycloalkyl substituted with from 0 to 4 C$_{1-4}$ alkyl; heterocyclyl including from 3-10 ring atoms, wherein from 1 to 3 ring atoms are each independently selected from NH, N(C$_{1-4}$ alkyl), O, and S, wherein the heterocyclyl is substituted with 0 to 4 independently selected C$_{1-4}$ alkyl; phenyl substituted with 0 to 3 R$^n$; and heteroaryl including from 5 to 10 ring atoms, wherein from 1 to 4 ring atoms are each independently selected from N, NH, N(C$_{1-4}$ alkyl), O, and S, wherein the heteroaryl is substituted with 0 to 3 R$^n$.

In one embodiment, R$^{1a}$ is independently C$_{1-6}$ alkyl substituted with 0 to 6 F, or C$_{3-6}$ cycloalkyl substituted with 0 to 6 F.

In one embodiment, R$^3$ is independently halo or —(C$_{0-3}$ alkylene)-(5-membered heteroaryl) wherein the heteroaryl includes 1 to 4 ring carbon atoms and 1 to 4 ring heteroatoms are each independently selected from: N, N(R$^f$), and S, and is substituted with from 0 to 3 R$^g$.

In one embodiment, R$^6$ is independently: OH, OR$^a$, —C(O)R$^a$, —C(O)OR$^a$, —NR$^b$R$^c$, —C(O)NR$^b$R$^k$, or heteroaryl including from 5 to 6 ring atoms, wherein from 1-4 ring atoms are each independently selected from N, N(R$^f$), O, and S, wherein the heteroaryl is substituted with from 0 to 3 R$^d$.

In one embodiment, R$^h$ is independently selected from C$_{1-6}$ alkyl, C$_{1-4}$ haloalkyl, and —(C$_{0-3}$ alkylene)-R$^p$.

In another aspect, the present invention provides a compound of Formula (I):
or a stereoisomer, a tautomer or a pharmaceutically acceptable salt thereof, wherein:

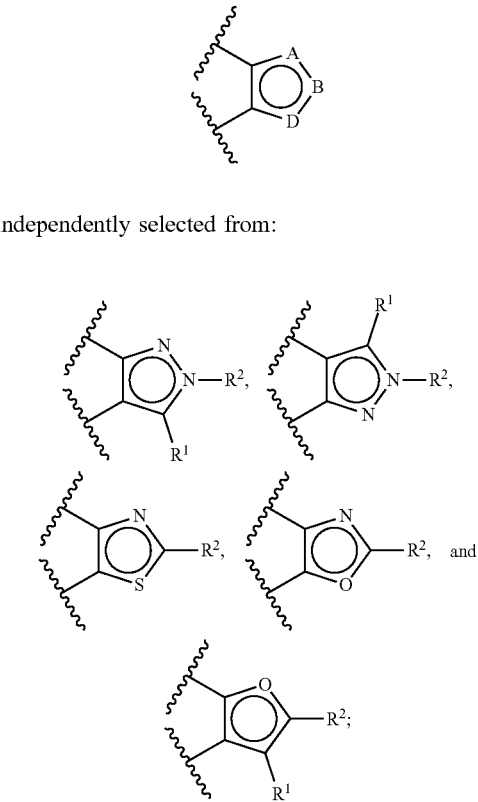

is independently selected from:

R$^1$ is, at each occurrence, independently:
(i) H;
(ii) halo;
(iii) X—R$^5$, wherein X is an unbranched C$_{1-6}$ alkylene, and R$^5$ is H, OH, cyano, C$_{1-4}$ alkoxy, C$_{1-4}$ haloalkoxy, —C(O)OR$^a$, —NR$^b$R$^c$, or —C(O)NR$^b$R$^k$;
(iv) (C$_{1-3}$ alkylene)-aryl, wherein the aryl is substituted with 0 to 3 R$^d$; or
(v) (C$_{1-3}$ alkylene)-heteroaryl including from 5 to 6 ring atoms, wherein from 1 to 4 ring atoms are each independently selected from N, N(R$^f$), O, and S, wherein the heteroaryl is substituted with 0 to 3 R$^d$;

R$^2$ is, at each occurrence, independently:
(i) H;
(ii) —Y—R$^6$;
(iii) —C(O)—Y—R$^6$;
wherein:
Y is independently C$_{1-8}$ alkylene substituted with from 0 to 4 R$^e$; and
R$^6$ is, at each occurrence, independently: OH, OR$^a$, —C(O)R$^a$, —C(O)OR$^a$, —NR$^b$R$^c$, —C(O)NR$^b$R$^k$, or heteroaryl including from 5 to 6 ring atoms, wherein from 1-4 ring atoms are each independently selected from N, N(R$^f$), O, and S, wherein the heteroaryl is substituted with from 0 to 3 R$^d$;
(iv) —(Y$^1$)$_n$—Y$^2$—(Y$^3$)$_p$—R$^7$, wherein:
each of n and p is independently 0 or 1;
each of Y$^1$ and Y$^3$ is, independently, C$_{1-3}$ alkylene substituted with from 0 to 2 R$^e$.

Y² is independently C$_{3-6}$ cycloalkylene substituted with from 0 to 4 R$^g$, or heterocycloalkylene including from 3-8 ring atoms, wherein from 1-2 ring atoms are each independently selected from N, N(R$^f$) and O, and wherein the heterocycloalkylene is substituted with from 0 to 4 R$^g$, and R⁷ is H, OH, —C(O)OR$^a$, —NR$^b$R$^c$, —C(O)NR$^b$R$^k$, or heteroaryl including from 5-6 ring atoms, wherein from 1-4 ring atoms are each independently selected from N, N(R$^f$), O, and S, and wherein the heteroaryl is substituted with from 0 to 4 R$^g$;

or (v) —Z¹—Z²—Z³—R⁸, wherein:
Z¹ is C$_{1-3}$ alkylene substituted with from 0 to 6 F;
Z² is —N(R$^f$)—, —O—, or —S—;
Z³ is C$_{2-5}$ alkylene substituted with from 0 to 6 F; and
R⁸ is OH, OR$^a$, —C(O)R$^a$, —C(O)OR$^a$; —NR$^b$R$^c$, —C(O)NR$^b$R$^k$, or heteroaryl including from 5-6 ring atoms, wherein from 1-4 ring atoms are each independently selected from N, N(R$^f$), O, and S, wherein the heteroaryl is substituted with from 0 to 3 R$^d$;

R³ is independently halo or —(C$_{0-3}$ alkylene)-(5-membered heteroaryl) wherein the heteroaryl includes 1 to 4 ring carbon atoms and 1 to 4 ring heteroatoms are each independently selected from: N, N(R$^f$), O, and S, and is substituted with from 0 to 3 R$^g$; provided that when R³ is furanyl, R² is other than C$_{1-4}$ alkyl;

R⁴ is independently selected from: H, halo, cyano, OH, C$_{1-4}$ alkoxy, C$_{1-4}$ haloalkyl, C$_{1-4}$ haloalkoxy, —C(O)OH, —C(O)OR$^a$, —NR$^j$R$^k$, —C(O)NR$^j$R$^k$, —SO$_{1-2}$R$^h$, and C$_{1-4}$ alkyl substituted with from 0 to 2 R$^e$;

R$^a$ is, at each occurrence, independently:
(i) C$_{1-6}$ alkyl substituted with from 0 to 2 R$^e$;
(ii) —(C$_{0-3}$ alkylene)-C$_{3-6}$ cycloalkyl, wherein the cycloalkyl is substituted with from 0 to 4 R$^g$;
(iii) —(C$_{0-3}$ alkylene)-heterocyclyl including from 3 to 10 ring atoms, wherein from 1 to 3 ring atoms are each independently selected from N(R$^f$), O, and S, wherein the heterocyclyl is substituted with from 0 to 4 R$^g$;
(iv) —(C$_{0-3}$ alkylene)-(C$_{6-10}$ aryl), wherein the aryl is substituted with from 0 to 5 R$^d$; or
(v) —(C$_{0-3}$ alkylene)-heteroaryl including from 5 to 10 ring atoms, wherein from 1 to 4 ring atoms are each independently selected from N, N(R$^f$), O, and S, wherein the heteroaryl is substituted with from 0 to 3 R$^d$;

R$^b$ is, at each occurrence, independently H or R$^a$;
R$^c$ is, at each occurrence, independently selected from: H, —C(O)R$^a$, —C(O)OR$^a$, —C(O)NR$^j$R$^k$, —S(O)$_{1-2}$R$^h$, C$_{1-6}$ alkyl substituted with from 0 to 2 R$^e$, —(C$_{0-3}$ alkylene)-(phenyl substituted with from 0 to 4 R$^n$), or —(C$_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 alternatively, R$^b$ and R$^c$, together with the nitrogen atom to which each is attached form heterocyclyl including from 3 to 10 ring atoms, wherein from 1 to 3 ring atoms are each independently selected from N(R$^f$), O, and S, and wherein the heterocyclyl is substituted with from 0 to 4 R$^g$;

R$^d$ is, at each occurrence, independently selected from: halo, OH, cyano, C$_{2-6}$ alkenyl, C$_{2-6}$ alkynyl, C$_{1-4}$ alkoxy, C$_{1-4}$ haloalkyl, C$_{1-4}$ haloalkoxy, —C(O)(C$_{1-4}$ alkyl), —C(O)OH, —C(O)O(C$_{1-4}$ alkyl), —NR$^j$R$^k$, —N(R$^m$)(C(O)(C$_{1-4}$ alkyl), —N(R$^m$)(C(O)O(C$_{1-4}$ alkyl), —C(O)NR$^j$R$^k$, —S(O)$_{1-2}$R$^h$, —S(O)$_{1-2}$NR$^h$R$^j$, C$_{1-6}$ alkyl substituted with from 0 to 2 R$^e$, and —(C$_{0-3}$ alkylene)-R$^p$;

R$^e$ is, at each occurrence, independently selected from: halo, OH, cyano, C$_{1-4}$ alkoxy, C$_{1-4}$ haloalkyl, C$_{1-4}$ haloalkoxy, —C(O)OR$^a$, —OC(O)R$^h$, —NR$^b$R$^c$, and —CONR$^b$R$^k$.

R$^f$ is, at each occurrence, independently selected from: H, OH, C$_{1-4}$ alkyl, C$_{1-4}$ alkoxy, —C(O)(C$_{1-4}$ alkyl), —C(O)O(C$_{1-4}$ alkyl), —C(O)NR$^j$R$^k$, —S(O)$_{1-2}$R$^h$, and —(C$_{0-3}$ alkylene)-phenyl;

R$^g$ is, at each occurrence, independently oxo or R$^d$;

R$^h$ is, at each occurrence, independently selected from C$_{1-6}$ alkyl, C$_{1-4}$ haloalkyl, and —(C$_{0-3}$ alkylene)-R$^p$;

R$^j$ and R$^m$ are, at each occurrence, independently H or C$_{1-4}$ alkyl;

R$^k$ is, at each occurrence, independently selected from H, C$_{1-4}$ alkyl, and —(C$_{0-2}$ alkylene)-phenyl;

R$^n$ is, at each occurrence, independently selected from: halo, OH, C$_{1-6}$ alkyl, C$_{1-4}$ haloalkyl, C$_{1-4}$ alkoxy, C$_{1-4}$ haloalkoxy, cyano, —C(O)OH, —C(O)O(C$_{1-4}$ alkyl), —NR$^j$R$^k$, and —CONR$^j$R$^k$; and R$^p$ is, at each occurrence, independently selected from: C$_{3-6}$ cycloalkyl substituted with from 0 to 4 C$_{1-4}$ alkyl; heterocyclyl including from 3-10 ring atoms, wherein from 1 to 3 ring atoms are each independently selected from NH, N(C$_{1-4}$ alkyl), O, and S, wherein the heterocyclyl is substituted with 0 to 4 independently selected C$_{1-4}$ alkyl; phenyl substituted with 0 to 3 R$^n$; and heteroaryl including from 5 to 10 ring atoms, wherein from 1 to 4 ring atoms are each independently selected from N, NH, N(C$_{1-4}$ alkyl), O, and S, wherein the heteroaryl is substituted with 0 to 3 R$^n$.

In a second aspect, the present invention provides a compound of Formula (I), or a stereoisomer, a tautomer or a pharmaceutically acceptable salt thereof, within the scope of the first aspect, wherein:
R³ is independently —(C$_{0-3}$ alkylene)-(5-membered heteroaryl) wherein the heteroaryl includes 2 to 4 ring carbon atoms and 1 to 3 ring heteroatoms are each independently selected from: N, N(R$^f$), and S, and is substituted with 0 to 3 R$^g$; and R⁶ is, at each occurrence, independently selected from: OH, OR$^a$, —C(O)R$^a$, —C(O)OR$^a$, —NR$^b$R$^c$, —C(O)NR$^b$R$^k$, —SO$_2$(C$_{1-4}$ alkyl), and heteroaryl including from 5 to 6 ring atoms, wherein from 1 to 4 ring atoms are each independently selected from N, N(R$^f$), O, and S, wherein the heteroaryl is substituted with from 0 to 3 R$^d$.

In another aspect, the present invention provides a compound of Formula (I), or a stereoisomer, a tautomer or a pharmaceutically acceptable salt thereof, within the scope of the first aspect, wherein:
R³ is independently —(C$_{0-3}$ alkylene)-(5-membered heteroaryl) wherein the heteroaryl includes 2 to 4 ring carbon atoms and 1 to 3 ring heteroatoms are each independently selected from: N, N(R$^f$), and S, and is substituted with 0 to 3 R$^g$; and R⁶ is, at each occurrence, independently: OH, OR$^a$, —C(O)R$^a$, —C(O)OR$^a$, —NR$^b$R$^c$, —C(O)NR$^b$R$^k$, or heteroaryl including from 5 to 6 ring atoms, wherein from 1 to 4 ring atoms are each independently selected from N, N(R$^f$), O, and S, wherein the heteroaryl is substituted with from 0 to 3 R$^d$.

In a third aspect, within the scope of the first or second aspect, the invention provides a compound of Formula (IIa), (IIb), (IIc), (IId), (IIe), (IIf), (IIg), (IIh) or (IIi):

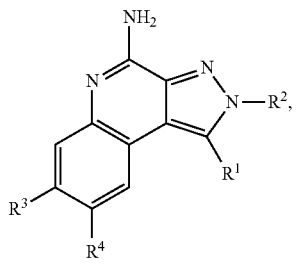
(IIa)
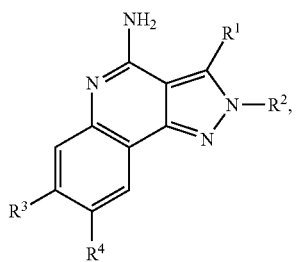
(IIb)
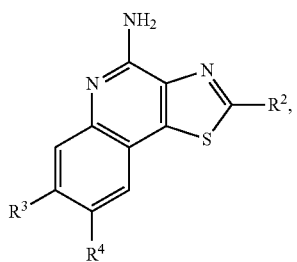
(IIc)
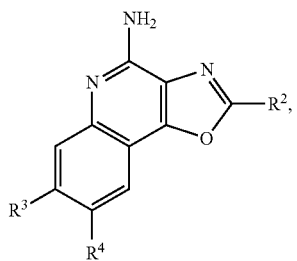
(IId)
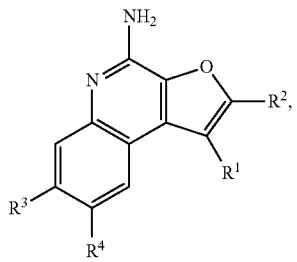
(IIe)
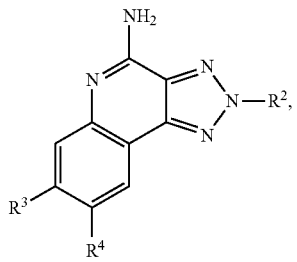
(IIf)
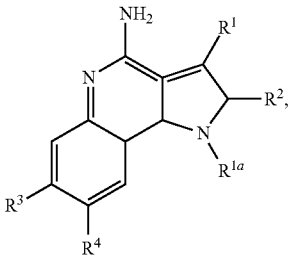
(IIg)
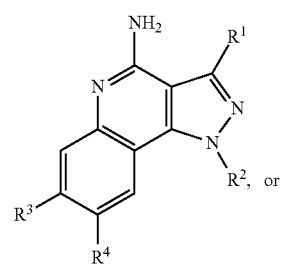
(IIh)
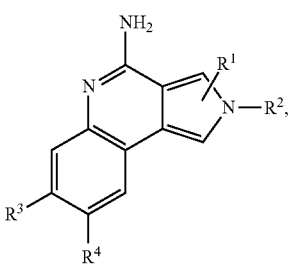
(IIi)
or a stereoisomer, a tautomer or a pharmaceutically acceptable salt thereof.
In another aspect, within the scope of the first or second aspect, the invention provides a compound of Formula (IIa), (IIb), (IIc), (IId), (IIe), (IIf), (IIg-1), or (IIh):
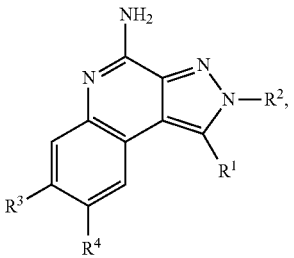
(IIa)
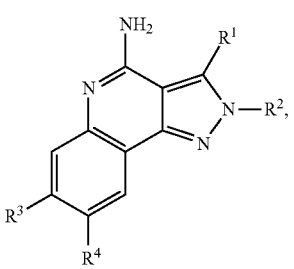
(IIb)

-continued

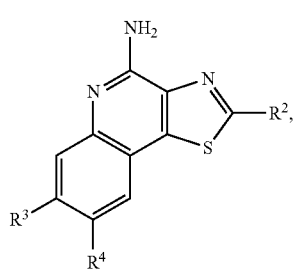
(IIc)

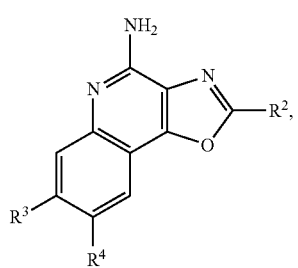
(IId)

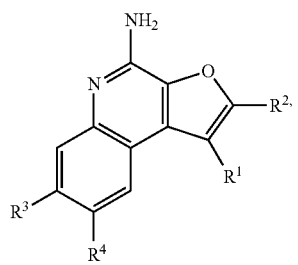
(IIe)

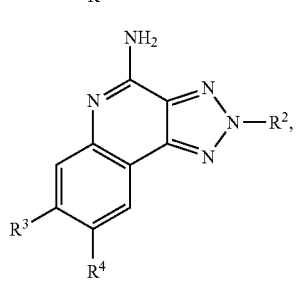
(IIf)

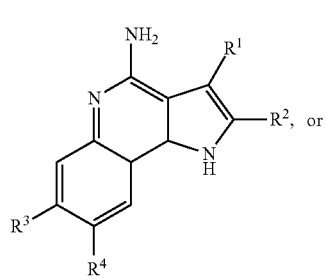
(IIg-1)

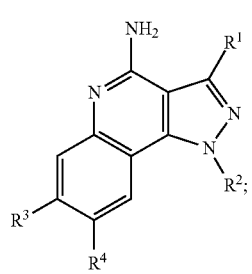
(IIh)

or a stereoisomer, a tautomer or a pharmaceutically acceptable salt thereof.

In another aspect, within the scope of the first or second aspect, the invention provides a compound of Formula (IIa), (IIb), (IIc), (IId) or (IIe):

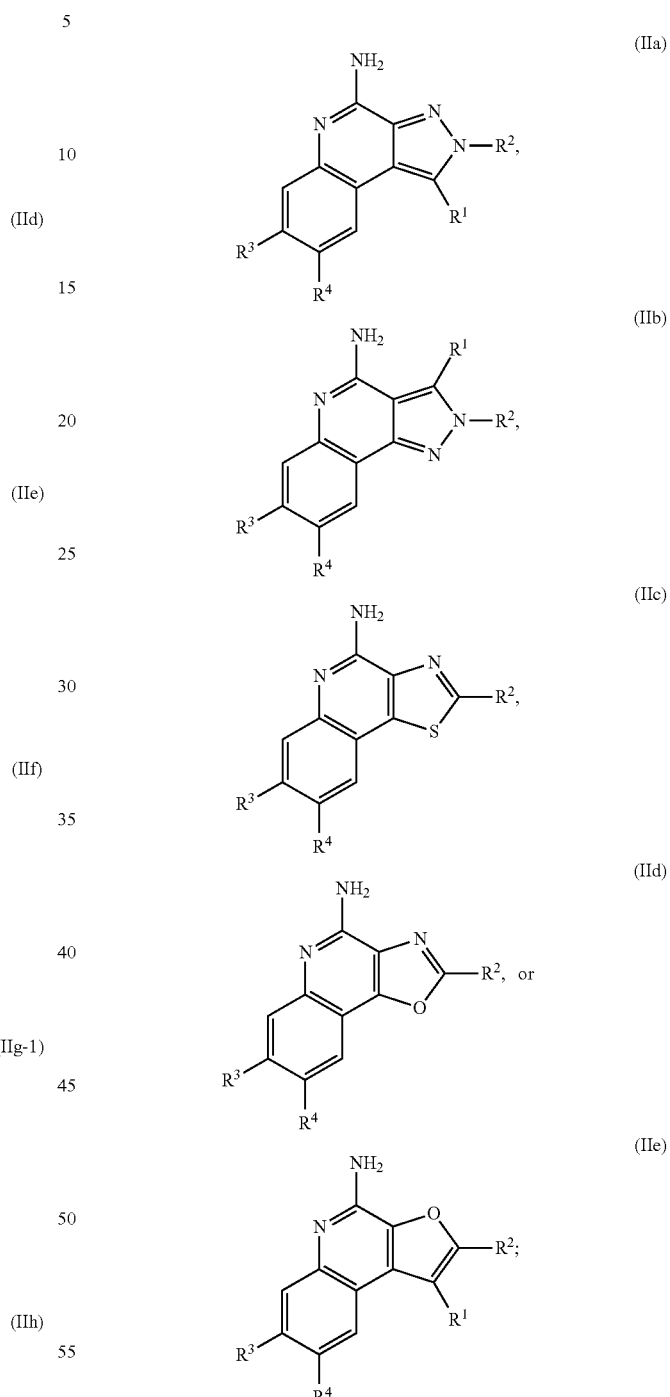

or a stereoisomer, a tautomer or a pharmaceutically acceptable salt thereof.

In a fourth aspect, within the scope of the first, second or third aspect, the invention provides a compound of Formula (IIa), (IIb), (IIc), (IId), (IIe), (IIf), (IIg), (IIh) or (IIi) or a stereoisomer, a tautomer or a pharmaceutically acceptable salt thereof, wherein:

$R^1$ is, at each occurrence, independently selected from H, halo and $C_{1-4}$ alkyl;

R² is, at each occurrence, independently selected from: H, C₁₋₄ alkyl substituted with 0 to 3 F, —Y—R⁶, —(CH₂)₁₋₃O(CH₂)₂₋₃ORᵃ, —(CH₂)₀₋₂—Y²—R⁷, and

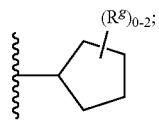

Y is independently C₁₋₆ alkylene substituted with from 0 to 3 Rᵉ;

R³ is, at each occurrence, independently —(C₀₋₂ alkylene)-(5-membered heteroaryl) wherein the heteroaryl includes 2 to 4 ring carbon atoms and 1 to 3 ring heteroatoms are each independently selected from: N, N(Rᶠ), and S, wherein the heteroaryl is substituted with from 0 to 2 Rᵍ; provided that when R³ is furanyl, R² is other than C₁₋₄ alkyl;

R⁴ is, at each occurrence, independently selected from H, halo and C₁₋₄ alkyl;

R⁶ is independently selected from: OH, CN, ORᵃ, —C(O)Rᵃ, NRᵇRᶜ, —C(O)NRᵇRᵏ, —SO₂(C₁₋₄ alkyl),

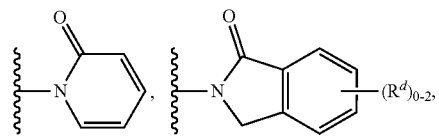

and heteroaryl including from 5 to 10 ring atoms, wherein from 1 to 4 ring atoms are each independently selected from N, N(Rᶠ), O, and S, wherein the heteroaryl is substituted with from 0 to 3 Rᵈ;

—Y²—R⁷ is independently selected from C₃₋₆ cycloalkyl substituted with 0 to 2 Rᵈ,

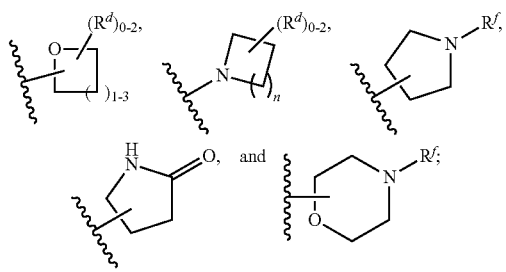

Rᵃ is, at each occurrence, independently:
(i) C₁₋₆ alkyl substituted with from 0 to 3 Rᵉ;
(ii) C₃₋₆ cycloalkyl substituted with from 0 to 2 Rᵍ;
(iii) —(C₀₋₂ alkylene)-heterocyclyl including from 4 to 10 ring atoms, wherein from 1 to 3 ring atoms are each independently selected from N(Rᶠ), O, and S, wherein the heterocyclyl is substituted with from 0 to 3 Rᵍ;
(iv) —(C₀₋₂ alkylene)-(C₆₋₁₀ aryl), wherein the aryl is substituted with from 0 to 3 Rᵈ; or
(v) —(C₀₋₂ alkylene)-heteroaryl including from 5 to 10 ring atoms, wherein from 1 to 3 ring atoms are each independently selected from N, N(Rᶠ), O, and S, wherein the heteroaryl is substituted with from 0 to 3 Rᵈ;

Rᵇ is, at each occurrence, independently H or Rᵃ;

Rᶜ is, at each occurrence, independently selected from: H, —C(O)Rᵃ, —C(O)ORᵃ, —C(O)NRʲRᵏ, —S(O)₂Rʰ, C₁₋₆ alkyl substituted with from 0 to 2 Rᵉ, —(C₀₋₃ alkylene)-(phenyl substituted with from 0 to 4 Rⁿ), and —(C₀₋₃ alkylene)-heteroaryl including from 5-6 ring atoms, wherein from 1-4 ring atoms are each independently selected from N, N(Rᶠ), O, and S, wherein the heteroaryl is substituted with from 0 to 3 Rⁿ;

alternatively, Rᵇ and Rᶜ, together with the nitrogen atom to which each is attached form heterocyclyl including from 3 to 10 ring atoms, wherein from 1 to 3 ring atoms are each independently selected from N(Rᶠ), O, and S, and wherein the heterocyclyl is substituted with from 0 to 3 Rᵍ;

Rᵈ is, at each occurrence, independently selected from: OH, halo, CN, C₁₋₄ alkoxy, C₁₋₄ haloalkyl, C₁₋₄ haloalkoxy, —C(O)O(C₁₋₄ alkyl), NH₂, N(C₁₋₄ alkyl)₂, —CONH₂, —CONH(C₁₋₄ alkyl), —NHC(O)(C₁₋₄ alkyl), —NHC(O)O(C₁₋₄ alkyl), —S(O)₂(C₁₋₄ alkyl), benzoxy, C₁₋₄ alkyl substituted with from 0 to 2 Rᵉ, phenyl, and heteroaryl including from 5 to 6 ring atoms, wherein from 1 to 4 ring atoms are each independently selected from N, N(Rᶠ), O, and S, wherein the heteroaryl is substituted with 0 to 2 Rⁿ;

Rᵉ is, at each occurrence, independently selected from: halo, OH, CN, C₁₋₄ alkoxy, C₁₋₄ haloalkyl, C₁₋₄ haloalkoxy, —CONH₂, and —CONH(C₁₋₄ alkyl);

Rᶠ is, at each occurrence, independently selected from H, C₁₋₄ alkyl, —C(O)C₁₋₄ alkyl, and —C(O)(C₁₋₄ haloalkyl);

Rᵍ is, at each occurrence, independently oxo or Rᵈ;

Rʰ is independently C₁₋₄ alkyl substituted with 0 to 2 Rⁿ, C₃₋₆ cycloalkyl, or phenyl;

Rʲ is independently H or C₁₋₄ alkyl;

Rᵏ is independently selected from H, C₁₋₄ alkyl and phenyl; and

Rⁿ is, at each occurrence, independently selected from: halo, C₁₋₄ alkyl, and C₁₋₄ alkoxy.

In one embodiment, Rᵇ is independently selected from H, C₁₋₄ alkyl, and —(C₀₋₂ alkylene)-phenyl.

In one embodiment, Rᵉ is independently selected from: halo, OH, C₁₋₄ alkoxy, C₁₋₄ haloalkyl, and C₁₋₄ haloalkoxy.

In one embodiment, R is independently selected from H, C₁₋₄ alkyl, and —C(O)C₁₋₄ alkyl.

In one embodiment, Rᵍ is independently OH or C₁₋₄ alkoxy.

In one embodiment, Rʰ is independently C₁₋₄ alkyl or phenyl.

In another aspect, within the scope of the first, second or third aspect, the invention provides a compound of Formula (IIa), (IIb), (IIc), (IId), or (IIe), or a stereoisomer, a tautomer or a pharmaceutically acceptable salt thereof, wherein:

R¹ is, at each occurrence, independently selected from H, halo and C₁₋₄ alkyl;

R² is, at each occurrence, independently selected from: H, —(CH₂)₁₋₃—R⁶, —(CH₂)₁₋₃O(CH₂)₂₋₃ORᵃ, and —(CH₂)₁₋₂—Y²—R⁷;

R³ is independently —(C₀₋₂ alkylene)-(5-membered heteroaryl) wherein the heteroaryl includes 2 to 4 ring carbon atoms and 1 to 3 ring heteroatoms are each independently selected from: N, N(Rᶠ), and S, wherein the heteroaryl is substituted with from 0 to 2 Rᵍ;

R⁴ is, at each occurrence, independently selected from H, halo and C₁₋₄ alkyl;

R⁶ is, at each occurrence, independently selected from: OH, ORᵃ, —NRᵇRᶜ, —C(O)NRᵇRᵏ, or heteroaryl including from 5 to 6 ring atoms, wherein from 1 to 4 ring atoms are each independently selected from N, N($R^f$), O, and S, wherein the heteroaryl is substituted with from 0 to 3 $R^d$;

—$Y^2$—$R^7$ is independently selected from and;

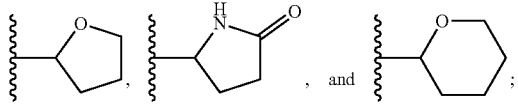

$R^a$ is, at each occurrence, independently:
(i) $C_{1-6}$ alkyl substituted with from 0 to 2 $R^e$;
(ii) $C_{3-6}$ cycloalkyl substituted with from 0 to 2 $R^g$;
(iii) —($C_{0-2}$ alkylene)-heterocyclyl including from 4 to 10 ring atoms, wherein from 1 to 3 ring atoms are each independently selected from N($R^f$), O, and S, wherein the heterocyclyl is substituted with from 0 to 3 $R^g$;
(iv) —($C_{0-2}$ alkylene)-($C_{6-10}$ aryl), wherein the aryl is substituted with from 0 to 3 $R^d$; or
(v) —($C_{0-2}$ alkylene)-heteroaryl including from 5 to 10 ring atoms, wherein from 1 to 3 ring atoms are each independently selected from N, N($R^f$), O, and S, wherein the heteroaryl is substituted with from 0 to 3 $R^d$;

$R^b$ is, at each occurrence, independently selected from H, $C_{1-4}$ alkyl, and —($C_{0-2}$ alkylene)-phenyl;

$R^c$ is, at each occurrence, independently selected from: H, —C(O)$R^a$, —C(O)O$R^a$, —C(O)N$R^j R^k$, —S(O)$_2 R^h$, $C_{1-6}$ alkyl substituted with from 0 to 2 $R^e$, —($C_{0-3}$ alkylene)-(phenyl substituted with from 0 to 4 $R^n$), and —($C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;

alternatively, $R^b$ and $R^c$, together with the nitrogen atom to which each is attached form heterocyclyl including from 3 to 10 ring atoms, wherein from 1 to 3 ring atoms are each independently selected from N($R^f$), O, and S, and wherein the heterocyclyl is substituted with from 0 to 3 $R^g$;

$R^d$ is, at each occurrence, independently selected from: halo, CN, $C_{1-4}$ alkoxy, $C_{1-4}$ haloalkyl, $C_{1-4}$ haloalkoxy, —C(O)O($C_{1-4}$ alkyl), —NHC(O)($C_{1-4}$ alkyl), —NHC(O)O($C_{1-4}$ alkyl), —S(O)$_2$($C_{1-4}$ alkyl), benzoxy, $C_{1-4}$ alkyl substituted with from 0 to 2 $R^e$, and heteroaryl including from 5 to 6 ring atoms, wherein from 1 to 4 ring atoms are each independently selected from N, N($R^f$), O, and S, wherein the heteroaryl is substituted with 0 to 2 $R^n$;

$R^e$ is, at each occurrence, independently selected from: F, Cl, OH, $C_{1-4}$ alkoxy, $C_{1-4}$ haloalkyl, and $C_{1-4}$ haloalkoxy;

$R^f$ is, at each occurrence, independently H or $C_{1-4}$ alkyl;

$R^h$ is independently $C_{1-4}$ alkyl or phenyl;

$R^j$ is independently H or $C_{1-4}$ alkyl;

$R^k$ is independently selected from H, $C_{1-4}$ alkyl and phenyl; and $R^n$ is, at each occurrence, independently selected from: F, Cl, $C_{1-4}$ alkyl, and $C_{1-4}$ alkoxy.

In a fifth aspect, within the scope of any of the first to fourth aspects, the invention provides a compound of Formula (IIa):

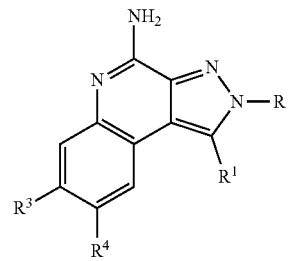

(IIa)

or a stereoisomer, a tautomer or a pharmaceutically acceptable salt thereof, wherein:

$R^1$ is independently selected from H, F and $C_{1-4}$ alkyl;

$R^2$ is independently selected from: H, $C_{1-4}$ alkyl substituted with 0 to 3 F, —(CH$_2$)$_{1-3}$—$R^6$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O($C_{1-4}$ alkyl), —(CH$_2$)$_{1-3}$O(CH$_2$)$_{2-3}$O$R^a$, —CH$_2$CH(CH$_3$)NHC(O)$R^a$, and —(CH$_2$)$_{1-2}$—$Y^2$—$R^7$;

$R^3$ is independently 5-membered heteroaryl wherein the heteroaryl includes 3 to 4 ring carbon atoms and 1 to 2 ring heteroatoms are each independently selected from: N, NH, and S; provided that when $R^3$ is furanyl, $R^2$ is other than $C_{1-4}$ alkyl;

$R^4$ is independently selected from H, halo and $C_{1-4}$ alkyl;

$R^6$ is independently selected from: OH, O$R^a$, N$R^b R^c$, —N$R^b$C(O)$R^a$, —C(O)N$R^b R^k$, —NHC(O)O$R^a$, —NHC(O)N$R^j R^k$, —NHS(O)$_2 R^h$, —SO$_2$($C_{1-4}$ alkyl),

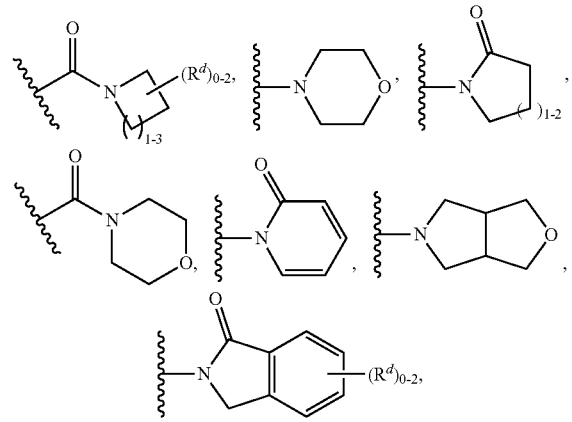

and heteroaryl including from 5 to 6 ring atoms, wherein from 1 to 4 ring atoms are each independently selected from N, N($R^f$), O, and S, wherein the heteroaryl is substituted with from 0 to 3 $R^d$;

—$Y^2$—$R^7$ is independently selected from $C_{3-6}$ cycloalkyl substituted with 0 to 2 $R^d$,

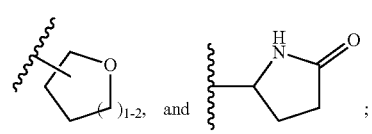

$R^a$ is, at each occurrence, independently selected from:
$C_{1-4}$ alkyl substituted with 0 to 2 $R^e$, $C_{3-6}$ cycloalkyl,

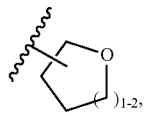

phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

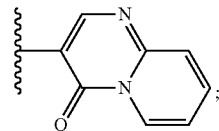 [SMILES: *c1cnc2ccccn2c1=O]

wherein each ring moiety is substituted with 0 to 3 $R^d$;
$R^b$ is, at each occurrence, independently H, $C_{1-4}$ alkyl, or phenyl substituted with 0 to 2 F;
$R^c$ is independently $C_{1-4}$ alkyl, —($C_{0-3}$ alkylene)-(phenyl substituted with from 0 to 3 $R^n$), or —($C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;
$R^d$ is, at each occurrence, independently selected from: halo, CN, —CH$_2$OH, $C_{1-4}$ alkyl, $C_{1-4}$ alkoxy, $C_{1-4}$ haloalkyl, $C_{1-4}$ haloalkoxy, —C(O)O($C_{1-4}$ alkyl), —CONH$_2$, NH$_2$, N($C_{1-4}$ alkyl)$_2$, —NHC(O)($C_{1-4}$ alkyl), —NHC(O)O($C_{1-4}$ alkyl), —S(O)$_2$($C_{1-4}$ alkyl), benzoxy, phenyl, and heteroaryl including from 5 to 6 ring atoms, wherein from 1 to 4 ring atoms are each independently selected from N, N($R^f$), O, and S, wherein the heteroaryl is substituted with 0 to 2 $R^n$;
$R^e$ is, at each occurrence, independently selected from: halo, OH, $C_{1-4}$ alkoxy, $C_{1-4}$ haloalkyl, and $C_{1-4}$ haloalkoxy;
$R^f$ is, at each occurrence, independently H or $C_{1-4}$ alkyl;
$R^h$ is independently $C_{1-4}$ alkyl or phenyl;
$R^j$ is independently H or $C_{1-4}$ alkyl;
$R^k$ is independently selected from H, $C_{1-4}$ alkyl and phenyl; and
$R^n$ is, at each occurrence, independently selected from: halo, $C_{1-4}$ alkyl, and $C_{1-4}$ alkoxy.

In another aspect, within the scope of any of the first to fourth aspects, the invention provides a compound of Formula (IIa), or a stereoisomer, a tautomer or a pharmaceutically acceptable salt thereof, wherein:
$R^1$ is independently selected from H, F and $C_{1-4}$ alkyl;
$R^2$ is independently selected from: H, $C_{1-4}$ alkyl substituted with 0 to 3 F, —(CH$_2$)$_{1-3}$—R$^6$, —(CH$_2$)$_{1-3}$O(CH$_2$)$_{2-3}$OR$^a$, and —(CH$_2$)$_{1-2}$—Y$^2$—R$^7$;
$R^3$ is independently 5-membered heteroaryl wherein the heteroaryl includes 3 to 4 ring carbon atoms and 1 to 2 ring heteroatoms are each independently selected from: N, NH, and S;
$R^4$ is independently selected from H, halo and $C_{1-4}$ alkyl;
$R^6$ is independently selected from: OH, OR$^a$, NR$^b$R$^c$, —NR$^b$C(O)R$^a$, —C(O)NHR$^k$, —NHC(O)OR$^a$, —NHC(O)NR$^j$R$^k$, —NHS(O)$_2$R$^h$, —SO$_2$($C_{1-4}$ alkyl),

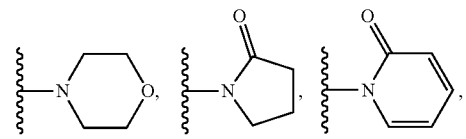

and heteroaryl including from 5 to 6 ring atoms, wherein from 1 to 4 ring atoms are each independently selected from N, N(R$^f$), O, and S, wherein the heteroaryl is substituted with from 0 to 3 $R^d$;
—Y$^2$—R$^7$ is independently selected from

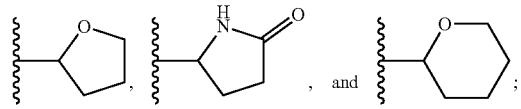

$R^a$ is, at each occurrence, independently selected from:
$C_{1-4}$ alkyl substituted with 0 to 1 $R^e$, $C_{3-6}$ cycloalkyl,

phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

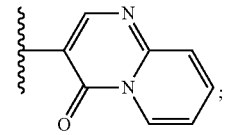 [SMILES: *c1cnc2ccccn2c1=O]

wherein each ring moiety is substituted with 0 to 3 $R^d$;
$R^b$ is, at each occurrence, independently H or $C_{1-4}$ alkyl;
$R^c$ is independently $C_{1-4}$ alkyl, —($C_{0-3}$ alkylene)-(phenyl substituted with from 0 to 3 $R^n$), or —($C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;
$R^d$ is, at each occurrence, independently selected from: halo, CN, —CH$_2$OH, $C_{1-4}$ alkyl, $C_{1-4}$ alkoxy, $C_{1-4}$ haloalkyl, $C_{1-4}$ haloalkoxy, —C(O)O($C_{1-4}$ alkyl), —NHC(O)O($C_{1-4}$ alkyl), —S(O)$_2$($C_{1-4}$ alkyl), benzoxy, phenyl, and heteroaryl including from 5 to 6 ring atoms, wherein from 1 to 4 ring atoms are each independently selected from N, N($R^f$), O, and S, wherein the heteroaryl is substituted with 0 to 2 $R^n$;
$R^e$ is, at each occurrence, independently selected from: halo, OH, $C_{1-4}$ alkoxy, $C_{1-4}$ haloalkyl, and $C_{1-4}$ haloalkoxy;

$R^1$ is, at each occurrence, independently H or $C_{1-4}$ alkyl;
$R^h$ is independently $C_{1-4}$ alkyl or phenyl;
$R^j$ is independently H or $C_{1-4}$ alkyl;
$R^k$ is independently selected from H, $C_{1-4}$ alkyl and phenyl; and
$R^n$ is, at each occurrence, independently selected from: halo, $C_{1-4}$ alkyl, and $C_{1-4}$ alkoxy.

In another aspect, within the scope of any of the first to fourth aspects, the invention provides a compound of Formula (IIa), or a stereoisomer, a tautomer or a pharmaceutically acceptable salt thereof, wherein:

$R^1$ is independently selected from H, F and $C_{1-4}$ alkyl;
$R^2$ is independently selected from: $-(CH_2)_{1-3}-R^6$, $-(CH_2)_{1-3}O(CH_2)_{2-3}OR^a$, and $-(CH_2)_{1-2}-Y^2-R^7$;
$R^3$ is independently 5-membered heteroaryl wherein the heteroaryl includes 3 to 4 ring carbon atoms and 1 to 2 ring heteroatoms are each independently selected from: N, NH, O, and S;
$R^4$ is independently selected from H, F and $C_{1-4}$ alkyl;
$R^6$ is independently selected from: OH, $OR^a$, $NR^bR^c$, $-NR^bC(O)R^a$, $-C(O)NHR^k$, $-NHC(O)OR^a$, $-NHC(O)NR^jR^k$, $-NHS(O)_2R^h$,

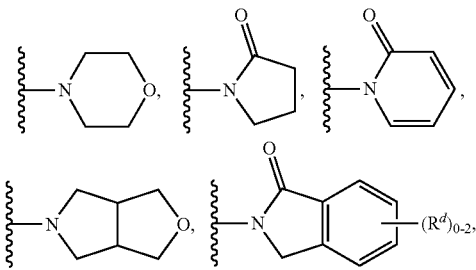

and heteroaryl including from 5 to 6 ring atoms, wherein from 1 to 4 ring atoms are each independently selected from N, N($R^f$), O, and S, wherein the heteroaryl is substituted with from 0 to 3 $R^d$;
$-Y^2-R^7$ is independently selected from

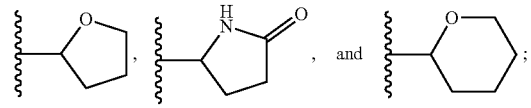

$R^a$ is, at each occurrence, independently selected from: $C_{1-4}$ alkyl substituted with 0 to 1 OH, tetrahydro-2H-pyranyl, phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

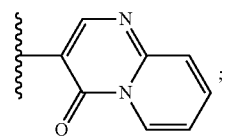 [SMILES: *c1cnc2ccccn2c1=O]

wherein each ring moiety is substituted with 0 to 3 $R^d$;
$R^b$ is, at each occurrence, independently H or $C_{1-4}$ alkyl;
$R^c$ is independently $C_{1-4}$ alkyl, $-(C_{0-3}$ alkylene)-(phenyl substituted with from 0 to 3 $R^n$), or $-(C_{0-3}$ alkylene)- heteroaryl including from 5-6 ring atoms, wherein from 1-4 ring atoms are each independently selected from N, N($R^f$), O, and S, wherein the heteroaryl is substituted with from 0 to 3 $R^n$;
$R^d$ is, at each occurrence, independently selected from: F, Cl, CN, $-CH_2OH$, $C_{1-4}$ alkyl, $C_{1-4}$ alkoxy, $C_{1-4}$ haloalkyl, $C_{1-4}$ haloalkoxy, $-C(O)O(C_{1-4}$ alkyl), $-NHC(O)O(C_{1-4}$ alkyl), $-S(O)_2(C_{1-4}$ alkyl), benzoxy, and heteroaryl including from 5 to 6 ring atoms, wherein from 1 to 4 ring atoms are each independently selected from N, N($R^f$), O, and S, wherein the heteroaryl is substituted with 0 to 2 $R^n$;
$R^f$ is, at each occurrence, independently H or $C_{1-4}$ alkyl;
$R^h$ is independently $C_{1-4}$ alkyl or phenyl;
$R^j$ is independently H or $C_{1-4}$ alkyl;
$R^k$ is independently selected from H, $C_{1-4}$ alkyl and phenyl; and
$R^n$ is, at each occurrence, independently selected from: F, Cl, $C_{1-4}$ alkyl, and $C_{1-4}$ alkoxy.

In a sixth aspect, within the scope of any of the first to fifth aspects, the invention provides a compound of Formula (IIa), or a stereoisomer, a tautomer, or a pharmaceutically acceptable salt thereof, wherein:
$R^1$ is H;
$R^2$ is independently selected from: H, $C_{1-4}$ alkyl substituted with 0 to 3 F, $-(CH_2)_{1-3}-R^6$, $-(CH_2)_{1-2}CH(CH_3)OH$, $-(CH_2)_{1-2}C(CH_3)_2OH$, $-(CH_2)_{1-2}CH(OCH_3)CH_2OH$, $-CH(CH_3)(CH_2)_{1-2}OH$, $-(CH_2)_{1-2}CH(OH)CH_2F$, $-(CH_2)_{1-2}CH(CH_3)O(C_{1-4}$ alkyl), $-(CH_2)_{1-3}O(CH_2)_{2-3}OR^a$, $-CH_2CH(CH_3)NHC(O)R^a$, and $-(CH_2)_{1-2}-Y^2-R^7$;
$R^3$ is independently selected from

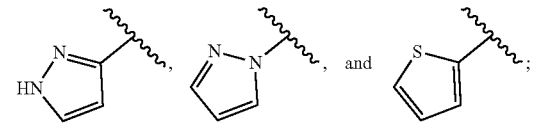 [SMILES: *c1cc[nH]n1 ; *n1cccn1 ; *c1cccs1]

$R^4$ is independently H, F, or Cl;
$R^6$ is independently selected from: OH, $OR^a$, $NR^bR^c$, $-NR^bC(O)R^a$, $-C(O)NR^bR^k$, $-NHC(O)O(C_{1-6}$ alkyl), $-NHC(O)OPh$, $-NHC(O)N(C_{1-4}$ alkyl)$_2$, $-NHC(O)N(C_{1-4}$ alkyl)Ph, $-NHS(O)_2(C_{1-4}$ alkyl), $-SO_2(C_{1-4}$ alkyl),

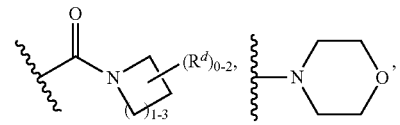

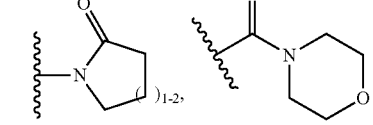

and heteroaryl including from 5 to 6 ring atoms, wherein from 1 to 4 ring atoms are each independently selected from N, N($R^f$), O, and S, wherein the heteroaryl is substituted with from 0 to 3 $R^d$;

—Y²—R⁷ is independently selected from: $C_{3-6}$ cycloalkyl substituted with 0 to 2 $R^d$,

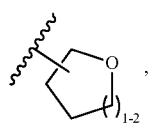, and 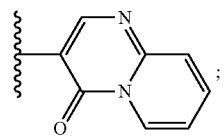;

$R^a$ is, at each occurrence, independently selected from: $C_{1-4}$ alkyl substituted with 0 to 2 $R^e$, $C_{3-6}$ cycloalkyl,

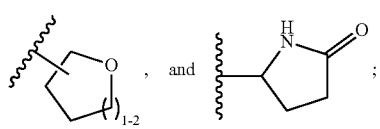, phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

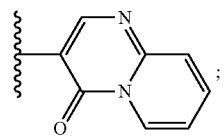;

wherein each ring moiety is substituted with 0 to 3 $R^d$;
$R^b$ is, at each occurrence, independently H, $C_{1-4}$ alkyl, or phenyl substituted with 0 to 2 F;
$R^c$ is independently $C_{1-4}$ alkyl, —($C_{0-3}$ alkylene)-(phenyl substituted with from 0 to 3 $R^n$), or —($C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;
$R^d$ is, at each occurrence, independently selected from: F, Cl, CN, —CH₂OH, $C_{1-4}$ alkyl, $C_{1-4}$ alkoxy, $C_{1-4}$ haloalkyl, $C_{1-4}$ haloalkoxy, —C(O)O($C_{1-4}$ alkyl), —CONH₂, NH₂, N($C_{1-4}$ alkyl)₂, —NHC(O)($C_{1-4}$ alkyl), —NHC(O)O($C_{1-4}$ alkyl), —S(O)₂($C_{1-4}$ alkyl), benzoxy, phenyl, and heteroaryl including from 5 to 6 ring atoms, wherein from 1 to 4 ring atoms are each independently selected from N, N($R^f$), O, and S, wherein the heteroaryl is substituted with 0 to 2 $R^n$;
$R^e$ is, at each occurrence, independently selected from: F, Cl, OH, $C_{1-4}$ alkoxy, $C_{1-4}$ haloalkyl, and $C_{1-4}$ haloalkoxy;
$R^f$ is, at each occurrence, independently H or $C_{1-4}$ alkyl;
$R^k$ is independently selected from H, $C_{1-4}$ alkyl and phenyl;
$R^n$ is, at each occurrence, independently selected from: F, Cl, $C_{1-4}$ alkyl, and $C_{1-4}$ alkoxy.

In another aspect, within the scope of any of the first to fifth aspects, the invention provides a compound of Formula (IIa), or a stereoisomer, a tautomer, or a pharmaceutically acceptable salt thereof, wherein:
$R^1$ is H;
$R^2$ is independently selected from: H, $C_{1-4}$ alkyl substituted with 0 to 3 F, —(CH₂)$_{1-3}$—R⁶, —(CH₂)$_{1-3}$O(CH₂)$_{2-3}$OR$^a$, and —(CH₂)$_{1-2}$—Y²—R⁷;

$R^3$ is independently selected from

$R^4$ is independently H, F, or Cl;
$R^6$ is independently selected from: OH, OR$^a$, NR$^b$R$^c$, —NR$^b$C(O)R$^a$, —C(O)NHR$^k$, —NHC(O)O($C_{1-6}$ alkyl), —NHC(O)N($C_{1-4}$ alkyl)₂, —NHS(O)₂($C_{1-4}$ alkyl), —SO₂($C_{1-4}$ alkyl),

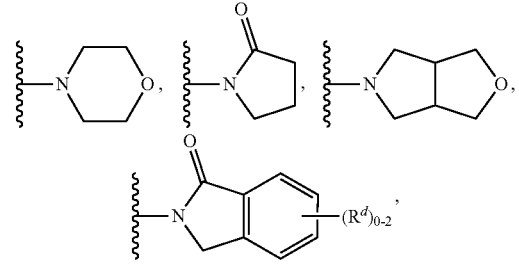

—NH(pyridyl), and heteroaryl including from 5 to 6 ring atoms, wherein from 1 to 4 ring atoms are each independently selected from N, N($R^f$), O, and S, wherein the heteroaryl is substituted with from 0 to 3 $R^d$;
—Y²—R⁷ is independently selected from:

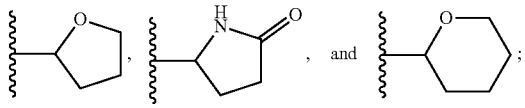

$R^a$ is, at each occurrence, independently selected from: $C_{1-4}$ alkyl substituted with 0 to 1 $R^e$, $C_{3-6}$ cycloalkyl,

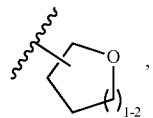, phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

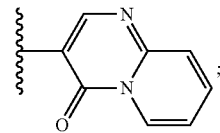 [SMILES: *c1cnc2ccccn2c1=O];

wherein each ring moiety is substituted with 0 to 3 $R^d$;
$R^b$ is, at each occurrence, independently H or $C_{1-4}$ alkyl;

$R^c$ is independently $C_{1-4}$ alkyl, —($C_{0-3}$ alkylene)-(phenyl substituted with from 0 to 3 $R^n$), or —($C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;

$R^d$ is, at each occurrence, independently selected from: F, Cl, CN, —CH$_2$OH, $C_{1-4}$ alkyl, $C_{1-4}$ alkoxy, $C_{1-4}$ haloalkyl, $C_{1-4}$ haloalkoxy, —C(O)O($C_{1-4}$ alkyl), —NHC(O)O($C_{1-4}$ alkyl), —S(O)$_2$($C_{1-4}$ alkyl), benzoxy, phenyl, and heteroaryl including from 5 to 6 ring atoms, wherein from 1 to 4 ring atoms are each independently selected from N, N($R^f$), O, and S, wherein the heteroaryl is substituted with 0 to 2 $R^n$;

$R^e$ is, at each occurrence, independently selected from: F, Cl, OH, $C_{1-4}$ alkoxy, $C_{1-4}$ haloalkyl, and $C_{1-4}$ haloalkoxy;

$R^f$ is, at each occurrence, independently H or $C_{1-4}$ alkyl;

$R^k$ is independently selected from H, $C_{1-4}$ alkyl and phenyl; and $R^n$ is, at each occurrence, independently selected from: F, Cl, $C_{1-4}$ alkyl, and $C_{1-4}$ alkoxy.

In another aspect, within the scope of any of the first to fifth aspects, the invention provides a compound of Formula (IIa), or a stereoisomer, a tautomer, or a pharmaceutically acceptable salt thereof, wherein:

$R^1$ is H;

$R^2$ is independently selected from —(CH$_2$)$_{1-3}$—$R^6$, —(CH$_2$)$_{1-3}$O(CH$_2$)$_{2-3}$OR$^a$, and —(CH$_2$)$_{1-2}$—Y$^2$—R$^7$;

$R^3$ is independently selected from

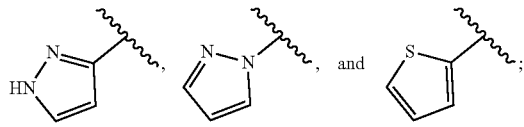 [SMILES: *c1cc[nH]n1 ; *n1cccn1 ; *c1cccs1]

$R^4$ is H;

$R^6$ is independently selected from: OH, OR$^a$, NR$^b$R$^c$, —NR$^b$C(O)R$^a$, —C(O)NH(C$_{1-4}$ alkyl), —C(O)NHPh, —NHC(O)O(C$_{1-6}$ alkyl), —NHC(O)N(C$_{1-4}$ alkyl)$_2$, —NHS(O)$_2$(C$_{1-4}$ alkyl),

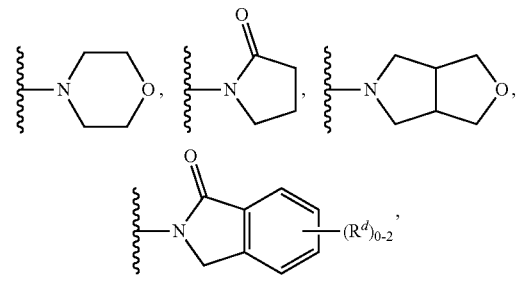

and heteroaryl including from 5 to 6 ring atoms, wherein from 1 to 4 ring atoms are each independently selected from N, N(R$^f$), O, and S, wherein the heteroaryl is substituted with from 0 to 3 R$^d$;

—Y$^2$—R$^7$ is independently selected from:

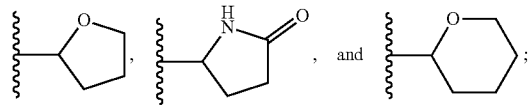

R$^a$ is, at each occurrence, independently selected from: $C_{1-4}$ alkyl substituted with 0 to 1 OH, tetrahydro-2H-pyranyl, phenyl, benzyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, pyrazolo[1,5-a]pyrimidinyl and

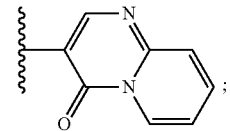 [SMILES: *c1cnc2ccccn2c1=O]

wherein each ring moiety is substituted with 0 to 3 R$^d$;

R$^b$ is, at each occurrence, independently H or $C_{1-4}$ alkyl;

R$^c$ is independently $C_{1-4}$ alkyl, —($C_{0-3}$ alkylene)-(phenyl substituted with from 0 to 3 R$^n$), or —($C_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 R$^n$;

R$^d$ is, at each occurrence, independently selected from: F, Cl, CN, —CH$_2$OH, $C_{1-4}$ alkyl, $C_{1-4}$ alkoxy, $C_{1-4}$ haloalkyl, $C_{1-4}$ haloalkoxy, —C(O)O($C_{1-4}$ alkyl), —NHC(O)O($C_{1-4}$ alkyl), —S(O)$_2$($C_{1-4}$ alkyl), benzoxy, and heteroaryl including from 5 to 6 ring atoms, wherein from 1 to 4 ring atoms are each independently selected from N, N(R$^f$), O, and S, wherein the heteroaryl is substituted with 0 to 2 R$^n$;

R$^f$ is, at each occurrence, independently H or $C_{1-4}$ alkyl; and

R$^n$ is, at each occurrence, independently selected from: F, Cl, $C_{1-4}$ alkyl, and $C_{1-4}$ alkoxy.

In a seventh aspect, within the scope of any of the first to sixth aspects, the invention provides a compound of Formula (IIa), or a tautomer, or a pharmaceutically acceptable salt thereof, wherein:

R$^1$ is H;

R$^2$ is independently selected from: H, $C_{1-4}$ alkyl substituted with 0 to 3 F, —(CH$_2$)$_{1-3}$—R$^6$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O($C_{1-4}$ alkyl), —CH$_2$CH(CH$_3$)NHC(O)R$^a$, and —(CH$_2$)$_{1-2}$—Y$^2$—R$^7$;

R$^3$ is independently

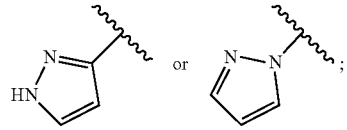 [SMILES: *c1cc[nH]n1 ; *n1cccn1]

R$^4$ is independently H, F, or Cl;

R$^6$ is independently selected from: OH, OR$^a$, N($C_{1-4}$ alkyl)$_2$, —NH($C_{1-4}$ alkyl), —NH(CH$_2$)$_{1-2}$(phenyl substituted with 0 to 1 $R^d$), —N($C_{1-2}$ alkyl)Bn, —NH(pyridyl), —$NR^bC(O)R^a$, —NHC(O)O($C_{1-6}$ alkyl), —NHC(O)OPh, —NHC(O)N($C_{1-4}$ alkyl)$_2$, —NHC(O)CH$_2$OCH$_2$CF$_3$, —NHC(O)N($C_{1-4}$ alkyl)Ph, —C(O)NH$_2$, —C(O)NH($C_{1-4}$ alkyl substituted with 0 to 2 $R^e$), —C(O)N(CH$_3$)($C_{1-4}$ alkyl substituted with 0 to 2 $R^e$), —C(O)NH($C_{3-6}$ cycloalkyl), —C(O)NH(phenyl substituted with 0 to 1 F), —C(O)NH(pyridyl), —NHS(O)$_2$($C_{1-4}$ alkyl), —SO$_2$($C_{1-4}$ alkyl),

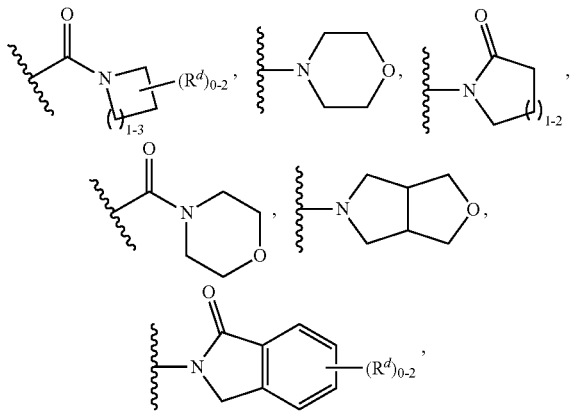

and heteroaryl selected from imidazolyl, pyrazolyl, oxazolyl, isoxazolyl, thiazolyl, oxadiazolyl and pyridyl, wherein the heteroaryl is substituted with 0 to 2 $R^d$;

—$Y^2$—$R^7$ is independently selected from: $C_{3-6}$ cycloalkyl substituted with 0 to 2 $R^d$,

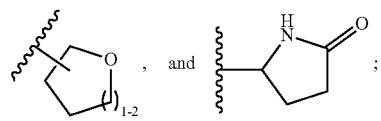

$R^a$ is, at each occurrence, independently selected from: $C_{1-4}$ alkyl substituted with 0 to 2 $R^e$, $C_{3-6}$ cycloalkyl,

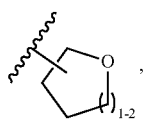

phenyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, and pyrazolo[1,5-a]pyrimidinyl; wherein each ring moiety is substituted with 0 to 3 $R^d$;

$R^b$ is independently H or $C_{1-2}$ alkyl;

$R^d$ is, at each occurrence, independently selected from: F, Cl, CN, —CH$_2$OH, $C_{1-4}$ alkyl, $C_{1-4}$ alkoxy, $C_{1-4}$ haloalkyl, $C_{1-4}$ haloalkoxy, —CONH$_2$, NH$_2$, N($C_{1-4}$ alkyl)$_2$, —C(O)O($C_{1-4}$ alkyl), benzoxy, phenyl, and pyridyl; and $R^e$ is independently selected from F, OH and $C_{1-4}$ alkoxy.

In another aspect, within the scope of any of the first to sixth aspects, the invention provides a compound of Formula (IIa), or a tautomer, or a pharmaceutically acceptable salt thereof, wherein:

$R^1$ is H;

$R^2$ is independently selected from: H, $C_{1-4}$ alkyl substituted with 0 to 3 F, or —(CH$_2$)$_{2-3}$—$R^6$;

$R^3$ is independently

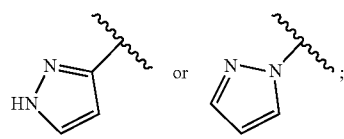 [SMILES: *c1cc[nH]n1 ; *n1cccn1]

$R^4$ is independently H, F, or Cl;

$R^6$ is independently selected from: OH, OR$^a$, N($C_{1-4}$ alkyl)$_2$, —$NR^bC(O)R^a$, —NHC(O)O($C_{1-6}$ alkyl), —NHC(O)N($C_{1-4}$ alkyl)$_2$, —NHC(O)CH$_2$OCH$_2$CF$_3$, —NHC(O)N($C_{1-4}$ alkyl)Ph, C(O)NH$_2$, —C(O)NHPh, —NHS(O)$_2$($C_{1-4}$ alkyl), —SO$_2$($C_{1-4}$ alkyl),

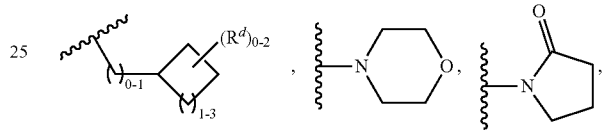

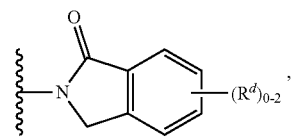

—NH(pyridyl), and heteroaryl selected from imidazolyl, pyrazolyl, oxazolyl, isoxazolyl, thiazolyl, oxadiazolyl and pyridyl, wherein heteroaryl is substituted with 0 to 2 $R^d$;

$R^a$ is, at each occurrence, independently selected from: $C_{1-4}$ alkyl, $C_{3-6}$ cycloalkyl,

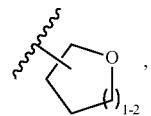

phenyl, oxazolyl, isoxazolyl, thiazolyl, N—($C_{1-4}$ alkyl)-pyrazolyl, pyrazol-1-yl, N—($C_{1-4}$ alkyl)-imidazolyl, pyridyl, pyridazinyl, pyrimidyl, pyrazinyl, N—($C_{1-4}$ alkyl)-benzimidazolyl, and pyrazolo[1,5-a]pyrimidinyl; wherein each ring moiety is substituted with 0 to 3 $R^d$;

$R^b$ is independently H or $C_{1-2}$ alkyl; and $R^d$ is, at each occurrence, independently selected from: F, Cl, CN, —CH$_2$OH, $C_{1-4}$ alkyl, $C_{1-4}$ alkoxy, $C_{1-4}$ haloalkyl, $C_{1-4}$ haloalkoxy, benzoxy, phenyl, and pyridyl.

In another aspect, within the scope of any of the first to sixth aspects, the invention provides a compound of Formula (IIa), or a tautomer, or a pharmaceutically acceptable salt thereof, wherein:

R[1] is H;
R[2] is —(CH$_2$)$_{2-3}$—R[6].
R[3] is independently

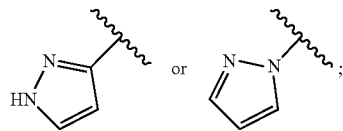

R[4] is H;
R[6] is independently selected from: OH, OR$^a$, N(C$_{1-4}$ alkyl)$_2$, —NR$^b$C(O)R$^a$, —C(O)NHPh, —NHC(O)O(C$_{1-6}$ alkyl), —NHC(O)N(C$_{1-4}$ alkyl)$_2$, —NHS(O)$_2$(C$_{1-4}$ alkyl),

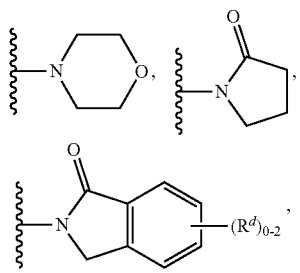

and pyrazol-1-yl substituted with 0 to 2 R$^d$;
R$^a$ is, at each occurrence, independently selected from: C$_{1-4}$ alkyl, tetrahydro-2H-pyranyl, phenyl, oxazolyl, isoxazolyl, thiazolyl, N—(C$_{1-4}$ alkyl)-pyrazolyl, pyrazol-1-yl, N—(C$_{1-4}$ alkyl)-imidazolyl, pyridyl, pyridazinyl, pyrimidyl, pyrazinyl, N—(C$_{1-4}$ alkyl)-benzimidazolyl, and pyrazolo[1,5-a]pyrimidinyl; wherein each ring moiety is substituted with 0 to 3 R$^d$;
R$^b$ is independently H or C$_{1-2}$ alkyl; and
R$^d$ is, at each occurrence, independently selected from: F, Cl, CN, —CH$_2$OH, C$_{1-4}$ alkyl, C$_{1-4}$ alkoxy, C$_{1-4}$ haloalkyl, C$_{1-4}$ haloalkoxy, benzoxy, and pyridyl.

In an eighth aspect, the invention provides a compound of Formula (IIIa-1):

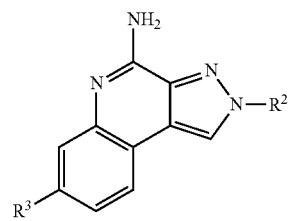

(IIIa-1)

or a stereoisomer, a tautomer or a pharmaceutically acceptable salt thereof, wherein:
R[2] is independently selected from: H, C$_{1-4}$ alkyl substituted with 0 to 3 F, —(CH$_2$)$_{1-2}$OCHF$_2$, —(CH$_2$)$_2$O(C$_{1-4}$ alkyl), —(CH$_2$)$_2$O(CH$_2$)$_2$(C$_{1-4}$ alkoxy), —(CH$_2$)$_{2-3}$OH, —(CH$_2$)$_{1-3}$OR$^a$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O(C$_{1-4}$ alkyl), —(CH$_2$)$_{2-3}$NHC(O)R$^a$, —CH$_2$CH(CH$_3$)NHC(O)R$^a$, —(CH$_2$)$_{2-3}$NHC(O)CH$_2$OCH$_2$CF$_3$, —(CH$_2$)$_{2-3}$N(CH$_3$)Bn, —(CH$_2$)$_{2-3}$N(CH$_3$)C(O)Ph, —(CH$_2$)$_{2-3}$NHC(O)O(C$_{1-4}$ alkyl), —(CH$_2$)$_{2-3}$NHC(O)OPh, —(CH$_2$)$_2$C(O)NH$_2$, —(CH$_2$)$_{2-3}$SO$_2$(C$_{1-4}$ alkyl), —(CH$_2$)$_{1-2}$NH(C$_{1-4}$ alkyl), —(CH$_2$)$_{1-2}$CONH(C$_{1-4}$ alkyl substituted with 0 to 2 R$^e$), —(CH$_2$)$_{1-2}$CON(CH$_3$)(C$_{1-4}$ alkyl substituted with 0 to 2 R$^e$), —(CH$_2$)$_{1-2}$NH(CH$_2$)$_{1-2}$(phenyl substituted with 0 to 1 R$^d$), —(CH$_2$)$_{2-3}$NH(pyridyl), —(CH$_2$)$_{1-2}$C(O)NH(pyridyl), —(CH$_2$)$_{1-2}$C(O)NH(phenyl substituted with 0 to 1 F), —(CH$_2$)$_{1-2}$CH(CH$_3$)NHSO$_2$(C$_{1-4}$ alkyl),

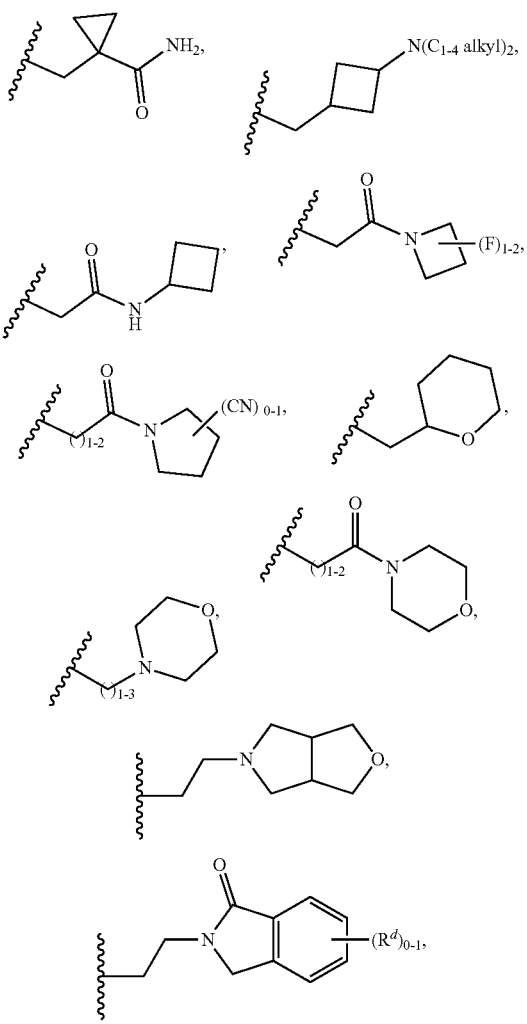

and —(CH$_2$)$_{1-3}$-(heteroaryl), wherein the heteroaryl is selected from imidazolyl, pyrazolyl, oxazolyl, isoxazolyl, thiazolyl, oxadiazolyl and pyridyl, and the heteroaryl is substituted with 0 to 2 R$^d$;

R[3] is independently

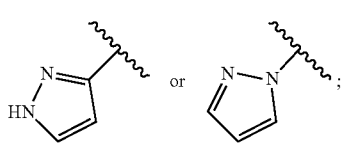 [SMILES: *c1cc[nH]n1 ; *n1cccn1]

$R^a$ is independently selected from: $C_{3-6}$ cycloalkyl,

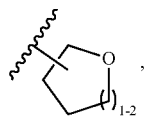

phenyl, oxazolyl, thiazolyl, N—($C_{1-4}$ alkyl)-pyrazolyl, N—($C_{1-4}$ alkyl)-imidazolyl, pyridyl, pyrimidyl, pyrazinyl, and N—($C_{1-4}$ alkyl)-benzimidazolyl; wherein each ring moiety is substituted with 0 to 2 $R^d$;

$R^d$ is, at each occurrence, independently selected from: F, Cl, CN, $C_{1-4}$ alkyl, $C_{1-4}$ alkoxy, $C_{1-4}$ haloalkyl, $C_{1-4}$ haloalkoxy, $NH_2$, —C(O)O($C_{1-4}$ alkyl), phenyl, and benzoxy; and $R^e$ is independently selected from F, OH and $C_{1-4}$ alkoxy.

In another aspect, the invention provides a compound of Formula (IIIa-1):

(IIIa-1)

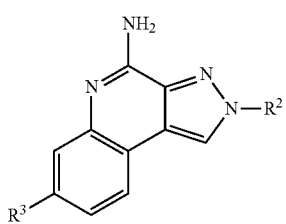

or a stereoisomer, a tautomer or a pharmaceutically acceptable salt thereof, wherein:

$R^2$ is independently selected from: H, $C_{1-4}$ alkyl substituted with 0 to 3 F, —$(CH_2)_2O(C_{1-4}$ alkyl), —$(CH_2)_{2-3}NHC(O)R^a$, —$(CH_2)_{2-3}NHC(O)CH_2OCH_2CF_3$, —$(CH_2)_{2-3}NHC(O)O(C_{1-4}$ alkyl), —$(CH_2)_2C(O)NH_2$, —$(CH_2)_{2-3}SO_2(C_{1-4}$ alkyl), —$(CH_2)_{2-3}NH$(pyridyl), —$(CH_2)_{1-2}C(O)NH$(phenyl substituted with 0 to 1 F),

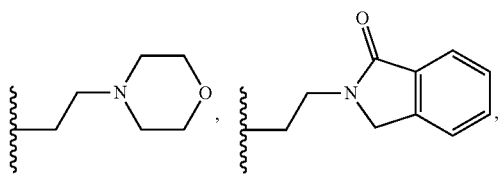

and —$(CH_2)_{1-3}$(heteroaryl), wherein heteroaryl is selected from imidazolyl, pyrazolyl, oxazolyl, isoxazolyl, thiazolyl, oxadiazolyl and pyridyl, and heteroaryl is substituted with 0 to 2 $R^d$;

$R^3$ is independently

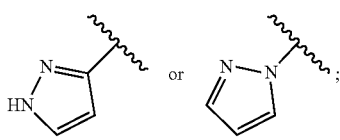

$R^a$ is independently selected from: $C_{3-6}$ cycloalkyl,

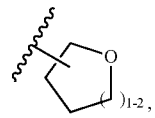

phenyl, oxazolyl, thiazolyl, N—($C_{1-4}$ alkyl)-pyrazolyl, N—($C_{1-4}$ alkyl)-imidazolyl, pyridyl, pyrimidyl, pyrazinyl, and N—($C_{1-4}$ alkyl)-benzimidazolyl; wherein each ring moiety is substituted with 0 to 2 $R^d$; and $R^d$ is, at each occurrence, independently selected from: F, Cl, CN, $C_{1-4}$ alkyl, $C_{1-4}$ alkoxy, $C_{1-4}$ haloalkyl, and phenyl.

In another aspect, the invention provides a compound of Formula (IIIa-1):

(IIIa-1)

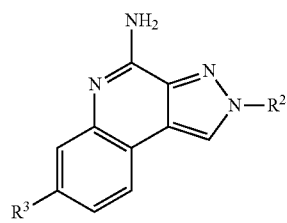

or a stereoisomer, a tautomer or a pharmaceutically acceptable salt thereof, wherein:

$R^2$ is independently selected from: H, $C_{1-4}$ alkyl substituted with 0 to 3 F, —$(CH_2)_2O(C_{1-4}$ alkyl), —$(CH_2)_{2-3}NHC(O)R^a$, —$(CH_2)_{2-3}NHC(O)CH_2OCH_2CF_3$, —$(CH_2)_{2-3}NHC(O)O(C_{1-4}$ alkyl), —$(CH_2)_2C(O)NH_2$, —$(CH_2)_{2-3}SO_2(C_{1-4}$ alkyl), —$(CH_2)_{2-3}NH$(pyridyl), —$(CH_2)_{1-2}C(O)NH$(phenyl substituted with 0 to 1 F),

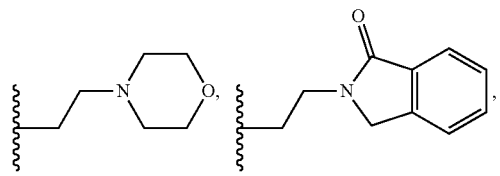

and —$(CH_2)_{1-3}$(heteroaryl), wherein heteroaryl is selected from imidazolyl, pyrazolyl, oxazolyl, isoxazolyl, thiazolyl, oxadiazolyl and pyridyl, and heteroaryl is substituted with 0 to 2 $R^d$;

$R^3$ is independently

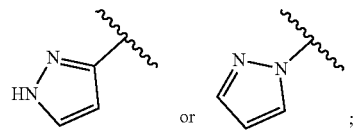 [SMILES: *c1cc[nH]n1 ; *n1cccn1]

$R^a$ is independently selected from: $C_{3-6}$ cycloalkyl, phenyl, oxazolyl, thiazolyl, N—($C_{1-4}$ alkyl)-pyrazolyl, N—($C_{1-4}$ alkyl)-imidazolyl, pyridyl, pyrimidyl, pyrazinyl, and N—($C_{1-4}$ alkyl)-benzimidazolyl; wherein each ring moiety is substituted with 0 to 2 $R^d$; and $R^d$ is, at each occurrence, independently selected from: F, Cl, CN, $C_{1-4}$ alkyl, $C_{1-4}$ alkoxy, $C_{1-4}$ haloalkyl, and phenyl.

In another aspect, the invention provides a compound of Formula (IIIa):

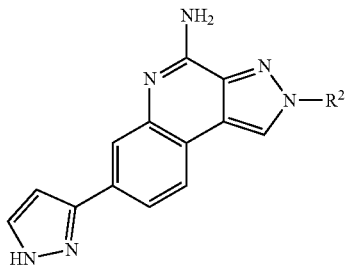

(IIIa)

or a tautomer or a pharmaceutically acceptable salt thereof, wherein:

R² is independently selected from —(CH₂)₂-—NHC(O)R^a,

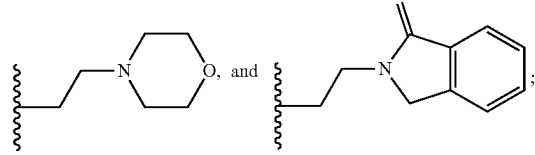

R^a is independently selected from: phenyl, oxazolyl, thiazolyl, N—(C₁₋₄ alkyl)-pyrazolyl, N—(C₁₋₄ alkyl)-imidazolyl, pyridyl, pyrimidyl, pyrazinyl, and N—(C₁₋₄ alkyl)-benzimidazolyl; wherein each ring moiety is substituted with 0 to 2 R^d; and R^d is, at each occurrence, independently selected from: F, Cl, CN, C₁₋₄ alkyl, C₁₋₄ alkoxy and C₁₋₄ haloalkyl.

In a ninth aspect, within the scope of the eighth aspect, the invention provides a compound of Formula (IIIa): or a tautomer or a pharmaceutically acceptable salt thereof, wherein:

R² is independently C₁₋₄ alkyl substituted with 0 to 3 F, —(CH₂)₂₋₄O(C₁₋₄ alkyl), —(CH₂)₂₋₃NHC(O)R^a, —(CH₂)₂₋₃NHC(O)O(C₁₋₄ alkyl), —(CH₂)₂C(O)NH₂, —(CH₂)₁₋₂C(O)NH(phenyl substituted with 0 to 1 F), —(CH₂)₁₋₃(heteroaryl), wherein heteroaryl is selected from imidazolyl, pyrazolyl, oxazolyl, isoxazolyl, thiazolyl, oxadiazolyl and pyridyl, and heteroaryl is substituted with 0 to 2 R^d;

R^a is independently selected from: oxazolyl, isoxazolyl, thiazolyl, N-methyl-imidazolyl, pyridyl and pyrazinyl; wherein each ring moiety is substituted with 0 to 2 R^d; and R^d is, at each occurrence, independently selected from F, Cl, C₁₋₄ alkyl, C₁₋₄ alkoxy and phenyl.

In another aspect, within the scope of the eighth aspect, the invention provides a compound of Formula (IIIa): or a tautomer or a pharmaceutically acceptable salt thereof, wherein:

R² is —(CH₂)₂-—NHC(O)R^a;

R^a is independently selected from: oxazolyl, thiazolyl, N-methyl-imidazolyl, pyridyl and pyrazinyl; wherein each ring moiety is substituted with 0 to 2 R^d; and R^d is, at each occurrence, independently selected from F, Cl and C₁₋₄ alkyl.

In a tenth aspect, within the scope of the ninth aspect, the invention provides a compound of Formula (IIIa): or a tautomer or a pharmaceutically acceptable salt thereof, wherein:

R^d is, at each occurrence, independently selected from F, Cl, CH₃, and OCH₃.

In another aspect, within the scope of the ninth aspect, the invention provides a compound of Formula (IIIa): or a tautomer or a pharmaceutically acceptable salt thereof, wherein:

R^d is, at each occurrence, independently selected from F, Cl and CH₃.

In an eleventh aspect, the invention provides a compound of Formula (IIIb-1):

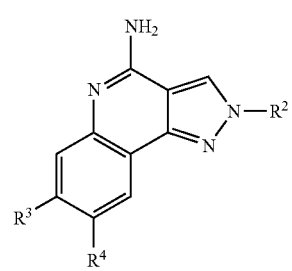

(IIIb-1)

or a stereoisomer, a tautomer or a pharmaceutically acceptable salt thereof, wherein:

R² is independently selected from H, C₁₋₄ alkyl substituted with 0 to 3 F, —(CH₂)₁₋₂CH(OH)CH₂F, —(CH₂)₁₋₂CH(OH)CF₃, —(CH₂)₁₋₂CH(OH)CH₂CF₃, —(CH₂)₁₋₂OCHF₂, —(CH₂)₁₋₃OCF₃, —(CH₂)₁₋₂OCH₂CF₃, —(CH₂)₂₋₅OH, —(CH₂)₂₋₅CN, —(CH₂)₁₋₂CH(CH₃)OH, —(CH₂)₁₋₂CH(CH₃)CH₂OH, —(CH₂)₁₋₂C(CH₃)₂OH, —C(CH₃)₂(CH₂)₁₋₂OH, —(CH₂)₁₋₂C(CH₃)₂CH₂OH, —CH₂CH(OH)CH₂OH, —CH₂CH(OH)(C₁₋₄ alkyl), —CH(CH₃)(CH₂)₁₋₂OH, —CH₂CH(C₁₋₂ alkyl)(CH₂)₁₋₂OH, —CH₂CH(C₁₋₄ alkoxy)(CH₂)₁₋₂OH, —(CH₂)₂₋₄O(C₁₋₄ alkyl substituted with 0 to 2 R^e), —(CH₂)₁₋₂CH(CH₃)O(C₁₋₄ alkyl), —(CH₂)₁₋₂C(CH₃)₂O(C₁₋₄ alkyl), —CH(CH₃)(CH₂)₁₋₂O(C₁₋₄ alkyl), —CH₂CH(OH)(CH₂)₁₋₂O(C₁₋₄ alkyl), —(CH₂)₁₋₂CH(CH₃)NH₂, —CH₂C(CH₃)₂NH₂, —(CH₂)₂₋₃NH(C₁₋₄ alkyl), —(CH₂)₂₋₃N(C₁₋₄ alkyl)₂, —(CH₂)₁₋₃C(O)NH₂, —(CH₂)₁₋₂C(CH₃)₂CONH₂, —(CH₂)₁₋₂C(O)NH(C₁₋₄ alkyl substituted with 0 to 2 R^e), —(CH₂)₁₋₂C(O)N(CH₃)(C₁₋₄ alkyl substituted with 0 to 2 R^e), —(CH₂)₀₋₁CH(CH₃)(CH₂)₀₋₁C(O)NH(C₁₋₄ alkyl), —(CH₂)₁₋₂C(O)N(C₁₋₄ alkyl)₂, —(CH₂)₀₋₁CH(CH₃)C(O)N(C₁₋₄ alkyl)₂, —(CH₂)₁₋₂C(O)N(C₁₋₂ alkyl)(CH₂)₂O(C₁₋₄ alkyl), —(CH₂)₂₋₃NHC(O)R^a, —(CH₂)₁₋₂CH(CH₃)NHC(O)R^a, —CH₂C(CH₃)₂NHC(O)R^a, —(CH₂)₂₋₃N(CH₃)C(O)R^a, —(CH₂)₂₋₃S(O)₂(C₁₋₄ alkyl), —CH₂CH(CH₃)S(O)₂(C₁₋₄ alkyl), —(CH₂)₂₋₃NHS(O)₂(C₁₋₄ alkyl), —CH₂CH(CH₃)NHS(O)₂(C₁₋₄ alkyl), —(CH₂)₂₋₃NHS(O)₂(C₃₋₆ cycloalkyl),

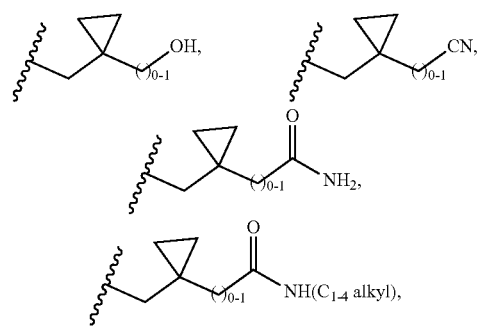

-continued

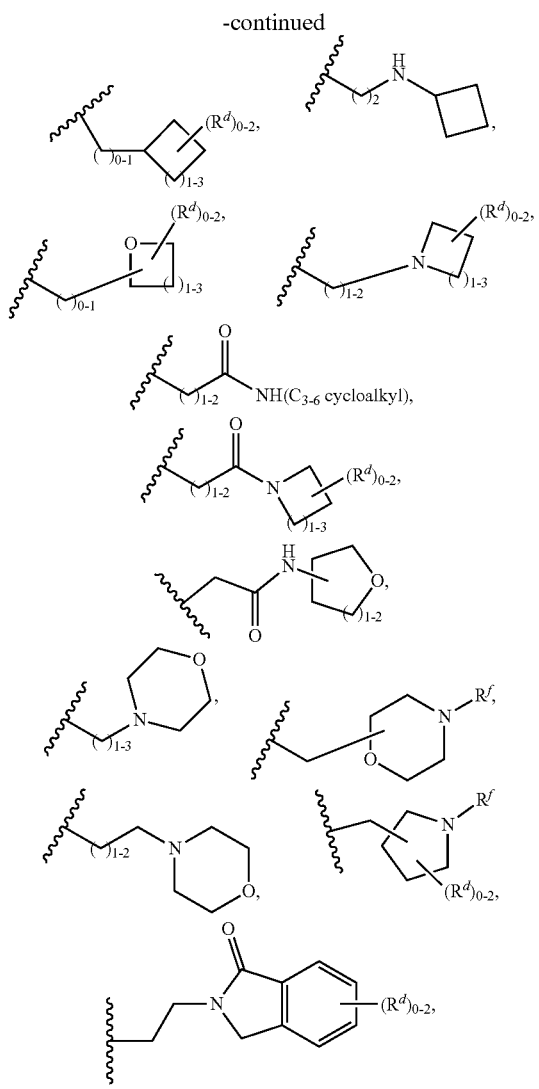

and —(CH$_2$)$_{1-3}$-(heteroaryl including from 5 to 10 ring atoms, wherein from 1 to 4 ring atoms are each independently selected from N, N(R$^f$), O, and S), and said heteroaryl is substituted with 0 to 2 R$^d$;
R$^3$ is independently

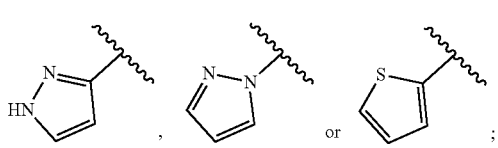 [SMILES: *c1cc[nH]n1 ; *n1cccn1 ; *c1cccs1]

R$^4$ is independently H or F;
R$^a$ is independently C$_{1-4}$ alkyl substituted with 0 to 1 R$^e$, C$_{3-6}$ cycloalkyl substituted with 0 to 2 R$^d$,

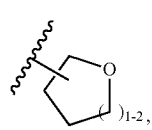

phenyl or heteroaryl selected from oxazolyl, isoxazolyl, thiazolyl, pyridyl and pyrazinyl, wherein said phenyl and heteroaryl are substituted with 0 to 2 R$^d$;
R$^d$ is, at each occurrence, independently selected from: F, Cl, OH, CN, C$_{1-4}$ alkyl, C$_{1-4}$ alkoxy, C$_{1-4}$ haloalkyl, NH$_2$, N(C$_{1-4}$ alkyl)$_2$, —NHC(O)(C$_{1-4}$ alkyl), and phenyl;
R$^e$ is independently selected from F, OH and C$_{1-4}$ alkoxy; and
R$^f$ is, at each occurrence, independently selected from: H, C$_{1-4}$ alkyl, —C(O)(C$_{1-4}$ alkyl), and —C(O)(C$_{1-4}$ haloalkyl).

In a twelfth aspect, within the scope of the eleventh aspect, the invention provides a compound of Formula (IIIb-1), or a stereoisomer, a tautomer or a pharmaceutically acceptable salt thereof, wherein:
R$^2$ is independently selected from H, C$_{1-4}$ alkyl substituted with 0 to 3 F, —(CH$_2$)$_{1-2}$CH(OH)CH$_2$F, —(CH$_2$)$_{1-2}$CH(OH)CF$_3$, —(CH$_2$)$_{1-2}$CH(OH)CH$_2$CF$_3$, —(CH$_2$)$_{1-2}$OCHF$_2$, —(CH$_2$)$_{1-3}$OCF$_3$, —(CH$_2$)$_{1-2}$OCH$_2$CF$_3$, —(CH$_2$)$_{2-4}$OH, —(CH$_2$)$_{2-4}$CN, —(CH$_2$)$_{1-2}$CH(CH$_3$)OH, —(CH$_2$)$_{1-2}$CH(CH$_3$)CH$_2$OH, —(CH$_2$)$_{1-2}$C(CH$_3$)$_2$OH, —C(CH$_3$)$_2$(CH$_2$)$_{1-2}$OH, —(CH$_2$)$_{1-2}$C(CH$_3$)$_2$CH$_2$OH, —CH$_2$CH(OH)CH$_2$OH, —CH$_2$CH(OH)(C$_{1-4}$ alkyl), —CH(CH$_3$)(CH$_2$)$_{1-2}$OH, —CH$_2$CH(C$_{1-2}$ alkyl)(CH$_2$)$_{1-2}$OH, —CH$_2$CH(C$_{1-4}$ alkoxy)(CH$_2$)$_{1-2}$OH, —(CH$_2$)$_{2-4}$O(C$_{1-4}$ alkyl substituted with 0 to 1 R$^e$), —(CH$_2$)$_{1-2}$CH(CH$_3$)O(C$_{1-4}$ alkyl), —(CH$_2$)$_{1-2}$C(CH$_3$)$_2$O(C$_{1-4}$ alkyl), —CH(CH$_3$)(CH$_2$)$_{1-2}$O(C$_{1-4}$ alkyl), —CH$_2$CH(OH)(CH$_2$)$_{1-2}$O(C$_{1-4}$ alkyl), —(CH$_2$)$_{1-2}$CH(CH$_3$)NH$_2$, —CH$_2$C(CH$_3$)$_2$NH$_2$, —(CH$_2$)$_{2-3}$NH(C$_{1-4}$ alkyl), —(CH$_2$)$_{2-3}$N(C$_{1-4}$ alkyl)$_2$, —(CH$_2$)$_{1-3}$C(O)NH$_2$, —(CH$_2$)$_{1-2}$C(CH$_3$)$_2$CONH$_2$, —(CH$_2$)$_{1-2}$C(O)NH(C$_{1-4}$ alkyl substituted with 0 to 2 R$^e$), —(CH$_2$)$_{1-2}$C(O)N(CH$_3$)(C$_{1-4}$ alkyl substituted with 0 to 2 R$^e$), —(CH$_2$)$_{0-1}$CH(CH$_3$)(CH$_2$)$_{0-1}$C(O)NH (C$_{1-4}$ alkyl), —(CH$_2$)$_{1-2}$C(O)N(C$_{1-4}$ alkyl)$_2$, —(CH$_2$)$_{0-1}$CH(CH$_3$)C(O)N(C$_{1-4}$ alkyl)$_2$, —(CH$_2$)$_{1-2}$C(O)N(C$_{1-2}$ alkyl)(CH$_2$)$_2$O(C$_{1-4}$ alkyl), —(CH$_2$)$_{2-3}$NHC(O)R$^a$, —CH$_2$CH(CH$_3$)NHC(O)R$^a$, —CH$_2$C(CH$_3$)$_2$NHC(O)R$^a$, —(CH$_2$)$_{2-3}$S(O)$_2$(C$_{1-4}$ alkyl), —CH$_2$CH(CH$_3$)S(O)$_2$(C$_{1-4}$ alkyl), —(CH$_2$)$_{2-3}$NHS(O)$_2$(C$_{1-4}$ alkyl), —CH$_2$CH(CH$_3$)NHS(O)$_2$(C$_{1-4}$ alkyl), —(CH$_2$)$_{2-3}$NHS(O)$_2$(C$_{3-6}$ cycloalkyl),

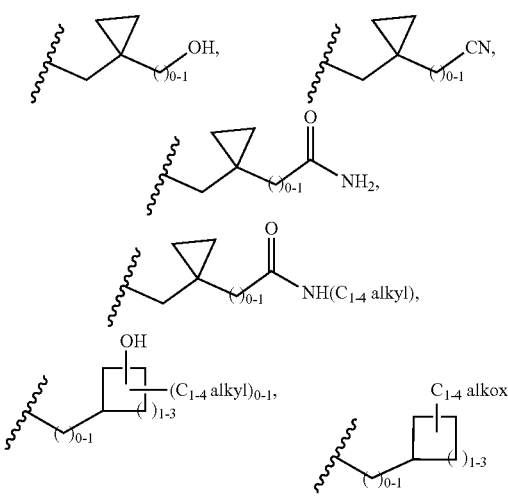

-continued

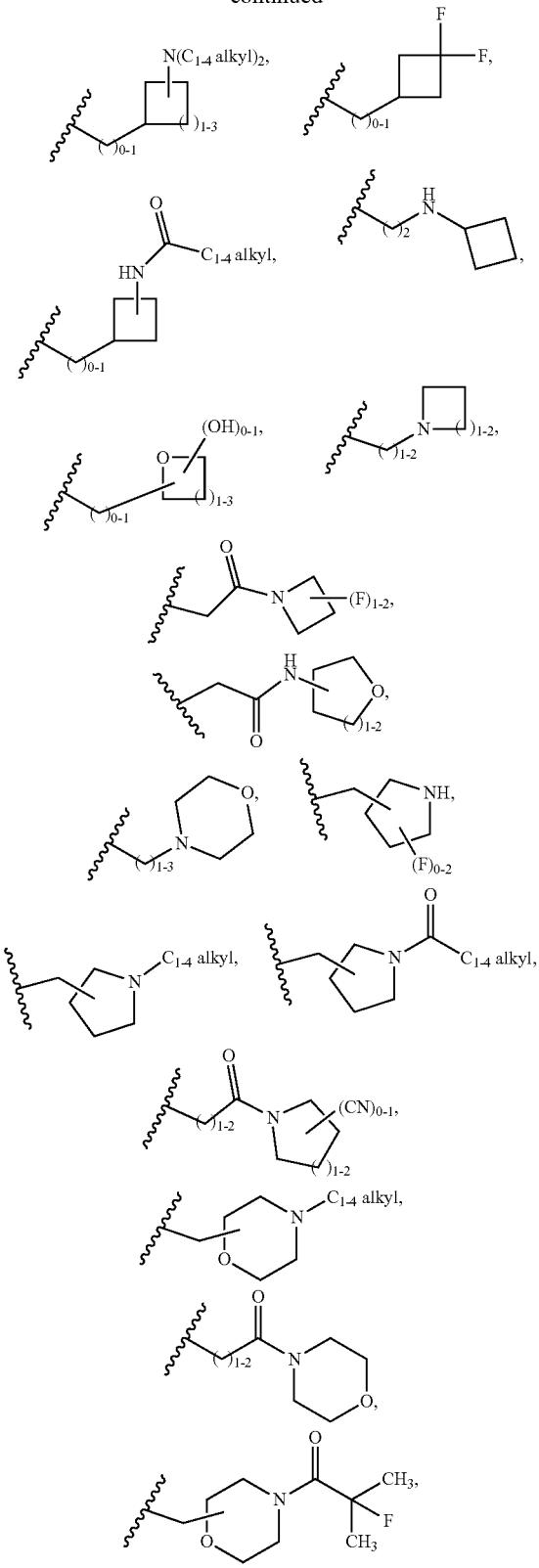

and —(CH$_2$)$_{1-2}$(heteroaryl), wherein the heteroaryl is selected from imidazolyl, pyrazolyl, oxazolyl, isoxazolyl, thiazolyl, oxadiazolyl, pyridyl and pyridazinyl, and the heteroaryl is substituted with 0 to 2 R$^d$;

R$^a$ is independently C$_{1-4}$ alkyl substituted with 0 to 1 R$^e$,

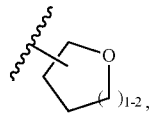

phenyl or heteroaryl selected from oxazolyl, pyridyl and pyrazinyl, wherein said phenyl and heteroaryl are substituted with 0 to 2 R$^d$; and R$^d$ is, at each occurrence, independently selected from: F, Cl, CN, C$_{1-4}$ alkyl, C$_{1-4}$ alkoxy, and C$_{1-4}$ haloalkyl.

In a thirteenth aspect, within the scope of the eleventh or twelfth aspects, the invention provides a compound of Formula (IIIb-1), or a stereoisomer, a tautomer or a pharmaceutically acceptable salt thereof, wherein:

R$^3$ is independently

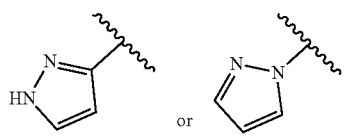

In a fourteenth aspect, the invention provides a compound of Formula (IIIb-2),

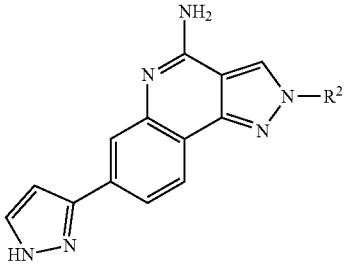

(IIIb-2)

or a stereoisomer, a tautomer or a pharmaceutically acceptable salt thereof, wherein:

R$^2$ is independently selected from H, C$_{1-4}$ alkyl substituted with 0 to 3 F, —(CH$_2$)$_{2-4}$OH, —(CH$_2$)$_{2-4}$CN, —(CH$_2$)$_{1-2}$CH(CH$_3$)OH, —(CH$_2$)$_{1-2}$C(CH$_3$)$_2$OH, —CH$_2$CH(OH)CH$_2$OH, —CH$_2$CH(OH)(C$_{1-4}$ alkyl), —CH(CH$_3$)(CH$_2$)$_{1-2}$OH, —CH$_2$CH(C$_{1-2}$ alkyl)(CH$_2$)$_{1-2}$OH, —CH$_2$CH(C$_{1-2}$ alkoxy)(CH$_2$)$_{1-2}$OH, —(CH$_2$)$_{2-4}$O(C$_{1-4}$ alkyl substituted with 0 to 2 R$^e$), —CH$_2$C(CH$_3$)$_2$NH$_2$, —(CH$_2$)$_{1-3}$C(O)NH$_2$, —(CH$_2$)$_{1-2}$C(CH$_3$)$_2$CONH$_2$, —(CH$_2$)$_{1-2}$C(O)NH(C$_{1-4}$ alkyl), —(CH$_2$)$_{0-1}$CH(CH$_3$)(CH$_2$)$_{0-1}$C(O)NH(C$_{1-4}$ alkyl), —(CH$_2$)$_{1-2}$C(O)N(C$_{1-4}$ alkyl)$_2$, —(CH$_2$)$_{0-1}$CH(CH$_3$)C(O)N(C$_{1-4}$ alkyl)$_2$, —(CH$_2$)$_{1-2}$C(O)NH(C$_{1-4}$ alkyl substituted with 0 to 2 R$^e$), —(CH$_2$)$_{1-2}$C(O)N(CH$_3$)(C$_{1-4}$ alkyl substituted with 0 to 2 R$^e$), —CH$_2$CH(CH$_3$)NHC(O)(C$_{1-4}$ alkyl), —(CH$_2$)$_{2-3}$S(O)$_2$(C$_{1-4}$ alkyl), —CH$_2$CH(CH$_3$)S(O)$_2$(C$_{1-4}$ alkyl), —(CH$_2$)$_{2-3}$NHS(O)$_2$(C$_{1-4}$ alkyl), —CH$_2$CH(CH$_3$)NHS(O)$_2$(C$_{1-4}$ alkyl), —(CH$_2$)$_{2-3}$NHS(O)$_2$(C$_{3-6}$ cycloalkyl),

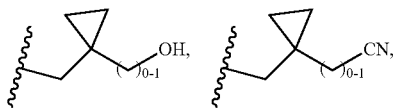

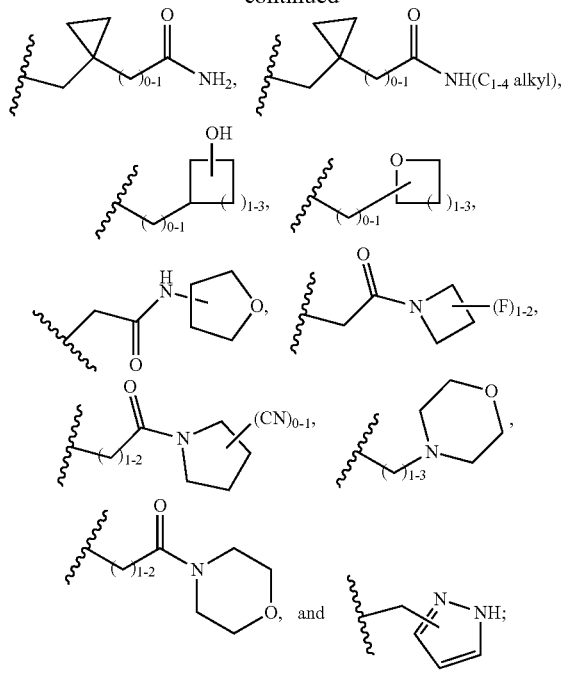

and $R^e$ is independently selected from F, OH and $C_{1-4}$ alkoxy.

In a fifthteenth aspect, the invention provides a compound of Formula (IIIb-2), or a stereoisomer, a tautomer or a pharmaceutically acceptable salt thereof, wherein:

$R^2$ is independently selected from H, —$CH_2CHF_2$, —$(CH_2)_{2-4}OH$, —$(CH_2)_{2-4}CN$, —$CH_2CH(CH_3)OH$, —$CH_2C(CH_3)_2OH$, —$CH_2CH(OH)CH_2OH$, —$CH_2CH(OH)CH_2CH_3$, —$CH(CH_3)(CH_2)_2OH$, —$CH_2CH(CH_3)CH_2OH$, —$CH_2CH(OCH_3)CH_2OH$, —$(CH_2)_2O(CH_2)_2OH$, —$(CH_2)_2O(CH_2)_2OCH_3$, —$CH_2C(CH_3)_2NH_2$, —$(CH_2)_{1-3}C(O)NH_2$, —$CH_2C(CH_3)_2CONH_2$, —$(CH_2)_{1-2}C(O)NH(CH_3)$, —$(CH_2)_{1-2}C(O)NH(CH_2CH_3)$, —$(CH_2)_{1-2}C(O)NH(CH(CH_3)_2)$, —$(CH_2)_{0-1}CH(CH_3)(CH_2)_{0-1}C(O)NH(CH_3)$, —$(CH_2)_{0-1}CH(CH_3)C(O)NH(CH(CH_3)_2)$, —$(CH_2)_{1-2}C(O)N(CH_3)_2$, —$(CH_2)_{0-1}CH(CH_3)C(O)N(CH_3)_2$, —$CH_2C(O)NH(CH_2CHF_2)$, —$CH(CH_3)C(O)NH(CH_2CHF_2)$, —$C(CH_3)_2C(O)NH(CH_2CHF_2)$, —$(CH_2)_{1-2}C(O)NH(CH_2)_2OH$, —$CH(CH_3)C(O)NH(CH_2)_{2-3}OH$, —$(CH_2)_{1-2}C(O)NH(C(CH_3)_2CH_2OH)$, —$(CH_2)_{1-2}C(O)NH(CH_2)_2OCH_3$, —$(CH_2)_{1-2}C(O)N(CH_3)(CH_2)_2OCH_3$, —$CH_2CH(CH_3)NHC(O)(CH_3)$, —$(CH_2)_{2-3}S(O)_2CH_3$, —$(CH_2)_{2-3}S(O)_2CH_2CH_3$, —$(CH_2)_{2-3}NHS(O)_2CH_3$, —$CH_2CH(CH_3)NHS(O)_2CH_3$, —$(CH_2)_{2-3}NHS(O)_2(cyclopropyl)$,

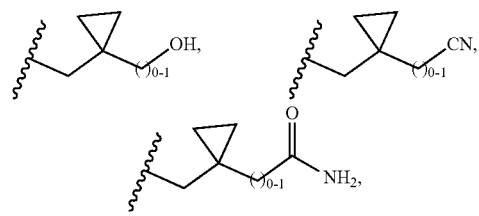

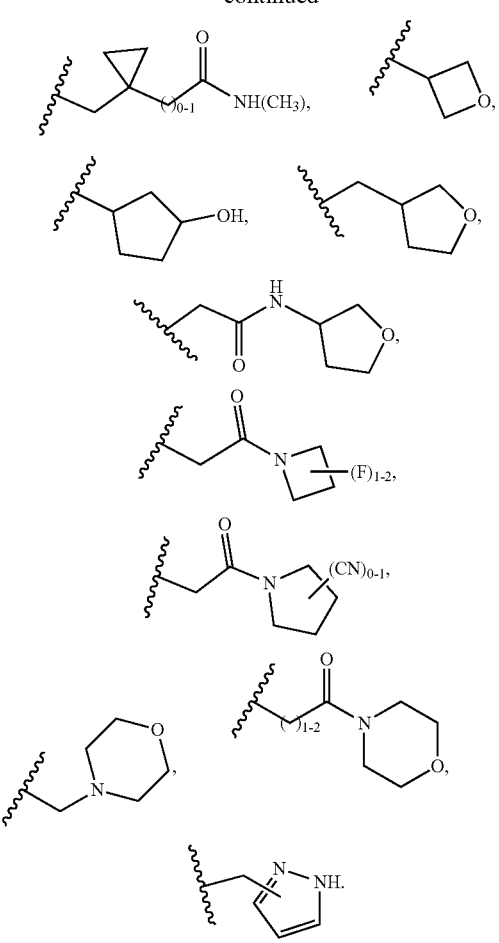

In another aspect, the invention provides a compound of Formula (IIIb):

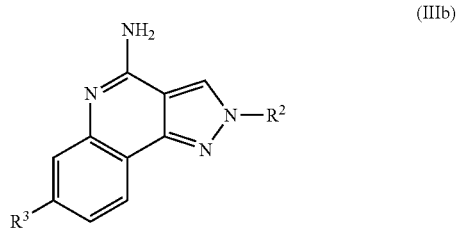

(IIIb)

or a tautomer or a pharmaceutically acceptable salt thereof, wherein:

$R^2$ is independently selected from H, $C_{1-4}$ alkyl substituted with 0 to 3 F, —$(CH_2)_{1-2}CH(OH)CF_3$, —$CH_2CH(CH_3)NHC(O)(C_{1-4}$ alkyl), —$CH_2C(CH_3)_2NHC(O)(C_{1-4}$ alkyl), —$(CH_2)_{2-3}NHC(O)R^a$, —$(CH_2)_{2-3}NHC(O)CF(CH_3)_2$, —$(CH_2)_{2-3}N(CH_3)C(O)R^a$, —$(CH_2)_{2-3}OH$, —$(CH_2)_{1-2}CH(CH_3)OH$, —$(CH_2)_{1-2}C(CH_3)_2OH$, —$CH_2CH(OH)CH_2OH$, —$CH(CH_3)(CH_2)_{1-2}OH$, —$(CH_2)_{2-4}O(C_{1-4}$ alkyl), —$CH_2CH(CH_3)NH_2$, —$CH_2C(CH_3)_2NH_2$, —$(CH_2)_{2-3}NH(C_{1-4}$ alkyl), —$(CH_2)_{2-3}N(C_{1-4}$ alkyl)$_2$, —$(CH_2)_{2-3}NHS(O)_2(C_{1-4}$ alkyl), —$(CH_2)_{2-3}S(O)_2(C_{1-4}$ alkyl),

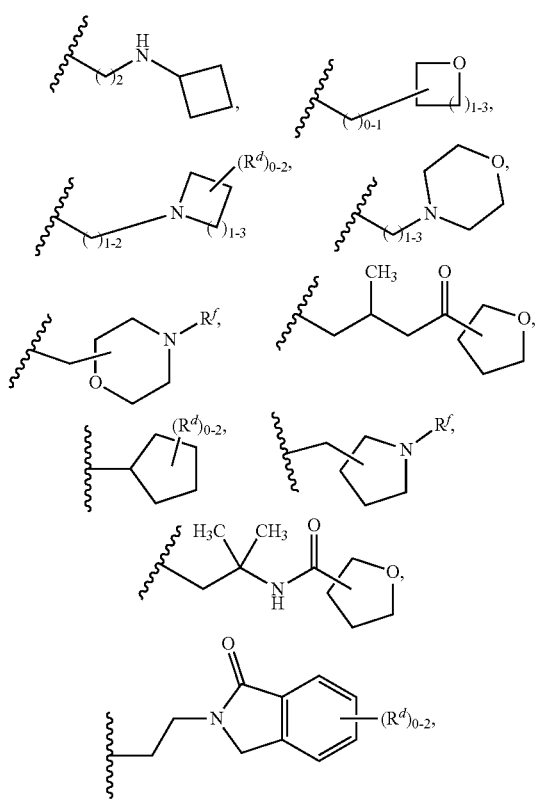

and —(CH$_2$)$_{1-3}$(heteroaryl), wherein heteroaryl is selected from imidazolyl, pyrazolyl, oxazolyl, isoxazolyl, thiazolyl, oxadiazolyl and pyridyl, and heteroaryl is substituted with 0 to 2 R$^d$;
R$^3$ is independently

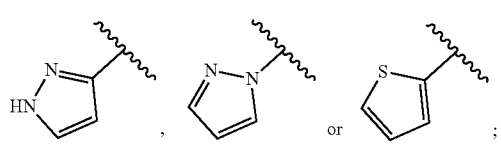

R$^a$ is independently C$_{1-4}$ alkyl, C$_{3-6}$ cycloalkyl,

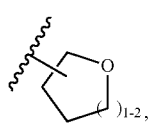

phenyl or heteroaryl selected from oxazolyl, isoxazolyl, thiazolyl, pyridyl and pyrazinyl, wherein said phenyl and heteroaryl are substituted with 0 to 2 R$^d$;
R$^d$ is, at each occurrence, independently selected from: F, Cl, CN, C$_{1-4}$ alkyl, C$_{1-4}$ alkoxy, C$_{1-4}$ haloalkyl and phenyl; and
R$^1$ is, at each occurrence, independently selected from: H, C$_{1-4}$ alkyl, C(O)(C$_{1-4}$ alkyl), and C(O)(C$_{1-4}$ haloalkyl).

In another aspect, within the scope of the above aspect, the invention provides a compound of Formula (IIIb), or a tautomer or a pharmaceutically acceptable salt thereof, wherein:

R$^2$ is independently selected from H, C$_{1-4}$ alkyl, —(CH$_2$)$_{1-2}$CHF$_2$, —(CH$_2$)$_{1-2}$CH(OH)CF$_3$, —CH$_2$C(CH$_3$)$_2$NHC(O)(C$_{1-4}$ alkyl), —(CH$_2$)$_{2-3}$NHC(O)R$^a$, —(CH$_2$)$_{2-3}$OH, —(CH$_2$)$_{1-2}$CH(CH$_3$)OH, —(CH$_2$)$_{1-2}$C(CH$_3$)$_2$OH, —CH$_2$CH(OH)CH$_2$OH, —CH(CH$_3$)(CH$_2$)$_{1-2}$OH, —(CH$_2$)$_{2-4}$O(C$_{1-4}$ alkyl), —CH$_2$CH(CH$_3$)NH$_2$, —CH$_2$C(CH$_3$)$_2$NH$_2$, —(CH$_2$)$_{2-3}$NH(C$_{1-4}$ alkyl), —(CH$_2$)$_{2-3}$N(C$_{1-4}$ alkyl)$_2$, —(CH$_2$)$_{2-3}$NHS(O)$_2$(C$_{1-4}$ alkyl), —(CH$_2$)$_{2-3}$S(O)$_2$(C$_{1-4}$ alkyl),

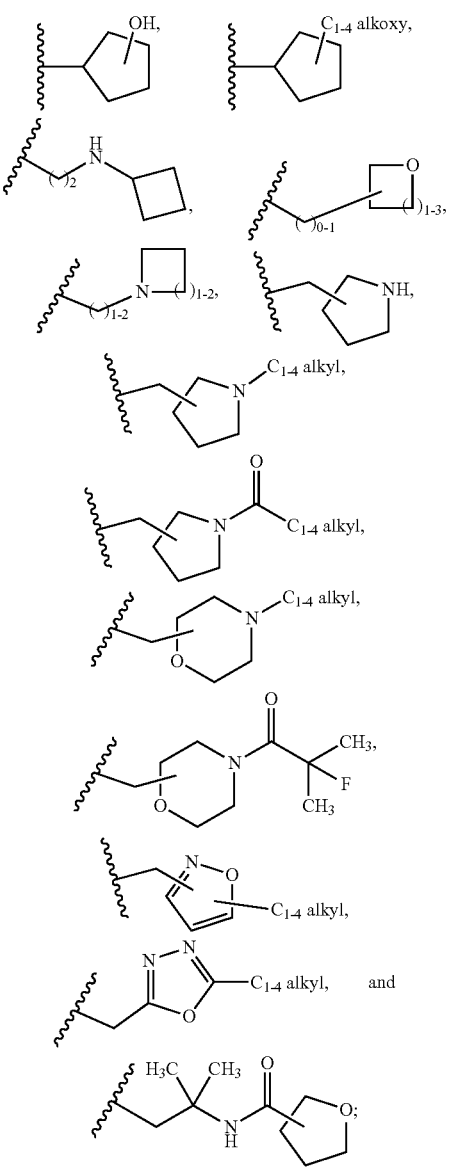

and
R$^a$ is independently C$_{1-4}$ alkyl,

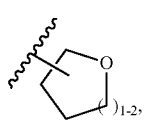

phenyl or heteroaryl selected from oxazolyl, pyridyl and pyrazinyl, wherein said phenyl and heteroaryl are substituted with 0 to 2 $R^d$.

In another aspect, within the scope of any of the above two aspects, the invention provides a compound of Formula (IIIb), or a tautomer or a pharmaceutically acceptable salt thereof, wherein:

$R^3$ is independently or

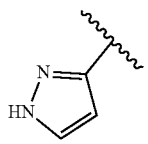 or 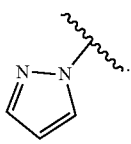.

In a sixteenth aspect, the invention provides a compound of Formula (IIIf):

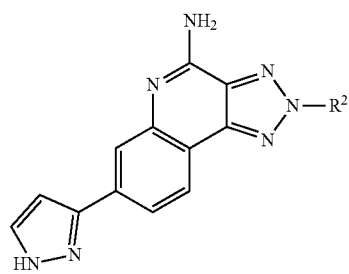

(IIIf)

or a tautomer or a pharmaceutically acceptable salt thereof, wherein:

$R^2$ is independently selected from —(CH$_2$)$_2$N(C$_{1-4}$ alkyl)$_2$, —(CH$_2$)$_2$—OR$^a$, —(CH$_2$)$_2$—NHC(O)R$^a$, and

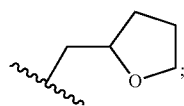 [SMILES: *CC1CCCO1];

$R^a$ is independently selected from: C$_{1-4}$ alkyl substituted with from 0 to 2 F,

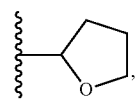, and heteroaryl selected from thiazolyl and pyridyl, wherein said heteroaryl is substituted with 0 to 2 $R^d$; and $R^d$ is, at each occurrence, independently selected from: F, Cl, CN, C$_{1-4}$ alkyl, C$_{1-4}$ alkoxy and C$_{1-4}$ haloalkyl.

In a seventeenth aspect, the invention provides a compound of Formula (IIIg-1):

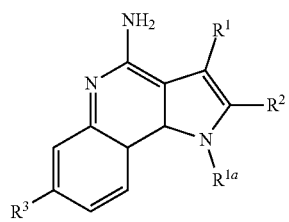

(IIIg-1)

or a tautomer or a pharmaceutically acceptable salt thereof, wherein:

$R^1$ is independently H, Cl or C$_{1-4}$ alkyl;

$R^{1a}$ is independently H or C$_{1-4}$ alkyl;

$R^2$ is independently selected from —(CH$_2$)$_{1-4}$—OH, —(CH$_2$)$_{1-2}$—OR$^a$, —(CH$_2$)$_{1-2}$NH$_2$, —(CH$_2$)$_{1-2}$NH(C$_{1-4}$ alkyl substituted with 0 to 1 R$^e$), —(CH$_2$)$_{1-2}$N(C$_{1-4}$ alkyl)$_2$, —(CH$_2$)$_{1-2}$—NHC(O)R$^a$, —(CH$_2$)$_{2-3}$NHS(O)$_2$(C$_{1-4}$ alkyl), —(CH$_2$)$_{2-3}$NHS(O)$_2$Ph,

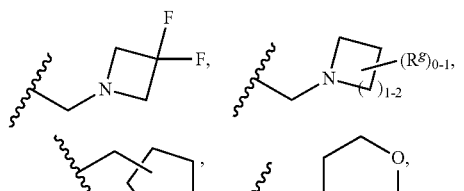

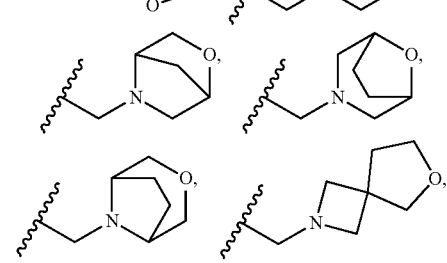

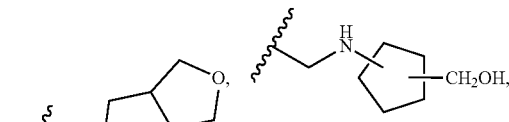

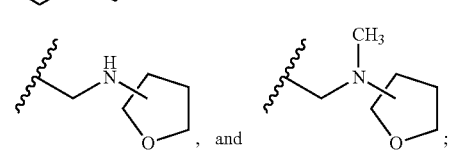, and

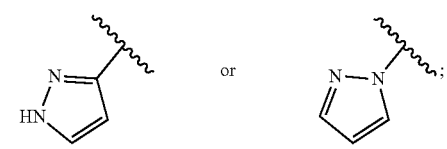 [SMILES: *c1cc[nH]n1 ; *n1cccn1];

$R^3$ is independently

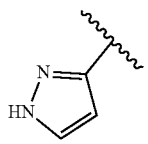 or 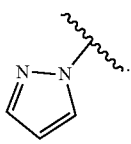;

R$^a$ is independently selected from: C$_{1-4}$ alkyl substituted with from 0 to 2 F,

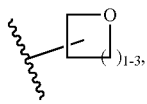

and heteroaryl selected from thiazolyl, oxazolyl, N—C$_{1-4}$ alkyl-imidazolyl, and pyridyl, wherein said heteroaryl is substituted with 0 to 2 R$^d$;

R$^d$ is, at each occurrence, independently selected from: F, Cl, OH, CN, C$_{1-4}$ alkyl, C$_{1-4}$ alkoxy, C$_{1-4}$ haloalkyl, and —NHC(O)(C$_{1-4}$ alkyl); and R$^e$ is independently selected from F, OH, C$_{1-4}$ alkoxy and C$_{1-4}$ haloalkyl.

In another aspect, the invention provides a compound of Formula (IIIg-1):

or a tautomer or a pharmaceutically acceptable salt thereof, wherein:

R$^{1a}$ is H;

R$^2$ is independently selected from —(CH$_2$)$_{1-4}$—OH,

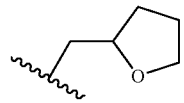 and 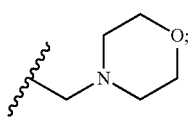

and

R$^3$ is independently

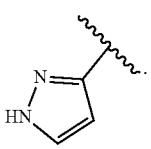

In an eighteenth aspect, the invention provides a compound of Formula (IIIg):

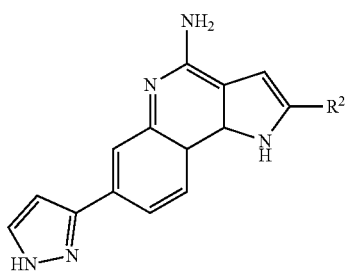

(IIIg)

or a stereoisomer, a tautomer or a pharmaceutically acceptable salt thereof, wherein:

R$^2$ is independently selected from —(CH$_2$)$_{1-2}$NH$_2$, —(CH$_2$)$_{1-2}$N(C$_{1-4}$ alkyl)$_2$, —(CH$_2$)$_{1-2}$NH(C$_{1-4}$ alkyl substituted with 0 to 1 R$^e$), —(CH$_2$)$_{1-2}$—NHC(O)R$^a$;

R$^a$ is independently selected from: C$_{1-4}$ alkyl substituted with from 0 to 2 F,

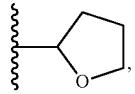

and heteroaryl selected from thiazolyl and pyridyl, wherein said heteroaryl is substituted with 0 to 2 R$^d$; and R$^d$ is, at each occurrence, independently selected from: F, Cl, CN, C$_{1-4}$ alkyl, C$_{1-4}$ alkoxy and C$_{1-4}$ haloalkyl; and R$^e$ is independently selected from F, OH, OCH$_3$, CHF$_2$, and CF$_3$.

In another aspect, the invention provides a compound of Formula (IIIg):

or a tautomer or a pharmaceutically acceptable salt thereof, wherein:

R$^2$ is independently selected from —(CH$_2$)$_2$N(C$_{1-4}$ alkyl)$_2$, —(CH$_2$)$_2$—OR$^a$, —(CH$_2$)$_2$—NHC(O)R$^a$, and

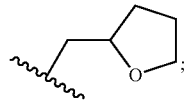 [SMILES: *CC1CCCO1]

R$^a$ is independently selected from: C$_{1-4}$ alkyl substituted with from 0 to 2 F,

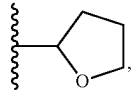

and heteroaryl selected from thiazolyl and pyridyl, wherein said heteroaryl is substituted with 0 to 2 R$^d$; and R$^d$ is, at each occurrence, independently selected from: F, Cl, CN, C$_{1-4}$ alkyl, C$_{1-4}$ alkoxy and C$_{1-4}$ haloalkyl.

In a nineteenth aspect, the invention provides a compound of Formula (IIIh):

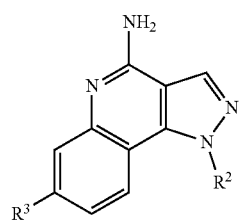

(IIIh)

or a stereoisomer, a tautomer or a pharmaceutically acceptable salt thereof, wherein:

R$^2$ is independently selected from C$_{1-4}$ alkyl, —(CH$_2$)$_{1-2}$CHF$_2$, —(CH$_2$)$_{2-4}$OH, —CH$_2$CH(CH$_3$)(CH$_2$)$_{0-2}$OH, —CH$_2$CH(OH)CH$_2$CH$_3$, —(CH$_2$)$_{1-2}$C(CH$_3$)$_2$OH, —(CH$_2$)$_2$O(CH$_2$)$_{1-2}$OH, —(CH$_2$)$_{2-4}$O(C$_{1-4}$ alkyl), —CH$_2$CH(OH)(CH$_2$)$_{1-2}$O(C$_{1-4}$ alkyl), —(CH$_2$)$_{2-3}$NH(C$_{1-4}$ alkyl), —(CH$_2$)$_{2-3}$N(C$_{1-4}$ alkyl)$_2$, —(CH$_2$)$_2$(pyridyl),

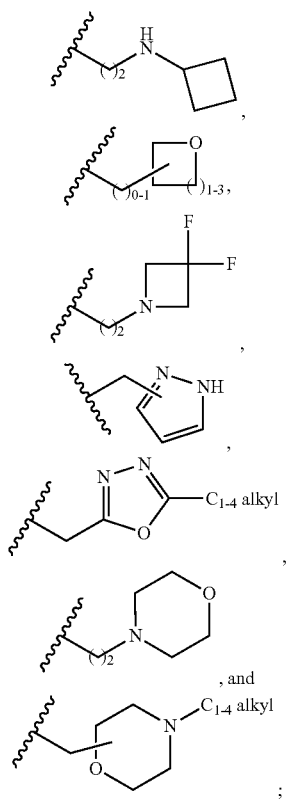

and
R³ is independently

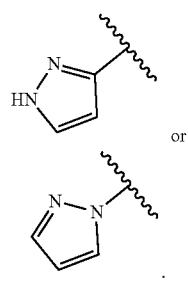

In another aspect, the invention provides a compound of Formula (IIIh):
or a tautomer or a pharmaceutically acceptable salt thereof, wherein:

R² is independently selected from —(CH₂)₂₋₄OH, —CH₂CH(CH₃)(CH₂)₀₋₂OH, —CH₂CH(OH)CH₂CH₃, —(CH₂)₁₋₂C(CH₃)₂OH, and —(CH₂)₂O(CH₂)₁₋₂OH; and R³ is independently

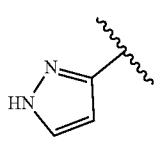

In another aspect, the invention provides a compound of Formula (IIIh):

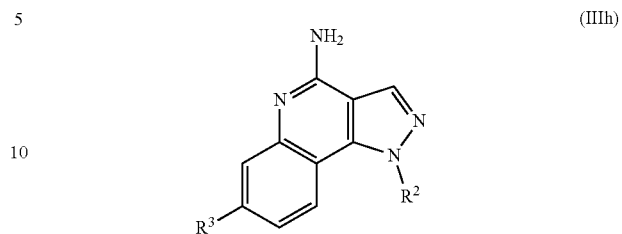

or a tautomer or a pharmaceutically acceptable salt thereof, wherein:

R² is independently selected from C₁₋₄ alkyl, —(CH₂)₁₋₂CHF₂, —(CH₂)₂₋₄OH, —CH₂CH(CH₃)(CH₂)₁₋₂OH, —(CH₂)₂O(CH₂)₁₋₂OH, —(CH₂)₂₋₄O(C₁₋₄ alkyl), —CH₂CH(OH)(CH₂)₂O(C₁₋₄ alkyl), —(CH₂)₂₋₃NH(C₁₋₄ alkyl), —(CH₂)₂₋₃N(C₁₋₄ alkyl)₂, —(CH₂)₂(pyridyl),

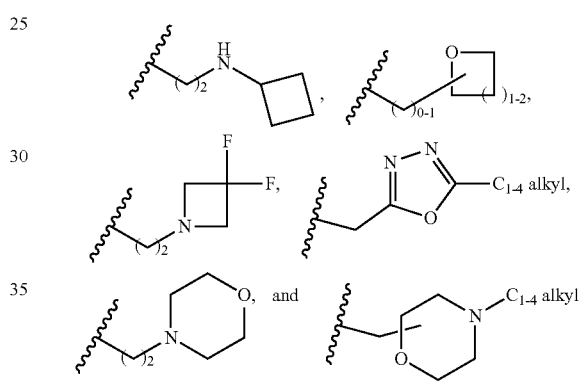

and
R³ is independently

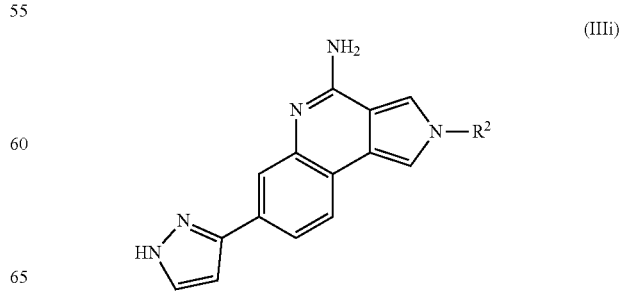

In a 20th aspect, the invention provides a compound of Formula (IIIi):

or a tautomer or a pharmaceutically acceptable salt thereof, wherein:

$R^2$ is independently selected from: —$(CH_2)_{2-4}OH$, —$(CH_2)_{2-4}O(C_{1-4}$ alkyl), —$(CH_2)_{2-3}N(C_{1-4}$ alkyl)$_2$, and —$(CH_2)_{2-3}NHC(O)R^a$.

$R^a$ is independently $C_{3-6}$ cycloalkyl,

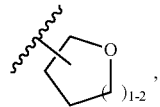

phenyl or heteroaryl selected from oxazolyl, isoxazolyl, thiazolyl, pyridyl and pyrazinyl, wherein said phenyl and heteroaryl are substituted with 0 to 2 $R^d$; and $R^d$ is, at each occurrence, independently selected from: F, Cl, CN, $C_{1-4}$ alkyl, $C_{1-4}$ alkoxy, and $C_{1-4}$ haloalkyl.

In another aspect, the invention provides a compound of Formula (IIIi):

or a tautomer or a pharmaceutically acceptable salt thereof, wherein:

$R^2$ is independently —$(CH_2)_{2-4}OH$ or —$(CH_2)_{2-4}O(C_{1-4}$ alkyl).

In another aspect, the invention provides a compound selected from the exemplified examples or a stereoisomer, a tautomer or a pharmaceutically acceptable salt thereof.

In another aspect, the invention provides a compound selected from the Examples 1 to 151 or a stereoisomer, a tautomer or a pharmaceutically acceptable salt thereof.

In another aspect, the invention provides a compound selected from the Examples 1 to 285 or a stereoisomer, a tautomer or a pharmaceutically acceptable salt thereof.

In another aspect, the invention provides a compound selected from the Examples 1 to 624 or a stereoisomer, a tautomer or a pharmaceutically acceptable salt thereof.

In another aspect, the invention provides a compound selected from

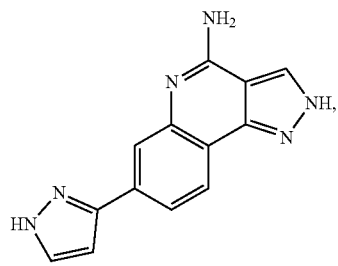

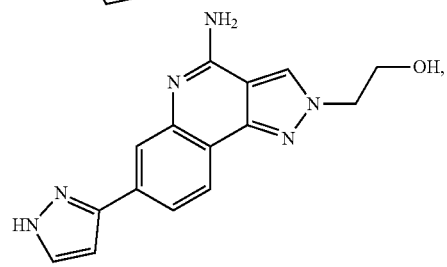

-continued

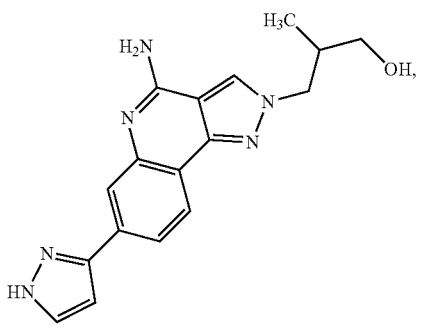

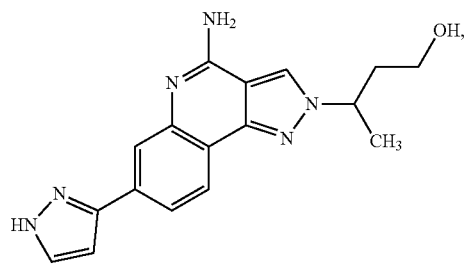

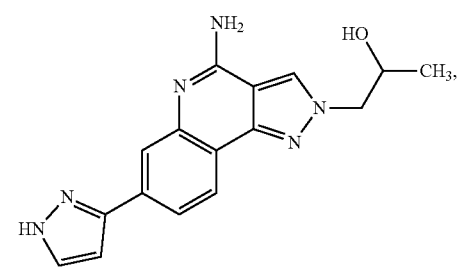

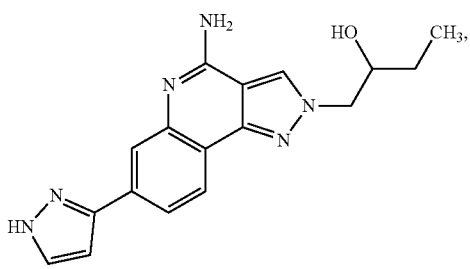

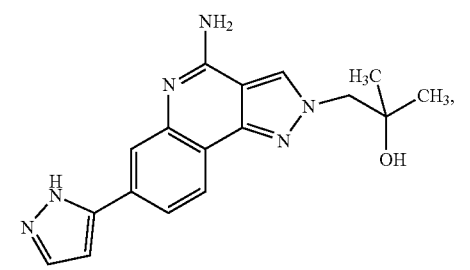

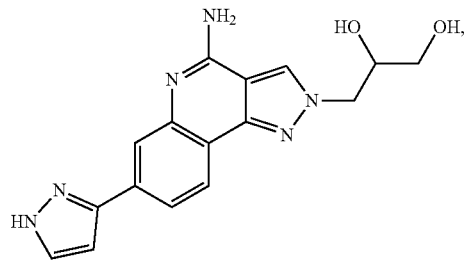

-continued
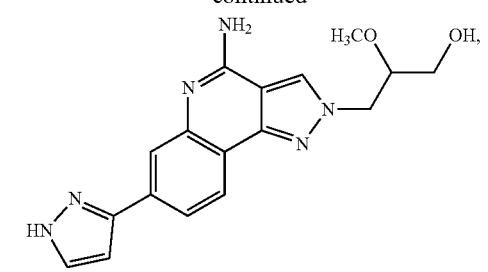
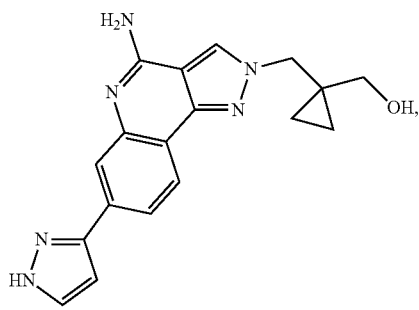
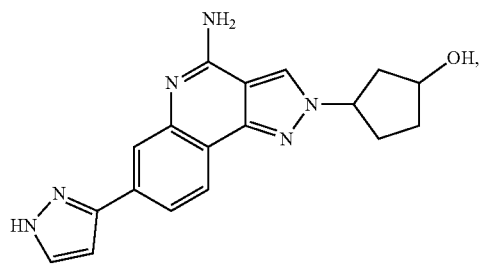
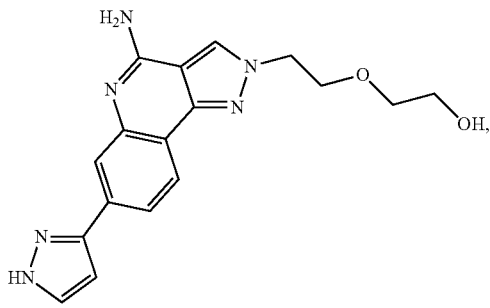 [SMILES: Nc1nc2cc(-c3cc[nH]n3)ccc2c2nn(CCOCCO)cc12]
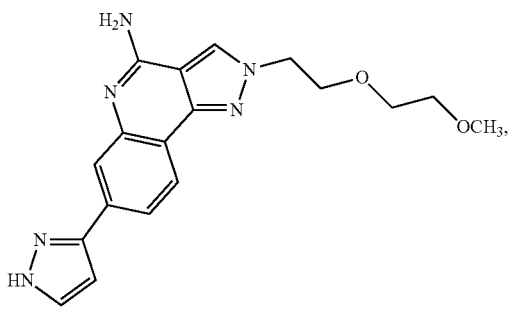
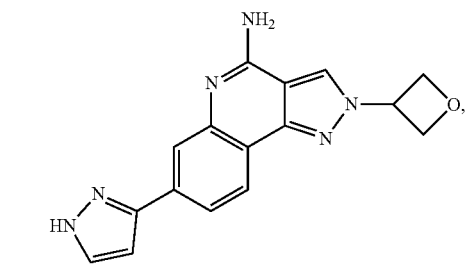
-continued
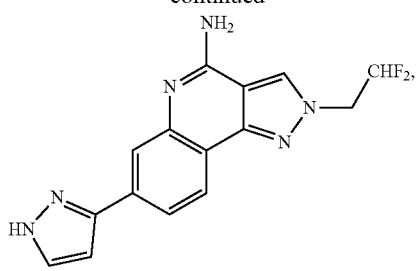
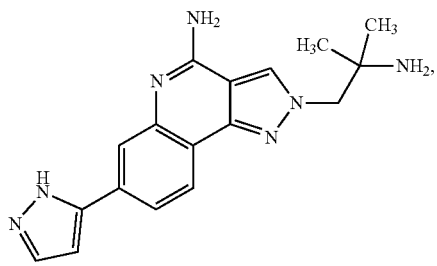
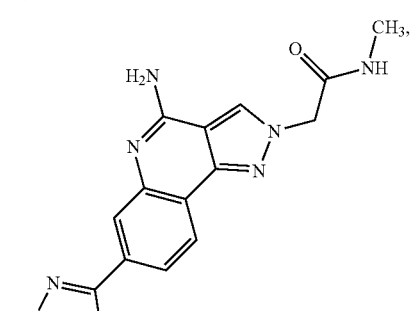
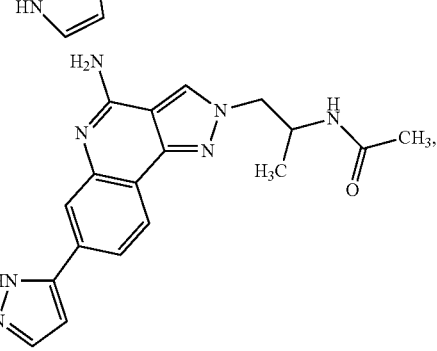
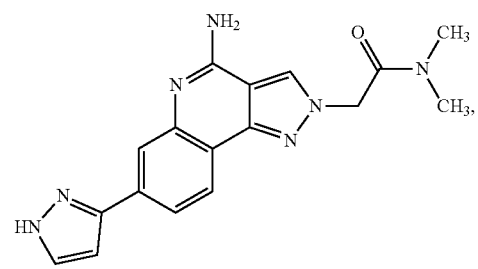
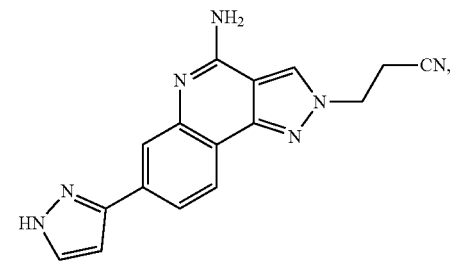

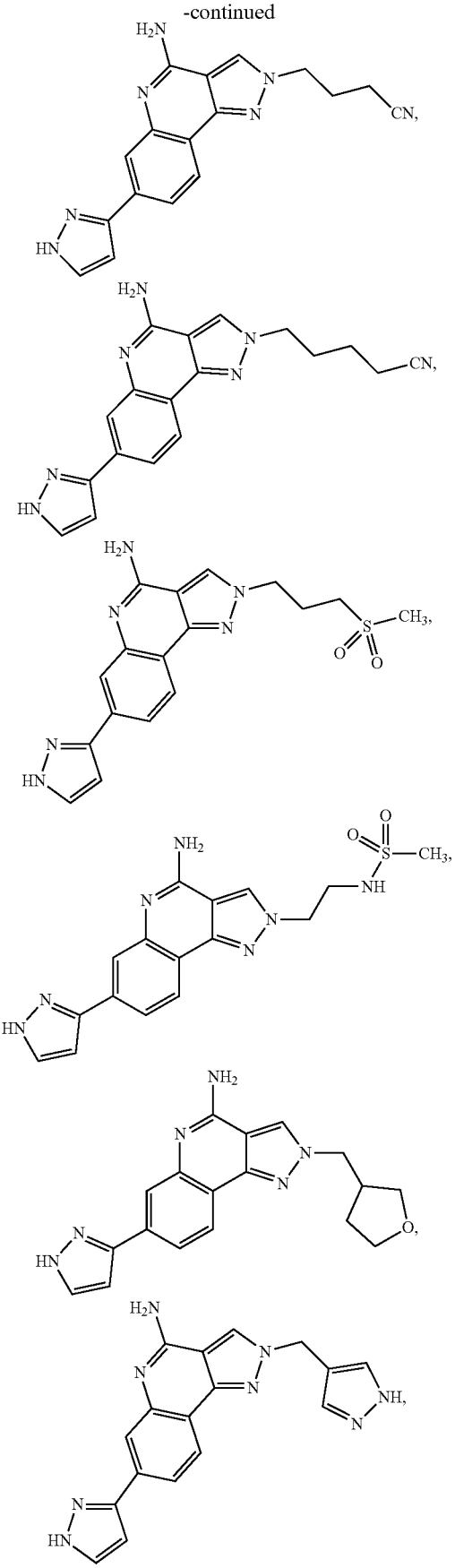
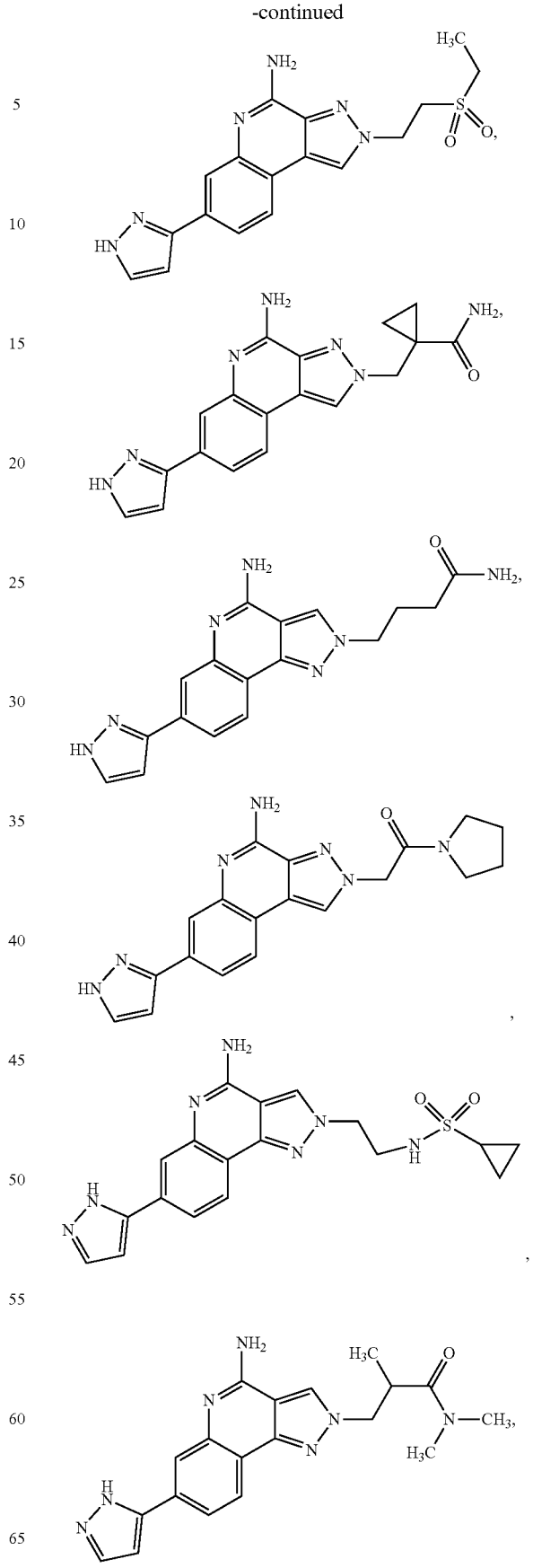

-continued
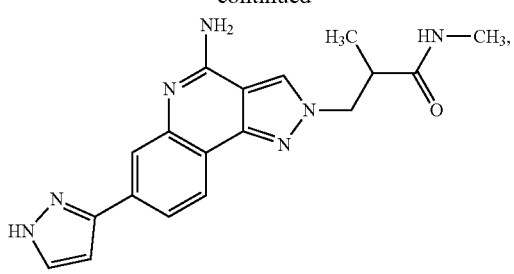
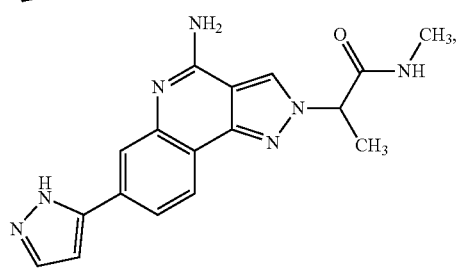
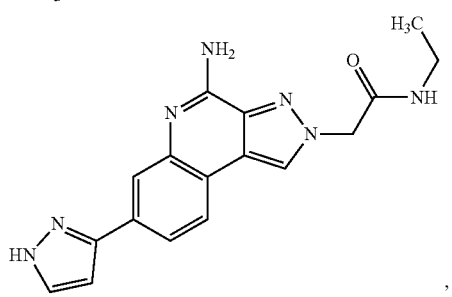
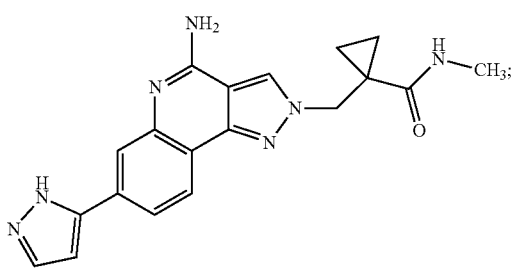
or a stereoisomer, a tautomer or a pharmaceutically acceptable salt thereof.
In another aspect, the invention provides a compound selected from
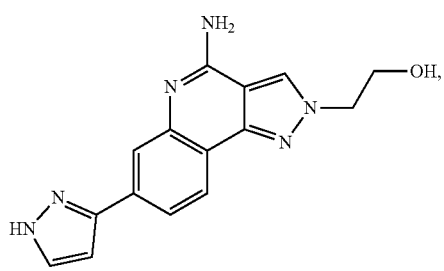
-continued
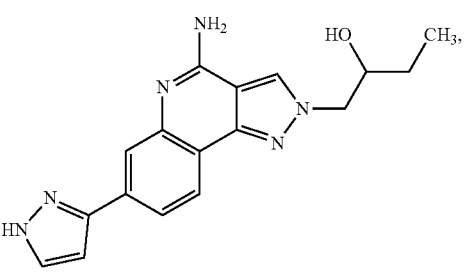
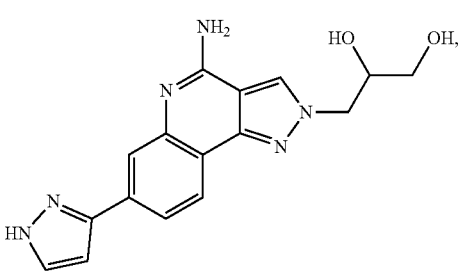
, and -continued
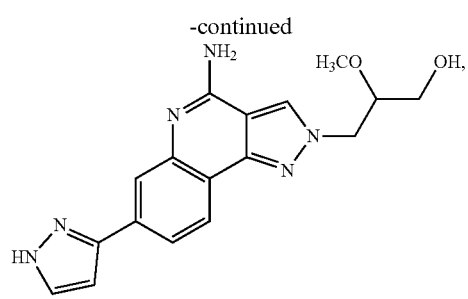
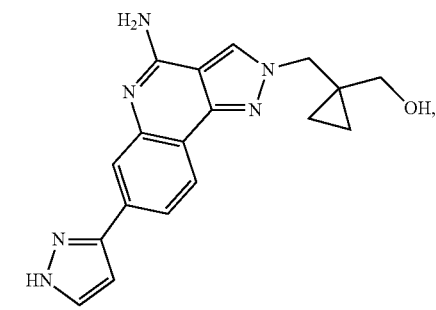
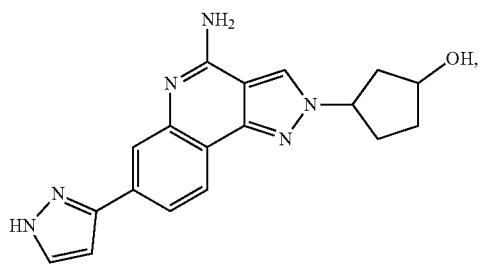
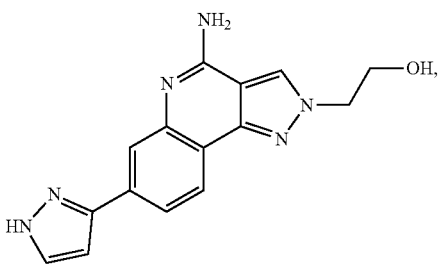
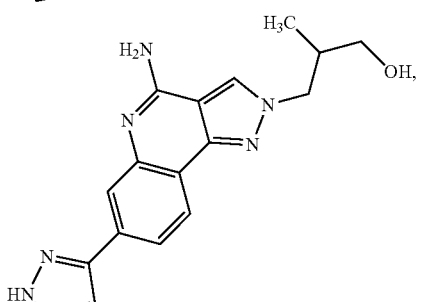
or a stereoisomer, a tautomer or a pharmaceutically acceptable salt thereof.
In another aspect, the invention provides a compound selected from
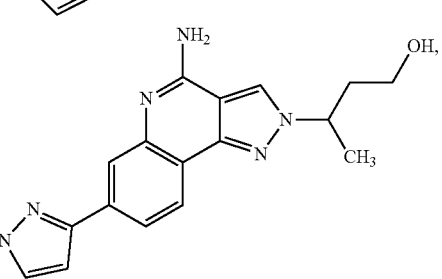
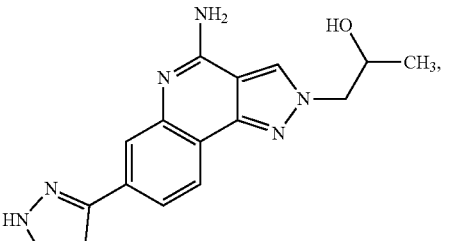
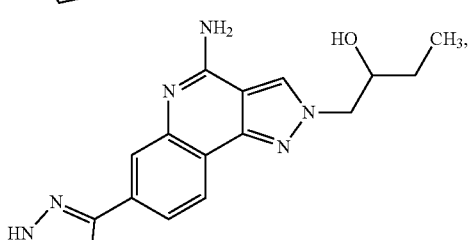
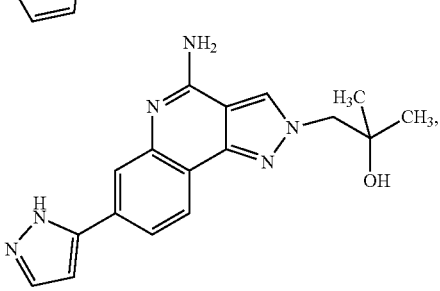

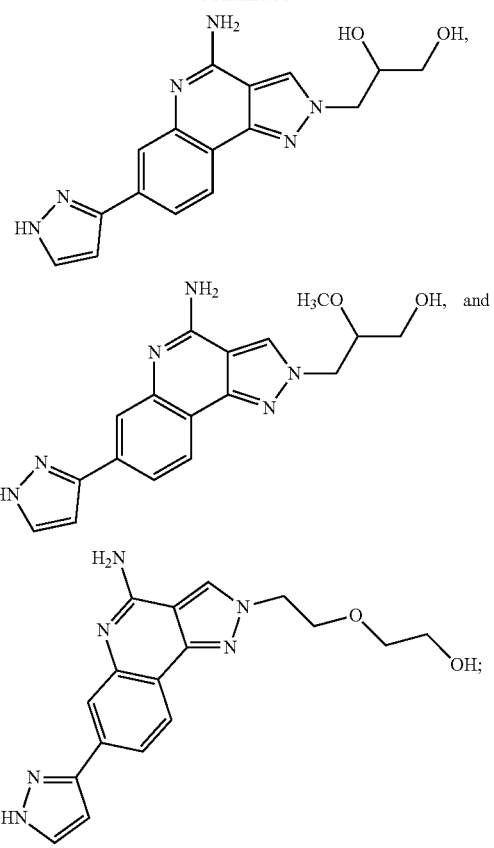
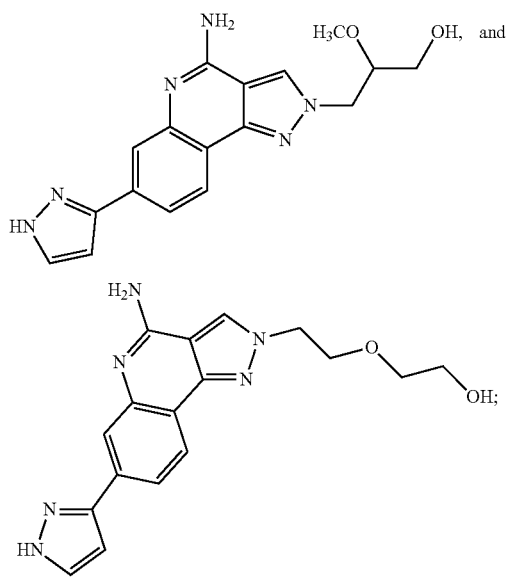
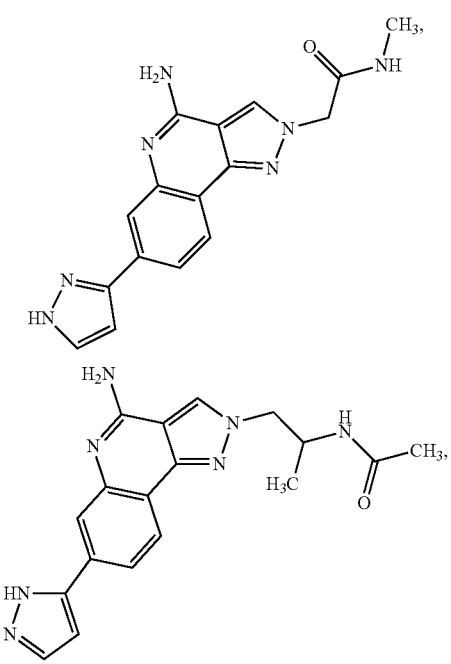
or a stereoisomer, a tautomer or a pharmaceutically acceptable salt thereof.
In another aspect, the invention provides a compound selected from
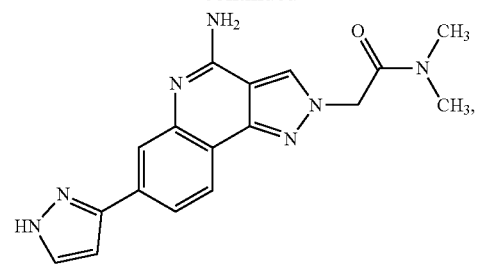
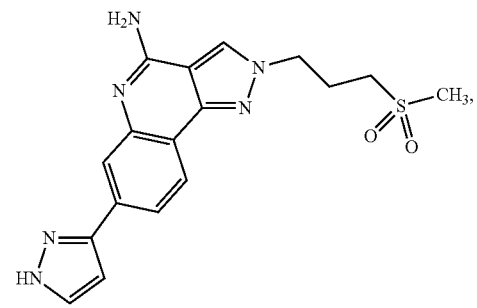
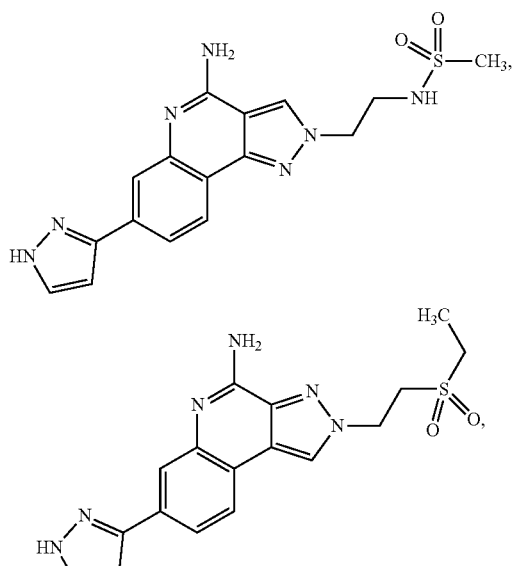
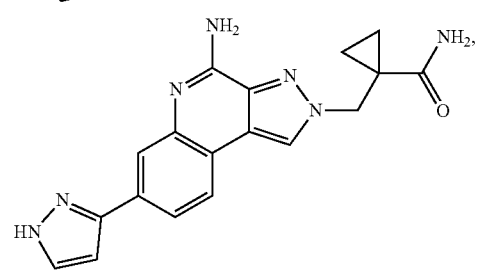
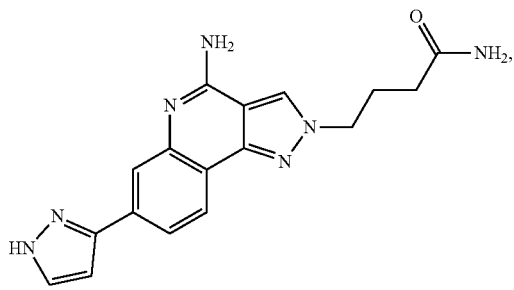

-continued
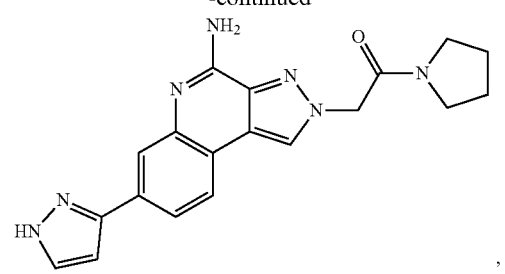
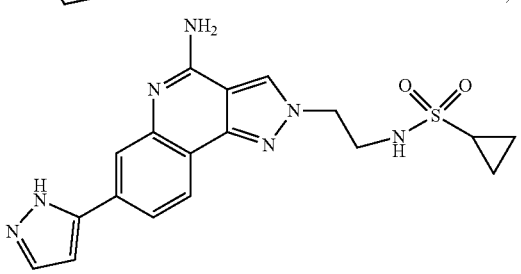
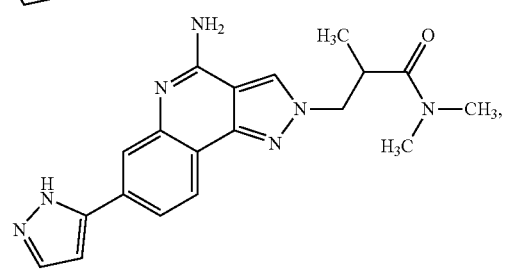
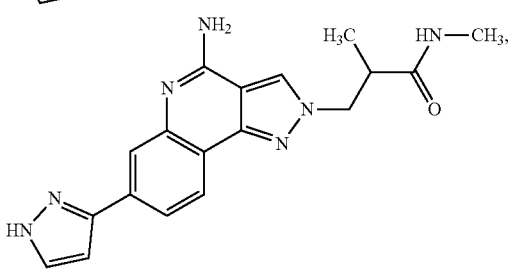
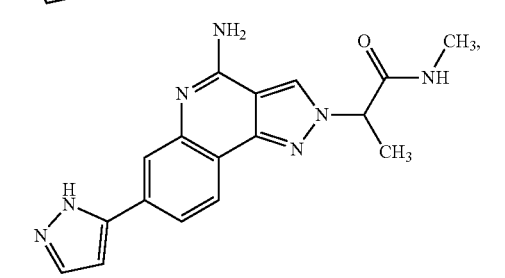
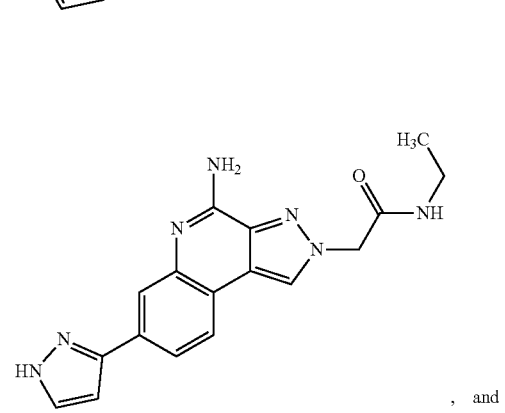
, and
-continued
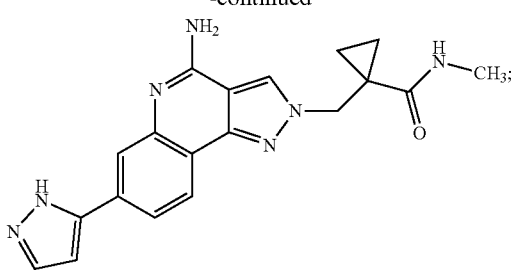
or a stereoisomer, a tautomer or a pharmaceutically acceptable salt thereof.
In another aspect, the invention provides a compound selected from
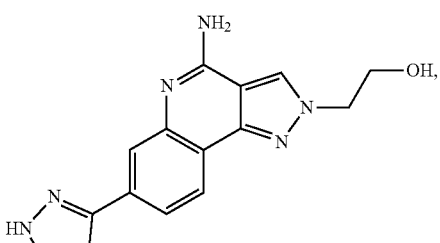
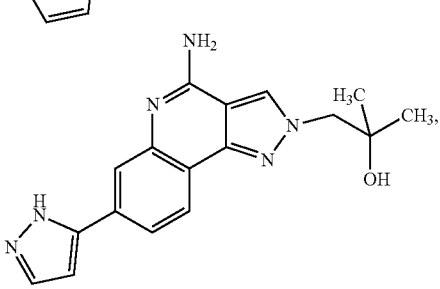
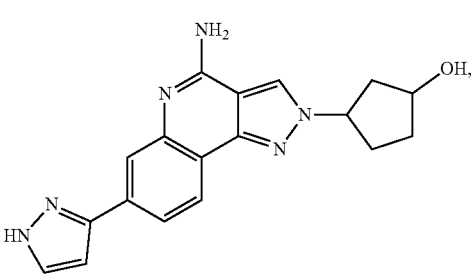
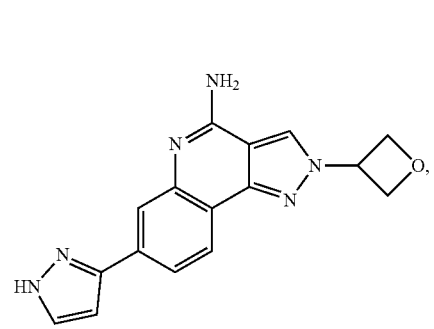

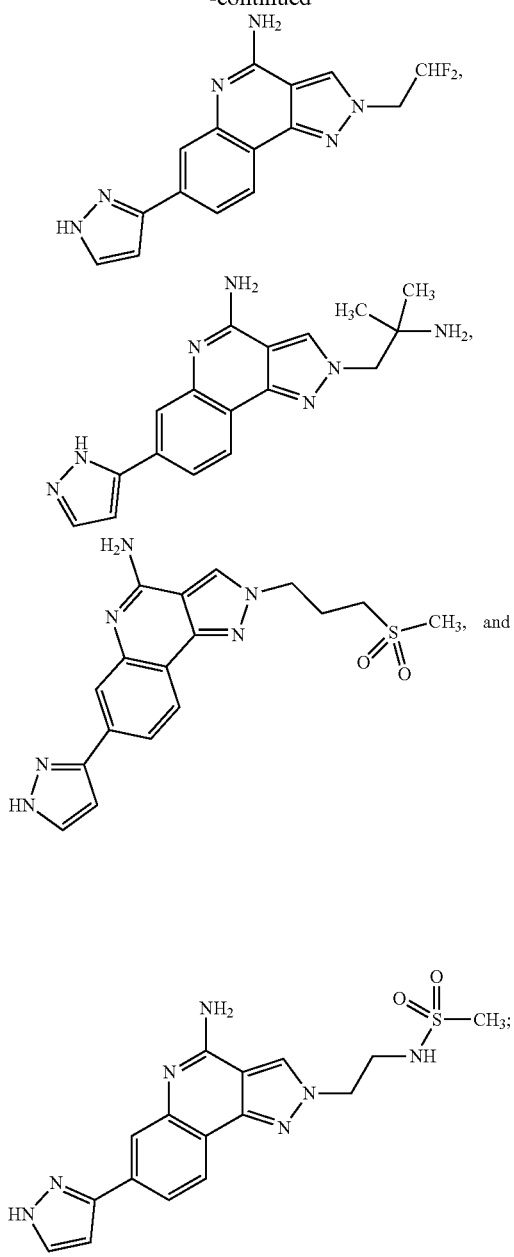
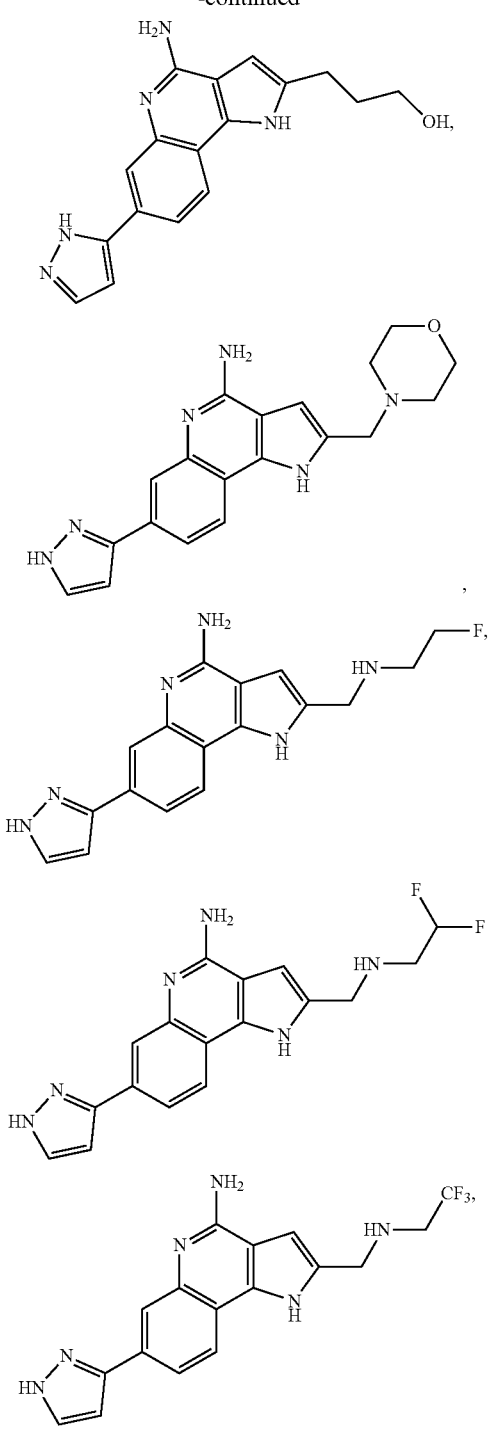
or a stereoisomer, a tautomer or a pharmaceutically acceptable salt thereof.
In another aspect, the invention provides a compound selected from
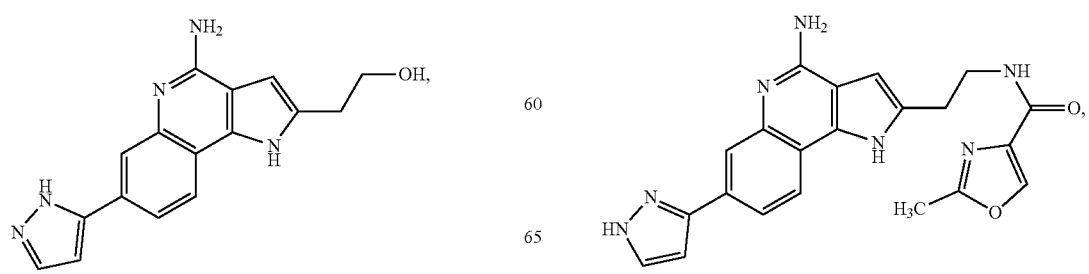

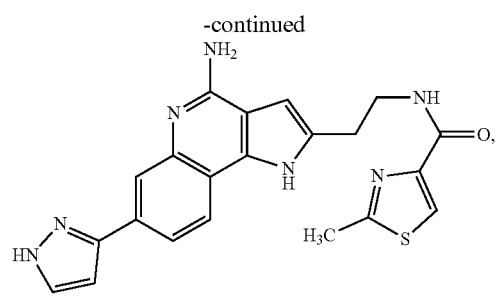
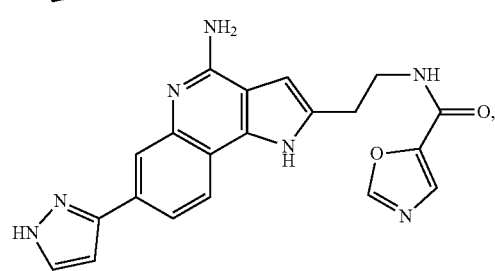
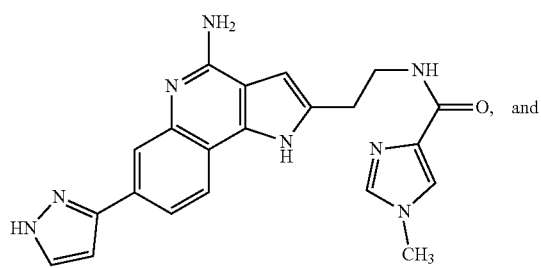
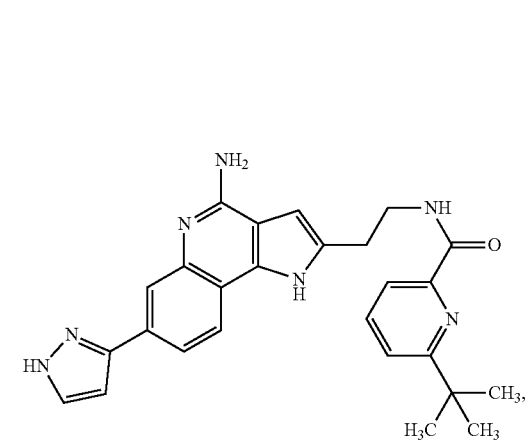
or a stereoisomer, a tautomer or a pharmaceutically acceptable salt thereof.
In another aspect, the invention provides a compound selected from
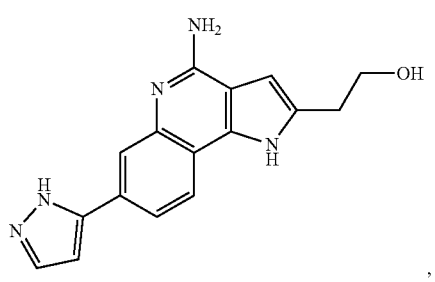
,
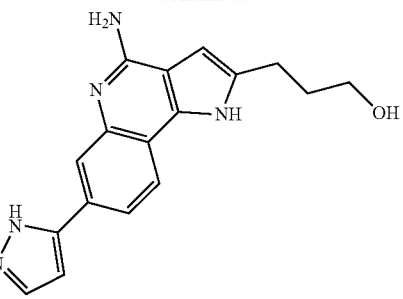
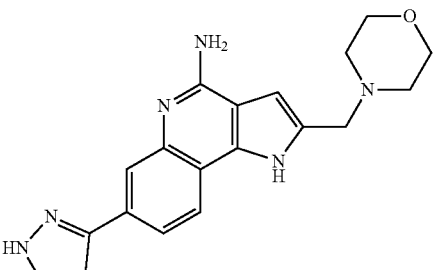
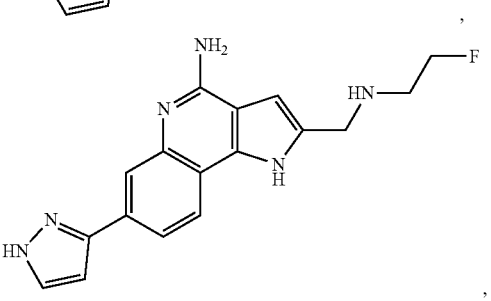
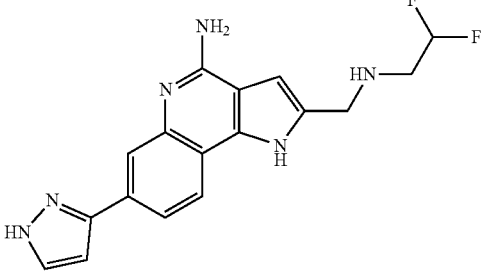
and
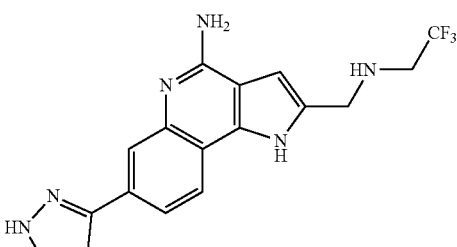
;
or a stereoisomer, a tautomer or a pharmaceutically acceptable salt thereof.

In another aspect, the invention provides a compound selected from

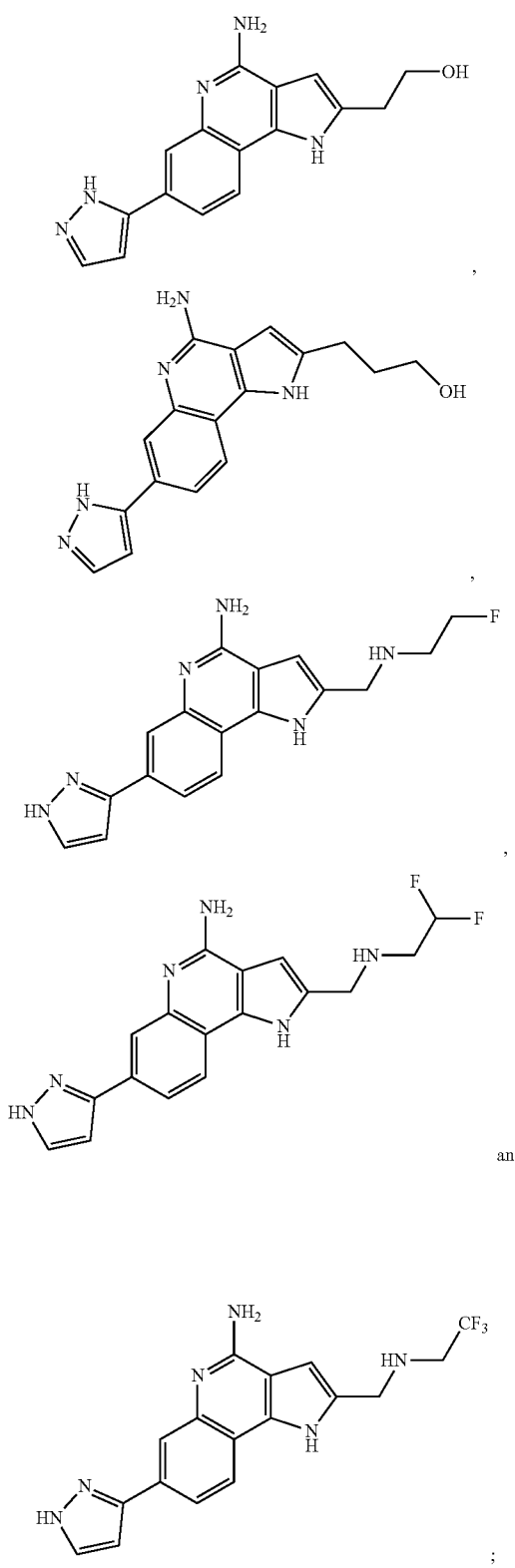

or a stereoisomer, a tautomer or a pharmaceutically acceptable salt thereof.

In another aspect, the invention provides a compound selected from

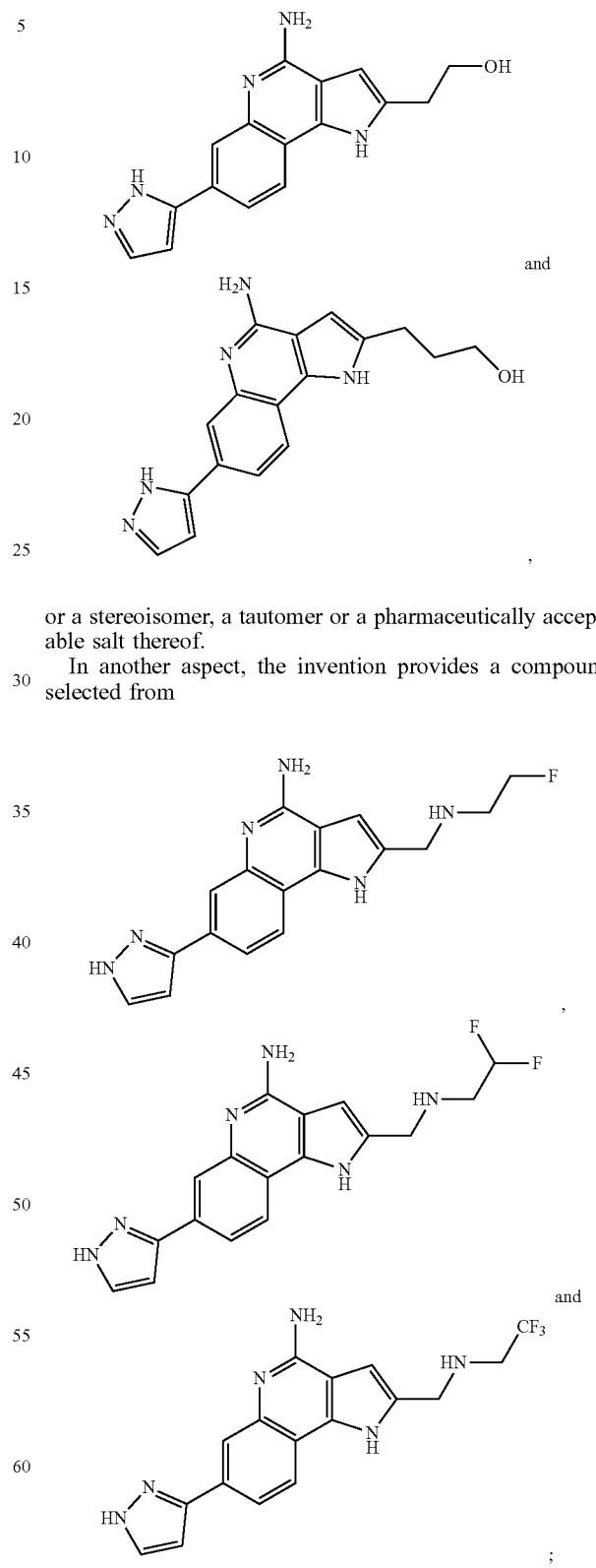

or a stereoisomer, a tautomer or a pharmaceutically acceptable salt thereof.

In another aspect, the invention provides a compound selected from or a stereoisomer, a tautomer or a pharmaceutically acceptable salt thereof.

In another aspect, the invention provides a compound selected from

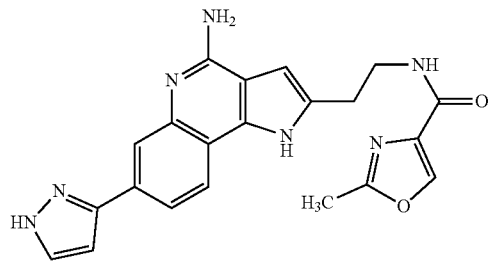

,

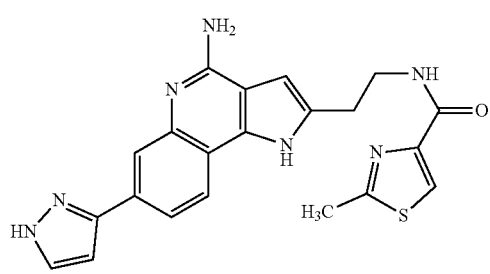

,

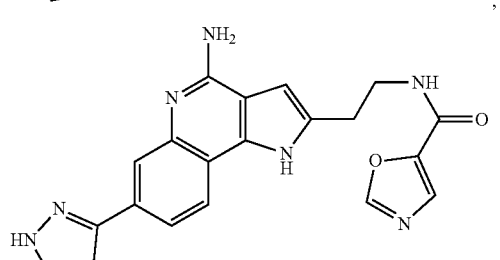

,

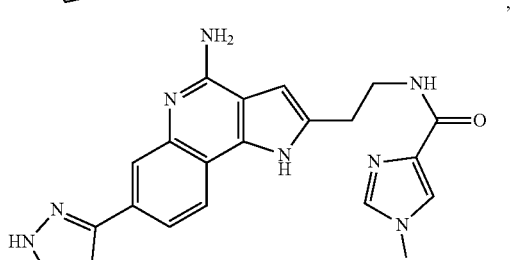

, and

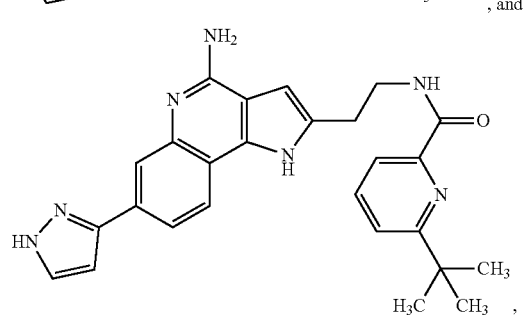

, or a stereoisomer, a tautomer or a pharmaceutically acceptable salt thereof.

In another aspect, the present invention provides a compound selected from any subset list of compounds or a single compound from the exemplified examples within the scope of any of the above aspects.

In some embodiments, the invention provides a compound of Formula (IIa):

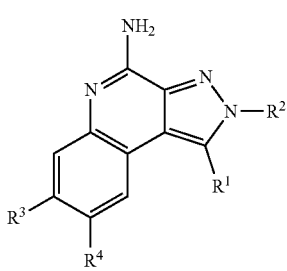

(IIa)

or a tautomer or a pharmaceutically acceptable salt thereof.

In some embodiments, the invention provides a compound of Formula (IIb):

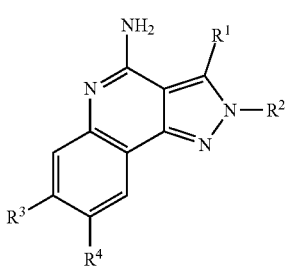

(IIb)

or a tautomer or a pharmaceutically acceptable salt thereof.

In some embodiments, the invention provides a compound of Formula (IIc):

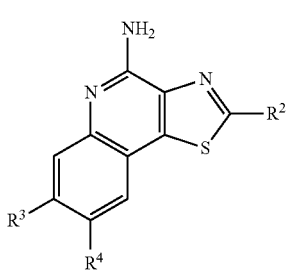

(IIc)

or a tautomer or a pharmaceutically acceptable salt thereof.

In some embodiments, the invention provides a compound of Formula (IId):

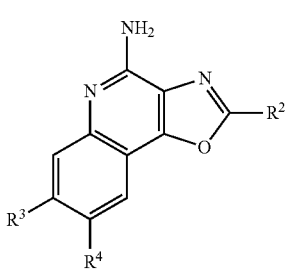

(IId)

or a tautomer or a pharmaceutically acceptable salt thereof.

In some embodiments, the invention provides a compound of Formula (IIe):

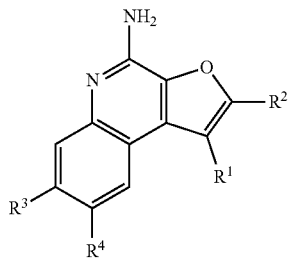

(IIe)

or a stereoisomer, a tautomer or a pharmaceutically acceptable salt thereof.

In some embodiments, the invention provides a compound of Formula (IIf):

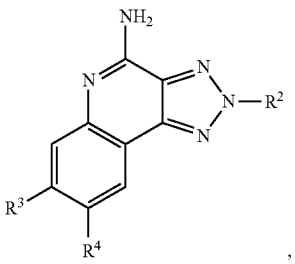

(IIf)

or a stereoisomer, a tautomer or a pharmaceutically acceptable salt thereof.

In some embodiments, the invention provides a compound of Formula (IIg):

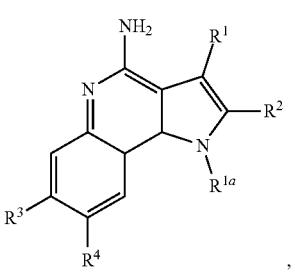

(IIg)

or a stereoisomer, a tautomer or a pharmaceutically acceptable salt thereof.

In some embodiments, the invention provides a compound of Formula (IIg-I):

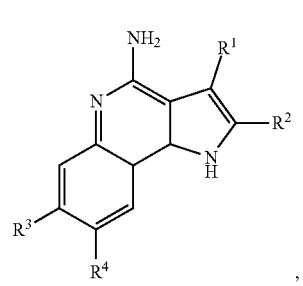

(IIg-1)

or a stereoisomer, a tautomer or a pharmaceutically acceptable salt thereof.

In some embodiments, the invention provides a compound of Formula (IIh):

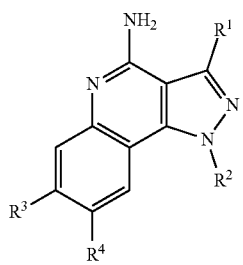

(IIh)

or a stereoisomer, a tautomer or a pharmaceutically acceptable salt thereof.

In some embodiments, the invention provides a compound of Formula (IIi):

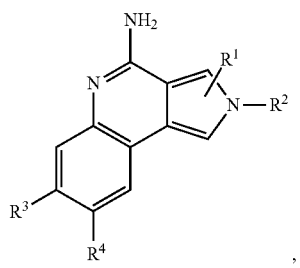

(IIi)

or a stereoisomer, a tautomer or a pharmaceutically acceptable salt thereof.

In some embodiments, $R^1$ is H or X—$R^5$, wherein X is an unbranched $C_{1-6}$ alkylene, and $R^5$ is H, OH, cyano, $C_{1-4}$ alkoxy, $C_{1-4}$ haloalkoxy, —C(O)OR$^a$, —NR$^b$R$^c$, or —C(O)NR$^b$R$^k$. In other embodiments, $R^1$ is H or halo. In other embodiments, $R^1$ is H. In other embodiments, $R^1$ is H or X—$R^5$, wherein X is an unbranched $C_{1-6}$ alkylene, and $R^5$ is H, OH, cyano, $C_{1-4}$ alkoxy, $C_{1-4}$ haloalkoxy, —C(O)OR$^a$, —NR$^b$R$^c$, or —C(O)NR$^b$R$^k$. In other embodiments, $R^1$ is ($C_{1-3}$ alkylene)-aryl, wherein the aryl is substituted with 0 to 3 R$^d$; or ($C_{1-3}$ alkylene)-heteroaryl including from 5 to 6 ring atoms, wherein from 1 to 4 ring atoms are each independently selected from N, N(R$^f$), O, and S, wherein the heteroaryl is substituted with 0 to 3 R$^d$. In other embodiments, $R^1$ is ($C_{1-3}$ alkylene)-aryl, wherein the aryl is substituted with 0 to 3 R$^d$. In other embodiments, $R^1$ is ($C_{1-3}$ alkylene)-heteroaryl including from 5 to 6 ring atoms, wherein from 1 to 4 ring atoms are each independently selected from N, N(R$^f$), O, and S, wherein the heteroaryl is substituted with 0 to 3 R$^d$. In other embodiments, $R^1$ is H, halo or $C_{1-4}$ alkyl. In other embodiments, $R^1$ is H, F or $C_{1-4}$ alkyl.

In some embodiments, $R^2$ is H, —Y—$R^6$, or —C(O)—Y—$R^6$; wherein: Y is independently $C_{1-8}$ alkylene substituted with from 0 to 4 R$^e$; and $R^6$ is, at each occurrence, independently: H, OH, OR$^a$, —C(O)R$^a$, —C(O)OR$^a$, —NR$^b$R$^c$, —C(O)NR$^b$R$^k$, or heteroaryl including from 5 to 6 ring atoms, wherein from 1-4 ring atoms are each independently selected from N, N(R$^f$), O, and S, wherein the heteroaryl is substituted with from 0 to 3 R$^d$. In other embodiments, $R^2$ is —Y—$R^6$, or —C(O)—Y—$R^6$. In other embodiments, $R^2$ is —Y—$R^6$. In other embodiments, $R^2$ is —$(Y^1)_n$—$Y^2$—$(Y^3)_p$—$R^7$, wherein: each of n and p is independently 0 or 1; each of $Y^1$ and $Y^3$ is, independently, $C_{1-3}$ alkylene substituted with from 0 to 2 $R^e$; $Y^2$ is independently $C_{3-6}$ cycloalkylene substituted with from 0 to 4 $R^g$, or heterocycloalkylene including from 3-8 ring atoms, wherein from 1-2 ring atoms are each independently selected from N, N($R^f$) and O, and wherein the heterocycloalkylene is substituted with from 0 to 4 $R^g$, and $R^7$ is H, OH, —C(O)O$R^a$, —NR$^b$R$^c$, —C(O)NR$^b$R$^k$, or heteroaryl including from 5-6 ring atoms, wherein from 1-4 ring atoms are each independently selected from N, N($R^f$), O, and S, and wherein the heteroaryl is substituted with from 0 to 4 $R^g$. In other embodiments, $R^2$ is —$Z^1$—$Z^2$—$Z^3$—$R^8$, wherein: $Z^1$ is $C_{1-3}$ alkylene substituted with from 0 to 6 F; $Z^2$ is —N($R^f$)—, —O—, or —S—; $Z^3$ is $C_{2-5}$ alkylene substituted with from 0 to 6 F; and $R^8$ is OH, OR$^a$, —C(O)R$^a$, —C(O)OR$^a$; —NR$^b$R$^c$, —C(O)NR$^b$R$^k$, or heteroaryl including from 5-6 ring atoms, wherein from 1-4 ring atoms are each independently selected from N, N($R^f$), O, and S, wherein the heteroaryl is substituted with from 0 to 3 $R^d$.

In some embodiments, $R^2$ is H, —$(CH_2)_{1-3}$—$R^6$, —$(CH_2)_{1-3}$O$(CH_2)_{2-3}$OR$^a$, or —$(CH_2)_{1-2}$—$Y^2$—$R^7$. In other embodiments, $R^2$ is —$(CH_2)_{1-3}$—$R^6$, —$(CH_2)_{1-3}$O$(CH_2)_{2-3}$OR$^a$, or —$(CH_2)_{1-2}$—$Y^2$—$R^7$. In other embodiments, $R^2$ is —$(CH_2)_{2-3}$—$R^6$. In other embodiments, $R^2$ is —$(CH_2)_2$—NHC(O)R$^a$,

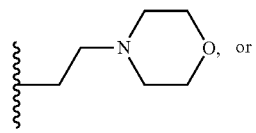, or

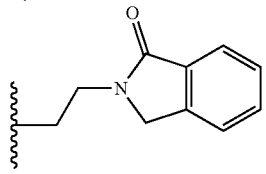

In other embodiments, $R^2$ is —$(CH_2)_2$—NHC(O)R$^a$.

In some embodiments, $R^3$ is —($C_{0-3}$ alkylene)-(5-membered heteroaryl) wherein the heteroaryl includes 2 to 4 ring carbon atoms and 1 to 3 ring heteroatoms are each independently selected from: N, N($R^f$), O, and S, and is substituted with 0 to 3 $R^g$. In other embodiments, $R^3$ is —($C_{0-2}$ alkylene)-(5-membered heteroaryl) wherein the heteroaryl includes 2 to 4 ring carbon atoms and 1 to 3 ring heteroatoms are each independently selected from: N, N($R^f$), O, and S, wherein the heteroaryl is substituted with from 0 to 2 $R^g$. In other embodiments, $R^3$ is 5-membered heteroaryl wherein the heteroaryl includes 3 to 4 ring carbon atoms and 1 to 2 ring heteroatoms are each independently selected from: N, NH, O, and S. In other embodiments, $R^3$ is

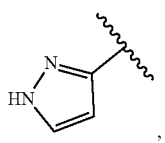,

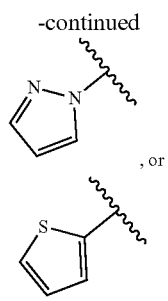

In other embodiments, $R^3$ is

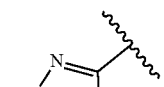

In other embodiments, $R^3$ is

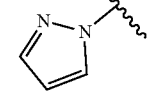

In some embodiments, $R^4$ is H, halo or $C_{1-4}$ alkyl. In other embodiments, $R^4$ is H, F or $C_{1-4}$ alkyl.

In some embodiments, $R^6$ is OH, OR$^a$, —NR$^b$R$^c$, —C(O)NR$^b$R$^k$, or heteroaryl including from 5 to 6 ring atoms, wherein from 1 to 4 ring atoms are each independently selected from N, N($R^f$), O, and S, wherein the heteroaryl is substituted with from 0 to 3 $R^d$. In other embodiments, $R^6$ is OH, OR$^a$, NR$^b$R$^c$, —NR$^b$C(O)R$^a$, —C(O)NHR$^k$, —NHC(O)OR$^a$, —NHC(O)NR$^j$R$^k$, —NHS(O)$_2$R$^h$,

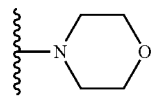,

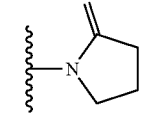,

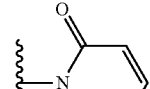,

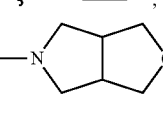,

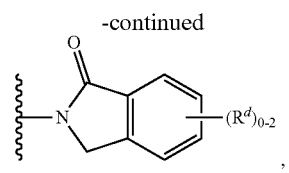
, or heteroaryl including from 5 to 6 ring atoms, wherein from 1 to 4 ring atoms are each independently selected from N, N($R^f$), O, and S, wherein the heteroaryl is substituted with from 0 to 3 $R^d$. In other embodiments, $R^6$ is OH, $OR^a$, $NR^bR^c$, —$NR^bC(O)R^a$, —C(O)NH($C_{1-4}$ alkyl), —C(O)NHPh, —NHC(O)O($C_{1-6}$ alkyl), —NHC(O)N($C_{1-4}$ alkyl)$_2$, —NHS(O)$_2$($C_{1-4}$ alkyl),

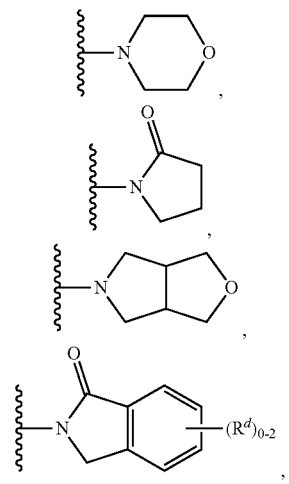

or heteroaryl including from 5 to 6 ring atoms, wherein from 1 to 4 ring atoms are each independently selected from N, N($R^f$), O, and S, wherein the heteroaryl is substituted with from 0 to 3 $R^d$. In other embodiments, $R^6$ is independently selected from: OH, $OR^a$, N($C_{1-4}$ alkyl)$_2$, —$NR^bC(O)R^a$, —C(O)NHPh, —NHC(O)O($C_{1-6}$ alkyl), —NHC(O)N($C_{1-4}$ alkyl)$_2$, —NHS(O)$_2$($C_{1-4}$ alkyl),

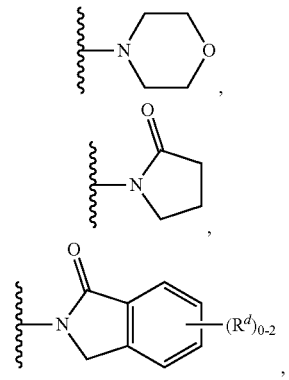

and pyrazol-1-yl substituted with 0 to 2 $R^d$. In other embodiments, $R^6$ is OH, $OR^a$, —$NR^bR^c$, or —C(O)$NR^bR^k$. In other embodiments, $R^6$ is —$NR^bR^c$, or —C(O)$NR^bR^k$.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

Other Aspects and Embodiments of the Invention

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer.

In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., cancer therapies that include administering one or more (e.g., two, three, four, five, six, or more) additional anticancer agents. Non-limiting examples of additional anticancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine, Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, *chlamydia, Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, Kingella kingae infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, *salmonellosis*, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, *Tinea barabe, Tinea capitis, Tinea corporis, Tinea cruris, Tinea manum, Tinea nigra, Tinea pedis, Tinea unguium, Tinea versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —OCH$_3$ is attached through the oxygen atom.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 22nd Edition, Pharmaceutical Press, London, U K (2012); *Handbook of Pharmaceutical Excipients,* 6th ed.; Rowe et al., Eds.; The Pharmaceutical Press and the American Pharmaceutical Association: (2009); *Handbook of Pharmaceutical Additives,* 3rd ed.; Ash and Ash Eds.; Gower Publishing Company: (2007); *Pharmaceutical Preformulation and Formulation,* 2nd ed.; Gibson Ed.; CRC Press LLC: Boca Raton, FL, (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "alkylene" refers to a branched or unbranched divalent alkyl (e.g., —$CH_2$—).

The term "haloalkyl" refers to an alkyl, in which one or more hydrogen atoms is/are replaced with an independently selected halo.

The term "alkoxy" refers to an —O-alkyl radical (e.g., —$OCH_3$).

The term "haloalkoxy" refers to an —O-haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aromatic" refers generally to a ring that includes a cyclic array of resonance-stabilized 4n+2 pi electrons, wherein n is an integer (e.g., 1 or 2). Aromatic moieties include aryl and heteroaryl groups. The term "non-aromatic" describes any moiety that does not fall within the definition of "aromatic".

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 7-12 membered bicyclic or bridged, or 11-14 membered tricyclic ring system having 1-3 heteroatoms if monocyclic, 1-6 heteroatoms if bicyclic, spiro, or bridged, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Pharmaceutical Compositions and Administration

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., *"Effect of Intratumoral Injection on the Biodistribution and the Therapeutic Potential of HPMA Copolymer-Based Drug Delivery Systems"* Neoplasia. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 1 1 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 1 1 months, 12 months, or more. In a further embodiment, a period of during which administration is stopped is for 1 day, 2 days, 3 days, 4 days, 5 days, 6 days, 7 days, 8 days, 9 days, 10 days, 1 1 days, 12 days, 13 days, 14 days, 3 weeks, 4 weeks, 5 weeks, 6 weeks, 7 weeks, 8 weeks, 9 weeks, 10 weeks, 1 1 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a mycobacterium.

Non-limiting examples of infectious disease include: *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, Kingella kingae infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, *Tinea barabe, Tinea capitis, Tinea corporis, Tinea cruris, Tinea manum, Tinea nigra, Tinea pedis, Tinea unguium, Tinea versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J. Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics), IBI308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MED16469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MED16469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MED14736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semi-synthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a *vinca* alkaloid, a podophyllotoxin and/or a taxane. *Vinca* alkaloids, in general, bind to specific sites on tubulin, inhibiting the assembly of tubulin into microtubules, generally during the M phase of the cell cycle. In an embodiment, a *vinca* alkaloid is derived, without limitation, from the Madagascar periwinkle, *Catharanthus roseus* (formerly known as *Vinca rosea*). In an embodiment, a *vinca* alkaloid includes, without limitation, Vincristine, Vinblastine, Vinorelbine and/or Vindesine. In an embodiment, a taxane includes, but is not limited to, Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaftate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer. In certain embodiments, the compounds of the invention may be used for the manufacture of a medicament for modulating NLRP3 activity. In certain embodiments, the modulating comprises agonizing NLRP3.

Methods of Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224, the contents of each of which are hereby incorporated by reference in their entirety. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

The following abbreviations have the indicated meanings:
ACN=acetonitrile
AcOH=acetic acid
$CDCl_3$=chloroform-d
$CD_3OD$=methanol-d
$CH_2Cl_2$=dichloromethane
$CH_3ReO_3$=methyltrioxorhenium
$Cs_2CO_3$=cesium carbonate
CuI=copper (I) iodide
d=doublet
DCM=dichloromethane
DIEA=N,N-diethylisopropylamine
DMF=N,N-dimethylformamide
DMSO=dimethylsulfoxide
ES=electrospray ionization
$Et_2O$=diethyl ether
EtOAc=ethyl acetate
EtOH=ethanol
equiv=equivalents
g=grams
h or hr=hour(s)
HCl=hydrogen chloride (usually as a solution)
$H_2O$=water
$H_2O_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
$I_2$=iodine
$K_2CO_3$=potassium carbonate
$K_2HPO_4$=potassium phosphate, dibasic
KI=potassium iodide LC/MS=liquid chromatography mass spectrometer
LiBH$_4$=lithium borohydride
m=multiplet
m/z=mass to charge ratio
M=molar
m-CPBA=meta-chloroperoxybenzoic acid
mg=milligram(s)
MeOH=methanol
MHz=megahertz
mL=milliliter(s)
mmol=millimole(s)
MTO=methyltrioxorhenium
NaHCO$_3$=sodium hydrogen carbonate
Na$_2$CO$_3$=sodium carbonate
NaOH=sodium hydroxide
Na$_2$SO$_4$=sodium sulfate
NEt$_3$ and TEA=trimethylamine
NH$_4$OH or NH$_3$H$_2$O=ammonium hydroxide
NH$_4$HCO$_3$=ammonium hydrogen carbonate
nm=nanometer
PdCl$_2$(PPh$_3$)$_2$=bis(triphenylphosphine)palladium (II) dichloride
Pd(dppf)Cl$_2$=1,1'-Bis(diphenylphosphino)ferrocene
Pd(dppf)Cl$_2$DCM=1,1'-Bis(diphenylphosphino)ferrocene-dichloromethane complex
Pd(OH)$_2$=palladium hydroxide
PMB=para-methoxybenzyl
POCl$_3$=phosphorous oxychloride
ppm=parts per million
Pt=platinum
Pt/C=platinum on carbon
rt=room temperature
RT=retention time
s=singlet
t=triplet
TFA=trifluoroacetic acid
TLC=thin layer chromatography
TosMIC=toluenesulfonylmethyl isocyanide
TsCl=para-toluenesulfonyl chloride
° C.=degrees Celsius
μmol=micromole(s)

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section (e.g., Schemes 1 to 11).

Compound 10 may be prepared by a synthetic sequence outlined in Scheme 1. Indole 1, where the Hal group is a halide such as bromide, can be converted to intermediate 2 with a reagent such as ethyl 2-chloro-2-oxoacetate. Treatment of intermediate 2 with an appropriately functionalized hydrazine (NH$_2$—NH-PG$^1$) in the presence of an acid, such as acetic acid, provides intermediate 3, which can then be converted to intermediate 4 with a chlorinating reagent such as POCl$_3$. Addition of ammonia or an appropriately functionalized amine (NH$_2$-PG$^2$) to intermediate 4 affords intermediate 5. The de-protection of intermediate 5 may be accomplished in several ways known to one skilled in the art. For example, where PG$^1$=PG$^2$=PMB, intermediate d 5 may be treated with a reagent such as TFA to afford intermediate 6. Coupling between intermediate 6 and a coupling reagent 7 by the action of a suitable catalyst affords intermediate 8. For example, this step may be accomplished by treating intermediate 6 with a suitable boronic ester, such as 3-(tetramethyl-1,3,2-dioxaborolan-2-yl)-1H-pyrazole, in the presence of a catalyst such as Pd(dppf)Cl$_2$ to give intermediate 8. Alternatively, this step may be accomplished by treating intermediate 6 with a suitable heterocycle, such as pyrazole, in the presence of a copper catalyst, such as copper(I) iodide, and a ligand, such as N,N'-dimethylethylenediamine to give intermediate 8. In the last step of Scheme 1, compound 10 can be prepared by treating intermediate 8 with an appropriately functionalized alkylating reagent (R$^2$—X), where X is a leaving group such as a halide, in the presence of a base such as potassium carbonate. Optionally, if R$^3$ contains a protecting group, it may be removed at this stage under suitable conditions. For example, if R$^3$-M was 1-(tetrahydro-2H-pyran-2-yl)-5-(4,4,5,5-tetramethyl-1,3,2-dioxaborolan-2-yl)-1H-pyrazole, the tetrahydropyran group can be removed by treatment with a reagent such as TFA.

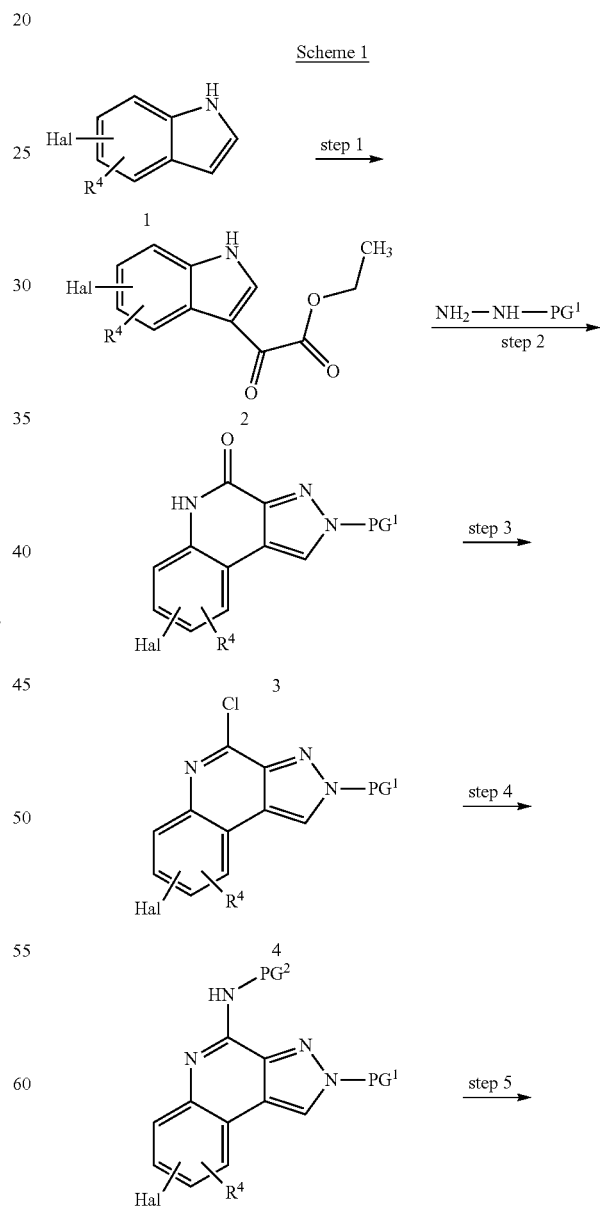

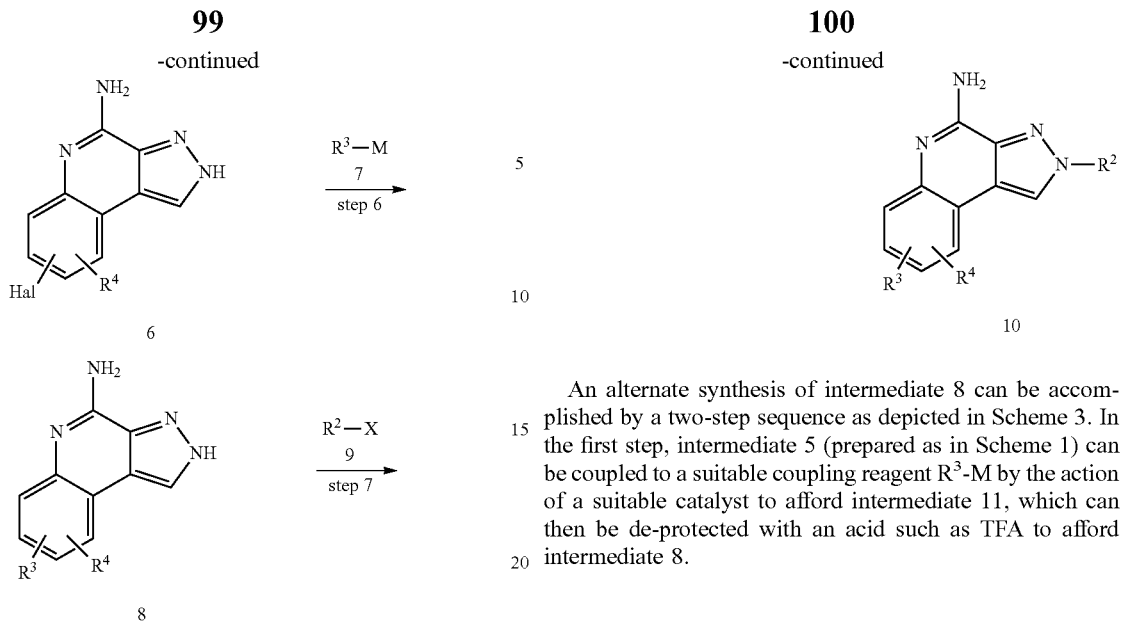

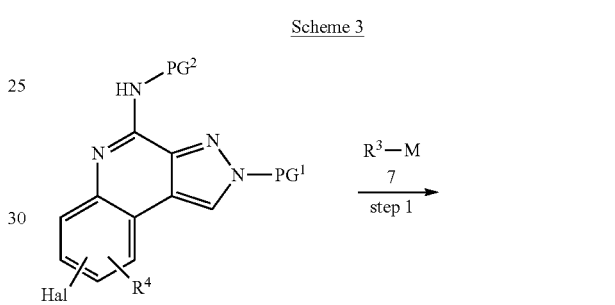

Alternatively, intermediate 6 may be functionalized first with an alkylating reagent R²—X to give compound 10a and then converted to compound 10 with a suitable coupling partner R³-M under the action of an catalyst as shown in Scheme 2.

Scheme 2

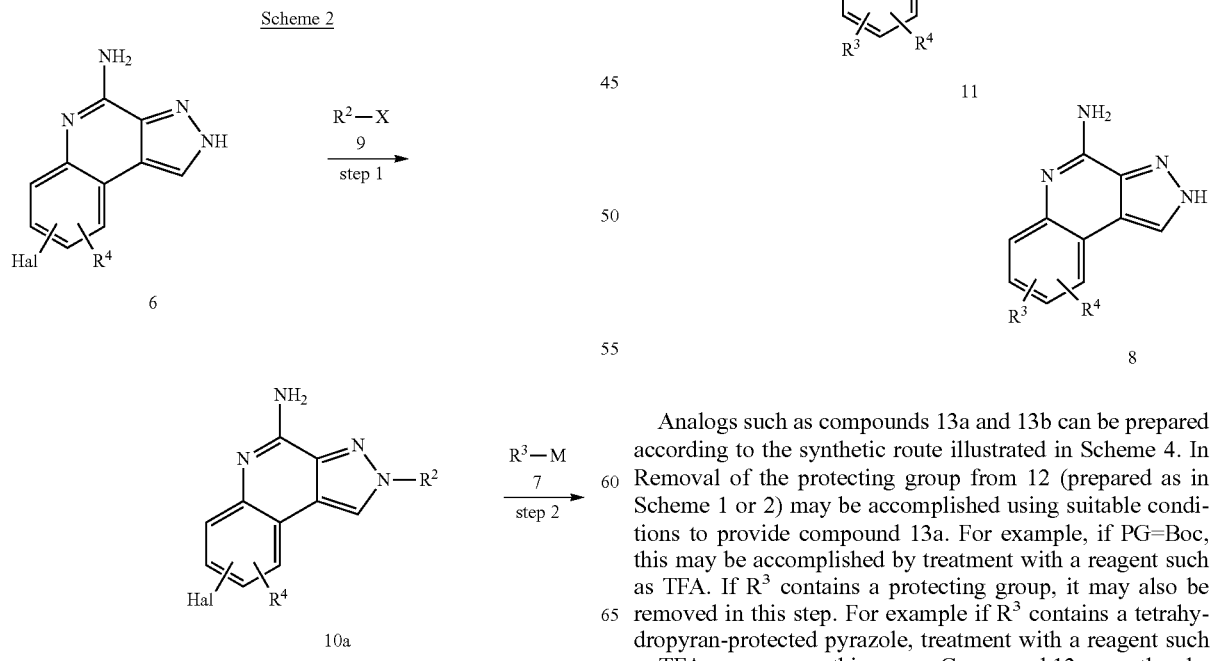

An alternate synthesis of intermediate 8 can be accomplished by a two-step sequence as depicted in Scheme 3. In the first step, intermediate 5 (prepared as in Scheme 1) can be coupled to a suitable coupling reagent R³-M by the action of a suitable catalyst to afford intermediate 11, which can then be de-protected with an acid such as TFA to afford intermediate 8.

Scheme 3

Analogs such as compounds 13a and 13b can be prepared according to the synthetic route illustrated in Scheme 4. In Removal of the protecting group from 12 (prepared as in Scheme 1 or 2) may be accomplished using suitable conditions to provide compound 13a. For example, if PG=Boc, this may be accomplished by treatment with a reagent such as TFA. If R³ contains a protecting group, it may also be removed in this step. For example if R³ contains a tetrahydropyran-protected pyrazole, treatment with a reagent such as TFA may remove this group. Compound 13a may then be converted to the desired final product by treatment with the appropriate reagents. For example, 13a may be converted to an amide by treatment with an appropriately-substituted carboxylic acid in the presence of a suitable coupling reagent, such as HATU, and a base, such as N,N-diisopropylethylamine. Alternatively, compound 13a may by converted to an isoindolinone by treatment with a reagent such as methyl 2-(bromomethyl)benzoate, or an appropriately-substituted analog thereof, in the presence of a base, such as N,N-diisopropylethylamine. Alternatively, compound 13a may be alkylated by treatment with an appropriately-substituted aldehyde or ketone in the presence of a suitable reducing agent, such as sodium triacetoxyborohydride. Alternatively, compound 13a may be converted to a sulfonamide by treatment with an appropriately-substituted sulfonyl chloride in the presence of a base, such as triethylamine. Alternatively, compound 13a may be converted to a urea by treatment with an appropriately-substituted isocyanate or carbamoyl chloride in the presence of a base, such as triethylamine. Alternatively, compound 13a may be converted to a carbamate by treatment with an appropriately-substituted chloroformate in the presence of a base, such as triethyl amine.

if PG=TBS, this may be accomplished by treatment with a reagent such as TBAF. Compound 15a may then be converted compound 15b by treatment with the appropriate reagents. For example, compound 15a may be converted to an aryl or heteroaryl ether by treatment with an appropriately-substituted phenol in the presence of suitable reagents, such as DIAD and triphenylphosphine. In a final step, if $R^3$ contains a protecting group, it may be removed using suitable conditions. For example if $R^3$ contains a tetrahydropyran-protected pyrazole, treatment with a reagent such as TFA may remove this group.

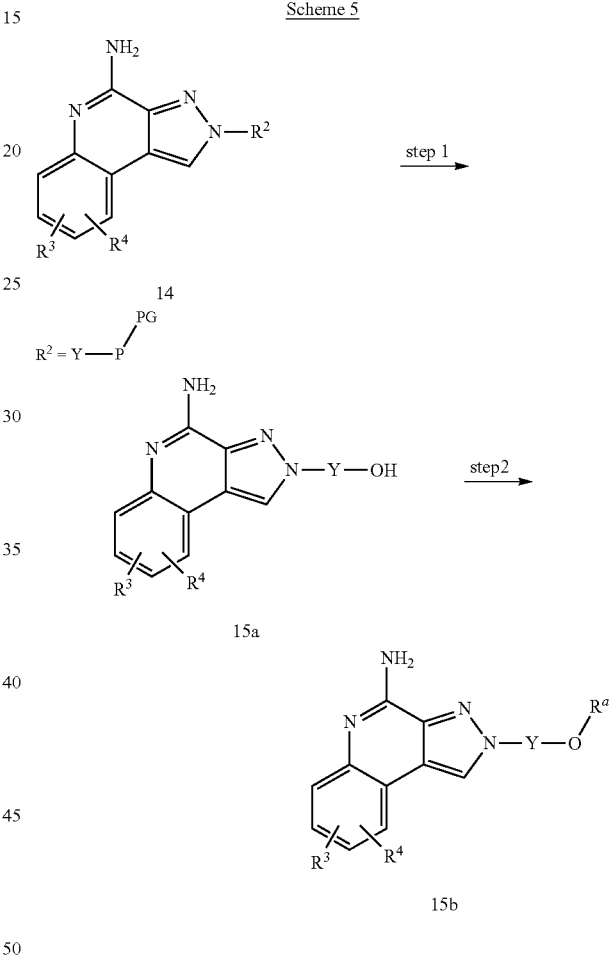

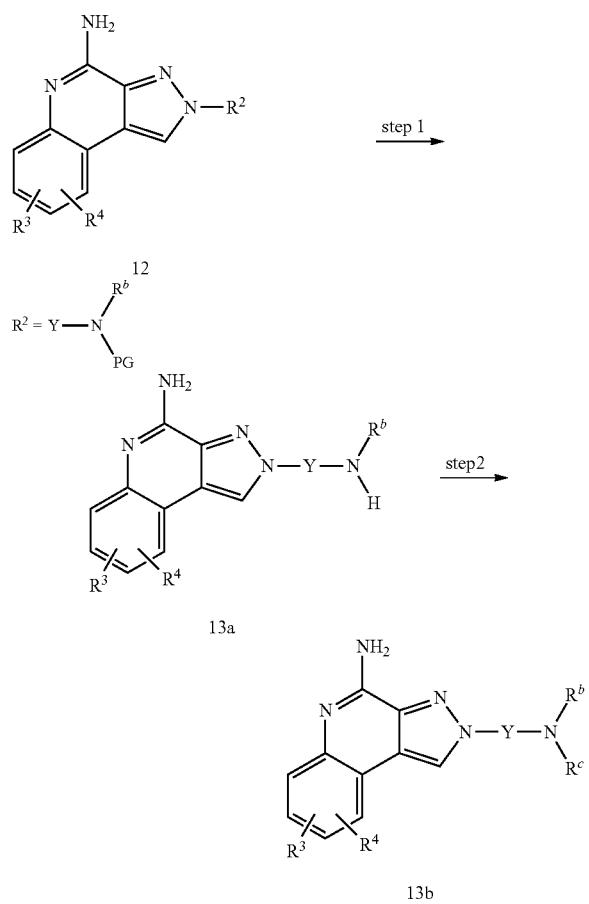

Analogs such as compounds 15a and 15b can be prepared according to the synthetic route illustrated in Scheme 5. Removal of the protecting group from intermediate 14 (prepared as in Scheme 1 or 2) may be accomplished using suitable conditions to provide compound 15a. For example, Compound 22 may be prepared by a synthetic sequence outlined in Scheme 6. Intermediate 17 can be prepared by treating quinoline 16 with an appropriate halogenating reagent, such as iodine, in the presence of a base, such as sodium hydroxide. Intermediate 17 can then be coupled to an appropriately substituted alkyne 18 under the action of a suitable catalyst, such as $Pd(Ph_3)_4$, to provide cyclized product 19. Further elaboration to compound 21 may be accomplished with a two-step sequence by first treating intermediate 19 with a suitable oxidant, such as m-CPBA, to give oxide 20, which may be converted to compound 21 with a reagent, such as tosyl chloride, and an amine, such as ammonia. Cross-coupling reaction between compound 21 with a suitable coupling partner by the action of a catalyst then provides compound 22.

Scheme 6

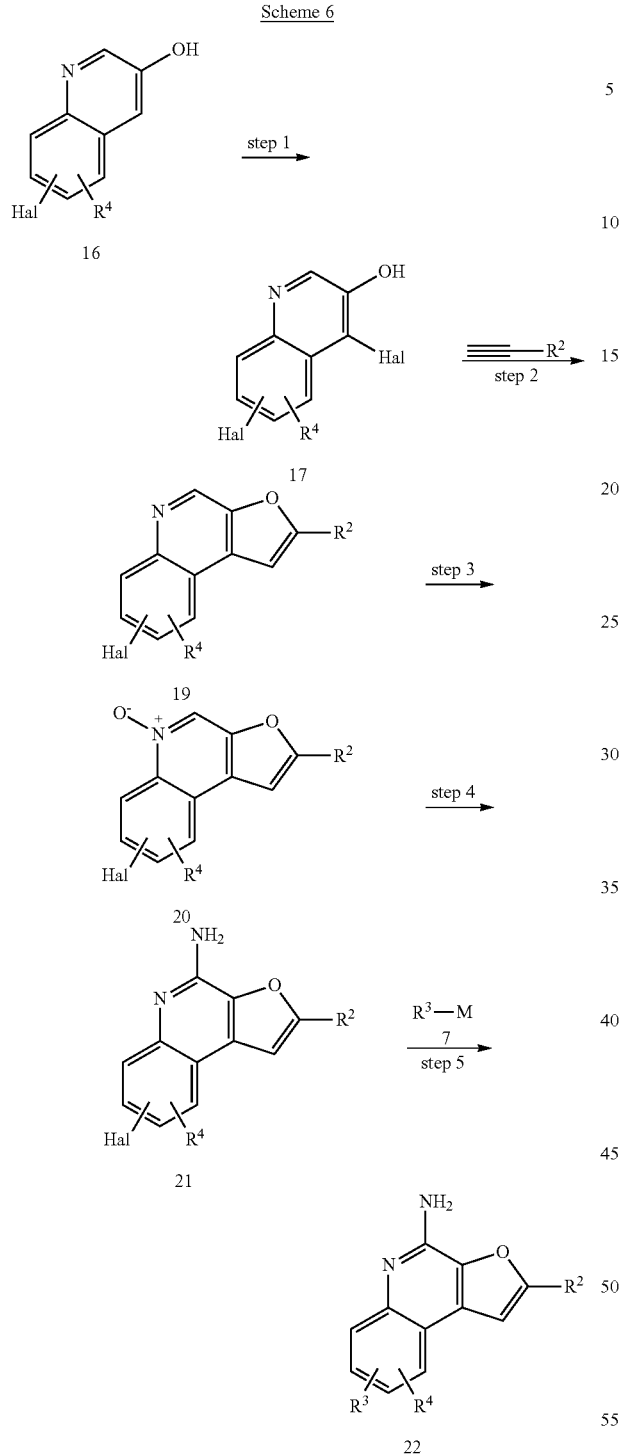

which was then converted to compound 28 with a reagent, such as tosyl chloride, and an amine, such as ammonia. Cross-coupling reaction between compound 28 with a suitable coupling partner by the action of a catalyst then provides compound 29.

Scheme 7

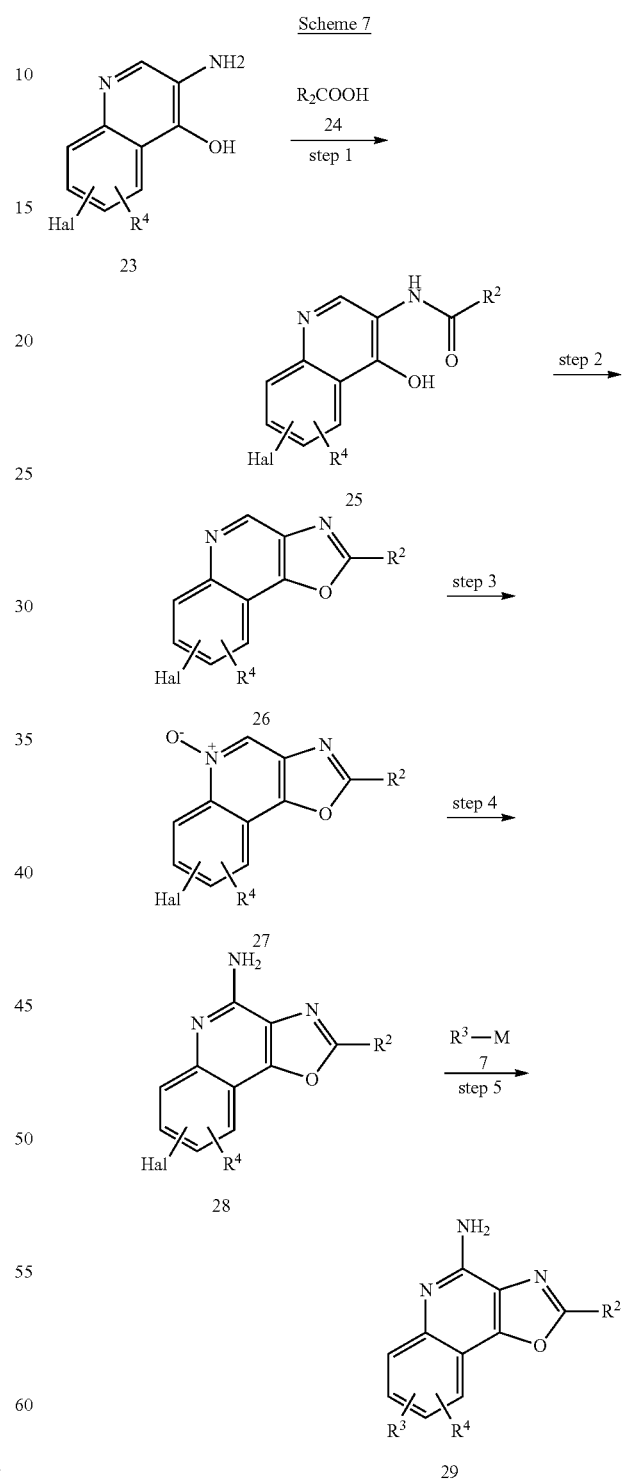

Analogs such as compound 29 can be prepared according to the synthetic route depicted in Scheme 7. In Scheme 7, amide bond formation between intermediate 23 and acid 24 in the presence of a suitable coupling reagent, such as HATU, provides intermediate 25. Intermediate 25 can undergo cyclization reaction in the presence of suitable reagents such as $C_2Cl_6$ and $PPh_3$ to provide intermediate 26. Further elaboration to compound 28 may be accomplished with a two-step sequence by first treating intermediate 26 with a suitable oxidant, such as m-CPBA, to give oxide 27, Analogs such as compound 33 can be prepared according to the synthetic route depicted in Scheme 8. In Scheme 8, intermediate 25 (prepared as shown in Scheme 7) can be converted to intermediate 30 with a suitable reagent, such as Lawesson's reagent, in the presence of a base, such as pyridine. Further elaboration to compound 32 may be accomplished with a two-step sequence by first treating compound 30 with a suitable oxidant, such as m-CPBA, to give oxide 31, which may be converted to compound 32 with a reagent, such as tosyl chloride, and an amine, such as ammonia. Cross-coupling reaction between compound 32 with a suitable coupling partner by the action of a catalyst then provides compound 33.

such as $POCl_3$. Addition of ammonia or an appropriately functionalized amine ($NH_2$-$PG^2$) to intermediate 36 affords intermediate 37. The de-protection of intermediate 37 may be accomplished in several ways known to one skilled in the art. For example, where $PG^1$=$PG^2$=PMB, compound 5 may be treated with a reagent such as TFA to afford intermediate 38. Compound 39 can be prepared by treating intermediate 38 with an appropriately functionalized alkylating reagent ($R^2$—X), where X is a leaving group such as a halide, in the presence of a base such as potassium carbonate. Coupling between compound 39 and a coupling reagent by the action of a suitable catalyst affords compound 40. Optionally, if $R^3$ contains a protecting group, it may be removed at this stage using suitable conditions. For example, if $R^3$-M was 1-(tetrahydro-2H-pyran-2-yl)-5-(4,4,5,5-tetramethyl-1,3,2-dioxaborolan-2-yl)-1H-pyrazole, the tetrahydropyran group can be removed by treatment with a reagent such as TFA.

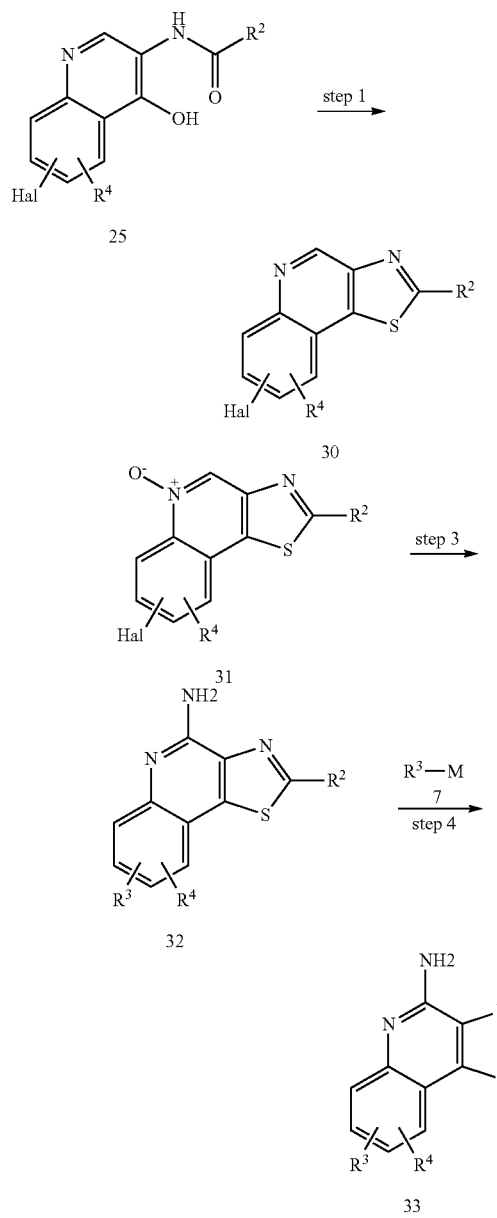

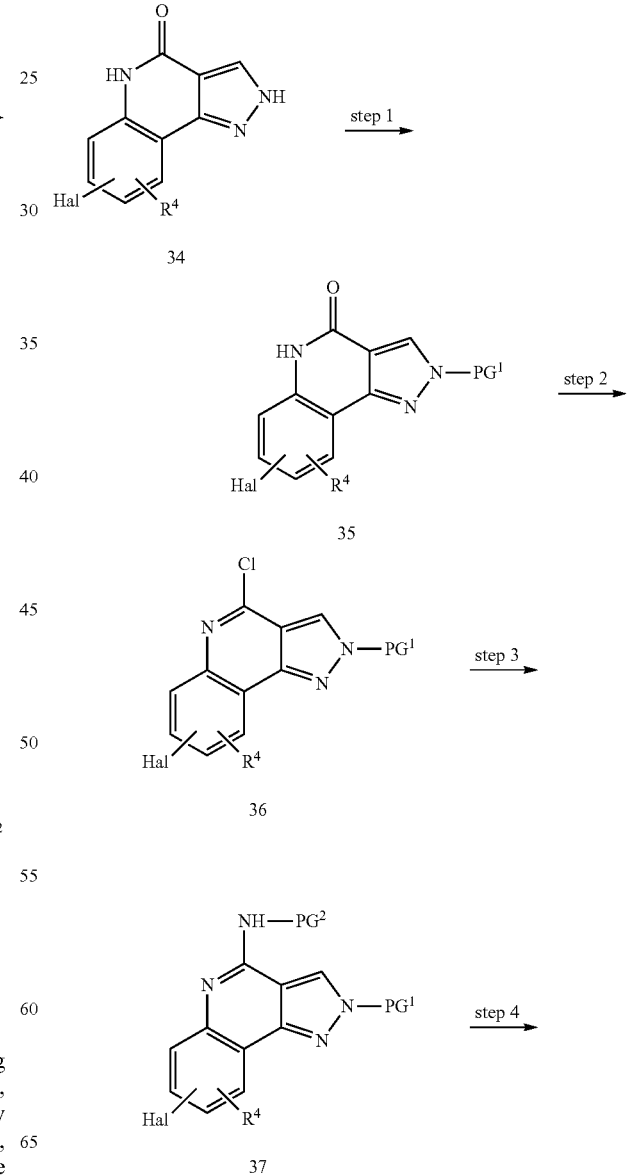

Analogs such as compound 40 can be prepared according to the synthetic routes depicted in Scheme 9. In Scheme 9, compound 34 (prepared according to WO2013/045400) may be protected with a suitable protecting group, such as PMB, to provide intermediate 35. Intermediate 35 may then be converted to intermediate 36 with a chlorinating reagent -continued

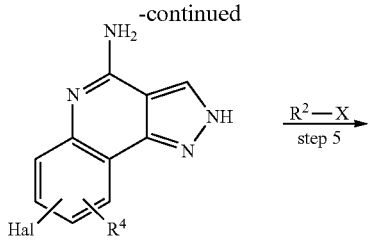

38

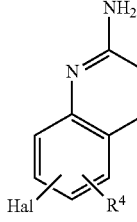

40

Scheme 10

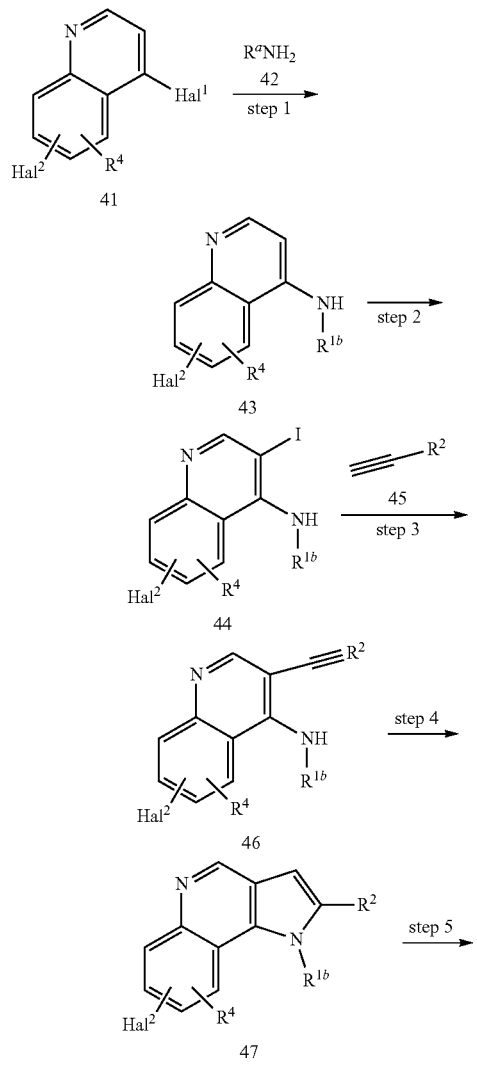

-continued

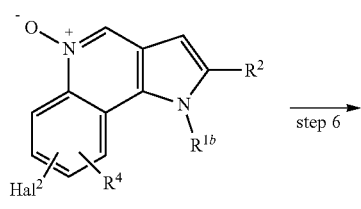

48

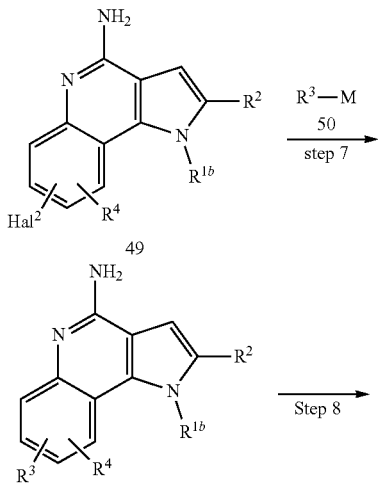

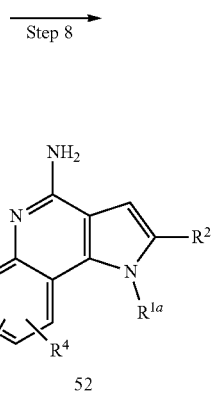

52

Compound 52 may be prepared by a synthetic sequence outlined in Scheme 10. In Scheme 10, treatment of quinoline 41, where the Hal$^1$ group is a halide such as bromide, with a substituted amine 42, where R$^{1b}$ is H, a protecting group such as PMB, or Ria provides compound 43. Treatment of compound 43 with an iodinating reagent such as NIS, provides compound 44, which can be coupled with an appropriately substituted alkyne 45 by the action of a suitable catalyst such as Pd(Ph$_3$)$_2$Cl$_2$ and CuI to provide compound 46. The cyclization of compound 46 may be accomplished by the action of a base such as NaOH to give compound 47. Conversion to compound 48 may be accomplished by treating compound 47 with a suitable oxidant, such as m-CPBA. Treatment of compound 48 with a reagent, such as tosyl chloride, and an amine, such as ammonia, provides compound 49. Coupling between compound 49 and a coupling reagent 50 by the action of a suitable catalyst affords compound 51. For example, this step may be accomplished by treating compound 49 with a suitable boronic ester, such as 3-(tetramethyl-1,3,2-dioxaborolan-2-yl)-1H-pyrazole, in the presence of a catalyst such as Pd(dppf)Cl$_2$ to give compound 51. Alternatively, this step may be accomplished by treating compound 49 with a suitable heterocycle, such as pyrazole, in the presence of a copper catalyst, such as copper(I) iodide, and a ligand, such as N,N'-dimethylethylenediamine to give compound 51. In the last step of scheme 10, compound 52 can be prepared by deprotection of compound 51 with a suitable reagent such as TFA.

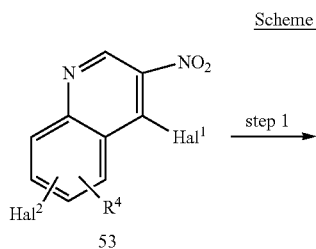

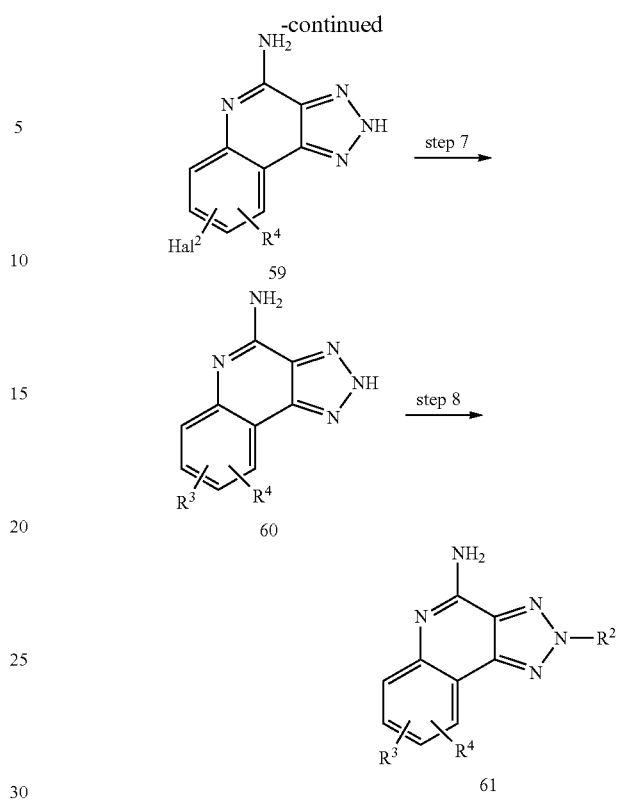

Compound 61 may be prepared by a synthetic sequence outlined in Scheme 11. In Scheme 11, treatment of quinoline 53, where $Hal^1$ group is a halide such as chloride, with an appropriately substituted hydrazine, such as (4-methoxybenzyl)hydrazine, provides compound 54. Treatment of compound 54 with a suitable reagent, such as $PCl_3$ in a suitable solvent such as toluene, provides compound 55. Conversion to compound 56 may be accomplished by treating compound 55 with a suitable oxidant, such as MTO. Compound 56 can then be further converted to compound 57 by a suitable reagent such as $POCl_3$. Treatment of compound 57 with an amine, such as ammonia, provides compound 58. Deprotection of compound 58 may be accomplished by the action of an acid, such as TFA, to provide compound 59. Coupling between compound 59 and a suitable coupling reagent by the action of a suitable catalyst affords compound 60. For example, this step may be accomplished by treating compound 59 with a suitable boronic ester, such as 3-(tetramethyl-1,3,2-dioxaborolan-2-yl)-1H-pyrazole, in the presence of a catalyst such as $Pd(dppf)Cl_2$ to give compound 60. Compound 61 can be prepared by treating compound 60 with an appropriately functionalized alkylating reagent ($R^2$—X), where X is a leaving group such as a halide, in the presence of a base such as potassium carbonate Optionally, if $R^2$ or $R^3$ contains a protecting group, it may be removed at this stage using suitable conditions. For example, if $R^3$-M was 1-(tetrahydro-2H-pyran-2-yl)-5-(4,4,5,5-tetramethyl-1,3,2-dioxaborolan-2-yl)-1H-pyrazole, the tetrahydropyran group can be removed by treatment with a reagent such as TFA.

EXAMPLES

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

Example 1. Preparation of 3-[4-amino-7-(1H-pyrazol-3-yl)-2H-pyrazolo[3,4-c]quinolin-2-yl]propan-1-ol

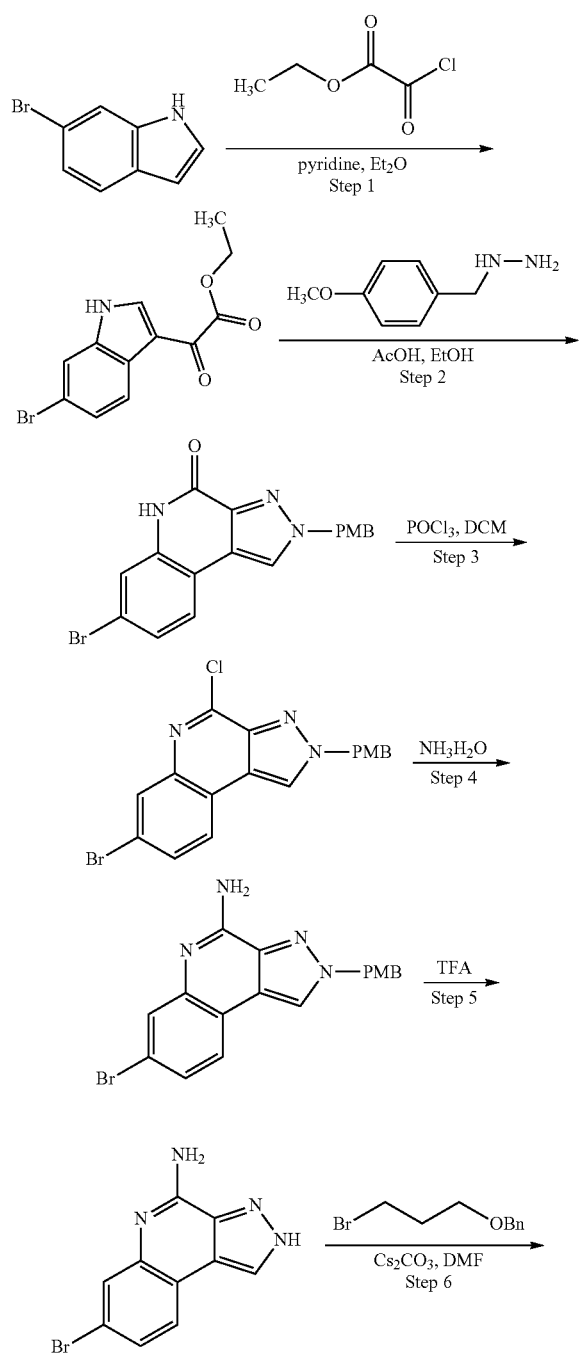

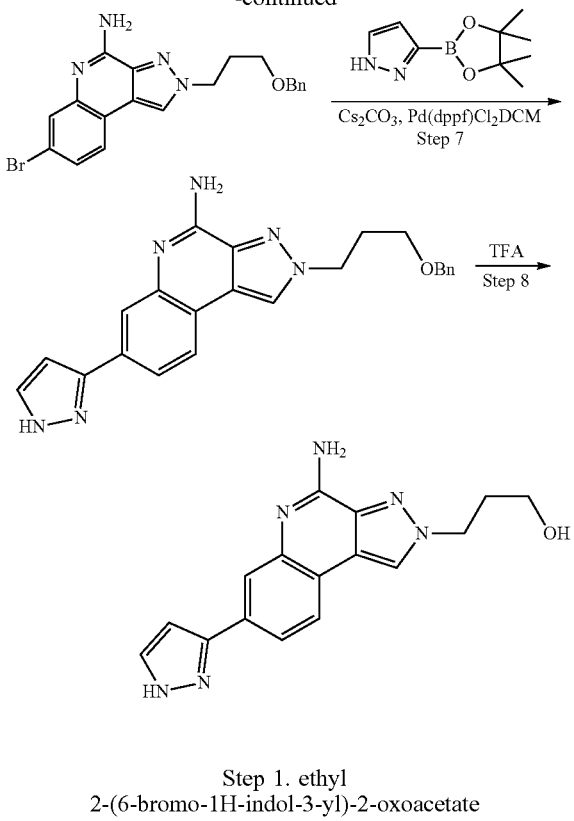

Step 1. ethyl 2-(6-bromo-1H-indol-3-yl)-2-oxoacetate

Into a 150-mL round-bottom flask was placed 6-bromo-1H-indole (1.15 g, 5.89 mmol, 1.00 equiv) in Et$_2$O (30 mL). Then ethyl 2-chloro-2-oxoacetate (922 mg, 6.78 mmol, 1.15 equiv) and pyridine (3 mL) were added. The resulting solution was stirred at rt overnight. The reaction was then quenched by the addition of water. The resulting solution was extracted with ethyl acetate and the combined organic layers were concentrated in vacuo. The residue was purified on a silica gel column eluting with ethyl acetate/petroleum ether (1:3) to provide ethyl 2-(6-bromo-1H-indol-3-yl)-2-oxoacetate (900 mg, 60%) as a solid. LC-MS m/z 296.1 [M+H]$^+$.

Step 2. 7-bromo-2-[(4-methoxyphenyl)methyl]-2H, 4H,5H-pyrazolo[3,4-c]quinolin-4-one Into a 250-mL round-bottom flask was placed a solution of ethyl 2-(6-bromo-1H-indol-3-yl)-2-oxoacetate (1.7 g, 5.74 mmol, 1.00 equiv) and [(4-methoxyphenyl)methyl] hydrazine (1.007 g, 6.62 mmol, 1.15 equiv) in ethanol (25 mL) and acetic acid (3 mL). The resulting solution was stirred overnight at 80° C. The reaction was then quenched by the addition of water. The resulting solution was extracted with ethyl acetate and the organic layers combined. The solution was dried over anhydrous sodium sulfate and concentrated under vacuum. The residue was purified on a silica gel column with ethyl acetate/petroleum ether (4:1) to provide 7-bromo-2-[(4-methoxyphenyl)methyl]-2H,4H, 5H-pyrazolo[3,4-c]quinolin-4-one (1.5 g, 68%) as a solid. LC-MS m/z 384.1 [M+H]$^+$.

Step 3. 7-bromo-4-chloro-2-[(4-methoxyphenyl) methyl]-2H-pyrazolo[3,4-c]quinoline Into a 250-mL round-bottom flask, was placed a solution of 7-bromo-2-[(4-methoxyphenyl)methyl]-2H,4H,5H-pyrazolo[3,4-c]quinolin-4-one (1.3 g, 3.38 mmol, 1.00 equiv) in dichloromethane (10 mL). To the solution were added DMF (0.5 mL) and POCl₃ (1.031 g, 6.72 mmol, 2.00 equiv). The resulting solution was stirred for 6 h at 25° C. The reaction was then quenched by the addition of aq. K₂HPO₄. The resulting solution was extracted with dichloromethane and the combined organic layers were dried over anhydrous sodium sulfate and concentrated in vacuo to give 7-bromo-4-chloro-2-[(4-methoxyphenyl)methyl]-2H-pyrazolo[3,4-c]quinoline (1.17 g, 86%) of as an off-white solid. LC-MS m/z 402.3 [M+H]⁺.

Step 4. 7-bromo-2-[(4-methoxyphenyl)methyl]-2H, 6H,7H-pyrazolo[3,4-c]quinolin-4-amine Into a 50-mL sealed tube, was placed a solution of 7-bromo-4-chloro-2-[(4-methoxyphenyl)methyl]-2H-pyrazolo[3,4-c]quinoline (180 mg, 0.45 mmol, 1.00 equiv) and ammonia (3 mL, 5.00 equiv) in dioxane (3 mL). The resulting solution was stirred overnight at 80° C. The reaction was then quenched by the addition of water. The resulting solution was extracted with dichloromethane:CH₃OH (5:1) and the combined organic layers were concentrated in vacuo. The residue was purified on a silica gel column with dichloromethane/methanol (10:1) to give 7-bromo-2-[(4-methoxyphenyl)methyl]-2H,6H,7H-pyrazolo[3,4-c]quinolin-4-amine (140 mg, 81%) as a solid. LC-MS m/z 383.2 [M+H]⁺.

Step 5. 7-bromo-2H-pyrazolo[3,4-c]quinolin-4-amine

Into a 30-mL sealed tube was placed a solution of 7-bromo-2-[(4-methoxyphenyl)methyl]-2H,6H,7H-pyrazolo[3,4-c]quinolin-4-amine (400 mg, 1.04 mmol, 1.00 equiv) in trifluoroacetic acid (5 mL). The resulting solution was stirred overnight at 80° C. The resulting mixture was concentrated in vacuo. The residue was purified on a silica gel column with dichloromethane/methanol (12:1) to give 7-bromo-2H-pyrazolo[3,4-c]quinolin-4-amine (250 mg, 92%) as an off-white solid. LC-MS m/z 263.1 [M+H]⁺.

Step 6. 2-[3-(benzyloxy)propyl]-7-bromo-2H-pyrazolo[3,4-c]quinolin-4-amine

Into a 100-mL sealed tube was placed a solution of 7-bromo-2H-pyrazolo[3,4-c]quinolin-4-amine (688 mg, 2.62 mmol, 1.00 equiv) in DMF (8 mL). To the solution were added Cs₂CO₃ (1.029 g, 3.16 mmol, 1.20 equiv) and [(3-bromopropoxy)methyl]benzene (624.24 mg, 2.72 mmol, 1.10 equiv). The resulting solution was stirred overnight at 25° C. The reaction was then quenched by the addition of water. The resulting solution was extracted with dichloromethane:CH₃OH (5:1) and the combined organic layers were dried over anhydrous sodium sulfate and concentrated in vacuo. The residue was purified on a silica gel column with dichloromethane/methanol (20:1) to give 2-[3-(benzyloxy) propyl]-7-bromo-2H-pyrazolo[3,4-c]quinolin-4-amine (500 mg, 46%) as a dark red solid. LC-MS m/z 411.3 [M+H]t.

Step 7. 2-[3-(benzyloxy)propyl]-7-(1H-pyrazol-3-yl)-[1,3]oxazolo[5,4-c]quinolin-4-amine Into a 50-mL sealed tube was placed a solution of 2-[3-(benzyloxy)propyl]-7-bromo-[1,3]oxazolo[5,4-c]quinolin-4-amine (500 mg, 1.21 mmol, 1.00 equiv), 3-(tetram-ethyl-1,3,2-dioxaborolan-2-yl)-1H-pyrazole (472 mg, 2.43 mmol, 2.00 equiv) and Cs₂CO₃ (1.193 mg, 3.00 equiv) in dioxane/water (10:1, 11 mL). To the solution was added Pd(dppf)Cl₂DCM (199.3 mg, 0.20 equiv) under nitrogen. The resulting solution was stirred overnight at 100° C. The reaction was then quenched by the addition of water. The resulting solution was extracted with dichloromethane:CH₃OH (5:1) and the organic layers combined. The solution was dried over anhydrous sodium sulfate and concentrated under vacuum. The residue was purified on a silica gel column with dichloromethane/methanol (15:1) to give 2-[3-(benzyloxy)propyl]-7-(1H-pyrazol-3-yl)-[1,3]oxazolo[5,4-c]quinolin-4-amine (300 mg, 62%) of as a solid. LC-MS m/z 399.2 [M+H]⁺.

Step 8. 3-[4-amino-7-(1H-pyrazol-3-yl)-2H-pyrazolo[3,4-c]quinolin-2-yl]propan-1-ol Into a 50-mL sealed tube was placed a solution of 2-[3-(benzyloxy)propyl]-7-(1H-pyrazol-3-yl)-2H-pyrazolo[3,4-c]quinolin-4-amine (100 mg, 0.25 mmol, 1.00 equiv) in trifluoroacetic acid (5 mL). The resulting solution was stirred overnight at 70° C. The reaction was then quenched by the addition of water. The resulting mixture was concentrated in vacuo. The crude product was purified by Prep-HPLC with the following conditions: Column, XBridge Shield RP18 OBD Column, 19×250 mm, 10 um; mobile phase, Water (10 mM NH₄HCO₃) and ACN (20.0% ACN up to 55.0% in 9 min); Detector, UV 254/210 nm. This provided 3-[4-amino-7-(1H-pyrazol-3-yl)-2H-pyrazolo[3,4-c]quinolin-2-yl]propan-1-ol (11.6 mg, 15%) as a white solid. ¹H NMR (400 MHz, CD₃OD-d₄) δ 8.55 (s, 1H), 7.97-7.92 (m, 2H), 7.68 (br s, 2H), 6.72 (s, 1H), 4.60 (t, J=6.8 Hz, 2H), 3.60 (t, J=6.4 Hz, 2H), 2.26-2.21 (m, 2H). LC-MS m/z 309.1 [M+H]⁺.

Example 2. Preparation of 2-(3-phenoxypropyl)-7-(1H-pyrazol-3-yl)-2H-pyrazolo[3,4-c]quinolin-4-amine

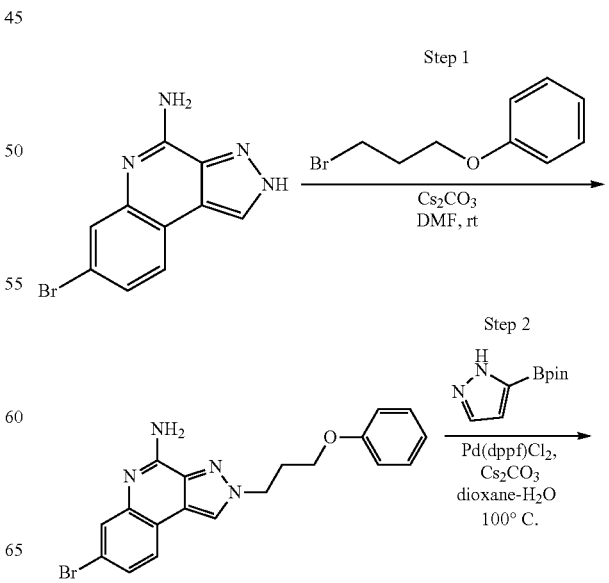

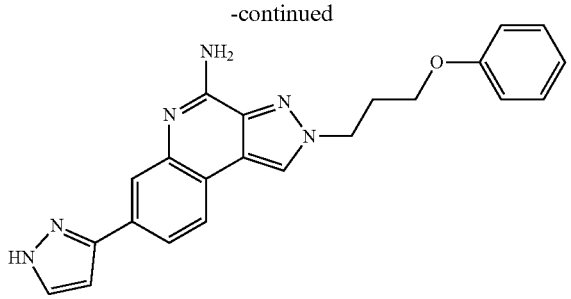

Step 1. 7-bromo-2-(3-phenoxypropyl)-2H-pyrazolo[3,4-c]quinolin-4-amine

To a rt solution of 7-bromo-2H-pyrazolo[3,4-c]quinolin-4-amine (16.9 mg, 0.064 mmol) in DMF (214 µl) was added cesium carbonate (25.1 mg, 0.077 mmol), followed by (3-bromopropoxy)benzene (15.2 mg, 0.071 mmol). The reaction was stirred at rt for 3 h. The reaction was diluted with EtOAc (20 mL), washed with H$_2$O (20 mL) and sat. aq. NaCl (20 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide 7-bromo-2-(3-phenoxypropyl)-2H-pyrazolo[3,4-c]quinolin-4-amine (17.1 mg, 67%). LC-MS m/z 397/399 [M+H]$^+$.

Step 2. 2-(3-phenoxypropyl)-7-(1H-pyrazol-3-yl)-2H-pyrazolo[3,4-c]quinolin-4-amine A rt mixture of 7-bromo-2-(3-phenoxypropyl)-2H-pyrazolo[3,4-c]quinolin-4-amine (17.1 mg, 0.043 mmol), 3-(4,4,5,5-tetramethyl-1,3,2-dioxaborolan-2-yl)-1H-pyrazole (16.7 mg, 0.086 mmol), and cesium carbonate (42.1 mg, 0.129 mmol) in a mixture of dioxane (387 µl) and H$_2$O (43.0 µl) was sparged with N$_2$ for 5 min, then [1,1'-bis(diphenylphosphino)ferrocene]dichloropalladium(II) (6.3 mg, 8.6 µmol) was added. The reaction was sealed and stirred at 100° C. for 21 h. The reaction was cooled to rt, diluted with EtOAc (20 mL), washed with H$_2$O (20 mL) and sat. aq. NaCl (20 mL), dried over Na$_2$SO$_4$, filtered, and concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 16% B, 16-56% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide to provide 2-(3-phenoxypropyl)-7-(1H-pyrazol-3-yl)-2H-pyrazolo[3,4-c]quinolin-4-amine (3.6 mg, 22%). $^1$H NMR (500 MHz, DMSO-d$_6$) δ 8.71-8.66 (m, 1H), 7.92-7.88 (m, 2H), 7.66 (s, 1H), 7.61 (dd, J=8.0, 1.5 Hz, 1H), 7.29-7.23 (m, 2H), 6.94-6.90 (m, 3H), 6.70 (d, J=2.1 Hz, 1H), 6.66-6.42 (m, 2H), 4.62 (t, J=7.0 Hz, 2H), 4.06-4.02 (m, 2H), 2.41 (quin, J=6.4 Hz, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 385.3 [M+H]$^+$; RT: 1.39 min.

Examples 3 and 4. Preparation of 7-(1H-pyrazol-3-yl)-2-[3-(pyridin-2-yloxy)propyl]-2H-pyrazolo[3,4-c]quinolin-4-amine and 1-{3-[4-amino-7-(1H-pyrazol-3-yl)-2H-pyrazolo[3,4-c]quinolin-2-yl]propyl}-1,2-dihydropyridin-2-one

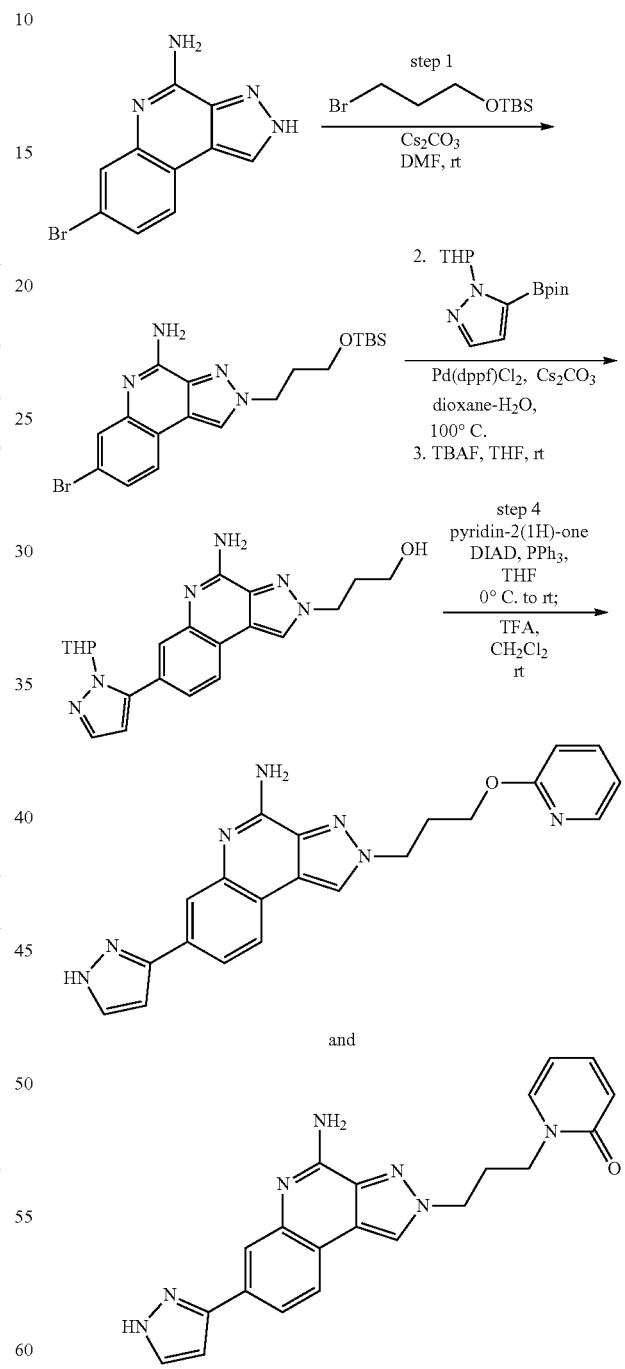

Step 1. 7-bromo-2-(3-((tert-butyldimethylsilyl)oxy)propyl)-2H-pyrazolo[3,4-c]quinolin-4-amine To a rt solution of 7-bromo-2H-pyrazolo[3,4-c]quinolin-4-amine, TFA (240 mg, 0.636 mmol) in DMF (2121 µl) was added cesium carbonate (622 mg, 1.91 mmol) followed by (3-bromopropoxy)(tert-butyl)dimethylsilane (162 µl, 0.700 mmol). The suspension was stirred at rt for 16 h. The reaction was diluted with EtOAc (50 mL) and H$_2$O (50 mL). The layers were separated and the aqueous layer was extracted with EtOAc (50 mL). The combined organic layers were washed with sat. aq. NaCl (50 mL), dried over Na$_2$SO$_4$, filtered, and concentrated in vacuo. The crude material was purified by flash chromatography (24 g silica gel; linear gradient 0-10% MeOH—CH$_2$Cl$_2$) to provide 7-bromo-2-(3-((tert-butyldimethylsilyl)oxy)propyl)-2H-pyrazolo[3,4-c]quinolin-4-amine (214 mg, 77%) as a white solid, mixed with ~5% of the regioisomeric product. 15 $^1$H NMR (400 MHz, DMSO-d$_6$) δ 8.73 (s, 1H), 7.85 (d, J=8.4 Hz, 1H), 7.58 (d, J=2.0 Hz, 1H), 7.31 (dd, J=8.4, 2.0 Hz, 1H), 6.96 (br s, 2H), 4.49 (t, J=7.1 Hz, 2H), 3.63 (t, J=6.0 Hz, 2H), 2.14 (quin, J=6.6 Hz, 2H), 0.86 (s, 9H), 0.02 (s, 6H); LC-MS m/z 435 [M+H]$^+$.

Step 2. 2-(3-((tert-butyldimethylsilyl)oxy)propyl)-7-(1-(tetrahydro-2H-pyran-2-yl)-1H-pyrazol-5-yl)-2H-pyrazolo[3,4-c]quinolin-4-amine A mixture of 7-bromo-2-(3-((tert-butyldimethylsilyl)oxy) propyl)-2H-pyrazolo[3,4-c]quinolin-4-amine (214 mg, 0.491 mmol), 1-(tetrahydro-2H-pyran-2-yl)-5-(4,4,5,5-tetramethyl-1,3,2-dioxaborolan-2-yl)-1H-pyrazole (205 mg, 0.737 mmol), and cesium carbonate (480 mg, 1.474 mmol) was evacuated and back-filled with N$_2$, then 1,4-dioxane (4423 µl) and H$_2$O (491 µl) were added. The resulting mixture was sparged with N$_2$ for 10 min, then [1,1'-bis (diphenylphosphino)ferrocene]dichloropalladium(II) (17.98 mg, 0.025 mmol) was added. The mixture was sparged with N$_2$ for 1 min, then it was sealed and stirred at 100° C. for 30 min. The reaction was cooled to rt, diluted with EtOAc (50 mL), washed with H$_2$O (50 mL) and sat. aq. NaCl (50 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide 2-(3-((tert-butyldimethylsilyl)oxy)propyl)-7-(1-(tetrahydro-2H-pyran-2-yl)-1H-pyrazol-5-yl)-2H-pyrazolo[3,4-c]quinolin-4-amine (242 mg, 97%) as a brown foam. $^1$H NMR (400 MHz, DMSO-d$_6$) δ 8.76 (s, 1H), 8.01 (d, J=8.0 Hz, 1H), 7.62 (d, J=1.7 Hz, 1H), 7.58 (d, J=1.7 Hz, 1H), 7.32 (dd, J=8.0, 1.7 Hz, 1H), 6.86 (br s, 2H), 6.48 (d, J=1.7 Hz, 1H), 5.30 (dd, J=9.9, 2.0 Hz, 1H), 4.51 (t, J=7.1 Hz, 2H), 4.09-4.00 (m, 1H), 3.64 (t, J=6.0 Hz, 2H), 3.62-3.53 (m, 1H), 2.48-2.37 (m, 1H), 2.21-2.12 (m, 2H), 2.00-1.90 (m, 1H), 1.79 (br d, J=12.5 Hz, 1H), 1.63-1.48 (m, 3H), 0.88 (s, 9H), 0.06-0.01 (m, 6H); LC-MS m/z 507 [M+H]$^+$.

Step 3. 3-(4-amino-7-(1-(tetrahydro-2H-pyran-2-yl)-1H-pyrazol-5-yl)-2H-pyrazolo[3,4-c]quinolin-2-yl)propan-1-ol To a rt solution of 2-(3-((tert-butyldimethylsilyl)oxy)propyl)-7-(1-(tetrahydro-2H-pyran-2-yl)-1H-pyrazol-5-yl)-2H-pyrazolo[3,4-c]quinolin-4-amine (182 mg, 0.359 mmol) in THF (1796 µl) was added tetrabutylammonium fluoride (1 M solution in THF) (431 µl, 0.431 mmol). The reaction was stirred at rt for 1 h. The reaction was concentrated in vacuo. The crude material was purified by flash chromatography (24 g silica gel; linear gradient 0-100% EtOAc—CH$_2$Cl$_2$ then 0-10% MeOH—CH$_2$Cl$_2$) to provide 3-(4-amino-7-(1-(tetrahydro-2H-pyran-2-yl)-1H-pyrazol-5-yl)-2H-pyrazolo [3,4-c]quinolin-2-yl)propan-1-ol (128 mg, 91%). $^1$H NMR (400 MHz, DMSO-d$_6$) δ 8.78 (s, 1H), 8.01 (d, J=8.0 Hz, 1H), 7.62 (d, J=1.6 Hz, 1H), 7.58 (d, J=1.7 Hz, 1H), 7.32 (dd, J=8.0, 1.8 Hz, 1H), 6.90 (br s, 2H), 6.48 (d, J=1.8 Hz, 1H), 5.30 (dd, J=10.0, 2.0 Hz, 1H), 4.69 (t, J=5.0 Hz, 1H), 4.52 (t, J=7.1 Hz, 2H), 4.07-4.00 (m, 1H), 3.62-3.54 (m, 1H), 3.45 (q, J=6.0 Hz, 2H), 2.47-2.37 (m, 1H), 2.10 (quin, J=6.6 Hz, 2H), 1.94 (br s, 1H), 1.79 (br d, J=12.6 Hz, 1H), 1.64-1.47 (m, 3H); LC-MS m/z 393 [M+H]$^+$.

Step 4. 7-(1H-pyrazol-3-yl)-2-[3-(pyridin-2-yloxy) propyl]-2H-pyrazolo[3,4-c]quinolin-4-amine and 1-{3-[4-amino-7-(1H-pyrazol-3-yl)-2H-pyrazolo[3,4-c]quinolin-2-yl]propyl}-1,2-dihydropyridin-2-one To a 0° C. solution of 3-(4-amino-7-(1-(tetrahydro-2H-pyran-2-yl)-1H-pyrazol-5-yl)-2H-pyrazolo[3,4-c]quinolin-2-yl)propan-1-ol (40 mg, 0.102 mmol), pyridin-2(1H)-one (10.7 mg, 0.112 mmol), and triphenylphosphine (32.1 mg, 0.122 mmol) in THF (1019 µl) was added diisopropyl azodicarboxylate (24.1 µl, 0.122 mmol), dropwise. The reaction was stirred at rt for 1 h. The reaction was concentrated in vacuo.

The crude material was dissolved in CH$_2$Cl$_2$ (250 µL) and TFA (250 µL) was added. The reaction was stirred at rt for 1 h. The reaction was concentrated in vacuo. The crude material was taken up in CH$_2$Cl$_2$ and concentrated again. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 3% B, 3-43% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide 7-(1H-pyrazol-3-yl)-2-(3-(pyridin-2-yloxy)propyl)-2H-pyrazolo[3,4-c]quinolin-4-amine, TFA (28.5 mg, 56%) and 1-(3-(4-amino-7-(1H-pyrazol-3-yl)-2H-pyrazolo[3,4-c]quinolin-2-yl)propyl)pyridin-2(1H)-one, TFA (11.6 mg, 23%).

Characterization data for 7-(1H-pyrazol-3-yl)-2-(3-(pyridin-2-yloxy)propyl)-2H-pyrazolo[3,4-c]quinolin-4-amine, TFA: $^1$H NMR (500 MHz, DMSO-d$_6$) δ 9.03 (s, 1H), 8.86 (s, 1H), 8.15-8.07 (m, 2H), 7.90 (br d, J=7.7 Hz, 1H), 7.87-7.78 (m, 1H), 7.72-7.65 (m, 1H), 6.99-6.92 (m, 1H), 6.79 (s, 1H), 6.75 (d, J=8.3 Hz, 1H), 4.70 (t, J=6.7 Hz, 2H), 4.33 (t, J=6.1 Hz, 2H), 2.49-2.42 (m, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 386.3 [M+H]$^+$; RT: 1.18 min.

Characterization data for 1-(3-(4-amino-7-(1H-pyrazol-3-yl)-2H-pyrazolo[3,4-c]quinolin-2-yl)propyl)pyridin-2(1H)-one, TFA: 0.78 (br s, 1H), 6.39 (d, J=9.1 Hz, 1H), 6.24 (t, J=6.2 Hz, 1H), 4.55 (br t, J=6.9 Hz, 2H), 4.01 (br t, J=6.9 Hz, 2H), 2.40-2.32 (m, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 386.3 [M+H]$^+$; RT 1.03 min.

Examples 5 to 9 were prepared according to synthetic procedures similar to those described for Example 3 from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex. No. | Structure | LC/MS [M + H]+ | RT (min) | 1H NMR (500 MHZ, DMSO-d6) |
|---|---|---|---|---|
| 5 | 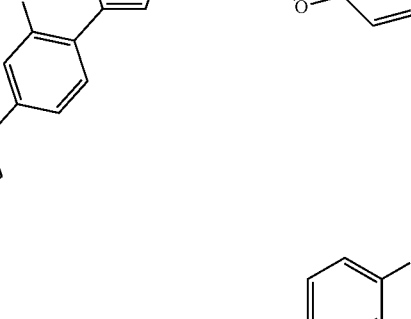 | 403.1 | 1.55 | δ 13.23-12.68 (m, 1H), 9.46-9.07 (m, 2H), 9.01 (s, 1H), 8.11 (br s, 1H), 8.09 (d, J = 8.2 Hz, 1H), 7.89 (br d, J = 8.2 Hz, 1H), 7.79 (br s, 1H), 7.29 (q, J = 8.1 Hz, 1H), 6.78-6.72 (m, 4H), 4.70 (t, J = 6.9 Hz, 2H), 4.12 (t, J = 6.0 Hz, 2H), 2.49-2.43 (m, 2H) |
| 6 | 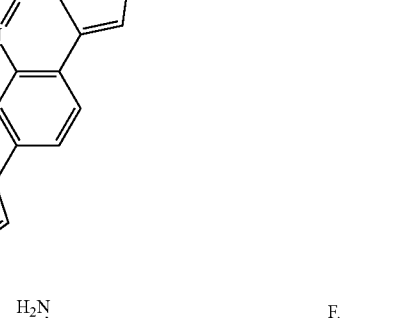 | 403.3 | 1.67 | δ 13.65-12.80 (m, 1H), 9.47-9.17 (m, 2H), 9.01 (s, 1H), 8.12 (br s, 1H), 8.09 (d, J = 8.2 Hz, 1H), 7.89 (br d, J = 8.1 Hz, 1H), 7.80 (br s, 1H), 7.12-7.05 (m, 2H), 6.95-6.91 (m, 2H), 6.77 (d, J = 2.1 Hz, 1H), 4.70 (t, J = 6.9 Hz, 2H), 4.06 (t, J = 6.0 Hz, 2H), 2.45 (quin, J = 6.5 Hz, 2H) |
| 7 | 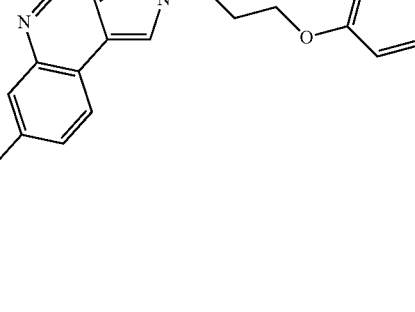 | 403.1 | 1.60 | δ 13.77-12.92 (m, 1H), 9.86-9.17 (m, 2H), 9.05 (s, 1H), 8.16-8.12 (m, 1H), 8.10 (br d, J = 8.3 Hz, 1H), 7.90 (br d, J = 7.7 Hz, 1H), 7.86-7.79 (m, 1H), 7.22-7.14 (m, 2H), 7.13-7.08 (m, 1H), 6.97-6.91 (m, 1H), 6.78 (s, 1H), 4.72 (br t, J = 6.7 Hz, 2H), 4.16 (br t, J = 5.6 Hz, 2H), 2.49-2.45 (m, 2H) |
| 8 | 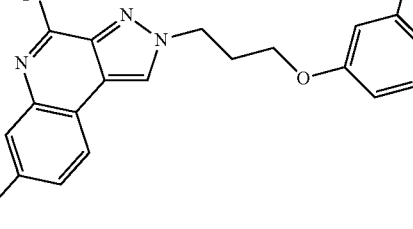 | 398.9 | 1.74 | δ 13.12-12.96 (m, 1H), 9.01 (s, 1H), 8.16-8.10 (m, 1H), 8.08 (br d, J=8.0 Hz, 1H), 7.91-7.78 (m, 2H), 7.16-7.11 (m, 1H), 6.78 (br s, 1H), 6.74 (br d, J = 7.2 Hz, 1H), 6.69 (s, 2H), 4.69 (br t, J = 6.6 Hz, 2H), 4.04 (br t, J = 5.9 Hz, 2H), 2.43 (br t, J = 6.1 Hz, 2H), 2.23 (s, 3H) |

| Ex. No. | Structure | LC/MS [M + H]+ | RT (min) | 1H NMR (500 MHZ, DMSO-d6) |
|---|---|---|---|---|
| 9 | 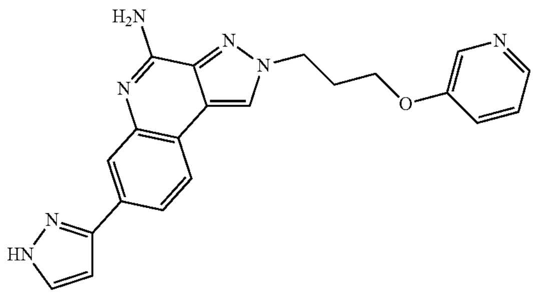 [SMILES: Nc1nc2cc(-c3cc[nH]n3)ccc2c2cn(CCCOc3cccnc3)nc12] | 386.1 | 0.89 | δ 8.75 (s, 1H), 8.28 (d, J = 2.5 Hz, 1H), 8.16 (d, J = 3.9 Hz, 1H), 7.92-7.88 (m, 2H), 7.69 (br s, 1H), 7.62 (br d, J = 8.0 Hz, 1H), 7.40-7.35 (m, 1H), 7.33-7.29 (m, 1H), 6.81-6.68 (m, 3H), 4.63 (br t, J = 7.0 Hz, 2H), 4.11 (t, J = 5.9 Hz, 2H), 2.46-2.41 (m, 2H) |

Example 10. Preparation of 2-(2-ethoxyethyl)-7-(1H-pyrazol-1-yl)-2H-pyrazolo[3,4-c]quinolin-4-amine

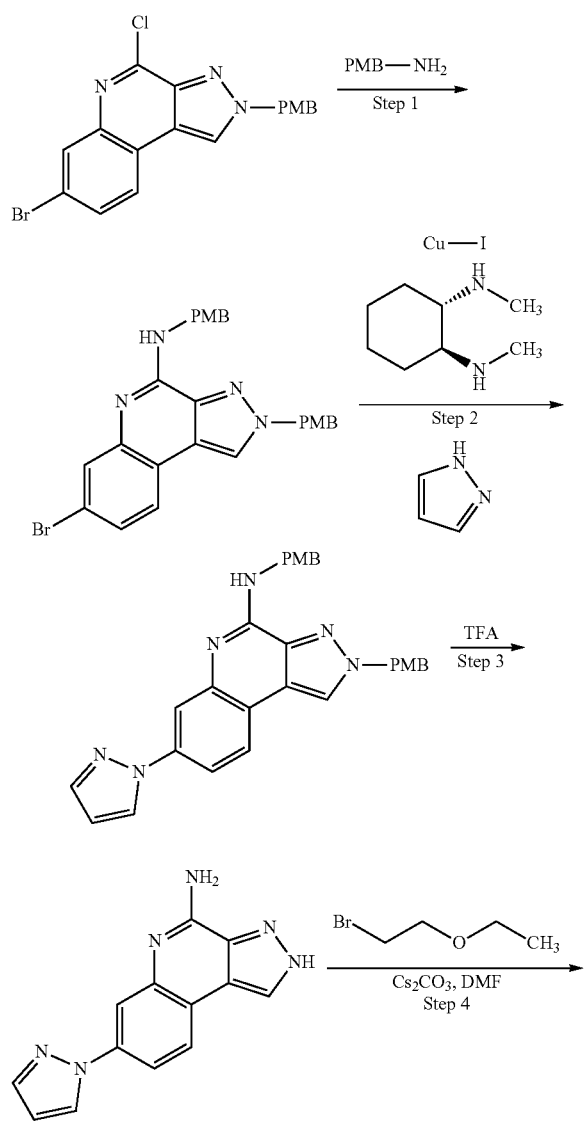

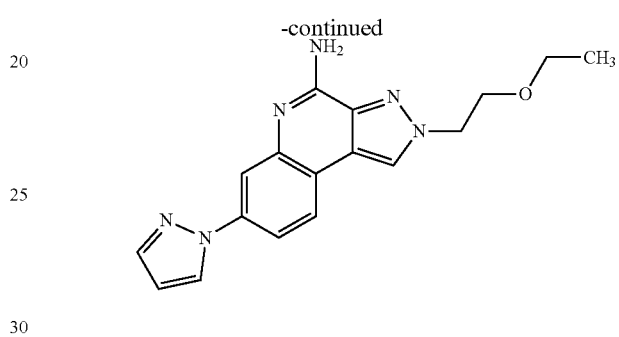

Step 1. 7-bromo-N,2-bis(4-methoxybenzyl)-2H-pyrazolo[3,4-c]quinolin-4-amine

To a rt solution of 7-bromo-4-chloro-2-(4-methoxybenzyl)-2H-pyrazolo[3,4-c]quinoline (2.428 g, 6.03 mmol) in DMSO (20.10 ml) was added (4-methoxyphenyl)methanamine (1.576 ml, 12.06 mmol), followed by N,N-diisopropylethylamine (3.15 ml, 18.09 mmol). The reaction was stirred at 70° C. for 18 h. The reaction was cooled to rt, diluted with EtOAc (500 mL), washed with H$_2$O (2×250 mL) and sat. aq. NaCl (250 mL), dried over Na$_2$SO$_4$, filtered, and concentrated in vacuo to provide a brown oil. The crude material was purified by flash chromatography (40 g silica gel; linear gradient 0-100% EtOAc-hexanes) to provide 7-bromo-N,2-bis(4-methoxybenzyl)-2H-pyrazolo[3,4-c]quinolin-4-amine (2.880 g, 95%) as an off-white foam. 1H NMR (400 MHz, DMSO-d$_6$) δ 8.79 (s, 1H), 7.96 (t, J=6.2 Hz, 1H), 7.85 (d, J=8.3 Hz, 1H), 7.63 (d, J=2.0 Hz, 1H), 7.37 (d, J=8.7 Hz, 2H), 7.32-7.27 (m, 3H), 6.95-6.90 (m, 2H), 6.87-6.82 (m, 2H), 5.58 (s, 2H), 4.66 (d, J=6.0 Hz, 2H), 3.72 (s, 3H), 3.69 (s, 3H); LC-MS m/z 503/505 [M+H]+.

Step 2. N,2-bis(4-methoxybenzyl)-7-(1H-pyrazol-1-yl)-2H-pyrazolo[3,4-c]quinolin-4-amine To a solution of pyrazole (97 mg, 1.43 mmol), 7-bromo-N,2-bis(4-methoxybenzyl)-2H-pyrazolo[3,4-c]quinolin-4-amine (600 mg, 1.19 mmol), copper(I) iodide (11.35 mg, 0.060 mmol), and (1S,2S)—N1,N2-dimethylcyclohexane-1,2-diamine (33.9 mg, 0.238 mmol) in toluene (2.5 mL) was added potassium carbonate (362 mg, 2.62 mmol). The reaction was purged with N$_2$ and stirred at 120° C. for 24 h. The reaction was then cooled to rt, diluted with EtOAc, and filtered through a pad of Celite. The filtrate was concentrated and purified by flash chromatography (40 g silica gel; linear gradient 0-100% EtOAc-Hexane) to provide N,2-bis(4-methoxybenzyl)-7-(1H-pyrazol-1-yl)-2H-pyrazolo[3,4-c]quinolin-4-amine (495 mg, 85%). LC-MS m/z 491.4 [M+H]⁺.

Step 3. 7-(1H-pyrazol-1-yl)-2H-pyrazolo[3,4-c]quinolin-4-amine

To a solution of N,2-bis(4-methoxybenzyl)-7-(1H-pyrazol-1-yl)-2H-pyrazolo[3,4-c]quinolin-4-amine (501 mg, 1.02 mmol) in TFA (3934 µl, 51.1 mmol) was added anisole (1116 µl, 10.2 mmol). The reaction was stirred at 80° C. overnight. The reaction was cooled to rt and concentrated in vacuo. The crude material was triturated with Et₂O, and then filtered to give 7-(1H-pyrazol-1-yl)-2H-pyrazolo[3,4-c]quinolin-4-amine, TFA salt (350 mg, 94%). ¹H NMR (400 MHz, METHANOL-d₄) δ 8.81 (s, 1H), 8.39 (d, J=2.3 Hz, 1H), 8.26 (d, J=8.6 Hz, 1H), 8.11 (d, J=1.9 Hz, 1H), 7.92 (dd, J=8.6, 1.9 Hz, 1H), 7.83 (d, J=1.2 Hz, 1H), 6.63 (d, J=1.8 Hz, 1H); LC-MS m/z 251.1 [M+H]⁺.

Step 4. 2-(2-ethoxyethyl)-7-(1H-pyrazol-1-yl)-2H-pyrazolo[3,4-c]quinolin-4-amine To a solution of 1-bromo-2-ethoxyethane (9.17 mg, 0.060 mmol) and 7-(1H-pyrazol-1-yl)-2H-pyrazolo[3,4-c]quinolin-4-amine (15 mg, 0.060 mmol) in DMF (0.3 mL) was added Cs₂CO₃ (78 mg, 0.240 mmol). The reaction was stirred at rt for 12 h before it was filtered. The crude product was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 6% B, 6-46% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-ethoxyethyl)-7-(1H-pyrazol-1-yl)-2H-pyrazolo[3,4-c]quinolin-4-amine (6.9 mg, 26%). ¹H NMR (500 MHz, DMSO-d₆) δ 8.70 (s, 1H), 8.49 (d, J=2.0 Hz, 1H), 8.03 (d, J=8.4 Hz, 1H), 7.88 (d, J=2.0 Hz, 1H), 7.75 (s, 1H), 7.68 (dd, J=8.4, 2.1 Hz, 1H), 6.54 (s, 1H), 4.60 (t, J=5.3 Hz, 2H), 3.92 (t, J=5.3 Hz, 2H), 3.48 (q, J=6.9 Hz, 2H), 1.08 (t, J=6.9 Hz, 3H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 323.2 [M+H]⁺; RT: 1.03 min.

Examples 11 to 19 were prepared according to the synthetic procedures described for Example 10 from the appropriate starting materials. LC/MS method: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex No. | Structure | LC/MS [M + H]⁺ | RT (min) | ¹H NMR (500 MHZ, DMSO-d₆) |
|---|---|---|---|---|
| 11 | 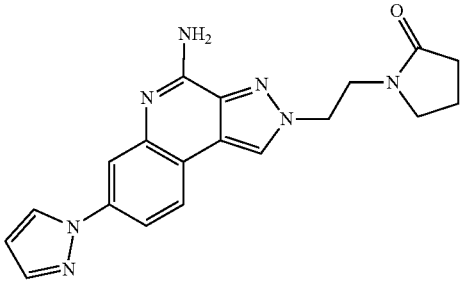 [SMILES: Nc1nc2cc(-n3cccn3)ccc2c2cn(CCN3CCCC3=O)nc12] | 362.2 | 0.85 | δ 8.72 (s, 1H), 8.53 (s, 1H), 7.99 (d, J = 8.5 Hz, 1H), 7.86 (s, 1H), 7.74 (s, 1H), 7.67 (br d, J = 7.3 Hz, 1H), 6.54 (br s, 1H), 4.57 (br t, J = 5.6 Hz, 2H), 3.71 (br t, J = 5.6 Hz, 2H), 3.17 (br d, J = 6.7 Hz, 2H), 2.15 (br t, J = 7.9 Hz, 2H), 1.88-1.80 (m, 2H) |
| 12 | 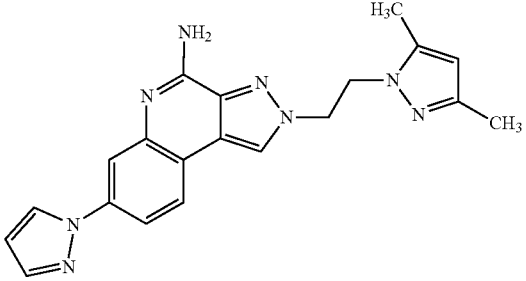 [SMILES: Cc1cc(C)n(CCn2cc3c(n2)c(N)nc2cc(-n4cccn4)ccc23)n1] | 373.0 | 1.18 | δ 8.47 (s, 1H), 8.40 (s, 1H), 7.93 (d, J = 8.4 Hz, 1H), 7.87 (d, J = 1.7 Hz, 1H), 7.74 (s, 1H), 7.65 (dd, J = 8.4, 1.8 Hz, 1H), 6.54 (s, 1H), 5.70 (s, 1H), 4.81 (br t, J = 5.9 Hz, 2H), 4.50 (br t, J = 5.9 Hz, 2H), 2.10 (s, 3H), 1.88 (s, 3H) |

| Ex No. | Structure | LC/MS [M + H]+ | RT (min) | 1H NMR (500 MHZ, DMSO-d6) |
|---|---|---|---|---|
| 13 | 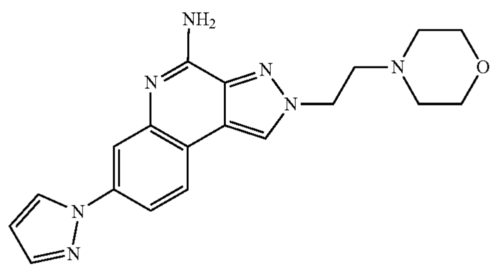 [SMILES: Nc1nc2cc(-n3cccn3)ccc2c2cn(CCN3CCOCC3)nc12] | 364.2 | 1.01 | δ 8.71 (s, 1H), 8.47 (d, J = 2.1 Hz, 1H), 8.01 (d, J = 8.4 Hz, 1H), 7.87 (s, 1H), 7.74 (s, 1H), 7.70-7.63 (m, 1H), 6.54 (s, 1H), 4.57 (t, J = 6.4 Hz, 2H), 3.66-3.46 (m, 4H), 2.91 (t, J = 6.4 Hz, 2H), 2.49-2.43 (m, 4H) |
| 14 | 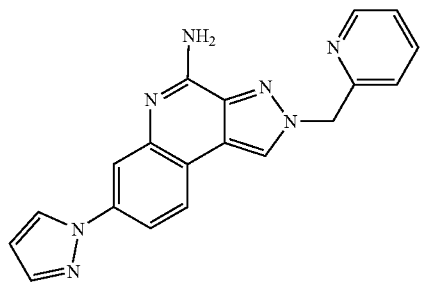 [SMILES: Nc1nc2cc(-n3cccn3)ccc2c2cn(Cc3ccccn3)nc12] | 342.0 | 1.08 | δ 8.83 (s, 1H), 8.56 (br d, J = 4.8 Hz, 1H), 8.48 (s, 1H), 8.04 (d, J = 8.4 Hz, 1H), 7.88 (d, J = 1.6 Hz, 1H), 7.81 (t, J = 7.7 Hz, 1H), 7.74 (s, 1H), 7.67 (dd, J = 8.4, 1.9 Hz, 1H), 7.35 (dd, J = 7.3, 5.0 Hz, 1H), 7.26 (d, J = 7.8 Hz, 1H), 6.54 (s, 1H), 5.79 (s, 2H) |
| 15 | 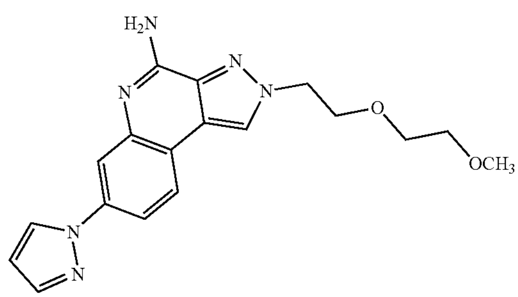 [SMILES: COCCOCCn1cc2c(n1)c(N)nc1cc(-n3cccn3)ccc12] | 353.0 | 1.19 | δ 8.70 (s, 1H), 8.47 (br s, 1H), 8.02 (d, J = 8.4 Hz, 1H), 7.89 (br d, J = 1.8 Hz, 1H), 7.75 (s, 1H), 7.68 (br dd, J = 8.5, 2.0 Hz, 1H), 6.55 (s, 1H), 4.61 (br t, J = 5.2 Hz, 2H), 3.96 (br t, J = 5.1 Hz, 2H), 3.65-3.51 (m, 2H), 3.44-3.35 (m, 2H), 3.20 (s, 3H) |
| 16 | 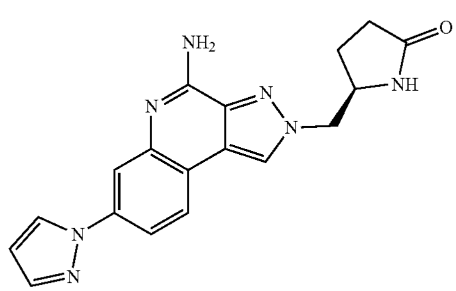 [SMILES: Nc1nc2cc(-n3cccn3)ccc2c2cn(C[C@H]3CCC(=O)N3)nc12] | 348.2 | 0.95 | δ 8.70 (s, 1H), 8.54 (d, J = 2.1 Hz, 1H), 8.01 (d, J = 8.5 Hz, 1H), 7.94-7.86 (m, 2H), 7.76 (s, 1H), 7.70 (dd, J = 8.4, 1.7 Hz, 1H), 6.56 (s, 1H), 4.59-4.48 (m, 1H), 4.48-4.35 (m, 1H), 4.16-3.99 (m, 1H), 2.25-2.02 (m, 3H), 1.97-1.79 (m, 1H) |
| 17 | 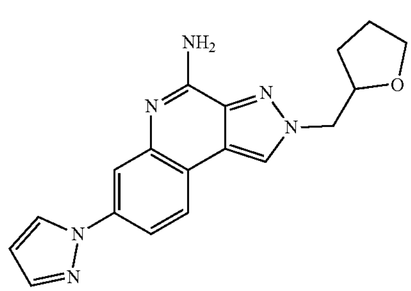 [SMILES: Nc1nc2cc(-n3cccn3)ccc2c2cn(CC3CCCO3)nc12] | 335.2 | 1.24 | δ 8.68 (s, 1H), 8.50 (d, J = 1.5 Hz, 1H), 8.03 (d, J = 8.2 Hz, 1H), 7.86 (s, 1H), 7.75 (s, 1H), 7.66 (br d, J = 7.0 Hz, 1H), 6.55 (s, 1H), 4.59-4.48 (m, 1H), 4.47-4.39 (m, 1H), 4.37-4.25 (m, 1H), 3.78 (br d, J = 7.3 Hz, 2H), 2.01 (br dd, J = 12.1, 6.0 Hz, 1H), 1.89-1.75 (m, 2H), 1.72-1.59 (m, 1H) |

-continued

| Ex No. | Structure | LC/MS [M + H]+ | RT (min) | 1H NMR (500 MHZ, DMSO-d6) |
|---|---|---|---|---|
| 18 | 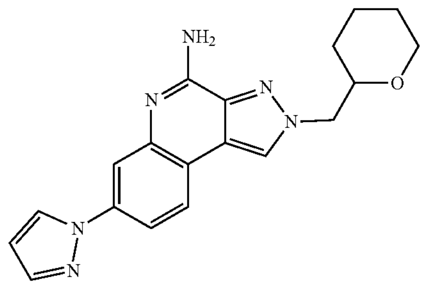 [SMILES: Nc1nc2cc(-n3cccn3)ccc2c2cn(CC3CCCCO3)nc12] | 349.2 | 1.16 | δ 8.67 (s, 1H), 8.53 (d, J = 1.8 Hz, 1H), 8.02 (d, J = 8.2 Hz, 1H), 7.86 (s, 1H), 7.75 (s, 1H), 7.67 (dd, J = 8.4, 1.7 Hz, 1H), 6.55 (s, 1H), 4.58-4.33 (m, 2H), 3.84 (br t, J = 11.7 Hz, 2H), 3.31 (br t, J = 9.3 Hz, 1H), 1.81 (br d, J = 11.0 Hz, 1H), 1.64 (br d, J = 12.5 Hz, 1H), 1.53-1.38 (m, 3H), 1.34-1.18 (m, 1H) |
| 19 | 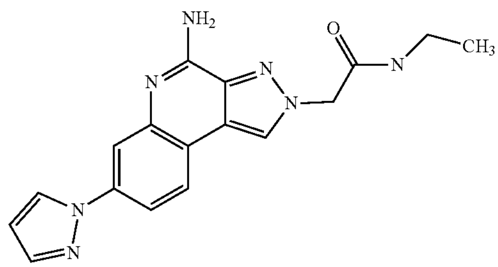 [SMILES: CCNC(=O)Cn1cc2c(n1)c(N)nc1cc(-n3cccn3)ccc12] | 336.3 | 1.03 | δ 8.68 (s, 1H), 8.50 (d, J = 2.3 Hz, 1H), 8.16 (br s, 1H), 8.04 (d, J = 8.4 Hz, 1H), 7.88 (d, J = 2.0 Hz, 1H), 7.75 (s, 1H), 7.68 (dd, J = 8.4, 2.1 Hz, 1H), 6.54 (s, 1H), 5.13 (s, 2H), 3.17 (m, 2H), 1.09 (t, J = 7.2 Hz, 3H) |

Example 20. Preparation of 2-[2-(morpholin-4yl)ethyl]-7-(1H-pyrazol-3-yl)-2H- pyrazolo[3,4-c]quinolin-4-amine

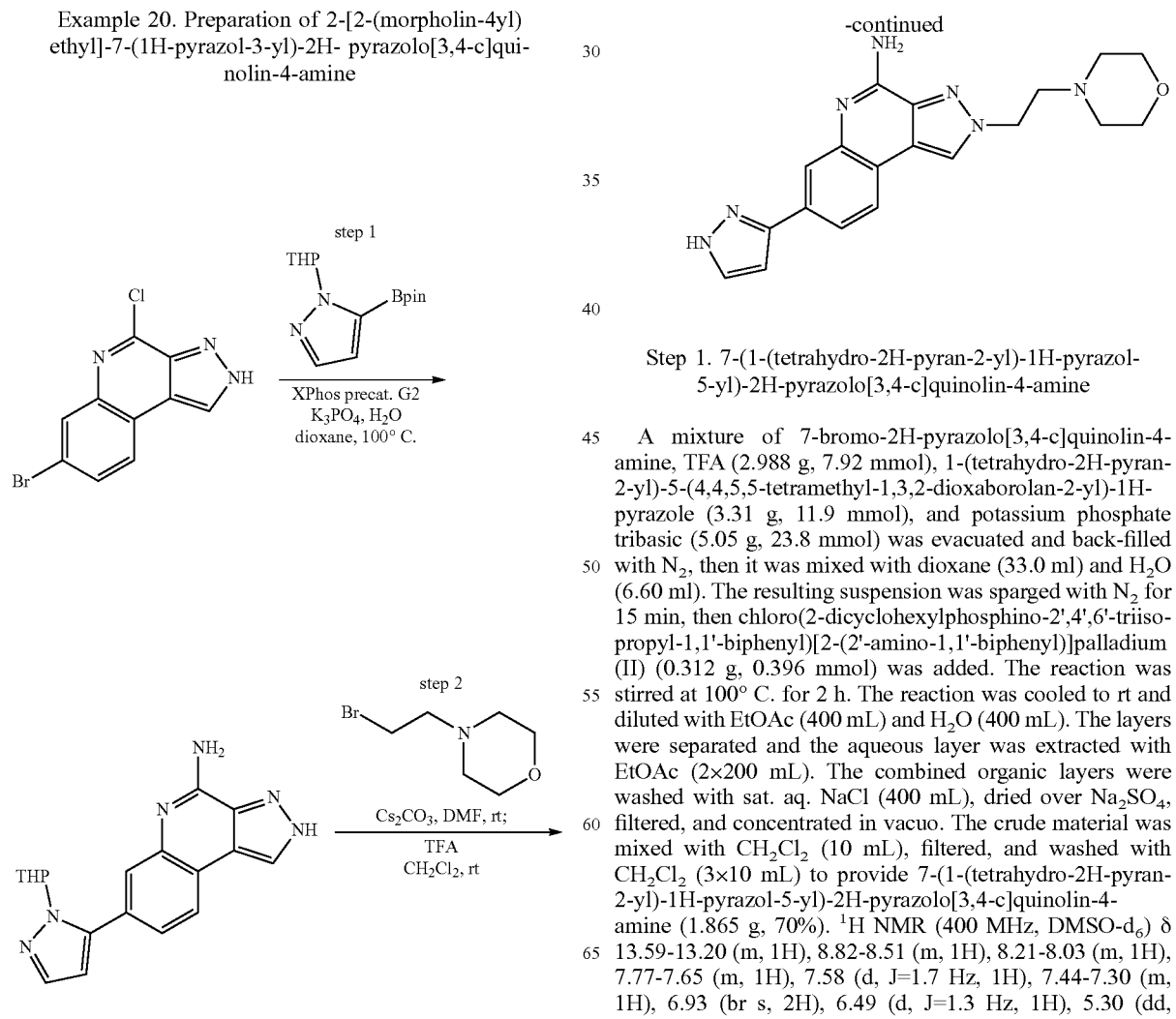

Step 1. 7-(1-(tetrahydro-2H-pyran-2-yl)-1H-pyrazol-5-yl)-2H-pyrazolo[3,4-c]quinolin-4-amine A mixture of 7-bromo-2H-pyrazolo[3,4-c]quinolin-4-amine, TFA (2.988 g, 7.92 mmol), 1-(tetrahydro-2H-pyran-2-yl)-5-(4,4,5,5-tetramethyl-1,3,2-dioxaborolan-2-yl)-1H-pyrazole (3.31 g, 11.9 mmol), and potassium phosphate tribasic (5.05 g, 23.8 mmol) was evacuated and back-filled with N₂, then it was mixed with dioxane (33.0 ml) and H₂O (6.60 ml). The resulting suspension was sparged with N₂ for 15 min, then chloro(2-dicyclohexylphosphino-2',4',6'-triisopropyl-1,1'-biphenyl)[2-(2'-amino-1,1'-biphenyl)]palladium (II) (0.312 g, 0.396 mmol) was added. The reaction was stirred at 100° C. for 2 h. The reaction was cooled to rt and diluted with EtOAc (400 mL) and H₂O (400 mL). The layers were separated and the aqueous layer was extracted with EtOAc (2×200 mL). The combined organic layers were washed with sat. aq. NaCl (400 mL), dried over Na₂SO₄, filtered, and concentrated in vacuo. The crude material was mixed with CH₂Cl₂ (10 mL), filtered, and washed with CH₂Cl₂ (3×10 mL) to provide 7-(1-(tetrahydro-2H-pyran-2-yl)-1H-pyrazol-5-yl)-2H-pyrazolo[3,4-c]quinolin-4-amine (1.865 g, 70%). ¹H NMR (400 MHz, DMSO-d₆) δ 13.59-13.20 (m, 1H), 8.82-8.51 (m, 1H), 8.21-8.03 (m, 1H), 7.77-7.65 (m, 1H), 7.58 (d, J=1.7 Hz, 1H), 7.44-7.30 (m, 1H), 6.93 (br s, 2H), 6.49 (d, J=1.3 Hz, 1H), 5.30 (dd, J=10.0, 2.0 Hz, 1H), 4.08-4.02 (m, 1H), 3.62-3.55 (m, 1H), 2.47-2.37 (m, 1H), 1.97-1.91 (m, 1H), 1.79 (br d, J=13.1 Hz, 1H), 1.62-1.49 (m, 3H); LC-MS m/z 335 [M+H]$^+$.

Step 2. 2-[2-(morpholin-4-yl)ethyl]-7-(1H-pyrazol-3-yl)-2H-pyrazolo[3,4-c]quinolin-4-amine To a rt solution of 7-(1-(tetrahydro-2H-pyran-2-yl)-1H-pyrazol-5-yl)-2H-pyrazolo[3,4-c]quinolin-4-amine (16.3 mg, 0.049 mmol) in DMF (162 µl) was added cesium carbonate (47.6 mg, 0.146 mmol) followed by 4-(2-bromoethyl)morpholine, hydrobromide (14.7 mg, 0.054 mmol). The suspension was stirred at rt for 16 h. The reaction was diluted with H$_2$O (2 mL) and extracted with EtOAc (3×2 mL). The combined organic layers were concentrated.

The crude material was mixed with CH$_2$Cl$_2$ (200 µL) and TFA (200 µL) and stirred at rt for 1.5 h. The reaction was concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-46% B over 20 minutes, then a 4-minute hold at 100% B; Flow Rate: 20 mL/min; Column Temperature: 25° C. Fraction collection was triggered by MS signals. Fractions containing the desired product (the more polar of the two observed regioisomeric products) were combined and dried via centrifugal evaporation to provide 2-(2-morpholinoethyl)-7-(1H-pyrazol-3-yl)-2H-pyrazolo[3,4-c]quinolin-4-amine (10.8 mg, 59%). $^1$H NMR (500 MHz, DMSO-d$_6$) δ 8.73 (s, 1H), 7.93 (d, J=8.0 Hz, 1H), 7.90 (s, 1H), 7.70 (br s, 1H), 7.64 (br d, J=7.4 Hz, 1H), 6.97-6.80 (m, 2H), 6.73 (d, J=1.9 Hz, 1H), 4.56 (t, J=6.3 Hz, 2H), 3.57-3.53 (m, 4H), 2.88 (br t, J=6.5 Hz, 2H), 2.48-2.43 (m, 4H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 363.9 [M+H]$^+$; RT: 0.84 min.

Examples 21 to 28 were prepared according to synthetic procedures similar to those described for Example 20 from the appropriate starting materials. For Example 27, the reaction was stirred at 50° C. for 4 h. For reactions where two regioisomeric peaks were observed by HPLC, the product was typically the major peak, and was the more polar of the two peaks observed under the HPLC conditions used. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex No. | Structure | LC/MS [M + H]$^+$ | RT (min) | $^1$H NMR (500 MHZ, DMSO-d$_6$) |
|---|---|---|---|---|
| 21 | (structure) | 322.2 | 0.61 | δ 9.00 (s, 1H), 8.14-8.08 (m, 2H), 7.90 (d, J = 8.3 Hz, 1H), 7.79 (s, 1H), 6.77 (d, J = 2.1 Hz, 1H), 4.94 (br t, J = 5.9 Hz, 2H), 3.75-3.69 (m, 2H), 2.87 (s, 6H |
| 22 | (structure) | 336.1 | 0.86 | δ 13.27-12.87 (m, 1H), 9.98-9.19 (m, 2H), 8.99 (s, 1H), 8.15-8.07 (m, 2H), 7.91 (br d, J = 7.7 Hz, 1H), 7.83 (br s, 1H), 6.79 (d, J = 1.7 Hz, 1H), 4.61 (t, J = 6.6 Hz, 2H), 3.17-3.12 (m, 2H), 2.79 (s, 6H), 2.39-2.30 (m, 2H) |
| 23 | (structure) | 398.1 | 1.21 | δ 10.11 (s, 1H), 8.97 (s, 1H), 8.12 (d, J = 8.3 Hz, 1H), 8.08 (br s, 1H), 7.88 (br d, J = 8.5 Hz, 1H), 7.52 (br d, J = 8.3 Hz, 2H), 7.30-7.24 (m, 3H), 7.07-7.00 (m, 1H), 6.78 (s, 1H), 4.82 (br t, J = 6.5 Hz, 2H), 3.13 (br t, J = 6.3 Hz, 2H) |

| Ex No. | Structure | LC/MS [M + H]+ | RT (min) | ¹H NMR (500 MHZ, DMSO-d₆) |
|---|---|---|---|---|
| 24 | 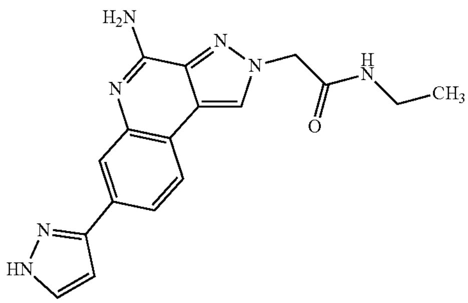 [SMILES: CCNC(=O)Cn1cc2c(n1)c(N)nc1cc(-c3cc[nH]n3)ccc12] | 336.4 | 0.80 | δ 8.68 (s, 1H), 8.27 (br t, J = 5.1 Hz, 1H), 7.96 (br d, J = 8.0 Hz, 1H), 7.90 (s, 1H), 7.76-7.59 (m, 2H), 6.89-6.79 (m, 2H), 6.74 (s, 1H), 5.13 (s, 2H), 3.18-3.11 (m, 2H), 1.06 (t, J = 7.3 Hz, 3H) |
| 25 | 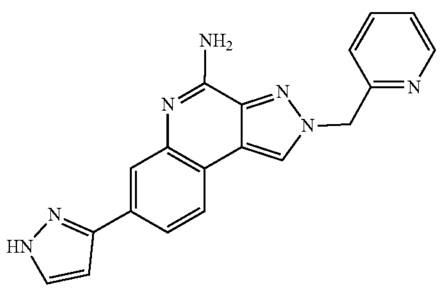 [SMILES: Nc1nc2cc(-c3cc[nH]n3)ccc2c2cn(Cc3ccccn3)nc12] | 342.1 | 1.02 | δ 9.03 (s, 1H), 8.54 (br d, J = 4.4 Hz, 1H), 8.10 (d, J = 8.3 Hz, 1H), 8.05 (br d, J = 0.8 Hz, 1H), 7.86-7.73 (m, 3H), 7.39-7.31 (m, 2H), 6.78 (s, 1H), 5.85 (s, 2H) |
| 26 | 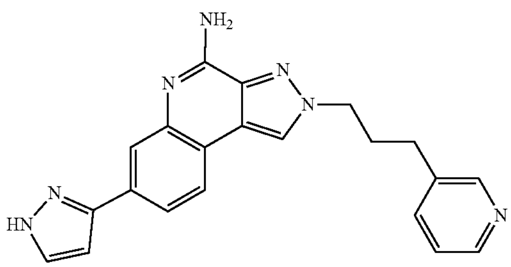 [SMILES: Nc1nc2cc(-c3cc[nH]n3)ccc2c2cn(CCCc3cccnc3)nc12] | 370.2 | 0.95 | δ 8.71 (s, 1H), 8.43 (s, 1H), 8.37 (br d, J = 3.6 Hz, 1H), 7.93 (d, J = 8.3 Hz, 1H), 7.88 (s, 1H), 7.70-7.65 (m, 2H), 7.63 (br d, J = 8.3 Hz, 1H), 7.31 (dd, J = 7.4, 5.0 Hz, 1H), 6.80-6.66 (m, 3H), 4.45 (br t, J = 6.9 Hz, 2H), 2.66-2.61 (m, 2H), 2.30-2.22 (m, 2H) |
| 27 | 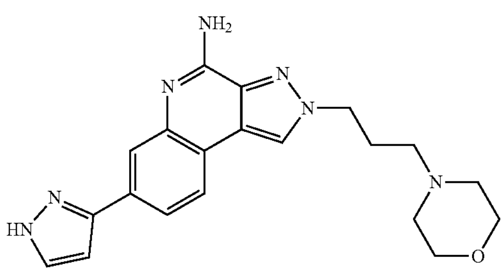 [SMILES: Nc1nc2cc(-c3cc[nH]n3)ccc2c2cn(CCCN3CCOCC3)nc12] | 378.0 | 0.92 | δ 13.41-12.76 (m, 1H), 8.73 (s, 1H), 7.96-7.87 (m, 2H), 7.81-7.56 (m, 2H), 7.02-6.80 (m, 2H), 6.74 (br s, 1H), 4.47 (br t, J = 6.7 Hz, 2H), 3.59-3.53 (m, 4H), 2.37-2.32 (m, 4H), 2.31 (br t, J = 7.0 Hz, 2H), 2.14-2.07 (m, 2H) |
| 28 | 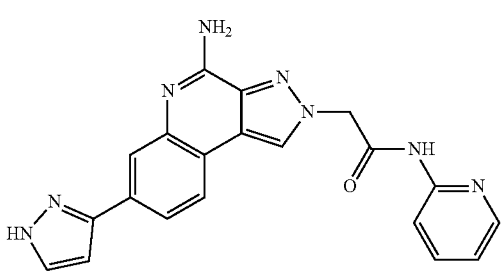 [SMILES: Nc1nc2cc(-c3cc[nH]n3)ccc2c2cn(CC(=O)Nc3ccccn3)nc12] | 385.0 | 0.87 | δ 11.01 (br s, 1H), 8.76 (s, 1H), 8.37 (br d, J = 1.4 Hz, 1H), 8.04-7.96 (m, 2H), 7.91 (br s, 1H), 7.83-7.78 (m, 1H), 7.76-7.60 (m, 2H), 7.18-7.11 (m, 1H), 7.00-6.82 (m, 2H), 6.75 (br s, 1H), 5.49 (br s, 2H) |

Example 29. Preparation of N-[2-[4-amino-7-(1H-pyrazol-3-yl)-2H-pyrazolo[3,4-c]quinolin-2-yl]ethyl]-N-ethylacetamide

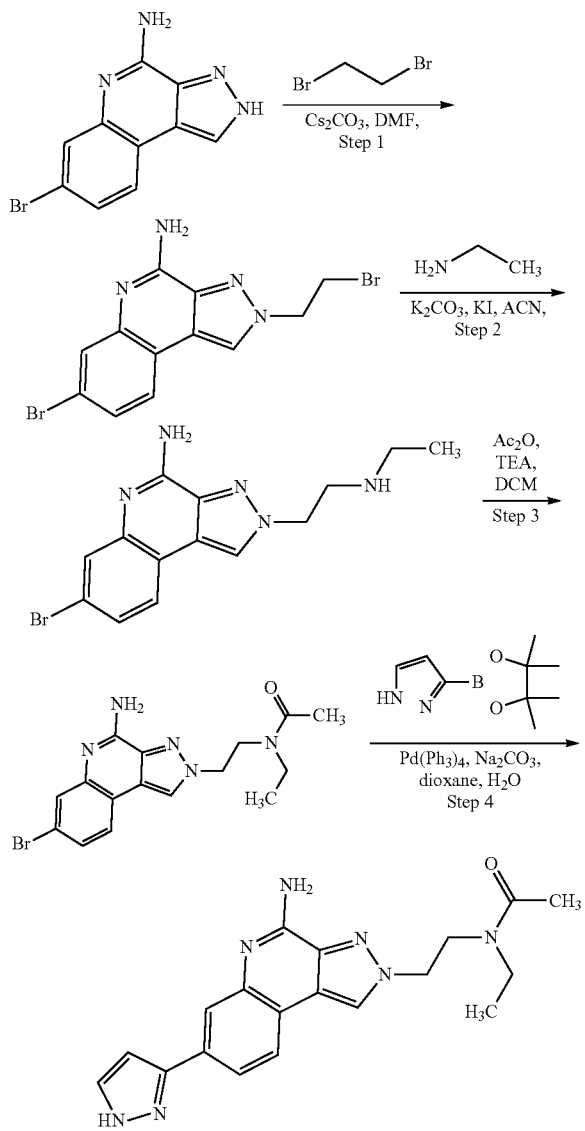

Step 1. 7-bromo-2-(2-bromoethyl)-2H-pyrazolo[3,4-c]quinolin-4-amine

Into a 250-mL round-bottom flask was placed 7-bromo-2H-pyrazolo[3,4-c]quinolin-4-amine (2 g, 7.60 mmol, 1 equiv), DMF (70 mL, 957.67 mmol), Cs$_2$CO$_3$ (5.0 g, 15.20 mmol, 2 equiv), and 1,2-dibromoethane (2.1 g, 11.40 mmol, 1.5 equiv). The resulting solution was stirred for 5 h at rt and then diluted with EtOAc (350 mL). The resulting mixture was washed with H$_2$O (2×100 mL) and brine (2×100 mL). Then the mixture was concentrated and the residue was purified on a silica gel column with ethyl acetate/petroleum ether (0-70%) to provide 7-bromo-2-(2-bromoethyl)-2H-pyrazolo[3,4-c]quinolin-4-amine (1.5 g, 53%) as a solid. LC-MS m/z [M+H]$^+$=368.9.

Step 2. 7-bromo-2-[2-(ethylamino)ethyl]-2H-pyrazolo[3,4-c]quinolin-4-amine

Into a 30-mL sealed tube was placed 7-bromo-2-(2-bromoethyl)-2H-pyrazolo[3,4-c]quinolin-4-amine (500 mg, 1.35 mmol, 1 equiv), ACN (10 mL, 0.24 mmol), K$_2$CO$_3$ (373.5 mg, 2.70 mmol, 2 equiv), KI (22.4 mg, 0.14 mmol, 0.1 equiv), and ethanamine (609.2 mg, 13.51 mmol, 10 equiv). The resulting solution was stirred for 16 h at 65° C. The reaction was filtered and the filtrate was concentrated in vacuo. The residue was purified on a silica gel column with dichloromethane/methanol (0-10%) to provide 7-bromo-2-[2-(ethylamino)ethyl]-2H-pyrazolo[3,4-c]quinolin-4-amine (250 mg, 55%) as a solid. LC-MS m/z [M+H]$^+$=334.1.

Step 3. N-(2-[4-amino-7-bromo-2H-pyrazolo[3,4-c]quinolin-2-yl]ethyl)-N-ethylacetamide Into a 25-mL 3-necked round-bottom flask purged and maintained with an inert atmosphere of nitrogen was placed 7-bromo-2-[2-(ethylamino)ethyl]-2H-pyrazolo[3,4-c]quinolin-4-amine (250 mg, 0.75 mmol, 1 equiv), DCM (10 mL, 157.30 mmol), TEA (227.1 mg, 2.24 mmol, 3 equiv), and Ac$_2$O (91.6 mg, 0.90 mmol, 1.2 equiv). The resulting solution was stirred for 5 h at rt. The resulting mixture was concentrated in vacuo and the residue was purified on a silica gel column with dichloromethane/methanol (0-10%) to provide N-(2-[4-amino-7-bromo-2H-pyrazolo[3,4-c]quinolin-2-yl]ethyl)-N-ethylacetamide (200 mg, 71%) as a solid. LC-MS m/z [M+H]$^+$=376.1.

Step 4. N-[2-[4-amino-7-(1H-pyrazol-3-yl)-2H-pyrazolo[3,4-c]quinolin-2-yl]ethyl]-N-ethylacetamide Into a 25-mL round-bottom flask was placed N-(2-[4-amino-7-bromo-2H-pyrazolo[3,4-c]quinolin-2-yl]ethyl)-N-ethylacetamide (200 mg, 0.53 mmol, 1 equiv), Na$_2$CO$_3$ (112.7 mg, 1.06 mmol, 2 equiv), 3-(tetramethyl-1,3,2-dioxaborolan-2-yl)-1H-pyrazole (206.3 mg, 1.06 mmol, 2 equiv), Pd(PPh$_3$)$_4$ (61.4 mg, 0.05 mmol, 0.1 equiv) in dioxane (5 mL, 0.06 mmol) and H$_2$O (1.25 mL, 620.08 mmol). The resulting solution was stirred for 16 h at 80° C. in an oil bath. The resulting mixture was concentrated and the residue was purified on a silica gel column with dichloromethane/methanol (10:1). The crude product was purified by Prep-HPLC with the following conditions: Column: XBridge Shield RP18 OBD Column 19*250 mm, 10 um; Mobile Phase A: Water (10 mM NH$_4$HCO$_3$), Mobile Phase B: ACN; Flow rate: 25 mL/min; Gradient: 13% B to 40% B in 7 min; 254/210 nm; RT: 6.55 min. This provided N-[2-[4-amino-7-(1H-pyrazol-3-yl)-2H-pyrazolo[3,4-c]quinolin-2-yl]ethyl]-N-ethylacetamide (82.6 mg, 43%) as a white solid. $^1$H-NMR: (300 MHz, DMSO-d$_6$, ppm): δ 13.33-12.84 (m, 1H), 8.72 (s, 1H), 7.94-7.64 (m, 4H), 6.80-6.74 (m, 3H), 4.65-4.54 (m, 2H), 3.85-3.73 (m, 2H), 3.34-3.06 (m, 2H), 2.01 (s, 2H), 1.70 (s, 1H), 1.02-0.94 (m, 3H). LC Methods: Column: Kinetex EVO 3.0 mm×50 mm, 2.6 μm particles; Mobile Phase A: water with 0.03% NH$_3$H$_2$O; Mobile Phase B: acetonitrile; Temperature: 40° C.; Gradient: 10% B to 95% B over 2 min, then a 0.60 min hold at 95% B; Flow: 1.2 mL/min. m/z [M+H]$^+$=336.3. LC RT: 1.030 min.

Example 30. Preparation of 2-(2-{hexahydro-1H-furo[3,4-c]pyrrol-5-yl}ethyl)-7-(1H-pyrazol-3-yl)-2H-pyrazolo[3,4-c]quinolin-4-amine

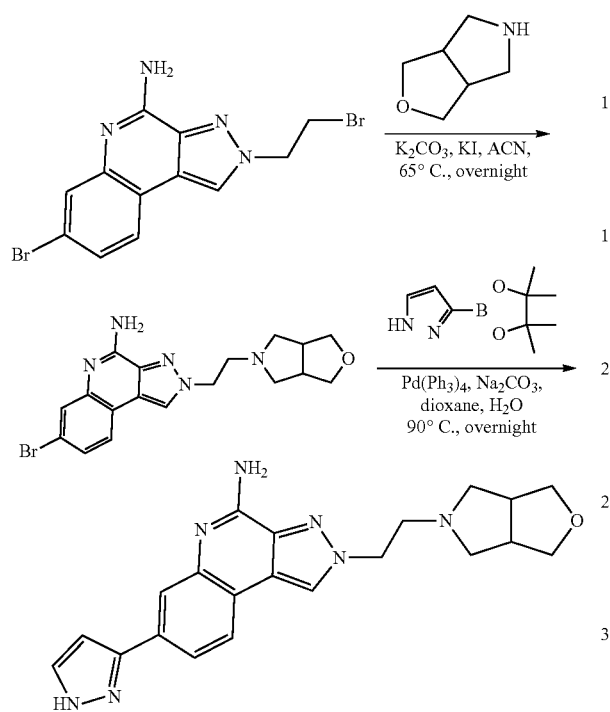

Step 1. 7-bromo-2-(2-[hexahydro-1H-furo[3,4-c]pyrrol-5-yl]ethyl)-2H-pyrazolo[3,4-c]quinolin-4-amine Into a 30-mL sealed tube was placed 7-bromo-2-(2-bromoethyl)-2H-pyrazolo[3,4-c]quinolin-4-amine (400 mg, 1.08 mmol, 1 equiv), K₂CO₃ (298.8 mg, 2.16 mmol, 2 equiv), KI (17.9 mg, 0.11 mmol, 0.1 equiv), and hexahydro-1H-furo[3,4-c]pyrrole (611.6 mg, 5.40 mmol, 5 equiv) in ACN (10 mg, 0.24 mmol, 0.225 equiv). The resulting solution was stirred for 16 h at 65° C. The reaction was filtered and the filtrate was concentrated in vacuo. The residue was the purified on a silica gel column with dichloromethane/methanol (0-10%) to provide 7-bromo-2-(2-[hexahydro-1H-furo[3,4-c]pyrrol-5-yl]ethyl)-2H-pyrazolo[3,4-c]quinolin-4-amine (120 mg, 28%) as a solid. LC-MS: (ES, m/z): [M+H]⁺=402.1.

Step 2. 2-(2-[hexahydro-1H-furo[3,4-c]pyrrol-5-yl]ethyl)-7-(1H-pyrazol-3-yl)-2H-pyrazolo[3,4-c]quinolin-4-amine Into a 30-mL sealed tube was placed 7-bromo-2-(2-[hexahydro-1H-furo[3,4-c]pyrrol-5-yl]ethyl)-2H-pyrazolo[3,4-c]quinolin-4-amine (120 mg, 0.30 mmol, 1 equiv), Na₂CO₃ (63.2 mg, 0.60 mmol, 2 equiv), 3-(tetramethyl-1,3,2-dioxaborolan-2-yl)-1H-pyrazole (115.8 mg, 0.60 mmol, 2 equiv), Pd(PPh₃)₄ (34.5 mg, 0.03 mmol, 0.1 equiv) in dioxane (4 mL) and H₂O (1 mL). The resulting solution was stirred for 16 h at 80° C. The resulting mixture was cooled to rt and concentrated. The residue was purified on a silica gel column with dichloromethane/methanol (0-10%). The crude product was purified again by Prep-HPLC with the following conditions: Column: XBridge Shield RP18 OBD Column 19*250 mm, 10 um; Mobile Phase A: Water (10 mM NH₄HCO₃), Mobile Phase B: ACN; Flow rate: 25 mL/min; Gradient: 15% B to 40% B in 7.5 min; 210/254 nm; RT: 6.90 min. This provided 2-(2-[hexahydro-1H-furo[3,4-c]pyrrol-5-yl]ethyl)-7-(1H-pyrazol-3-yl)-2H-pyrazolo[3,4-c]quinolin-4-amine (27.9 mg, 24%) as a solid. ¹H-NMR: (300 MHz, DMSO-d₆, ppm): δ 13.28-12.85 (m, 1H), 8.74 (s, 1H), 7.91-7.63 (m, 4H), 6.77-6.74 (m, 3H), 4.56-4.51 (m, 2H), 3.72-3.67 (m, 2H), 3.35-3.31 (m, 2H), 2.95-2.91 (m, 2H), 2.67-2.55 (m, 4H), 2.40-2.36 (m, 2H). LC Methods: Column: Kinetex EVO 3.0 mm×50 mm, 2.6 µm particles; Mobile Phase A: water with 0.03% NH₃H₂O; Mobile Phase B: acetonitrile; Temperature: 40° C.; Gradient: 10% B to 95% B over 2 min, then a 0.60 min hold at 95% B; Flow: 1.2 mL/min. m/z [M+H]⁺=390.2. LC RT: 1.030 min.

Example 31. Preparation of N-{2-[4-amino-7-(1H-pyrazol-3-yl)-2H-pyrazolo[3,4-c]quinolin-2-yl]ethyl}-5-fluoropyridine-2-carboxamide

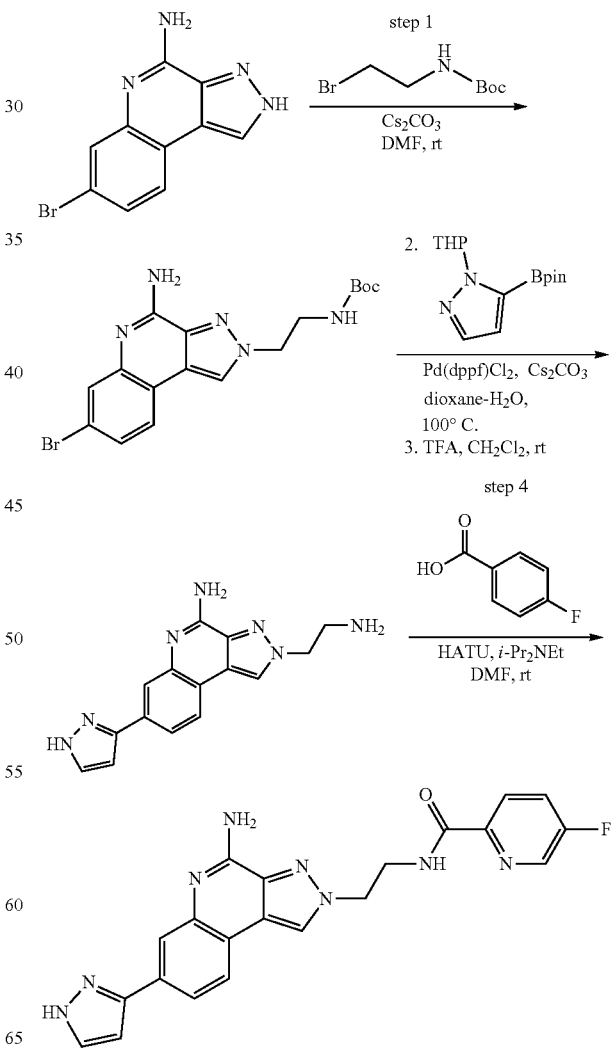

Step 1. tert-butyl (2-(4-amino-7-bromo-2H-pyrazolo[3,4-c]quinolin-2-yl)ethyl)carbamate To a rt solution of 7-bromo-2H-pyrazolo[3,4-c]quinolin-4-amine, TFA (3.00 g, 7.96 mmol) in DMF (22.73 ml) was added cesium carbonate (7.78 g, 23.87 mmol) followed by tert-butyl (2-bromoethyl)carbamate (1.961 g, 8.75 mmol). The suspension was stirred at rt for 20 h. The reaction was diluted with EtOAc (300 mL) and H$_2$O (300 mL). The layers were separated and the aqueous layer was extracted with EtOAc (100 mL). The combined organic layers were washed with sat. aq. NaCl (300 mL), dried over Na$_2$SO$_4$ and filtered. Celite was added, and the mixture was concentrated in vacuo. This material was dry loaded onto a column and purified by flash chromatography (80 g silica gel with 25 g solid load cartridge; linear gradient 0-10% MeOH—CH$_2$Cl$_2$) to provide tert-butyl (2-(4-amino-7-bromo-2H-pyrazolo[3,4-c]quinolin-2-yl)ethyl)carbamate (2.06 g, 64%) as a white solid. $^1$H NMR (400 MHz, DMSO-d$_6$) δ 8.67 (s, 1H), 7.85 (d, J=8.3 Hz, 1H), 7.58 (d, J=2.0 Hz, 1H), 7.30 (dd, J=8.3, 2.0 Hz, 1H), 7.05 (br t, J=5.4 Hz, 1H), 6.98 (br s, 2H), 4.45 (br t, J=6.1 Hz, 2H), 3.48 (q, J=6.0 Hz, 2H), 1.33 (s, 9H); LC-MS m/z 406/408 [M+H]$^+$.

Step 2. tert-butyl (2-(4-amino-7-(1-(tetrahydro-2H-pyran-2-yl)-1H-pyrazol-5-yl)-2H-pyrazolo[3,4-c]quinolin-2-yl)ethyl)carbamate A mixture of tert-butyl (2-(4-amino-7-bromo-2H-pyrazolo[3,4-c]quinolin-2-yl)ethyl)carbamate (1.01 g, 2.49 mmol), 1-(tetrahydro-2H-pyran-2-yl)-5-(4,4,5,5-tetramethyl-1,3,2-dioxaborolan-2-yl)-1H-pyrazole (1.037 g, 3.73 mmol), and cesium carbonate (2.430 g, 7.46 mmol) was evacuated and back-filled with N$_2$, then 1,4-dioxane (22.37 ml) and H$_2$O (2.486 ml) were added. The resulting mixture was sparged with N$_2$ for 15 min, then [1,1'-bis(diphenylphosphino)ferrocene]dichloropalladium(II) (0.091 g, 0.124 mmol) was added. The mixture was sparged with N$_2$ for 1 min, then it was stirred at 100° C. for 30 min. The reaction was cooled to rt, diluted with EtOAc (300 mL), washed with H$_2$O (150 mL) and sat. aq. NaCl (150 mL), dried over Na$_2$SO$_4$, filtered, and concentrated in vacuo. The crude material was purified by flash chromatography (80 g silica gel; linear gradient 0-10% MeOH—CH$_2$Cl$_2$) to provide tert-butyl (2-(4-amino-7-(1-(tetrahydro-2H-pyran-2-yl)-1H-pyrazol-5-yl)-2H-pyrazolo[3,4-c]quinolin-2-yl)ethyl)carbamate (1.2 g, quant.) as a yellow solid. $^1$H NMR (400 MHz, DMSO-d$_6$) δ 8.71 (s, 1H), 8.01 (d, J=8.1 Hz, 1H), 7.62 (d, J=1.6 Hz, 1H), 7.57 (d, J=1.7 Hz, 1H), 7.32 (dd, J=8.0, 1.8 Hz, 1H), 7.07 (br t, J=5.7 Hz, 1H), 6.89 (br s, 2H), 6.48 (d, J=1.7 Hz, 1H), 5.30 (dd, J=10.0, 2.0 Hz, 1H), 4.48 (br t, J=6.1 Hz, 2H), 4.07-4.01 (m, 1H), 3.61-3.54 (m, 1H), 3.50 (q, J=6.0 Hz, 2H), 2.47-2.36 (m, 1H), 1.99-1.90 (m, 1H), 1.79 (br d, J=13.4 Hz, 1H), 1.64-1.48 (m, 3H), 1.35 (s, 9H); LC-MS m/z 478 [M+H]$^+$.

Step 3. 2-(2-aminoethyl)-7-(1H-pyrazol-3-yl)-2H-pyrazolo[3,4-c]quinolin-4-amine, 2 TFA To a rt solution of tert-butyl (2-(4-amino-7-(1-(tetrahydro-2H-pyran-2-yl)-1H-pyrazol-5-yl)-2H-pyrazolo[3,4-c]quinolin-2-yl)ethyl)carbamate (1.2 g, 2.5 mmol) in CH$_2$Cl$_2$ (6.17 ml) was added TFA (6.17 ml). The reaction was stirred at rt for 2 h. The reaction was concentrated to remove about half the volume, then it was added dropwise to Et$_2$O (75 mL). The resulting solid was collected by vacuum filtration and washed with Et$_2$O (3×10 mL) to provide 2-(2-aminoethyl)-7-(1H-pyrazol-3-yl)-2H-pyrazolo[3,4-c]quinolin-4-amine, 2 TFA (1.121 g, 87%) as an off-white solid. $^1$H NMR (400 MHz, DMSO-d$_6$) δ 13.69-12.94 (m, 1H), 9.85-9.68 (m, 1H), 9.38-9.22 (m, 1H), 9.02 (s, 1H), 8.17-8.13 (m, 2H), 8.09 (br s, 2H), 7.94 (d, J=7.2 Hz, 1H), 7.85 (br s, 1H), 6.80 (d, J=2.1 Hz, 1H), 4.77 (t, J=5.7 Hz, 2H), 3.55-3.49 (m, 2H); LC-MS m/z 294 [M+H]$^+$.

Step 4. N-{2-[4-amino-7-(1H-pyrazol-3-yl)-2H-pyrazolo[3,4-c]quinolin-2-yl]ethyl}-5-fluoropyridine-2-carboxamide To a rt solution of 2-(2-aminoethyl)-7-(1H-pyrazol-3-yl)-2H-pyrazolo[3,4-c]quinolin-4-amine, 2 TFA (40 mg, 0.077 mmol) and 5-fluoropicolinic acid (10.8 mg, 0.077 mmol) in DMF (384 µl) was added N,N-diisopropylethylamine (53.5 µl, 0.307 mmol), followed by HATU (29.2 mg, 0.077 mmol). The reaction was stirred at rt for 30 min. The reaction was diluted with H$_2$O (0.2 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 0.10% trifluoroacetic acid; Mobile Phase B: 95:5 acetonitrile:water with 0.10% trifluoroacetic acid; Gradient: a 0-minute hold at 2% B, 2-42% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(1H-pyrazol-3-yl)-2H-pyrazolo[3,4-c]quinolin-2-yl)ethyl)-5-fluoropicolinamide, 2 TFA (15.8 mg, 31%). $^1$H NMR (500 MHz, DMSO-d$_6$) δ 9.06 (br t, J=5.8 Hz, 1H), 8.93 (s, 1H), 8.61 (d, J=2.5 Hz, 1H), 8.12-8.02 (m, 3H), 7.90-7.77 (m, 3H), 6.78 (s, 1H), 4.71 (br t, J=5.9 Hz, 2H), 3.94-3.86 (m, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 417.3 [M+H]$^+$; RT: 1.13 min.

Alternate procedure for the preparation of N-{2-[4-amino-7-(1H-pyrazol-3-yl)-2H-pyrazolo[3,4-c]quinolin-2-yl]ethyl}-5-fluoropyridine-2-carboxamide To a rt solution of 5-fluoropicolinic acid (29.8 mg, 0.211 mmol) in DMF (479 µl) was added N,N-diisopropylethylamine (66.8 µl, 0.384 mmol), followed by HATU (72.9 mg, 0.192 mmol). This solution was stirred at rt for 5 min, then it was added, dropwise, to a solution of 2-(2-aminoethyl)-7-(1H-pyrazol-3-yl)-2H-pyrazolo[3,4-c]quinolin-4-amine, 2 TFA (100 mg, 0.192 mmol) and N,N-diisopropylethylamine (100 µl, 0.575 mmol) in DMF (479 µl). The reaction was stirred at rt for 30 min. The reaction was diluted with EtOAc (50 mL) and H$_2$O (50 mL). The layers were separated and the aqueous layer was extracted EtOAc (50 mL). The combined organic layers were washed with 10% aq. LiCl (2×50 mL) and sat. aq. NaCl (50 mL), dried over Na$_2$SO$_4$, filtered, and concentrated in vacuo. The crude material was taken up in MeOH—CH$_2$Cl$_2$, Celite was added, and the mixture was concentrated in vacuo. This material was dry loaded onto a column and purified by flash chromatography (24 g RediSep Gold silica gel with 5 g solid load cartridge; linear gradient 0-20% MeOH—CH$_2$Cl$_2$) to provide N-(2-

(4-amino-7-(1H-pyrazol-3-yl)-2H-pyrazolo[3,4-c]quinolin-2-yl)ethyl)-5-fluoropicolinamide (33.7 mg, 42%) as a white solid. ¹H NMR (400 MHz, DMSO-d₆) δ 13.33-12.77 (m, 1H), 9.04 (t, J=5.9 Hz, 1H), 8.69 (br s, 1H), 8.62 (d, J=2.7 Hz, 1H), 8.09 (dd, J=8.7, 4.7 Hz, 1H), 7.93-7.84 (m, 3H), 7.82-7.64 (m, 1H), 7.64-7.51 (m, 1H), 6.84-6.76 (m, 1H), 6.74 (br s, 2H), 4.65 (t, J=6.2 Hz, 2H), 3.88 (q, J=6.2 Hz, 2H); LC-MS m/z 417 [M+H]⁺.

Examples 32 to 101 were prepared according to synthetic procedures similar to those described for Example 31 from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex No. | Structure | LC/MS [M + H]⁺ | RT (min) | ¹H NMR (500 MHZ, DMSO-d₆) |
|---|---|---|---|---|
| 32 | 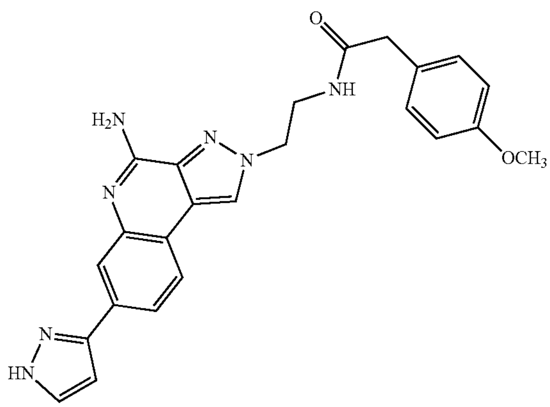 [SMILES: COc1ccc(CC(=O)NCCn2cc3c(n2)c(N)nc2cc(-c4cc[nH]n4)ccc23)cc1] | 442.3 | 0.98 | δ 8.54 (s, 1H), 8.12 (br t, J = 5.6 Hz, 1H), 7.91-7.87 (m, 2H), 7.70 (br s, 1H), 7.64 (br d, J = 7.7 Hz, 1H), 7.06 (d, J = 8.3 Hz, 2H), 6.80 (br s, 2H), 6.75-6.71 (m, 3H), 4.49 (br t, J = 5.8 Hz, 2H), 3.65 (s, 3H), 3.63-3.59 (m, 2H), 3.30 (s, 2H) |
| 33 | 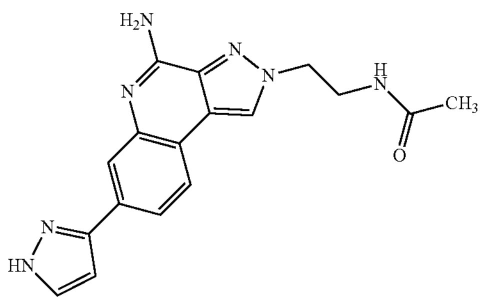 [SMILES: CC(=O)NCCn1cc2c(n1)c(N)nc1cc(-c3cc[nH]n3)ccc12] | 336.1 | 0.73 | δ 8.63 (s, 1H), 7.96-7.92 (m, 2H), 7.89 (s, 1H), 7.67 (s, 1H), 7.64 (d, J = 8.0 Hz, 1H), 6.71 (s, 1H), 4.49 (t, J = 6.0 Hz, 2H), 3.65-3.58 (m, 2H), 1.81 (s, 3H) |
| 34 | 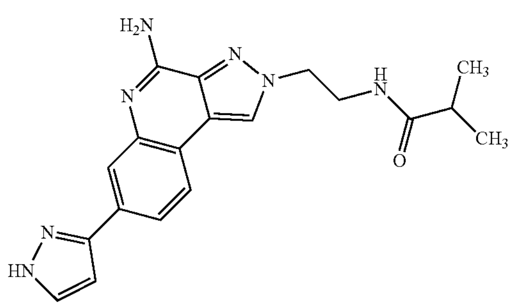 [SMILES: CC(C)C(=O)NCCn1cc2c(n1)c(N)nc1cc(-c3cc[nH]n3)ccc12] | 364.2 | 0.86 | δ 8.61 (s, 1H), 7.94-7.85 (m, 3H), 7.81-7.54 (m, 1H), 6.90-6.64 (m, 2H), 4.48 (br t, J = 5.8 Hz, 2H), 3.60-3.55 (m, 2H), 2.30 (quin, J = 6.8 Hz, 1H), 0.95 (d, J = 6.9 Hz, 6H) |
| 35 | 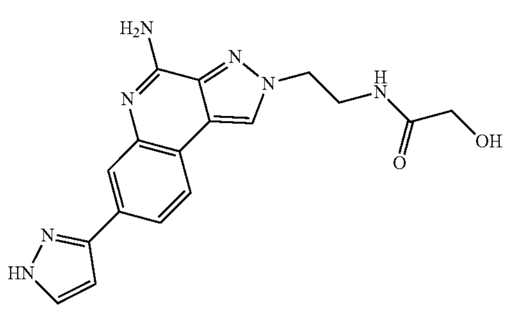 | 352.2 | 0.69 | δ 8.67 (s, 1H), 8.02 (br t, J = 5.6 Hz, 1H), 7.93 (br d, J = 7.4 Hz, 1H), 7.89 (br s, 1H), 7.79-7.57 (m, 2H), 6.86-6.76 (m, 2H), 6.73 (s, 1H), 5.54 (br t, J = 5.5 Hz, 1H), 4.53 (br t, J = 5.9 Hz, 2H), 3.80 (br d, J = 5.2 Hz, 2H), 3.71-3.65 (m, 2H) |

-continued

| Ex No. | Structure | LC/MS [M + H]+ | RT (min) | 1H NMR (500 MHZ, DMSO-d6) |
|---|---|---|---|---|
| 36 | 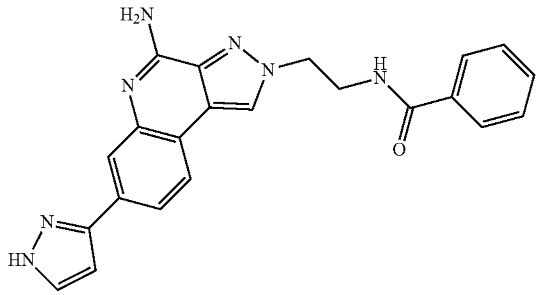 [SMILES: Nc1nc2cc(-c3cc[nH]n3)ccc2c2cn(CCNC(=O)c3ccccc3)nc12] | 398.2 | 0.98 | δ 8.70 (s, 1H), 8.67 (br t, J = 5.9 Hz, 1H), 7.90 (d, J = 8.5 Hz, 1H), 7.88 (s, 1H), 7.79 (d, J = 7.4 Hz, 2H), 7.69 (br s, 1H), 7.60 (br d, J = 8.0 Hz, 1H), 7.54-7.49 (m, 1H), 7.47-7.41 (m, 2H), 6.73 (s, 1H), 6.82-6.69 (m, 2H), 4.63 (br t, J = 5.9 Hz, 2H), 3.82 (q, J = 5.7 Hz, 2H) |
| 37 | 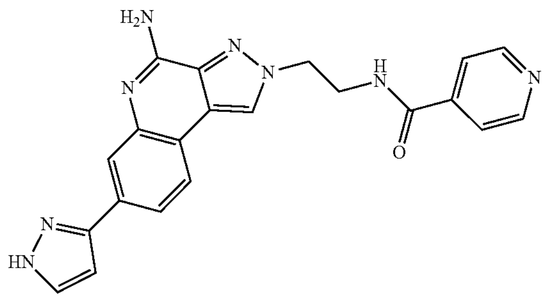 [SMILES: Nc1nc2cc(-c3cc[nH]n3)ccc2c2cn(CCNC(=O)c3ccncc3)nc12] | 399.3 | 0.95 | δ 13.71-13.34 (m, 1H), 9.91-9.67 (m, 1H), 9.33-9.12 (m, 1H), 9.02 (s, 1H), 8.97 (br s, 1H), 8.71 (br d, J = 3.6 Hz, 2H), 8.13 (s, 1H), 8.10 (br d, J = 8.5 Hz, 1H), 7.97-7.88 (m, 1H), 7.82 (s, 1H), 7.68 (br d, J = 4.1 Hz, 2H), 6.78 (s, 1H), 4.74-4.69 (m, 2H), 3.91-3.84 (m, 2H) |
| 38 | 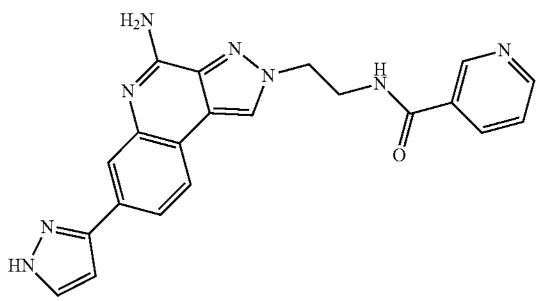 [SMILES: Nc1nc2cc(-c3cc[nH]n3)ccc2c2cn(CCNC(=O)c3cccnc3)nc12] | 399.2 | 0.95 | δ 8.94 (s, 1H), 8.88 (br t, J = 4.7 Hz, 1H), 8.72 (s, 1H), 8.69 (br d, J = 4.7 Hz, 1H), 8.13 (br d, J = 8.0 Hz, 1H), 7.92-7.87 (m, 2H), 7.69 (br s, 1H), 7.60 (br d, J = 8.3 Hz, 1H), 7.48 (dd, J = 7.3, 4.8 Hz, 1H), 6.80-6.70 (m, 3H), 4.63 (br t, J = 5.5 Hz, 2H), 3.87-3.81 (m, 2H) |
| 39 | 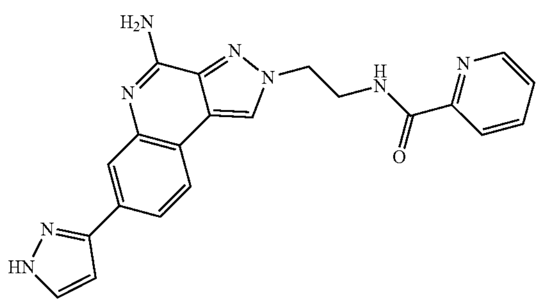 [SMILES: Nc1nc2cc(-c3cc[nH]n3)ccc2c2cn(CCNC(=O)c3ccccn3)nc12] | 399.3 | 1.06 | δ 13.54-13.37 (m, 1H), 9.89-9.76 (m, 1H), 9.24-9.13 (m, 1H), 9.11 (br t, J = 5.6 Hz, 1H), 8.98 (s, 1H), 8.62 (br d, J = 4.4 Hz, 1H), 8.12 (br s, 1H), 8.09 (br d, J = 8.5 Hz, 1H), 8.01-7.95 (m, 2H), 7.88 (br d, J = 8.0 Hz, 1H), 7.82 (br s, 1H), 7.60 (br t, J = 4.5 Hz, 1H), 6.78 (s, 1H), 4.74 (br t, J = 5.2 Hz, 2H), 3.96-3.90 (m, 2H) |
| 40 | 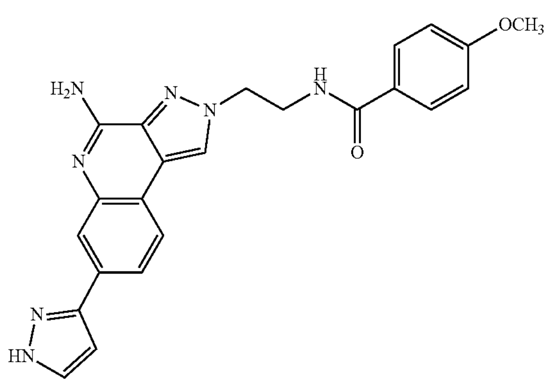 [SMILES: COc1ccc(C(=O)NCCn2cc3c(n2)c(N)nc2cc(-c4cc[nH]n4)ccc23)cc1] | 428.1 | 1.16 | δ 8.70 (s, 1H), 8.53 (t, J = 5.2 Hz, 1H), 7.96-7.88 (m, 2H), 7.78 (d, J = 8.5 Hz, 2H), 7.71-7.67 (m, 1H), 7.62 (br d, J = 9.1 Hz, 1H), 6.97 (d, J = 8.5 Hz, 2H), 6.97-6.80 (m, 2H), 6.73 (s, 1H), 4.61 (br t, J = 6.1 Hz, 2H), 3.83-3.78 (m, 5H) |

-continued
| Ex No. | Structure | LC/MS [M + H]+ | RT (min) | 1H NMR (500 MHZ, DMSO-d6) |
|---|---|---|---|---|
| 41 | 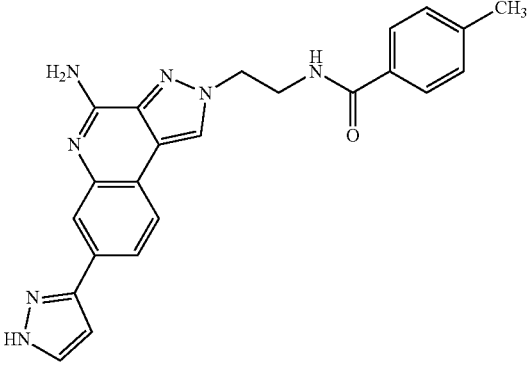 [SMILES: Cc1ccc(C(=O)NCCn2cc3c(n2)c(N)nc2cc(-c4cc[nH]n4)ccc23)cc1] | 412.2 | 1.20 | δ 8.71-8.67 (m, 1H), 8.59 (br t, J = 4.7 Hz, 1H), 7.92-7.87 (m, 2H), 7.73-7.67 (m, 3H), 7.60 (br d, J = 8.0 Hz, 1H), 7.24 (br d, J = 7.4 Hz, 2H), 6.79-6.74 (m, 2H), 6.73 (s, 1H), 4.62 (br t, J = 5.4 Hz, 2H), 3.83-3.77 (m, 2H), 2.33 (s, 3H) |
| 42 | 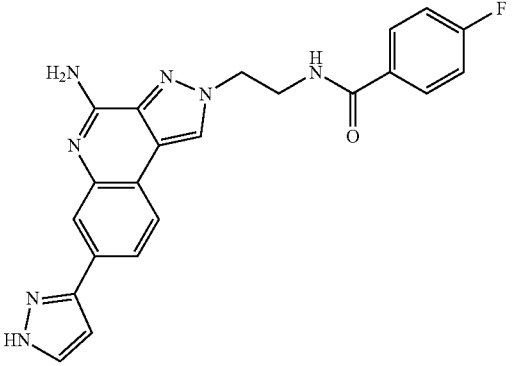 [SMILES: Nc1nc2cc(-c3cc[nH]n3)ccc2c2cn(CCNC(=O)c3ccc(F)cc3)nc12] | 416.1 | 1.17 | δ 8.99 (s, 1H), 8.73-8.67 (m, 1H), 8.17-8.05 (m, 2H), 7.92-7.79 (m, 4H), 7.27 (br t, J = 8.8 Hz, 2H), 6.80-6.75 (m, 1H), 4.72-4.67 (m, 2H), 3.85 (q, J = 5.4 Hz, 2H) |
| 43 | 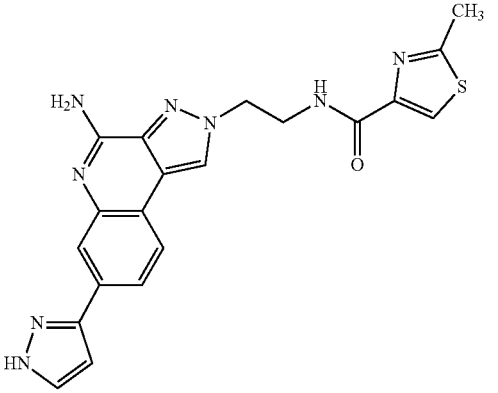 [SMILES: Cc1nc(C(=O)NCCn2cc3c(n2)c(N)nc2cc(-c4cc[nH]n4)ccc23)cs1] | 419.2 | 1.06 | δ 8.70-8.66 (m, 1H), 8.62 (br t, J = 5.5 Hz, 1H), 8.07 (s, 1H), 7.91 (br d, J = 8.0 Hz, 1H), 7.88 (s, 1H), 7.72-7.65 (m, 1H), 7.64-7.58 (m, 1H), 6.73 (br s, 3H), 4.62 (br t, J = 6.2 Hz, 2H), 3.83 (q, J = 6.3 Hz, 2H), 2.67 (s, 3H) |
| 44 | 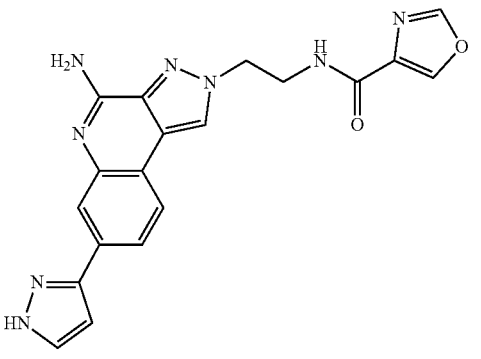 [SMILES: Nc1nc2cc(-c3cc[nH]n3)ccc2c2cn(CCNC(=O)c3cocn3)nc12] | 389.3 | 0.75 | δ 13.16-12.98 (m, 1H), 8.99-8.92 (m, 1H), 8.63-8.57 (m, 2H), 8.48 (s, 1H), 8.18-8.05 (m, 2H), 7.94-7.78 (m, 2H), 6.78 (br s, 1H), 4.68 (br t, J = 5.5 Hz, 2H), 3.87-3.82 (m, 2H) |

| Ex No. | Structure | LC/MS [M + H]+ | RT (min) | 1H NMR (500 MHZ, DMSO-d6) |
|---|---|---|---|---|
| 45 | 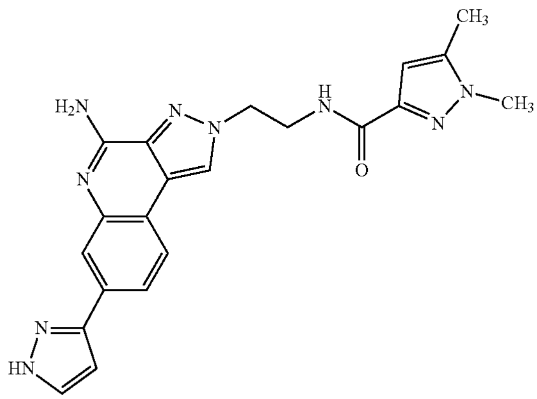 [SMILES: Cc1cc(C(=O)NCCn2cc3c(n2)c(N)nc2cc(-c4cc[nH]n4)ccc23)nn1C] | 416.3 | 0.84 | δ 8.67 (s, 1H), 8.25 (br t, J = 5.9 Hz, 1H), 7.91 (br d, J = 8.3 Hz, 1H), 7.89 (s, 1H), 7.69 (br s, 1H), 7.61 (br d, J = 8.3 Hz, 1H), 6.82-6.74 (m, 2H), 6.73 (d, J = 1.4 Hz, 1H), 6.38 (s, 1H), 4.59 (br t, J = 6.2 Hz, 2H), 3.81-3.76 (m, 2H), 3.74 (s, 3H), 2.24 (s, 3H) |
| 46 | 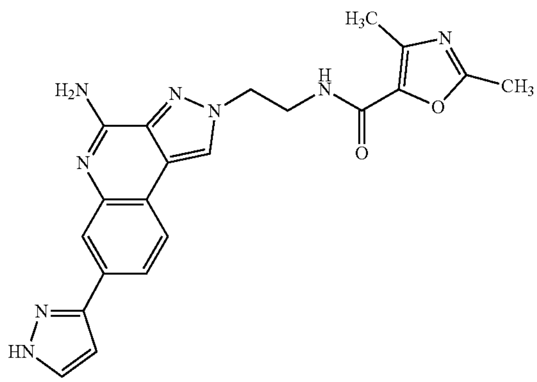 [SMILES: Cc1nc(C)c(C(=O)NCCn2cc3c(n2)c(N)nc2cc(-c4cc[nH]n4)ccc23)o1] | 417.4 | 0.32 | δ 8.69 (s, 1H), 8.47 (br t, J = 5.6 Hz, 1H), 7.92 (br d, J = 8.0 Hz, 1H), 7.88 (s, 1H), 7.75-7.64 (m, 1H), 7.64-7.58 (m, 1H), 6.73 (br s, 3H), 4.58 (br t, J = 6.1 Hz, 2H), 3.77 (q, J = 5.6 Hz, 2H), 2.39 (s, 3H), 2.28 (s, 3H) |
| 47 | 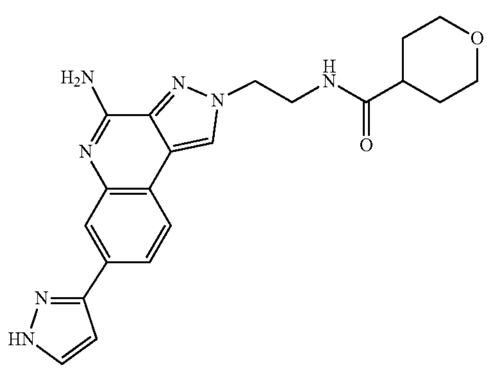 [SMILES: Nc1nc2cc(-c3cc[nH]n3)ccc2c2cn(CCNC(=O)C3CCOCC3)nc12] | 406.2 | 0.96 | δ 8.88 (s, 1H), 8.08 (br d, J = 8.3 Hz, 2H), 7.97 (br t, J = 5.6 Hz, 1H), 7.89-7.83 (m, 1H), 7.83-7.77 (m, 1H), 6.78 (s, 1H), 4.55 (br t, J = 5.8 Hz, 2H), 3.82-3.77 (m, 2H), 3.62 (q, J = 5.4 Hz, 2H), 3.28-3.21 (m, 2H), 2.34-2.26 (m, 1H), 1.55-1.48 (m, 4H) |
| 48 | 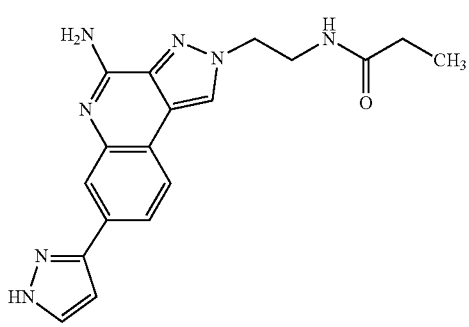 [SMILES: CCC(=O)NCCn1cc2c(n1)c(N)nc1cc(-c3cc[nH]n3)ccc12] | 350.2 | 0.97 | δ 13.55-12.85 (m, 1H), 9.59-9.01 (m, 2H), 8.92 (s, 1H), 8.16-8.08 (m, 2H), 7.90 (br d, J = 8.1 Hz, 1H), 7.86 (br t, J = 5.4 Hz, 1H), 7.83-7.77 (m, 1H), 6.77 (d, J = 1.8 Hz, 1H), 4.57 (t, J = 6.0 Hz, 2H), 3.65 (q, J = 5.7 Hz, 2H), 2.07 (q, J = 7.5 Hz, 2H), 0.98 (t, J = 7.6 Hz, 3H) |

| Ex No. | Structure | LC/MS [M + H]+ | RT (min) | ¹H NMR (500 MHZ, DMSO-d₆) |
|---|---|---|---|---|
| 49 | (structure) | 413.0 | 1.27 | δ 13.35-12.51 (m, 1H), 8.83-8.76 (m, 1H), 8.69 (s, 1H), 7.92-7.88 (m, 2H), 7.86-7.80 (m, 2H), 7.76-7.54 (m, 2H), 7.45-7.41 (m, 1H), 6.71 (d, J = 1.3 Hz, 1H), 6.68-6.53 (m, 2H), 4.68 (t, J = 6.3 Hz, 2H), 3.91 (q, J = 6.1 Hz, 2H), 2.52 (s, 3H) |
| 50 | (structure) | 413.9 | 1.05 | δ 12.99-12.71 (m, 1H), 9.17-9.12 (m, 1H), 8.92 (d, J = 4.7 Hz, 1H), 8.71 (s, 1H), 7.93-7.88 (m, 2H), 7.77 (d, J = 5.0 Hz, 1H), 7.75-7.57 (m, 2H), 6.96-6.78 (m, 2H), 6.73 (s, 1H), 4.66 (br t, J = 6.1 Hz, 2H), 3.89 (q, J = 5.8 Hz, 2H), 2.69 (s, 3H) |
| 51 | (structure) | 430.2 | 0.96 | δ 8.68 (s, 1H), 8.63-8.58 (m, 1H), 7.93-7.90 (m, 2H), 7.81 (d, J = 9.6 Hz, 1H), 7.70-7.59 (m, 2H), 6.98 (d, J = 9.6 Hz, 1H), 6.83-6.59 (m, 3H), 4.64 (t, J = 6.3 Hz, 2H), 3.87-3.81 (m, 2H), 3.70 (s, 3H) |
| 52 | (structure) | 414.3 | 1.04 | δ 9.06 (br t, J = 5.6 Hz, 1H), 8.97 (s, 1H), 8.69 (s, 1H), 8.54 (s, 1H), 7.88 (br d, J = 7.3 Hz, 2H), 7.77-7.50 (m, 2H), 6.69 (br s, 1H), 4.62 (br t, J = 5.6 Hz, 2H), 3.85 (br d, J = 5.8 Hz, 2H), 2.53 (s, 3H) |

-continued

| Ex No. | Structure | LC/MS [M + H]+ | RT (min) | 1H NMR (500 MHZ, DMSO-d6) |
|---|---|---|---|---|
| 53 | 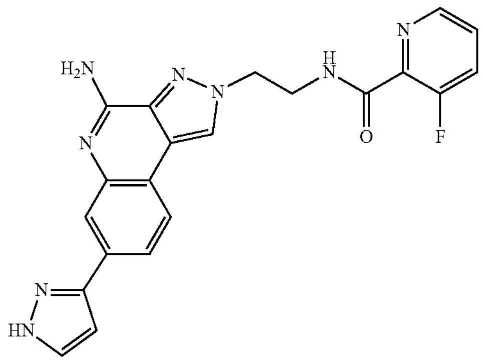 [SMILES: Nc1nc2cc(-c3cc[nH]n3)ccc2c2cn(CCNC(=O)c3ncccc3F)nc12] | 416.9 | 1.09 | δ 13.87-12.93 (m, 1H), 9.81-9.11 (m, 2H), 9.01-8.94 (m, 2H), 8.46 (br d, J = 4.4 Hz, 1H), 8.16-8.06 (m, 2H), 7.90-7.79 (m, 3H), 7.66 (dt, J = 8.4, 4.1 Hz, 1H), 6.78 (s, 1H), 4.71 (br t, J = 5.8 Hz, 2H), 3.89 (q, J = 5.9 Hz, 2H) |
| 54 | 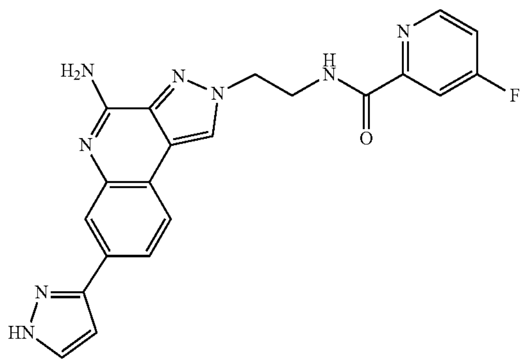 [SMILES: Nc1nc2cc(-c3cc[nH]n3)ccc2c2cn(CCNC(=O)c3cc(F)ccn3)nc12] | 416.8 | 1.13 | δ 13.81-13.44 (m, 1H), 9.92-9.71 (m, 1H), 9.42-9.23 (m, 1H), 9.19 (br t, J = 5.8 Hz, 1H), 8.99 (s, 1H), 8.69-8.65 (m, 1H), 8.13-8.06 (m, 2H), 7.88 (br d, J = 8.3 Hz, 1H), 7.82 (br s, 1H), 7.78 (br d, J = 9.9 Hz, 1H), 7.59-7.51 (m, 1H), 6.78 (s, 1H), 4.73 (br t, J = 5.6 Hz, 2H), 3.92 (q, J = 5.5 Hz, 2H) |
| 55 | 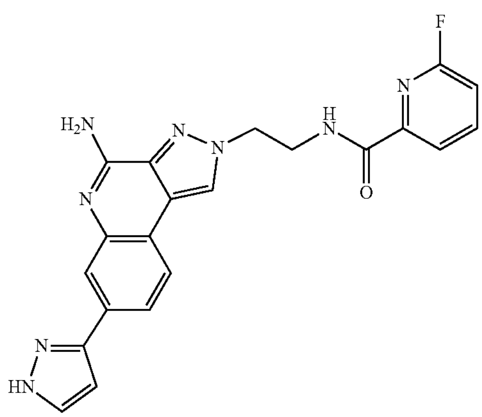 [SMILES: Nc1nc2cc(-c3cc[nH]n3)ccc2c2cn(CCNC(=O)c3cccc(F)n3)nc12] | 417.1 | 1.12 | δ 13.60-12.92 (m, 1H), 9.91-9.60 (m, 1H), 9.28-9.06 (m, 1H), 9.01 (br t, J = 5.6 Hz, 1H), 8.97 (s, 1H), 8.19-8.06 (m, 3H), 7.92 (br d, J = 7.7 Hz, 1H), 7.88 (br d, J = 8.0 Hz, 1H), 7.85-7.77 (m, 1H), 7.41 (br d, J = 8.8 Hz, 1H), 6.78 (s, 1H), 4.72 (br t, J = 5.8 Hz, 2H), 3.90 (q, J = 6.1 Hz, 2H) |
| 56 | 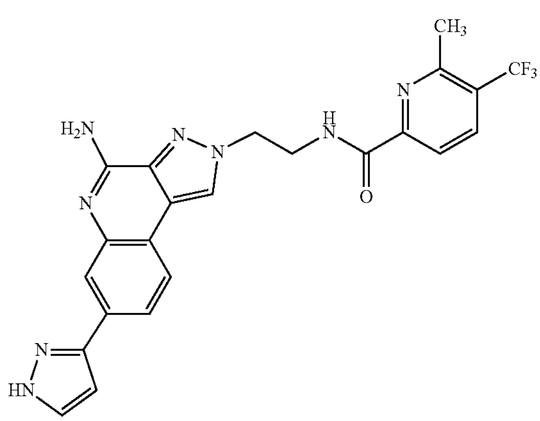 [SMILES: Cc1nc(C(=O)NCCn2cc3c(n2)c(N)nc2cc(-c4cc[nH]n4)ccc23)ccc1C(F)(F)F] | 481.3 | 1.38 | δ 13.75-12.92 (m, 1H), 9.92-9.57 (m, 1H), 9.46-9.17 (m, 1H), 9.16-9.09 (m, 1H), 8.99 (s, 1H), 8.27 (d, J = 8.3 Hz, 1H), 8.14-8.06 (m, 2H), 7.96 (br d, J = 8.0 Hz, 1H), 7.88 (br d, J = 8.3 Hz, 1H), 7.84-7.79 (m, 1H), 6.78 (s, 1H), 4.74 (br t, J = 5.8 Hz, 2H), 3.94 (q, J = 6.1 Hz, 2H), 2.69 (s, 3H) |

-continued

| Ex No. | Structure | LC/MS [M + H]+ | RT (min) | ¹H NMR (500 MHZ, DMSO-d₆) |
|---|---|---|---|---|
| 57 | 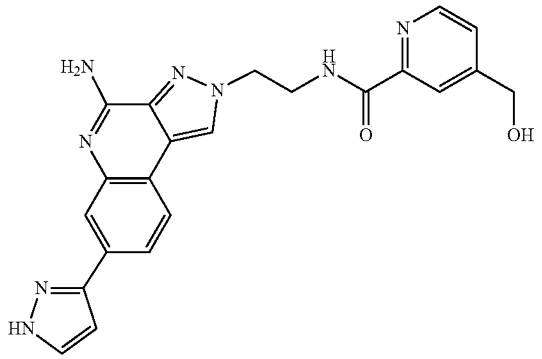 [SMILES: Nc1nc2cc(-c3cc[nH]n3)ccc2c2cn(CCNC(=O)c3cc(CO)ccn3)nc12] | 429.0 | 0.87 | δ 9.10-9.03 (m, 1H), 8.71 (s, 1H), 8.54 (br d, J = 4.6 Hz, 1H), 7.99 (s, 1H), 7.93-7.86 (m, 2H), 7.62 (br s, 1H), 7.50 (br d, J = 4.3 Hz, 1H), 6.73 (br s, 1H), 4.69-4.63 (m, 2H), 4.60 (br d, J = 5.2 Hz, 2H), 3.90 (br d, J = 5.5 Hz, 2H) |
| 58 | 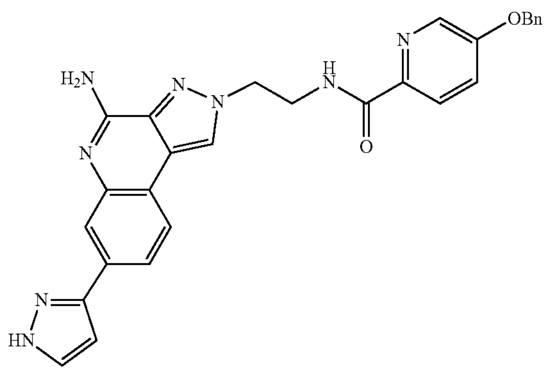 [SMILES: Nc1nc2cc(-c3cc[nH]n3)ccc2c2cn(CCNC(=O)c3ccc(OCc4ccccc4)cn3)nc12] | 505.0 | 1.47 | δ 8.96 (s, 1H), 8.93 (br t, J = 5.8 Hz, 1H), 8.34 (br s, 1H), 8.11 (br s, 1H), 8.08 (br d, J = 7.9 Hz, 1H), 7.95 (br d, J = 8.5 Hz, 1H), 7.87 (br d, J = 7.6 Hz, 1H), 7.82 (br s, 1H), 7.59 (br d, J = 8.5 Hz, 1H), 7.49-7.43 (m, 2H), 7.40 (br t, J = 7.3 Hz, 2H), 7.37-7.31 (m, 1H), 6.78 (br s, 1H), 5.24 (s, 2H), 4.71 (br t, J = 5.5 Hz, 2H), 3.90 (br d, J = 5.8 Hz, 2H) |
| 59 | 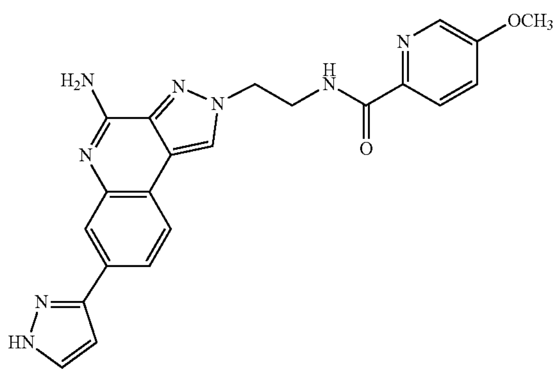 [SMILES: COc1ccc(C(=O)NCCn2cc3c(n2)c(N)nc2cc(-c4cc[nH]n4)ccc23)nc1] | 429.0 | 1.23 | δ 8.90-8.83 (m, 1H), 8.72 (s, 1H), 8.27 (br s, 1H), 7.98 (br d, J = 8.5 Hz, 1H), 7.92 (br d, J = 7.3 Hz, 2H), 7.64 (br s, 1H), 7.52 (br dd, J = 8.4, 2.0 Hz, 1H), 6.74 (br s, 1H), 4.65 (br t, J = 5.8 Hz, 2H), 3.91-3.84 (m, 5H) |
| 60 | 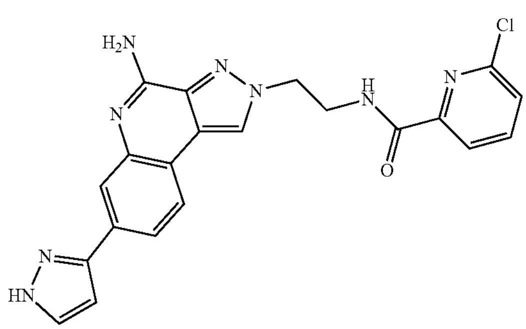 [SMILES: Nc1nc2cc(-c3cc[nH]n3)ccc2c2cn(CCNC(=O)c3cccc(Cl)n3)nc12] | 433.1 | 1.25 | δ 9.04-8.95 (m, 2H), 8.16-8.07 (m, 2H), 8.07-8.01 (m, 1H), 7.97 (br d, J = 7.3 Hz, 1H), 7.88 (br d, J = 7.3 Hz, 1H), 7.83 (br s, 1H), 7.73 (br d, J = 7.9 Hz, 1H), 6.78 (br s, 1H), 4.73 (br t, J = 5.6 Hz, 2H), 3.91 (br d, J = 6.1 Hz, 2H) |

-continued

| Ex No. | Structure | LC/MS [M + H]⁺ | RT (min) | ¹H NMR (500 MHZ, DMSO-d₆) |
|---|---|---|---|---|
| 61 | 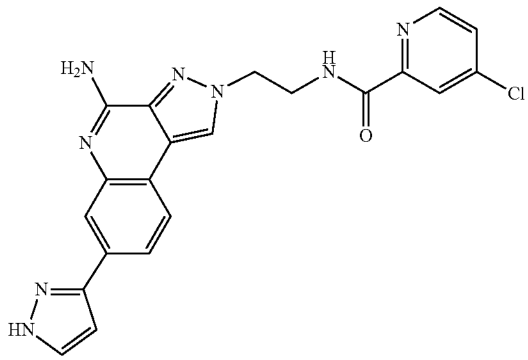 [SMILES: Nc1nc2cc(-c3cc[nH]n3)ccc2c2cn(CCNC(=O)c3cc(Cl)ccn3)nc12] | 433.3 | 1.20 | δ 9.18 (br t, J = 5.3 Hz, 1H), 8.96 (s, 1H), 8.60 (br d, J = 5.2 Hz, 1H), 8.13-8.04 (m, 2H), 7.98 (s, 1H), 7.87 (br d, J = 7.9 Hz, 1H), 7.81 (br s, 1H), 7.75 (br d, J = 4.0 Hz, 1H), 6.78 (br s, 1H), 4.73 (br t, J = 5.3 Hz, 2H), 3.92 (br d, J = 5.5 Hz, 2H) |
| 62 | 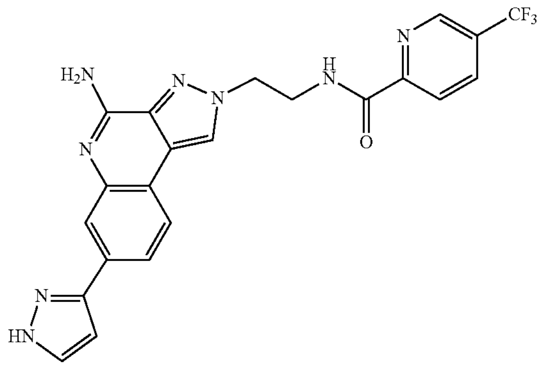 [SMILES: Nc1nc2cc(-c3cc[nH]n3)ccc2c2cn(CCNC(=O)c3ccc(C(F)(F)F)cn3)nc12] | 467.1 | 1.37 | δ 9.33-9.26 (m, 1H), 9.02 (s, 1H), 8.98 (s, 1H), 8.41 (br d, J = 7.9 Hz, 1H), 8.18 (br d, J = 8.2 Hz, 1H), 8.12 (br s, 1H), 8.08 (br d, J = 8.2 Hz, 1H), 7.91-7.80 (m, 2H), 6.78 (br s, 1H), 4.74 (br t, J = 5.5 Hz, 2H), 3.94 (br d, J = 5.5 Hz, 2H) |
| 63 | 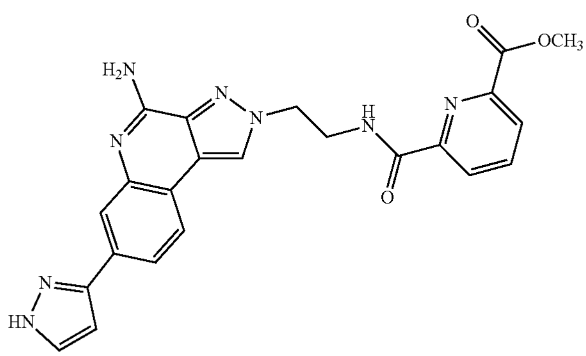 [SMILES: COC(=O)c1cccc(C(=O)NCCn2cc3c(n2)c(N)nc2cc(-c4cc[nH]n4)ccc23)n1] | 457.4 | 1.01 | δ 8.95-8.89 (m, 1H), 8.72 (s, 1H), 8.25-8.15 (m, 3H), 7.93-7.86 (m, 2H), 7.69 (br s, 1H), 7.60 (br d, J = 7.6 Hz, 1H), 6.73 (s, 1H), 4.69 (br t, J = 5.6 Hz, 2H), 3.97-3.90 (m, 2H), 3.89 (s, 3H) |
| 64 | 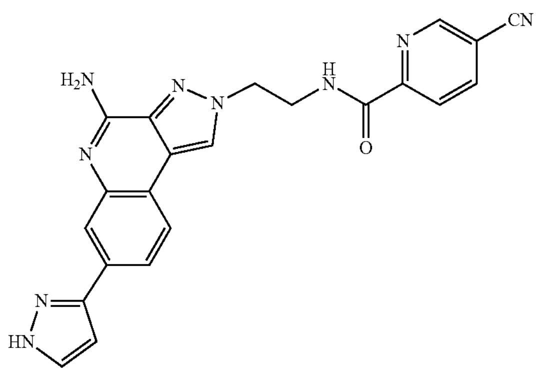 [SMILES: N#Cc1ccc(C(=O)NCCn2cc3c(n2)c(N)nc2cc(-c4cc[nH]n4)ccc23)nc1] | 424.4 | 0.98 | δ 9.31 (br t, J = 5.5 Hz, 1H), 9.10 (s, 1H), 8.97 (s, 1H), 8.50 (br d, J = 7.9 Hz, 1H), 8.13 (br d, J = 8.2 Hz, 1H), 8.08 (br d, J = 7.9 Hz, 1H), 7.87 (br d, J = 7.0 Hz, 2H), 6.77 (br s, 1H), 4.73 (br t, J = 5.6 Hz, 2H), 3.93 (br d, J = 5.8 Hz, 2H) |

| Ex No. | Structure | LC/MS [M + H]+ | RT (min) | ¹H NMR (500 MHZ, DMSO-d₆) |
|---|---|---|---|---|
| 65 | 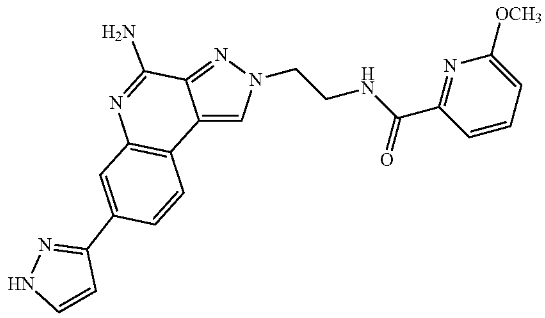 [SMILES: COc1cccc(C(=O)NCCn2cc3c(n2)c(N)nc2cc(-c4cc[nH]n4)ccc23)n1] | 429.3 | 1.19 | δ 8.72 (s, 2H), 7.92-7.82 (m, 3H), 7.77-7.57 (m, 3H), 7.00 (d, J = 8.2 Hz, 1H), 6.73 (s, 1H), 4.66 (br t, J = 6.0 Hz, 2H), 3.89 (br d, J = 6.1 Hz, 2H), 3.87 (s, 3H) |
| 66 | 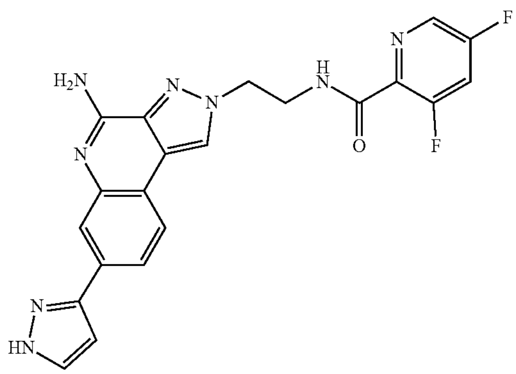 [SMILES: Nc1nc2cc(-c3cc[nH]n3)ccc2c2cn(CCNC(=O)c3ncc(F)cc3F)nc12] | 435.3 | 0.96 | δ 8.99 (s, 1H), 8.97-8.93 (m, 1H), 8.55 (br s, 1H), 8.16-8.02 (m, 3H), 7.89 (br d, J = 7.9 Hz, 1H), 7.83 (br s, 1H), 6.78 (br s, 1H), 4.71 (br s, 2H), 3.88 (br d, J = 5.2 Hz, 2H) |
| 67 | 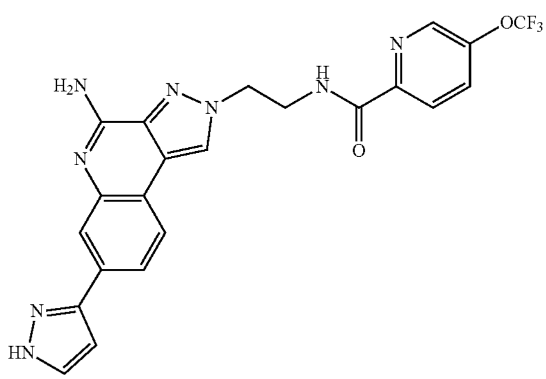 [SMILES: Nc1nc2cc(-c3cc[nH]n3)ccc2c2cn(CCNC(=O)c3ccc(OC(F)(F)F)cn3)nc12] | 483.3 | 1.26 | δ 9.12 (br t, J = 5.3 Hz, 1H), 8.71 (s, 2H), 8.15 (br d, J = 8.5 Hz, 1H), 8.06 (br d, J = 8.8 Hz, 1H), 7.92-7.85 (m, 2H), 7.69 (br s, 1H), 7.61 (br d, J = 5.5 Hz, 1H), 6.73 (s, 1H), 4.66 (br t, J = 5.8 Hz, 2H), 3.89 (br q, J = 5.5 Hz, 2H) |
| 68 | 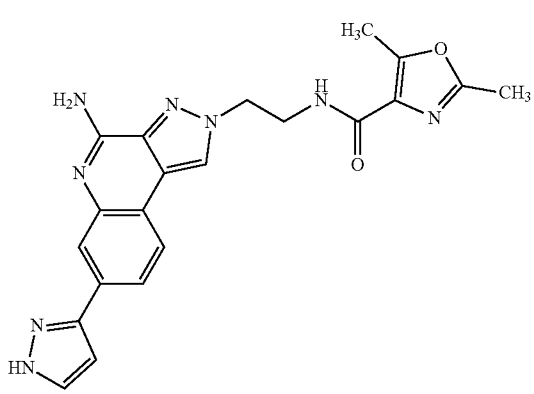 [SMILES: Cc1nc(C(=O)NCCn2cc3c(n2)c(N)nc2cc(-c4cc[nH]n4)ccc23)c(C)o1] | 417.3 | 1.12 | δ 8.68 (s, 1H), 8.32 (br t, J = 5.5 Hz, 1H), 7.95-7.84 (m, 2H), 7.77-7.55 (m, 2H), 6.73 (br s, 1H), 4.59 (br t, J = 5.8 Hz, 2H), 3.78 (br d, J = 5.8 Hz, 2H), 2.47 (s, 3H), 2.35 (s, 3H) |

| Ex No. | Structure | LC/MS [M + H]+ | RT (min) | ¹H NMR (500 MHZ, DMSO-d₆) |
|---|---|---|---|---|
| 69 | 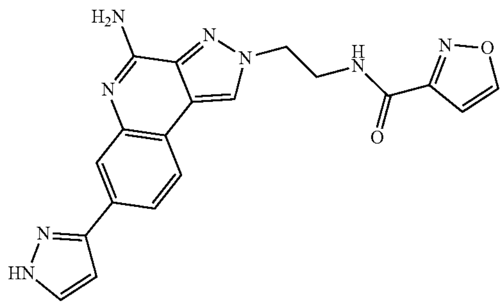 [SMILES: Nc1nc2cc(-c3cc[nH]n3)ccc2c2cn(CCNC(=O)c3ccon3)nc12] | 389.3 | 0.86 | δ 9.07-8.97 (m, 2H), 8.91 (br s, 1H), 8.12 (br s, 1H), 8.05 (br d, J = 7.9 Hz, 1H), 7.83 (br s, 2H), 6.83 (s, 1H), 6.78 (br s, 1H), 4.68 (br t, J = 5.3 Hz, 2H), 3.85 (br q, J = 5.3 Hz, 2H) |
| 70 | 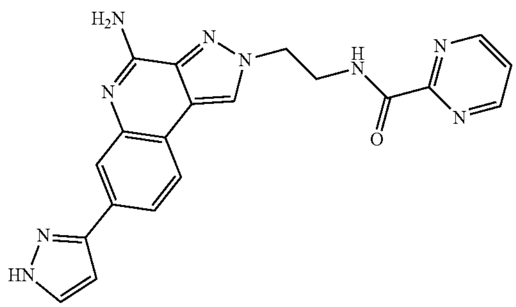 [SMILES: Nc1nc2cc(-c3cc[nH]n3)ccc2c2cn(CCNC(=O)c3ncccn3)nc12] | 400.3 | 0.79 | δ 9.22 (br s, 1H), 8.94 (br d, J = 4.6 Hz, 3H), 8.12-8.07 (m, 1H), 8.05 (br d, J = 8.2 Hz, 1H), 7.83 (br s, 2H), 7.67 (br t, J = 4.6 Hz, 1H), 6.77 (br s, 1H), 4.76-4.68 (m, 2H), 3.95-3.88 (m, 2H) |
| 71 | 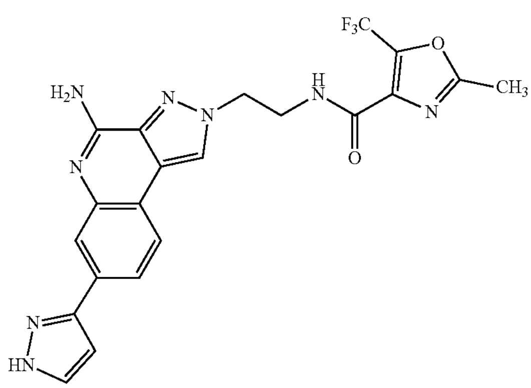 [SMILES: Cc1nc(C(=O)NCCn2cc3c(n2)c(N)nc2cc(-c4cc[nH]n4)ccc23)c(C(F)(F)F)o1] | 471.2 | 1.21 | δ 8.96 (s, 1H), 8.89 (br t, J = 5.6 Hz, 1H), 8.10 (br d, J = 8.5 Hz, 2H), 7.90 (br d, J = 8.2 Hz, 1H), 7.82 (br s, 1H), 6.79 (s, 1H), 4.68 (br t, J = 5.5 Hz, 2H), 3.84 (br d, J = 5.8 Hz, 2H), 2.52 (br s, 3H) |
| 72 | 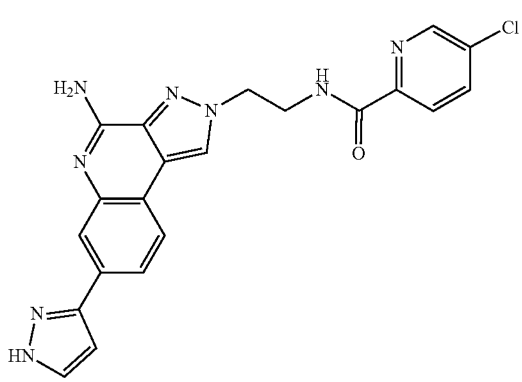 [SMILES: Nc1nc2cc(-c3cc[nH]n3)ccc2c2cn(CCNC(=O)c3ccc(Cl)cn3)nc12] | 433.3 | 1.25 | δ 9.09 (br t, J = 5.5 Hz, 1H), 8.70 (s, 1H), 8.67 (s, 1H), 8.10 (br d, J = 7.9 Hz, 1H), 8.02 (br d, J = 8.5 Hz, 1H), 7.93-7.86 (m, 2H), 7.63 (br s, 1H), 6.73 (br s, 1H), 4.65 (br t, J = 5.8 Hz, 2H), 3.88 (br d, J = 5.8 Hz, 2H) |

| Ex No. | Structure | LC/MS [M + H]+ | RT (min) | ¹H NMR (500 MHZ, DMSO-d₆) |
|---|---|---|---|---|
| 73 | 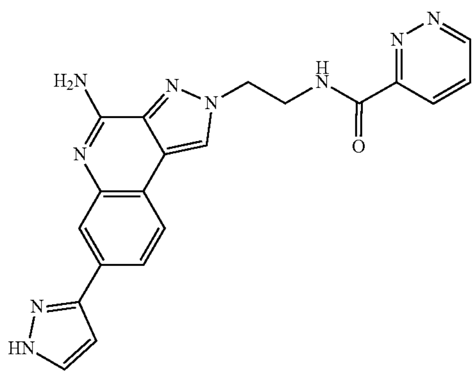 [SMILES: Nc1nc2cc(-c3cc[nH]n3)ccc2c2cn(CCNC(=O)c3cccnn3)nc12] | 400.2 | 0.97 | δ 9.56 (br t, J = 5.6 Hz, 1H), 9.39 (br d, J = 4.9 Hz, 1H), 8.87 (br s, 1H), 8.17 (br d, J = 8.2 Hz, 1H), 8.00 (br d, J = 8.2 Hz, 2H), 7.89 (br dd, J = 8.2, 5.2 Hz, 1H), 7.76 (br s, 2H), 6.76 (br s, 1H), 4.73 (br t, J = 5.6 Hz, 2H), 3.95 (br d, J = 5.8 Hz, 2H) |
| 74 | 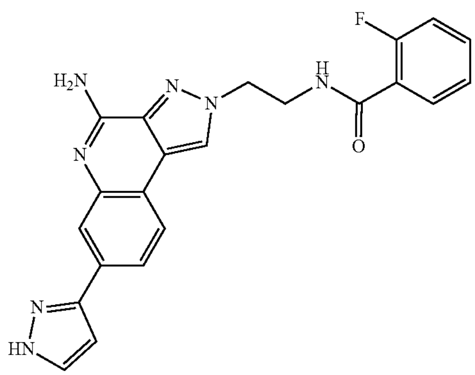 [SMILES: Nc1nc2cc(-c3cc[nH]n3)ccc2c2cn(CCNC(=O)c3ccccc3F)nc12] | 416.1 | 1.19 | δ 8.71 (s, 1H), 8.53 (br s, 1H), 7.94-7.84 (m, 2H), 7.69 (br s, 1H), 7.63 (br d, J = 7.6 Hz, 1H), 7.59 (br t, J = 7.2 Hz, 1H), 7.55-7.45 (m, 1H), 7.32-7.21 (m, 2H), 6.74 (s, 1H), 4.63 (br t, J = 5.6 Hz, 2H), 3.82 (br d, J = 5.8 Hz, 2H) |
| 75 | 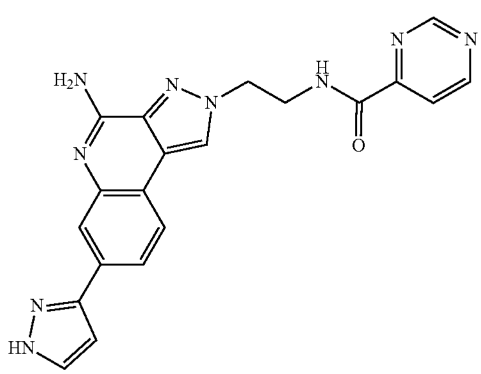 [SMILES: Nc1nc2cc(-c3cc[nH]n3)ccc2c2cn(CCNC(=O)c3ccncn3)nc12] | 400.2 | 1.00 | δ 9.30 (br s, 2H), 9.04 (br d, J = 4.9 Hz, 1H), 8.71 (s, 1H), 7.98 (br d, J = 4.6 Hz, 1H), 7.94-7.86 (m, 2H), 7.69 (br s, 1H), 7.63 (br d, J = 6.7 Hz, 1H), 6.73 (s, 1H), 4.66 (br t, J = 5.8 Hz, 2H), 3.90 (br d, J = 5.8 Hz, 2H) |
| 76 | 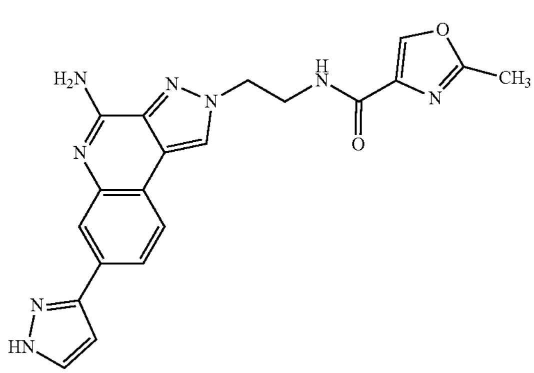 [SMILES: Cc1nc(C(=O)NCCn2cc3c(n2)c(N)nc2cc(-c4cc[nH]n4)ccc23)co1] | 403.4 | 0.91 | δ 8.69 (s, 1H), 8.49 (br t, J = 5.3 Hz, 1H), 8.43 (s, 1H), 7.95-7.88 (m, 2H), 7.77-7.58 (m, 2H), 6.74 (br s, 1H), 4.60 (br t, J = 6.0 Hz, 2H), 3.80 (br d, J = 5.8 Hz, 2H), 2.43 (s, 3H) |

-continued

| Ex No. | Structure | LC/MS [M + H]+ | RT (min) | 1H NMR (500 MHZ, DMSO-d6) |
|---|---|---|---|---|
| 77 | 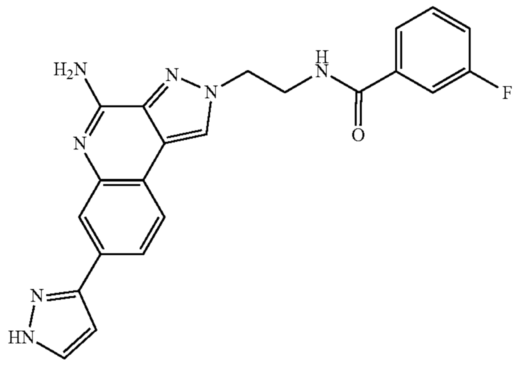 [SMILES: Nc1nc2cc(-c3cc[nH]n3)ccc2c2cn(CCNC(=O)c3cccc(F)c3)nc12] | 415.8 | 1.23 | δ 8.80-8.75 (m, 1H), 8.71 (s, 1H), 7.93-7.87 (m, 2H), 7.69 (br s, 1H), 7.65 (br d, J = 7.6 Hz, 1H), 7.63-7.56 (m, 2H), 7.54-7.47 (m, 1H), 7.37 (br t, J = 7.6 Hz, 1H), 6.73 (s, 1H), 4.62 (br t, J = 5.5 Hz, 2H), 3.82 (br d, J = 5.8 Hz, 2H) |
| 78 | 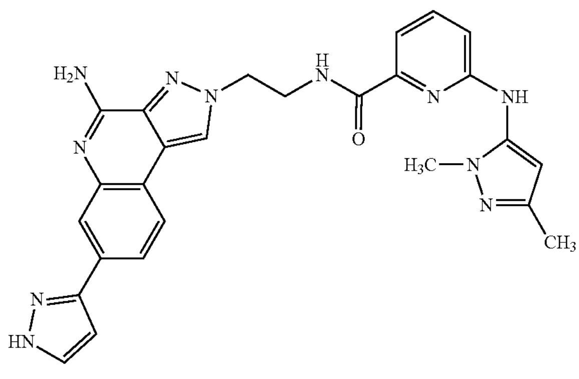 [SMILES: Cc1cc(Nc2cccc(C(=O)NCCn3cc4c(n3)c(N)nc3cc(-c5cc[nH]n5)ccc34)n2)n(C)n1] | 508.1 | 0.96 | δ 8.87 (s, 1H), 8.71 (s, 1H), 8.28-8.23 (m, 1H), 7.89 (br d, J = 4.9 Hz, 2H), 7.75-7.69 (m, 2H), 7.61 (br s, 1H), 7.40 (br d, J = 7.0 Hz, 1H), 6.90 (br d, J = 8.2 Hz, 1H), 6.73 (br s, 1H), 5.97 (s, 1H), 4.65 (br s, 2H), 3.89 (br d, J = 5.5 Hz, 2H), 3.54 (s, 3H), 1.96 (s, 3H) |
| 79 | 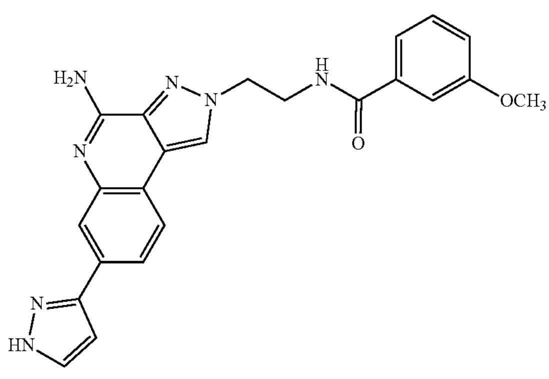 [SMILES: COc1cccc(C(=O)NCCn2cc3c(n2)c(N)nc2cc(-c4cc[nH]n4)ccc23)c1] | 428.3 | 1.16 | δ 8.70 (s, 1H), 8.66 (br t, J = 5.0 Hz, 1H), 7.94-7.87 (m, 2H), 7.61 (br s, 1H), 7.39-7.30 (m, 3H), 7.07 (br d, J = 7.3 Hz, 1H), 6.73 (s, 1H), 4.62 (br t, J = 5.5 Hz, 2H), 3.81 (br d, J = 5.2 Hz, 2H), 3.75 (s, 3H) |
| 80 | 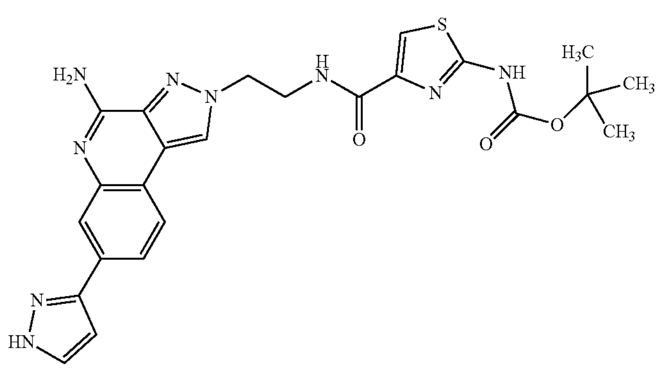 [SMILES: CC(C)(C)OC(=O)Nc1nc(C(=O)NCCn2cc3c(n2)c(N)nc2cc(-c4cc[nH]n4)ccc23)cs1] | 520.1 | 1.41 | δ 8.74 (s, 1H), 8.06 (br t, J = 5.3 Hz, 1H), 7.97-7.89 (m, 2H), 7.73 (s, 1H), 7.66 (br s, 1H), 6.74 (br s, 1H), 4.63 (br t, J = 5.5 Hz, 2H), 3.85 (br d, J = 5.8 Hz, 2H), 1.47 (s, 9H) |

| Ex No. | Structure | LC/MS [M + H]+ | RT (min) | 1H NMR (500 MHZ, DMSO-d6) |
| --- | --- | --- | --- | --- |
| 81 | 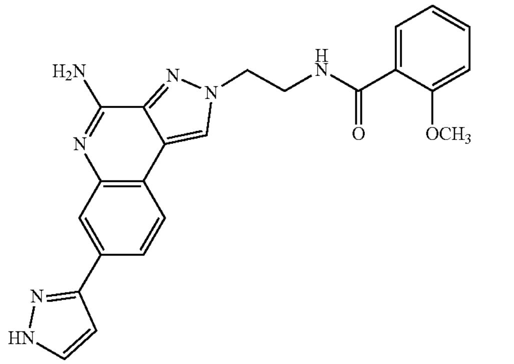 [SMILES: COc1ccccc1C(=O)NCCn1cc2c(n1)c(N)nc1cc(-c3cc[nH]n3)ccc12] | 428.1 | 1.23 | δ 8.98 (s, 1H), 8.37-8.32 (m, 1H), 8.11 (br d, J = 8.2 Hz, 2H), 7.89 (br d, J = 7.6 Hz, 1H), 7.83 (br s, 1H), 7.67 (br d, J = 7.3 Hz, 1H), 7.44 (br t, J = 7.8 Hz, 1H), 7.08 (br d, J = 8.2 Hz, 1H), 7.00 (br t, J = 7.3 Hz, 1H), 6.79 (br s, 1H), 4.71 (br t, J = 4.9 Hz, 2H), 3.89 (br d, J = 5.2 Hz, 2H), 3.74 (s, 3H) |
| 82 | 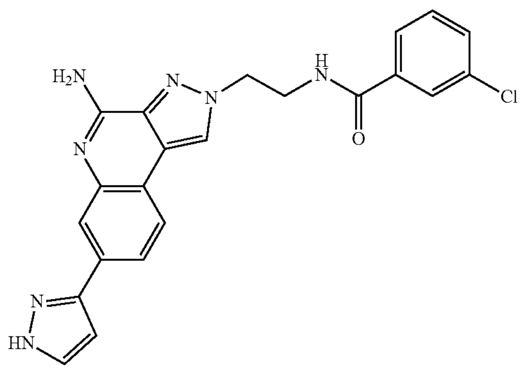 [SMILES: Nc1nc2cc(-c3cc[nH]n3)ccc2c2cn(CCNC(=O)c3cccc(Cl)c3)nc12] | 432.0 | 1.24 | δ 8.79 (br t, J = 5.2 Hz, 1H), 8.70 (s, 1H), 7.92-7.86 (m, 2H), 7.81 (s, 1H), 7.74 (br d, J = 7.6 Hz, 1H), 7.69 (br s, 1H), 7.61 (br d, J = 7.9 Hz, 1H), 7.58 (br d, J = 7.9 Hz, 1H), 7.48 (t, J = 7.8 Hz, 1H), 6.73 (s, 1H), 4.62 (br t, J = 5.6 Hz, 2H), 3.82 (br d, J = 5.5 Hz, 2H) |
| 83 | 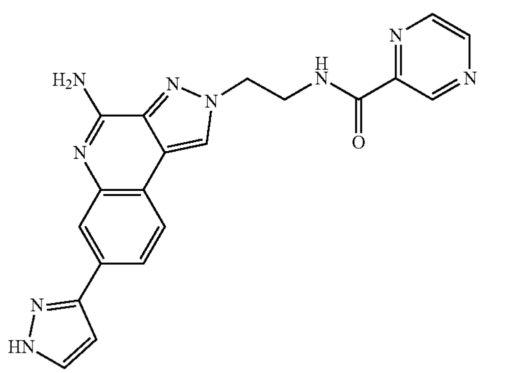 [SMILES: Nc1nc2cc(-c3cc[nH]n3)ccc2c2cn(CCNC(=O)c3cnccn3)nc12] | 400.3 | 1.02 | δ 9.22-9.13 (m, 2H), 8.86 (s, 1H), 8.70 (br s, 2H), 7.92-7.86 (m, 2H), 7.69 (br s, 1H), 7.60 (br d, J = 7.9 Hz, 1H), 6.73 (s, 1H), 4.66 (br t, J = 5.8 Hz, 2H), 3.93-3.86 (m, 2H) |
| 84 | 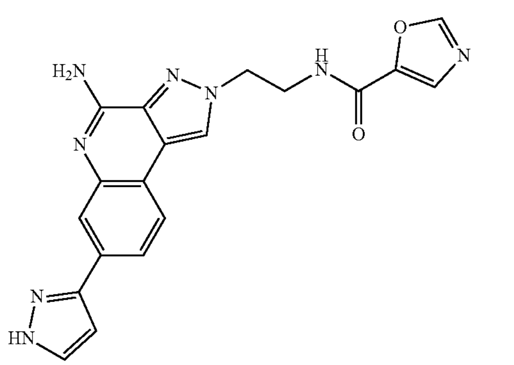 [SMILES: Nc1nc2cc(-c3cc[nH]n3)ccc2c2cn(CCNC(=O)c3cnco3)nc12] | 389.3 | 0.79 | δ 8.99 (br s, 1H), 8.85 (br s, 2H), 8.55 (s, 1H), 8.15 (br s, 1H), 8.10 (br d, J = 7.9 Hz, 1H), 7.87 (br d, J = 19.5 Hz, 2H), 7.74 (s, 1H), 6.79 (br s, 1H), 4.68 (br s, 2H), 3.83 (br d, J = 4.9 Hz, 2H) |

| Ex No. | Structure | LC/MS [M + H]⁺ | RT (min) | ¹H NMR (500 MHZ, DMSO-d₆) |
|---|---|---|---|---|
| 85 | 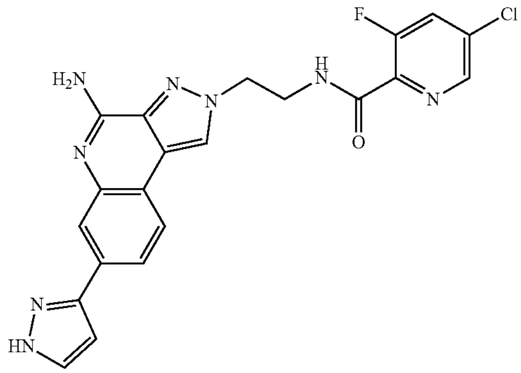 [SMILES: Nc1nc2cc(-c3cc[nH]n3)ccc2c2cn(CCNC(=O)c3ncc(Cl)cc3F)nc12] | 451.3 | 1.36 | δ 8.97 (br s, 1H), 8.68 (s, 1H), 8.53 (br s, 1H), 8.19 (br d, J = 10.1 Hz, 1H), 7.93-7.86 (m, 2H), 7.68 (br s, 1H), 7.61 (br d, J = 7.3 Hz, 1H), 6.73 (br s, 1H), 4.63 (br s, 2H), 3.85 (br d, J = 5.2 Hz, 2H) |
| 86 | 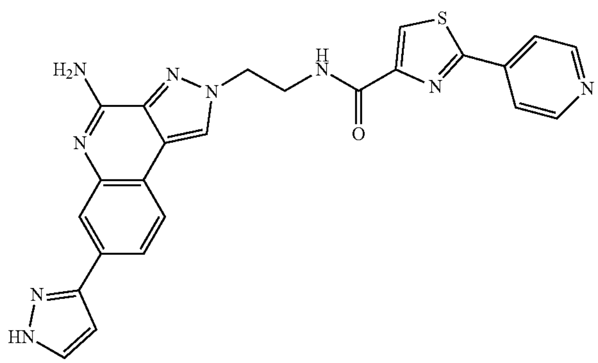 [SMILES: Nc1nc2cc(-c3cc[nH]n3)ccc2c2cn(CCNC(=O)c3csc(-c4ccncc4)n3)nc12] | 482.2 | 0.95 | δ 8.81 (br t, J = 5.6 Hz, 1H), 8.75 (s, 1H), 8.72 (br d, J = 4.9 Hz, 2H), 8.45 (s, 1H), 7.95 (br d, J = 4.9 Hz, 2H), 7.93-7.87 (m, 2H), 7.69 (br s, 1H), 7.61 (br d, J = 7.9 Hz, 1H), 6.73 (s, 1H), 4.68 (br t, J = 6.0 Hz, 2H), 3.90 (br d, J = 4.9 Hz, 2H) |
| 87 | 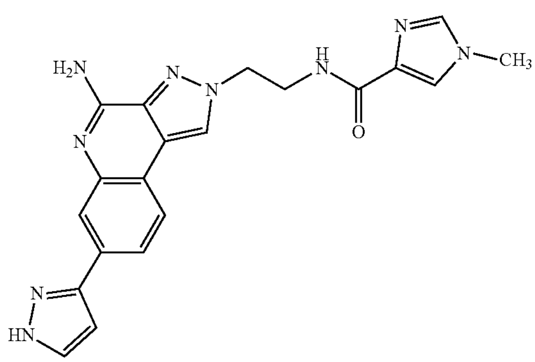 [SMILES: Cn1cnc(C(=O)NCCn2cc3c(n2)c(N)nc2cc(-c4cc[nH]n4)ccc23)c1] | 402.0 | 0.72 | δ 8.95 (s, 1H), 8.27 (br t, J = 5.0 Hz, 1H), 8.13-8.06 (m, 2H), 7.89 (br d, J = 8.2 Hz, 1H), 7.81 (br s, 1H), 7.70 (s, 1H), 7.61 (s, 1H), 6.79 (s, 1H), 4.67 (br t, J = 5.6 Hz, 2H), 3.84 (br d, J = 5.8 Hz, 2H), 3.66 (s, 3H) |
| 88 | 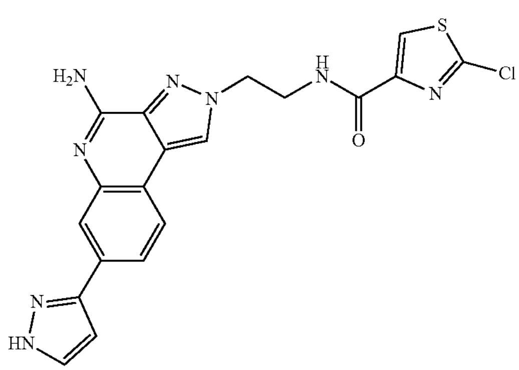 [SMILES: Nc1nc2cc(-c3cc[nH]n3)ccc2c2cn(CCNC(=O)c3csc(Cl)n3)nc12] | 439.2 | 1.16 | δ 8.95 (s, 1H), 8.79 (br t, J = 5.5 Hz, 1H), 8.21 (s, 1H), 8.09 (br d, J = 6.7 Hz, 2H), 7.88 (br d, J = 8.2 Hz, 1H), 7.81 (s, 1H), 6.78 (br s, 1H), 4.68 (br t, J = 5.5 Hz, 2H), 3.85 (br d, J = 5.5 Hz, 2H) |

-continued

| Ex No. | Structure | LC/MS [M + H]+ | RT (min) | 1H NMR (500 MHZ, DMSO-d6) |
|---|---|---|---|---|
| 89 | 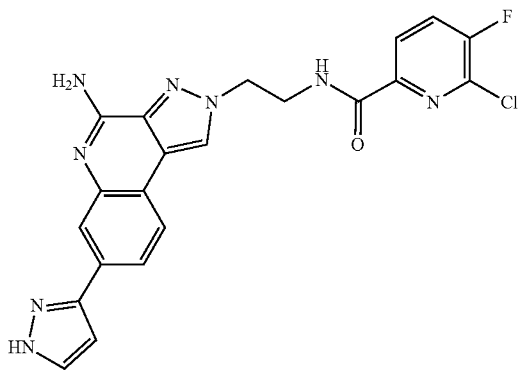 [SMILES: Nc1nc2cc(-c3cc[nH]n3)ccc2c2cn(CCNC(=O)c3ccc(F)c(Cl)n3)nc12] | 451.0 | 1.27 | δ 9.00 (br t, J = 5.8 Hz, 1H), 8.73 (s, 1H), 8.11-8.04 (m, 2H), 7.93 (br d, J = 8.2 Hz, 2H), 7.84-7.58 (m, 2H), 6.74 (br s, 1H), 4.66 (br t, J = 5.8 Hz, 2H), 3.87 (br d, J = 5.8 Hz, 2H) |
| 90 | 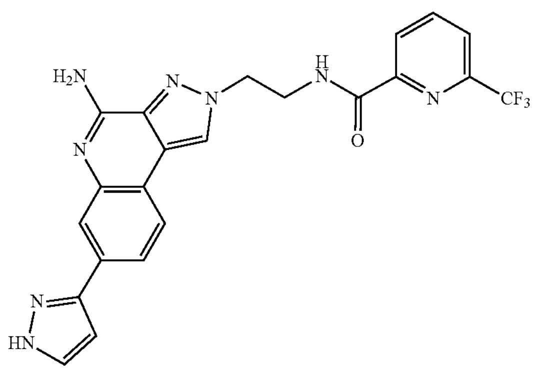 [SMILES: Nc1nc2cc(-c3cc[nH]n3)ccc2c2cn(CCNC(=O)c3cccc(C(F)(F)F)n3)nc12] | 467.1 | 1.30 | δ 8.99 (s, 2H), 8.30-8.22 (m, 2H), 8.10 (br dd, J = 13.7, 7.6 Hz, 3H), 7.88 (br d, J = 7.6 Hz, 1H), 7.83 (br s, 1H), 6.78 (br s, 1H), 4.75 (br t, J = 5.8 Hz, 2H), 3.94 (br d, J = 5.8 Hz, 2H) |
| 91 | 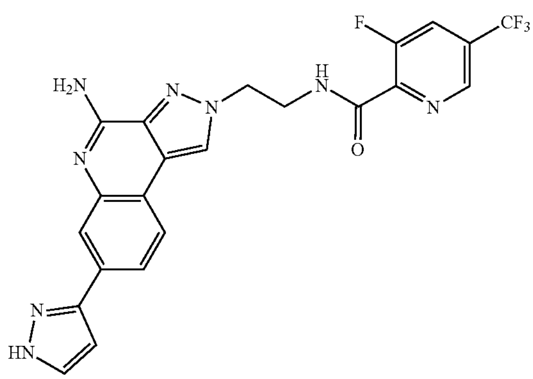 [SMILES: Nc1nc2cc(-c3cc[nH]n3)ccc2c2cn(CCNC(=O)c3ncc(C(F)(F)F)cc3F)nc12] | 485.3 | 1.18 | δ 9.09 (br t, J = 5.5 Hz, 1H), 8.87 (s, 1H), 8.70 (s, 1H), 8.45 (br d, J = 10.4 Hz, 1H), 7.93-7.86 (m, 2H), 7.69 (br s, 1H), 7.61 (br d, J = 7.6 Hz, 1H), 6.73 (d, J = 1.5 Hz, 1H), 4.65 (br t, J = 5.8 Hz, 2H), 3.88 (br d, J = 6.1 Hz, 2H) |
| 92 | 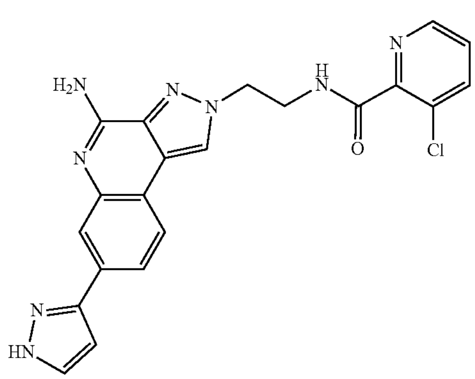 [SMILES: Nc1nc2cc(-c3cc[nH]n3)ccc2c2cn(CCNC(=O)c3ncccc3Cl)nc12] | 432.9 | 1.05 | δ 8.97 (s, 1H), 8.93-8.87 (m, 1H), 8.53 (dd, J = 4.5, 1.2 Hz, 1H), 8.16-8.06 (m, 2H), 8.01-7.96 (m, 1H), 7.89 (br d, J = 7.2 Hz, 1H), 7.85-7.77 (m, 1H), 7.53 (dd, J = 8.3, 4.7 Hz, 1H), 6.78 (br s, 1H), 4.75-4.64 (m, 2H), 3.94-3.83 (m, 2H) |

-continued

| Ex No. | Structure | LC/MS [M + H]⁺ | RT (min) | ¹H NMR (500 MHZ, DMSO-d₆) |
|---|---|---|---|---|
| 93 | 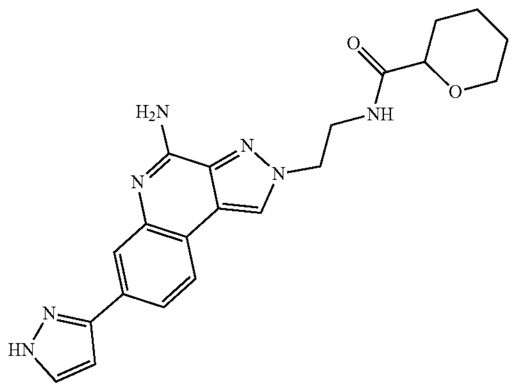 [SMILES: Nc1nc2cc(-c3cc[nH]n3)ccc2c2cn(CCNC(=O)C3CCCCO3)nc12] | 406.4 | 1.02 | δ 8.88 (s, 1H), 8.12-8.08 (m, 2H), 7.94-7.87 (m, 2H), 7.81 (br s, 1H), 6.79 (s, 1H), 4.58 (q, J = 5.6 Hz, 2H), 3.48 (br s, 4H), 3.39 (br t, J = 10.2 Hz, 1H), 1.77-1.67 (m, 2H), 1.51-1.39 (m, 3H), 1.29-1.17 (m, 1H) |
| 94 | 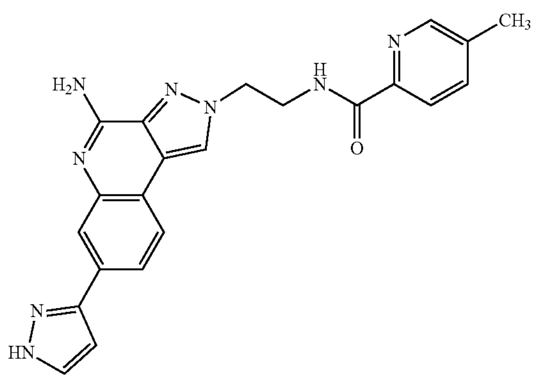 [SMILES: Cc1ccc(C(=O)NCCn2cc3c(n2)c(N)nc2cc(-c4cc[nH]n4)ccc23)nc1] | 413.0 | 1.04 | δ 9.01-8.95 (m, 1H), 8.69 (s, 1H), 8.44 (s, 1H), 7.89 (br s, 3H), 7.77 (br d, J = 8.2 Hz, 1H), 7.69 (br s, 1H), 7.62 (br d, J = 7.6 Hz, 1H), 6.73 (s, 1H), 4.65 (br t, J = 5.6 Hz, 2H), 3.88 (br d, J = 3.7 Hz, 2H), 2.35 (s, 3H) |
| 95 | 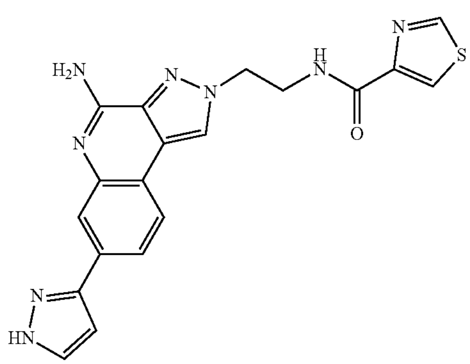 [SMILES: Nc1nc2cc(-c3cc[nH]n3)ccc2c2cn(CCNC(=O)c3cscn3)nc12] | 405.1 | 0.88 | δ 9.13 (d, J = 1.5 Hz, 1H), 8.74 (br t, J = 5.6 Hz, 1H), 8.70 (s, 1H), 8.29 (d, J = 1.5 Hz, 1H), 7.94-7.86 (m, 2H), 7.69 (br s, 1H), 7.62 (br d, J = 7.3 Hz, 1H), 6.73 (d, J = 1.5 Hz, 1H), 4.64 (br t, J = 6.0 Hz, 2H), 3.86 (br d, J = 6.1 Hz, 2H) |
| 96 | 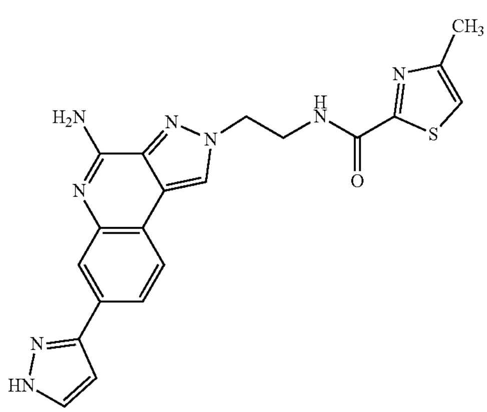 [SMILES: Cc1csc(C(=O)NCCn2cc3c(n2)c(N)nc2cc(-c4cc[nH]n4)ccc23)n1] | 419.3 | 1.14 | δ 9.00 (br t, J = 5.9 Hz, 1H), 8.89 (s, 1H), 8.08-8.01 (m, 2H), 7.81 (br dd, J = 15.1, 6.6 Hz, 2H), 7.56 (s, 1H), 6.77 (s, 1H), 4.69 (br t, J = 5.9 Hz, 2H), 3.89-3.83 (m, 2H), 2.40 (s, 3H) |

| Ex No. | Structure | LC/MS [M + H]+ | RT (min) | ¹H NMR (500 MHZ, DMSO-d₆) |
|---|---|---|---|---|
| 97 | 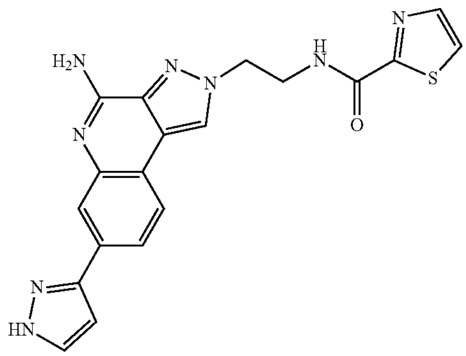 [SMILES: Nc1nc2cc(-c3cc[nH]n3)ccc2c2cn(CCNC(=O)c3nccs3)nc12] | 405.2 | 1.00 | δ 9.14-9.07 (m, 1H), 8.97 (s, 1H), 8.15-8.05 (m, 2H), 8.04-7.97 (m, 2H), 7.88 (br d, J = 5.8 Hz, 1H), 7.83 (br s, 1H), 6.79 (br s, 1H), 4.72 (br t, J = 5.6 Hz, 2H), 3.89 (br d, J = 5.2 Hz, 2H) |
| 98 | 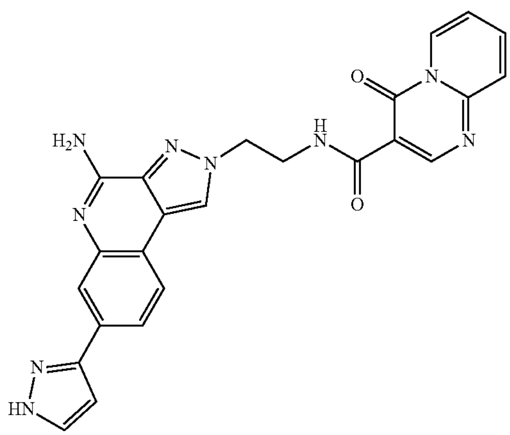 [SMILES: Nc1nc2cc(-c3cc[nH]n3)ccc2c2cn(CCNC(=O)c3cnc4ccccn4c3=O)nc12] | 466.3 | 1.05 | δ 9.19 (br t, J = 5.5 Hz, 1H), 9.12 (br d, J = 7.0 Hz, 1H), 8.99 (d, J = 3.7 Hz, 2H), 8.21-8.15 (m, 1H), 8.10 (br s, 1H), 8.08 (br d, J = 8.2 Hz, 1H), 7.90-7.84 (m, 2H), 7.82 (br s, 1H), 7.58 (br t, J = 6.9 Hz, 1H), 6.78 (s, 1H), 4.74 (br t, J = 5.5 Hz, 2H), 3.99 (br d, J = 5.8 Hz, 2H) |
| 99 | 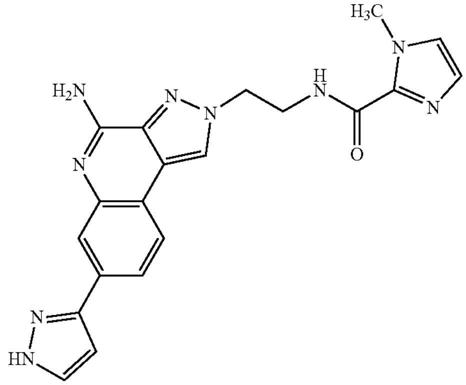 [SMILES: Cn1ccnc1C(=O)NCCn1cc2c(n1)c(N)nc1cc(-c3cc[nH]n3)ccc12] | 402.2 | 0.79 | δ 8.76-8.62 (m, 2H), 7.93-7.86 (m, 2H), 7.69 (br s, 1H), 7.62 (br d, J = 7.9 Hz, 1H), 7.32 (s, 1H), 6.96 (s, 1H), 6.73 (s, 1H), 4.61 (br t, J = 5.8 Hz, 2H), 3.90 (s, 3H), 3.80 (br d, J = 5.8 Hz, 2H) |

| Ex No. | Structure | LC/MS [M + H]+ | RT (min) | 1H NMR (500 MHZ, DMSO-d6) |
|---|---|---|---|---|
| 100 | 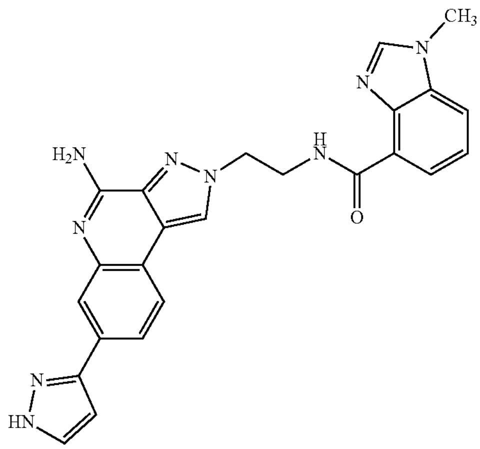 [SMILES: Cn1cnc2c(C(=O)NCCn3cc4c(n3)c(N)nc3cc(-c5cc[nH]n5)ccc34)cccc21] | 452.3 | 0.98 | δ 9.83 (br d, J = 5.5 Hz, 1H), 9.01 (s, 1H), 8.38 (s, 1H), 8.10 (s, 1H), 8.03 (br d, J = 8.2 Hz, 1H), 7.94 (s, 1H), 7.88 (br dd, J = 12.5, 7.9 Hz, 2H), 7.83-7.78 (m, 2H), 7.41 (br t, J = 7.8 Hz, 1H), 6.78 (s, 1H), 4.81-4.75 (m, 2H), 4.07 (br d, J = 5.5 Hz, 2H), 3.87 (s, 3H) |
| 101 | 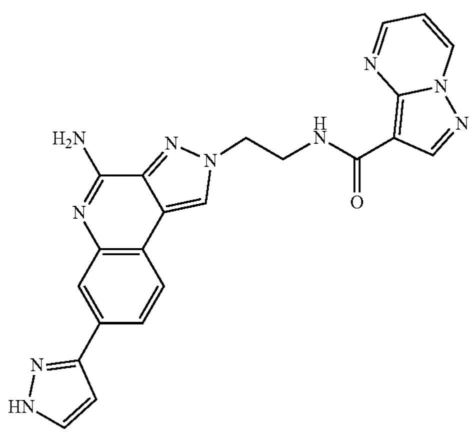 [SMILES: Nc1nc2cc(-c3cc[nH]n3)ccc2c2cn(CCNC(=O)c3cnn4cccnc34)nc12] | 439.3 | 1.04 | δ 9.25 (br d, J = 7.0 Hz, 1H), 8.73 (s, 1H), 8.62 (br d, J = 3.4 Hz, 1H), 8.57 (s, 1H), 8.18 (br t, J = 5.2 Hz, 1H), 7.92-7.86 (m, 2H), 7.69 (br s, 1H), 7.61 (br d, J = 7.6 Hz, 1H), 7.21 (dd, J = 6.7, 4.3 Hz, 1H), 6.73 (s, 1H), 4.67 (br t, J = 5.6 Hz, 2H), 3.96 (br d, J = 5.5 Hz, 2H) |

Example 102. Preparation of 2-{2-[4-amino-7-(1H-pyrazol-3-yl)-2H-pyrazolo[3,4-c]quinolin-2-yl]ethyl}-2,3-dihydro-1H-isoindol-1-one

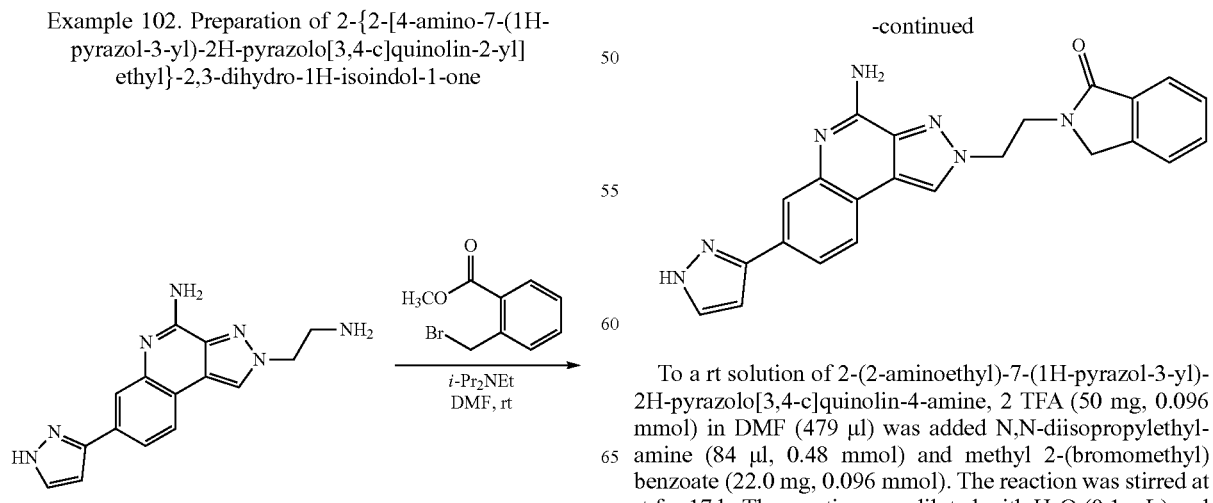

To a rt solution of 2-(2-aminoethyl)-7-(1H-pyrazol-3-yl)-2H-pyrazolo[3,4-c]quinolin-4-amine, 2 TFA (50 mg, 0.096 mmol) in DMF (479 μl) was added N,N-diisopropylethylamine (84 μl, 0.48 mmol) and methyl 2-(bromomethyl)benzoate (22.0 mg, 0.096 mmol). The reaction was stirred at rt for 17 h. The reaction was diluted with H2O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-(4-amino-7-(1H-pyrazol-3-yl)-2H-pyrazolo[3,4-c]quinolin-2-yl)ethyl)isoindolin-1-one (6.5 mg, 16%). $^1$H NMR (500 MHz, DMSO-d$_6$) δ 8.73 (s, 1H), 7.88 (br s, 1H), 7.86 (br d, J=7.7 Hz, 1H), 7.76-7.52 (m, 5H), 7.48-7.43 (m, 1H), 6.72 (br s, 1H), 6.82-6.70 (m, 2H), 4.73 (br t, J=5.8 Hz, 2H), 4.33 (s, 2H), 4.12 (br t, J=5.5 Hz, 2H). Analytical LC/MS conditions Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 410.0 [M+H]$^+$; RT: 1.11 min.

Example 103. Preparation of 2-{2-[4-amino-7-(1H-pyrazol-3-yl)-2H-pyrazolo[3,4-c]quinolin-2-yl]ethyl}-6-fluoro-2,3-dihydro-1H-isoindol-1-one

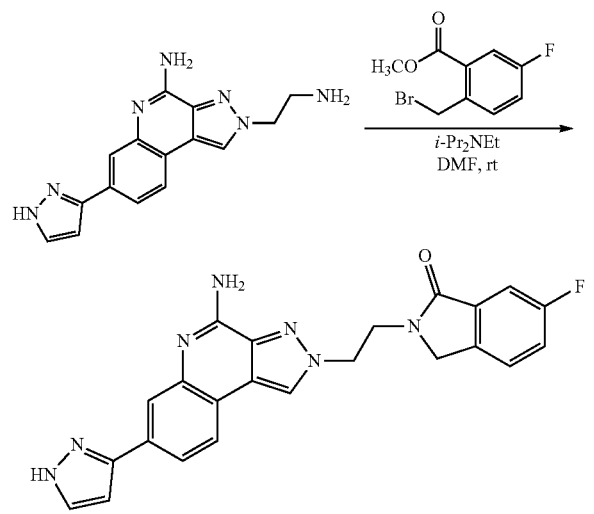

To a rt solution of 2-(2-aminoethyl)-7-(1H-pyrazol-3-yl)-2H-pyrazolo[3,4-c]quinolin-4-amine, 2 TFA (50 mg, 0.096 mmol) in DMF (479 µl) was added N,N-diisopropylethylamine (84 µl, 0.48 mmol) and methyl 2-(bromomethyl)-5-fluorobenzoate (23.7 mg, 0.096 mmol. The reaction was stirred at rt for 2 h. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 4% B, 4-44% B over 20 minutes, then a 4-minute hold at 100% B; Flow Rate: 20 mL/min; Column Tempera-ture: 25° C. Fraction collection was triggered by MS signals. Fractions containing the desired product were combined and dried via centrifugal evaporation to provide 2-(2-(4-amino-7-(1H-pyrazol-3-yl)-2H-pyrazolo[3,4-c]quinolin-2-yl)ethyl)-6-fluoroisoindolin-1-one, TFA (16.1 mg, 30%). $^1$H NMR (500 MHz, DMSO-d$_6$) δ 8.96 (s, 1H), 8.14-8.05 (m, 1H), 8.02 (br d, J=8.3 Hz, 1H), 7.89-7.76 (m, 2H), 7.61 (dd, J=8.3, 4.4 Hz, 1H), 7.47-7.33 (m, 2H), 6.77 (s, 1H), 4.81 (br t, J=5.6 Hz, 2H), 4.39 (s, 2H), 4.14 (br t, J=5.5 Hz, 2H). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). m/z 428.3 [M+H]$^+$; RT: 1.35 min.

Example 104. Preparation of 2-{2-[4-amino-7-(1H-pyrazol-3-yl)-2H-pyrazolo[3,4-c]quinolin-2-yl]ethyl}-5-chloro-2,3-dihydro-1H-isoindol-1-one

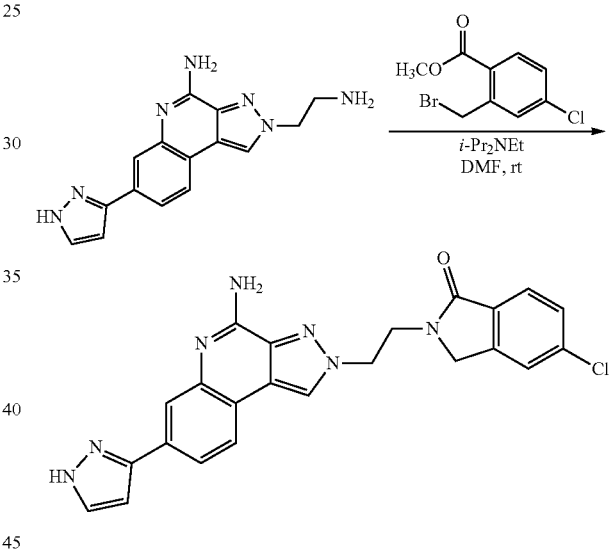

To a rt solution of 2-(2-aminoethyl)-7-(1H-pyrazol-3-yl)-2H-pyrazolo[3,4-c]quinolin-4-amine, 2 TFA (50 mg, 0.096 mmol) in DMF (479 µl) was added N,N-diisopropylethylamine (84 µl, 0.479 mmol) and methyl 2-(bromomethyl)-4-chlorobenzoate (25.3 mg, 0.096 mmol). The reaction was stirred at rt for 2 h. The reaction was diluted with H$_2$O (0.1 mL) and DMF (to a total volume of 2 mL), filtered (syringe filter), and via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 11% B, 11-51% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide 2-(2-(4-amino-7-(1H-pyrazol-3-yl)-2H-pyrazolo[3,4-c]quinolin-2-yl)ethyl)-5-chloroisoindolin-1-one (11.9 mg, 28%). $^1$H NMR (500 MHz, DMSO-d$_6$) δ 8.77 (s, 1H), 7.93 (br s, 1H), 7.89 (br d, J=8.3 Hz, 1H), 7.77-7.59 (m, 4H), 7.50 (br d, J=8.0 Hz, 1H), 6.74 (s, 1H), 4.74 (br t, J=5.5 Hz, 2H), 4.35 (s, 2H), 4.10 (br t, J=5.4 Hz, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 mm, then a 0.0 mi hold at 100% B; Flow: 1 mL/min; Detection: MS and UV (220 nm). m/z 444.1 [M+H]*; RT: 1.37 min.

Example 105. Preparation of 2-(2-{[(2-methylphenyl)methyl]amino}ethyl)-7-(1H-pyrazol-3-yl)-2H-pyrazolo[3,4-c]quinolin-4-amine

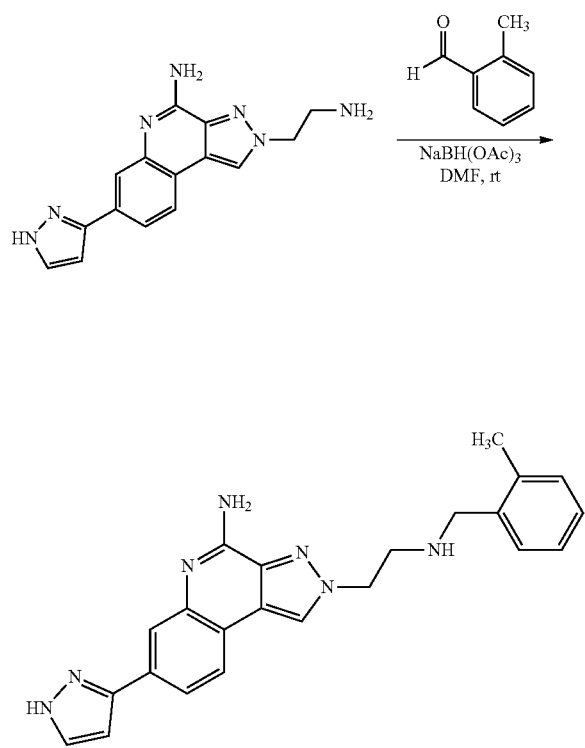

To a rt solution of 2-(2-aminoethyl)-7-(1H-pyrazol-3-yl)-2H-pyrazolo[3,4-c]quinolin-4-amine, 2 TFA (35 mg, 0.067 mmol) in DMF (336 μl) was added 2-methylbenzaldehyde (10.1 μl, 0.087 mmol), followed by sodium triacetoxyborohydride (42.7 mg, 0.201 mmol). The reaction was stirred at rt for 1 h. The reaction was diluted with H$_2$O (100 μL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 0% B, 0-60% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-((2-methylbenzyl)amino)ethyl)-7-(1H-pyrazol-3-yl)-2H-pyrazolo[3,4-c]quinolin-4-amine, 2 TFA (17.5 mg, 40%). $^1$H NMR (500 MHz, DMSO-d$_6$) δ 9.02 (s, 1H), 8.16-8.10 (m, 2H), 7.92 (br d, J=8.3 Hz, 1H), 7.83 (br s, 1H), 7.44 (br d, J=7.2 Hz, 1H), 7.34-7.29 (m, 1H), 7.29-7.24 (m, 2H), 6.80 (s, 1H), 4.91 (br t, J=5.6 Hz, 2H), 4.28 (s, 2H), 3.76-3.69 (m, 2H), 2.36 (s, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 398.1 [M+H]$^+$; RT: 1.08 min.

Examples 106 to 112 were prepared according to synthetic procedures similar to those described for Example 105 from the appropriate starting materials. For Examples 106 and 108, triethylamine (2.5 equiv.) was added to the starting material prior to addition of the other reagents. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex No. | Structure | LC/MS [M + H]$^+$ | RT (min) | $^1$H NMR (500 MHZ, DMSO-d$_6$) |
|---|---|---|---|---|
| 106 | 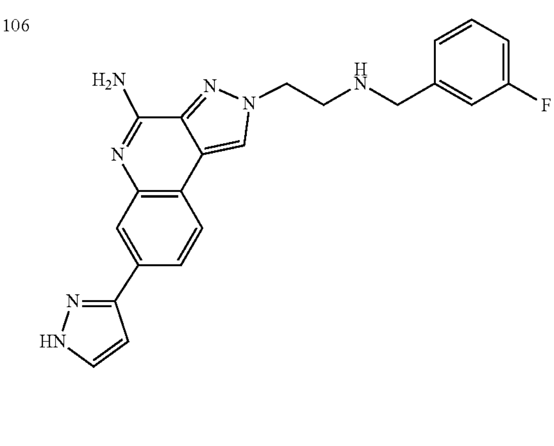 | 402.2 | 0.84 | δ 8.66 (s, 1H), 7.92 (d, J = 8.1 Hz, 1H), 7.89 (s, 1H), 7.67 (br s, 1H), 7.62 (br d, J = 7.8 Hz, 1H), 7.33-7.27 (m, 1H), 7.13-7.07 (m, 2H), 6.99 (br t, J = 8.5 Hz, 1H), 6.71 (s, 1H), 6.53 (br s, 2H), 4.51 (t, J = 6.0 Hz, 2H), 3.75 (s, 2H), 3.06 (t, J = 6.1 Hz, 2H) |

| Ex No. | Structure | LC/MS [M + H]+ | RT (min) | ¹H NMR (500 MHZ, DMSO-d₆) |
|---|---|---|---|---|
| 107 | 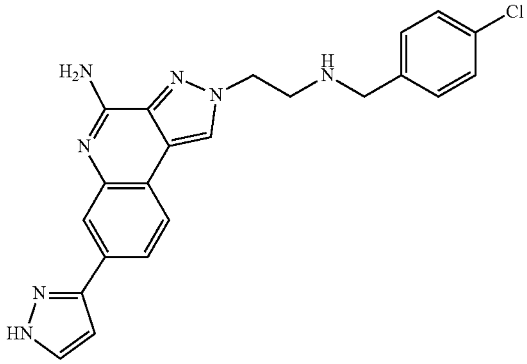 [SMILES: Nc1nc2cc(-c3cc[nH]n3)ccc2c2cn(CCNCc3ccc(Cl)cc3)nc12] | 418.2 | 0.92 | δ 8.66 (s, 1H), 7.93 (d, J = 8.1 Hz, 1H), 7.90 (d, J = 1.1 Hz, 1H), 7.67 (d, J = 1.7 Hz, 1H), 7.64 (dd, J = 8.1, 1.4 Hz, 1H), 7.30 (s, 4H), 6.71 (d, J = 2.1 Hz, 1H), 4.51 (t, J = 6.1 Hz, 2H), 3.72 (s, 2H), 3.07 (t, J = 6.1 Hz, 2H) |
| 108 | 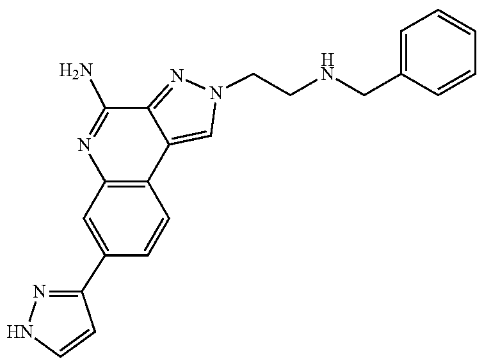 [SMILES: Nc1nc2cc(-c3cc[nH]n3)ccc2c2cn(CCNCc3ccccc3)nc12] | 384.1 | 0.98 | δ 8.69 (s, 1H), 7.92 (d, J = 8.0 Hz, 1H), 7.88 (s, 1H), 7.69 (br s, 1H), 7.62 (br d, J = 8.5 Hz, 1H), 7.30-7.24 (m, 4H), 7.23-7.17 (m, 1H), 6.73 (d, J = 1.9 Hz, 1H), 6.81-6.65 (m, 2H), 4.50 (t, J = 6.1 Hz, 2H), 3.72 (s, 2H), 3.04 (br t, J = 6.2 Hz, 2H) |
| 109 | 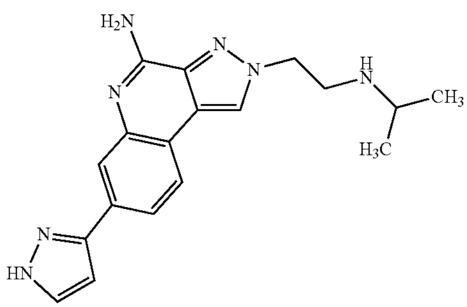 [SMILES: CC(C)NCCn1cc2c(n1)c(N)nc1cc(-c3cc[nH]n3)ccc12] | 336.0 | 1.04 | δ 8.67 (s, 1H), 7.92 (d, J = 8.0 Hz, 1H), 7.89 (d, J = 1.4 Hz, 1H), 7.67 (s, 1H), 7.64-7.61 (m, 1H), 6.71 (d, J = 2.0 Hz, 1H), 4.47 (t, J = 6.3 Hz, 2H), 3.09 (t, J = 6.4 Hz, 2H), 2.79-2.73 (m, 1H), 0.97 (d, J = 6.3 Hz, 6H) |
| 110 | 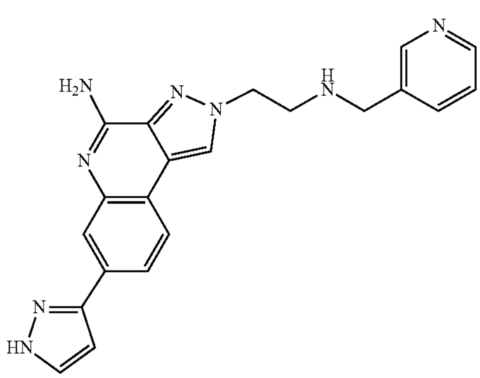 [SMILES: Nc1nc2cc(-c3cc[nH]n3)ccc2c2cn(CCNCc3cccnc3)nc12] | 385.0 | 0.92 | δ 8.68 (s, 1H), 8.46 (s, 1H), 8.39 (d, J = 4.7 Hz, 1H), 7.93 (d, J = 8.0 Hz, 1H), 7.88 (s, 1H), 7.70-7.66 (m, 2H), 7.63 (d, J = 7.7 Hz, 1H), 7.29 (dd, J = 7.8, 4.8 Hz, 1H), 6.73 (d, J = 1.7 Hz, 1H), 4.51 (br t, J = 5.9 Hz, 2H), 3.04 (br t, J = 5.8 Hz, 3H) |

| Ex No. | Structure | LC/MS [M + H]⁺ | RT (min) | ¹H NMR (500 MHZ, DMSO-d₆) |
|---|---|---|---|---|
| 111 | 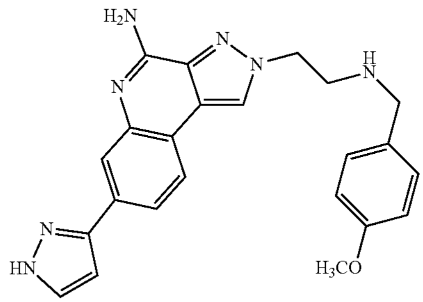 [SMILES: COc1ccc(CNCCn2cc3c(n2)c(N)nc2cc(-c4cc[nH]n4)ccc23)cc1] | 414.1 | 0.99 | δ 8.69 (s, 1H), 7.92 (d, J = 8.3 Hz, 1H), 7.89 (s, 1H), 7.69 (br s, 1H), 7.62 (br d, J = 8.3 Hz, 1H), 7.21 (d, J = 8.5 Hz, 2H), 6.84 (d, J = 8.5 Hz, 2H), 6.73 (s, 1H), 6.80-6.70 (m, 2H), 4.51 (br t, J = 6.2 Hz, 2H), 3.70 (s, 3H), 3.68 (s, 2H), 3.05 (br t, J = 6.1 Hz, 2H) |
| 112 | 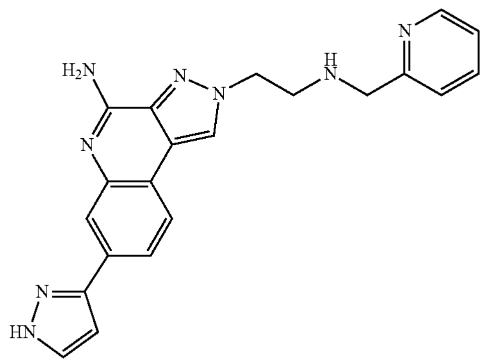 [SMILES: Nc1nc2cc(-c3cc[nH]n3)ccc2c2cn(CCNCc3ccccn3)nc12] | 385.3 | 0.94 | δ 8.75 (s, 1H), 8.49 (br d, J = 4.3 Hz, 1H), 7.95 (br d, J = 7.9 Hz, 1H), 7.92 (br s, 1H), 7.72 (br d, J = 7.6 Hz, 2H), 7.66 (br d, J = 7.3 Hz, 1H), 7.37 (br d, J = 7.6 Hz, 1H), 7.30-7.24 (m, 1H), 6.74 (s, 1H), 4.63-4.58 (m, 2H), 3.96 (s, 2H), 3.22 (br t, J = 6.0 Hz, 2H) |

Example 113. Preparation of N-{2-[4-amino-7-(1H-pyrazol-3-yl)-2H-pyrazolo[3,4-c]quinolin-2-yl]ethyl}methanesulfonamide

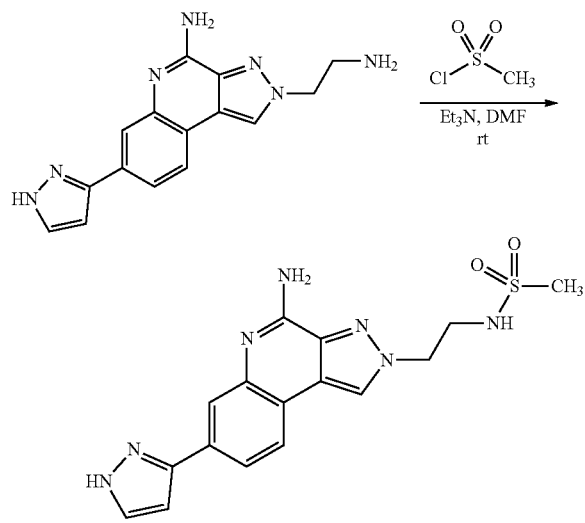

To a rt solution of 2-(2-aminoethyl)-7-(1H-pyrazol-3-yl)-2H-pyrazolo[3,4-c]quinolin-4-amine, 2 TFA (35 mg, 0.067 mmol) in DMF (224 μl) was added triethylamine (37.4 μl, 0.269 mmol), followed by methanesulfonyl chloride (8.1 mg, 0.070 mmol). The reaction was stirred at rt for 1 h. The reaction was diluted with H₂O (0.1 mL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 13% B, 13-36% B over 25 minutes, then a 2-minute hold at 100% B; Flow Rate: 20 mL/min; Column Temperature: 25° C. Fraction collection was triggered by UV signals. Fractions containing the desired product were combined and dried via centrifugal evaporation to provide N-(2-(4-amino-7-(1H-pyrazol-3-yl)-2H-pyrazolo[3,4-c]quinolin-2-yl)ethyl)methanesulfonamide, TFA (6.1 mg, 19%). ¹H NMR (500 MHz, DMSO-d₆) δ 8.97 (s, 1H), 8.16-8.09 (m, 2H), 7.90 (br d, J=8.5 Hz, 1H), 7.82 (br s, 1H), 7.33 (br t, J=5.8 Hz, 1H), 6.80 (s, 1H), 4.62 (br t, J=5.6 Hz, 2H), 3.60-3.56 (m, 2H), 2.90 (s, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 372 [M+H]⁺; RT: 0.94 min.

Example 114. Preparation of N-{2-[4-amino-7-(1H-pyrazol-3-yl)-2H-pyrazolo[3,4-c]quinolin-2-yl]ethyl}benzenesulfonamide

Example 115. Preparation of 3-{2-[4-amino-7-(1H-pyrazol-3-yl)-2H-pyrazolo[3,4-c]quinolin-2-yl]ethyl}-1-phenylurea

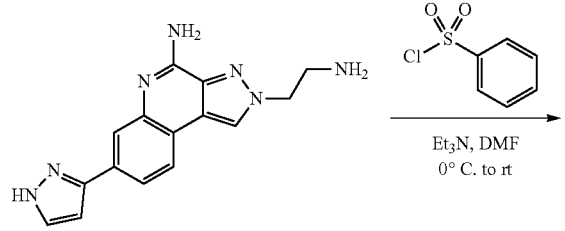

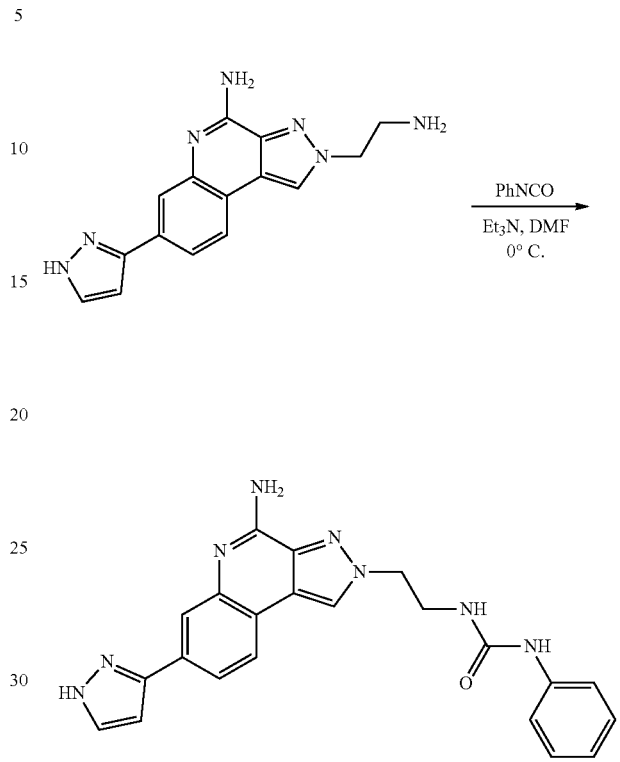

To a 0° C. solution of 2-(2-aminoethyl)-7-(1H-pyrazol-3-yl)-2H-pyrazolo[3,4-c]quinolin-4-amine, 2 TFA (51 mg, 0.098 mmol) in DMF (326 µl) was added triethylamine (54.5 µl, 0.391 mmol), followed by benzenesulfonyl chloride (13.1 µl, 0.103 mmol), dropwise. The reaction was stirred at rt for 1 h. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 11% B, 11-51% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide N-(2-(4-amino-7-(1H-pyrazol-3-yl)-2H-pyrazolo[3,4-c]quinolin-2-yl)ethyl)benzenesulfonamide (34.3 mg, 80%). $^1$H NMR (500 MHz, DMSO-d$_6$) δ 8.59 (s, 1H), 7.92-7.88 (m, 2H), 7.87-7.80 (m, 1H), 7.78-7.74 (m, 2H), 7.71-7.60 (m, 2H), 7.58-7.48 (m, 3H), 6.72 (d, J=2.0 Hz, 1H), 6.68-6.52 (m, 2H), 4.49 (t, J=6.1 Hz, 2H), 3.40 (br t, J=6.1 Hz, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). m/z 434.3 [M+H]$^+$; RT: 1 min.

To a 0° C. solution of 2-(2-aminoethyl)-7-(1H-pyrazol-3-yl)-2H-pyrazolo[3,4-c]quinolin-4-amine, 2 TFA (40 mg, 0.077 mmol) in DMF (384 µl) was added triethylamine (42.8 µl, 0.307 mmol), followed by phenyl isocyanate (8.3 µl, 0.077 mmol). The reaction was stirred at 0° C. for 1 h. The reaction was diluted with H$_2$O (0.2 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 1-(2-(4-amino-7-(1H-pyrazol-3-yl)-2H-pyrazolo[3,4-c]quinolin-2-yl)ethyl)-3-phenylurea (16.5 mg, 52%). $^1$H NMR (500 MHz, DMSO-d$_6$) δ 8.73 (s, 1H), 8.55 (s, 1H), 7.93 (br d, J=8.0 Hz, 1H), 7.89 (s, 1H), 7.72-7.66 (m, 1H), 7.62 (br d, J=8.0 Hz, 1H), 7.37 (br d, J=7.7 Hz, 2H), 7.21 (t, J=8.0 Hz, 2H), 6.89 (t, J=7.3 Hz, 1H), 6.83-6.75 (m, 2H), 6.73 (d, J=1.7 Hz, 1H), 6.33-6.29 (m, 1H), 4.53 (br t, J=5.5 Hz, 2H), 3.72-3.66 (m, 2H). Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 413.1 [M+H]$^+$; RT: 1.14 min.

Example 116. Preparation of 1-{2-[4-amino-7-(1H-pyrazol-3-yl)-2H-pyrazolo[3,4-c]quinolin-2-yl]ethyl}-3,3-dimethylurea

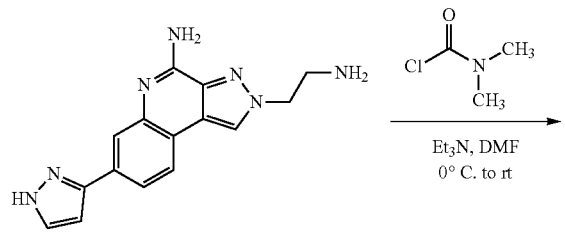

Example 117. Preparation of phenyl N-{2-[4-amino-7-(1H-pyrazol-3-yl)-2H-pyrazolo[3,4-c]quinolin-2-yl]ethyl}carbamate

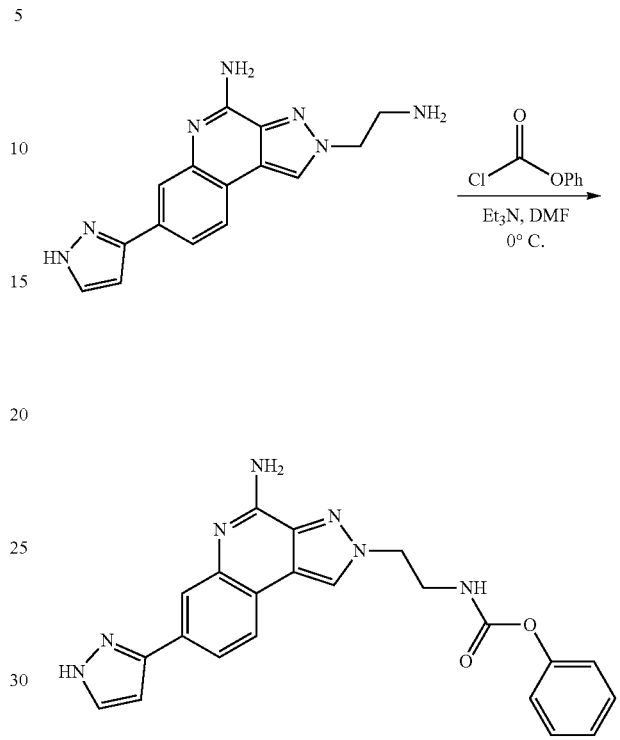

To a 0° C. solution of 2-(2-aminoethyl)-7-(1H-pyrazol-3-yl)-2H-pyrazolo[3,4-c]quinolin-4-amine, 2 TFA (40 mg, 0.077 mmol) in DMF (384 µl) was added triethylamine (42.8 µl, 0.307 mmol), followed by dimethylcarbamyl chloride (7.1 µl, 0.077 mmol). The reaction was stirred at 0° C. for 30 min, then at rt for 1.5 h. The reaction was diluted with H$_2$O (0.2 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 3-(2-(4-amino-7-(1H-pyrazol-3-yl)-2H-pyrazolo[3,4-c]quinolin-2-yl)ethyl)-1,1-dimethylurea (20.5 mg, 73%). $^1$H NMR (500 MHz, DMSO-d$_6$) δ 8.64 (s, 1H), 7.94 (br d, J=8.3 Hz, 1H), 7.88 (s, 1H), 7.76-7.54 (m, 2H), 6.73 (br s, 3H), 6.50 (br t, J=5.4 Hz, 1H), 4.47 (br t, J=5.9 Hz, 2H), 3.57-3.52 (m, 2H), 2.75 (s, 6H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 365.3 [M+H]$^+$; RT: 0.89 min.

To a 0° C. solution of 2-(2-aminoethyl)-7-(1H-pyrazol-3-yl)-2H-pyrazolo[3,4-c]quinolin-4-amine, 2 TFA (40 mg, 0.077 mmol) in DMF (384 µl) was added triethylamine (42.8 µl, 0.307 mmol), followed by phenyl chloroformate (9.6 µl, 0.077 mmol). The reaction was stirred at 0° C. for 30 min. The reaction was diluted with H$_2$O (0.2 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 5% B, 5-45% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide phenyl (2-(4-amino-7-(1H-pyrazol-3-yl)-2H-pyrazolo[3,4-c]quinolin-2-yl)ethyl)carbamate, TFA (4.9 mg, 12%). $^1$H NMR (500 MHz, DMSO-d$_6$) δ 9.95-9.67 (m, 1H), 9.34-9.20 (m, 1H), 9.01 (s, 1H), 8.15 (br d, J=8.5 Hz, 1H), 8.12 (br s, 1H), 7.96 (br t, J=5.9 Hz, 1H), 7.92 (br d, J=8.0 Hz, 1H), 7.82 (br s, 1H), 7.30 (br t, J=7.6 Hz, 2H), 7.19-7.14 (m, 1H), 7.02 (br d, J=7.7 Hz, 2H), 6.80 (s, 1H), 4.64 (br t, J=5.4 Hz, 2H), 3.70-3.65 (m, 2H). Analytical LC/MS conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. m/z 414.4 [M+H]$^+$; RT: 1.26 min.

Example 118. Preparation of tert-butyl N-{2-[4-amino-7-(1H-pyrazol-3-yl)-2H-pyrazolo[3,4-c]quinolin-2-yl]ethyl}carbamate

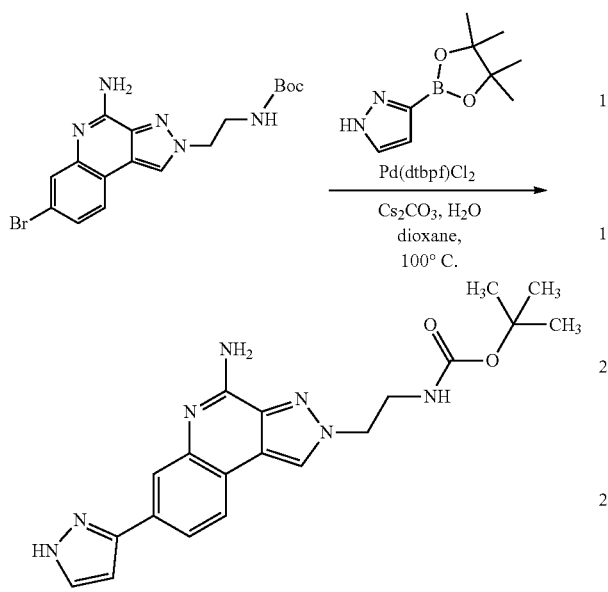

A mixture of tert-butyl (2-(4-amino-7-bromo-2H-pyrazolo[3,4-c]quinolin-2-yl)ethyl)carbamate (39 mg, 0.096 mmol), 3-(4,4,5,5-tetramethyl-1,3,2-dioxaborolan-2-yl)-1H-pyrazole (37.3 mg, 0.192 mmol), and cesium carbonate (94 mg, 0.29 mmol) was evacuated and back-filled with $N_2$, then 1,4-dioxane (864 µl) and $H_2O$ (96 µl) were added. The resulting mixture was sparged with $N_2$ for 10 min, then 1,1'-bis(di-tert-butylphosphino)ferrocene palladium dichloride (6.26 mg, 9.60 µmol) was added. The mixture was sparged with $N_2$ for 1 min, then it was sealed and stirred at 100° C. for 1 h. The reaction was cooled to rt, diluted with EtOAc (30 mL), and washed with $H_2O$ (30 mL). The aqueous layer was extracted with EtOAc and the combined organic layers were washed with sat. aq. NaCl (30 mL), dried over $Na_2SO_4$, filtered, and concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-45% B over 25 minutes, then a 7-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge Phenyl, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 9% B, 9-49% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide tert-butyl (2-(4-amino-7-(1H-pyrazol-3-yl)-2H-pyrazolo[3,4-c]quinolin-2-yl)ethyl)carbamate (5.7 mg, 15%). $^1H$ NMR (500 MHz, DMSO-$d_6$) δ 8.66 (s, 1H), 7.97-7.88 (m, 2H), 7.73-7.67 (m, 1H), 7.64 (br d, J=6.6 Hz, 1H), 7.05 (br d, J=4.7 Hz, 1H), 7.02-6.83 (m, 2H), 6.74 (s, 1H), 4.47 (br t, J=5.0 Hz, 2H), 3.53-3.46 (m, 2H), 1.34 (s, 9H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 394.1 $[M+H]^+$; RT: 1.18 min.

Example 119. Preparation of N-{2-[4-amino-7-(1H-pyrazol-3-yl)-2H-pyrazolo[3,4-c]quinolin-2-yl]ethyl}-N-methylacetamide

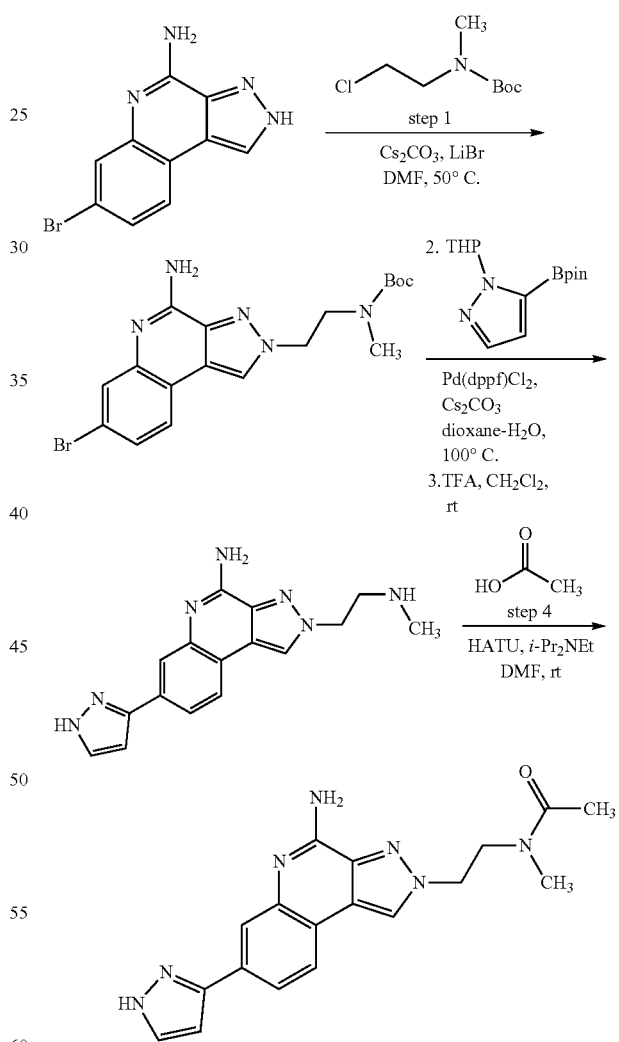

Step 1. tert-butyl (2-(4-amino-7-bromo-2H-pyrazolo[3,4-c]quinolin-2-yl)ethyl)(methyl)carbamate To a rt solution of 7-bromo-2H-pyrazolo[3,4-c]quinolin-4-amine, TFA (513 mg, 1.36 mmol) in DMF (4534 µl) was added cesium carbonate (1330 mg, 4.08 mmol) followed by tert-butyl (2-chloroethyl)(methyl)carbamate (290 mg, 1.50 mmol) and lithium bromide (11.8 mg, 0.136 mmol). The suspension was stirred at rt for 19 h, then at 50° C. for 16 h. The reaction was diluted with EtOAc (100 mL), washed with 10% aq. LiCl (2×50 mL) and sat. aq. NaCl (50 mL), dried over $Na_2SO_4$, and filtered. Celite was added, and the mixture was concentrated in vacuo. This material was dry loaded onto a column and purified by flash chromatography (40 g silica gel with 25 g solid load cartridge; linear gradient 0-10% MeOH—$CH_2Cl_2$) to provide tert-butyl (2-(4-amino-7-bromo-2H-pyrazolo[3,4-c]quinolin-2-yl)ethyl)(methyl)carbamate (321 mg, 56%) as a yellow foam. NMR is consistent with ~2:1 ratio of rotamers. $^1$H NMR (400 MHz, DMSO-$d_6$) δ 8.70-8.64 (m, 1H), 7.85 (br d, J=8.3 Hz, 1H), 7.58 (d, J=2.0 Hz, 1H), 7.30 (dd, J=8.4, 2.0 Hz, 1H), 6.95 (br s, 2H), 4.54 (t, J=5.5 Hz, 2H), 3.70 (br d, J=3.0 Hz, 2H), 2.79-2.71 (m, 3H), 1.29 (br s, 3H), 1.01 (s, 6H). LC-MS m/z 420/422 [M+H]$^+$.

Step 2. tert-butyl (2-(4-amino-7-(1-(tetrahydro-2H-pyran-2-yl)-1H-pyrazol-5-yl)-2H-pyrazolo[3,4-c]quinolin-2-yl)ethyl)(methyl)carbamate A mixture of tert-butyl (2-(4-amino-7-bromo-2H-pyrazolo[3,4-c]quinolin-2-yl)ethyl)(methyl)carbamate (320 mg, 0.761 mmol), 1-(tetrahydro-2H-pyran-2-yl)-5-(4,4,5,5-tetramethyl-1,3,2-dioxaborolan-2-yl)-1H-pyrazole (318 mg, 1.14 mmol), and cesium carbonate (744 mg, 2.28 mmol) was evacuated and back-filled with $N_2$, then 1,4-dioxane (6852 μl) and $H_2O$ (761 μl) were added. The resulting mixture was sparged with $N_2$ for 10 min, then [1,1'-bis(diphenylphosphino)ferrocene]dichloropalladium(II) (27.9 mg, 0.038 mmol) was added. The mixture was sparged with $N_2$ for 1 min, then it was sealed and stirred at 100° C. for 30 min. The reaction was cooled to rt, diluted with EtOAc (100 mL), washed with $H_2O$ (100 mL) and sat. aq. NaCl (100 mL), dried over $Na_2SO_4$, filtered, and concentrated in vacuo. The crude material was purified by flash chromatography (40 g silica gel; linear gradient 0-10% MeOH—$CH_2Cl_2$) to provide tert-butyl (2-(4-amino-7-(1-(tetrahydro-2H-pyran-2-yl)-1H-pyrazol-5-yl)-2H-pyrazolo[3,4-c]quinolin-2-yl)ethyl)(methyl)carbamate (305 mg, 81%) as a yellow foam. NMR is consistent with ~2:1 ratio of rotamers. $^1$H NMR (400 MHz, DMSO-$d_6$) δ 8.74-8.66 (m, 1H), 8.01 (br d, J=7.9 Hz, 1H), 7.62 (d, J=1.6 Hz, 1H), 7.57 (d, J=1.8 Hz, 1H), 7.31 (dd, J=8.0, 1.8 Hz, 1H), 6.85 (br s, 2H), 6.48 (s, 1H), 5.30 (dd, J=9.9, 2.0 Hz, 1H), 4.57 (br t, J=5.5 Hz, 2H), 4.08-4.00 (m, 1H), 3.73 (br s, 2H), 3.63-3.53 (m, 1H), 2.77-2.69 (m, 3H), 2.46-2.37 (m, 1H), 2.01-1.89 (m, 1H), 1.79 (br d, J=12.3 Hz, 1H), 1.63-1.48 (m, 3H), 1.32 (br s, 3H), 1.13-1.02 (m, 6H). LC-MS m/z 492 [M+H]$^+$.

Step 3. 2-(2-(methylamino)ethyl)-7-(1H-pyrazol-3-yl)-2H-pyrazolo[3,4-c]quinolin-4-amine To a rt solution of tert-butyl (2-(4-amino-7-(1-(tetrahydro-2H-pyran-2-yl)-1H-pyrazol-5-yl)-2H-pyrazolo[3,4-c]quinolin-2-yl)ethyl)(methyl)carbamate (304 mg, 0.618 mmol) in $CH_2Cl_2$ (1546 μl) was added TFA (1546 μl). The reaction was stirred at rt for 2 h. The reaction was concentrated under a stream of $N_2$ to remove about half the volume, then it was added dropwise to $Et_2O$ (20 mL). The resulting solid was collected by vacuum filtration and washed with $Et_2O$ (3×2 mL) to provide 2-(2-(methylamino)ethyl)-7-(1H-pyrazol-3-yl)-2H-pyrazolo[3,4-c]quinolin-4-amine, 2 TFA (272 mg, 82%) as an off-white solid. $^1$H NMR (400 MHz, DMSO-$d_6$) δ 13.70-12.93 (m, 1H), 9.84-9.66 (m, 1H), 9.45-9.26 (m, 1H), 9.03 (s, 1H), 8.79-8.65 (m, 2H), 8.19-8.10 (m, 2H), 7.93 (br d, J=8.0 Hz, 1H), 7.85 (br s, 1H), 6.80 (d, J=2.0 Hz, 1H), 4.85 (br t, J=5.6 Hz, 2H), 3.61 (br s, 2H), 2.70 (br s, 3H). LC-MS m/z 308 [M+H]$^+$.

Step 4. N-{2-[4-amino-7-(1H-pyrazol-3-yl)-2H-pyrazolo[3,4-c]quinolin-2-yl]ethyl}-N-methylacetamide To a rt solution of 2-(2-(methylamino)ethyl)-7-(1H-pyrazol-3-yl)-2H-pyrazolo[3,4-c]quinolin-4-amine, 2 TFA (20 mg, 0.037 mmol) in DMF (208 μl) was added acetic acid (2.136 μl, 0.037 mmol), followed by N,N-diisopropylethylamine (26.0 μl, 0.149 mmol) and HATU (14.20 mg, 0.037 mmol). The reaction was stirred at rt for 1 h. The reaction was diluted with $H_2O$ (0.1 mL) and DMF (to a total volume of 2 mL), filtered (syringe filter), and via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by UV signals. Fractions containing the desired product were combined and dried via centrifugal evaporation to provide N-(2-(4-amino-7-(1H-pyrazol-3-yl)-2H-pyrazolo[3,4-c]quinolin-2-yl)ethyl)-N-methylacetamide, TFA (14.1 mg, 80%). NMR is consistent with ~2:1 ratio of rotamers. $^1$H NMR (500 MHz, DMSO-$d_6$) δ 8.86 (s, 1H), 8.07-7.99 (m, 2H), 7.80 (br dd, J=8.1, 6.6 Hz, 1H), 7.75 (br d, J=1.5 Hz, 1H), 6.74 (s, 1H), 4.70 (br t, J=5.9 Hz, 0.67H), 4.61 (br t, J=6.1 Hz, 1.33H), 3.92-3.86 (m, 0.67H), 3.83 (br t, J=6.1 Hz, 1.33H), 2.87 (s, 2H), 2.79 (s, 1H), 1.96 (s, 2H), 1.91 (s, 1H). Analytical LC/MS conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. m/z 350.3 [M+H]$^+$; RT: 0.87 min.

Example 120. Preparation of N-{2-[4-amino-7-(1H-pyrazol-3-yl)-2H-pyrazolo[3,4-c]quinolin-2-yl]ethyl}-N-methylbenzamide

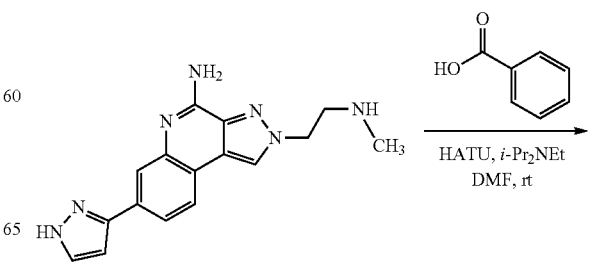

191

-continued

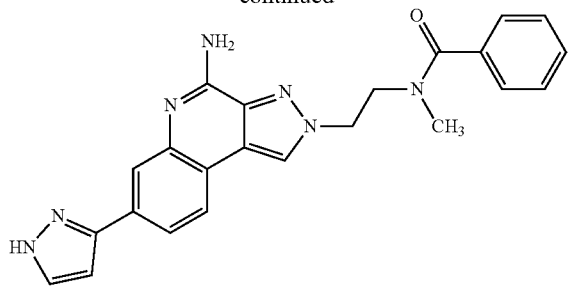

To benzoic acid (12.6 mg, 0.103 mmol) was added N,N-diisopropylethylamine (0.5 M solution in DMF) (0.374 mL, 0.187 mmol), followed by HATU (0.4 M solution in DMF) (0.233 mL, 0.093 mmol). The reaction was stirred at rt for 5 min, then it was added, dropwise, to a solution of 2-(2-(methylamino)ethyl)-7-(1H-pyrazol-3-yl)-2H-pyrazolo [3,4-c]quinolin-4-amine, 2 TFA (0.25 M solution in DMF with 0.75 M N,N-diisopropylethylamine) (0.374 mL, 0.093 mmol). The clear orange solution was stirred at rt for 1 h. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-47% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(1H-pyrazol-3-yl)-2H-pyrazolo[3,4-c]quinolin-2-yl) ethyl)-N-methylbenzamide (30.5 mg, 79%). NMR is consistent with ~2:1 ratio of rotamers. $^1$H NMR (500 MHz, DMSO-d$_6$) δ 8.81 (br s, 0.67H), 8.63-8.54 (m, 0.33H), 7.98-7.85 (m, 2H), 7.72-7.67 (m, 1H), 7.64 (br d, J=7.4 Hz, 1H), 7.46-7.12 (m, 4H), 6.94-6.56 (m, 4H), 4.74-4.68 (m, 1.33H), 4.60-4.54 (m, 067H), 4.01-3.95 (m, 1.33H), 3.82-3.75 (m, 0.67H), 3.02 (br s, 1H), 2.74 (br s, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 412.1 [M+H]$^+$; RT: 1.21 min.

Example 121. Preparation of 2-{2-[benzyl(methyl) amino]ethyl}-7-(1H-pyrazol-3-yl)-2H-pyrazolo[3,4-c]quinolin-4-amine

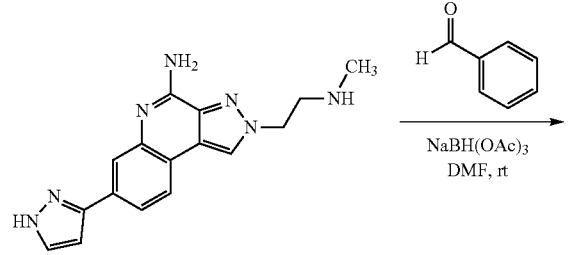

192

-continued

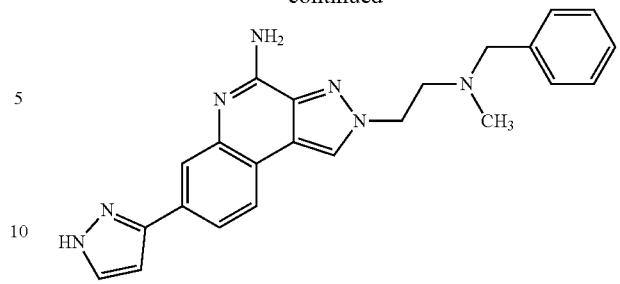

To a rt solution of 2-(2-(methylamino)ethyl)-7-(1H-pyrazol-3-yl)-2H-pyrazolo[3,4-c]quinolin-4-amine, 2 TFA (20 mg, 0.037 mmol) in DMF (187 μl) was added benzaldehyde (5.0 μl, 0.049 mmol), followed by sodium triacetoxyborohydride (23.8 mg, 0.112 mmol). The reaction was stirred at rt for 1 h. The reaction was diluted with H$_2$O (100 μL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 12% B, 12-37% B over 25 minutes, then a 2-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-(benzyl(methyl)amino)ethyl)-7-(1H-pyrazol-3-yl)-2H-pyrazolo[3,4-c]quinolin-4-amine, TFA (10.0 mg, 50%). $^1$H NMR (500 MHz, DMSO-d$_6$) δ 8.98 (s, 1H), 8.14 (s, 1H), 8.12 (d, J=8.3 Hz, 1H), 7.93 (dd, J=8.2, 1.4 Hz, 1H), 7.81 (d, J=1.9 Hz, 1H), 7.38-7.29 (m, 5H), 6.78 (d, J=2.3 Hz, 1H), 4.91-4.81 (m, 2H), 4.23-3.97 (m, 2H). Analytical LC/MS conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. m/z 398 [M+H]$^+$; RT: 1.03 min.

Example 122. Preparation of 1-{2-[4-amino-7-(1H-pyrazol-3-yl)-2H-pyrazolo[3,4-c]quinolin-2-yl] ethyl}pyrrolidin-2-one

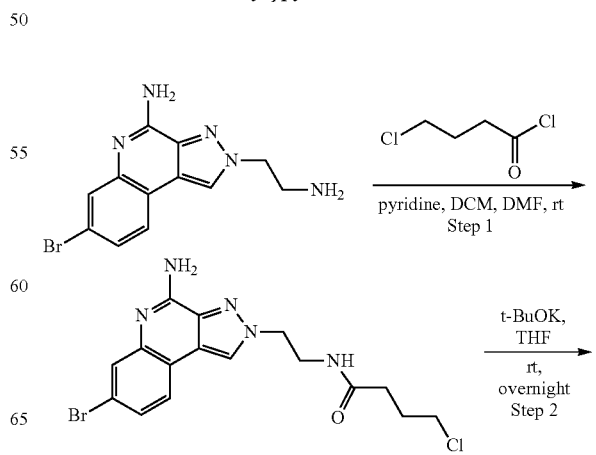

193

-continued

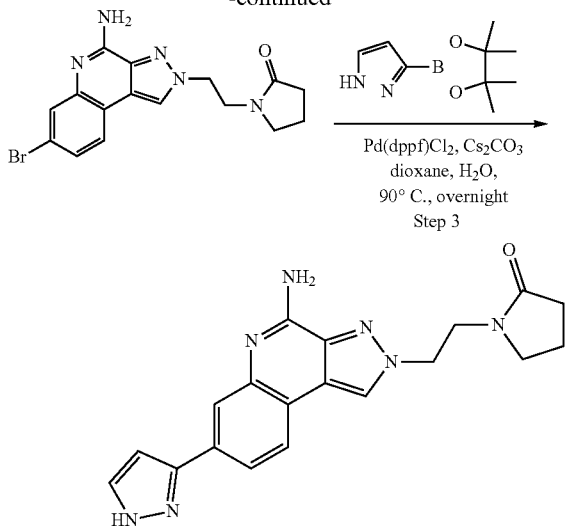

Pd(dppf)Cl₂, Cs₂CO₃
dioxane, H₂O,
90° C., overnight
Step 3

Step 1. N-(2-[7-bromo-2H-pyrazolo[3,4-c]quinolin-2-yl]ethyl)-4-chlorobutanamide Into a 100-mL 3-necked round-bottom flask was placed 2-(2-aminoethyl)-7-bromo-2H-pyrazolo[3,4-c]quinolin-4-amine (900 mg, 2.94 mmol, 1 equiv), DCM (30 mL), pyridine (697.6 mg, 8.82 mmol, 3 equiv), and 4-chlorobutanoyl chloride (829.0 mg, 5.88 mmol, 2 equiv). The resulting solution was stirred for 16 h at rt. The reaction was then quenched by the addition of MeOH. The resulting mixture was concentrated. The residue was applied onto a silica gel column with dichloromethane/methanol (10:1) to provide N-(2-[7-bromo-2H-pyrazolo[3,4-c]quinolin-2-yl]ethyl)-4-chlorobutanamide (240 mg, 21%) as a light yellow solid. LC-MS m/z [M+H]⁺=390.1.

Step 2. 1-(2-[4-amino-7-bromo-2H-pyrazolo[3,4-c]quinolin-2-yl]ethyl)pyrrolidin-2-one Into a 25-mL round-bottom flask, was placed N-(2-[4-amino-7-bromo-2H-pyrazolo[3,4-c]quinolin-2-yl]ethyl)-4-chlorobutanamide (300 mg, 0.73 mmol, 1 equiv) in THF (7 mL). Then t-BuOK (163.9 mg, 1.46 mmol, 2 equiv) was added. The resulting solution was stirred for 16 h at rt. The reaction was quenched by the addition of H₂O (20 mL). The resulting solution was extracted with ethyl acetate (3×20 mL). The resulting mixture was concentrated. The residue was applied onto a silica gel column with dichloromethane/methanol (10:1) to provide 1-(2-[4-amino-7-bromo-2H-pyrazolo[3,4-c]quinolin-2-yl]ethyl)pyrrolidin-2-one (200 mg, 73%) as a light yellow solid. LC-MS: (ES, m/z): [M+H]⁺=374.1.

Step 3. 1-[2-[4-amino-7-(1H-pyrazol-3-yl)-2H-pyrazolo[3,4-c]quinolin-2-yl]ethyl]pyrrolidin-2-one Into a 20-mL sealed tube purged and maintained with an inert atmosphere of nitrogen was placed 1-(2-[4-amino-7-bromo-2H-pyrazolo[3,4-c]quinolin-2-yl]ethyl)pyrrolidin-2-one (200 mg, 0.53 mmol, 1 equiv), Cs₂CO₃ (348.3 mg, 1.07 mmol, 2 equiv), 3-(tetramethyl-1,3,2-dioxaborolan-2-yl)-1H-pyrazole (207.4 mg, 1.07 mmol, 2 equiv), Pd(dppf)Cl₂ (39.1 mg, 0.05 mmol, 0.1 equiv) in dioxane (5 mL) and H₂O (1.25 mL). The resulting solution was stirred for 16 h at 80° C. The resulting mixture was cooled to rt and concentrated. The residue was applied onto a silica gel column with dichloromethane/methanol (10:1). The crude product was purified by Prep-HPLC with the following conditions: Column, XBridge Shield RP18 OBD Column, 19*250 mm, 10 um; mobile phase, Water (10 mM NH₄HCO₃) and ACN (15% PhaseB up to 40% in 7 min); Detector, UV. This provided 1-[2-[4-amino-7-(1H-pyrazol-3-yl)-2H-pyrazolo[3,4-c]quinolin-2-yl]ethyl]pyrrolidin-2-one (35.4 mg, 18%) as a white solid. ¹H-NMR: (300 MHz, DMSO-d₆, ppm): δ 13.32-12.85 (m br, 1H), 8.72 (s, 1H), 7.90-7.52 (m, 4H), 6.86 (s, 1H), 6.76 (s, 2H), 4.58-4.56 (m, 2H), 3.74-3.71 (m, 2H), 3.28-3.25 (m, 2H), 2.18-2.14 (m, 2H), 1.96-1.83 (m, 2H). LC Methods: Column: Kinetex EVO 3.0 mm×50 mm, 2.6 μm particles; Mobile Phase A: water with 0.03% NH₃H₂O; Mobile Phase B: acetonitrile; Temperature: 40° C.; Gradient: 10% B to 95% B over 2 min, then a 0.60 min hold at 95% B; Flow: 1.2 mL/min. m/z 362.2 [M+H]⁺. RT: 0.939 min.

Example 123. Preparation of N-{3-[4-amino-7-(1H-pyrazol-3-yl)-2H-pyrazolo[3,4-c]quinolin-2-yl]propyl}benzamide

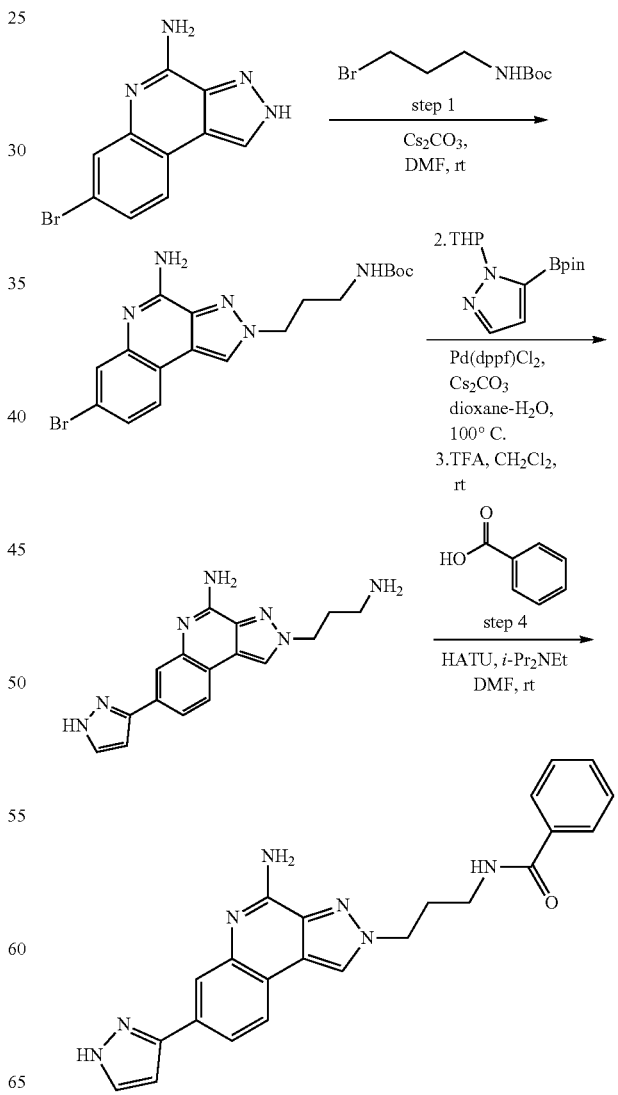

Step 1. tert-butyl (3-(4-amino-7-bromo-2H-pyrazolo [3,4-c]quinolin-2-yl)propyl)carbamate To a rt solution of 7-bromo-2H-pyrazolo[3,4-c]quinolin-4-amine, TFA (0.40 g, 1.06 mmol) in DMF (3.54 ml) was added cesium carbonate (1.037 g, 3.18 mmol) followed by tert-butyl (3-bromopropyl)carbamate (0.278 g, 1.17 mmol). The suspension was stirred at rt for 40 h. The reaction was diluted with EtOAc (50 mL) and $H_2O$ (50 mL). The layers were separated and the aqueous layer was extracted with EtOAc (50 mL). The combined organic layers were washed with sat. aq. NaCl (50 mL), dried over $Na_2SO_4$, filtered, and concentrated in vacuo. The crude material was purified by flash chromatography (24 g silica gel; linear gradient 0-10% MeOH—$CH_2Cl_2$) to provide tert-butyl (3-(4-amino-7-bromo-2H-pyrazolo[3,4-c]quinolin-2-yl)propyl)carbamate (379 mg, 85%) as a white foam. $^1$H NMR (400 MHz, DMSO-$d_6$) δ 8.74 (s, 1H), 7.83 (d, J=8.3 Hz, 1H), 7.59 (d, J=2.0 Hz, 1H), 7.31 (dd, J=8.3, 2.1 Hz, 1H), 7.02-6.92 (m, 3H), 4.43 (t, J=7.0 Hz, 2H), 3.01-2.92 (m, 2H), 2.04 (quin, J=6.9 Hz, 2H), 1.37 (s, 9H). LC-MS m/z 420/422 $[M+H]^+$.

Step 2. tert-butyl (3-(4-amino-7-(1-(tetrahydro-2H-pyran-2-yl)-1H-pyrazol-5-yl)-2H-pyrazolo[3,4-c]quinolin-2-yl)propyl)carbamate A mixture of tert-butyl (3-(4-amino-7-bromo-2H-pyrazolo[3,4-c]quinolin-2-yl)propyl)carbamate (378 mg, 0.899 mmol), 1-(tetrahydro-2H-pyran-2-yl)-5-(4,4,5,5-tetramethyl-1,3,2-dioxaborolan-2-yl)-1H-pyrazole (375 mg, 1.35 mmol), and cesium carbonate (879 mg, 2.70 mmol) was evacuated and back-filled with $N_2$, then 1,4-dioxane (8094 µl) and $H_2O$ (899 µl) were added. The resulting mixture was sparged with $N_2$ for 10 min, then [1,1'-bis(diphenylphosphino)ferrocene]dichloropalladium(II) (32.9 mg, 0.045 mmol) was added. The mixture was sparged with $N_2$ for 1 min, then it was stirred at 100° C. for 30 min. The reaction was cooled to rt, diluted with EtOAc (200 mL), washed with $H_2O$ (100 mL) and sat. aq. NaCl (100 mL), dried over $Na_2SO_4$, filtered, and concentrated in vacuo. The crude material was purified by flash chromatography (40 g silica gel; linear gradient 0-10% MeOH—$CH_2Cl_2$) to provide tert-butyl (3-(4-amino-7-(1-(tetrahydro-2H-pyran-2-yl)-1H-pyrazol-5-yl)-2H-pyrazolo[3,4-c]quinolin-2-yl)propyl)carbamate (474 mg, quant.) as a brown foam. $^1$H NMR (400 MHz, DMSO-$d_6$) δ 8.77 (s, 1H), 7.99 (d, J=8.0 Hz, 1H), 7.62 (d, J=1.7 Hz, 1H), 7.58 (d, J=1.7 Hz, 1H), 7.32 (dd, J=8.0, 1.7 Hz, 1H), 6.98 (br t, J=5.4 Hz, 1H), 6.89 (s, 2H), 6.48 (d, J=1.8 Hz, 1H), 5.30 (dd, J=9.9, 2.0 Hz, 1H), 4.46 (t, J=6.9 Hz, 2H), 4.04 (br d, J=9.3 Hz, 1H), 3.62-3.53 (m, 1H), 2.97 (q, J=6.5 Hz, 2H), 2.46-2.36 (m, 1H), 2.11-2.01 (m, 2H), 1.99-1.89 (m, 1H), 1.79 (br d, J=12.5 Hz, 1H), 1.64-1.48 (m, 3H), 1.38 (s, 9H). LC-MS m/z 492 $[M+H]^+$.

Step 3. 2-(3-aminopropyl)-7-(1H-pyrazol-3-yl)-2H-pyrazolo[3,4-c]quinolin-4-amine, 2 TFA To a rt solution of tert-butyl (3-(4-amino-7-(1-(tetrahydro-2H-pyran-2-yl)-1H-pyrazol-5-yl)-2H-pyrazolo[3,4-c]quinolin-2-yl)propyl)carbamate (442 mg, 0.899 mmol) in $CH_2Cl_2$ (2248 µl) was added TFA (2248 µl). The reaction was stirred at rt for 2 h. The reaction was concentrated to remove about half the volume, then it was added dropwise to $Et_2O$ (50 mL). The resulting solid was collected by vacuum filtration and washed with $Et_2O$ (3×2 mL) to provide 2-(3-aminopropyl)-7-(1H-pyrazol-3-yl)-2H-pyrazolo[3,4-c]quinolin-4-amine, 2 TFA (423 mg, 88%) as an off-white solid. $^1$H NMR (400 MHz, DMSO-$d_6$) δ 13.51 (br s, 1H), 9.86-9.70 (m, 1H), 9.29-9.17 (m, 1H), 9.01 (s, 1H), 8.15 (br s, 1H), 8.13 (d, J=8.3 Hz, 1H), 7.92 (dd, J=8.3, 1.1 Hz, 1H), 7.83 (br d, J=9.2 Hz, 4H), 6.80 (d, J=2.2 Hz, 1H), 4.63 (t, J=6.7 Hz, 2H), 2.94-2.84 (m, 2H), 2.29-2.19 (m, 2H). LC-MS m/z 308 $[M+H]^+$.

Step 4. N-{3-[4-amino-7-(1H-pyrazol-3-yl)-2H-pyrazolo[3,4-c]quinolin-2-yl]propyl}benzamide To a rt solution of 2-(3-aminopropyl)-7-(1H-pyrazol-3-yl)-2H-pyrazolo[3,4-c]quinolin-4-amine, 2 TFA (40 mg, 0.075 mmol) and benzoic acid (9.1 mg, 0.075 mmol) in DMF (374 µl) was added N,N-diisopropylethylamine (52.1 µl, 0.299 mmol), followed by HATU (28.4 mg, 0.075 mmol). The reaction was stirred at rt for 30 min. The reaction was diluted with $H_2O$ (0.2 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-47% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(3-(4-amino-7-(1H-pyrazol-3-yl)-2H-pyrazolo[3,4-c]quinolin-2-yl)propyl)benzamide (10.4 mg, 34%). $^1$H NMR (500 MHz, DMSO-$d_6$) δ 8.76 (s, 1H), 8.58 (br t, J=5.2 Hz, 1H), 7.92 (d, J=8.3 Hz, 1H), 7.90 (s, 1H), 7.83 (br d, J=7.4 Hz, 2H), 7.69 (br s, 1H), 7.64 (br d, J=7.7 Hz, 1H), 7.54-7.49 (m, 1H), 7.47-7.43 (m, 2H), 6.99-6.76 (m, 2H), 6.73 (s, 1H), 4.51 (br t, J=6.7 Hz, 2H), 3.38-3.31 (m, 2H), 2.26-2.17 (m, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 412.1 $[M+H]^+$; RT: 1.17 min.

Examples 124 to 126 were prepared according to synthetic procedures similar to those described for Example 123 from the appropriate starting materials. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection MS and UV (220 nm).

| Ex No. | Structure | LC/MS [M + H]+ | RT (min) | 1H NMR |
|---|---|---|---|---|
| 124 | 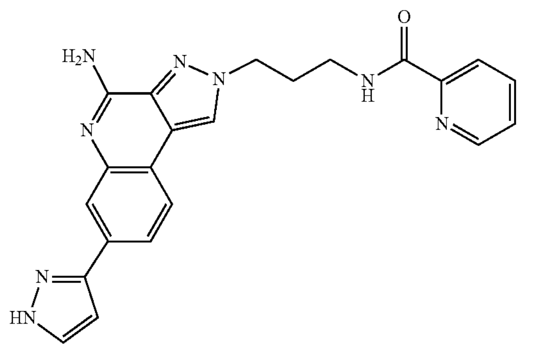 [SMILES: Nc1nc2cc(-c3cc[nH]n3)ccc2c2cn(CCCNC(=O)c3ccccn3)nc12] | 413.3 | 1.01 | 1H NMR (400 MHZ, METHANOL-d4) δ 8.65 (s, 1H), 8.43-8.37 (m, 1H), 7.97-7.96 (m, 1H), 7.95-7.93 (m, 1H), 7.91 (d, J = 1.4 Hz, 1H), 7.82-7.78 (m, 1H), 7.78-7.75 (m, 1H), 7.71 (d, J = 2.2 Hz, 1H), 7.37 (ddd, J = 7.6, 4.8, 1.2 Hz, 1H), 6.77 (d, J = 2.2 Hz, 1H), 4.63 (t, J = 6.4 Hz, 2H), 3.59 (t, J = 6.3 Hz, 2H), 2.41 (quin, J = 6.4 Hz, 2H) |
| 125 | 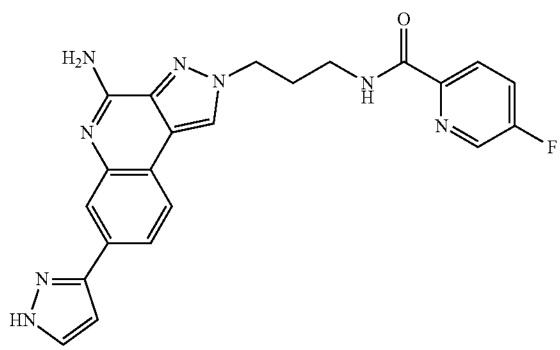 [SMILES: Nc1nc2cc(-c3cc[nH]n3)ccc2c2cn(CCCNC(=O)c3ccc(F)cn3)nc12] | 431.1 | 1.16 | 1H NMR (400 MHZ, METHANOL-d4) δ 8.63 (s, 1H), 8.25 (d, J = 2.7 Hz, 1H), 8.00 (dd, J = 8.7, 4.5 Hz, 1H), 7.94 (d, J = 8.2 Hz, 1H), 7.91 (d, J = 1.2 Hz, 1H), 7.78-7.74 (m, 1H), 7.71 (d, J = 2.1 Hz, 1H), 7.54 (td, J = 8.5, 2.8 Hz, 1H), 6.76 (d, J = 2.2 Hz, 1H), 4.63 (t, J = 6.4 Hz, 2H), 3.58 (t, J = 6.3 Hz, 2H), 2.41 (quin, J = 6.3 Hz, 2H) |
| 126 | 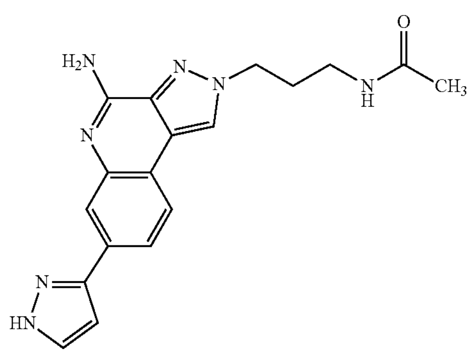 [SMILES: CC(=O)NCCCn1cc2c(n1)c(N)nc1cc(-c3cc[nH]n3)ccc12] | 350.1 | 1.03 | 1H NMR (500 MHZ, DMSO-d6) δ 13.70-12.87 (m, 1H), 9.91-9.08 (m, 2H), 9.00 (s, 1H), 8.15-8.08 (m, 2H), 8.01-7.97 (m, 1H), 7.90 (br d, J = 8.3 Hz, 1H), 7.83 (br s, 1H), 6.79 (s, 1H), 4.53 (br t, J = 6.9 Hz, 2H), 3.11 (q, J = 6.1 Hz, 2H), 2.14-2.07 (m, 2H), 1.82 (s, 3H) |

Example 127. Preparation of tert-butyl N-{2-[4-amino-7-(thiophen-2-yl)-2H-pyrazolo[3,4-c]quinolin-2-yl]ethyl}carbamate

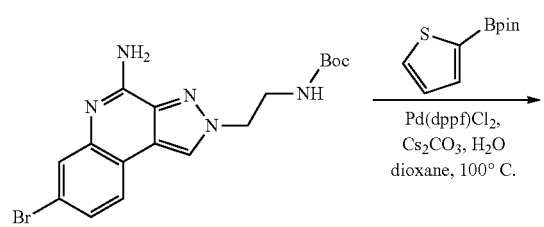

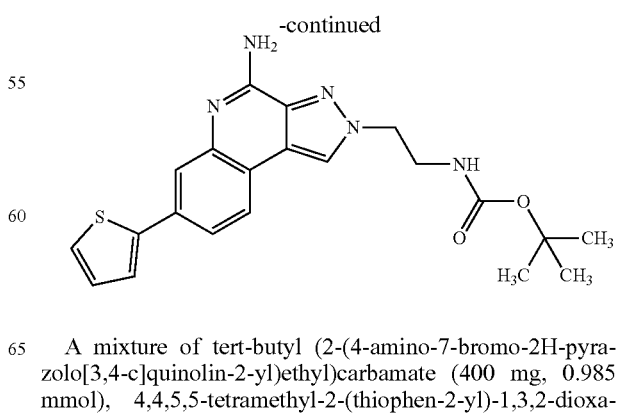

A mixture of tert-butyl (2-(4-amino-7-bromo-2H-pyrazolo[3,4-c]quinolin-2-yl)ethyl)carbamate (400 mg, 0.985 mmol), 4,4,5,5-tetramethyl-2-(thiophen-2-yl)-1,3,2-dioxaborolane (310 mg, 1.48 mmol), and cesium carbonate (962 mg, 2.95 mmol) was evacuated and back-filled with $N_2$, then 1,4-dioxane (8861 μl) and $H_2O$ (985 μl) were added. The resulting mixture was sparged with $N_2$ for 10 min, then [1,1'-bis(diphenylphosphino)ferrocene]dichloropalladium (II) (36.0 mg, 0.049 mmol) was added. The mixture was sparged with $N_2$ for 1 min, then it was sealed and stirred at 100° C. for 1 h. The reaction was cooled to rt, diluted with EtOAc (100 mL), washed with $H_2O$ (100 mL) and sat. aq. NaCl (100 mL), dried over $Na_2SO_4$, filtered, and concentrated in vacuo. The crude material was purified by flash chromatography (40 g silica gel; linear gradient 0-10% MeOH—$CH_2Cl_2$) to provide tert-butyl (2-(4-amino-7-(thiophen-2-yl)-2H-pyrazolo[3,4-c]quinolin-2-yl)ethyl)carbamate (396 mg, 98%) as an off-white solid. $^1$H NMR (400 MHz, DMSO-$d_6$) δ 8.66 (s, 1H), 7.92 (d, J=8.1 Hz, 1H), 7.70 (d, J=1.8 Hz, 1H), 7.55 (dd, J=3.6, 1.0 Hz, 1H), 7.53 (dd, J=5.1, 1.0 Hz, 1H), 7.49 (dd, J=8.1, 1.9 Hz, 1H), 7.15 (dd, J=5.0, 3.6 Hz, 1H), 7.07 (br t, J=5.7 Hz, 1H), 6.82 (br s, 2H), 4.46 (br t, J=6.1 Hz, 2H), 3.49 (q, J=6.0 Hz, 2H), 1.34 (s, 9H); LC-MS m/z 410 $[M+H]^+$.

Example 128. Preparation of N-{2-[4-amino-7-(thiophen-2-yl)-2H-pyrazolo[3,4-c]quinolin-2-yl]ethyl}-2-methyl-1,3-oxazole-4-carboxamide

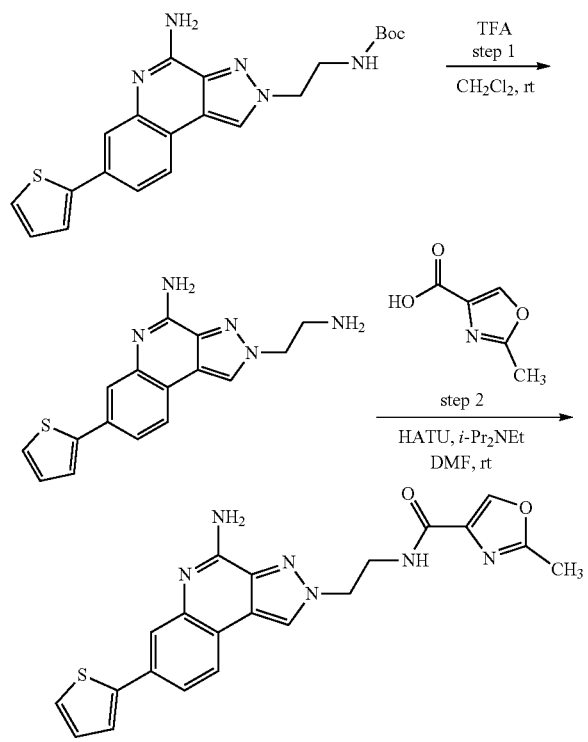

Step 1. 2-(2-aminoethyl)-7-(thiophen-2-yl)-2H-pyrazolo[3,4-c]quinolin-4-amine, 2 TFA To a rt suspension of tert-butyl (2-(4-amino-7-(thiophen-2-yl)-2H-pyrazolo[3,4-c]quinolin-2-yl)ethyl)carbamate (376 mg, 0.918 mmol) in $CH_2Cl_2$ (2295 μl) was added TFA (2295 μl), causing the mixture to become an orange solution (rapid gas evolution noted). The reaction was stirred at rt for 30 min. The reaction was concentrated to remove about half the volume, then it was added dropwise to $Et_2O$ (25 mL). The resulting solid was collected by vacuum filtration and washed with $Et_2O$ (3×10 mL) to provide 2-(2-aminoethyl)-7-(thiophen-2-yl)-2H-pyrazolo[3,4-c]quinolin-4-amine, 2 TFA (428.6 mg, 87%) as an off-white solid. $^1$H NMR (400 MHz, DMSO-$d_6$) δ 9.95-9.10 (m, 2H), 9.02 (s, 1H), 8.13 (d, J=8.2 Hz, 1H), 8.17-8.05 (m, 2H), 7.93 (d, J=1.3 Hz, 1H), 7.83 (br d, J=8.1 Hz, 1H), 7.65 (dd, J=5.1, 1.0 Hz, 1H), 7.63 (dd, J=3.6, 1.1 Hz, 1H), 7.21 (dd, J=5.1, 3.7 Hz, 1H), 4.76 (t, J=5.7 Hz, 2H), 3.55-3.48 (m, 2H); LC-MS m/z 310 $[M+H]^+$.

Step 2. N-{2-[4-amino-7-(thiophen-2-yl)-2H-pyrazolo[3,4-c]quinolin-2-yl]ethyl}-2-methyl-1,3-oxazole-4-carboxamide To 2-methyloxazole-4-carboxylic acid (13.0 mg, 0.092 mmol) was added N,N-diisopropylethylamine (0.5 M solution in DMF) (0.335 mL, 0.167 mmol), followed by HATU (0.4 M solution in DMF) (0.209 mL, 0.084 mmol). The reaction was stirred at rt for 5 min, then it was added, dropwise, to a suspension of 2-(2-aminoethyl)-7-(thiophen-2-yl)-2H-pyrazolo[3,4-c]quinolin-4-amine, 2 TFA (0.25 M in DMF with 0.75 M N,N-diisopropylethylamine) (0.335 mL, 0.084 mmol). The reaction was stirred at rt for 2 h. The reaction was diluted with $H_2O$ (0.1 mL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 16% B, 16-56% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(thiophen-2-yl)-2H-pyrazolo[3,4-c]quinolin-2-yl)ethyl)-2-methyloxazole-4-carboxamide (22.9 mg, 59%). $^1$H NMR (500 MHz, DMSO-$d_6$) δ 8.74 (s, 1H), 8.49 (br t, J=5.6 Hz, 1H), 8.41 (s, 1H), 7.95 (d, J=8.0 Hz, 1H), 7.74 (d, J=1.4 Hz, 1H), 7.57-7.50 (m, 3H), 7.40-7.24 (m, 2H), 7.15 (dd, J=5.0, 3.9 Hz, 1H), 4.61 (br t, J=6.1 Hz, 2H), 3.80 (q, J=5.8 Hz, 2H), 2.42 (s, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 419 $[M+H]^+$; RT: 1.34 min.

Examples 129 to 131 were prepared according to synthetic procedures similar to those described for Example 128 from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

| Ex No. | Structure | LC/MS [M + H]+ | RT (min) | 1H NMR |
|---|---|---|---|---|
| 129 | 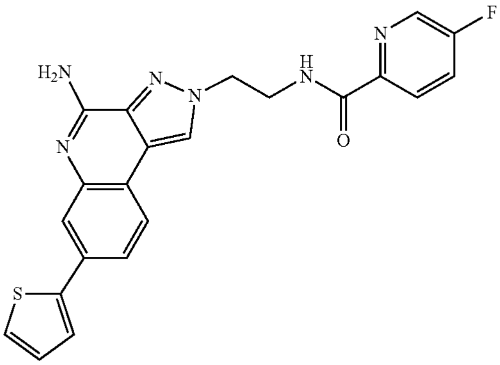 [SMILES: Nc1nc2cc(-c3cccs3)ccc2c2cn(CCNC(=O)c3ccc(F)cn3)nc12] | 433.2 | 1.44 | 1H NMR (500 MHZ, DMSO-d6) δ 9.02 (br t, J = 5.8 Hz, 1H), 8.68 (s, 1H), 8.59 (d, J = 2.2 Hz, 1H), 8.07 (dd, J = 8.5, 4.4 Hz, 1H), 7.92-7.82 (m, 2H), 7.69 (s, 1H), 7.53-7.49 (m, 2H), 7.47 (br d, J = 8.0 Hz, 1H), 7.14 (t, J = 4.3 Hz, 1H), 6.82-6.72 (m, 2H), 4.64 (br t, J = 5.8 Hz, 2H), 3.88 (q, J = 6.1 Hz, 2H) |
| 130 | 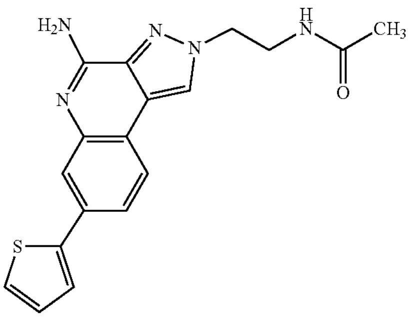 [SMILES: CC(=O)NCCn1cc2c(n1)c(N)nc1cc(-c3cccs3)ccc12] | 352.2 | 1.2 | 1H NMR (400 MHZ, METHANOL-d4) δ 8.73 (s, 1H), 8.08 (d, J = 8.3 Hz, 1H), 7.87 (d, J = 1.6 Hz, 1H), 7.78 (dd, J = 8.2, 1.7 Hz, 1H), 7.55 (dd, J = 3.6, 1.0 Hz, 1H), 7.49 (dd, J = 5.1, 0.9 Hz, 1H), 7.17 (dd, J = 5.1, 3.7 Hz, 1H), 4.64 (t, J = 5.9 Hz, 2H), 3.79 (t, J = 5.8 Hz, 2H), 1.91 (s, 3H) |
| 131 | 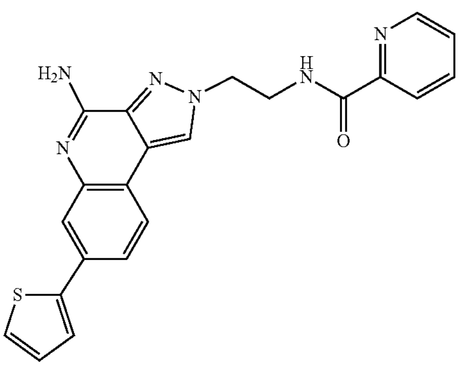 [SMILES: Nc1nc2cc(-c3cccs3)ccc2c2cn(CCNC(=O)c3ccccn3)nc12] | 415.2 | 1.42 | 1H NMR (500 MHz, DMSO-d6) δ 9.08-9.02 (m, 1H), 8.66 (s, 1H), 8.59 (br d, J = 3.9 Hz, 1H), 8.01-7.93 (m, 2H), 7.88 (br d, J = 8.0 Hz, 1H), 7.69 (s, 1H), 7.59-7.55 (m, 1H), 7.53-7.45 (m, 3H), 7.16-7.11 (m, 1H), 6.84-6.62 (m, 2H), 4.64 (br t, J = 5.6 Hz, 2H), 3.91-3.87 (m, 2H) |

Example 132. Preparation of N-{2-[4-amino-7-(1H-pyrazol-1-yl)-2H-pyrazolo[3,4-c]quinolin-2-yl]ethyl}benzamide

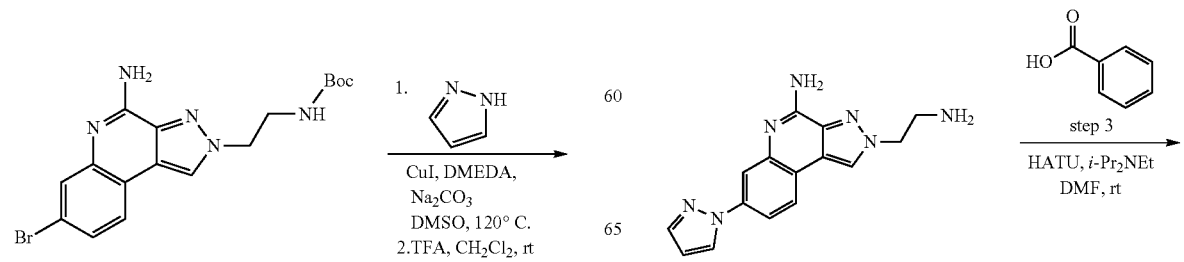

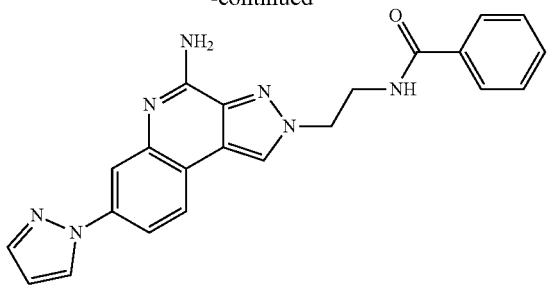

Step 1. tert-butyl (2-(4-amino-7-(1H-pyrazol-1-yl)-2H-pyrazolo[3,4-c]quinolin-2-yl)ethyl)carbamate A mixture of tert-butyl (2-(4-amino-7-bromo-2H-pyrazolo[3,4-c]quinolin-2-yl)ethyl)carbamate (0.498 g, 1.23 mmol), 1H-pyrazole (0.125 g, 1.84 mmol), and sodium carbonate (0.520 g, 4.90 mmol) was evacuated and backfilled with $N_2$, then DMSO (12.26 ml) was added. The resulting mixture was sparged with $N_2$ for 10 min, then N,N'-dimethylethylenediamine (0.396 ml, 3.68 mmol) and copper(I) iodide (0.350 g, 1.84 mmol) were added. The mixture was sparged with $N_2$ for 1 min, then it was sealed and stirred at 120° C. for 1 h. The reaction was cooled to rt. The reaction was diluted with EtOAc (200 mL), washed with $H_2O$ (200 mL), 1:1 $H_2O$-aq. $NH_4OH$ (200 mL), and sat. aq. NaCl (200 mL), dried over $Na_2SO_4$, filtered, and concentrated in vacuo. The crude material was purified by flash chromatography (80 g silica gel; linear gradient 0-10% MeOH—$CH_2Cl_2$) to provide tert-butyl (2-(4-amino-7-(1H-pyrazol-1-yl)-2H-pyrazolo[3,4-c]quinolin-2-yl)ethyl)carbamate (395 mg, 82%). $^1$H NMR (400 MHz, DMSO-$d_6$) δ 8.66 (s, 1H), 8.55 (d, J=2.2 Hz, 1H), 7.99 (d, J=8.4 Hz, 1H), 7.87 (d, J=2.1 Hz, 1H), 7.75 (d, J=1.5 Hz, 1H), 7.67 (dd, J=8.4, 2.3 Hz, 1H), 7.07 (br t, J=5.5 Hz, 1H), 6.89 (br s, 2H), 6.55-6.53 (m, 1H), 4.46 (br t, J=6.0 Hz, 2H), 3.49 (q, J=6.0 Hz, 2H), 1.34 (s, 9H); LC-MS m/z 394 [M+H]$^+$.

Step 2. 2-(2-aminoethyl)-7-(1H-pyrazol-1-yl)-2H-pyrazolo[3,4-c]quinolin-4-amine, 2 TFA To a rt solution of tert-butyl (2-(4-amino-7-(1H-pyrazol-1-yl)-2H-pyrazolo[3,4-c]quinolin-2-yl)ethyl)carbamate (396 mg, 1.01 mmol) in $CH_2Cl_2$ (2516 μl) was added TFA (2516 μl) (gas evolution was noted). The reaction was stirred at rt for 30 min. The reaction was concentrated to remove about half the volume, then it was added dropwise to $Et_2O$ (25 mL). The resulting solid was collected by vacuum filtration and washed with $Et_2O$ (3×10 mL) to provide 2-(2-aminoethyl)-7-(1H-pyrazol-1-yl)-2H-pyrazolo[3,4-c]quinolin-4-amine, 2 TFA (464 mg, 88%) as a white solid. $^1$H NMR (400 MHz, DMSO-$d_6$) δ 9.94-9.69 (m, 1H), 9.52-9.28 (m, 1H), 9.02 (s, 1H), 8.62 (d, J=2.5 Hz, 1H), 8.27-8.21 (m, 2H), 8.16-8.06 (m, 3H), 8.01-7.97 (m, 1H), 7.85 (d, J=1.4 Hz, 1H), 6.67-6.60 (m, 1H), 4.77 (t, J=5.6 Hz, 2H), 3.51 (br d, J=3.8 Hz, 2H); LC-MS m/z 294 [M+H]$^+$.

Step 3. N-{2-[4-amino-7-(1H-pyrazol-1-yl)-2H-pyrazolo[3,4-c]quinolin-2-yl]ethyl}benzamide To benzoic acid (11.6 mg, 0.095 mmol) was added N,N-diisopropylethylamine (0.5 M solution in DMF) (0.345 mL, 0.173 mmol), followed by HATU (0.4 M solution in DMF) (0.216 mL, 0.086 mmol). The reaction was stirred at rt for 5 min, then it was added, dropwise, to a suspension of 2-(2-aminoethyl)-7-(1H-pyrazol-1-yl)-2H-pyrazolo[3,4-c]quinolin-4-amine, 2 TFA (0.25 M in DMF with 0.75 M N,N-diisopropylethylamine) (0.345 mL, 0.086 mmol). The reaction was stirred at rt for 2 h. The reaction was diluted with $H_2O$ (0.1 mL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 25 minutes, then a 7-minute hold at 100% B; Flow Rate: 20 mL/min; Column Temperature: 25° C. Fraction collection was triggered by MS signals. Fractions containing the desired product were combined and dried via centrifugal evaporation to provide N-(2-(4-amino-7-(1H-pyrazol-1-yl)-2H-pyrazolo[3,4-c]quinolin-2-yl)ethyl)benzamide (23.1 mg, 67%). $^1$H NMR (500 MHz, DMSO-$d_6$) δ 8.72 (s, 1H), 8.70-8.66 (m, 1H), 8.54 (br d, J=1.9 Hz, 1H), 8.01-7.95 (m, 1H), 7.87 (br s, 1H), 7.84-7.78 (m, 2H), 7.74 (s, 1H), 7.68-7.64 (m, 1H), 7.54-7.49 (m, 1H), 7.48-7.42 (m, 2H), 6.89 (br s, 2H), 6.54 (br s, 1H), 4.66-4.60 (m, 2H), 3.85-3.80 (m, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 398.1 [M+H]$^+$; RT: 1.24 min.

Example 133. Preparation of N-{2-[4-amino-7-(1H-pyrazol-1-yl)-2H-pyrazolo[3,4-c]quinolin-2-yl]ethyl}pyridine-2-carboxamide

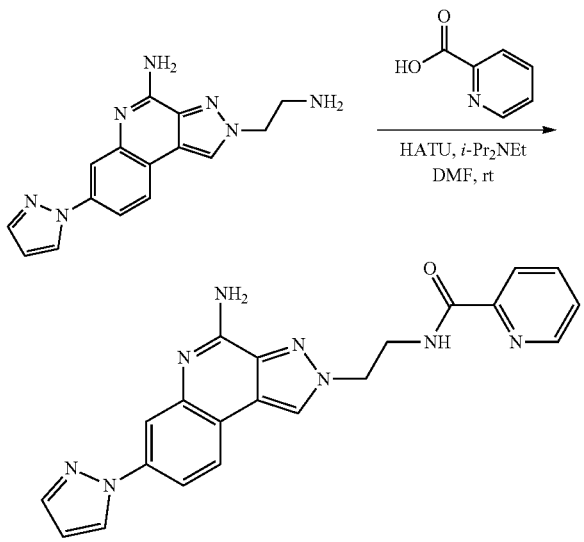

To picolinic acid (11.7 mg, 0.095 mmol) was added N,N-diisopropylethylamine (0.5 M solution in DMF) (0.345 mL, 0.173 mmol), followed by HATU (0.4 M solution in DMF) (0.216 mL, 0.086 mmol). The reaction was stirred at rt for 5 min, then it was added, dropwise, to a suspension of 2-(2-aminoethyl)-7-(1H-pyrazol-1-yl)-2H-pyrazolo[3,4-c]quinolin-4-amine, 2 TFA (0.25 M in DMF with 0.75 M N,N-diisopropylethylamine) (0.345 mL, 0.086 mmol). The reaction was stirred at rt for 2 h. The reaction was diluted with H₂O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 23 minutes, then a 6-minute hold at 100% B; Flow Rate: 20 mL/min; Column Temperature: 25° C. Fraction collection was triggered by MS signals. Fractions containing the desired product were combined and dried via centrifugal evaporation to provide N-(2-(4-amino-7-(1H-pyrazol-1-yl)-2H-pyrazolo[3,4-c]quinolin-2-yl)ethyl)picolinamide (11.4 mg, 33%). $^1$H NMR (500 MHz, DMSO-d₆) δ 9.07 (br t, J=6.1 Hz, 1H), 8.71 (s, 1H), 8.61 (d, J=4.7 Hz, 1H), 8.52 (d, J=2.2 Hz, 1H), 8.02-7.94 (m, 3H), 7.85 (d, J=1.9 Hz, 1H), 7.74 (s, 1H), 7.65 (dd, J=8.5, 1.9 Hz, 1H), 7.59 (br t, J=5.5 Hz, 1H), 6.86 (br s, 2H), 6.54 (s, 1H), 4.67-4.63 (m, 2H), 3.90 (q, J=5.9 Hz, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 399.0 [M+H]⁺; RT: 0.98 min.

Example 134. Preparation of methyl N-[[4-amino-7-(1H-pyrazol-5-yl)-[1,3]thiazolo[4,5-c]quinolin-2-yl]methyl]carbamate

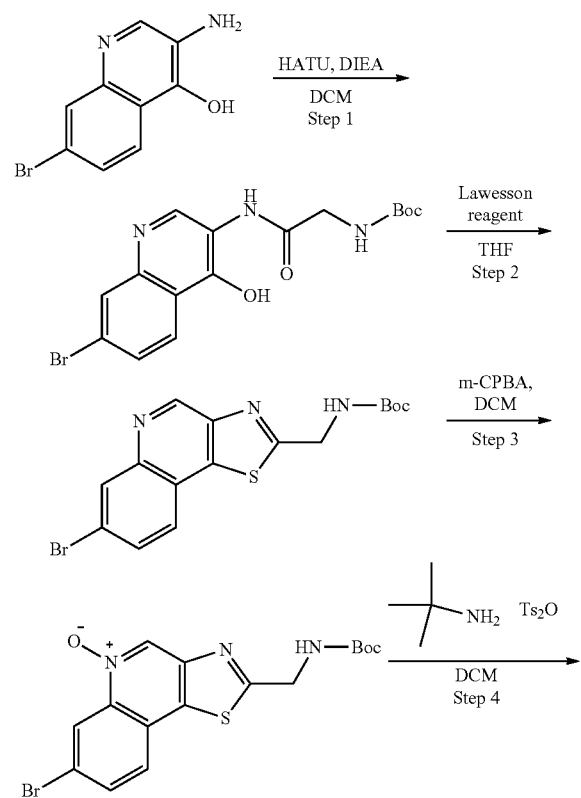

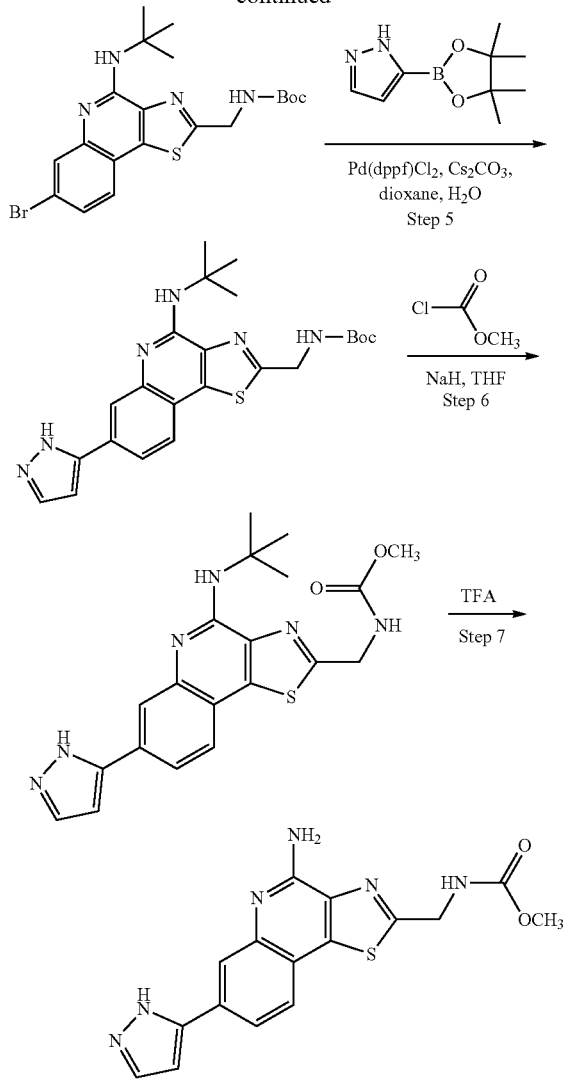

Step 1. tert-butyl N-[[(7-bromo-4-hydroxyquinolin-3-yl)carbamoyl]methyl]carbamate Into a 500-mL round-bottom flask, was placed 3-amino-7-bromoquinolin-4-ol (10 g, 41.83 mmol, 1 equiv), HATU (23.9 g, 62.74 mmol, 1.5 equiv), 2-[[(tert-butoxy) carbonyl]amino]acetic acid (7.3 g, 41.83 mmol, 1 equiv), DCM (100 mL), DIEA (16.2 g, 125.35 mmol, 3.0 equiv). The resulting solution was stirred for 1 h at rt. The resulting solution was washed with 30 mL of EtOAc and filtered. The filtrate was concentrated in vacuo. This provided 15 g (90.5%) of tert-butyl N-[[(7-bromo-4-hydroxyquinolin-3-yl)carbamoyl]methyl]carbamate as a pink solid.

Step 2. tert-butyl N-([7-bromo-[1,3]thiazolo[4,5-c]quinolin-2-yl]methyl)carbamate Into a 500-mL round-bottom flask, was placed tert-butyl N-[[(7-bromo-4-hydroxyquinolin-3-yl)carbamoyl]methyl]carbamate (20 g, 50.47 mmol, 1 equiv), THF (250 mL), Lawesson reagent (16.3 g, 40.38 mmol, 0.8 equiv). The resulting solution was stirred for 3 h at 70° C. The reaction was then quenched by the addition of 200 mL of aq.

NaHCO$_3$. The mixture was extracted with EtOAc (500 mL). The combined organic layers were dried over anhydrous sodium sulfate and concentrated in vacuo. This provided 9 g (45.2%) of tert-butyl N-([7-bromo-[1,3]thiazolo[4,5-c]quinolin-2-yl]methyl)carbamate as alight yellow solid. LC-MS: (ES, m/z): [M+H]$^+$=386.1.

Step 3. 7-bromo-2-(((tert-butoxycarbonyl)amino)methyl)thiazolo[4,5-c]quinoline 5-oxide Into a 100-mL round-bottom flask, was placed tert-butyl N-([7-bromo-[1,3]thiazolo[4,5-c]quinolin-2-yl]methyl)carbamate (1.3 g, 3.30 mmol, 1 equiv), DCM (20 mL), m-CPBA (3.3 g, 13.19 mmol, 4 equiv, 70%). The resulting solution was stirred for 5 hr at rt. The residue was applied onto a silica gel column with dichloromethane/methanol (70:1). This resulted in 1 g (73.92%) of 7-bromo-2-([[(tert-butoxy)carbonyl]amino]methyl)-[1,3]thiazolo[4,5-c]quinolin-5-ium-5-olate as a light yellow solid. LC-MS: (ES, m/z): [M+H]$^+$=412.1.

Step 4. tert-butyl N-[[7-bromo-4-(tert-butylamino)-[1,3]thiazolo[4,5-c]quinolin-2-yl]methyl]carbamate Into a 100-mL round-bottom flask was placed 7-bromo-2-([[(tert-butoxy)carbonyl]amino]methyl)-[1,3]thiazolo[4,5-c]quinolin-5-ium-5-olate (700 mg, 1.71 mmol, 1 equiv), DCM (20 mL), 2-methylpropan-2-amine (623.9 mg, 8.53 mmol, 5 equiv), (4-methylbenzene)sulfonyl 4-methylbenzene-1-sulfonate (1.1 g, 3.41 mmol, 2 equiv). The resulting solution was stirred for 1 h at rt. The resulting mixture was concentrated. The crude product was purified by Prep-TLC (PE/EA=2:1). This provided 680 mg (85.6%) of tert-butyl N-[[7-bromo-4-(tert-butylamino)-[1,3]thiazolo[4,5-c]quinolin-2-yl]methyl]carbamate as a light yellow solid. LC-MS: (ES, m/z): [M+H]+=466.2.

Step 5. tert-butyl N-[[4-(tert-butylamino)-7-(1H-pyrazol-5-yl)-[1,3]thiazolo[4,5-c]quinolin-2-yl]methyl]carbamate Into a 30-mL sealed tube purged and maintained with an inert atmosphere of nitrogen was placed tert-butyl N-[[7-bromo-4-(tert-butylamino)-[1,3]thiazolo[4,5-c]quinolin-2-yl]methyl]carbamate (680 mg, 1.46 mmol, 1 equiv), 5-(4,4,5,5-tetramethyl-1,3,2-dioxaborolan-2-yl)-1H-pyrazole (567.0 mg, 2.92 mmol, 2 equiv), Cs$_2$CO$_3$ (1.4 g, 4.38 mmol, 3 equiv), dioxane (10 mL), H$_2$O (1 mL), Pd(dppf)Cl$_2$ (213.8 mg, 0.29 mmol, 0.2 equiv). The resulting solution was stirred for 16 h at 100° C. The resulting solution was extracted with EtOAc and the combined organic layers was concentrated in vacuo.

The crude product was purified by Prep-TLC (PE/EA=1:2). This provided 420 mg (63.52%) of tert-butyl N-[[4-(tert-butylamino)-7-(1H-pyrazol-5-yl)-[1,3]thiazolo[4,5-c]quinolin-2-yl]methyl]carbamate as a light yellow solid. LC-MS: (ES, m/z): [M+H]+=453.2.

Step 6. methyl N-[[4-(tert-butylamino)-7-(1H-pyrazol-5-yl)-[1,3]thiazolo[4,5-c]quinolin-2-yl]methyl]carbamate Into a 50-mL round-bottom flask was placed a solution of tert-butyl N-[[4-(tert-butylamino)-7-(1H-pyrazol-5-yl)-[1,3]thiazolo[4,5-c]quinolin-2-yl]methyl]carbamate (150 mg, 0.33 mmol, 1 equiv) in THF (10 mL). NaH (26.5 mg, 0.66 mmol, 2 equiv, 60%) was added followed by methyl carbonochloridate (62.6 mg, 0.66 mmol, 2 equiv). The resulting solution was stirred for 1 h at rt. The reaction was then quenched by the addition of MeOH. The resulting mixture was concentrated and heated at reflux in MeOH for 2 h. The reaction was then cooled to rt and purified by Prep-TLC (EA:PE=1:2). This provided 80 mg (58.80%) of methyl N-[[4-(tert-butylamino)-7-(1H-pyrazol-5-yl)-[1,3]thiazolo[4,5-c]quinolin-2-yl]methyl]carbamate as a light yellow solid. LC-MS: (ES, m/z): [M+H]$^+$=411.1.

Step 7. methyl N-[[4-amino-7-(1H-pyrazol-5-yl)-[1,3]thiazolo[4,5-c]quinolin-2-yl]methyl]carbamate Into a 25-mL round-bottom flask was placed methyl N-[[4-(tert-butylamino)-7-(1H-pyrazol-5-yl)-[1,3]thiazolo[4,5-c]quinolin-2-yl]methyl]carbamate (80 mg, 0.19 mmol, 1 equiv) and TFA (5 mL). The resulting solution was stirred at 70° C. for 16 h. The resulting mixture was concentrated in vacuo and purified by Prep-HPLC with the following conditions: Column, XBridge Shield RP18 OBD Column, 19×250 mm, 10 um; mobile phase, Water (10 mM NH$_4$HCO$_3$) and ACN (10% PhaseB up to 60% in 7 min); Detector, UV 254 nm. This provided 25.9 mg (37.50%) of methyl N-[[4-amino-7-(1H-pyrazol-5-yl)-[1,3]thiazolo[4,5-c]quinolin-2-yl]methyl]carbamate as a white solid. LC Methods: Column: Kinetex 2.6 um EVO C18 100A 3.0 mm×50 mm, 2.6 μm particles; Mobile Phase A: Water-5 mM NH$_4$HCO$_3$; Mobile Phase B: acetonitrile; Temperature: 40° C.; Gradient: 10% B to 95% B over 2.1 min, then a 0.7 min hold at 95% B; Flow: 1.2 mL/min. LC RT: 1.073 min. LC-MS: (ES, m/z): [M+H]$^+$=355.1. 1H-NMR: (300 MHz, DMSO-d$_6$, ppm) δ 13.45-12.97 (m, 1H), 8.31 (s, 1H), 8.01 (s, 1H), 7.89-7.57 (m, 3H), 7.02-6.93 (m, 2H), 6.84 (s, 1H), 4.67 (d, J=5.9 Hz, 2H), 3.64 (s, 3H).

Example 135. Preparation of N-(2-(4-amino-7-(1H-pyrazol-5-yl)thiazolo[4,5-c]quinolin-2-yl)ethyl) benzamide

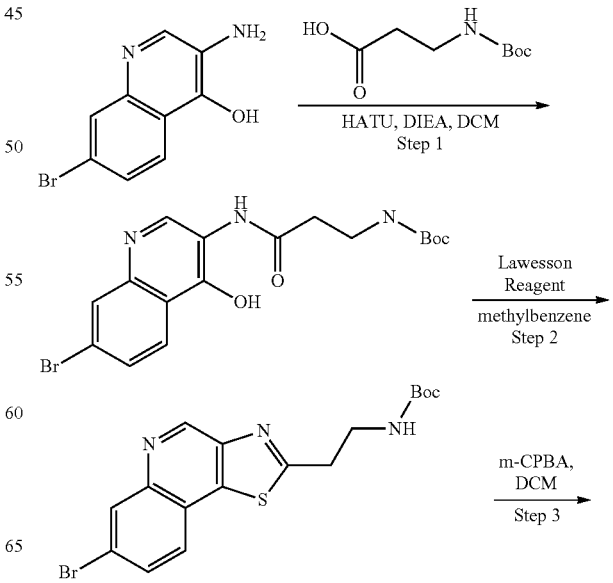

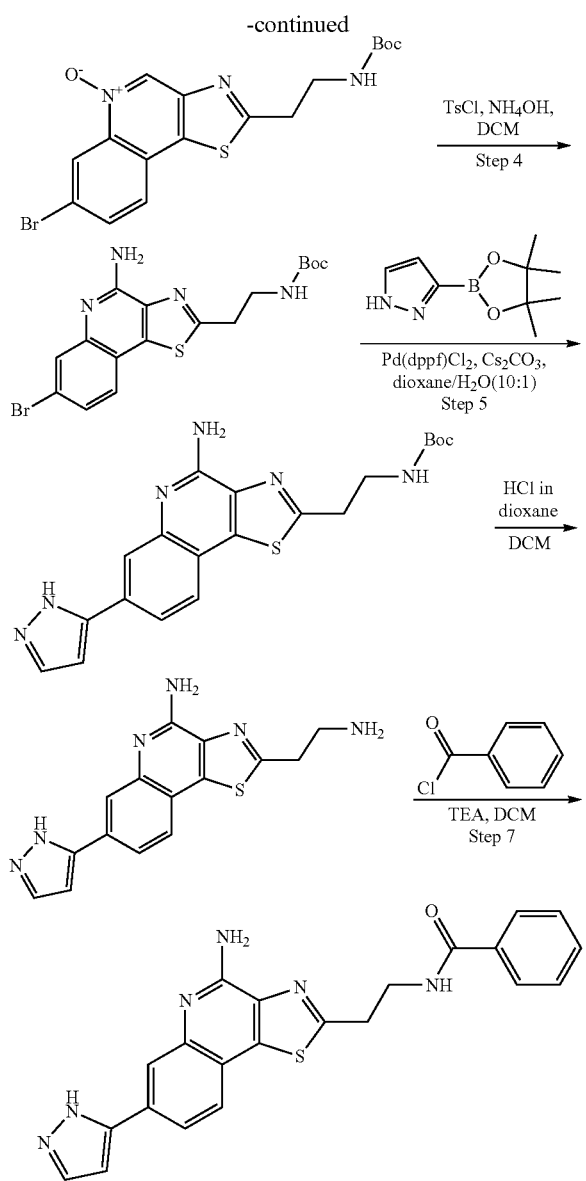

Step 1. tert-butyl N-[2-[(7-bromo-4-hydroxyquinolin-3-yl)carbamoyl]ethyl]carbamate A solution of 3-amino-7-bromoquinolin-4-ol hydrochloride (25 g, 90.73 mmol, 1 equiv), 3-[[(tert-butoxy)carbonyl]amino]propanoic acid (20.6 g, 108.87 mmol, 1.20 equiv), HATU (51.7 g, 136.10 mmol, 1.5 equiv) and DIEA (35.2 g, 272.20 mmol, 3 equiv) in DCM (200 mL) was stirred at 25° C. for 3 h. The resulting mixture was diluted with water (200 mL). The resulting mixture was extracted with $CH_2Cl_2$ (2×200 mL). The combined organic layers were washed with brine (1×200 mL), dried over anhydrous $Na_2SO_4$, and concentrated in vacuo. The residue was washed with EtOAc (3×100 mL) to provide tert-butyl N-[2-[(7-bromo-4-hydroxyquinolin-3-yl)carbamoyl]ethyl]carbamate (35 g, 94.02%) as a red solid. LC-MS: (ES, m/z): [M+H]$^+$=410.1.

Step 2. tert-butyl N-(2-[7-bromo-[1,3]thiazolo[4,5-c]quinolin-2-yl]ethyl)carbamate A solution of tert-butyl N-[2-[(7-bromo-4-hydroxyquinolin-3-yl)carbamoyl]ethyl]carbamate (3.7 g, 9.02 mmol, 1 equiv) and Lawesson Reagent (3.6 g, 8.90 mmol, 0.99 equiv) in methylbenzene (30 mL) was stirred for 1 h at 100° C. The resulting mixture was diluted with water (100 mL). The mixture was basified to pH 8 with saturated aq. $NaHCO_3$. The resulting mixture was extracted with EtOAc (3×100 mL). The combined organic layers were washed with brine (1×100 mL), dried over anhydrous $Na_2SO_4$, and concentrated in vacuo. The residue was purified by silica gel column chromatography, eluting with PE/EtOAc (5:1) to afford tert-butyl N-(2-[7-bromo-[1,3]thiazolo[4,5-c]quinolin-2-yl]ethyl)carbamate (830 mg, 22.54%) as a yellow solid. LC-MS: (ES, m/z): [M+H]$^+$=408.0. $^1$H-NMR: $^1$H NMR (400 MHz, Methanol-$d_4$) δ 9.35 (s, 1H), 8.36 (d, J=2.0 Hz, 1H), 8.05 (d, J=8.7 Hz, 1H), 7.86 (m, 1H), 3.65 (t, J=6.5 Hz, 2H), 3.45 (t, J=6.5 Hz, 2H), 1.42 (s, 9H).

Step 3. 7-bromo-2-(2-[[(tert-butoxy)carbonyl]amino]ethyl)-[1,3]thiazolo[4,5-c]quinolin-5-ium-5-olate A solution of tert-butyl N-(2-[7-bromo-[1,3]thiazolo[4,5-c]quinolin-2-yl]ethyl)carbamate (800 mg, 1.96 mmol, 1 equiv) and m-CPBA (676.2 mg, 3.92 mmol, 2 equiv) in DCM (20 mL) was stirred at rt for 4 h. The resulting mixture was concentrated in vacuo. The residue was purified by silica gel column chromatography, eluting with $CH_2Cl_2$/MeOH (50:1) to afford 7-bromo-2-(2-[[(tert-butoxy)carbonyl]amino]ethyl)-[1,3]thiazolo[4,5-c]quinolin-5-ium-5-olate (432 mg, 51.96%) as a yellow solid. LC-MS: (ES, m/z): [M+H]$^+$=424.0.

Step 4. tert-butyl N-(2-[4-amino-7-bromo-[1,3]thiazolo[4,5-c]quinolin-2-yl]ethyl)carbamate To a stirred solution of 7-bromo-2-(2-[[(tert-butoxy)carbonyl]amino]ethyl)-[1,3]thiazolo[4,5-c]quinolin-5-ium-5-olate (2 g, 4.71 mmol, 1 equiv) and $NH_4OH$ (10 mL) in DCM (30 mL) was added TsCl (1.8 g, 9.44 mmol, 2.00 equiv). The resulting mixture was stirred at rt for 5 h. The resulting mixture was concentrated in vacuo. The residue was purified by silica gel column chromatography, eluting with PE/EtOAc (1:1) to afford tert-butyl N-(2-[4-amino-7-bromo-[1,3]thiazolo[4,5-c]quinolin-2-yl]ethyl)carbamate (1.2 g, 60.14%) as a yellow solid. LC-MS: (ES, m/z): [M+H]$^+$=423.0. H-NMR: $^1$H NMR (400 MHz, DMSO-$d_6$) δ 7.76-7.74 (m, 2H), 7.39 (m, 1H), 7.17 (d, J=14.8 Hz, 3H), 3.46 (m, 2H), 3.32 (m, 2H), 1.37 (s, 9H).

Step 5. tert-butyl N-[2-[4-amino-7-(1H-pyrazol-5-yl)-[1,3]thiazolo[4,5-c]quinolin-2-yl]ethyl]carbamate To a stirred solution of tert-butyl N-(2-[4-amino-7-bromo-[1,3]thiazolo[4,5-c]quinolin-2-yl]ethyl)carbamate (1.1 g, 2.60 mmol, 1 equiv), 3-(4,4,5,5-tetramethyl-1,3,2-dioxaborolan-2-yl)-1H-pyrazole (1.1 g, 5.67 mmol, 2.18 equiv) and $Cs_2CO_3$ (2.5 g, 7.80 mmol, 3 equiv) in dioxane (15 mL) and $H_2O$ (1.5 mL) was added Pd(dppf)Cl$_2$ (0.4 g, 0.52 mmol, 0.2 equiv) at rt under nitrogen atmosphere. The resulting mixture was stirred for 16 h at 90° C. under nitrogen atmosphere. The resulting mixture was concentrated in vacuo. The residue was purified by Prep-TLC ($CH_2Cl_2$/MeOH 10:1) to afford tert-butyl N-[2-[4-amino-7-(1H-pyrazol-5-yl)-[1,3]thiazolo[4,5-c]quinolin-2-yl]ethyl]carbamate (690 mg, 64.69%) as a light yellow solid. LC-MS: (ES, m/z): [M+H]+=411.2.

Step 6. 2-(2-aminoethyl)-7-(1H-pyrazol-5-yl)-[1,3]thiazolo[4,5-c]quinolin-4-amine Into a 25-mL round-bottom flask was placed tert-butyl N-[2-[4-amino-7-(1H-pyrazol-5-yl)-[1,3]thiazolo[4,5-c]quinolin-2-yl]ethyl]carbamate (80 mg, 0.19 mmol, 1 equiv), DCM (4 mL), HCl in dioxane (4 mL). The resulting solution was stirred at rt for 6 h. The resulting mixture was concentrated. The crude product was purified by Prep-HPLC with the following conditions: Column, XBridge Shield RP18 OBD Column, 5 um, 19×150 mm; mobile phase, Water (10 mM NH$_4$HCO$_3$) and ACN (20% Phase B up to 45% in 8 min); Detector, UV 210/254 nm. This provided 2-(2-aminoethyl)-7-(1H-pyrazol-5-yl)-[1,3]thiazolo[4,5-c]quinolin-4-amine (15 mg, 24.80%) as a light yellow solid. LC-MS: (ES, m/z): [M+H]$^+$=311.0. H-NMR: $^1$H NMR (400 MHz, DMSO-d$_6$) δ 13.04-12.91 (m, 1H), 8.05 (s, 1H), 7.96-7.62 (m, 3H), 6.94-6.82 (m, 3H), 3.29 (t, J=6.6 Hz, 2H), 3.07 (t, J=6.6 Hz, 2H), 1.86 (s, 2H).

Step 7. N-(2-(4-amino-7-(1H-pyrazol-5-yl)thiazolo[4,5-c]quinolin-2-yl)ethyl) benzamide Into a 25-mL round-bottom flask, was placed 2-(2-aminoethyl)-7-(1H-pyrazol-5-yl)-[1,3]thiazolo[4,5-c]quinolin-4-amine (80 mg, 0.26 mmol, 1 equiv), DCM (5 mL), TEA (78.2 mg, 0.77 mmol, 3 equiv), benzoyl chloride (43.5 mg, 0.31 mmol, 1.2 equiv). The resulting solution was stirred at rt for 16 h. The resulting mixture was concentrated. The crude product was purified by Prep-HPLC with the following conditions: Column, Sunfire Prep C18 OBD Column, 10 um, 19×250 mm; mobile phase, Water (0.05% TFA) and CAN (10% Phase B up to 60% in 7 min); Detector, UV 210/254 nm. This provided 15.5 mg (11.38%) of N-(2-(4-amino-7-(1H-pyrazol-5-yl)thiazolo[4,5-c]quinolin-2-yl)ethyl)benzamide 2,2,2-trifluoroacetate as a light pink solid. LC Methods: Column: Agilent Poroshell HPH-C$_{18}$ 3.0 mm×50 mm, 2.7 μm particles; Mobile Phase A: water/5 mmol NH$_4$HCO$_3$; Mobile Phase B: acetonitrile; Temperature: 40° C.; Gradient: 10% B to 95% B over 2.1 min, then a 0.6 min hold at 95% B; Flow: 1.0 mL/min. LC RT: 1.236 min. LC-MS: (ES, m/z): [M+H]$^+$=415.2. $^1$H-NMR: (400 MHz, DMSO-d$_6$, ppm) δ 9.29-9.08 (m, 1H), 8.78 (t, J=5.8 Hz, 1H), 8.26 (s, 1H), 8.09-8.07 (m, 2H), 8.00-7.98 (m, 3H), 7.56-7.45 (m, 3H), 6.87 (d, J=2.4 Hz, 1H), 3.83 (t, J=6.3 Hz, 2H), 3.55 (t, J=6.6 Hz, 2H).

Examples 136 to 141 were prepared according to synthetic procedures similar to those described for Example 135 from the appropriate starting materials.

Example 136. N-[2-[4-amino-7-(1H-pyrazol-5-yl)-[1,3]thiazolo[4,5-c]quinolin-2-yl]ethyl]pyridine-2-carboxamide

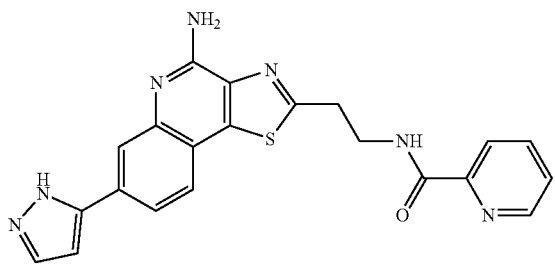 [SMILES: Nc1nc2cc(-c3ccn[nH]3)ccc2c2sc(CCNC(=O)c3ccccn3)nc12]

LC Methods: Column: Kinetex EVO 3.0 mm×50 mm, 2.6 μm particles; Mobile Phase A: water/5 mmol NH$_4$HCO$_3$; Mobile Phase B: acetonitrile; Temperature: 40° C.; Gradient: 10% B to 95% B over 2 min, then a 0.6 min hold at 95% B; Flow: 1.2 mL/min. LC RT: 1.207 min. LC-MS: (ES, m/z): [M+H]$^+$=416.0. $^1$H-NMR: (400 MHz, DMSO-d$_6$, ppm) δ 13.42-12.94 (m, 1H), 9.20 (t, J=6.0 Hz, 1H), 8.66 (d, J=5.0 Hz, 1H), 8.10-8.00 (m, 3H), 7.98-7.56 (m, 4H), 6.98-6.81 (m, 3H), 3.91 (m, 2H), 3.51 (t, J=6.9 Hz, 2H).

Example 137. N-[2-[4-amino-7-(1H-pyrazol-5-yl)-[1,3]thiazolo[4,5-c]quinolin-2-yl]ethyl]oxetane-2-carboxamide

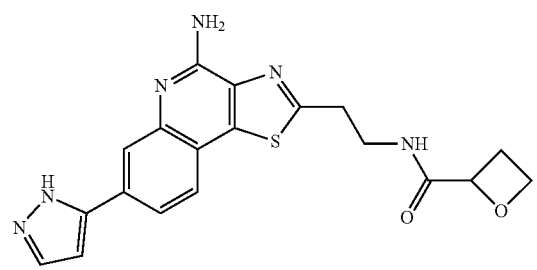 [SMILES: Nc1nc2cc(-c3ccn[nH]3)ccc2c2sc(CCNC(=O)C3CCO3)nc12]

LC Methods: Column: Express C18 2.1 mm×50 mm, 2.7 μm particles; Mobile Phase A: Water+0.05% TFA; Mobile Phase B: Acetonitrile+0.05% TFA; Temperature: 40° C.; Gradient: 5% B to 100% B over 2 min, then a 0.7 min hold at 100% B; Flow: 1.0 mL/min. LC RT: 0.829 min. LC-MS: (ES, m/z): [M+H]$^+$=395.1. $^1$H-NMR: (400 MHz, DMSO-d$_6$, ppm) δ 13.34 (s, 1H), 8.39 (d, J=6.2 Hz, 1H), 8.01 (s, 1H), 7.83-7.75 (m, 3H), 6.98-6.82 (m, 3H), 4.92 (m, 1H), 4.65-4.51 (m, 2H), 3.70 (m, 2H), 3.41 (t, J=6.7 Hz, 2H), 2.94-2.85 (m, 1H), 2.45 (m, 1H).

Example 138. 2-(3-aminopropyl)-7-(1H-pyrazol-5-yl)-1,3]thiazolo[4,5-c]quinolin-4-amine

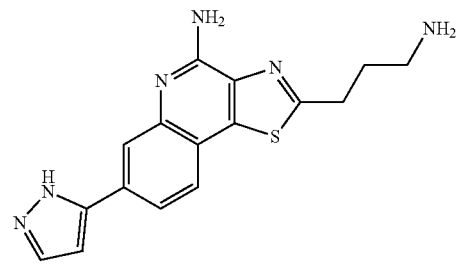 [SMILES: NCCCc1nc2c(N)nc3cc(-c4ccn[nH]4)ccc3c2s1]

LC Methods: Column: Shim-pack XR-ODS, 3.0 mm×50 mm, 2.2 μm particles; Mobile Phase A: water with 0.05% TFA; Mobile Phase B: acetonitrile with 0.05% TFA; Temperature: 40° C.; Gradient: 5% B to 95% B over 2 min, then a 0.7 min hold at 95% B; Flow: 1.5 mL/min. LC RT: 0.776 min. LC-MS: (ES, m/z): [M+H]$^+$=325.3. $^1$H NMR: (400 MHz, Methanol-d$_4$, ppm) δ 8.01 (d, J=1.6 Hz, 1H), 7.83-7.69 (m, 3H), 6.77 (d, J=2.3 Hz, 1H), 3.26 (t, J=7.5 Hz, 2H), 2.97-2.89 (m, 2H), 2.18-2.11 (m, 2H).

Example 139. N-[3-[4-amino-7-(1H-pyrazol-5-yl)-[1,3]thiazolo[4,5-c]quinolin-2-yl]propyl]acetamide

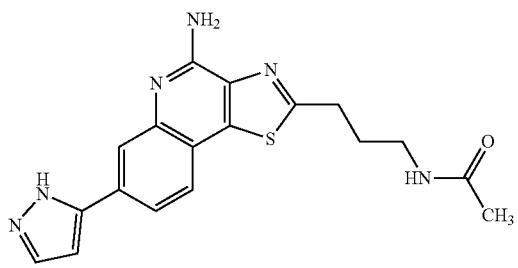 [SMILES: CC(=O)NCCCc1nc2c(N)nc3cc(-c4ccn[nH]4)ccc3c2s1]

LC Methods: Column: Kinetex EVO, 3.0 mm×50 mm, 2.6 μm particles; Mobile Phase A: water with 10 mM NH$_4$HCO$_3$; Mobile Phase B: acetonitrile; Temperature: 40° C.; Gradient: 10% B to 95% B over 2 min, then a 0.6 min hold at 95% B; Flow: 1.2 mL/min. LC RT: 1.020 min. LC-MS: (ES, m/z): [M+H]$^+$=366.95. $^1$H NMR (400 MHz, DMSO-d$_6$, ppm) δ 13.45-12.96 (m, 1H), 8.02-7.96 (m, 2H), 7.83-7.79 (m, 3H), 6.98-6.85 (m, 3H), 3.22-3.17 (m, 4H), 2.08-1.95 (m, 2H), 1.83 (s, 3H).

Example 140. N-{[4-amino-7-(1H-pyrazol-3-yl)-[1,3]thiazolo[4,5-c]quinolin-2-yl]methyl}-N-ethylacetamide

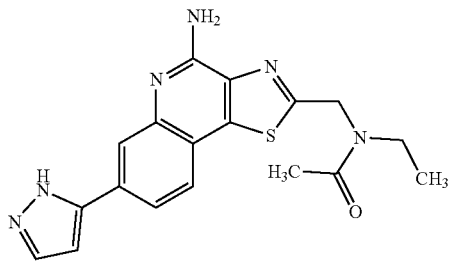 [SMILES: CCN(Cc1nc2c(N)nc3cc(-c4ccn[nH]4)ccc3c2s1)C(C)=O]

LC Methods: Column: Shim-pack XR-ODS, 3.0 mm×50 mm, 2.2 μm particles; Mobile Phase A: water with 0.05% TFA; Mobile Phase B: acetonitrile with 0.05% TFA; Temperature: 40° C.; Gradient: 5% B to 50% B over 2 min, 50% B to 100% B over 0.3 min, then a 0.4 min hold at 100% B; Flow: 1.2 mL/min. LC RT: 1.679 min. LC-MS: (ES, m/z): [M+H]$^+$=367.1. H-NMR: (CD$_3$OD, ppm): δ 8.061 (s, 1H), 7.848-7.741 (m, 3H), 6.785 (s, 1H), 5.091-4.990 (m, 2H), 3.654-3.572 (m, 2H), 2.252 (s, 3H), 1.301-1.166 (m, 3H).

Example 141. 2-[3-(benzyloxy)propyl]-7-(1H-pyrazol-3-yl)-[1,3]thiazolo[4,5-c]quinolin-4-amine

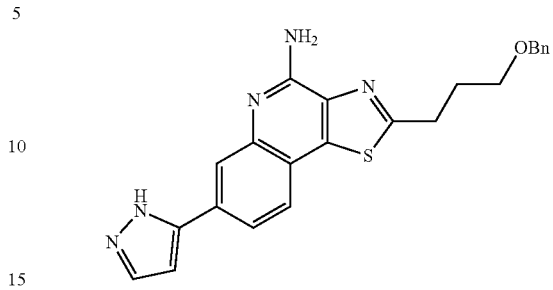

$^1$H NMR (400 MHz, METHANOL-d$_4$) δ 8.07 (br s, 1H), 7.81 (br s, 3H), 7.37-7.14 (m, 5H), 6.80 (br s, 1H), 4.53 (s, 2H), 3.66 (t, J=6.0 Hz, 2H), 2.37-2.14 (m, 2H). LC-MS: (ES, m/z): [M+H]$^+$=416.1.

Example 142. Preparation of 3-[4-amino-7-(1H-pyrazol-3-yl)-[1,3]thiazolo[4,5-c]quinolin-2-yl]propan-1-ol

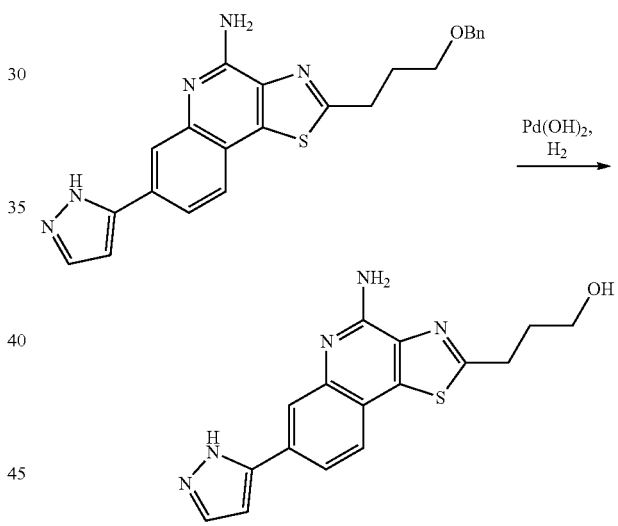

Into a 25-mL round-bottom flask, was placed a solution of 2-[3-(benzyloxy)propyl]-7-(1H-pyrazol-3-yl)-[1,3]thiazolo[4,5-c]quinolin-4-amine (290 mg, 0.70 mmol, 1.00 equiv) in ethanol (30 mL). To the solution was added Pd(OH)$_2$ (29 mg). The resulting solution was degassed and back filled with hydrogen. The resulting solution was stirred for 2 h at 80° C. in an oil bath. The solids were collected by filtration. The resulting mixture was concentrated under vacuum. The crude product was purified by Prep-HPLC with the following conditions (HPLC-10): Column, XBridge Shield RP18 OBD Column, 19*250 mm, 10 um; mobile phase, Water (10 mM NH$_4$HCO$_3$) and ACN (10.0% ACN up to 36.0% in 8 min); Detector, 254/210 nm. This provided 35.7 mg (16%) of 3-[4-amino-7-(1H-pyrazol-3-yl)-[1,3]thiazolo[4,5-c]quinolin-2-yl]propan-1-ol as a white solid. LC-MS: (ES, m/z): [M+H]$^+$=326.0. H-NMR: (DMSO-d$_6$, 300 MHz, ppm): δ 8.02 (s, 1H), 7.82-7.58 (m, 3H), 6.89-6.83 (m, 3H), 4.65 (t, J=5.1 Hz, 1H), 3.58-3.52 (m, 2H), 3.23 (t, J=5.1 Hz, 2H), 2.05-1.96 (m, 2H).

Example 143. Preparation of 2-[(dimethylamino)methyl]-7-(1H-pyrazol-5-yl)-[1,3]thiazolo[4,5-c]quinolin-4-amine

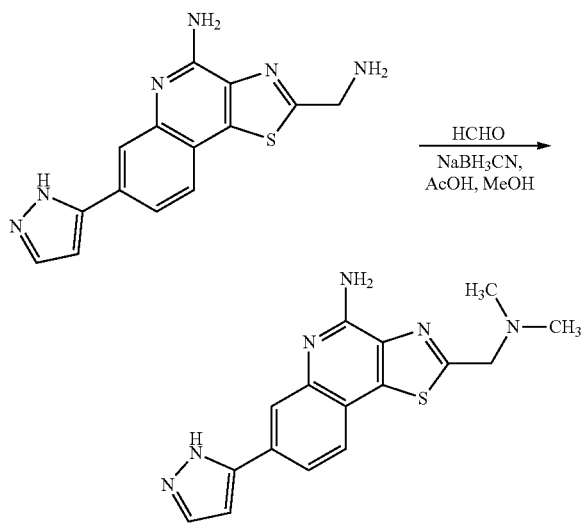

Into a 50-mL round-bottom flask was placed 2-(aminomethyl)-7-(1H-pyrazol-5-yl)-[1,3]thiazolo[4,5-c]quinolin-4-amine (50 mg, 0.17 mmol, 1 equiv), MeOH (5 mL), AcOH (0.1 mL), HCHO (41.1 mg, 0.51 mmol, 3.00 equiv, 37%), NaBH$_4$ (19.1 mg, 0.51 mmol, 3.00 equiv). The resulting solution was stirred for 2 h at rt. The resulting mixture was concentrated. The crude product was purified by Prep-HPLC with the following conditions: Column, XBridge Shield RP18 OBD Column, 19×250 mm, 10 um; mobile phase, Water (10 mM NH$_4$HCO$_3$) and ACN (20% Phase B up to 60% in 8 min); Detector, uv 254 nm. This provided 10.1 mg (18.45%) of 2-[(dimethylamino) methyl]-7-(1H-pyrazol-5-yl)-[1,3]thiazolo[4,5-c]quinolin-4-amine as a white solid. LC Methods: Column: Kinetex EVO C18 3.0 mm×50 mm, 2.6 μm particles; Mobile Phase A: water/5 mmol NH$_4$HCO$_3$; Mobile Phase B: acetonitrile; Temperature: 40° C.; Gradient: 10% B to 95% B over 2 min, then a 0.6 min hold at 95% B; Flow: 1.2 mL/min. LC RT: 0.81 min. LC-MS: (ES, m/z): [M+H]$^+$=325.0. $^1$H-NMR: (400 MHz, DMSO-d$_6$, ppm) δ 12.96 (s, 1H), 8.01 (s, 1H), 7.83-7.57 (m, 3H), 6.98 (s, 2H), 6.84 (s, 1H), 3.94 (s, 2H), 2.37 (s, 6H).

Example 144. Preparation of 2-[3-(diethylamino)propyl]-7-(1H-pyrazol-5-yl)-[1,3]thiazolo[4,5-c]quinolin-4-amine

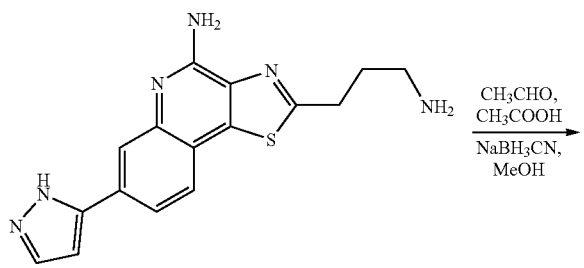

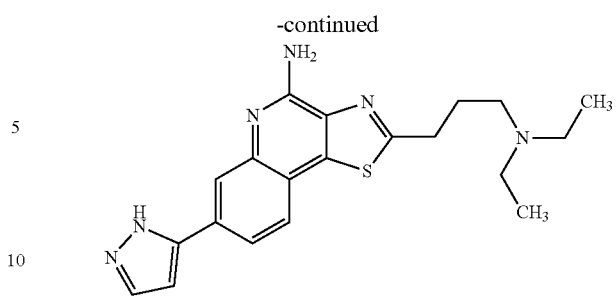

A solution of 2-(3-aminopropyl)-7-(1H-pyrazol-5-yl)-[1,3]thiazolo[4,5-c]quinolin-4-amine (70 mg, 0.22 mmol, 1 equiv), acetaldehyde (14.3 mg, 0.32 mmol, 1.5 equiv) and NaBH$_3$CN (27.1 mg, 0.43 mmol, 2 equiv) in CH$_3$COOH (0.5 mL) and MeOH (10 mL) was stirred for overnight at rt. The resulting mixture was concentrated under reduced pressure. The crude product was purified by Prep-HPLC with the following conditions (Column: XBridge Prep OBD C18 Column 30×150 mm 5 um; Mobile Phase A: Water (10 mM NH$_4$HCO$_3$), Mobile Phase B: ACN; Flow rate: 25 mL/min; Gradient: 25% B to 45% B in 10 min; 254/210 nm; RT: 8 min) to afford 2-[3-(diethylamino)propyl]-7-(1H-pyrazol-5-yl)-[1,3]thiazolo[4,5-c]quinolin-4-amine (9.8 mg, 11.94%) as an off-white solid. LC Methods: Column: Shim-pack XR-ODS 3.0 mm×50 mm, 2.2 μm particles; Mobile Phase A: water with 0.05% TFA; Mobile Phase B: acetonitrile with 0.05% TFA; Temperature: 40° C.; Gradient: 5% B to 95% B over 1.7 min, then a 1.0 min hold at 95% B; Flow: 1.5 mL/min. LC RT: 0.753 min. LC-MS: (ES, m/z): [M+H]$^+$=381.4. $^1$H-NMR: (300 MHz, CD$_3$OD, ppm) δ 8.03 (s, 1H), 7.83 (d, J=8.2 Hz, 1H), 7.77-7.70 (m, 2H), 6.78 (d, J=2.3 Hz, 1H), 3.23 (t, J=7.4 Hz, 2H), 2.67-2.60 (m, 6H), 2.16-2.08 (m, 2H), 1.09-1.05 (m, 6H).

Example 145. Preparation of 2-[(dimethylamino)methyl]-7-(1H-pyrazol-5-yl)-[1,3]oxazolo[4,5-c]quinolin-4-amine

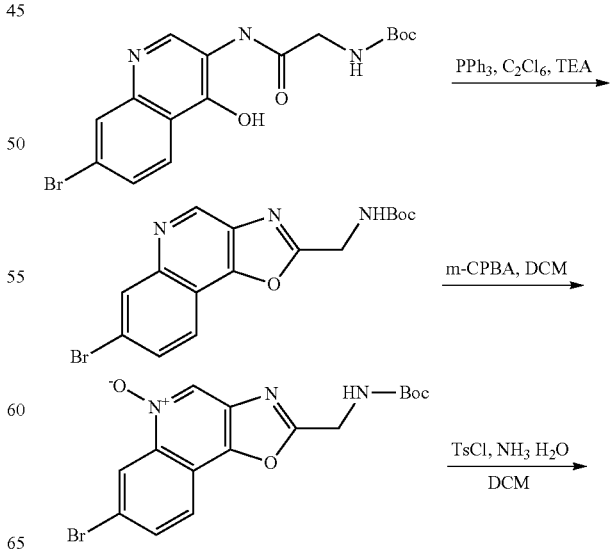

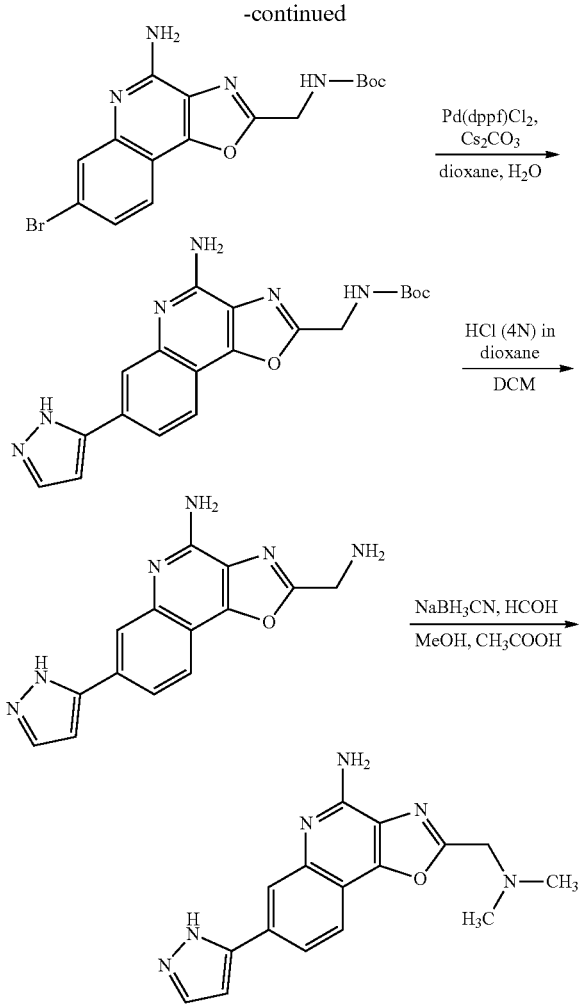

Step 1. tert-butyl N-([7-bromo-[1,3]oxazolo[4,5-c]quinolin-2-yl]methyl)carbamate Into a 500-mL round-bottom flask, was placed tert-butyl N-[[(7-bromo-4-hydroxyquinolin-3-yl)carbamoyl]methyl] carbamate (10 g, 25.24 mmol, 1 equiv), DCM (250 mL), CCl₃CCl₃ (9.0 g, 37.86 mmol, 1.50 equiv), TEA (10.2 g, 100.80 mmol, 3.99 equiv), PPh₃ (9.9 g, 37.75 mmol, 1.50 equiv). The resulting solution was stirred at rt for 1 h. The resulting mixture was diluted with water (200 mL). The resulting solution was extracted with 3×200 mL of dichloromethane and the combined organic layers were dried over anhydrous sodium sulfate and concentrated in vacuo. The residue was applied onto a silica gel column with ethyl acetate/petroleum ether (1:4) to provide 5 g (52.38%) of tert-butyl N-([7-bromo-[1,3]oxazolo[4,5-c]quinolin-2-yl] methyl) carbamate as a pink solid. LC-MS: (ES, m/z): [M+H]⁺=378.0.

Step 2. 7-bromo-2-([[(tert-butoxy)carbonyl]amino] methyl)-[1,3]oxazolo[4,5-c]quinolin-5-ium-5-olate Into a 100-mL round-bottom flask, was placed tert-butyl N-([7-bromo-[1,3]oxazolo[4,5-c]quinolin-2-yl]methyl)carbamate (4.2 g, 11.10 mmol, 1 equiv), DCM (50 mL), m-CPBA (9.6 g, 55.63 mmol, 5.01 equiv). The resulting solution was stirred at rt for 2 h. The resulting mixture was concentrated in vacuo. The residue was applied onto a silica gel column with dichloromethane/methanol (50:1). The resulting mixture was concentrated to provide 1.8 g (41.12%) of 7-bromo-2-([[(tert-butoxy)carbonyl]amino] methyl)-[1,3]oxazolo[4,5-c]quinolin-5-ium-5-olate as a yellow solid. LC-MS: (ES, m/z): [M+H]⁺=394.0.

Step 3. tert-butyl N-([4-amino-7-bromo-[1,3]oxazolo[4,5-c]quinolin-2-yl]methyl)carbamate Into a 100-mL round-bottom flask, was placed 7-bromo-2-([[(tert-butoxy) carbonyl]amino]methyl)-[1,3]oxazolo[4,5-c]quinolin-5-ium-5-olate (1.8 g, 4.57 mmol, 1 equiv) in DCM (5 mL) and NH₃H₂O (5 mL). Then TsCl (1.8 g, 9.44 mmol, 2.07 equiv) was added. The resulting solution was stirred for 1 h at rt. The resulting mixture was concentrated under vacuum. The residue was applied onto a silica gel column with dichloromethane/methanol (50:1). The resulting mixture was concentrated under vacuum. This provided 950 mg (52.91%) of tert-butyl N-([4-amino-7-bromo-[1,3] oxazolo[4,5-c]quinolin-2-yl]methyl)carbamate as an orange solid. LC-MS: (ES, m/z): [M+H]⁺=393.0.

Step 4. tert-butyl N-[[4-amino-7-(1H-pyrazol-5-yl)-[1,3]oxazolo[4,5-c]quinolin-2-yl]methyl]carbamate Into a 50-mL round-bottom flask, was placed tert-butyl N-([4-amino-7-bromo-[1,3]oxazolo[4,5-c]quinolin-2-yl] methyl)carbamate (900 mg, 2.29 mmol, 1 equiv), 5-(4,4,5,5-tetramethyl-1,3,2-dioxaborolan-2-yl)-1H-pyrazole (0.9 g, 4.58 mmol, 2.00 equiv), Cs₂CO₃ (2.2 g, 6.87 mmol, 3.00 equiv) and Pd(dppf)Cl₂ (334.9 mg, 0.46 mmol, 0.20 equiv) in dioxane (5 mL) and H₂O (0.5 mL) under N₂. The resulting mixture was stirred for overnight at 105° C. under nitrogen atmosphere. The resulting mixture was concentrated in vacuo. The residue was purified on a silica gel column with ethyl acetate/petroleum ether (1:4) to provide 680 mg (78.10%) of tert-butyl N-[[4-amino-7-(1H-pyrazol-5-yl)-[1,3]oxazolo[4,5-c]quinolin-2-yl]methyl]carbamate as a brown solid. LC-MS: (ES, m/z):[M+H]⁺=381.2.

Step 5. 2-(aminomethyl)-7-(1H-pyrazol-5-yl)-[1,3] oxazolo[4,5-c]quinolin-4-amine Into a 25-mL round-bottom flask, was placed tert-butyl N-[[4-amino-7-(1H-pyrazol-5-yl)-[1,3]oxazolo[4,5-c]quinolin-2-yl]methyl]carbamate (100 mg, 0.26 mmol, 1 equiv) in DCM (5 mL) and HCl (4N)/dioxane (2 mL). The resulting solution was stirred for 1.5 h at rt. The resulting mixture was concentrated in vacuo. The crude product was purified by Prep-HPLC with the following conditions: Column, XBridge Shield RP18 OBD Column, 5 um, 19×150 mm; mobile phase, Water (10 mM NH₄HCO₃) and ACN (15% Phase B up to 33% in 8 min); Detector, uv 254 nm. This provided 8.9 mg (12.08%) of 2-(aminomethyl)-7-(1H-pyrazol-5-yl)-[1,3]oxazolo[4,5-c]quinolin-4-amine as a yellow solid. LC-MS: (ES, m/z): [M+H]⁺=281.1. H-NMR: ¹H NMR (400 MHz, DMSO-d₆) δ 12.96 (s, 1H), 8.35 (m, 4H), 6.88 (d, J=34.5 Hz, 3H), 4.16 (s, 2H), 1.24 (s, 1H).

Step 6. 2-[(dimethylamino)methyl]-7-(1H-pyrazol-5-yl)-[1,3]oxazolo[4,5-c]quinolin-4-amine Into a 50-mL round-bottom flask, was placed 2-(aminomethyl)-7-(1H-pyrazol-5-yl)-[1, 3]oxazolo[4,5-c]quinolin-4-amine (40 mg, 0.14 mmol, 1 equiv), HCHO (12.9 mg, 0.43 mmol, 3.0 equiv) in MeOH (2 mL) and CH₃COOH (0.2 mL). Then NaBH₃CN (26.9 mg, 0.43 mmol, 3.0 equiv) was added. The resulting solution was stirred for 1 h at rt. The resulting mixture was concentrated. The crude product was purified by Prep-HPLC with the following conditions: Column: XBridge Prep OBD C18 Column 30×150 mm 5 um; Mobile Phase A: Water (10 mM NH₄HCO₃), Mobile Phase B: ACN; Flow rate: 25 mL/min; Gradient: 5% B to 40% B in 7.5 min; 254/210 nm; RT: 7.1 min. This provided 10 mg (22.73%) of 2-[(dimethylamino)methyl]-7-(1H-pyrazol-5-yl)-[1,3]oxazolo[4,5-c]quinolin-4-amine as a white solid. LC Methods: Column: Kinetex EVO C18 3.0 mm×50 mm, 2.6 μm particles; Mobile Phase A: water/5 mmol NH₄HCO₃; Mobile Phase B: acetonitrile; Temperature: 40° C.; Gradient: 10% B to 95% B over 2 min, then a 0.6 min hold at 95% B; Flow: 1.2 mL/min. LC RT: 1.039 min. LC-MS: (ES, m/z): [M+H]+=309.1. ¹H-NMR: (300 MHz, CD₃OD, ppm) δ 8.16-7.98 (m, 2H), 7.82 (d, J=37.3 Hz, 2H), 6.81 (s, 1H), 3.98 (s, 2H), 2.48 (s, 6H).

Example 146. 2-[3-(benzyloxy)propyl]-7-(1H-pyrazol-3-yl)-[1,3]oxazolo[4,5-c]quinolin-4-amine

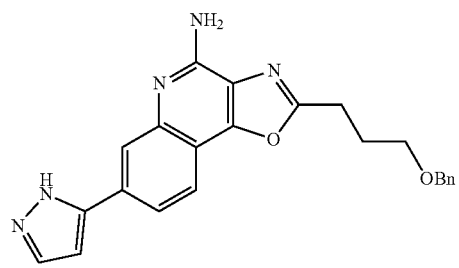 [SMILES: Nc1nc2cc(-c3ccn[nH]3)ccc2c2oc(CCCOCc3ccccc3)nc12]

Example 146 was prepared according to synthetic procedures similar to those described for Example 145 using appropriate starting materials. ¹H NMR (400 MHz, METHANOL-d₄) δ 8.02 (br s, 1H), 7.97 (d, J=8.3 Hz, 1H), 7.64 (br d, J=1.5 Hz, 1H), 7.53 (s, 1H), 7.31-7.16 (m, 5H), 6.74 (d, J=1.6 Hz, 1H), 4.51 (s, 2H), 3.66 (t, J=6.0 Hz, 2H), 3.17 (t, J=7.3 Hz, 2H), 2.33-2.18 (m, 2H). LC-MS: (ES, m/z): [M+H]⁺=400.2.

Example 147. Preparation 3-[4-amino-7-(1H-pyrazol-3-yl)-[1,3]oxazolo[4,5-c]quinolin-2-yl]propan-1-ol

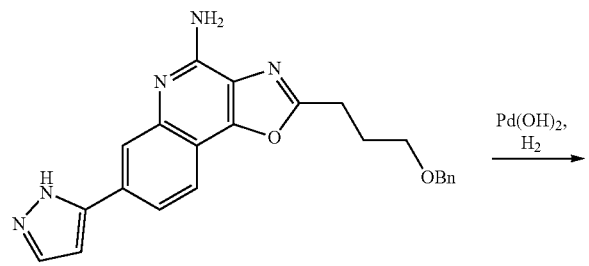

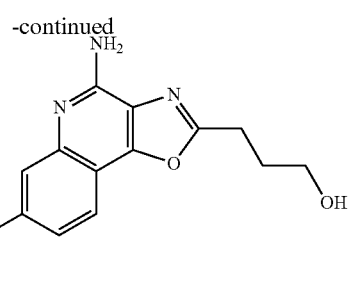

Into a 100-mL round-bottom flask, was placed a solution of 2-[3-(benzyloxy)propyl]-7-(1H-pyrazol-3-yl)-[1,3]oxazolo[4,5-c]quinolin-4-amine (200 mg, 0.50 mmol, 1.00 equiv) in ethanol (30 mL). To the solution was added Pd(OH)₂ (100 mg). The resulting solution was degassed and back filled with hydrogen. The resulting solution was stirred for 2 days at 70° C. in an oil bath. The solids were removed by filtration. The solution was concentrated under vacuum. The residue was purified by Prep-HPLC with the following conditions (HPLC-10): Column, X Bridge Shield RP18 OBD Column, 19×250 mm, 10 um; mobile phase, Water (10 mM NH₄HCO₃) and ACN (10.0% ACN up to 36.0% in 8 min); Detector, UV 254/210 nm. This provided 45 mg (29%) of 3-[4-amino-7-(1H-pyrazol-3-yl)-[1,3]oxazolo[4,5-c]quinolin-2-yl]propan-1-ol as a white solid. LC-MS: (ES, m/z): [M+H]⁺=310.1. H-NMR: (CD₃OD, 300 MHz, ppm): δ 8.14-7.96 (m, 2H), 7.85-7.81 (m, 1H), 7.78-7.68 (m, 1H), 6.79 (s, 1H), 3.74 (t, J=6.0 Hz, 2H), 3.17 (t, J=4.5 Hz, 2H), 2.21-2.12 (m, 2H).

Example 148. Preparation of 3-[4-amino-7-(1H-pyrazol-3-yl)furo[2,3-c]quinolin-2-yl]propan-1-ol

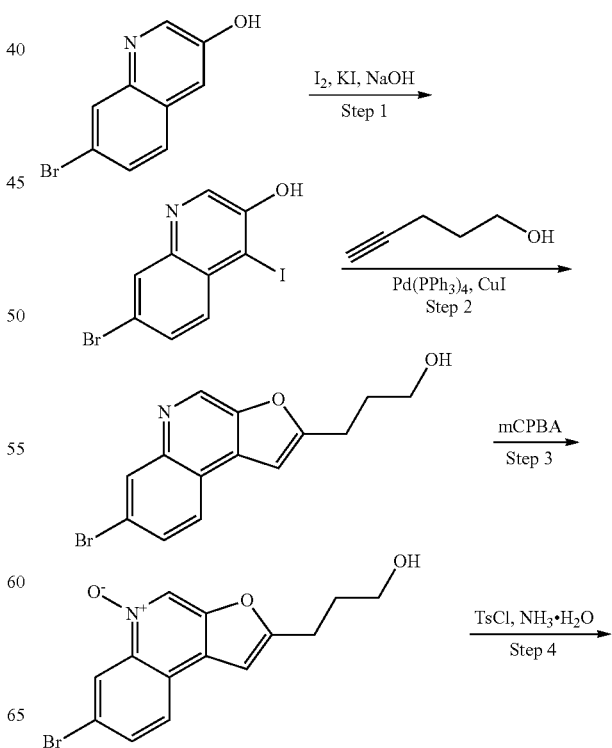

-continued

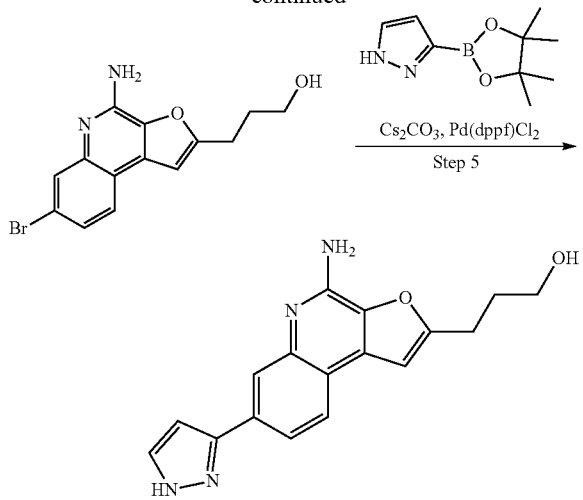

Step 1: 7-bromo-4-iodoquinolin-3-ol

Into a 250-mL round-bottom flask, was placed a solution of 7-bromoquinolin-3-ol (2000 mg, 8.93 mmol, 1.00 equiv) in 2 N NaOH solution (40 mL). To this mixture, a solution of iodine (4536 mg, 17.86 mmol) in 20% aqueous potassium iodide (40 mL) was added dropwise. The resulting solution was stirred for 3 h at 25° C. Then the pH value of the solution was adjusted to 6-7 with acetic acid. The solids were collected by filtration and washed with 15 mL of H$_2$O three times. This provided 2740 mg (88%) of 7-bromo-4-iodoquinolin-3-ol as a yellow solid. LC-MS: (ES, m/z): [M+H]$^+$=350.0.

Step 2. 3-[7-bromofuro[2,3-c]quinolin-2-yl]propan-1-ol

Into a 250-mL round-bottom flask purged and maintained with an inert atmosphere of nitrogen, was placed a solution of 7-bromo-4-iodoquinolin-3-ol (1575 mg, 4.50 mmol, 1.00 equiv) in CH$_3$CN (20 mL) and TEA (10 mL). To the solution were added pent-4-yn-1-ol (378 mg, 4.50 mmol, 1.00 equiv), Pd(PPh$_3$)$_4$ (156 mg, 0.14 mmol, 0.03 equiv) and CuI (27 mg, 0.14 mmol, 0.03 equiv). The resulting solution was stirred for 12 h at 70° C. in an oil bath. The resulting mixture was concentrated under vacuum. The residue was applied onto a silica gel column with ethyl acetate/petroleum ether (½). This provided 681 mg (49%) of 3-[7-bromofuro[2,3-c]quinolin-2-yl]propan-1-ol as a yellow solid. LC-MS: (ES, m/z): [M+H]$^+$=306.2.

Step 3: 7-bromo-2-(3-hydroxypropyl)furo[2,3-c]quinolin-5-ium-5-olate

Into a 250-mL round-bottom flask purged and maintained with an inert atmosphere of nitrogen, was placed a solution of 3-[7-bromofuro[2,3-c]quinolin-2-yl]propan-1-ol (681 mg, 2.22 mmol, 1.00 equiv) in dichloromethane (20 mL). To the solution was added m-CPBA (824 mg, 4.77 mmol, 2.15 equiv). The resulting solution was stirred for 2 h at 25° C. The resulting mixture was concentrated under vacuum. The residue was applied onto a silica gel column with dichloromethane/methanol (25/1). This provided 470 mg (66%) of 7-bromo-2-(3-hydroxypropyl)furo[2,3-c]quinolin-5-ium-5-olate as a yellow solid. LC-MS: (ES, m/z): [M+H]$^+$=322.2.

Step 4: 3-[4-amino-7-bromofuro[2,3-c]quinolin-2-yl]propan-1-ol

Into a 250-mL round-bottom flask, was placed a solution of 7-bromo-2-(3-hydroxypropyl)furo[2,3-c]quinolin-5-ium-5-olate (470 mg, 1.46 mmol, 1.00 equiv) in dichloromethane (20 mL). To the solution were added NH$_3$—H$_2$O (10 mL) and TsCl (416 mg, 2.18 mmol, 1.50 equiv). The resulting solution was stirred for 2 h at 25° C. The resulting mixture was concentrated under vacuum. The residue was applied onto a silica gel column with dichloromethane/methanol (10/1). This provided 390 mg (83%) of 3-[4-amino-7-bromofuro[2,3-c]quinolin-2-yl]propan-1-ol as a yellow solid. LC-MS: (ES, m/z): [M+H]$^+$=321.2.

Step 5: 3-[4-amino-7-(1H-pyrazol-3-yl)furo[2,3-c]quinolin-2-yl]propan-1-ol

Into a 100-mL round-bottom flask purged and maintained with an inert atmosphere of nitrogen, was placed a solution of 3-[4-amino-7-bromofuro[2,3-c]quinolin-2-yl]propan-1-ol (390 mg, 1.21 mmol, 1.00 equiv) in dioxane/water (15/3 mL). To the solution were added 3-(tetramethyl-1,3,2-dioxaborolan-2-yl)-1H-pyrazole (350 mg, 1.80 mmol, 1.49 equiv), Cs$_2$CO$_3$ (785 mg, 2.45 mmol, 2.01 equiv) and Pd(dppf)Cl$_2$·DCM (200 mg, 0.24 mmol, 0.20 equiv). The resulting solution was stirred for 12 h at 100° C. in an oil bath. The resulting mixture was concentrated under vacuum. The residue was applied onto a silica gel column with dichloromethane/methanol (10/1). The resulting crude product (250 mg) was purified by by Prep-HPLC with the following conditions (HPLC-10): Column, XBridge Shield RP18 OBD Column, 19*250 mm, 10 um; mobile phase, Water (10 mM NH$_4$HCO$_3$) and ACN (15.0% ACN up to 35.0% in 9 min); Detector, UV 254/210 nm. This provided 77 mg (21%) of 3-[4-amino-7-(1H-pyrazol-3-yl)furo[2,3-c]quinolin-2-yl]propan-1-ol as a white solid. LC-MS: (ES, m/z): [M+H]$^+$=309.1. H-NMR (CD$_3$OD, 400 MHz, ppm): δ 8.10-8.01 (m, 2H), 7.86-7.64 (m, 2H), 7.10 (s, 1H), 6.77 (s, 1H), 3.69 (t, J=6.4 Hz, 2H), 3.03 (t, J=7.2 Hz, 2H), 2.09-2.02 (m, 2H).

Example 149. Preparation of 2-(2-aminoethyl)-7-(1H-pyrazol-3-yl)-2H-pyrazolo[4,3-c]quinolin-4-amine

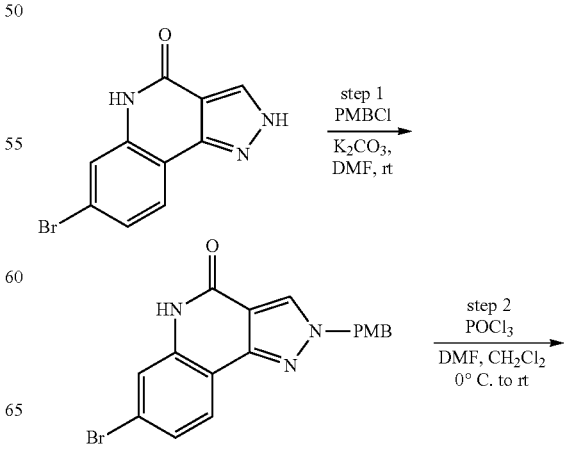

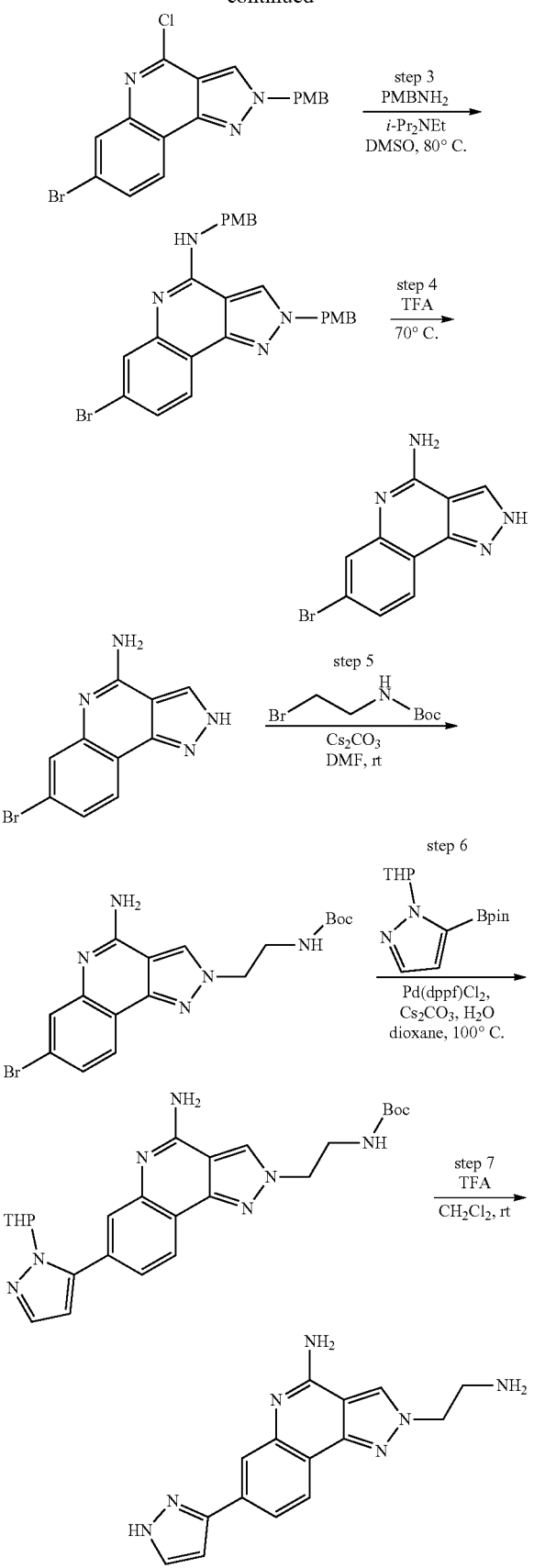

Step 1. 7-bromo-2-(4-methoxybenzyl)-2,5-dihydro-4H-pyrazolo[4,3-c]quinolin-4-one To a rt suspension of 7-bromo-2,5-dihydro-4H-pyrazolo[4,3-c]quinolin-4-one (256 mg, 0.969 mmol) (prepared according to WO 2013/045400) in DMF (9694 µl) was added potassium carbonate (402 mg, 2.91 mmol) and 1-(chloromethyl)-4-methoxybenzene (158 µl, 1.163 mmol). The reaction was stirred at rt for 2 days. The reaction was diluted with 10% MeOH-EtOAc (200 mL), washed with H$_2$O (200 mL) and sat. aq. NaCl (200 mL), dried over Na$_2$SO$_4$, filtered, and concentrated in vacuo. Used without further purification. LC-MS m/z 384/386 [M+H]$^+$. A minor amount of the regioisomeric product appears to be present, and was carried through the next three steps of the synthesis.

Step 2. 7-bromo-4-chloro-2-(4-methoxybenzyl)-2H-pyrazolo[4,3-c]quinoline

To a 0° C. mixture of 7-bromo-2-(4-methoxybenzyl)-2,5-dihydro-4H-pyrazolo[4,3-c]quinolin-4-one (crude material from previous reaction) in CH$_2$Cl$_2$ (4548 µl) and DMF (227 µl) was added phosphoryl chloride (107 µl, 1.146 mmol), dropwise. The solution was stirred at rt for 17 h. Added additional POCl$_3$ (53.5 µL) and stirred at rt for 1.5 h. Added additional DMF (0.5 mL) and stirred for 3 h. The reaction was quenched by slow addition to stirred 1.5 M aq. K$_2$HPO$_4$ (100 mL). The mixture was extracted with CH$_2$Cl$_2$ (2×100 mL). The combined organic layers were dried over Na$_2$SO$_4$, filtered, and concentrated in vacuo. The crude material was dissolved in a mixture of CH$_2$Cl$_2$ and MeOH, mixed with Celite, and concentrated in vacuo. This material was dry loaded onto a column and re-purified by flash chromatography (40 g silica gel; linear gradient 0-100% EtOAc-CH$_2$Cl$_2$) to provide 7-bromo-4-chloro-2-(4-methoxybenzyl)-2H-pyrazolo[4,3-c]quinoline (108 mg, 28%) as an off-white solid. LC-MS m/z 402/404 [M+H]$^+$.

Step 3. 7-bromo-N,2-bis(4-methoxybenzyl)-2H-pyrazolo[4,3-c]quinolin-4-amine

To a rt solution of 7-bromo-4-chloro-2-(4-methoxybenzyl)-2H-pyrazolo[4,3-c]quinoline (108 mg, 0.268 mmol) in DMSO (894 µl) was added (4-methoxyphenyl)methanamine (70.1 µl, 0.536 mmol) and N,N-diisopropylethylamine (140 µl, 0.805 mmol). The reaction was stirred at 80° C. for 22 h. The reaction was cooled to rt, diluted with EtOAc (20 mL), washed with H$_2$O (20 mL) and sat. aq. NaCl (20 mL), dried over Na$_2$SO$_4$, filtered, and concentrated in vacuo. This material was used without further purification. LC-MS m/z 503/505 [M+H]$^+$.

Step 4. 7-bromo-2H-pyrazolo[4,3-c]quinolin-4-amine, TFA

A solution of 7-bromo-N,2-bis(4-methoxybenzyl)-2H-pyrazolo[4,3-c]quinolin-4-amine (143 mg, 0.284 mmol) in TFA (568 µl) was sealed and stirred at 70° C. for 16 h. The reaction was cooled to rt and concentrated in vacuo. The crude material was concentrated from CH$_2$Cl$_2$ (2×2 mL). The crude material was mixed with CH$_2$Cl$_2$ (0.5 mL), filtered, and washed with CH$_2$Cl$_2$ (3×0.5 mL) to provide 7-bromo-2H-pyrazolo[4,3-c]quinolin-4-amine, TFA (99 mg, 92%) as a white solid. LC-MS m/z 263/265 [M+H]$^+$; $^1$H NMR (400 MHz, DMSO-d$_6$) δ 13.26-12.95 (m, 1H), 9.81-

9.57 (m, 1H), 8.95-8.56 (m, 2H), 8.18 (d, J=8.5 Hz, 1H), 7.93 (br s, 1H), 7.80-7.70 (m, 1H).

Step 5. tert-butyl (2-(4-amino-7-bromo-2H-pyrazolo [4,3-c]quinolin-2-yl)ethyl)carbamate To a rt solution of 7-bromo-2H-pyrazolo[4,3-c]quinolin-4-amine, TFA (98 mg, 0.26 mmol) in DMF (742 µl) was added cesium carbonate (254 mg, 0.780 mmol) followed by tert-butyl (2-bromoethyl)carbamate (64.1 mg, 0.286 mmol). The suspension was stirred at rt for 3 h. The reaction was diluted with EtOAc (20 mL) and H$_2$O (20 mL). The layers were separated and the aqueous layer was extracted with EtOAc (20 mL). The combined organic layers were washed with sat. aq. NaCl (20 mL), dried over Na$_2$SO$_4$, and filtered. Celite was added, and the mixture was concentrated in vacuo. This material was dry loaded onto a column and purified by flash chromatography (24 g silica gel with 5 g solid load cartridge; linear gradient 0-10% MeOH—CH$_2$Cl$_2$) to provide tert-butyl (2-(4-amino-7-bromo-2H-pyrazolo[4,3-c]quinolin-2-yl)ethyl)carbamate (54.2 mg, 51%). The product was the second of the two observed regioisomeric peaks to elute from the column; it was the less polar product observed under the LC-MS conditions. LC-MS m/z 406/408 [M+H]$^+$; $^1$H NMR (500 MHz, DMSO-d$_6$) δ 8.42 (s, 1H), 7.98 (d, J=8.3 Hz, 1H), 7.57 (d, J=2.0 Hz, 1H), 7.29 (dd, J=8.3, 2.0 Hz, 1H), 7.16-7.06 (m, 2H), 6.99 (br t, J=5.6 Hz, 1H), 4.43 (br t, J=5.9 Hz, 2H), 3.43 (q, J=5.9 Hz, 2H), 1.33 (s, 9H).

Step 6. tert-butyl (2-(4-amino-7-(1-(tetrahydro-2H-pyran-2-yl)-1H-pyrazol-5-yl)-2H-pyrazolo[4,3-c]quinolin-2-yl)ethyl)carbamate A mixture of tert-butyl (2-(4-amino-7-bromo-2H-pyrazolo[4,3-c]quinolin-2-yl)ethyl)carbamate (53.2 mg, 0.131 mmol), 1-(tetrahydro-2H-pyran-2-yl)-5-(4,4,5,5-tetramethyl-1,3,2-dioxaborolan-2-yl)-1H-pyrazole (54.6 mg, 0.196 mmol), and cesium carbonate (128 mg, 0.393 mmol) was evacuated and back-filled with N$_2$, then 1,4-dioxane (1178 µl) and H$_2$O (131 µl) were added. The resulting mixture was sparged with N$_2$ for 15 min, then [1,1'-bis (diphenylphosphino)ferrocene]dichloropalladium(II) (4.79 mg, 6.55 µmol) was added. The mixture was sparged with N$_2$ for 1 min, then it was stirred at 100° C. for 30 min. The reaction was cooled to rt, diluted with EtOAc (20 mL), washed with H$_2$O (20 mL) and sat. aq. NaCl (20 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide tert-butyl (2-(4-amino-7-(1-(tetrahydro-2H-pyran-2-yl)-1H-pyrazol-5-yl)-2H-pyrazolo[4,3-c]quinolin-2-yl)ethyl)carbamate. LC-MS m/z 478 [M+H]$^+$.

Step 7. 2-(2-aminoethyl)-7-(1H-pyrazol-3-yl)-2H-pyrazolo[4,3-c]quinolin-4-amine To a rt solution of tert-butyl (2-(4-amino-7-(1-(tetrahydro-2H-pyran-2-yl)-1H-pyrazol-5-yl)-2H-pyrazolo[4,3-c]quinolin-2-yl)ethyl)carbamate (62.6 mg, 0.131 mmol) in CH$_2$Cl$_2$ (328 µl) was added TFA (328 µl). The reaction was stirred at rt for 1.5 h. The reaction was concentrated to remove about half the volume, then it was added dropwise to Et$_2$O (4 mL). The resulting solid was collected by vacuum filtration and washed with Et$_2$O (3×1 mL) to provide 2-(2-aminoethyl)-7-(1H-pyrazol-3-yl)-2H-pyrazolo[4,3-c]quinolin-4-amine, 2 TFA (64.3 mg, 94%) as a white solid. A portion of this material (10 mg) was further purified via preparative LC/MS with the following conditions: Column: XBridge C18, 200 mm×19 mm, 5-µm particles; Mobile Phase A: 5:95 acetonitrile:water with 0.10% trifluoroacetic acid; Mobile Phase B: 95:5 acetonitrile:water with 0.10% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-aminoethyl)-7-(1H-pyrazol-3-yl)-2H-pyrazolo[4,3-c]quinolin-4-amine, 2 TFA (7.1 mg). $^1$H NMR (500 MHz, DMSO-d$_6$) δ 13.24-13.03 (m, 1H), 9.52-8.98 (m, 1H), 8.90 (s, 1H), 8.23 (d, J=8.2 Hz, 1H), 8.09 (br s, 1H), 7.92 (br d, J=5.9 Hz, 1H), 7.88-7.78 (m, 1H), 6.82 (d, J=2.1 Hz, 1H), 4.73 (br t, J=5.6 Hz, 2H), 3.48-3.44 (m, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 294.0 [M+H]$^+$; RT: 0.52 min.

Example 150. Preparation of N-{2-[4-amino-7-(1H-pyrazol-3-yl)-2H-pyrazolo[4,3-c]quinolin-2-yl]ethyl}pyridine-2-carboxamide

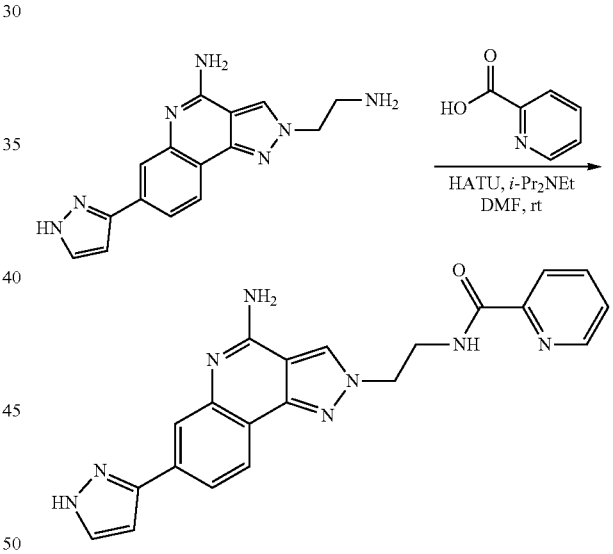

To a rt solution of picolinic acid (7.06 mg, 0.057 mmol) in DMF (174 µl) was added N,N-diisopropylethylamine (18.17 µl, 0.104 mmol), followed by HATU (19.84 mg, 0.052 mmol). This mixture was stirred at rt for 5 min, then it was added, dropwise, to a solution of 2-(2-aminoethyl)-7-(1H-pyrazol-3-yl)-2H-pyrazolo[4,3-c]quinolin-4-amine, 2 TFA (27.2 mg, 0.052 mmol) and N,N-diisopropylethylamine (27.3 µl, 0.157 mmol) in DMF (174 µl). The reaction was stirred at rt for 30 min. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 4% B, 4-44% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(1H-pyrazol-3-yl)-2H-pyrazolo[4,3-c]quinolin-2-yl)ethyl)picolinamide (14.2 mg, 68%). $^1$H NMR (500 MHz, DMSO-$d_6$) δ 9.10 (t, J=5.9 Hz, 1H), 8.62 (d, J=4.7 Hz, 1H), 8.46 (s, 1H), 8.08 (d, J=8.1 Hz, 1H), 8.03-7.95 (m, 2H), 7.87 (d, J=1.3 Hz, 1H), 7.71 (s, 1H), 7.64 (d, J=7.8 Hz, 1H), 7.61-7.57 (m, 1H), 7.07-6.84 (m, 2H), 6.75 (d, J=2.1 Hz, 1H), 4.63 (t, J=6.0 Hz, 2H), 3.86 (q, J=5.9 Hz, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 399. [M+H]$^+$; RT: 0.92 min.

Example 151. Preparation of N-{2-[4-amino-7-(1H-pyrazol-3-yl)-2H-pyrazolo[4,3-c]quinolin-2-yl]ethyl}-2-chloro-1,3-thiazole-4-carboxamide

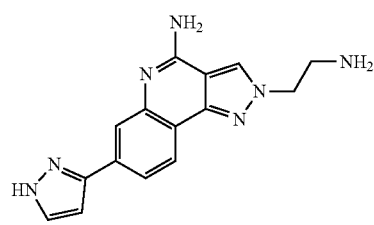
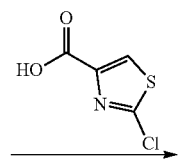
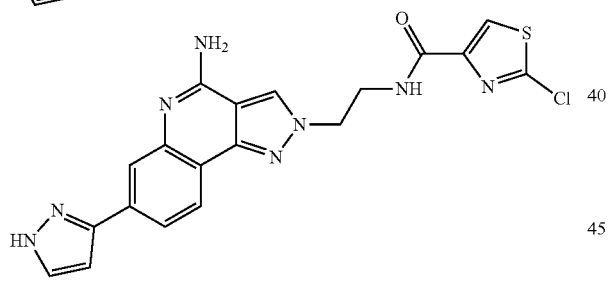

To a rt solution of 2-chlorothiazole-4-carboxylic acid (9.39 mg, 0.057 mmol) in DMF (130 μl) was added N,N-diisopropylethylamine (18.17 μl, 0.104 mmol), followed by HATU (19.84 mg, 0.052 mmol). This mixture was stirred at rt for 5 min, then it was added, dropwise, to a solution of 2-(2-aminoethyl)-7-(1H-pyrazol-3-yl)-2H-pyrazolo[4,3-c]quinolin-4-amine, 2 TFA (27.2 mg, 0.052 mmol) and N,N-diisopropylethylamine (27.3 μl, 0.157 mmol) in DMF (130 μl). The reaction was stirred at rt for 30 min. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-47% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(1H-pyrazol-3-yl)-2H-pyrazolo[4,3-c]quinolin-2-yl)ethyl)-2-chlorothiazole-4-carboxamide (14.7 mg, 64%). $^1$H NMR (500 MHz, DMSO-$d_6$) δ 8.83 (br t, J=5.5 Hz, 1H), 8.44 (s, 1H), 8.23 (s, 1H), 8.09 (d, J=8.3 Hz, 1H), 7.87 (s, 1H), 7.71 (br s, 1H), 7.63 (br d, J=7.7 Hz, 1H), 6.99-6.88 (m, 2H), 6.76 (d, J=1.9 Hz, 1H), 4.60 (br t, J=5.6 Hz, 2H), 3.82-3.75 (m, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 439.0 [M+H]$^+$; RT: 1.16 min.

Example 152. Preparation of 2-(2-aminoethyl)-7-(1H-pyrazol-5-yl)-1H-pyrrolo[3,2-c]quinolin-4-amine

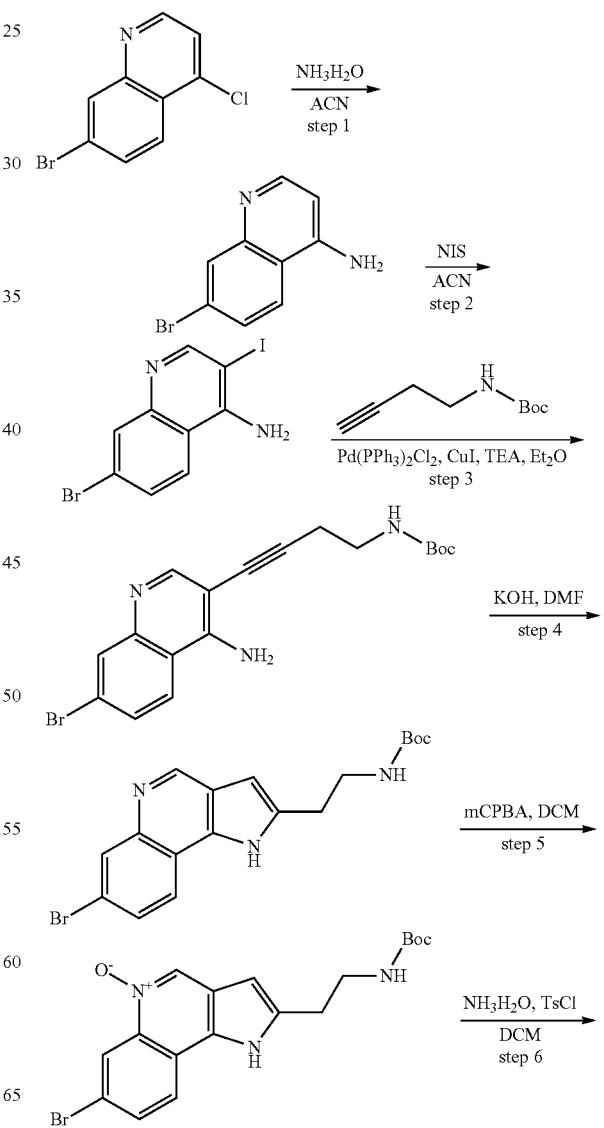

-continued

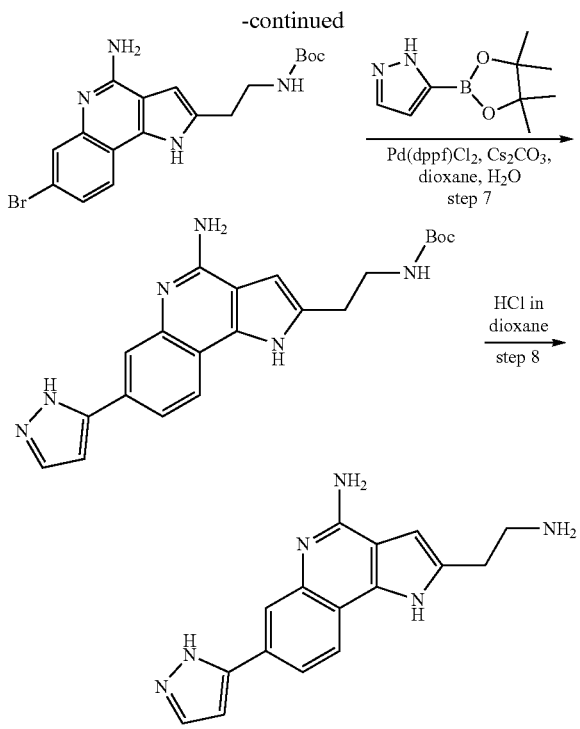

Step 1. Synthesis of 7-bromoquinolin-4-amine

A solution of 7-bromo-4-chloroquinoline (6.8 g, 28.04 mmol, 1 equiv) in aq. ammonia (20 mL) and CH$_3$CN (50 mL) was stirred for 2 days at 120° C. The resulting mixture was concentrated under reduced pressure. The residue was purified by silica gel column chromatography, eluted with PE/EtOAc (5:1) to afford 7-bromoquinolin-4-amine (1.1 g, 17.59%) as a yellow solid. LC-MS: (ES, m/z): [M+H]$^+$=223.0/225.0.

Step 2. Synthesis of 7-bromo-3-iodoquinolin-4-amine

A solution of 7-bromoquinolin-4-amine (1.1 g, 4.93 mmol, 1 equiv) and NIS (1029 mg, 5.92 mmol, 1.2 equiv) in CH$_3$CN (20 mL) was stirred for 2 h at 65° C. The resulting mixture was concentrated under reduced pressure. The residue was purified by silica gel column chromatography, eluted with PE/EtOAc (2:1) to afford 7-bromo-3-iodoquinolin-4-amine (850 mg, 49%) as a brown yellow solid. LC-MS: (ES, m/z):[M+H]+=249.9/251.9. $^1$H NMR (400 MHz, DMSO-d$_6$) δ 8.63 (s, 1H), 8.28 (d, J=9.0 Hz, 1H), 7.96 (d, J=1.7 Hz, 1H), 7.60 (dd, J=9.0, 1.7 Hz, 1H), 7.01 (s, 2H).

Step 3. Synthesis of tert-butyl N-[4-(4-amino-7-bromoquinolin-3-yl)but-3-yn-1-yl]carbamate A solution of 7-bromo-3-iodoquinolin-4-amine (3 g, 8.6 mmol, 1 equiv), tert-butyl N-(but-3-yn-1-yl)carbamate (1745 mg, 10.3 mmol, 1.2 equiv), CuI (163.7 mg, 0.86 mmol, 0.1 equiv), Pd(PPh$_3$)$_2$Cl$_2$ (603.4 mg, 0.86 mmol, 0.1 equiv) and TEA (4349 mg, 42.9 mmol, 5 equiv) in Et$_2$O (30 mL) was stirred for overnight at rt under nitrogen atmosphere. The resulting mixture was concentrated under reduced pressure. The residue was purified by silica gel column chromatography, eluted with PE/EtOAc (2:1) to afford tert-butyl N-[4-(4-amino-7-bromoquinolin-3-yl)but-3-yn-1-yl]carbamate (1.4 g, 41.7%) as a yellow solid. LC-MS: (ES, m/z): [M+H]$^+$=390.1/392.1.

Step 4. Synthesis of tert-butyl N-(2-[7-bromo-1H-pyrrolo[3,2-c]quinolin-2-yl]ethyl) carbamate A solution of tert-butyl N-[4-(4-amino-7-bromoquinolin-3-yl)but-3-yn-1-yl]carbamate (1.8 g, 4.612 mmol, 1 equiv) and KOH (5.17 g, 9.2 mmol, 2.0 equiv) in DMF (20 mL) was stirred for overnight at 40° C. under nitrogen atmosphere. The resulting mixture was concentrated under reduced pressure. The residue was purified by silica gel column chromatography, eluted with PE/EtOAc (1:1) to afford tert-butyl N-(2-[7-bromo-TH-pyrrolo[3,2-c]quinolin-2-yl]ethyl)carbamate (540 mg, 30%) as a yellow solid. LC-MS (ES, m/z): [M+H]$^+$=390.1/392.1. $^1$H NMR (400 MHz, DMSO-d$_6$) δ 12.38 (s, 1H), 9.02 (s, 1H), 8.31 (d, J=8.7 Hz, 1H), 8.18 (d, J=1.7 Hz, 1H), 7.74 (dd, J=8.8, 1.8 Hz, 1H), 7.04 (t, J=5.5 Hz, 1H), 6.54 (s, 1H), 3.39-3.35 (m, 2H), 2.96 (t, J=7.2 Hz, 2H), 1.37 (s, 9H).

Step 5. Synthesis of 7-bromo-2-(2-[[(tert-butoxy)carbonyl]amino]ethyl)-1H-pyrrolo[3,2-c]quinolin-5-ium-5-olate A solution of tert-butyl N-(2-[7-bromo-1H-pyrrolo[3,2-c]quinolin-2-yl]ethyl)carbamate (360 mg, 0.922 mmol, 1 equiv) and mCPBA (318.3 mg, 1.85 mmol, 2 equiv) in DCM (10 mL) was stirred for overnight at rt. The resulting mixture was concentrated under vacuum. The residue was purified by silica gel column chromatography, eluted with CH$_2$Cl$_2$/MeOH (20:1) to afford 7-bromo-2-(2-[[(tert-butoxy)carbonyl]amino]ethyl)-1H-pyrrolo[3,2-c]quinolin-5-ium-5-olate (120 mg, 32%) as a yellow solid. LC-MS (ES, m/z): [M+H]$^+$=406.1/408.1.

Step 6. Synthesis of tert-butyl N-(2-[4-amino-7-bromo-1H-pyrrolo[3,2-c]quinolin-2-yl]ethyl)carbamate A solution of 7-bromo-2-(2-[[(tert-butoxy)carbonyl]amino]ethyl)-1H-pyrrolo[3,2-c]quinolin-5-ium-5-olate (180 mg, 0.44 mmol, 1 equiv) and TsCl (168.9 mg, 0.88 mmol, 2 equiv) in NH$_3$H$_2$O (5 mL) and DCM (15 mL) was stirred for 2 h at rt. The resulting mixture was concentrated under reduced pressure. The residue was purified by silica gel column chromatography, eluted with CH$_2$Cl$_2$/MeOH (30:1) to afford tert-butyl N-(2-[4-amino-7-bromo-1H-pyrrolo[3,2-c]quinolin-2-yl]ethyl)carbamate (175 mg, 97.5%) as a yellow solid. LC-MS (ES, m/z): [M+H]$^+$=405.1/407.1.

Step 7. Synthesis of tert-butyl N-[2-[4-amino-7-(1H-pyrazol-5-yl)-1H-pyrrolo[3,2-c]quinolin-2-yl]ethyl]carbamate A solution of tert-butyl N-(2-[4-amino-7-bromo-1H-pyrrolo[3,2-c]quinolin-2-yl]ethyl)carbamate (175 mg, 0.43 mmol, 1 equiv), 3-(4,4,5,5-tetramethyl-1,3,2-dioxaborolan-2-yl)-4H-pyrazole (167.6 mg, 0.86 mmol, 2.0 equiv), Pd(dppf)Cl$_2$ (63.19 mg, 0.086 mmol, 0.2 equiv) and Cs$_2$CO$_3$ (422 mg, 1.295 mmol, 3 equiv) in dioxane (10 mL) and H$_2$O (1 mL) was stirred for overnight at 90° C. under nitrogen atmosphere. The resulting mixture was concentrated under reduced pressure. The residue was purified by silica gel column chromatography, eluted with CH$_2$Cl$_2$/MeOH (10:1) to afford tert-butyl N-[2-[4-amino-7-(1H-pyrazol-5-yl)-1H- pyrrolo[3,2-c]quinolin-2-yl]ethyl]carbamate (152 mg, 89.7%) as a yellow solid. LC-MS: (ES, m/z): [M+H]⁺=393.2.

Step 8. Synthesis of 2-(2-aminoethyl)-7-(1H-pyrazol-5-yl)-1H-pyrrolo[3,2-c]quinolin-4-amine A solution of tert-butyl N-[2-[4-amino-7-(1H-pyrazol-5-yl)-1H-pyrrolo[3,2-c]quinolin-2-yl]ethyl]carbamate (152 mg, 0.38 mmol, 1 equiv) in HCl in 1,4-dioxane (4N, 5 mL) was stirred for 2 h at rt. The resulting mixture was concentrated under vacuum and then purified by preparative HPLC with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 1-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation. LC-MS: (ES, m/z): [M+H]+=293.0. ¹H NMR (500 MHz, DMSO-d₆) δ 8.94-8.55 (m, 1H), 8.23 (br d, J=8.2 Hz, 1H), 8.17 (br d, J=0.8 Hz, 1H), 7.97 (br d, J=7.2 Hz, 1H), 7.92-7.81 (m, 1H), 6.94 (s, 1H), 6.84 (br s, 1H), 3.42-3.42 (m, 1H), 3.29-3.19 (m, 2H), 3.14 (br d, J=7.6 Hz, 2H).

Example 153. Preparation of 2-[2-(dimethylamino)ethyl]-7-(1H-pyrazol-5-yl)-1H-pyrrolo[3,2-c]quinolin-4-amine

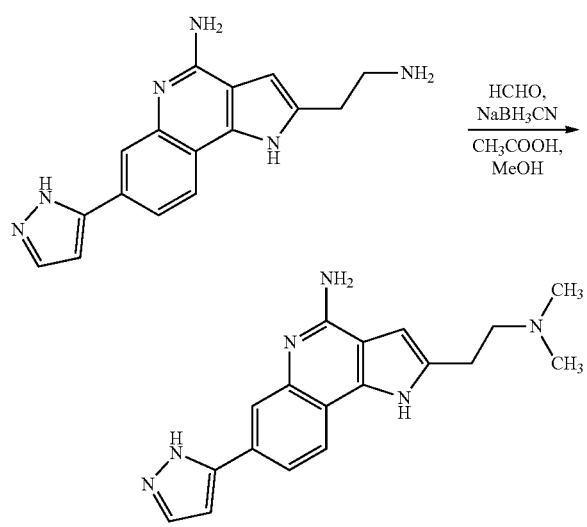

A solution of 2-(2-aminoethyl)-7-(1H-pyrazol-5-yl)-1H-pyrrolo[3,2-c]quinolin-4-amine (50 mg, 0.17 mmol, 1 equiv), HCHO (15.4 mg, 0.51 mmol, 3 equiv) and NaBH₃CN (21.5 mg, 0.34 mmol, 2 equiv) in MeOH (10 mL) and CH₃COOH (0.5 mL) was stirred for overnight at rt. The resulting mixture was concentrated under reduced pressure. The crude product was purified by Prep-HPLC with the following conditions (Column: Sunfire Prep C18 OBD Column, 10 um, 19*250 mm; Mobile Phase A: Water (0.05% TFA), Mobile Phase B: ACN; Flow rate: 25 mL/min; Gradient: 15% B to 30% B in 8 min; 254/210 nm; Rt: 6.37 min) to afford 2-[2-(dimethylamino)ethyl]-7-(1H-pyrazol-5-yl)-1H-pyrrolo[3,2-c]quinolin-4-amine; bis(trifluoroacetic acid) (13.4 mg, 14.29%) as an off-white solid. LC-MS: (ES, m/z): [M+H]⁺=321.2 ¹H NMR (400 MHz, Methanol-d₄, ppm) δ 8.17 (dd, J=8.5, 2.5 Hz, 1H), 8.06 (dt, J=3.7, 1.8 Hz, 1H), 7.95 (dt, J=8.3, 1.6 Hz, 1H), 7.77 (d, J=2.3 Hz, 1H), 6.92 (d, J=2.5 Hz, 1H), 6.84 (d, J=2.3 Hz, 1H), 3.60 (dd, J=8.9, 6.8 Hz, 2H), 3.36 (t, J=7.9 Hz, 2H), 3.01 (s, 6H).

Example 154. Preparation of N-{2-[4-amino-7-(1H-pyrazol-5-yl)-1H-pyrrolo[3,2-c]quinolin-2-yl]ethyl}propanamide

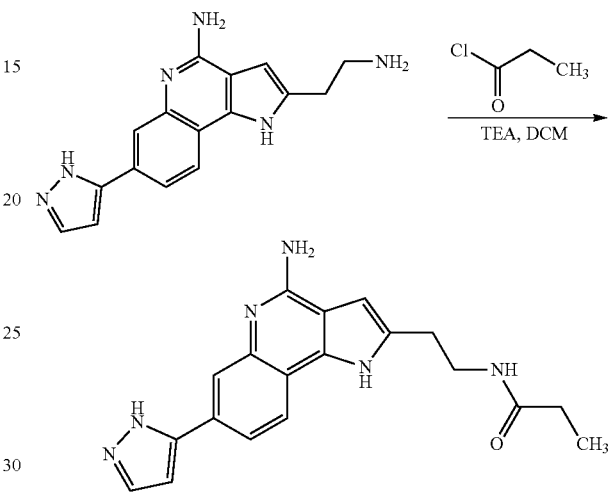

A solution of 2-(2-aminoethyl)-7-(1H-pyrazol-5-yl)-1H-pyrrolo[3,2-c]quinolin-4-amine (50 mg, 0.17 mmol, 1 equiv), propanoyl chloride (19.0 mg, 0.21 mmol, 1.2 equiv) and TEA (34.6 mg, 0.34 mmol, 2 equiv) in DCM (10 mL) was stirred for overnight at rt. The resulting mixture was concentrated under vacuum. The crude product was purified by Prep-HPLC with the following conditions (Column: Sunfire Prep C18 OBD Column, 10 um, 19*250 mm; Mobile Phase A: Water (0.05% TFA), Mobile Phase B: ACN; Flow rate: 25 mL/min; Gradient: 15% B to 30% B in 8 min; 254/210 nm; RT: 6.37 min) to afford 3,3,3-trifluoro-prop-1-en-2-ol N-[2-[4-amino-7-(1H-pyrazol-5-yl)-1H-pyrrolo[3,2-c]quinolin-2-yl]ethyl]propanamide hydrate (8.5 mg, 10.39%) as an off-white solid. LC-MS (ES, m/z): [M+H]⁺=349.2. ¹H NMR (400 MHz, Methanol-d₄, ppm) δ 8.16 (d, J=8.4 Hz, 1H), 8.04 (d, J=1.5 Hz, 1H), 7.94 (dd, J=8.4, 1.6 Hz, 1H), 7.76 (d, J=2.3 Hz, 1H), 6.83-6.80 (m, 2H), 3.59 (t, J=7.1 Hz, 2H), 3.05 (t, J=7.0 Hz, 2H), 2.20-2.18 (m, 2H), 1.10 (t, J=7.6 Hz, 3H).

Example 155. Preparation of N-[2-[4-amino-7-(1H-pyrazol-5-yl)-1H-pyrrolo[3,2-c]quinolin-2-yl]ethyl]pyridine-2-carboxamide

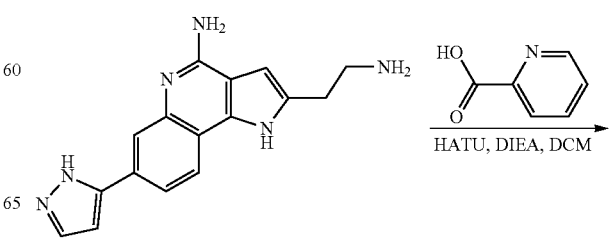

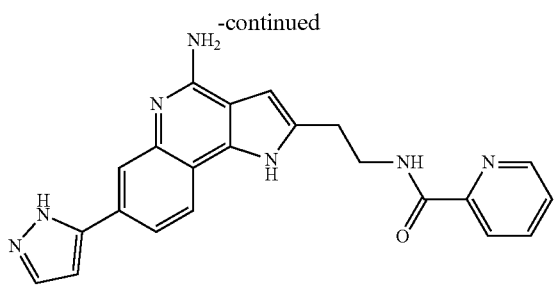

A solution of 2-(2-aminoethyl)-7-(1H-pyrazol-5-yl)-1H-pyrrolo[3,2-c]quinolin-4-amine (50 mg, 0.17 mmol, 1 equiv), pyridine-2-carboxylic acid (25.2 mg, 0.21 mmol, 1.2 equiv), HATU (130 mg, 0.34 mmol, 2 equiv) and DIEA (66.3 mg, 0.51 mmol, 3 equiv) in DCM (10 mL) was stirred for overnight at rt. The resulting mixture was concentrated under vacuum. The crude product was purified by Prep-HPLC with the following conditions (Column: Sunfire Prep C18 OBD Column, 10 um, 19*250 mm; Mobile Phase A: Water (0.05% TFA), Mobile Phase B: ACN; Flow rate: 25 mL/min; Gradient: 15% B to 40% B in 8 min; 254/210 nm; RT: 7.5 min) to afford N-[2-[4-amino-7-(1H-pyrazol-5-yl)-1H-pyrrolo[3,2-c]quinolin-2-yl]ethyl]pyridine-2-carboxamide; bis(trifluoroacetic acid)(11.1 mg, 10.4%) as a yellow solid. LC-MS: (ES, m/z): [M+H]$^+$=398.2. $^1$H NMR (300 MHz, Methanol-d$_4$, ppm) δ 8.62 (s, 1H), 8.09 (t, J=6.7 Hz, 2H), 7.97-7.89 (m, 3H), 7.77 (d, J=2.2 Hz, 1H), 7.56 (s, 1H), 6.81 (s, 2H), 3.86 (t, J=7.0 Hz, 2H), 3.31 (s, 4H), 3.18 (t, J=6.9 Hz, 2H).

Example 156. Preparation of 2-[(oxolan-2-yl)methyl]-7-(1H-pyrazol-5-yl)-1H-pyrrolo[3,2-c]quinolin-4-amine

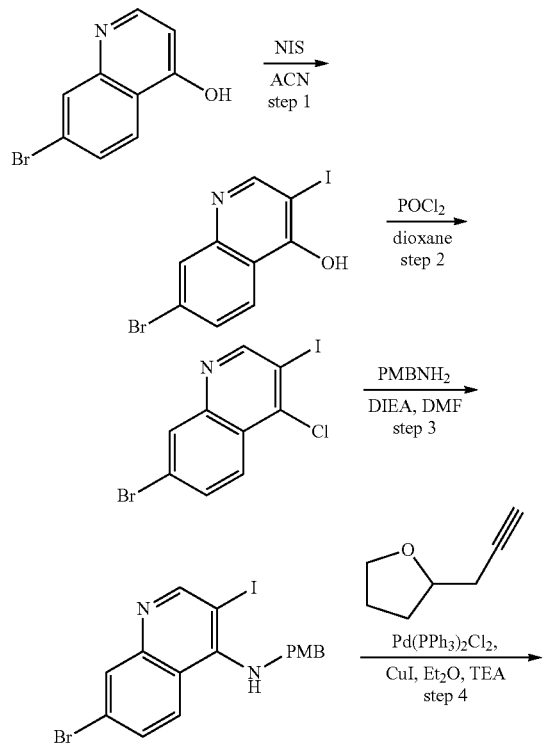

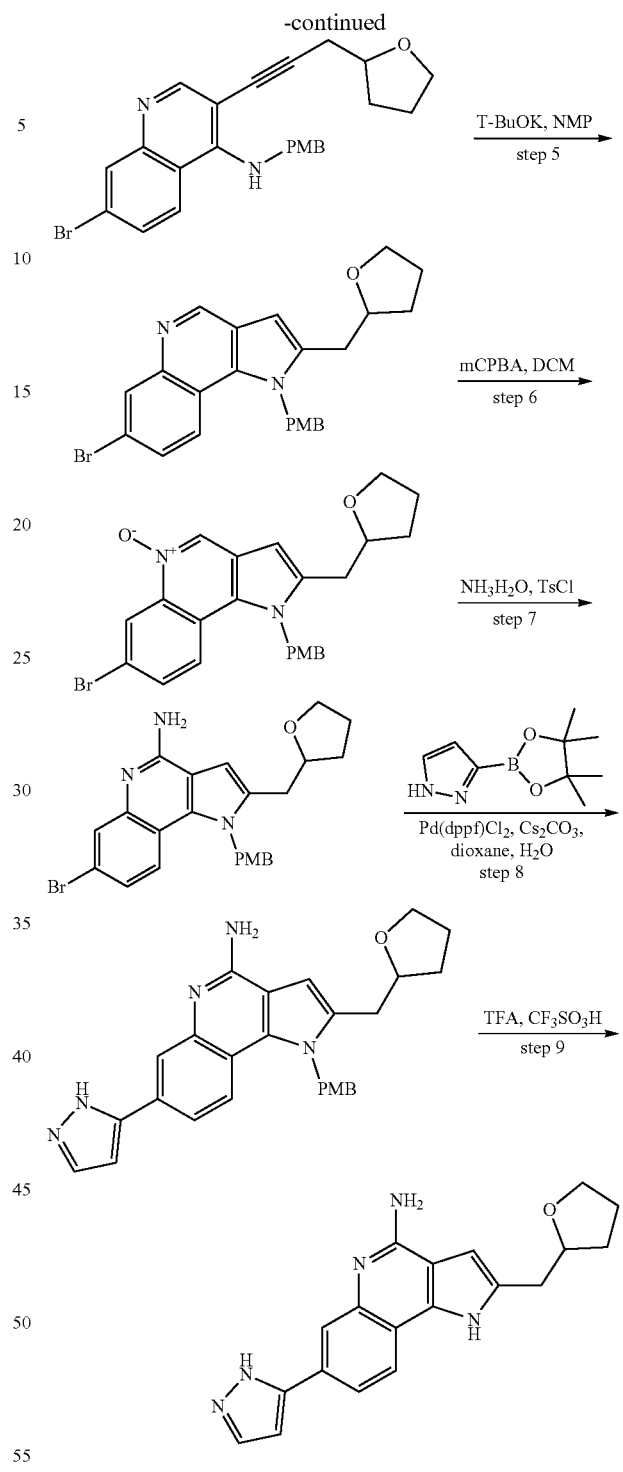

Step 1. Synthesis of 7-bromo-3-iodoquinolin-4-ol

A solution of 7-bromoquinolin-4-ol (11 g, 49.095 mmol, 1 equiv) and iodo (sulfanyl)amine (10.25 g, 58.9 mmol, 1.2 equiv) in CH$_3$CN (200 mL) was stirred for 2 h at 65° C. The precipitated solids were collected by filtration and washed with acetonitrile (3×10 mL). This resulted in 7-bromo-3-iodoquinolin-4-ol (15.7 g, 91.4%) as a yellow solid. LC-MS: (ES, m/z): [M+H]$^+$=349.9.

Step 2. Synthesis of 7-bromo-4-chloro-3-iodoquinoline

A solution of 7-bromo-3-iodoquinolin-4-ol (15.7 g, 44.8 mmol, 1 equiv) and phosphoroyl trichloride (20.64 g, 134.59 mmol, 3 equiv) in dioxane (400 mL, 4721.6 mmol, 105 equiv) was stirred for 2 h at 100° C. The reaction was quenched with water/ice. The mixture was neutralized to pH 8 with saturated aq. NaHCO$_3$. The precipitated solids were collected by filtration and washed with water (3×10 mL). This resulted in 7-bromo-4-chloro-3-iodoquinoline (16 g, 96.8%) as a yellow solid. LC-MS (ES, m/z): [M+H]$^+$=367.8.

Step 3. Synthesis of 7-bromo-3-iodo-N-[(4-methoxyphenyl)methyl]quinolin-4-amine A solution of 7-bromo-4-chloro-3-iodoquinoline (16 g, 43.43 mmol, 1 equiv) and 1-(4-methoxyphenyl)methanamine (11.9 g, 86.8 mmol, 2 equiv), Hunig's base (18.67 g, 130.3 mmol, 3 equiv) in DMF (400 mL) was stirred for overnight at 80° C. The resulting mixture was extracted with EtOAc (3×300 mL). The combined organic layers were washed with water (3×300 mL), dried over anhydrous Na$_2$SO$_4$. After filtration, the filtrate was concentrated under reduced pressure. The residue was dissolved in EtOAc (50 mL). The precipitated solids were collected by filtration and washed with EtOAc (3×10 mL). The resulting mixture was concentrated under reduced pressure. This resulted in 7-bromo-3-iodo-N-[(4-methoxyphenyl)methyl]quinolin-4-amine (7 g, 34.36%) as a yellow solid. LC-MS (ES, m/z): [M+H]$^+$=468.9. $^1$H NMR (400 MHz, DMSO-d$_6$) δ 8.75 (s, 1H), 8.21 (d, J=9.1 Hz, 1H), 8.01 (d, J=2.1 Hz, 1H), 7.60 (dd, J=9.1, 2.1 Hz, 1H), 7.24 (d, J=8.7 Hz, 2H), 6.85 (d, J=8.7 Hz, 2H), 6.45 (t, J=6.6 Hz, 1H), 4.83 (d, J=6.6 Hz, 2H), 3.70 (s, 3H).

Step 4. Synthesis of 7-bromo-N-[(4-methoxyphenyl)methyl]-3-[3-(oxolan-2-yl)prop-1-yn-1-yl]quinolin-4-amine A solution of 7-bromo-3-iodo-N-[(4-methoxyphenyl)methyl]quinolin-4-amine (1 g, 2.1 mmol, 1 equiv), 2-(prop-2-yn-1-yl)oxolane (704 mg, 6.4 mmol, 3 equiv), CuI (40 mg, 0.21 mmol, 0.1 equiv), Pd(PPh$_3$)$_2$Cl$_2$ (748 mg, 1.06 mmol, 0.5 equiv) and triethylamine (1.08 g, 10.66 mmol, 5 equiv) in ethoxyethane (20 mL) was stirred for overnight at rt under nitrogen atmosphere. The resulting mixture was concentrated under reduced pressure. The residue was purified by silica gel column chromatography, eluted with PE/EtOAc (2:1) to afford 7-bromo-N-[(4-methoxyphenyl)methyl]-3-[3-(oxolan-2-yl)prop-1-yn-1-yl]quinolin-4-amine (560 mg, 58.2%) as a yellow solid. LC-MS (ES, m/z): [M+H]$^+$=451.1.

Step 5. Synthesis of 7-bromo-1-[(4-methoxyphenyl)methyl]-2-[(oxolan-2-yl)methyl]-1H-pyrrolo[3,2-c]quinoline A solution of 7-bromo-N-[(4-methoxyphenyl)methyl]-3-[3-(oxolan-2-yl)prop-1-yn-1-yl]quinolin-4-amine (560 mg, 1.24 mmol, 1 equiv) and t-BuOK (278.44 mg, 2.48 mmol, 2 equiv) in 1-methylpyrrolidin-2-one (5 mL) was stirred for overnight at 65° C. under nitrogen atmosphere. The reaction was quenched with sat. NH$_4$Cl (aq.) at 0° C. The residue was purified by reverse flash chromatography with the following conditions: column, C18 silica gel; mobile phase, MeOH in water, 10% to 50% gradient in 10 min; detector, UV 254 nm. This resulted in 7-bromo-1-[(4-methoxyphenyl)methyl]-2-[(oxolan-2-yl)methyl]-1H-pyrrolo[3,2-c]quinoline (320 mg, 57.1%) as a yellow solid. LC-MS: (ES, m/z): [M+H]$^+$=451.1 $^1$H NMR (400 MHz, DMSO-d$_6$) δ 9.12 (s, 1H), 8.21 (d, J=2.1 Hz, 1H), 8.09 (d, J=9.1 Hz, 1H), 7.55 (dd, J=9.0, 2.1 Hz, 1H), 6.85 (s, 4H), 6.82 (s, 1H), 5.85 (s, 2H), 4.16 (q, J=6.4 Hz, 1H), 3.77 (q, J=6.9 Hz, 1H), 3.62 (q, J=7.4 Hz, 1H), 2.99 (dd, J=5.8, 4.0 Hz, 2H), 2.01 (ddd, J=12.1, 6.8, 4.4 Hz, 1H), 1.85-1.77 (m, 2H), 1.62-1.55 (m, 1H).

Step 6. Synthesis of 7-bromo-1-[(4-methoxyphenyl)methyl]-2-[(oxolan-2-yl)methyl]-1H-pyrrolo[3,2-c]quinolin-5-ium-5-olate A solution of 7-bromo-1-[(4-methoxyphenyl)methyl]-2-[(oxolan-2-yl)methyl]-1H-pyrrolo[3,2-c]quinoline (320 mg, 0.71 mmol, 1 equiv) and mCPBA (349 mg, 1.42 mmol, 2 equiv, 70%) in dichloromethane (10 mL) was stirred for 2 h at rt. The resulting mixture was concentrated under reduced pressure. The residue was purified by Prep-TLC (CH$_2$Cl$_2$/MeOH 30:1) to afford 7-bromo-1-[(4-methoxyphenyl)methyl]-2-[(oxolan-2-yl)methyl]-1H-pyrrolo[3,2-c]quinolin-5-ium-5-olate (200 mg, 60.4%) as a yellow solid. LC-MS: (ES, m/z): [M+H]$^+$=467.1.

Step 7. Synthesis of 7-bromo-1-[(4-methoxyphenyl)methyl]-2-[(oxolan-2-yl)methyl]-1H-pyrrolo[3,2-c]quinolin-4-amine A solution of 7-bromo-1-[(4-methoxyphenyl)methyl]-2-[(oxolan-2-yl)methyl]-1H-pyrrolo[3,2-c]quinolin-5-ium-5-olate (200 mg, 0.428 mmol, 1 equiv) and NH$_4$OH (3.00 mL, 85.601 mmol, 180.03 equiv) in dichloromethane (9 mL) was stirred for 5 min at rt. Then add TsCl (163.17 mg, 0.856 mmol, 2 equiv) to the above mixture was stirred for 2 h at rt. The resulting mixture was concentrated under reduced pressure. The residue was purified by Prep-TLC (CH$_2$Cl$_2$/MeOH 10:1) to afford 7-bromo-1-[(4-methoxyphenyl)methyl]-2-[(oxolan-2-yl)methyl]-1H-pyrrolo[3,2-c]quinolin-4-amine (160 mg, 80.17%) as a yellow solid. LC-MS (ES, m/z): [M+H]$^+$=466.1.

Step 8. Synthesis of 1-[(4-methoxyphenyl)methyl]-2-[(oxolan-2-yl)methyl]-7-(1H-pyrazol-5-yl)-1H-pyrrolo[3,2-c]quinolin-4-amine A solution of 7-bromo-1-[(4-methoxyphenyl)methyl]-2-[(oxolan-2-yl)methyl]-1H-pyrrolo[3,2-c]quinolin-4-amine (160 mg, 0.34 mmol, 1 equiv) and 3-(4,4,5,5-tetramethyl-1,3,2-dioxaborolan-2-yl)-1H-pyrazole (133 mg, 0.68 mmol, 2 equiv), Cs$_2$CO$_3$ (335 mg, 1.0 mmol, 3 equiv), Pd(dppf)Cl$_2$CH$_2$Cl$_2$ (56 mg, 0.069 mmol, 0.2 equiv) in 1,4-dioxane (5 mL), water (0.5 mL) was stirred for 3 h at 90° C. under nitrogen atmosphere. The resulting mixture was concentrated under reduced pressure. The residue was purified by Prep-TLC (CH$_2$Cl$_2$/MeOH 8:1) to afford 1-[(4-methoxyphenyl)methyl]-2-[(oxolan-2-yl)methyl]-7-(1H-pyrazol-5-yl)-1H-pyrrolo[3,2-c]quinolin-4-amine (100 mg, 64.27%) as a yellow solid. LC-MS (ES, m/z): [M+H]$^+$=454.2.

Step 9. Synthesis of 2-[(oxolan-2-yl)methyl]-7-(1H-pyrazol-5-yl)-1H-pyrrolo[3,2-c]quinolin-4-amine A solution of 1-[(4-methoxyphenyl)methyl]-2-[(oxolan-2-yl)methyl]-7-(1H-pyrazol-5-yl)-1H-pyrrolo[3,2-c]quinolin-4-amine (40 mg, 0.088 mmol, 1 equiv) and trifluoromethanesulfinic acid (0.5 mL) in 2,2,2-trifluoroacetaldehyde (2 mL) was stirred for 3 h at rt under nitrogen. The residue was basified to pH 8 with saturated aq. Na$_2$CO$_3$. The resulting mixture was concentrated under reduced pressure. The crude product (40 mg) was purified by Prep-HPLC with the following conditions (Column: XBridge Prep C18 OBD Column 19×150 mm 5 um; Mobile Phase A: Water (10 MMOL/L NH$_4$HCO$_3$+0.1% NH$_3$·H$_2$O), Mobile Phase B: ACN; Flow rate: 25 mL/min; Gradient: 15% B to 35% B in 7 min; 254/210 nm; RT: 6.37 min) to afford 2-[(oxolan-2-yl)methyl]-7-(1H-pyrazol-5-yl)-1H-pyrrolo[3,2-c]quinolin-4-amine (3.7 mg, 12.58%) as a light yellow solid. LC-MS: (ES, m/z): [M+H]$^+$=334.2. $^1$H NMR (400 MHz, Methanol-d$_4$) δ 8.10 (s, 1H), 7.98 (s, 1H), 7.81-7.79 (m, 1H), 7.71 (s, 1H), 6.78 (s, 1H), 6.69 (s, 1H), 4.29-4.22 (m, 1H), 3.95-3.90 (m, 1H), 3.81-3.76 (m, 1H), 3.31-3.30 (m, 2H), 2.18-2.05 (m, 1H), 1.97-1.90 (m, 3H), 1.74-1.66 (m, 1H), 1.28-1.23 (m, 1H).

Example 157. Preparation of N-{2-[4-amino-7-(1H-pyrazol-5-yl)-2H-[1,2,3]triazolo[4,5-c]quinolin-2-yl]ethyl}-2-fluoro-2-methylpropanamide

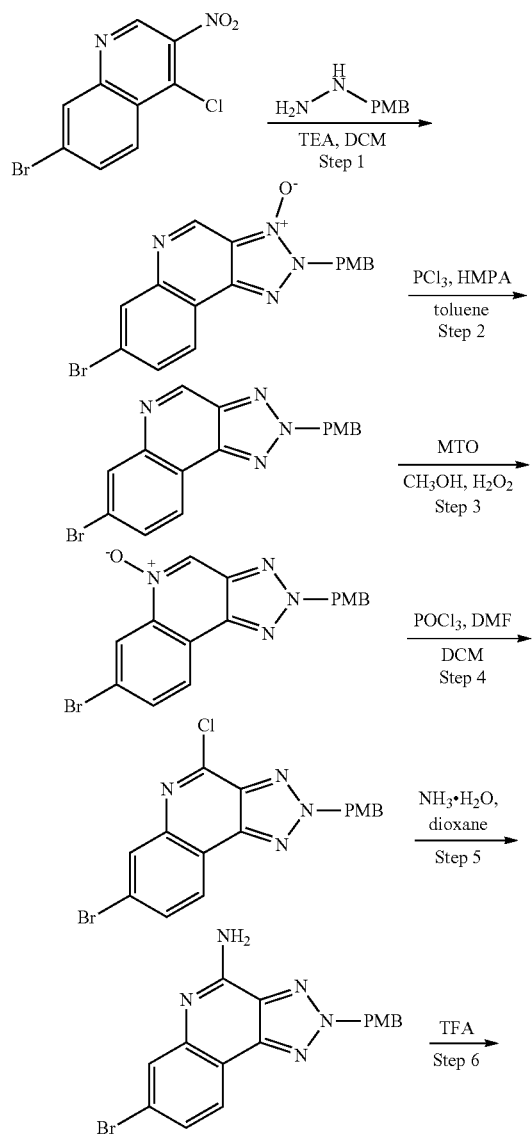

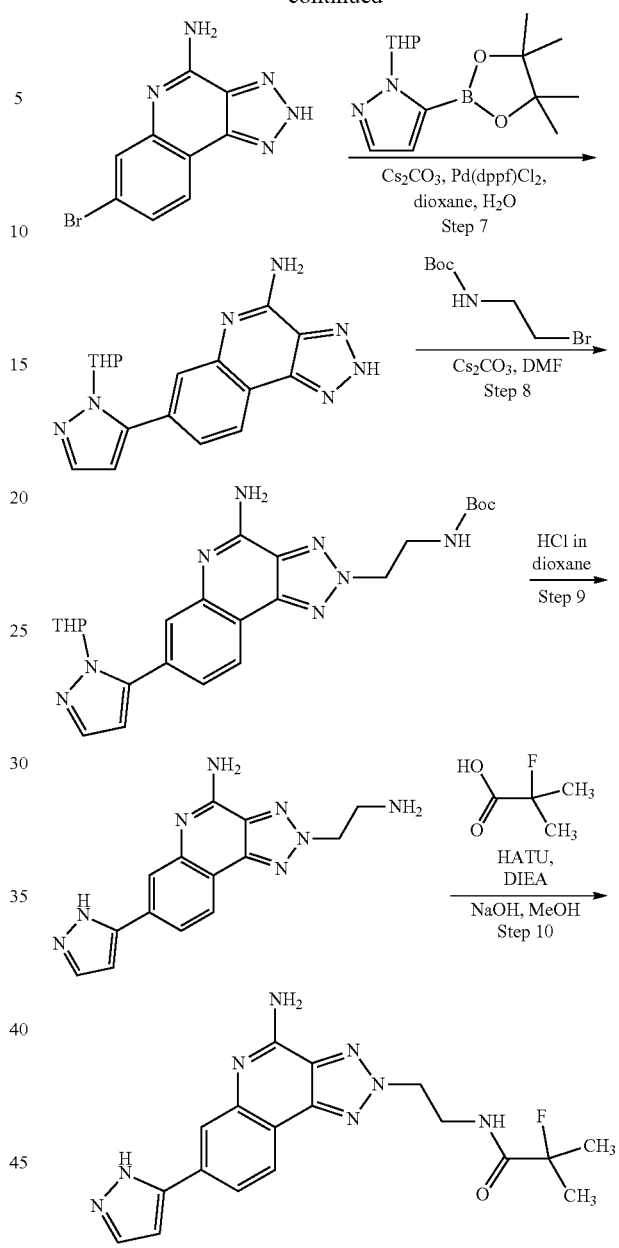

Step 1. Synthesis of 7-bromo-2-[(4-methoxyphenyl)methyl]-2H-[1,2,3]triazolo[4,5-c]quinolin-3-ium-3-olate Into a 500-mL round-bottom flask was placed 7-bromo-4-chloro-3-nitroquinoline (10.64 g, 37 mmol, 1 equiv) and TEA (22.47 g, 222 mmol, 6 equiv) in DCM (200 mL), then [(4-methoxyphenyl) methyl]hydrazine dihydrochloride (12.5 g, 55.5 mmol, 1.5 equiv) was added. The resulting solution was stirred for 1 day at rt. The resulting solution was extracted with 3×200 mL of dichloromethane and the organic layers combined and concentrated. This resulted in 11 g (77%) of 7-bromo-2-[(4-methoxyphenyl)methyl]-2H-[1,2,3]triazolo[4,5-c]quinolin-3-ium-3-olate as a red solid. LC-MS: (ES, m/z): [M+H]$^+$=385.2.

Step 2. Synthesis of 7-bromo-2-[(4-methoxyphenyl) methyl]-2H-[1,2,3]triazolo[4,5-c]quinoline Into a 500-mL round-bottom flask, was placed 7-bromo-2-[(4-methoxyphenyl) methyl]-2H-[1, 2, 3]triazolo[4,5-c]quinolin-3-ium-3-olate (11 g, 28.5 mmol, 1 equiv), in Toluene (100 mL) and $CHCl_3$ (100 mL), then HMPA (20 mL) and $PCl_3$ (31.07 g, 228 mmol, 8 equiv) were added subsequently. The resulting solution was stirred for 1 day at 100° C. The resulting mixture was concentrated. The pH value of the solution was adjusted to 7-8 with $NaHCO_3$. The residue was applied onto a silica gel column with dichloromethane/ethyl acetate (30:1). This resulted in 5.7 g (54%) of 7-bromo-2-[(4-methoxyphenyl)methyl]-2H-[1,2,3]triazolo[4,5-c]quinoline as a brown solid. LC-MS: (ES, m/z): [M+H]$^+$=369.2. $^1$H NMR (300 MHz, DMSO-$d_6$) δ 9.35 (s, 1H), 8.80 (d, J=1.7 Hz, 1H), 8.38 (d, J=8.5 Hz, 1H), 8.07 (dd, J=8.5, 1.9 Hz, 1H), 7.42 (d, J=8.6 Hz, 2H), 6.95 (d, J=8.6 Hz, 2H), 5.94 (s, 2H), 5.76 (s, 1H), 3.74 (s, 3H).

Step 3. Synthesis of 7-bromo-2-[(4-methoxyphenyl) methyl]-2H-[1,2,3]triazolo[4,5-c]quinolin-5-ium-5-olate Into a 500-mL round-bottom flask, was placed 7-bromo-2-[(4-methoxyphenyl) methyl]-2H-[1, 2, 3]triazolo[4, 5-c]quinoline (6.8 g, 18.4 mmol, 1 equiv) in MeOH (70 mL) and $H_2O_2$ (70 mL), then MTO (2.30 g, 9.2 mmol, 0.50 equiv) was added. The resulting solution was stirred for 16 hr at rt. The resulting mixture was concentrated. The residue was applied onto a silica gel column with dichloromethane/ethyl acetate (15:1). This resulted in 5.7 g (80%) of 7-bromo-2-[(4-methoxyphenyl)methyl]-2H-[1,2,3]triazolo[4,5-c]quinolin-5-ium-5-olate as a yellow solid. LC-MS: (ES, m/z): [M+H]+=385.2.

Step 4. Synthesis of 7-bromo-4-chloro-2-[(4-methoxyphenyl)methyl]-2H-[1,2,3]triazolo[4,5-c]quinoline Into a 500-mL round-bottom flask was placed 7-bromo-2-[(4-methoxyphenyl) methyl]-2H-[1, 2, 3]triazolo[4, 5-c]quinolin-5-ium-5-olate (4.2 g, 10.9 mmol, 1 equiv) and DMF (2 mL) in DCM (100 mL), then $POCl_3$ (2.51 g, 16.354 mmol, 1.5 equiv) was added. The resulting solution was stirred for 1 overnight at 40° C. The resulting solution was extracted with 3×100 mL of dichloromethane and the organic layers combined and concentrated. This resulted in 4.5 g of 7-bromo-4-chloro-2-[(4-methoxyphenyl)methyl]-2H-[1,2,3]triazolo[4,5-c]quinoline as a brown crude solid. LC-MS: (ES, m/z): [M+H]+=403.0.

Step 5. Synthesis of 7-bromo-2-[(4-methoxyphenyl) methyl]-2H-[1,2,3]triazolo[4,5-c]quinolin-4-amine Into a 250-mL sealed tube, was placed 7-bromo-4-chloro-2-[(4-methoxyphenyl) methyl]-2H-[1, 2, 3]triazolo[4, 5-c]quinoline (4.5 g, 11.148 mmol, 1 equiv) in dioxane (50 mL) and $NH_3H_2O$ (50 mL). The resulting solution was stirred for 1 overnight at 110° C. The resulting mixture was concentrated. The residue was applied onto a silica gel column with dichloromethane/ethyl acetate (10:1). The resulting mixture was concentrated. This resulted in 2.7 g (63%) of 7-bromo-2-[(4-methoxyphenyl)methyl]-2H-[1,2,3]triazolo[4,5-c]quinolin-4-amine as a brown solid. LC-MS: (ES, m/z): [M+H]+=384.2. $^1$H NMR (400 MHz, DMSO-$d_6$) δ 8.01 (d, J=8.4 Hz, 1H), 7.69 (d, J=1.5 Hz, 1H), 7.49 (s, 2H), 7.40 (dd, J=8.4, 1.7 Hz, 1H), 7.37 (d, J=8.5 Hz, 2H), 6.95 (d, J=8.6 Hz, 2H), 5.93 (s, 2H), 3.74 (s, 3H).

Step 6. Synthesis of 7-bromo-2H-[1,2,3]triazolo[4,5-c]quinolin-4-amine

Into a 250-mL round-bottom flask, was placed 7-bromo-2-[(4-methoxyphenyl)methyl]-2H-[1,2,3]triazolo[4,5-c]quinolin-4-amine (1.12 g, 2.9 mmol, 1 equiv) and TFA (30 mL). The resulting solution was stirred for 16 hr at 80° C. The resulting mixture was concentrated. This resulted in 1.3 of 7-bromo-2H-[1,2,3]triazolo[4,5-c]quinolin-4-amine as a brown crude solid. LC-MS: (ES, m/z): [M+H]$^+$=264.0.

Step 7. Synthesis of 7-[1-(oxan-2-yl)-1H-pyrazol-5-yl]-2H-[1,2,3]triazolo[4,5-c]quinolin-4-amine Into a 100-mL round-bottom flask purged and maintained with an inert atmosphere of nitrogen, was placed 7-bromo-2H-[1,2,3]triazolo[4,5-c]quinolin-4-amine (1.3 g, 4.923 mmol, 1 equiv), $Cs_2CO_3$ (4.81 g, 14.768 mmol, 3 equiv), 1-(oxan-2-yl)-5-(4,4,5,5-tetramethyl-1,3,2-dioxaborolan-2-yl)-1H-pyrazole (2.74 g, 9.845 mmol, 2.00 equiv), Pd(dppf)$Cl_2·CH_2Cl_2$ (804.00 mg, 0.985 mmol, 0.2 equiv) in dioxane (20 mL) and $H_2O$ (4 mL). The resulting solution was stirred for 16 hr at 90° C. The resulting mixture was concentrated. The residue was applied onto a silica gel column with dichloromethane/methanol (8:1). This resulted in 1.2 g (72%) of 7-[1-(oxan-2-yl)-1H-pyrazol-5-yl]-2H-[1,2,3]triazolo[4,5-c]quinolin-4-amine as a dark green solid. LC-MS: (ES, m/z): [M+H]$^+$=336.1.

Step 8. Synthesis of tert-butyl N-(2-[4-amino-7-[1-(oxan-2-yl)-1H-pyrazol-5-yl]-2H-[1,2,3]triazolo[4,5-c]quinolin-2-yl]ethyl)carbamate Into a 500-mL round-bottom flask, was placed 7-[1-(oxan-2-yl)-1H-pyrazol-5-yl]-2H-[1,2,3]triazolo[4,5-c]quinolin-4-amine (1.5 g, 4.47 mmol, 1 equiv) in DMF (30 mL), then tert-butyl N-(2-bromoethyl)carbamate (2.00 g, 8.9 mmol, 2 equiv) and $Cs_2CO_3$ (4.37 g, 13.4 mmol, 3 equiv) were added. The resulting solution was stirred for 16 hr at rt. The resulting mixture was concentrated. The solids were collected by filtration. This resulted in 1.5 g (70%) of tert-butyl N-(2-[4-amino-7-[1-(oxan-2-yl)-1H-pyrazol-5-yl]-2H-[1,2,3]triazolo[4,5-c]quinolin-2-yl]ethyl)carbamate as a brown solid. LC-MS: (ES, m/z): [M+H]$^+$=479.2. $^1$H NMR (300 MHz, DMSO-$d_6$) δ 8.18 (d, J=8.1 Hz, 1H), 7.71 (s, 1H), 7.61 (s, 1H), 7.43 (d, J=8.1 Hz, 1H), 7.36 (s, 2H), 7.07 (t, J=5.8 Hz, 1H), 6.55 (s, 1H), 5.37-5.26 (m, 1H), 4.79 (t, J=5.4 Hz, 2H), 4.12-3.98 (m, 1H), 3.58 (t, J=7.7 Hz, 3H), 2.49-2.31 (m, 2H), 2.04-1.89 (m, 1H), 1.87-1.74 (m, 1H), 1.69-1.49 (m, 3H), 1.31 (s, 9H).

Step 9. Synthesis of 2-(2-aminoethyl)-7-(1H-pyrazol-5-yl)-2H-[1,2,3]triazolo[4,5-c]quinolin-4-amine Into a 100-mL round-bottom flask, was placed tert-butyl N-(2-[4-amino-7-[1-(oxan-2-yl)-1H-pyrazol-5-yl]-2H-[1,2,3]triazolo[4,5-c]quinolin-2-yl]ethyl)carbamate (1.2 g, 2.508 mmol, 1 equiv) in HCl in 1,4-dioxane (4N, 20 mL). The resulting solution was stirred for 2 hr at rt. The resulting solution was concentrated. The resulting solution was extracted with 3×100 mL of dichloromethane and the aqueous layers combined. This resulted in 1.1 g of 2-(2-aminoethyl)-7-(1H-pyrazol-5-yl)-2H-[1,2,3]triazolo[4,5-c]quinolin-4-amine as a brown crude solid. LC-MS: (ES, m/z): [M+H]⁺=295.1.

Step 10. Synthesis of N-[2-[4-amino-7-(1H-pyrazol-5-yl)-2H-[1,2,3]triazolo[4,5-c]quinolin-2-yl]ethyl]-2-fluoro-2-methylpropanamide Into a 100-mL round-bottom flask, was placed 2-(2-aminoethyl)-7-(1H-pyrazol-5-yl)-2H-[1,2,3]triazolo[4,5-c]quinolin-4-amine (40 mg, 0.13 mmol, 1 equiv) and 2-fluoro-2-methylpropanoic acid (14.4 mg, 0.13 mmol, 1 equiv) in DCM (4 mL), then HATU (103.3 mg, 0.27 mmol, 2 equiv) and DIEA (52.6 mg, 0.4 mmol, 3 equiv) were added. The resulting solution was stirred for 16 hr at rt. The resulting mixture was concentrated. The crude product was dissolved in MeOH (4 mL), NaOH (10.8 mg, 0.27 mmol, 2 equiv) was added. The resulting solution was stirred for 2 hr at 70° C. The resulting mixture was concentrated. The residue was applied onto a silica gel column eluting with dichloromethane/methanol (10:1) to provide the crude product. The crude product was further purified by Prep-HPLC with the following conditions: Column: XBridge Prep OBD C18 Column 30×150 mm 5 um; Mobile Phase A: Water (10 MMOL/L NH₄HCO₃), Mobile Phase B: ACN; Flow rate: 60 mL/min; Gradient: 8% B to 45% B in 7 min; 254/210 nm; RT: 6.45 min. This resulted in 4 mg (7.70%) of N-[2-[4-amino-7-(1H-pyrazol-5-yl)-2H-[1,2,3]triazolo[4,5-c]quinolin-2-yl]ethyl]-2-fluoro-2-methylpropanamide as a white solid. LC-MS: (ES, m/z): [M+H]⁺=383.4. ¹H NMR (400 MHz, Methanol-d₄) δ 8.22 (d, J=8.2 Hz, 1H), 8.02 (s, 1H), 7.75 (s, 2H), 6.79 (s, 1H), 5.00-4.94 (m, 2H), 3.91 (t, J=5.7 Hz, 2H), 1.45 (d, J=21.8 Hz, 6H).

Examples 158 to 162 were prepared according to synthetic procedures similar to those described for Example 157 from the appropriate starting materials. Analytical LC/MS conditions:

A: Column: Ascentis Express C18, 3.0 mm×50 mm, 2.7 μm particles; Mobile Phase A: acetonitrile with 0.05% trifluoroacetic acid; Mobile Phase B: water with 0.05% trifluoroacetic acid; Temperature: 40° C.; Gradient: 5% B to 95% B over 2 min, then a 0.7 min hold at 95% B; Flow: 1.5 mL/min; Detection: MS and UV.

B: Column: PoroShell HPH C18, 3.0 mm×50 mm, 2.7 μm particles; Mobile Phase A: acetonitrile with 5 mM ammonium bicarbonate; Mobile Phase B: water with 5 mM ammonium bicarbonate; Temperature: 40° C.; Gradient: 5% B to 50% B over 3 min, then to 95% B in 0.2 min, then a 1.0 min hold at 95% B; Flow: 1 mL/min; Detection: MS and UV.

C: Column: PoroShell HPH C18, 3.0 mm×50 mm, 2.7 μm particles; Mobile Phase A: acetonitrile with 5 mM ammonium bicarbonate; Mobile Phase B: water with 5 mM ammonium bicarbonate; Temperature: 40° C.; Gradient: 5% B to 95% B over 2 min, then a 0.7 min hold at 95% B; Flow: 1 mL/min; Detection: MS and UV.

| Ex. No. | Structure | LC/MS [M + H]⁺ | RT (min)/ LC condition | ¹H NMR, unless otherwise indicated, 400 MHz, Methanol-d₄ |
|---|---|---|---|---|
| 158 | 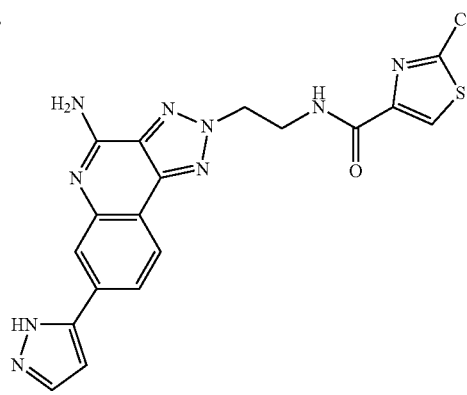 | 440.1 | 0.97/A | δ 8.20 (d, J = 8.2 Hz, 1H), 8.10 (s, 1H), 8.02 (s, 1H), 7.79 (d, J = 32.9 Hz, 2H), 6.79 (s, 1H), 5.05-4.98 (m, 2H), 4.08 (t, J = 5.8 Hz, 2H) |
| 159 | 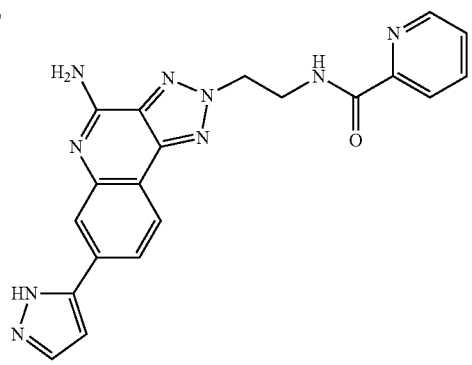 | 400.2 | 2.29/B | ¹H NMR (300 MHZ, Methanol-d₄) δ 8.60 (d, J = 4.7 Hz, 1H), 8.17 (d, J = 8.1 Hz, 1H), 8.06-7.96 (m, 2H), 7.94-7.86 (m, 1H), 7.84-7.67 (m, 2H), 7.58-7.48 (m, 1H), 6.79 (d, J = 2.3 Hz, 1H), 5.05 (t, J = 5.8 Hz, 2H), 4.16 (t, J = 5.9 Hz, 2H) |

| Ex. No. | Structure | LC/MS [M + H]+ | RT (min)/ LC condition | 1H NMR, unless otherwise indicated, 400 MHz, Methanol-d4 |
|---|---|---|---|---|
| 160 | 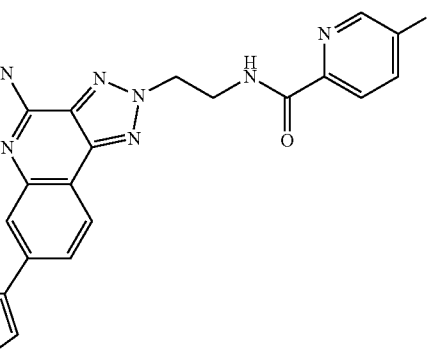 | 418.4 | 1.42/B | δ 8.49 (d, J = 2.9 Hz, 1H), 8.18 (d, J = 8.2 Hz, 1H), 8.10 (dd, J = 8.7, 4.6 Hz, 1H), 8.00 (s, 1H), 7.72 (td, J = 8.6, 2.8 Hz, 3H), 6.79 (d, J = 2.2 Hz, 1H), 5.04 (t, J = 5.8 Hz, 2H), 4.14 (t, J = 5.8 Hz, 2H) |
| 161 | 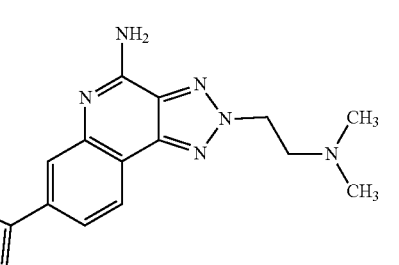 | 323.2 | 1.53/B | δ 8.24 (d, J = 8.3 Hz, 1H), 8.06 (s, 1H), 7.93-7.57 (m, 2H), 6.80 (s, 1H), 5.02-4.95 (m, 2H), 3.17 (t, J = 6.4 Hz, 2H), 2.37 (s, 6H) |
| 162 | 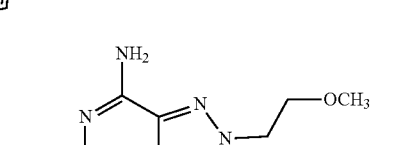 | 310.1 | 1.24/C | 1H NMR (300 MHZ, Methanol-d4) δ 8.24 (d, J = 8.2 Hz, 1H), 8.01 (s, 1H), 7.75 (d, J = 18.1 Hz, 2H), 6.79 (d, J = 2.2 Hz, 1H), 5.00-4.97 (m, 2H), 4.11 (t, J = 5.2 Hz, 2H), 3.38 (s, 3H) |

Examples 163 to 184 were prepared according to synthetic procedures similar to those described for Example 20, Example 31, or Example 132 from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 m hold at 100% B; Flow: 1 mL/min; Detection: MS and UV (220 nm).

| Ex. No. | Structure | LC/MS [M + H]+ | RT (min) | 1H NMR (500 MHz, DMSO-d6) |
|---|---|---|---|---|
| 163 | 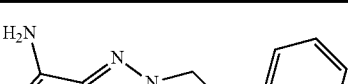 | 356.1 | 0.93 | δ 8.63 (s, 1H), 8.52 (br d, J = 4.1 Hz, 1H), 7.87 (br d, J = 5.5 Hz, 2H), 7.75-7.57 (m, 3H), 7.25-7.21 (m, 2H), 6.79 (br s, 2H), 6.72 (s, 1H), 4.84 (br t, J = 7.0 Hz, 2H); two CH protons are not visible, likely due to overlap with suppressed water peak. |

| Ex. No. | Structure | LC/MS [M + H]+ | RT (min) | ¹H NMR (500 MHz, DMSO-d₆) |
|---|---|---|---|---|
| 164 | 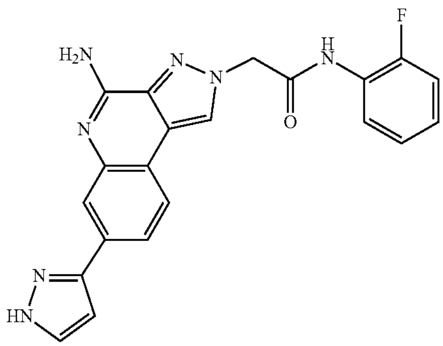 [SMILES: Nc1nc2cc(-c3cc[nH]n3)ccc2c2cn(CC(=O)Nc3ccccc3F)nc12] | 402.2 | 1.18 | δ 10.32 (br s, 1H), 8.74 (s, 1H), 7.97 (br d, J = 8.0 Hz, 1H), 7.90 (br s, 2H), 7.81-7.56 (m, 2H), 7.33-7.26 (m, 1H), 7.23-7.13 (m, 2H), 6.78 (br s, 2H), 6.74 (s, 1H), 5.49 (s, 2H) |
| 165 | 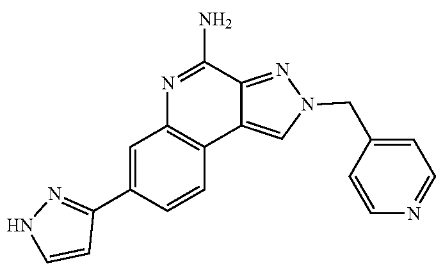 [SMILES: Nc1nc2cc(-c3cc[nH]n3)ccc2c2cn(Cc3ccncc3)nc12] | 342.2 | 0.57 | δ 13.79-13.51 (m, 1H), 13.24-12.90 (m, 1H), 9.84-9.26 (m, 2H), 9.13 (s, 1H), 8.59 (d, J = 5.8 Hz, 2H), 8.14 (br d, J = 8.0 Hz, 2H), 7.91 (br d, J = 8.5 Hz, 1H), 7.87-7.80 (m, 1H), 7.27 (d, J = 5.8 Hz, 2H), 6.79 (d, J = 1.7 Hz, 1H), 5.87 (s, 2H) |
| 166 | 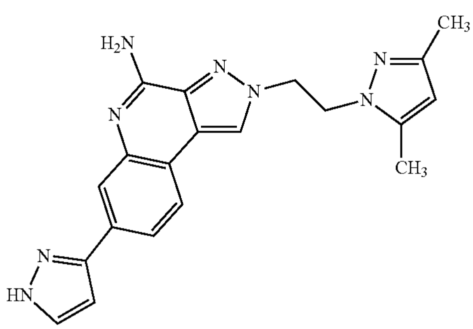 [SMILES: Cc1cc(C)n(CCn2cc3c(n2)c(N)nc2cc(-c4cc[nH]n4)ccc23)n1] | 372.9 | 1.13 | δ 8.40 (s, 1H), 7.87 (s, 1H), 7.84 (d, J = 8.0 Hz, 1H), 7.69 (br s, 1H), 7.60 (br d, J = 7.2 Hz, 1H), 6.83-6.74 (m, 2H), 6.72 (d, J = 1.9 Hz, 1H), 5.68 (s, 1H), 4.78 (br t, J = 5.8 Hz, 2H), 4.48 (br t, J = 5.8 Hz, 2H), 2.09 (s, 3H), 1.83 (s, 3H) |
| 167 | 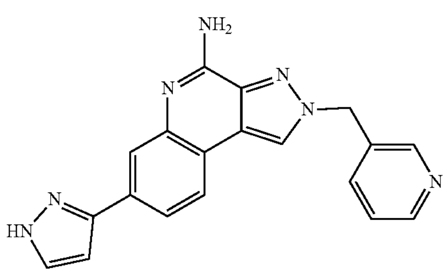 [SMILES: Nc1nc2cc(-c3cc[nH]n3)ccc2c2cn(Cc3cccnc3)nc12] | 342.1 | 0.75 | δ 8.85 (s, 1H), 8.64 (s, 1H), 8.54 (d, J = 3.9 Hz, 1H), 7.96-7.91 (m, 1H), 7.89 (s, 1H), 7.73 (br d, J = 8.0 Hz, 1H), 7.69 (br s, 1H), 7.62 (br d, J = 8.0 Hz, 1H), 7.41 (dd, J = 7.6, 4.5 Hz, 1H), 6.82-6.75 (m, 2H), 6.74 (d, J = 1.9 Hz, 1H), 5.74 (s, 2H) |
| 168 | 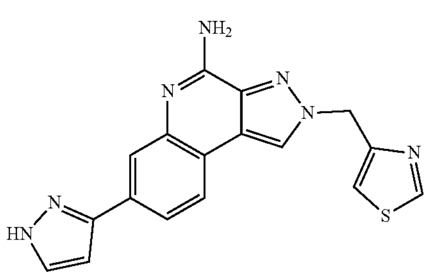 [SMILES: Nc1nc2cc(-c3cc[nH]n3)ccc2c2cn(Cc3cscn3)nc12] | 348.1 | 0.87 | δ 13.12-12.66 (m, 1H), 9.10 (d, J = 1.7 Hz, 1H), 8.79 (s, 1H), 7.96 (br d, J = 8.0 Hz, 1H), 7.89 (br s, 1H), 7.82-7.56 (m, 3H), 6.87-6.77 (m, 2H), 6.74 (s, 1H), 5.81 (s, 2H) |

| Ex. No. | Structure | LC/MS [M + H]+ | RT (min) | 1H NMR (500 MHz, DMSO-d6) |
|---|---|---|---|---|
| 169 | 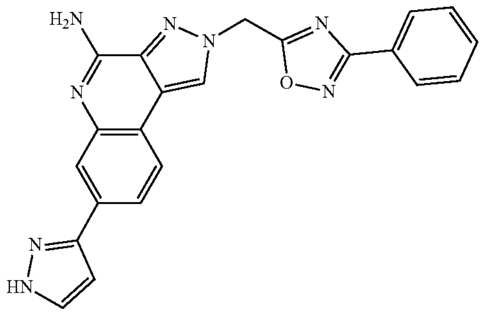 [SMILES: Nc1nc2cc(-c3cc[nH]n3)ccc2c2cn(Cc3nc(-c4ccccc4)no3)nc12] | 409.1 | 1.36 | δ 13.42-12.74 (m, 1H), 8.97 (s, 1H), 8.02-7.96 (m, 3H), 7.91 (s, 1H), 7.77-7.52 (m, 5H), 6.85 (br s, 2H), 6.75 (d, J = 1.7 Hz, 1H), 6.26 (s, 2H) |
| 170 | 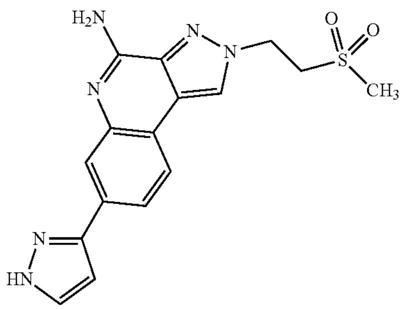 [SMILES: CS(=O)(=O)CCn1cc2c(n1)c(N)nc1cc(-c3cc[nH]n3)ccc12] | 357.3 | 0.93 | δ 8.81 (s, 1H), 7.94 (br d, J = 8.3 Hz, 1H), 7.85-7.52 (m, 2H), 7.22-6.84 (m, 2H), 6.74 (br s, 1H), 4.90 (t, J = 7.0 Hz, 2H), 3.90 (t, J = 6.6 Hz, 2H), 2.98 (s, 3H) |
| 171 | 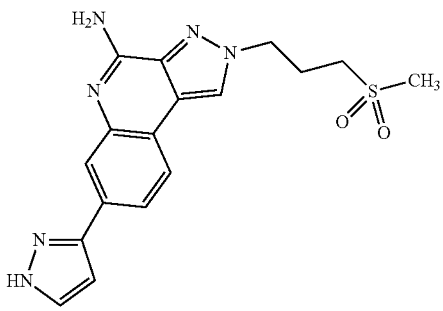 [SMILES: CS(=O)(=O)CCCn1cc2c(n1)c(N)nc1cc(-c3cc[nH]n3)ccc12] | 371.2 | 0.98 | δ 13.70-12.89 (m, 1H), 9.84-9.11 (m, 2H), 9.00 (s, 1H), 8.14-8.08 (m, 2H), 7.90 (d, J = 7.9 Hz, 1H), 7.82 (br s, 1H), 6.79 (d, J = 2.1 Hz, 1H), 4.67 (t, J = 7.0 Hz, 2H), 3.26-3.22 (m, 2H), 3.00 (s, 3H), 2.46-2.38 (m, 2H) |
| 172 | 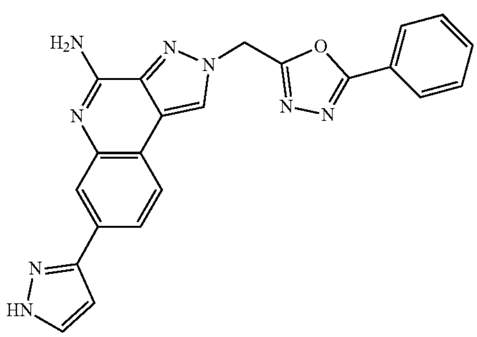 [SMILES: Nc1nc2cc(-c3cc[nH]n3)ccc2c2cn(Cc3nnc(-c4ccccc4)o3)nc12] | 409.1 | 1.22 | δ 13.04-12.70 (m, 1H), 8.97 (s, 1H), 8.00 (br d, J = 7.9 Hz, 1H), 7.98 (s, 1H), 7.97 (d, J = 1.5 Hz, 1H), 7.91 (br s, 1H), 7.83-7.56 (m, 5H), 7.05-6.91 (m, 2H), 6.75 (s, 1H), 6.17 (s, 2H) |
| 173 | 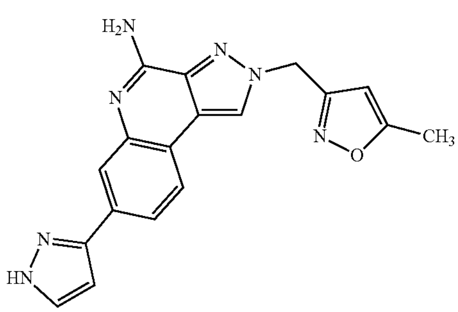 [SMILES: Cc1cc(Cn2cc3c(n2)c(N)nc2cc(-c4cc[nH]n4)ccc23)no1] | 346.1 | 1.11 | δ 13.44-12.75 (m, 1H), 8.84 (s, 1H), 7.95 (br d, J = 8.1 Hz, 1H), 7.90 (s, 1H), 7.80-7.57 (m, 2H), 6.98-6.79 (m, 2H), 6.74 (d, J = 1.7 Hz, 1H), 6.21 (s, 1H), 5.74 (s, 2H), 2.37 (s, 3H) |

| Ex. No. | Structure | LC/MS [M + H]⁺ | RT (min) | ¹H NMR (500 MHz, DMSO-d₆) |
| --- | --- | --- | --- | --- |
| 174 | 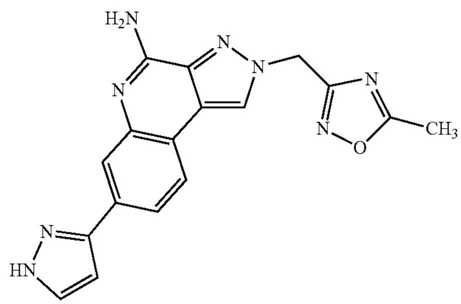 [SMILES: Cc1nc(Cn2cc3c(n2)c(N)nc2cc(-c4cc[nH]n4)ccc23)no1] | 347.3 | 0.84 | δ 13.43-12.77 (m, 1H), 8.85 (s, 1H), 7.97 (br d, J = 7.4 Hz, 1H), 7.89 (br s, 1H), 7.81-7.56 (m, 2H), 6.84-6.71 (m, 3H), 5.86 (s, 2H), 2.58-2.55 (m, 3H) |
| 175 | 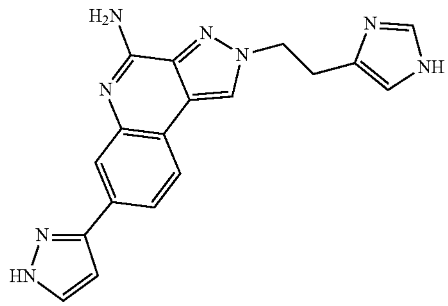 [SMILES: Nc1nc2cc(-c3cc[nH]n3)ccc2c2cn(CCc3c[nH]cn3)nc12] | 345.1 | 0.89 | δ 8.67 (s, 1H), 7.91 (br d, J = 7.7 Hz, 2H), 7.74-7.68 (m, 1H), 7.65 (br d, J = 7.4 Hz, 1H), 7.61 (s, 1H), 7.30-6.96 (m, 2H), 6.79 (s, 1H), 6.74 (d, J = 1.9 Hz, 1H), 4.69 (br t, J = 7.3 Hz, 2H), 3.21 (br t, J = 7.2 Hz, 2H) |
| 176 | 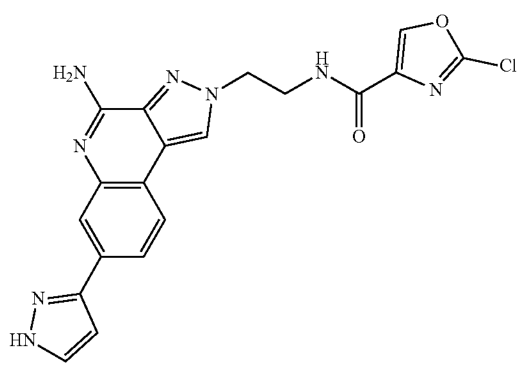 [SMILES: Nc1nc2cc(-c3cc[nH]n3)ccc2c2cn(CCNC(=O)c3coc(Cl)n3)nc12] | 423.2 | 1.12 | δ 8.91 (s, 1H), 8.71 (br t, J = 5.6 Hz, 1H), 8.67 (s, 1H), 8.11-8.05 (m, 2H), 7.88-7.76 (m, 2H), 6.78 (br s, 1H), 4.66 (br t, J = 5.5 Hz, 2H), 3.86-3.77 (m, 2H) |
| 177 | 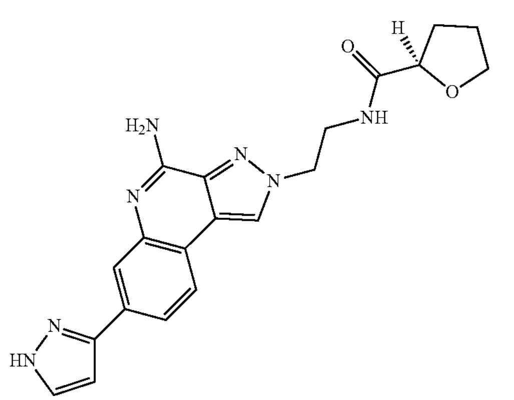 [SMILES: Nc1nc2cc(-c3cc[nH]n3)ccc2c2cn(CCNC(=O)[C@H]3CCCO3)nc12] | 392.2 | 0.79 | δ 8.62 (s, 1H), 7.97 (br t, J = 5.7 Hz, 1H), 7.94-7.87 (m, 2H), 7.69 (br s, 1H), 7.62 (br d, J = 7.9 Hz, 1H), 6.84-6.71 (m, 3H), 4.52 (br t, J = 5.8 Hz, 2H), 4.17-4.12 (m, 1H), 3.81-3.75 (m, 2H), 3.72-3.64 (m, 2H), 2.07-1.97 (m, 1H), 1.79-1.61 (m, 3H) |

| Ex. No. | Structure | LC/MS [M + H]+ | RT (min) | 1H NMR (500 MHz, DMSO-d6) |
|---|---|---|---|---|
| 178 | 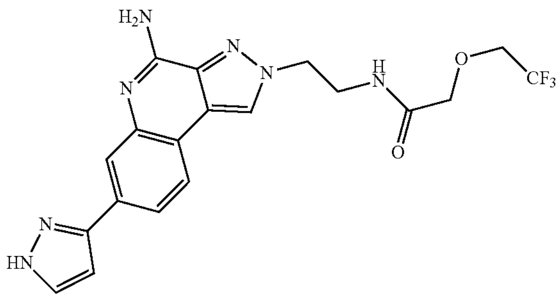 [SMILES: Nc1nc2cc(-c3cc[nH]n3)ccc2c2cn(CCNC(=O)COCC(F)(F)F)nc12] | 434.1 | 0.95 | δ 8.67 (s, 1H), 8.09 (t, J = 5.8 Hz, 1H), 7.92 (d, J = 8.1 Hz, 1H), 7.89 (d, J = 1.4 Hz, 1H), 7.69 (br s, 1H), 7.62 (br d, J = 8.5 Hz, 1H), 6.73 (d, J = 2.1 Hz, 1H), 6.88-6.71 (m, 2H), 4.53 (t, J = 6.0 Hz, 2H), 4.12-4.03 (m, 4H), 3.69-3.64 (m, 2H) |
| 179 | enantiomer 1 | 421.4 | 0.62 | δ 8.63 (s, 1H), 7.99-7.89 (m, 3H), 7.76-7.59 (m, 2H), 6.97-6.80 (m, 2H), 6.74 (d, J = 1.9 Hz, 1H), 4.57-4.45 (m, 2H), 3.86 (dd, J = 10.0, 2.6 Hz, 1H), 3.82 (br d, J = 11.3 Hz, 1H), 3.70-3.58 (m, 2H), 3.56-3.49 (m, 1H), 2.78 (br d, J = 11.0 Hz, 1H), 2.57-2.54 (m, 1H), 2.13 (s, 3H), 1.96 (td, J = 11.3, 2.9 Hz, 1H), 1.80 (t, J = 10.7 Hz, 1H) |
| 180 | enantiomer 2 | 421.1 | 0.62 | δ 8.64 (s, 1H), 7.99-7.89 (m, 3H), 7.76-7.59 (m, 2H), 7.01-6.83 (m, 2H), 6.74 (d, J = 1.7 Hz, 1H), 4.57-4.46 (m, 2H), 3.86 (dd, J = 10.0, 2.6 Hz, 1H), 3.82 (br d, J = 11.3 Hz, 1H), 3.70-3.58 (m, 2H), 3.53 (td, J = 11.1, 2.3 Hz, 1H), 2.78 (br d, J = 11.8 Hz, 1H), 2.57-2.54 (m, 1H), 2.13 (s, 3H), 1.96 (td, J = 11.2, 2.9 Hz, 1H), 1.80 (t, J = 10.7 Hz, 1H) |
| 181 | 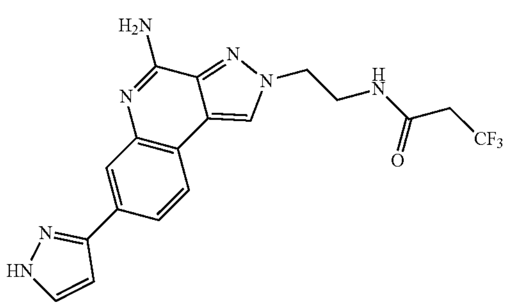 [SMILES: Nc1nc2cc(-c3cc[nH]n3)ccc2c2cn(CCNC(=O)CC(F)(F)F)nc12] | 404.1 | 1.02 | δ 8.65 (s, 1H), 8.46-8.39 (m, 1H), 7.93-7.86 (m, 2H), 7.69 (br s, 1H), 7.62 (br d, J = 7.7 Hz, 1H), 6.85-6.70 (m, 3H), 4.53-4.47 (m, 2H), 3.71-3.64 (m, 2H), 3.30-3.22 (m, 2H) |
| 182 | 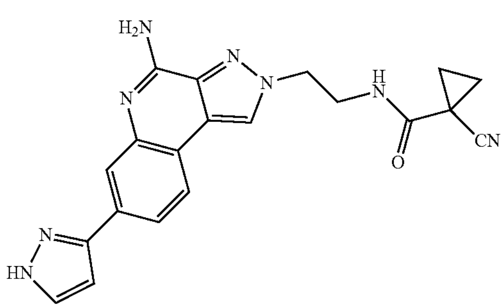 [SMILES: N#CC1(C(=O)NCCn2cc3c(n2)c(N)nc2cc(-c4cc[nH]n4)ccc23)CC1] | 387.2 | 1.01 | δ 8.65 (s, 1H), 8.38 (t, J = 5.5 Hz, 1H), 7.93 (d, J = 8.0 Hz, 1H), 7.88 (s, 1H), 7.74-7.65 (m, 1H), 7.63 (br d, J = 8.0 Hz, 1H), 6.75-6.65 (m, 3H), 4.53 (t, J = 5.6 Hz, 2H), 3.67-3.61 (m, 2H), 1.55-1.50 (m, 2H), 1.44-1.39 (m, 2H). |

-continued

| Ex. No. | Structure | LC/MS [M + H]⁺ | RT (min) | ¹H NMR (500 MHz, DMSO-d₆) |
|---|---|---|---|---|
| 183 | (structure: 4-amino-pyrazoloquinoline with ethyl-NHC(O)-2-methyloxazole and pyrazolyl substituent) | 403.1 | 1.13 | δ 8.67 (s, 1H), 8.47 (d, J = 2.1 Hz, 1H), 8.37 (s, 1H), 8.33 (br t, J = 5.1 Hz, 1H), 7.98 (d, J = 8.5 Hz, 1H), 7.87 (d, J = 1.8 Hz, 1H), 7.73 (s, 1H), 7.66 (dd, J = 8.4, 1.9 Hz, 1H), 6.68 (br s, 2H), 6.53 (s, 1H), 4.62 (t, J = 6.3 Hz, 2H), 3.83 (q, J = 6.1 Hz, 2H), 2.43 (s, 3H) |
| 184 | (structure: 4-amino-pyrazoloquinoline with ethyl-NHC(O)-5-fluoropyridine and pyrazolyl substituent) | 417.1 | 1.24 | δ 8.89 (br t, J = 5.6 Hz, 1H), 8.69 (s, 1H), 8.59 (d, J = 2.6 Hz, 1H), 8.47 (d, J = 2.2 Hz, 1H), 8.09 (dd, J = 8.8, 4.7 Hz, 1H), 7.97 (d, J = 8.5 Hz, 1H), 7.89-7.82 (m, 2H), 7.73 (s, 1H), 7.65 (dd, J = 8.3, 1.8 Hz, 1H), 6.68 (br s, 2H), 6.53 (s, 1H), 4.67 (t, J = 6.2 Hz, 2H), 3.91 (q, J = 6.3 Hz, 2H) |

Examples 185 to 193 were prepared according to synthetic procedures similar to those described for Example 20, Example 31, or Example 132 from the appropriate starting materials. Analytical LC/MS conditions:

A: Column: PoroShell HPH C18, 3.0 mm×50 mm, 2.7 µm particles; Mobile Phase A: water with 5 mM ammonium bicarbonate; Mobile Phase B: acetonitrile; Temperature: 40° C.; Gradient: 5% B to 95% B over 2 min, then a 0.6 min hold at 95% B; Flow: 1 mL/min; Detection: MS and UV.

B: Column: Shim-pack XR-ODS, 3.0 mm×50 mm, 2.2 µm particles; Mobile Phase A: water with with 0.0500 TFA; Mobile Phase B: acetonitrile with 0.05% TFA; Temperature: 40° C.; Gradient: 5% B to 95% B over 2 min, then a 0.7 min hold at 95% B; Flow: 1 mL/min; Detection: MS and UV.

C: Column: Kinetex EVO C18, 3.0 mm×50 mm, 2.2 µm particles; Mobile Phase A: water with with 5 mM ammonium bicarbonate; Mobile Phase B: acetonitrile; Temperature: 40° C.; Gradient: 10% B to 95% B over 2 min, then a 0.6 min hold at 95% B; Flow: 1 mL/min; Detection: MS and UV.

| Ex. No. | Structure | LC/MS [M + H]⁺ | RT (min)/ LC condition | ¹H NMR, unless otherwise indicated, 300 MHz, Methanol-d₄ |
|---|---|---|---|---|
| 185 | (structure: 4-amino-pyrazoloquinoline with ethyl-OCH₃ and pyrazolyl substituent) | 309.2 | 0.98/A | δ 8.59 (s, 1H), 7.98 (t, J = 10.2 Hz, 2H), 7.71 (s, 2H), 6.75 (s, 1H), 4.67 (t, J = 5.1 Hz, 2H), 3.94 (t, J = 5.1 Hz, 2H), 3.38 (s, 3H) |

-continued

| Ex. No. | Structure | LC/MS [M + H]+ | RT (min)/ LC condition | 1H NMR, unless otherwise indicated, 300 MHz, Methanol-d4 |
|---|---|---|---|---|
| 186 | 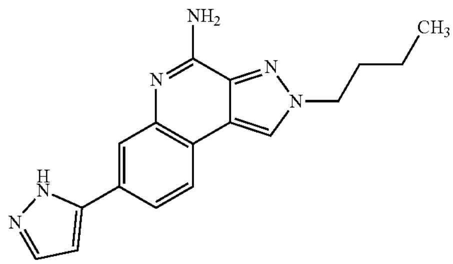 [SMILES: CCCCn1cc2c(n1)c(N)nc1cc(-c3ccn[nH]3)ccc12] | 307.2 | 1.13/B | 1H NMR (400 MHz, Methanol-d4) δ 8.77 (s, 1H), 8.09 (d, J = 8.3 Hz, 1H), 8.02 (d, J = 1.6 Hz, 1H), 8.02-7.97 (m, 1H), 7.77 (d, J = 2.3 Hz, 1H), 6.82 (d, J = 2.4 Hz, 1H), 4.57 (t, J = 7.1 Hz, 2H), 2.12-1.94 (m, 2H), 1.47 – 1.35 (m, 2H), 1.02 (t, J = 7.4 Hz, 3H) |
| 187 | 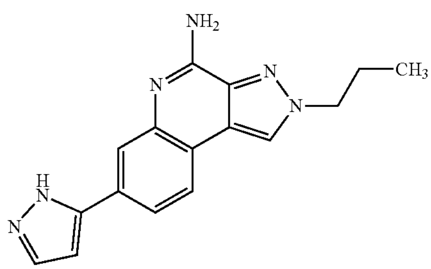 [SMILES: CCCn1cc2c(n1)c(N)nc1cc(-c3ccn[nH]3)ccc12] | 293.1 | 1.17/A | 1H NMR (300 MHz, DMSO-d6) δ 13.09 (d, J = 135.0 Hz, 1H), 8.73 (s, 1H), 8.11-7.89 (m, 2H), 7.88-7.49 (m, 2H), 6.93 – 6.62 (m, 3H), 4.41 (t, J = 7.0 Hz, 2H), 2.18-1.78 (m, 2H), 0.91 (t, J = 7.4 Hz, 3H) |
| 188 | 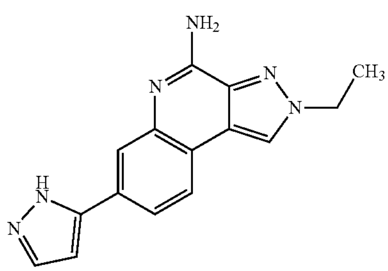 [SMILES: CCn1cc2c(n1)c(N)nc1cc(-c3ccn[nH]3)ccc12] | 279.1 | 1.08/C | δ 8.58 (s, 1H), 7.96 (t, J = 8.4 Hz, 2H), 7.70 (s, 2H), 6.74 (d, J = 2.2 Hz, 1H), 4.54 (q, J = 7.3 Hz, 2H), 1.66 (t, J = 7.3 Hz, 3H) |
| 189 | 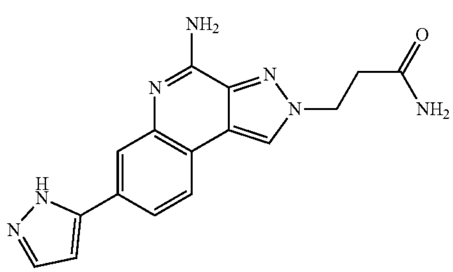 [SMILES: NC(=O)CCn1cc2c(n1)c(N)nc1cc(-c3ccn[nH]3)ccc12] | 322.1 | 0.84/C | δ 8.55 (s, 1H), 7.97 (d, J = 8.1 Hz, 2H), 7.71 (s, 2H), 6.74 (s, 1H), 4.79 (t, J = 6.6 Hz, 2H), 2.98 (t, J = 6.6 Hz, 2H) |
| 190 | 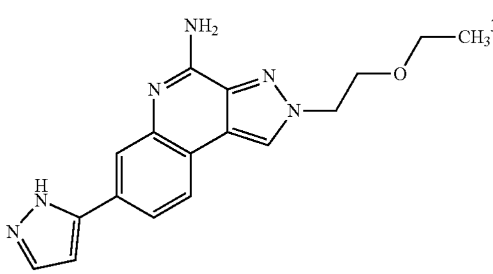 [SMILES: CCOCCn1cc2c(n1)c(N)nc1cc(-c3ccn[nH]3)ccc12] | 323.2 | 1.12/C | δ 8.57 (s, 1H), 7.97 (t, J = 9.0 Hz, 2H), 7.70 (s, 2H), 6.74 (s, 1H), 4.66 (t, J = 5.2 Hz, 2H), 3.98 (t, J = 5.2 Hz, 2H), 3.54 (q, J = 7.0 Hz, 2H), 1.16 (t, J = 7.0 Hz, 3H) |

-continued

| Ex. No. | Structure | LC/MS [M + H]⁺ | RT (min)/ LC condition | ¹H NMR, unless otherwise indicated, 300 MHz, Methanol-d₄ |
|---|---|---|---|---|
| 191 | 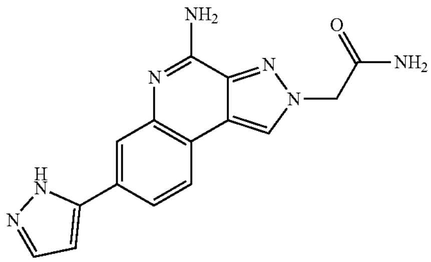 [SMILES: NC(=O)Cn1cc2c(n1)c(N)nc1cc(-c3ccn[nH]3)ccc12] | 308.1 | 0.76/A | δ 8.61 (s, 1H), 7.98 (t, J = 11.1 Hz, 2H), 7.70 (s, 2H), 6.74 (s, 1H), 5.25 (s, 2H) |
| 192 | 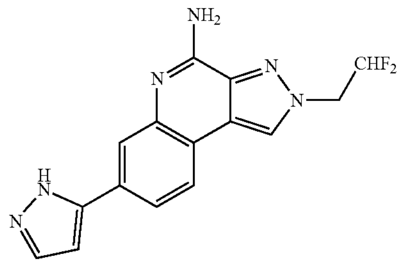 [SMILES: Nc1nc2cc(-c3ccn[nH]3)ccc2c2cn(CC(F)F)nc12] | 315.1 | 1.10/C | δ 8.64 (s, 1H), 8.12-7.89 (m, 2H), 7.71 (s, 2H), 6.74 (s, 1H), 6.60 – 6.21 (m, 1H), 5.02-4.91 (m, 2H) |
| 193 | 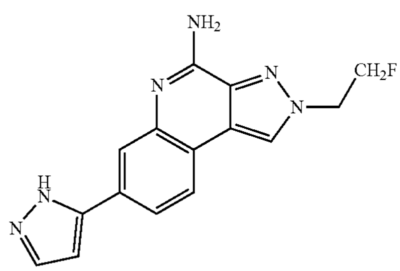 | 297.1 | 1.01/A | ¹H NMR (400 MHz, Methanol-d₄) δ 8.71-8.42 (m, 1H), 8.21 – 7.56 (m, 4H), 6.91-6.52 (m, 1H), 5.20 – 4.92 (m, 3H), 4.81-4.71 (m, 1H) |

Example 179 and Example 180

The racemic material was prepared from the appropriate starting materials and purified via preparative chiral SFC with the following conditions to provide Example 179 and Example 180 as single unassigned isomers: Instrument: Waters 100 Prep SFC; Column: Chiral AS, 30×250 mm. 5 micron; Mobile Phase: 65% CO₂/35% IPA w/0.1% DEA; Flow Conditions: 100 mL/min; Detector Wavelength: 220 nm. Example 179 (first-eluting isomer) RT: 3.87 min. Example 180 (second-eluting isomer) RT: 12.58 min.

Analytical Chiral SFC Conditions: Instrument: Shimadzu Nexera UC SFC; Column: Chiralpak AS, 4.6×100 mm, 5 micron; Mobile Phase: 65% CO₂/35% IPA w/0.1% DEA; Flow Conditions: 2 mL/min; Detector Wavelength: 220 nm. Example 179 (first-eluting isomer) RT: 2.5 min. Example 180 (second-eluting isomer) RT: 5.6 min.

Example 194. Preparation of 7-(1H-pyrazol-3-yl)-2-(2-(pyridin-2-ylamino)ethyl)-2H-pyrazolo[3,4-c]quinolin-4-amine

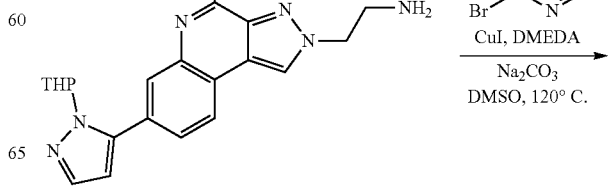

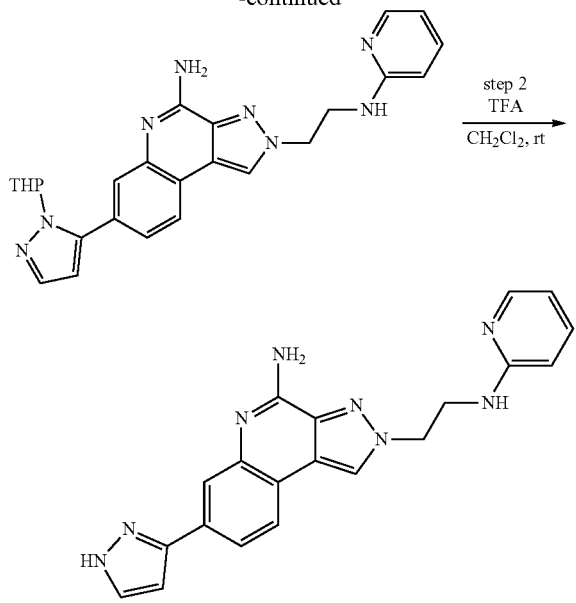

Step 1. 2-(2-(pyridin-2-ylamino)ethyl)-7-(1-(tetrahydro-2H-pyran-2-yl)-1H-pyrazol-5-yl)-2H-pyrazolo[3,4-c]quinolin-4-amine A mixture of 2-(2-aminoethyl)-7-(1-(tetrahydro-2H-pyran-2-yl)-1H-pyrazol-5-yl)-2H-pyrazolo[3,4-c]quinolin-4-amine (40 mg, 0.106 mmol) and sodium carbonate (44.9 mg, 0.424 mmol) was evacuated and back-filled with $N_2$, then DMSO (1060 μl) was added. The resulting mixture was sparged with $N_2$ for 10 min, then 2-bromopyridine (11.12 μl, 0.117 mmol), N,N'-dimethylethylenediamine (34.2 μl, 0.318 mmol), and copper(I) iodide (30.3 mg, 0.159 mmol) were added. The mixture was sparged with $N_2$ for 1 min, then it was sealed and stirred at 120° C. for 18 h. Additional 2-bromopyridine (11.12 μl, 0.117 mmol) was added and the reaction was stirred at 120° C. for 1 h. Additional 2-bromopyridine (25 μL) was added and the reaction was stirred at 120° C. for 4 h. The reaction was cooled to rt, diluted with EtOAc (20 mL), washed with $H_2O$ (20 mL), 1:1 $H_2O$-aq. $NH_4OH$ (20 mL), and sat. aq. NaCl (20 mL), dried over $Na_2SO_4$, filtered, and concentrated in vacuo. The crude material was purified by flash chromatography (12 g silica gel; linear gradient 0-10% MeOH—$CH_2Cl_2$) to provide 2-(2-(pyridin-2-ylamino)ethyl)-7-(1-(tetrahydro-2H-pyran-2-yl)-1H-pyrazol-5-yl)-2H-pyrazolo[3,4-c]quinolin-4-amine (4.3 mg, 9%). LC-MS m/z 455 [M+H]$^+$.

Step 2. 7-(1H-pyrazol-3-yl)-2-(2-(pyridin-2-ylamino)ethyl)-2H-pyrazolo[3,4-c]quinolin-4-amine To a rt solution of 2-(2-(pyridin-2-ylamino)ethyl)-7-(1-(tetrahydro-2H-pyran-2-yl)-1H-pyrazol-5-yl)-2H-pyrazolo[3,4-c]quinolin-4-amine (4.3 mg, 9.46 μmol) in $CH_2Cl_2$ (0.1 mL) was added TFA (0.1 mL). The reaction was stirred at rt for 2 h. The reaction was concentrated in vacuo. The crude material was dissolved in $CH_2Cl_2$ and concentrated. The crude material was dissolved in DMF (2 mL), filtered (syringe filter), and purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 2-minute hold at 1% B, 1-23% B over 25 minutes, then a 2-minute hold at 100% B; Flow Rate: 20 mL/min; Column Temperature: 25° C. Fraction collection was triggered by MS signals. Fractions containing the desired product were combined and dried via centrifugal evaporation to provide 7-(1H-pyrazol-3-yl)-2-(2-(pyridin-2-ylamino)ethyl)-2H-pyrazolo[3,4-c]quinolin-4-amine, 2 TFA (2.6 mg, 46%). $^1$H NMR (500 MHz, DMSO-$d_6$) δ 8.96 (s, 1H), 8.13-8.09 (m, 2H), 7.99 (br d, J=6.0 Hz, 1H), 7.90 (d, J=8.5 Hz, 1H), 7.79 (s, 1H), 7.55-7.48 (m, 1H), 6.77 (d, J=2.0 Hz, 1H), 6.67-6.60 (m, 2H), 4.73 (t, J=5.9 Hz, 2H), 3.94 (br t, J=5.8 Hz, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 371.1 [M+H]$^+$; RT: 0.92 min.

Example 195. Preparation of N-(2-(4-amino-8-chloro-7-(1H-pyrazol-3-yl)-2H-pyrazolo[3,4-c]quinolin-2-yl)ethyl)-5-fluoropicolinamide

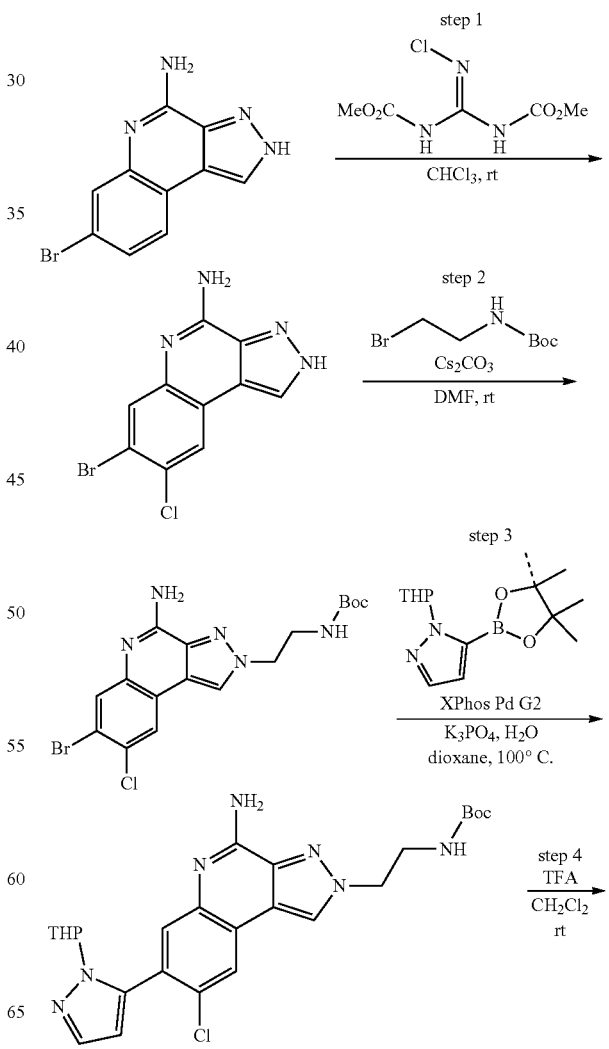

261
-continued step 5

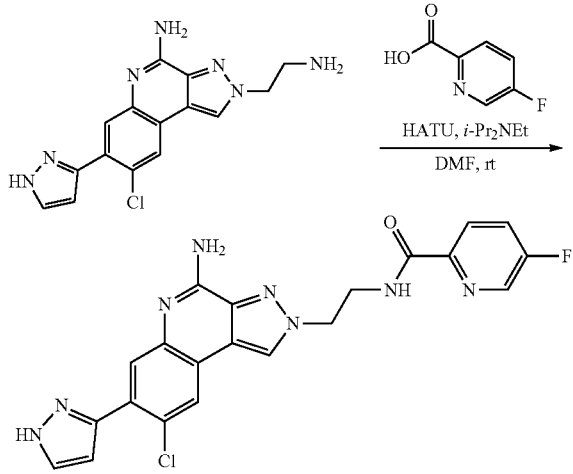

Step 1. 7-bromo-8-chloro-2H-pyrazolo[3,4-c]quinolin-4-amine

To a rt suspension of 7-bromo-2H-pyrazolo[3,4-c]quinolin-4-amine, TFA (0.500 g, 1.326 mmol) in CHCl$_3$ (13.26 ml) was added 2-chloro-1,3-bis(methoxycarbonyl)guanidine (0.333 g, 1.591 mmol). The reaction was stirred at rt for 2 days. The reaction was diluted with 10% MeOH—CH$_2$Cl$_2$ (200 mL), and it was washed with sat. aq. NaHCO$_3$ (200 mL). The aqueous layer was extracted with 10% MeOH—CH$_2$Cl$_2$ (3×100 mL). The combined organic layers were dried over Na$_2$SO$_4$ and filtered. Celite was added, and the mixture was concentrated in vacuo. This material was loaded onto a column and purified by flash chromatography (80 g RediSep Gold silica gel with 25 g solid load cartridge; linear gradient 0-7% MeOH—CH$_2$Cl$_2$) to provide 7-bromo-8-chloro-2H-pyrazolo[3,4-c]quinolin-4-amine (31 mg, 8%). LC-MS m/z 297/299 [M+H]$^+$.

Step 2. tert-butyl (2-(4-amino-7-bromo-8-chloro-2H-pyrazolo[3,4-c]quinolin-2-yl)ethyl)carbamate To a rt solution of 7-bromo-8-chloro-2H-pyrazolo[3,4-c]quinolin-4-amine (31 mg, 0.104 mmol) in DMF (417 µl) was added cesium carbonate (102 mg, 0.313 mmol) followed by tert-butyl (2-bromoethyl)carbamate (25.7 mg, 0.115 mmol). The reaction was stirred at rt for 16 h. additional cesium carbonate (51 mg, 0.16 mmol) and tert-butyl (2-bromoethyl) carbamate (11.7 mg, 0.0522 mmol) were added. The reaction was stirred at 40° C. for 2 h. The reaction was diluted with EtOAc (20 mL) and H$_2$O (20 mL). The layers were separated and the aqueous layer was extracted with EtOAc (20 mL). The combined organic layers were washed with sat. aq. NaCl (20 mL), dried over Na$_2$SO$_4$, and filtered. Celite was added, and the mixture was concentrated in vacuo. This material was dry loaded onto a column and purified by flash chromatography (12 g silica gel with 5 g solid load cartridge; linear gradient 0-10% MeOH—CH$_2$Cl$_2$) to provide tert-butyl (2-(4-amino-7-bromo-8-chloro-2H-pyrazolo[3,4-c]quinolin-2-yl)ethyl)carbamate (37 mg, 81%) as a white solid. LC-MS m/z [M+H]$^+$; $^1$H NMR (400 MHz, DMSO-d$_6$) δ 8.73 (s, 1H), 8.21 (s, 1H), 7.73 (s, 1H), 7.10 (br s, 2H), 7.05 (br t, J=5.8 Hz, 1H), 4.45 (br t, J=6.0 Hz, 2H), 3.47 (q, J=5.9 Hz, 2H), 1.33 (s, 9H).

262

Step 3. tert-butyl (2-(4-amino-8-chloro-7-(1-(tetrahydro-2H-pyran-2-yl)-1H-pyrazol-5-yl)-2H-pyrazolo[3,4-c]quinolin-2-yl)ethyl)carbamate A mixture of tert-butyl (2-(4-amino-7-bromo-8-chloro-2H-pyrazolo[3,4-c]quinolin-2-yl)ethyl)carbamate (20 mg, 0.045 mmol), 1-(tetrahydro-2H-pyran-2-yl)-5-(4,4,5,5-tetramethyl-1,3,2-dioxaborolan-2-yl)-1H-pyrazole (15.15 mg, 0.054 mmol), and potassium phosphate tribasic (28.9 mg, 0.136 mmol) was evacuated and back-filled with N$_2$, then 1,4-dioxane (189 µl) and H$_2$O (37.8 µl) were added. The resulting mixture was sparged with N$_2$ for 15 min, then chloro(2-dicyclohexylphosphino-2',4',6'-triisopropyl-1,1'-biphenyl)[2-(2'-amino-1,1'-biphenyl)]palladium(II) (1.785 mg, 2.269 µmol) was added. The mixture was sparged with N$_2$ for 1 min, then it was sealed and stirred at 100° C. for 1 h. The reaction was cooled to rt, diluted with EtOAc (20 mL), washed with H$_2$O (20 mL) and sat. aq. NaCl (20 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide tert-butyl (2-(4-amino-8-chloro-7-(1-(tetrahydro-2H-pyran-2-yl)-1H-pyrazol-5-yl)-2H-pyrazolo[3,4-c]quinolin-2-yl)ethyl)carbamate (17.3 mg, 75%). LC-MS m/z 512 [M+H]$^+$.

Step 4. 2-(2-aminoethyl)-8-chloro-7-(1H-pyrazol-3-yl)-2H-pyrazolo[3,4-c]quinolin-4-amine, 2 TFA To a rt solution of tert-butyl (2-(4-amino-8-chloro-7-(1-(tetrahydro-2H-pyran-2-yl)-1H-pyrazol-5-yl)-2H-pyrazolo[3,4-c]quinolin-2-yl)ethyl)carbamate (17.3 mg, 0.034 mmol) in CH$_2$Cl$_2$ (169 µl) was added TFA (169 µl). The reaction was stirred at rt for 1.5 h. The reaction was concentrated to remove about half the volume, then it was added dropwise to Et$_2$O (2 mL). The resulting solid was collected by vacuum filtration and washed with Et$_2$O (3×1 mL). The solids were dissolved in CH$_2$Cl$_2$-MeOH and concentrated in vacuo to provide 2-(2-aminoethyl)-8-chloro-7-(1H-pyrazol-3-yl)-2H-pyrazolo[3,4-c]quinolin-4-amine, 2 TFA (17.2 mg, 92%) as an off-white solid. LC-MS m/z 328 [M+H]$^+$.

Step 5. N-(2-(4-amino-8-chloro-7-(1H-pyrazol-3-yl)-2H-pyrazolo[3,4-c]quinolin-2-yl)ethyl)-5-fluoropicolinamide To a rt solution of 5-fluoropicolinic acid (4.80 mg, 0.034 mmol) in DMF (155 µl) was added N,N-diisopropylethylamine (10.78 µl, 0.062 mmol), followed by HATU (11.77 mg, 0.031 mmol). This mixture was stirred at rt for 5 min, then it was added, dropwise, to a solution of 2-(2-aminoethyl)-8-chloro-7-(1H-pyrazol-3-yl)-2H-pyrazolo[3,4-c]quinolin-4-amine, 2 TFA (17.2 mg, 0.031 mmol) and N,N-diisopropylethylamine (16.17 µl, 0.093 mmol) in DMF (155 µl). The reaction was stirred at rt for 15 min. The reaction was diluted with H$_2$O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 110% B, 11-51% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-8-chloro-7-(1H-pyrazol-3-yl)-2H-pyrazolo[3,4-c]quinolin-2-yl)ethyl)-5-fluoropicolinamide (4.2 mg, 29%). ¹H NMR (500 MHz, DMSO-d₆) δ 13.33-12.92 (m, 1H), 9.06 (t, J=6.0 Hz, 1H), 8.79 (s, 1H), 8.61 (d, J=2.6 Hz, 1H), 8.12-8.06 (m, 2H), 7.88 (td, J=8.7, 2.8 Hz, 1H), 7.85-7.66 (m, 2H), 7.36-6.96 (m, 2H), 6.72 (br s, 1H), 4.65 (br t, J=6.1 Hz, 2H), 3.88 (q, J=6.1 Hz, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 451.0 [M+H]⁺; RT: 1.15 min.

Examples 196 to 204 were prepared according to synthetic procedures similar to those described for Examples 150 and 151 from the appropriate starting materials. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

| Ex. No. | Structure | LC/MS [M + H]⁺ | RT (min) | ¹H NMR (500 MHz, DMSO-d₆) |
|---|---|---|---|---|
| 196 | 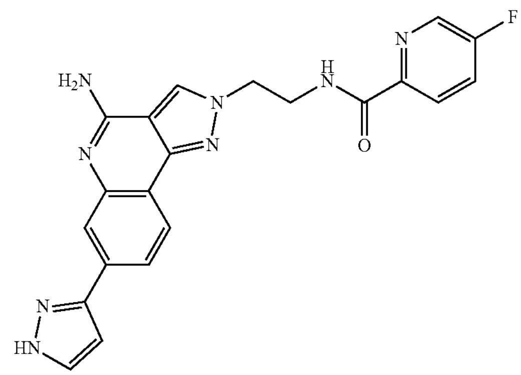 [SMILES: Nc1nc2cc(-c3cc[nH]n3)ccc2c2nn(CCNC(=O)c3ccc(F)cn3)cc12] | 417.1 | 1.19 | δ 9.06 (br t, J = 5.9 Hz, 1H), 8.64 (d, J = 2.5 Hz, 1H), 8.45 (s, 1H), 8.12 – 8.06 (m, 2H), 7.92 – 7.86 (m, 2H), 7.71 (br s, 1H), 7.63 (br d, J = 7.4 Hz, 1H), 7.11 – 6.84 (m, 2H), 6.75 (d, J = 1.9 Hz, 1H), 4.63 (br t, J = 5.9 Hz, 2H), 3.85 (q, J = 6.1 Hz, 2H) |
| 197 | 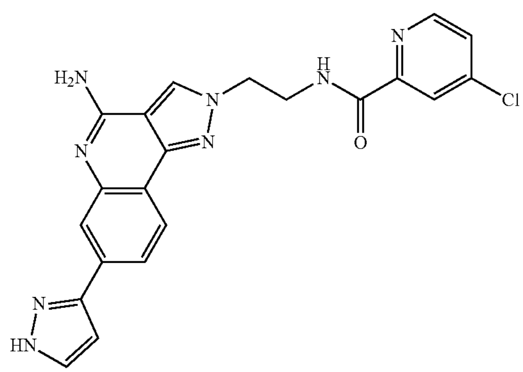 [SMILES: Nc1nc2cc(-c3cc[nH]n3)ccc2c2nn(CCNC(=O)c3cc(Cl)ccn3)cc12] | 433.2 | 1.11 | δ 9.18 (br t, J = 5.8 Hz, 1H), 8.62 (d, J = 5.2 Hz, 1H), 8.53 (br s, 1H), 8.08 (d, J = 8.0 Hz, 1H), 7.99 (d, J = 1.7 Hz, 1H), 7.92 (br s, 1H), 7.80 – 7.61 (m, 3H), 6.76 (s, 1H), 4.65 (br t, J = 5.9 Hz, 2H), 3.85 (q, J = 6.0 Hz, 2H) |
| 198 | 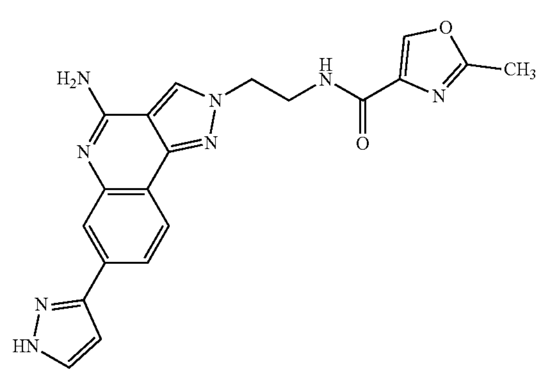 [SMILES: Cc1nc(C(=O)NCCn2cc3c(N)nc4cc(-c5cc[nH]n5)ccc4c3n2)co1] | 403.0 | 0.87 | δ 8.85 (s, 1H), 8.50 (t, J = 5.9 Hz, 1H), 8.40 (s, 1H), 8.19 (d, J = 8.3 Hz, 1H), 8.09 (br s, 1H), 7.91 (br d, J = 8.0 Hz, 1H), 7.84 (br s, 1H), 6.82 (d, J = 1.9 Hz, 1H), 4.64 (br t, J = 5.5 Hz, 2H), 3.77 (q, J = 5.9 Hz, 2H), 2.43 (s, 3H) |

| Ex. No. | Structure | LC/MS [M + H]+ | RT (min) | 1H NMR (500 MHz, DMSO-d6) |
|---|---|---|---|---|
| 199 | 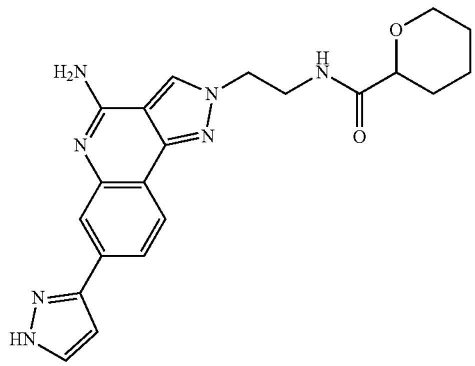 [SMILES: Nc1nc2cc(-c3cc[nH]n3)ccc2c2nn(CCNC(=O)C3CCCCO3)cc12] | 405.9 | 1.15 | δ 8.42 (s, 1H), 8.07 (d, J = 8.0 Hz, 1H), 7.90 – 7.86 (m, 2H), 7.71 (br s, 1H), 7.63 (br d, J = 8.0 Hz, 1H), 7.09 – 6.88 (m, 2H), 6.75 (d, J = 2.2 Hz, 1H), 4.50 (br t, J = 5.4 Hz, 2H), 3.92 (br d, J = 11.0 Hz, 1H), 3.69 (dd, J = 10.9, 2.3 Hz, 1H), 3.64 – 3.56 (m, 3H), 1.84 – 1.78 (m, 1H), 1.74 (br d, J = 10.7 Hz, 1H), 1.52 – 1.39 (m, 3H), 1.34 – 1.24 (m, 1H) |
| 200 | 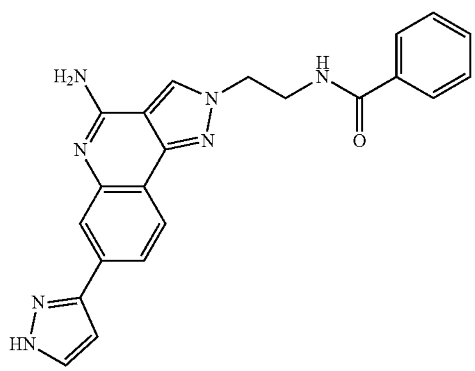 [SMILES: Nc1nc2cc(-c3cc[nH]n3)ccc2c2nn(CCNC(=O)c3ccccc3)cc12] | 398.2 | 1.16 | δ 8.68 (t, J = 5.5 Hz, 1H), 8.46 (s, 1H), 8.08 (d, J = 8.1 Hz, 1H), 7.88 (s, 1H), 7.80 – 7.76 (m, 2H), 7.76 – 7.69 (m, 1H), 7.64 (br d, J = 6.0 Hz, 1H), 7.54 – 7.49 (m, 1H), 7.47 – 7.42 (m, 2H), 7.01 (br s, 2H), 6.76 (d, J = 2.1 Hz, 1H), 4.61 (br t, J = 5.8 Hz, 2H), 3.78 (q, J = 5.7 Hz, 2H) |
| 201 | 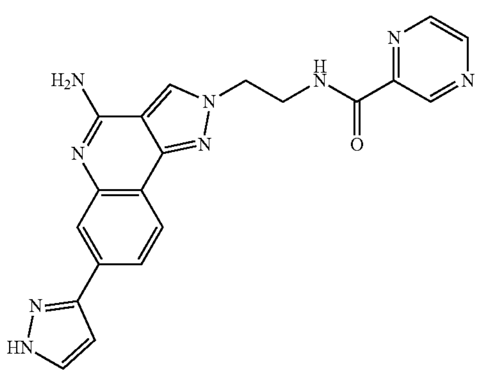 [SMILES: Nc1nc2cc(-c3cc[nH]n3)ccc2c2nn(CCNC(=O)c3cnccn3)cc12] | 399.9 | 1.06 | δ 9.22 (br t, J = 5.9 Hz, 1H), 9.15 (d, J = 1.1 Hz, 1H), 8.86 (d, J = 2.4 Hz, 1H), 8.74 – 8.69 (m, 1H), 8.43 (s, 1H), 8.05 (d, J = 8.1 Hz, 1H), 7.86 (s, 1H), 7.79 – 7.58 (m, 2H), 6.95 – 6.83 (m, 2H), 6.75 (d, J = 1.9 Hz, 1H), 4.64 (br t, J = 5.8 Hz, 2H), 3.86 (q, J = 5.9 Hz, 2H) |
| 202 | 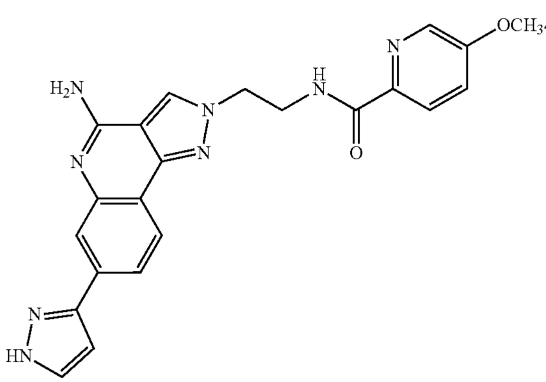 | 428.9 | 1.17 | δ 8.90 (br t, J = 5.9 Hz, 1H), 8.45 (s, 1H), 8.27 (br s, 1H), 8.08 (d, J = 8.2 Hz, 1H), 7.96 (d, J = 8.8 Hz, 1H), 7.87 (br s, 1H), 7.76 – 7.59 (m, 2H), 7.54 – 7.48 (m, 1H), 7.05 – 6.88 (m, 2H), 6.76 (d, J = 2.0 Hz, 1H), 4.61 (br t, J = 5.6 Hz, 2H), 3.87 (s, 3H), 3.85 – 3.80 (m, 2H) |

| Ex. No. | Structure | LC/MS [M + H]⁺ | RT (min) | ¹H NMR (500 MHz, DMSO-d₆) |
|---|---|---|---|---|
| 203 | 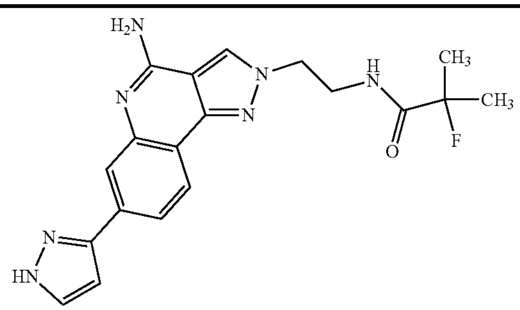 | 382.2 | 0.89 | δ 8.41 (s, 1H), 8.25 (br d, J = 2.5 Hz, 1H), 8.06 (d, J = 8.0 Hz, 1H), 7.87 (s, 1H), 7.70 (br s, 1H), 7.62 (br d, J = 7.7 Hz, 1H), 7.09 – 6.92 (m, 2H), 6.75 (d, J = 1.9 Hz, 1H), 4.51 (br t, J = 5.6 Hz, 2H), 3.63 – 3.58 (m, 2H), 1.41 (s, 3H), 1.37 (s, 3H) |
| 204 | 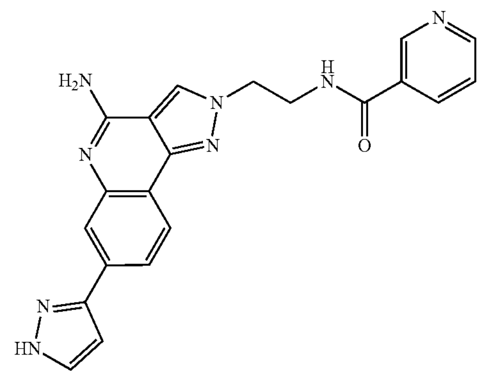 [SMILES: Nc1nc2cc(-c3cc[nH]n3)ccc2c2nn(CCNC(=O)c3cccnc3)cc12] | 399.2 | 1.00 | δ 8.93 (br s, 1H), 8.87 (t, J = 5.6 Hz, 1H), 8.68 (br d, J = 2.7 Hz, 1H), 8.46 (s, 1H), 8.11 (br d, J = 7.2 Hz, 1H), 8.07 (d, J = 8.2 Hz, 1H), 7.87 (s, 1H), 7.78 – 7.67 (m, 1H), 7.66 – 7.59 (m, 1H), 7.51 – 7.46 (m, 1H), 6.93 (br s, 2H), 6.75 (s, 1H), 4.61 (br t, J = 5.1 Hz, 2H), 3.79 (q, J = 5.9 Hz, 2H) |

Example 205. Preparation of 2-(2-(4-amino-7-(1H-pyrazol-3-yl)-2H-pyrazolo[4,3-c]quinolin-2-yl)ethyl)-6-fluoroisoindolin-1-one

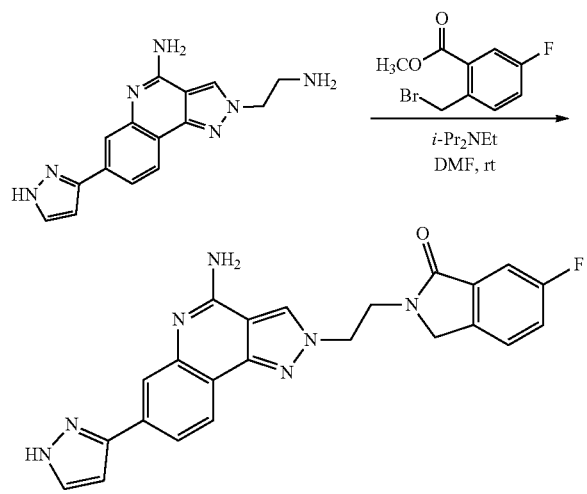

To a rt solution of 2-(2-aminoethyl)-7-(1H-pyrazol-3-yl)-2H-pyrazolo[4,3-c]quinolin-4-amine, 2 TFA (40 mg, 0.077 mmol) in DMF (384 µl) was added N,N-diisopropylethylamine (66.8 µl, 0.384 mmol) and methyl 2-(bromomethyl)-5-fluorobenzoate (18.95 mg, 0.077 mmol). The reaction was stirred at rt for 1.5 h. The was diluted with H₂O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 21% B, 21-61% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-(4-amino-7-(1H-pyrazol-3-yl)-2H-pyrazolo[4,3-c]quinolin-2-yl)ethyl)-6-fluoroisoindolin-1-one (23.1 mg, 70% yield). ¹H NMR (500 MHz, DMSO-d₆) δ 13.30-12.70 (m, 1H), 8.43 (s, 1H), 7.96 (d, J=7.9 Hz, 1H), 7.86 (s, 1H), 7.79-7.65 (m, 1H), 7.64-7.56 (m, 2H), 7.46-7.36 (m, 2H), 6.91 (br d, J=0.7 Hz, 2H), 6.75 (d, J=1.5 Hz, 1H), 4.72 (br t, J=5.4 Hz, 2H), 4.31 (s, 2H), 4.07 (br t, J=5.7 Hz, 2H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 428 [M+H]⁺; RT: 1.18 min.

Example 206. Preparation of N-(2-(4-amino-7-(1H-pyrazol-3-yl)-2H-pyrazolo[4,3-c]quinolin-2-yl)ethyl)methanesulfonamide

Examples 207 and 208. Preparation of 2-(2-methoxyethyl)-7-(1H-pyrazol-3-yl)-2H-pyrazolo[4,3-c]quinolin-4-amine and 1-(2-methoxyethyl)-7-(1H-pyrazol-3-yl)-1H-pyrazolo[4,3-c]quinolin-4-amine

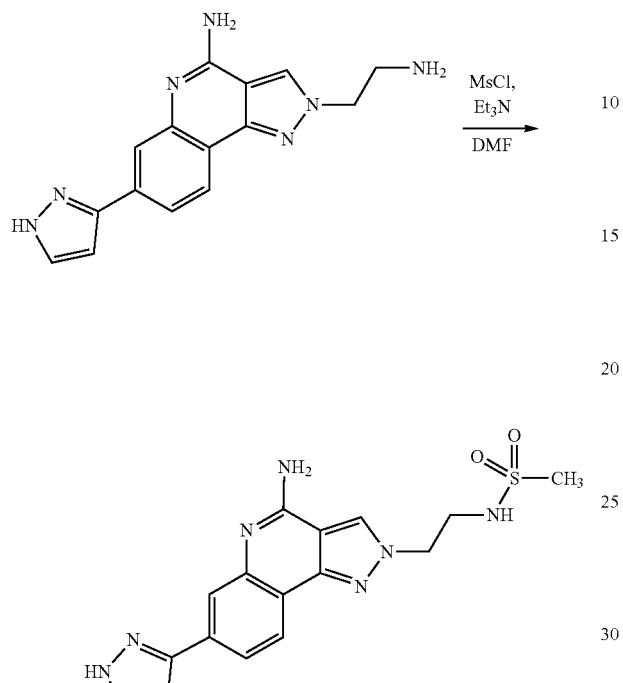

To a 0° C. solution of 2-(2-aminoethyl)-7-(1H-pyrazol-3-yl)-2H-pyrazolo[4,3-c]quinolin-4-amine, 2 TFA (40 mg, 0.077 mmol) in DMF (256 µl) was added triethylamine (42.8 µl, 0.307 mmol) and methanesulfonyl chloride (6.23 µl, 0.081 mmol). The reaction was stirred at rt for 1 h. The reaction was diluted with H₂O (0.1 mL) and DMF (to a total volume of 2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 8% B, 8-48% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide N-(2-(4-amino-7-(1H-pyrazol-3-yl)-2H-pyrazolo[4,3-c]quinolin-2-yl)ethyl)methanesulfonamide (18.3 mg, 64%). ¹H NMR (500 MHz, DMSO-d₆) δ 8.50 (s, 1H), 8.08 (d, J=8.1 Hz, 1H), 7.88 (br s, 1H), 7.82-7.55 (m, 2H), 7.32-7.25 (m, 1H), 6.76 (d, J=1.1 Hz, 1H), 4.50 (br t, J=5.4 Hz, 2H), 3.60-3.52 (m, 2H), 2.85 (d, J=2.4 Hz, 3H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 372.2 [M+H]⁺; RT: 0.93 min.

Step 1. 7-(1-(tetrahydro-2H-pyran-2-yl)-1H-pyrazol-5-yl)-2H-pyrazolo[4,3-c]quinolin-4-amine A mixture of 7-bromo-2H-pyrazolo[4,3-c]quinolin-4-amine, TFA (0.932 g, 2.47 mmol), 1-(tetrahydro-2H-pyran-2-yl)-5-(4,4,5,5-tetramethyl-1,3,2-dioxaborolan-2-yl)-1H-pyrazole (1.031 g, 3.71 mmol), and potassium phosphate tribasic (1.574 g, 7.41 mmol) was evacuated and back-filled with N₂, then it was mixed with 1,4-dioxane (10.30 ml) and H₂O (2.059 ml). The resulting suspension was sparged with N₂ for 15 min, then chloro(2-dicyclohexylphosphino-2',4',6'-triisopropyl-1,1'-biphenyl)[2-(2'-amino-1,1'-biphenyl)]palladium(II) (0.039 g, 0.049 mmol) was added. The reaction was stirred at 100° C. for 1 h. The reaction was cooled to rt and diluted with EtOAc (10 mL) and H₂O (10 mL). This mixture was filtered and the solid was washed with H₂O (2×2 mL) and EtOAc (2×2 mL), then dried under vacuum to provide 7-(1-(tetrahydro-2H-pyran-2-yl)-1H-pyrazol-5-yl)-

2H-pyrazolo[4,3-c]quinolin-4-amine (670 mg, 81%). LC-MS m/z 335 [M+H]$^+$; $^1$H NMR (400 MHz, DMSO-d$_6$) δ 8.32 (br s, 1H), 8.19 (d, J=8.2 Hz, 1H), 7.69 (s, 1H), 7.59 (d, J=1.5 Hz, 1H), 7.37 (br d, J=7.7 Hz, 1H), 7.08 (br s, 2H), 6.52 (d, J=1.5 Hz, 1H), 5.31 (dd, J=9.8, 1.9 Hz, 1H), 4.07-3.99 (m, 1H), 3.62-3.57 (m, 1H), 2.47-2.36 (m, 1H), 2.00-1.92 (m, 1H), 1.80 (br d, J=12.9 Hz, 1H), 1.64-1.49 (m, 3H).

Step 2. 2-(2-methoxyethyl)-7-(1H-pyrazol-3-yl)-2H-pyrazolo[4,3-c]quinolin-4-amine and 1-(2-methoxyethyl)-7-(1H-pyrazol-3-yl)-1H-pyrazolo[4,3-c]quinolin-4-amine To a rt suspension of 7-(1-(tetrahydro-2H-pyran-2-yl)-1H-pyrazol-5-yl)-2H-pyrazolo[4,3-c]quinolin-4-amine (29 mg, 0.087 mmol) in DMF (289 μl) was added cesium carbonate (85 mg, 0.260 mmol) followed by 2-bromoethyl methyl ether (8.97 μl, 0.095 mmol). The suspension was stirred at rt for 20 h. The reaction was diluted with H$_2$O (2 mL) and extracted with EtOAc (3×2 mL). The combined organic layers were concentrated.

The crude material was mixed with CH$_2$Cl$_2$ (200 μL) and TFA (200 μL) and stirred at rt for 2 h. The reaction was concentrated in vacuo. The crude material was dissolved in DMF (2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 2% B, 2-42% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide provide 2-(2-methoxyethyl)-7-(1H-pyrazol-3-yl)-2H-pyrazolo[4,3-c]quinolin-4-amine (7.3 mg, 27%). The other regioisomer was also isolated and further purified via preparative LC/MS with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide 1-(2-methoxyethyl)-7-(1H-pyrazol-3-yl)-1H-pyrazolo[4,3-c]quinolin-4-amine, TFA (3.8 mg, 9.8%).

Characterization data for 2-(2-methoxyethyl)-7-(1H-pyrazol-3-yl)-2H-pyrazolo[4,3-c]quinolin-4-amine (Example 207): $^1$H NMR (500 MHz, DMSO-d$_6$) δ 8.50 (s, 1H), 8.08 (br d, J=7.6 Hz, 1H), 7.87 (br s, 1H), 7.71 (br s, 1H), 7.64 (br d, J=7.9 Hz, 1H), 7.13-6.95 (m, 2H), 6.75 (br s, 1H), 4.57 (br s, 2H), 3.83-3.79 (m, 2H), 3.25 (s, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 309.2 [M+H]$^+$; RT: 1.02 min.

Characterization data for 1-(2-methoxyethyl)-7-(1H-pyrazol-3-yl)-1H-pyrazolo[4,3-c]quinolin-4-amine (Example 208): $^1$H NMR (500 MHz, DMSO-d$_6$) δ 8.64 (s, 1H), 8.43 (d, J=8.5 Hz, 1H), 8.18 (br s, 1H), 7.97 (br d, J=8.5 Hz, 1H), 7.85 (br s, 1H), 6.86 (d, J=2.2 Hz, 1H), 4.97 (t, J=5.1 Hz, 2H), 3.88 (t, J=5.1 Hz, 2H), 3.18 (s, 3H). Analytical LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). m/z 309.0 [M+H]$^+$; RT: 0.97 min.

Example 209. Preparation of 2-(4-amino-7-(1H-pyrazol-3-yl)-2H-pyrazolo[4,3-c]quinolin-2-yl)ethan-1-ol

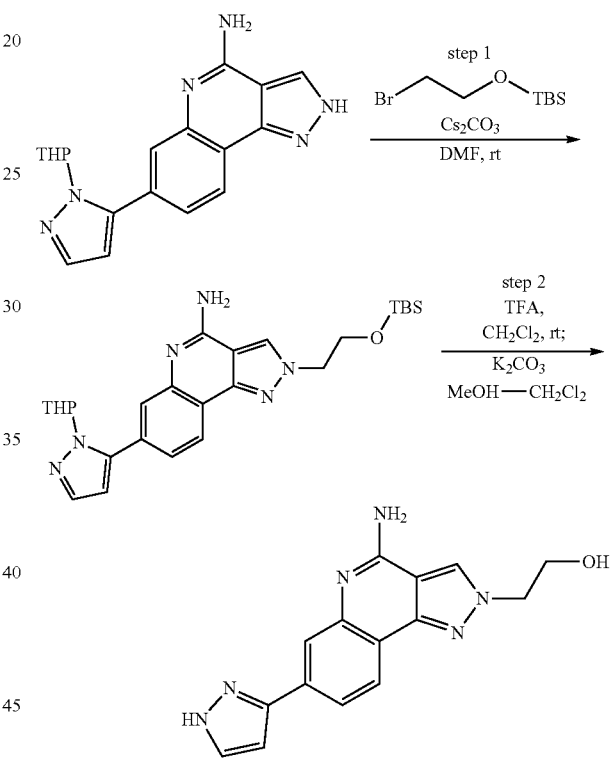

Step 1. 2-(2-((tert-butyldimethylsilyl)oxy)ethyl)-7-(1-(tetrahydro-2H-pyran-2-yl)-1H-pyrazol-5-yl)-2H-pyrazolo[4,3-c]quinolin-4-amine To a rt suspension of 7-(1-(tetrahydro-2H-pyran-2-yl)-1H-pyrazol-5-yl)-2H-pyrazolo[4,3-c]quinolin-4-amine (80 mg, 0.239 mmol) in DMF (797 μl) was added cesium carbonate (234 mg, 0.718 mmol) followed by (2-bromoethoxy)(tert-butyl)dimethylsilane (56.5 μl, 0.263 mmol). The reaction was stirred at rt for 2 h. The reaction was diluted with EtOAc (20 mL) and H$_2$O (20 mL). The aqueous layer was extracted with EtOAc (20 mL). The combined organic layers were washed with sat. aq. NaCl (20 mL), dried over Na$_2$SO$_4$, filtered, and concentrated in vacuo. The crude material was purified by flash chromatography (24 g RediSep Gold silica gel; linear gradient 0-10% MeOH—CH$_2$Cl$_2$). The second eluting regioisomer was isolated to provide 2-(2-((tert-butyldimethylsilyl)oxy)ethyl)-7-(1-(tetrahydro-2H-pyran-2-yl)-1H-pyrazol-5-yl)-2H-pyrazolo[4,3-c]quinolin-4-amine (58.5 mg, 50%). LC-MS m/z 493 [M+H]⁺; 1H NMR (400 MHz, DMSO-d₆) Shift 8.57 (br s, 1H), 8.18 (d, J=8.1 Hz, 1H), 7.64 (s, 1H), 7.60 (d, J=1.7 Hz, 1H), 7.37 (br d, J=6.9 Hz, 1H), 7.53-7.07 (m, 2H), 6.52 (d, J=1.8 Hz, 1H), 5.32 (dd, J=10.0, 2.2 Hz, 1H), 4.54 (t, J=4.8 Hz, 2H), 4.08-4.01 (m, 3H), 3.63-3.56 (m, 1H), 2.48-2.36 (m, 1H), 1.99-1.93 (m, 1H), 1.80 (br d, J=12.5 Hz, 1H), 1.64-1.49 (m, 3H), 0.80-0.74 (m, 9H), −0.13 (s, 6H).

Step 2. 2-(4-amino-7-(1H-pyrazol-3-yl)-2H-pyrazolo[4,3-c]quinolin-2-yl)ethan-1-ol To a rt suspension of 2-(2-((tert-butyldimethylsilyl)oxy)ethyl)-7-(1-(tetrahydro-2H-pyran-2-yl)-1H-pyrazol-5-yl)-2H-pyrazolo[4,3-c]quinolin-4-amine (58 mg, 0.118 mmol) in CH₂Cl₂ (294 µl) was added TFA (294 µl). The resulting clear orange solution was stirred at rt for 2 h. The reaction was concentrated. The crude material was taken up in CH₂Cl₂ (500 µL) and concentrated.

This material was dissolved in a mixture of CH₂Cl₂ (300 µL) and MeOH (300 µL), and potassium carbonate (81 mg, 0.589 mmol) was added. The reaction was stirred at rt for 15 min. The reaction was diluted with EtOAc (20 mL) and sat. aq. NaHCO₃ (20 mL). The layers were separated and the organic layer was extracted with 5% MeOH-EtOAc (5×10 mL). The combined organic layers were washed with sat. aq. NaCl (10 mL), dried over Na₂SO₄, filtered, and concentrated in vacuo. The crude material was dissolved in MeOH—CH₂Cl₂ and Celite was added. The mixture was concentrated in vacuo, dry loaded onto a column, and purified by flash chromatography (12 g RediSep Gold silica gel with 5 g solid load cartridge; linear gradient 0-60% MeOH—CH₂Cl₂) to provide 2-(4-amino-7-(1H-pyrazol-3-yl)-2H-pyrazolo[4,3-c]quinolin-2-yl)ethan-1-ol (23 mg, 66%) as a white solid. ¹H NMR (400 MHz, DMSO-d₆) δ 13.38-12.79 (m, 1H), 8.49 (s, 1H), 8.07 (br d, J=8.0 Hz, 1H), 7.88 (br s, 1H), 7.83-7.47 (m, 2H), 7.04-6.83 (m, 2H), 6.75 (br s, 1H), 5.04 (t, J=5.3 Hz, 1H), 4.45 (t, J=5.1 Hz, 2H), 3.87 (q, J=5.2 Hz, 2H). Analytical LC/MS conditions: Column: Acquity UPLC BEH C18, 2.1 mm×50 mm, 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). m/z 295.0 [M+H]⁺; RT: 0.62 min.

Example 210. Preparation of cis-3-(4-amino-7-(1H-pyrazol-3-yl)-2H-pyrazolo[4,3-c]quinolin-2-yl)cyclopentan-1-ol

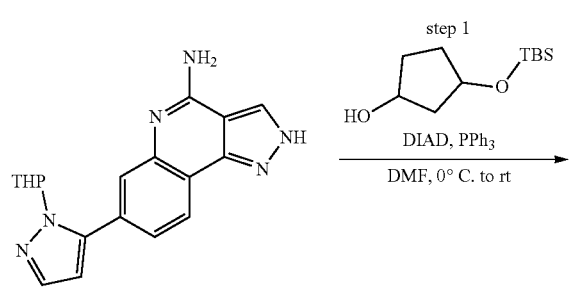

Step 1. 2-(cis-3-((tert-butyldimethylsilyl)oxy)cyclopentyl)-7-(1-(tetrahydro-2H-pyran-2-yl)-1H-pyrazol-5-yl)-2H-pyrazolo[4,3-c]quinolin-4-amine

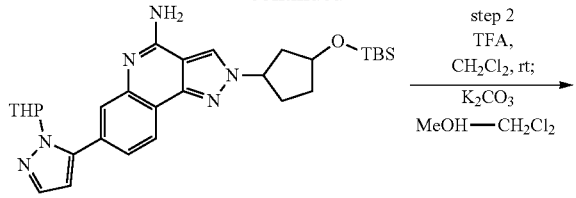

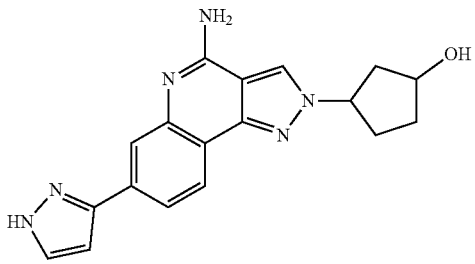

To a 0° C. suspension of 7-(1-(tetrahydro-2H-pyran-2-yl)-1H-pyrazol-5-yl)-2H-pyrazolo[4,3-c]quinolin-4-amine (30 mg, 0.090 mmol), triphenylphosphine (24.71 mg, 0.094 mmol), and trans-3-((tert-butyldimethylsilyl)oxy)cyclopentan-1-ol (20.39 mg, 0.094 mmol) in DMF (897 µl) was added diisopropyl azodicarboxylate (17.66 µl, 0.090 mmol). The reaction was stirred at 0° C. for 5 min, then at rt for 17 h. Additional trans-3-((tert-butyldimethylsilyl)oxy)cyclopentan-1-ol (20.39 mg, 0.094 mmol), triphenylphosphine (24.71 mg, 0.094 mmol), and diisopropyl azodicarboxylate (17.66 µl, 0.090 mmol) and stirred at rt for 1 h. The reaction was diluted with EtOAc (20 mL), washed with H₂O (20 mL) and sat. aq. NaCl (20 mL), dried over Na₂SO₄, filtered, and concentrated in vacuo. The crude material was purified by flash chromatography (12 g RediSep gold silica gel; linear gradient 0-10% MeOH—CH₂Cl₂). The second eluting regioisomer was isolated to provide 2-(cis-3-((tert-butyldimethylsilyl)oxy)cyclopentyl)-7-(1-(tetrahydro-2H-pyran-2-yl)-1H-pyrazol-5-yl)-2H-pyrazolo[4,3-c]quinolin-4-amine (17.6 mg, 37%). LC-MS m/z 533 [M+H]⁺; ¹H NMR (400 MHz, DMSO-d₆) δ 8.60 (s, 1H), 8.16 (d, J=8.0 Hz, 1H), 7.59 (dd, J=8.1, 1.5 Hz, 2H), 7.31 (dd, J=8.1, 1.6 Hz, 1H), 6.96 (br s, 2H), 6.50 (d, J=1.8 Hz, 1H), 5.30 (dd, J=10.0, 2.0 Hz, 1H), 5.00 (quin, J=7.7 Hz, 1H), 4.41 (quin, J=5.8 Hz, 1H), 4.06-4.01 (m, 1H), 3.63-3.52 (m, 1H), 2.63-2.55 (m, 1H), 2.47-2.37 (m, 1H), 2.26 (qd, J=7.5, 3.8 Hz, 2H), 2.09-1.92 (m, 3H), 1.88-1.76 (m, 2H), 1.64-1.49 (m, 3H), 0.86 (d, J=1.0 Hz, 9H), 0.08 (s, 3H), 0.06 (s, 3H).

Step 2. cis-3-(4-amino-7-(1H-pyrazol-3-yl)-2H-pyrazolo[4,3-c]quinolin-2-yl)cyclopentan-1-ol To a rt solution of 2-(cis-3-((tert-butyldimethylsilyl)oxy)cyclopentyl)-7-(1-(tetrahydro-2H-pyran-2-yl)-1H-pyrazol-5-yl)-2H-pyrazolo[4,3-c]quinolin-4-amine (17 mg, 0.032 mmol) in CH₂Cl₂ (160 µl) was added TFA (160 µl). The reaction was stirred at rt for 1 h. The reaction was concentrated in vacuo. The crude material was dissolved in CH₂Cl₂ (300 µL) and concentrated in vacuo.

The crude material was mixed with CH₂Cl₂ (150 µL) and MeOH (150 µL), and potassium carbonate (22 mg, 0.16 mmol) was added. The suspension was stirred at rt for 15 min. The reaction was diluted with 1:1 MeOH—CH₂Cl₂ (1 mL), filtered, and washed with 1:1 MeOH—CH₂Cl₂ (2×0.5 mL). The filtrate was concentrated in vacuo, then it was mixed with DMF (2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 3% B, 3-43% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide cis-3-(4-amino-7-(1H-pyrazol-3-yl)-2H-pyrazolo[4,3-c]quinolin-2-yl)cyclopentan-1-ol (6.3 mg, 59%). ¹H NMR (500 MHz, DMSO-d₆) δ 8.63 (s, 1H), 8.07 (d, J=8.3 Hz, 1H), 7.88 (s, 1H), 7.71 (br s, 1H), 7.63 (br d, J=8.5 Hz, 1H), 7.09-6.96 (m, 2H), 6.75 (d, J=1.4 Hz, 1H), 5.04-4.96 (m, 2H), 4.29-4.24 (m, 1H), 2.32-2.23 (m, 1H), 2.22-2.14 (m, 1H), 2.01-1.95 (m, 1H), 1.90-1.78 (m, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 335.2 [M+H]⁺; RT: 0.87 min.

Examples 211 to 246 were prepared according to synthetic procedures similar to those described for Examples 207 and 208, 209, or 210 from the appropriate alkyl halide, mesylate, or alcohol starting materials. The temperature for the alkylation reactions ranged from rt to 90° C., and, in some cases, additional equivalents of the alkylating reagent were added. Analytical LC/MS conditions: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/mm; Detection: MS and UV (220 nm).

| Ex. No. | Structure | LC/MS [M + H]⁺ | RT (min) | ¹H NMR (500 MHz, DMSO-d₆) |
|---|---|---|---|---|
| 211 | 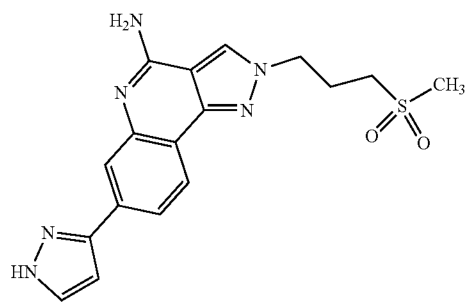 [SMILES: CS(=O)(=O)CCCn1cc2c(N)nc3cc(-c4cc[nH]n4)ccc3c2n1] | 371.1 | 1.04 | δ 13.22 – 13.01 (m, 1H), 8.92 (s, 1H), 8.21 (d, J = 8.3 Hz, 1H), 8.11 (br s, 1H), 7.92 (br d, J = 6.9 Hz, 1H), 7.88 – 7.80 (m, 1H), 6.81 (s, 1H), 4.63 (t, J = 6.9 Hz, 2H), 3.22 – 3.17 (m, 2H), 3.00 (s, 3H), 2.42 – 2.35 (m, 2H) |
| 212 | 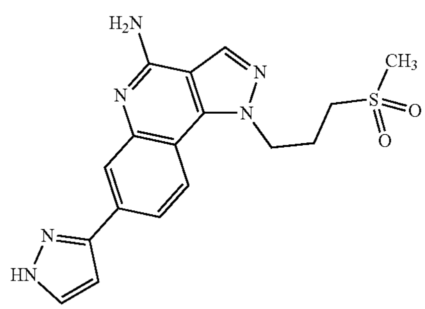 [SMILES: CS(=O)(=O)CCCn1ncc2c(N)nc3cc(-c4cc[nH]n4)ccc3c21] | 371.1 | 0.951 | δ 8.63 (s, 1H), 8.38 (d, J = 8.5 Hz, 1H), 8.19 (br s, 1H), 7.99 (br d, J = 8.0 Hz, 1H), 7.85 (br s, 1H), 6.87 (d, J = 2.2 Hz, 1H), 4.94 (br t, J = 7.2 Hz, 2H), 3.31 – 3.24 (m, 3H), 2.97 (s, 4H), 2.35 (quin, J = 7.2 Hz, 2H) |
| 213 | 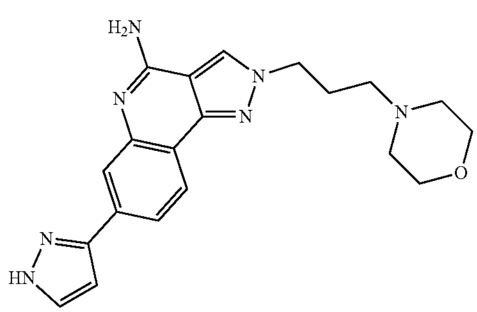 [SMILES: Nc1nc2cc(-c3cc[nH]n3)ccc2c2nn(CCCN3CCOCC3)cc12] | 378.2 | 0.67 | δ 8.64 – 8.58 (m, 1H), 8.11 (d, J = 8.0 Hz, 1H), 7.95 (br s, 1H), 7.80 – 7.68 (m, 2H), 6.77 (d, J = 1.9 Hz, 1H), 4.48 (br t, J = 6.7 Hz, 2H), 3.57 (br t, J = 4.3 Hz, 4H), 2.40 – 2.24 (m, 6H), 2.09 (dt, J = 13.5, 6.5 Hz, 2H) |

| Ex. No. | Structure | LC/MS [M + H]+ | RT (min) | ¹H NMR (500 MHz, DMSO-d₆) |
|---|---|---|---|---|
| 214 | 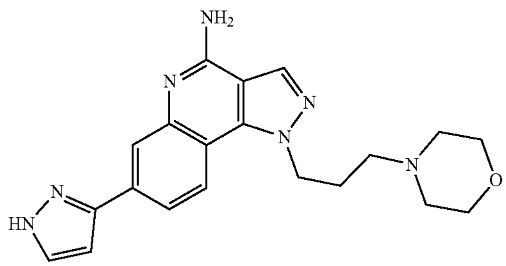 [SMILES: Nc1nc2cc(-c3cc[nH]n3)ccc2c2c1cnn2CCCN1CCOCC1] | 378.2 | 0.56 | δ 8.39 (br t, J = 7.3 Hz, 1H), 8.29 (br d, J = 7.7 Hz, 1H), 8.10 – 7.99 (m, 1H), 7.91 – 7.73 (m, 2H), 6.83 (s, 1H), 4.81 (br t, J = 6.3 Hz, 2H), 3.54 (br s, 4H), 2.47 – 2.27 (m, 6H), 2.11 – 2.02 (m, 2H) |
| 215 | 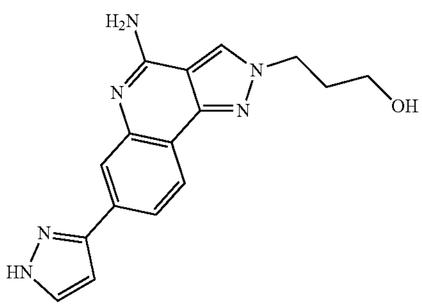 [SMILES: Nc1nc2cc(-c3cc[nH]n3)ccc2c2nn(CCCO)cc12] | 309.1 | 1.04 | δ 8.91 (s, 1H), 8.20 (d, J = 8.3 Hz, 1H), 8.10 (br s, 1H), 7.91 (br d, J = 8.0 Hz, 1H), 7.88 – 7.81 (m, 1H), 6.81 (d, J = 1.9 Hz, 1H), 4.85 – 4.72 (m, 1H), 4.55 (t, J = 7.0 Hz, 2H), 3.43 (s, 2H), 2.09 (quin, J = 6.5 Hz, 2H) |
| 216 | 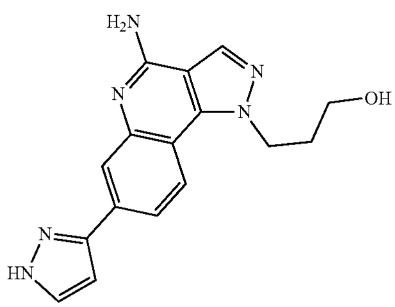 [SMILES: Nc1nc2cc(-c3cc[nH]n3)ccc2c2c1cnn2CCCO] | 308.9 | 1.01 | δ 8.54 (br s, 1H), 8.35 (br d, J = 8.5 Hz, 1H), 8.23 – 8.10 (m, 1H), 8.00 – 7.80 (m, 2H), 6.86 (s, 1H), 4.88 – 4.76 (m, 3H), 3.57 – 3.50 (m, 2H), 2.09 – 1.99 (m, 2H) |
| 217 | 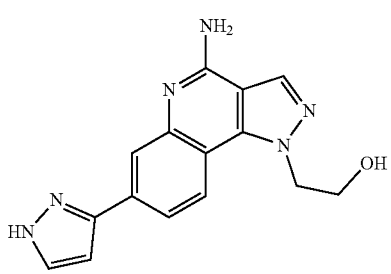 [SMILES: Nc1nc2cc(-c3cc[nH]n3)ccc2c2c1cnn2CCO] | 295.2 | 0.86 | δ 13.26 – 13.09 (m, 1H), 8.64 (s, 1H), 8.48 (d, J = 8.8 Hz, 1H), 8.19 (br s, 1H), 7.96 (br d, J = 8.3 Hz, 1H), 7.91 – 7.84 (m, 1H), 6.86 (s, 1H), 5.14 – 5.06 (m, 1H), 4.86 (br t, J = 5.4 Hz, 2H), 3.93 (br s, 2H) |
| 218 | 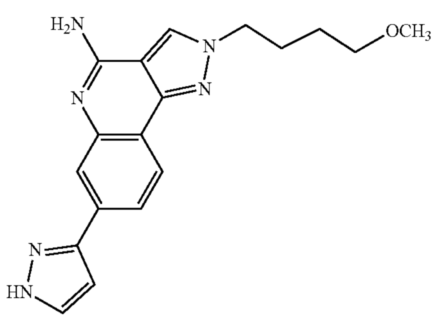 [SMILES: COCCCCn1cc2c(N)nc3cc(-c4cc[nH]n4)ccc3c2n1] | 337.2 | 1.03 | δ 8.49 (s, 1H), 8.08 (d, J = 8.2 Hz, 1H), 7.88 (s, 1H), 7.78 – 7.68 (m, 1H), 7.64 (br d, J = 7.5 Hz, 1H), 7.13 – 6.94 (m, 2H), 6.75 (d, J = 1.9 Hz, 1H), 4.43 (t, J = 7.0 Hz, 2H), 3.34 (t, J = 6.3 Hz, 2H), 3.21 (s, 3H), 1.95 (quin, J = 7.3 Hz, 2H), 1.54 – 1.47 (m, 2H) |

| Ex. No. | Structure | LC/MS [M + H]+ | RT (min) | ¹H NMR (500 MHz, DMSO-d₆) |
|---|---|---|---|---|
| 219 | 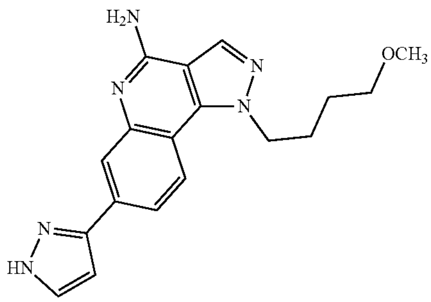 [SMILES: COCCCCn1ncc2c(N)nc3cc(-c4cc[nH]n4)ccc3c21] | 337.4 | 0.99 | δ 8.28 (s, 1H), 8.17 (d, J = 8.5 Hz, 1H), 8.00 (s, 1H), 7.80 – 7.71 (m, 2H), 7.17 – 7.05 (m, 2H), 6.81 (d, J = 2.1 Hz, 1H), 4.74 (br t, J = 7.1 Hz, 2H), 3.33 (t, J = 6.3 Hz, 2H), 3.19 (s, 3H), 1.94 – 1.87 (m, 2H), 1.59 – 1.52 (m, 2H) |
| 220 | 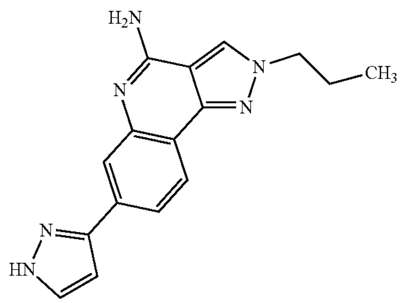 [SMILES: CCCn1cc2c(N)nc3cc(-c4cc[nH]n4)ccc3c2n1] | 293.1 | 1.02 | δ 8.49 (s, 1H), 8.09 (d, J = 8.1 Hz, 1H), 7.87 (d, J = 1.2 Hz, 1H), 7.71 (s, 1H), 7.64 (br d, J = 7.8 Hz, 1H), 7.23 – 6.93 (m, 2H), 6.76 (s, 1H), 4.36 (t, J = 6.9 Hz, 2H), 1.95 – 1.90 (m, 2H), 0.86 (br t, J = 7.1 Hz, 3H) |
| 221 | 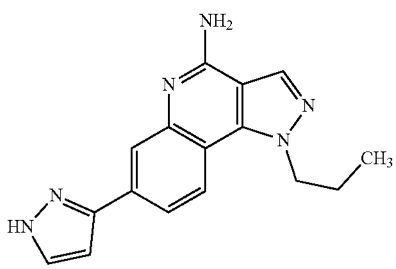 [SMILES: CCCn1ncc2c(N)nc3cc(-c4cc[nH]n4)ccc3c21] | 293.0 | 1.00 | δ 8.28 (s, 1H), 8.16 (br d, J = 8.5 Hz, 1H), 8.00 (br s, 1H), 7.85 – 7.66 (m, 2H), 7.06 (br d, J = 4.4 Hz, 2H), 6.80 (s, 1H), 4.69 (br t, J = 7.2 Hz, 2H), 1.94 – 1.85 (m, 2H), 0.91 (t, J = 7.3 Hz, 3H) |
| 222 | 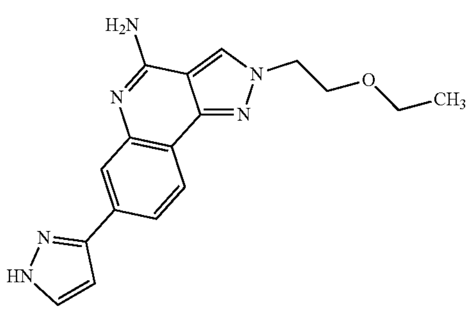 [SMILES: CCOCCn1cc2c(N)nc3cc(-c4cc[nH]n4)ccc3c2n1] | 323.2 | 1.12 | δ 8.92 (s, 1H), 8.19 (d, J = 8.3 Hz, 1H), 8.09 (br s, 1H), 7.91 (br d, J = 8.5 Hz, 1H), 7.84 (br s, 1H), 6.82 (s, 1H), 4.64 (br t, J = 4.7 Hz, 2H), 3.86 (br t, J = 4.7 Hz, 2H), 3.49 – 3.44 (m, 2H), 1.07 (t, J = 7.0 Hz, 3H) |
| 223 | 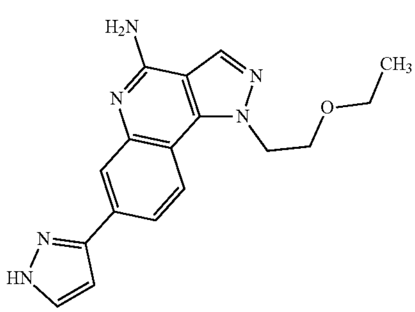 [SMILES: CCOCCn1ncc2c(N)nc3cc(-c4cc[nH]n4)ccc3c21] | 323.1 | 1.21 | δ 8.48 (br s, 1H), 8.37 (br d, J = 8.7 Hz, 1H), 8.07 (br s, 1H), 7.86 (br dd, J = 6.4, 1.2 Hz, 1H), 7.80 (br s, 1H), 6.84 (d, J = 2.2 Hz, 1H), 4.92 (br t, J = 4.8 Hz, 2H), 3.90 – 3.87 (m, 2H), 3.38 – 3.32 (m, 2H), 0.94 – 0.86 (m, 3H) |

| Ex. No. | Structure | LC/MS [M + H]⁺ | RT (min) | ¹H NMR (500 MHz, DMSO-d₆) |
|---|---|---|---|---|
| 224 | 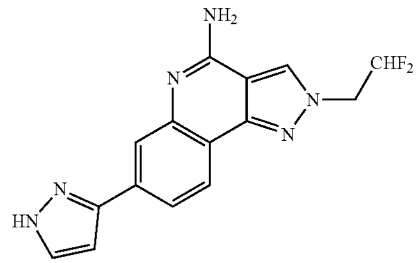 [SMILES: Nc1nc2cc(-c3cc[nH]n3)ccc2c2nn(CC(F)F)cc12] | 315.1 | 0.95 | δ 9.01 (s, 1H), 8.20 (d, J = 8.3 Hz, 1H), 8.14 – 8.05 (m, 1H), 7.93 (br d, J = 8.0 Hz, 1H), 7.84 (br s, 1H), 6.82 (d, J = 1.9 Hz, 1H), 6.70 – 6.43 (m, 1H), 5.11 (td, J = 15.1, 2.3 Hz, 2H) |
| 225 | 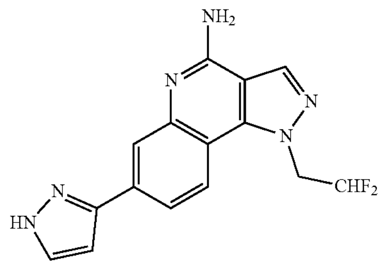 [SMILES: Nc1nc2cc(-c3cc[nH]n3)ccc2c2c1cnn2CC(F)F] | 315.1 | 1.00 | δ 8.73 (s, 1H), 8.44 (d, J = 8.8 Hz, 1H), 8.26 – 8.16 (m, 1H), 7.97 (br d, J = 8.3 Hz, 1H), 7.88 (br d, J = 1.9 Hz, 1H), 6.88 (d, J = 1.9 Hz, 1H), 6.74 – 6.49 (m, 1H), 5.44 – 5.35 (m, 2H) |
| 226 | 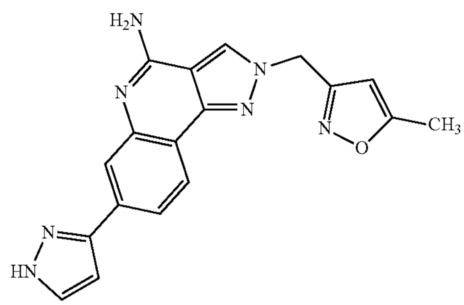 [SMILES: Cc1cc(Cn2cc3c(N)nc4cc(-c5cc[nH]n5)ccc4c3n2)no1] | 346.3 | 1.00 | δ 9.00 (s, 1H), 8.17 (d, J = 8.3 Hz, 1H), 8.05 (br s, 1H), 7.90 (br d, J = 8.3 Hz, 1H), 7.81 (br s, 1H), 6.81 (d, J = 1.7 Hz, 1H), 6.27 (s, 1H), 5.80 (s, 2H), 2.38 (s, 3H) |
| 227 | 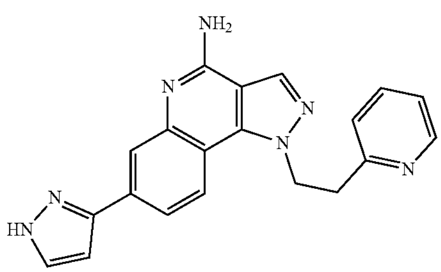 [SMILES: Nc1nc2cc(-c3cc[nH]n3)ccc2c2c1cnn2CCc1ccccn1] | 356.1 | 0.66 | δ 8.57 (s, 1H), 8.47 (d, J = 4.4 Hz, 1H), 8.43 (d, J = 8.5 Hz, 1H), 8.20 (br s, 1H), 7.99 (br d, J = 8.5 Hz, 1H), 7.91 – 7.83 (m, 1H), 7.67 (td, J = 7.6, 1.7 Hz, 1H), 7.25 (d, J = 7.7 Hz, 1H), 7.21 (dd, J = 7.4, 5.2 Hz, 1H), 6.87 (d, J = 1.7 Hz, 1H), 5.18 (t, J = 7.2 Hz, 2H), 3.42 – 3.39 (m, 2H) |
| 228 | 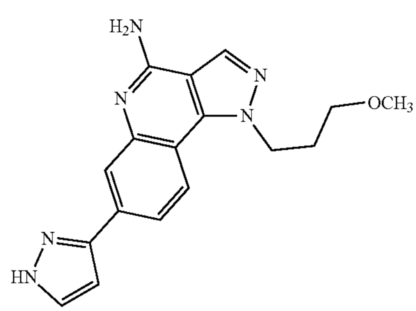 [SMILES: COCCCn1ncc2c(N)nc3cc(-c4cc[nH]n4)ccc3c21] | 323.2 | 0.95 | δ 13.19 (br s, 1H), 8.62 (s, 1H), 8.35 (d, J = 8.6 Hz, 1H), 8.22 (br s, 1H), 8.00 (br d, J = 7.9 Hz, 1H), 7.89 (br s, 1H), 6.88 (br s, 1H), 4.84 (t, J = 7.0 Hz, 2H), 3.37 – 3.33 (m, 2H), 3.23 (s, 3H), 2.13 (quin, J = 6.5 Hz, 2H) |

| Ex. No. | Structure | LC/MS [M + H]+ | RT (min) | ¹H NMR (500 MHz, DMSO-$d_6$) |
|---|---|---|---|---|
| 229 | 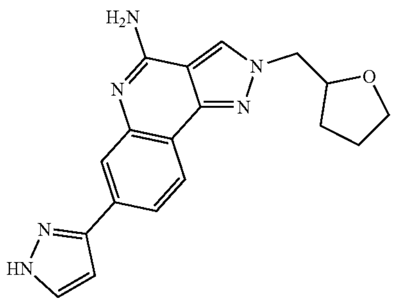 [SMILES: Nc1nc2cc(-c3cc[nH]n3)ccc2c2nn(CC3CCCO3)cc12] | 335.2 | 0.96 | δ 8.92 (s, 1H), 8.19 (d, J = 8.5 Hz, 1H), 8.08 (br s, 1H), 7.91 (br d, J = 7.7 Hz, 1H), 7.83 (br s, 1H), 6.82 (s, 1H), 4.62 – 4.57 (m, 1H), 4.51 – 4.45 (m, 1H), 4.33 – 4.26 (m, 1H), 3.78 (q, J = 7.0 Hz, 1H), 3.71 – 3.65 (m, 1H), 2.11 – 2.00 (m, 1H), 1.88 – 1.75 (m, 2H), 1.71 – 1.58 (m, 1H) |
| 230 | 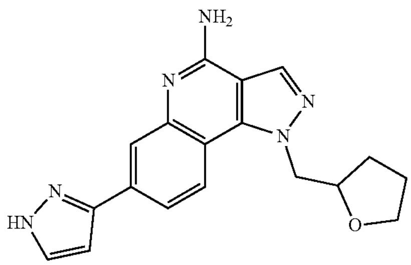 [SMILES: Nc1nc2cc(-c3cc[nH]n3)ccc2c2c1cnn2CC1CCCO1] | 335.2 | 1.09 | δ 8.70 (s, 1H), 8.09 (d, J = 8.0 Hz, 1H), 7.88 (s, 1H), 7.73 – 7.69 (m, 1H), 7.66 – 7.62 (m, 1H), 6.75 (s, 1H), 5.73 (dd, J = 8.7, 3.2 Hz, 1H), 4.01 (br d, J = 11.0 Hz, 1H), 3.79 – 3.72 (m, 1H), 3.58 – 3.53 (m, 2H), 2.03 – 1.95 (m, 1H), 1.82 – 1.70 (m, 1H), 1.65 – 1.57 (m, 2H) |
| 231 | 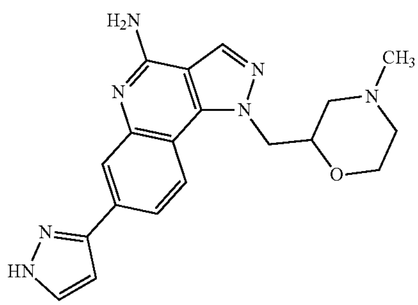 [SMILES: CN1CCOC(Cn2ncc3c(N)nc4cc(-c5cc[nH]n5)ccc4c32)C1] | 363.9 | 0.93 | δ 8.72 – 8.65 (m, 1H), 8.46 (d, J = 8.5 Hz, 1H), 8.20 (br s, 1H), 7.95 (br d, J = 8.3 Hz, 1H), 7.87 (br s, 1H), 6.87 (d, J = 2.1 Hz, 1H), 5.07 – 5.00 (m, 1H), 4.99 – 4.93 (m, 1H), 4.32 – 4.21 (m, 1H), 3.94 – 3.85 (m, 1H), 3.64 – 3.54 (m, 2H), 3.27 (br d, J = 9.5 Hz, 1H), 3.03 – 2.86 (m, 2H), 2.79 (br s, 3H) |
| 232 | 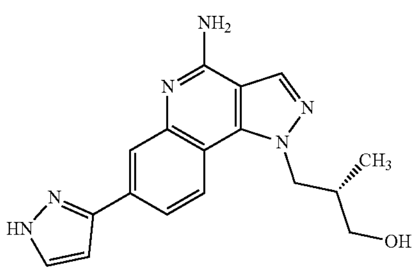 [SMILES: C[C@H](CO)Cn1ncc2c(N)nc3cc(-c4cc[nH]n4)ccc3c21] | 323.3 | 1.01 | δ 8.58 (br s, 1H), 8.41 (d, J = 8.5 Hz, 1H), 8.18 (br s, 1H), 7.94 (br dd, J = 5.8, 3.9 Hz, 1H), 7.89 – 7.78 (m, 1H), 6.87 (s, 1H), 4.98 – 4.91 (m, 2H), 4.48 (dd, J = 14.3, 9.4 Hz, 1H), 2.29 – 2.20 (m, 1H), 0.86 (d, J = 6.6 Hz, 3H); two CH protons are not visible, likely due to overlap with suppressed water peak. |
| 233 | 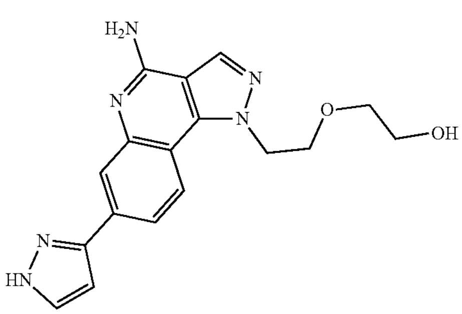 [SMILES: Nc1nc2cc(-c3cc[nH]n3)ccc2c2c1cnn2CCOCCO] | 339.2 | 0.73 | δ 8.61 (s, 1H), 8.45 (br d, J = 8.8 Hz, 1H), 8.15 (br s, 1H), 7.96 (br d, J = 8.3 Hz, 1H), 7.84 (br s, 1H), 6.86 (s, 1H), 4.95 (br t, J = 5.2 Hz, 2H), 3.96 (br t, J = 5.1 Hz, 2H), 3.39 – 3.36 (m, 2H), 3.34 (br d, J = 4.7 Hz, 2H) |

| Ex. No. | Structure | LC/MS [M + H]⁺ | RT (min) | ¹H NMR (500 MHz, DMSO-d₆) |
|---|---|---|---|---|
| 234 | 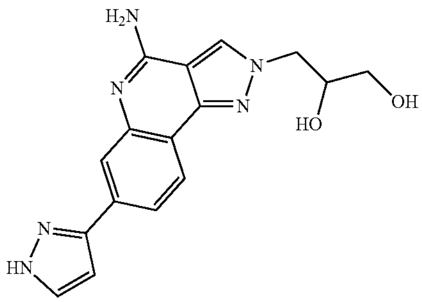 [SMILES: Nc1nc2cc(-c3cc[nH]n3)ccc2c2nn(CC(O)CO)cc12] | 325.1 | 0.68 | δ 8.92 (s, 1H), 8.20 (d, J = 8.2 Hz, 1H), 8.11 (br s, 1H), 7.92 (br d, J = 7.6 Hz, 1H), 7.86 (br s, 1H), 6.82 (s, 1H), 5.31 (br d, J = 5.0 Hz, 1H), 4.98 (br s, 1H), 4.60 (br d, J = 13.7 Hz, 1H), 4.35 (dd, J = 13.5, 8.7 Hz, 1H), 3.94 (br s, 1H) |
| 235 | 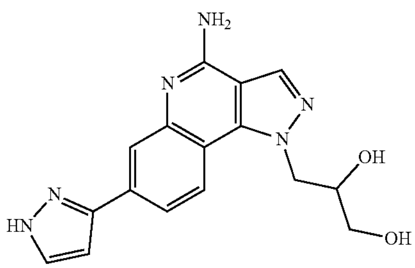 [SMILES: Nc1nc2cc(-c3cc[nH]n3)ccc2c2c1cnn2CC(O)CO] | 325.1 | 0.64 | δ 8.62 (s, 1H), 8.52 (d, J = 8.6 Hz, 1H), 8.17 (br s, 1H), 7.94 (br d, J = 8.5 Hz, 1H), 7.85 (br s, 1H), 6.87 (d, J = 1.7 Hz, 1H), 5.26 (br d, J = 0.6 Hz, 1H), 5.14 – 5.00 (m, 1H), 4.90 – 4.81 (m, 1H), 4.78 – 4.71 (m, 1H), 4.02 (br d, J = 1.6 Hz, 1H) |
| 236 | 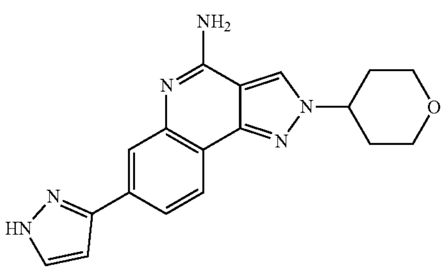 [SMILES: Nc1nc2cc(-c3cc[nH]n3)ccc2c2nn(C3CCOCC3)cc12] | 335.1 | 0.97 | δ 13.10 – 12.78 (m, 1H), 8.58 (s, 1H), 8.09 (d, J = 8.0 Hz, 1H), 7.88 (br s, 1H), 7.83 – 7.58 (m, 2H), 7.08 – 6.91 (m, 2H), 6.75 (d, J = 1.5 Hz, 1H), 4.77 – 4.69 (m, 1H), 4.02 (br dd, J = 11.0, 2.9 Hz, 2H), 2.18 – 2.12 (m, 2H), 2.11 – 2.01 (m, 2H); four CH protons are not visible, likely due to overlap with suppressed water peak. |
| 237 | 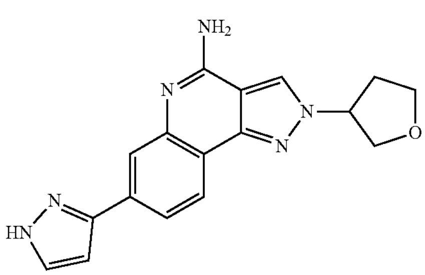 [SMILES: Nc1nc2cc(-c3cc[nH]n3)ccc2c2nn(C3CCOC3)cc12] | 321.1 | 0.89 | δ 13.42 – 13.09 (m, 1H), 9.68 – 9.47 (m, 1H), 9.03 (s, 1H), 9.13 – 8.92 (m, 1H), 8.21 (d, J = 8.2 Hz, 1H), 8.13 (br s, 1H), 7.93 (br d, J = 8.3 Hz, 1H), 7.91 – 7.86 (m, 1H), 6.83 (s, 1H), 5.47 (td, J = 5.4, 2.9 Hz, 1H), 4.16 – 4.06 (m, 3H), 3.92 (td, J = 8.5, 5.4 Hz, 1H), 2.65 – 2.56 (m, 1H), 2.40 – 2.33 (m, 1H) |

| Ex. No. | Structure | LC/MS [M + H]+ | RT (min) | 1H NMR (500 MHz, DMSO-d6) |
|---|---|---|---|---|
| 238 | 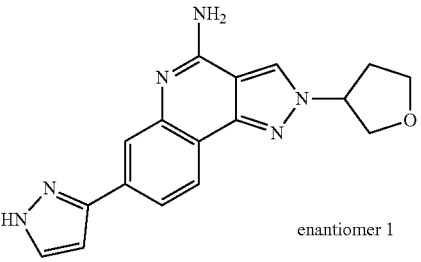 [SMILES: Nc1nc2cc(-c3cc[nH]n3)ccc2c2nn(C3CCOC3)cc12]<br>enantiomer 1 | 321.3 | 1.04 | δ 8.56 (s, 1H), 8.08 (d, J = 8.0 Hz, 1H), 7.86 (s, 1H), 7.73 – 7.67 (m, 1H), 7.64 – 7.60 (m, 1H), 6.91 – 6.79 (m, 2H), 6.74 (s, 1H), 5.36 – 5.31 (m, 1H), 4.13 – 4.03 (m, 3H), 3.93 – 3.85 (m, 1H), 2.60 – 2.54 (m, 1H), 2.38 – 2.30 (m, 1H) |
| 239 | 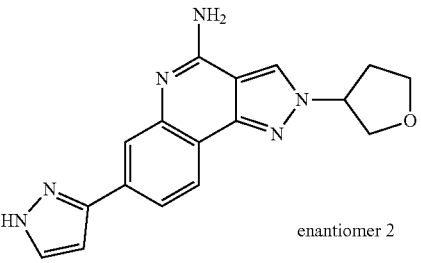 [SMILES: Nc1nc2cc(-c3cc[nH]n3)ccc2c2nn(C3CCOC3)cc12]<br>enantiomer 2 | 321.3 | 1.04 | δ 8.57 (s, 1H), 8.08 (d, J = 8.0 Hz, 1H), 7.86 (s, 1H), 7.70 (br s, 1H), 7.62 (br d, J = 8.5 Hz, 1H), 6.91 – 6.80 (m, 2H), 6.74 (s, 1H), 5.36 – 5.32 (m, 1H), 4.13 – 4.04 (m, 3H), 3.92 – 3.86 (m, 1H), 2.60 – 2.53 (m, 1H), 2.34 (br dd, J = 9.2, 5.4 Hz, 1H) |
| 240 | 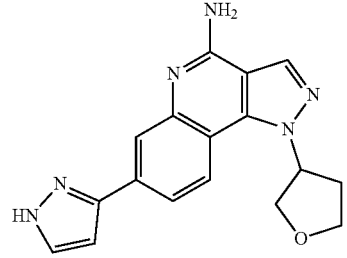 [SMILES: Nc1nc2cc(-c3cc[nH]n3)ccc2c2c1cnn2C1CCOC1] | 321.1 | 1.03 | δ 8.68 – 8.62 (m, 1H), 8.45 (br d, J = 8.8 Hz, 1H), 8.20 (br s, 1H), 8.00 (br d, J = 8.5 Hz, 1H), 7.91 – 7.83 (m, 1H), 6.88 (br d, J = 2.2 Hz, 1H), 5.97 – 5.89 (m, 1H), 4.25 – 4.17 (m, 2H), 4.07 – 4.01 (m, 1H), 3.99 – 3.92 (m, 1H), 2.63 – 2.56 (m, 1H), 2.55 – 2.52 (m, 1H) |
| 241 | 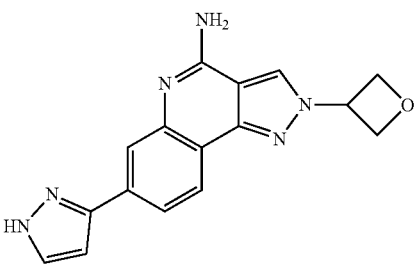 [SMILES: Nc1nc2cc(-c3cc[nH]n3)ccc2c2nn(C3COC3)cc12] | 307.2 | 0.84 | δ 8.82 (s, 1H), 8.21 (d, J = 8.2 Hz, 1H), 7.99 (br s, 1H), 7.79 (br d, J = 8.2 Hz, 2H), 6.80 (d, J = 2.1 Hz, 1H), 5.92 (quin, J = 6.7 Hz, 1H), 5.08 – 5.04 (m, 2H), 5.03 – 5.00 (m, 2H) |
| 242 | 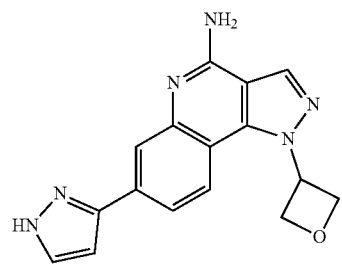 [SMILES: Nc1nc2cc(-c3cc[nH]n3)ccc2c2c1cnn2C1COC1] | 307.1 | 0.98 | δ 8.76 (s, 1H), 8.19 (br d, J = 8.5 Hz, 2H), 7.97 (br d, J = 8.8 Hz, 1H), 7.88 (br s, 1H), 6.86 (d, J = 2.1 Hz, 1H), 6.39 (quin, J = 6.2 Hz, 1H), 5.20 – 5.17 (m, 2H), 5.15 – 5.11 (m, 2H) |

| Ex. No. | Structure | LC/MS [M + H]⁺ | RT (min) | ¹H NMR (500 MHz, DMSO-d₆) |
|---|---|---|---|---|
| 243 | 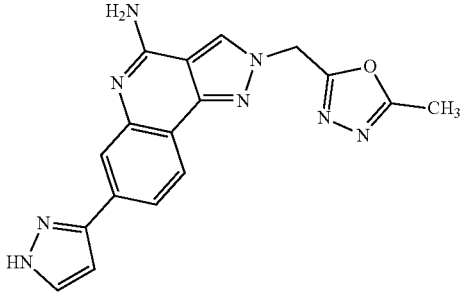 [SMILES: Cc1nnc(Cn2cc3c(N)nc4cc(-c5cc[nH]n5)ccc4c3n2)o1] | 347.0 | 0.78 | δ 8.67 (s, 1H), 8.04 (d, J = 8.0 Hz, 1H), 7.87 (s, 1H), 7.71 (br s, 1H), 7.63 (br d, J = 8.0 Hz, 1H), 7.13 – 6.98 (m, 2H), 6.75 (d, J = 1.9 Hz, 1H), 6.03 (s, 2H), 2.48 (s, 3H) |
| 244 | 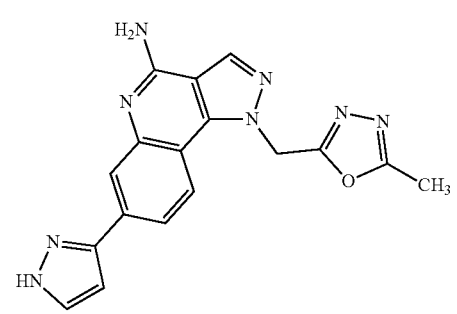 [SMILES: Cc1nnc(Cn2ncc3c(N)nc4cc(-c5cc[nH]n5)ccc4c32)o1] | 347.1 | 0.80 | δ 8.68 (s, 1H), 8.36 (d, J = 8.5 Hz, 1H), 8.18 (br s, 1H), 7.95 (br d, J = 8.8 Hz, 1H), 7.84 (br s, 1H), 6.88 (d, J = 1.7 Hz, 1H), 6.37 (s, 2H), 2.45 (s, 3H) |
| 245 | 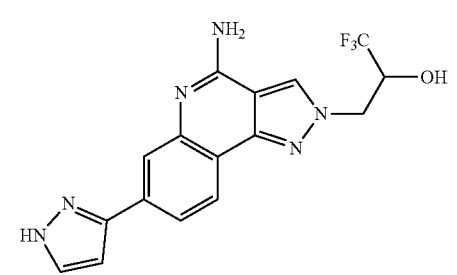 [SMILES: Nc1nc2cc(-c3cc[nH]n3)ccc2c2nn(CC(O)C(F)(F)F)cc12] | 363.2 | 1.00 | δ 8.64 (br s, 1H), 8.12 (d, J = 8.2 Hz, 1H), 7.92 (br s, 1H), 7.79 – 7.66 (m, 2H), 7.04 – 6.91 (m, 1H), 6.77 (d, J = 1.6 Hz, 1H), 4.76 – 4.69 (m, 1H), 4.62 – 4.54 (m, 2H) |
| 246 | 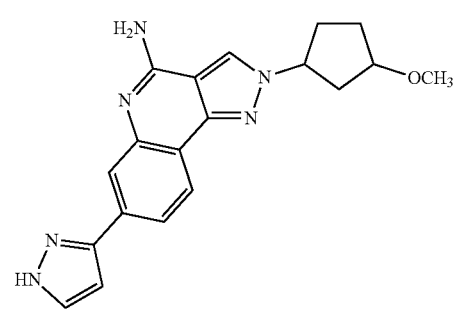 [SMILES: COC1CCC(n2cc3c(N)nc4cc(-c5cc[nH]n5)ccc4c3n2)C1] | 349.1 | 1.13 | δ 8.56 (s, 1H), 8.08 (d, J = 8.0 Hz, 1H), 7.88 (s, 1H), 7.71 (br s, 1H), 7.63 (br d, J = 8.3 Hz, 1H), 7.12 – 6.91 (m, 2H), 6.75 (d, J = 1.7 Hz, 1H), 5.14 – 5.07 (m, 1H), 4.11 – 4.06 (m, 1H), 3.25 (s, 3H), 2.38 – 2.25 (m, 3H), 2.20 – 2.12 (m, 1H), 2.08 – 1.99 (m, 1H), 1.84 – 1.74 (m, 1H) |

Example 238 and Example 239

The racemic material, Example 237, was prepared from the appropriate starting materials and purified via preparative chiral SFC with the following conditions to provide Example 238 and Example 239 as single unassigned isomers: Instrument: Waters 100 Prep SFC; Column: Chiral AD, 30×250 mm. 5 micron; Mobile Phase: 80% CO₂/20% MeOH w/0.1% DEA; Flow Conditions: 100 mL/min; Detector Wavelength: 220 nm. Example 238 (first-eluting isomer) RT: 25.73 min. Example 239 (second-eluting isomer) RT: 30.37 min.

Analytical Chiral SFC Conditions: Instrument: Shimadzu Nexera UC SFC; Column: Chiralpak AD, 4.6×100 mm, 5 micron; Mobile Phase: 80% CO₂/20% IPA w/0.1% DEA; Flow Conditions: 2 mL/min; Detector Wavelength: 220 nm. Example 238 (first-eluting isomer) RT: 11.4 min. Example 239 (second-eluting isomer) RT: 13.3 min.

Example 247. Preparation of 2-(2-methoxyethyl)-7-(1H-pyrazol-1-yl)-2H-pyrazolo[4,3-c]quinolin-4-amine

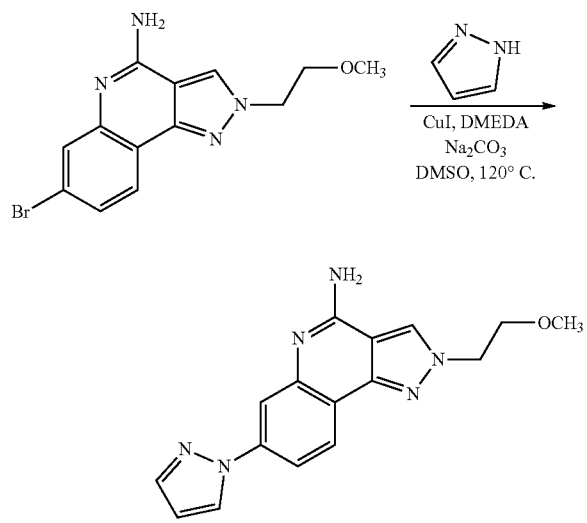

A mixture of 7-bromo-2-(2-methoxyethyl)-2H-pyrazolo[4,3-c]quinolin-4-amine (33 mg, 0.103 mmol), 1H-pyrazole (10.49 mg, 0.154 mmol), and sodium carbonate (43.6 mg, 0.411 mmol) was evacuated and back-filled with $N_2$, then DMSO (1027 µl) was added. The resulting mixture was sparged with $N_2$ for 10 min, then N,N'-dimethylethylenediamine (33.2 µl, 0.308 mmol) and copper(I) iodide (29.4 mg, 0.154 mmol) were added. The mixture was sparged with $N_2$ for 1 min, then it was sealed and stirred at 120° C. for 1 h. The reaction was cooled to rt, diluted with EtOAc (20 mL), washed with $H_2O$ (20 mL), 1:1 $H_2O$-aq. $NH_4OH$ (20 mL), and sat. aq. NaCl (20 mL), dried over $Na_2SO_4$, filtered, and concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 3% B, 3-43% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-methoxyethyl)-7-(1H-pyrazol-1-yl)-2H-pyrazolo[4,3-c]quinolin-4-amine (17.4 mg, 52%). $^1$H NMR (500 MHz, DMSO-$d_6$) δ 8.52 (d, J=2.2 Hz, 1H), 8.51 (s, 1H), 8.14 (d, J=8.5 Hz, 1H), 7.85 (d, J=2.2 Hz, 1H), 7.76 (d, J=1.1 Hz, 1H), 7.67 (dd, J=8.4, 2.1 Hz, 1H), 7.10-7.00 (m, 2H), 6.55 (s, 1H), 4.57 (t, J=5.0 Hz, 2H), 3.81 (t, J=5.0 Hz, 2H), 3.25 (s, 3H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 308.9 [M+H]$^+$; RT: 1.13 min.

Example 248. Preparation of 2-(2-methoxyethyl)-7-(thiophen-2-yl)-2H-pyrazolo[4,3-c]quinolin-4-amine

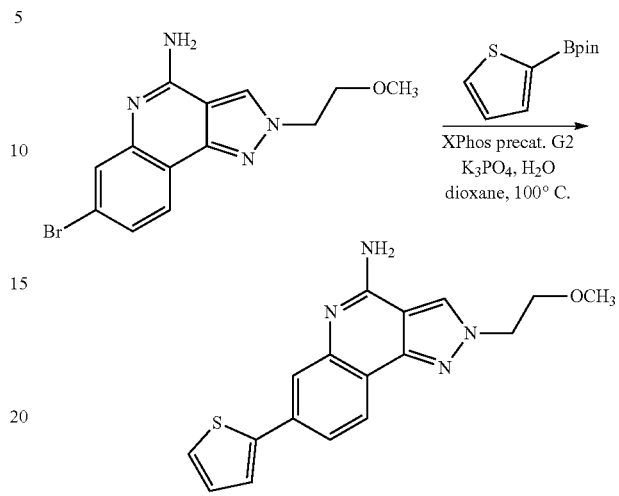

A mixture of 7-bromo-2-(2-methoxyethyl)-2H-pyrazolo[4,3-c]quinolin-4-amine (33 mg, 0.103 mmol), 4,4,5,5-tetramethyl-2-(thiophen-2-yl)-1,3,2-dioxaborolane (32.4 mg, 0.154 mmol), and potassium phosphate tribasic (65.4 mg, 0.308 mmol) was evacuated and back-filled with $N_2$, then 1,4-dioxane (428 µl) and $H_2O$ (86 µl) were added. The resulting mixture was sparged with $N_2$ for 15 min, then chloro(2-dicyclohexylphosphino-2',4',6'-triisopropyl-1,1'-biphenyl)[2-(2'-amino-1,1'-biphenyl)]palladium(II) (2.021 mg, 2.57 µmol) was added. The mixture was sparged with $N_2$ for 1 min, then it was sealed and stirred at 100° C. for 20 min. The reaction was cooled to rt, diluted with EtOAc (20 mL) and washed with $H_2O$ (20 mL). The aqueous layer was extracted with EtOAc (20 mL), and the combined organic layers were washed with sat. aq. NaCl (20 mL), dried over $Na_2SO_4$, filtered, and concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 14% B, 14-54% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to provide 2-(2-methoxyethyl)-7-(thiophen-2-yl)-2H-pyrazolo[4,3-c]quinolin-4-amine (26.9 mg, 81%). $^1$H NMR (500 MHz, DMSO-$d_6$) δ 8.51 (s, 1H), 8.08 (d, J=8.2 Hz, 1H), 7.69 (d, J=1.5 Hz, 1H), 7.55 (d, J=3.7 Hz, 1H), 7.54-7.50 (m, 2H), 7.15 (dd, J=5.0, 3.7 Hz, 1H), 7.21-7.05 (m, 2H), 4.56 (t, J=4.9 Hz, 2H), 3.82-3.79 (m, 2H), 3.24 (s, 3H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z: 325.2 [M+H]$^+$; RT: 1.28 min.

Examples 249 and 250. Preparation of 2-(4-amino-7-(1H-pyrazol-1-yl)-2H-pyrazolo[4,3-c]quinolin-2-yl)ethan-1-ol and 2-(4-amino-7-(1H-pyrazol-1-yl)-1H-pyrazolo[4,3-c]quinolin-1-yl)ethan-1-ol

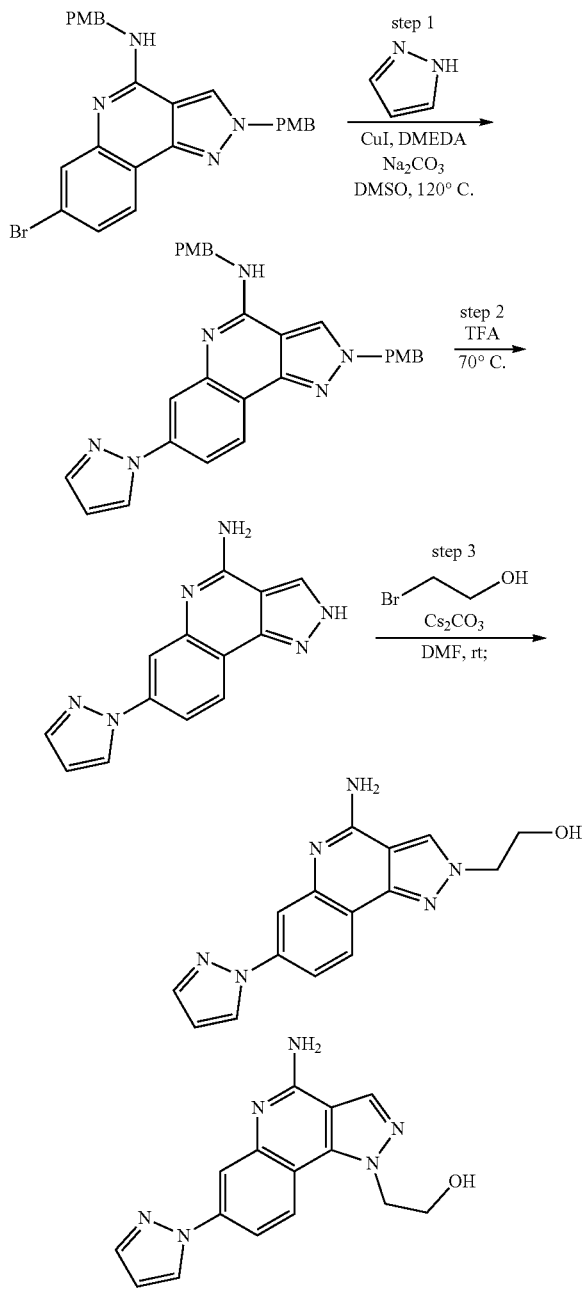

Step 1. N,2-bis(4-methoxybenzyl)-7-(1H-pyrazol-1-yl)-2H-pyrazolo[4,3-c]quinolin-4-amine A mixture of 7-bromo-N,2-bis(4-methoxybenzyl)-2H-pyrazolo[4,3-c]quinolin-4-amine (102 mg, 0.203 mmol), 1H-pyrazole (20.69 mg, 0.304 mmol), and sodium carbonate (86 mg, 0.810 mmol) was evacuated and back-filled with $N_2$, then DMSO (2026 µl) was added. The resulting mixture was sparged with $N_2$ for 10 min, then N,N'-dimethylethylenediamine (65.4 µl, 0.608 mmol) and copper(I) iodide (57.9 mg, 0.304 mmol) were added. The mixture was sparged with $N_2$ for 1 min, then it was sealed and stirred at 120° C. for 1 h. The reaction was cooled to rt, diluted with EtOAc (20 mL), washed with $H_2O$ (20 mL), 1:1 $H_2O$-aq. $NH_4OH$ (20 mL), and sat. aq. NaCl (20 mL), dried over $Na_2SO_4$, filtered, and concentrated in vacuo. The crude material was purified by flash chromatography (12 g silica gel; linear gradient 0-100% EtOAc-$CH_2Cl_2$) to provide N,2-bis(4-methoxybenzyl)-7-(1H-pyrazol-1-yl)-2H-pyrazolo[4,3-c]quinolin-4-amine (83.5 mg, 84%) as a white solid. LC-MS m/z 491 [M+H]$^+$; $^1$H NMR (400 MHz, DMSO-$d_6$) δ 8.61 (d, J=2.1 Hz, 1H), 8.47 (s, 1H), 8.13 (d, J=8.5 Hz, 1H), 7.95 (br t, J=5.3 Hz, 1H), 7.90 (d, J=2.0 Hz, 1H), 7.75 (d, J=1.6 Hz, 1H), 7.69 (dd, J=8.5, 2.2 Hz, 1H), 7.35 (d, J=7.8 Hz, 4H), 6.99-6.94 (m, 2H), 6.91-6.85 (m, 2H), 6.55-6.53 (m, 1H), 5.57 (s, 2H), 4.71 (d, J=5.6 Hz, 2H), 3.74 (s, 3H), 3.71 (s, 3H).

Step 2. 7-(1H-pyrazol-1-yl)-2H-pyrazolo[4,3-c]quinolin-4-amine, TFA

A solution of N,2-bis(4-methoxybenzyl)-7-(1H-pyrazol-1-yl)-2H-pyrazolo[4,3-c]quinolin-4-amine (82.5 mg, 0.168 mmol) in TFA (336 µl) was sealed and stirred at 70° C. for 18 h, then it was cooled to rt and concentrated in vacuo. The crude material was concentrated from $CH_2Cl_2$ (4×2 mL). The crude material was triturated with $CH_2Cl_2$ by mixing it with $CH_2Cl_2$ (1 mL), filtering, and then washing with $CH_2Cl_2$ (3×1 mL) to provide 7-(1H-pyrazol-1-yl)-2H-pyrazolo[4,3-c]quinolin-4-amine, TFA (52.8 mg, 86%) as an off-white solid. LC-MS m/z 251 [M+H]$^+$; $^1$H NMR (400 MHz, DMSO-$d_6$) δ 13.35-13.08 (m, 1H), 9.78-9.51 (m, 1H), 8.88-8.59 (m, 3H), 8.34 (br d, J=7.4 Hz, 1H), 8.25 (br s, 1H), 8.13-8.00 (m, 1H), 7.88 (br s, 1H), 6.66 (br s, 1H).

Step 3. 2-(4-amino-7-(1H-pyrazol-1-yl)-2H-pyrazolo[4,3-c]quinolin-2-yl)ethan-1-ol and 2-(4-amino-7-(1H-pyrazol-1-yl)-1H-pyrazolo[4,3-c]quinolin-1-yl)ethan-1-ol To a rt suspension of 7-(1H-pyrazol-1-yl)-2H-pyrazolo[4,3-c]quinolin-4-amine, TFA (26 mg, 0.071 mmol) in DMF (238 µl) was added cesium carbonate (69.8 mg, 0.214 mmol) followed by 2-bromoethan-1-ol (5.56 µl, 0.079 mmol). The suspension was stirred at rt for 18 h and at 50° C. for 6 h. The reaction was diluted with $H_2O$ (2 mL) and extracted with EtOAc (3×2 mL). The combined organic layers were concentrated in vacuo. The crude material was dissolved in DMF (2 mL), filtered (syringe filter), and purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to provide 2-(4-amino-7-(1H-pyrazol-1-yl)-1H-pyrazolo[4,3-c]quinolin-1-yl)ethan-1-ol, TFA (4.1 mg, 14%). The other regioisomer was also isolated and further purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 25 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to provide 2-(4-amino-7-(1H-pyrazol-1-yl)-2H-pyrazolo[4,3-c]quinolin-2-yl)ethan-1-ol, TFA (4 mg, 13%).

Characterization data for 2-(4-amino-7-(1H-pyrazol-1-yl)-2H-pyrazolo[4,3-c]quinolin-2-yl)ethan-1-ol (Example 249): $^1$H NMR (500 MHz, DMSO-$d_6$) δ 8.80 (s, 1H), 8.57 (s, 1H), 8.22 (d, J=8.5 Hz, 1H), 8.04 (s, 1H), 7.86 (br d, J=9.1 Hz, 1H), 7.82 (s, 1H), 6.60 (s, 1H), 5.16 (br d, J=1.9 Hz, 1H), 4.50 (br t, J=5.0 Hz, 2H), 3.88 (br s, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 295.1 [M+H]$^+$; RT: 0.81 min.

Characterization data for 2-(4-amino-7-(1H-pyrazol-1-yl)-1H-pyrazolo[4,3-c]quinolin-1-yl)ethan-1-ol (Example 250): $^1$H NMR (500 MHz, DMSO-$d_6$) δ 8.68-8.64 (m, 1H), 8.62 (s, 1H), 8.54 (d, J=9.0 Hz, 1H), 8.22 (br s, 1H), 7.98 (dd, J=8.8, 1.3 Hz, 1H), 7.87 (d, J=1.0 Hz, 1H), 6.66 (d, J=1.7 Hz, 1H), 5.19-5.07 (m, 1H), 4.86 (br t, J=5.1 Hz, 2H), 3.93 (br t, J=4.8 Hz, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 295.2 [M+H]$_+$; RT: 0.97 min.

Examples 251 and 252. Preparation of 3-(4-amino-7-(1H-pyrazol-1-yl)-2H-pyrazolo[4,3-c]quinolin-2-yl)propan-1-ol and 3-(4-amino-7-(1H-pyrazol-1-yl)-1H-pyrazolo[4,3-c]quinolin-1-yl)propan-1-ol

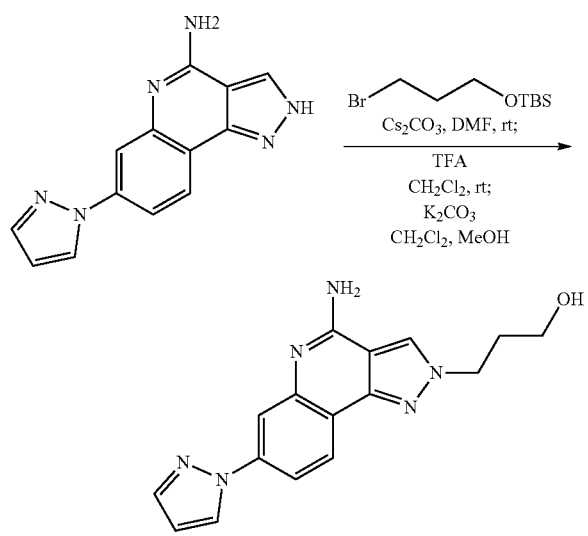

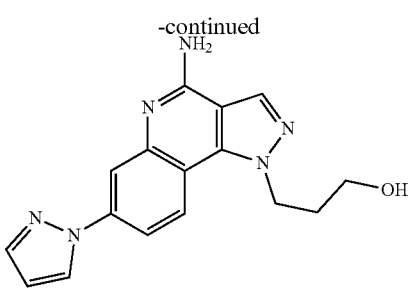

To a rt suspension of 7-(1H-pyrazol-1-yl)-2H-pyrazolo[4,3-c]quinolin-4-amine, TFA (26 mg, 0.071 mmol) in DMF (238 μl) was added cesium carbonate (69.8 mg, 0.214 mmol) followed by (3-bromopropoxy)(tert-butyl)dimethylsilane (18.19 μl, 0.079 mmol). The suspension was stirred at rt for 2 h The reaction was diluted with H$_2$O (2 mL) and extracted with EtOAc (3×2 mL). The combined organic layers were concentrated in vacuo.

The crude material was dissolved in CH$_2$Cl$_2$ (150 μL) and TFA (150 μL) was added. The reaction was stirred at rt for 1.5 h. The reaction was concentrated in vacuo. The crude material was concentrated from CH$_2$Cl$_2$ (300 μL).

The crude material was mixed with CH$_2$Cl$_2$ (150 μL) and MeOH (150 μL), and potassium carbonate (49 mg, 0.36 mmol) was added. The suspension was stirred at rt for 15 min. The reaction was diluted with 1:1 MeOH—CH$_2$Cl$_2$ (1 mL) and filtered (pipette filter). The filtrate was concentrated in vacuo, then it was mixed with DMF (2 mL), filtered (syringe filter), and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. Each product was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-20% B over 25 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to provide 3-(4-amino-7-(1H-pyrazol-1-yl)-2H-pyrazolo[4,3-c]quinolin-2-yl)propan-1-ol, TFA (12.2 mg, 41%) and 3-(4-amino-7-(1H-pyrazol-1-yl)-1H-pyrazolo[4,3-c]quinolin-1-yl)propan-1-ol, TFA (4.1 mg, 14%).

Characterization data for 3-(4-amino-7-(1H-pyrazol-1-yl)-2H-pyrazolo[4,3-c]quinolin-2-yl)propan-1-ol (Example 251): $^1$H NMR (500 MHz, DMSO-$d_6$) δ 8.90-8.88 (m, 1H), 8.61-8.57 (m, 1H), 8.26 (d, J=8.7 Hz, 1H), 8.15-8.12 (m, 1H), 7.95 (br d, J=8.2 Hz, 1H), 7.84 (s, 1H), 6.63 (s, 1H), 4.91-4.75 (m, 1H), 4.54 (br t, J=7.0 Hz, 2H), 3.45 (br t, J=6.0 Hz, 2H), 2.08 (quin, J=6.4 Hz, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 309.1 [M+H]+, RT: 0.83 min.

Characterization data for and 3-(4-amino-7-(1H-pyrazol-1-yl)-1H-pyrazolo[4,3-c]quinolin-1-yl)propan-1-ol (Example 252): $^1$H NMR (500 MHz, DMSO-$d_6$) δ 8.68 (d, J=2.4 Hz, 1H), 8.62 (s, 1H), 8.46 (d, J=9.0 Hz, 1H), 8.26 (d, J=1.9 Hz, 1H), 8.04 (dd, J=8.9, 1.7 Hz, 1H), 7.88 (s, 1H), 6.66 (s, 1H), 4.85 (br t, J=7.2 Hz, 2H), 3.55-3.51 (m, 2H), 2.10-2.02 (m, 2H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 309.2 [M+H]$^+$; RT: 0.75 min.

Example 253. Preparation of 2-[4-amino-7-(1H-pyrazol-5-yl)-2H-pyrazolo[4,3-c]quinolin-2-yl]propan-1-ol

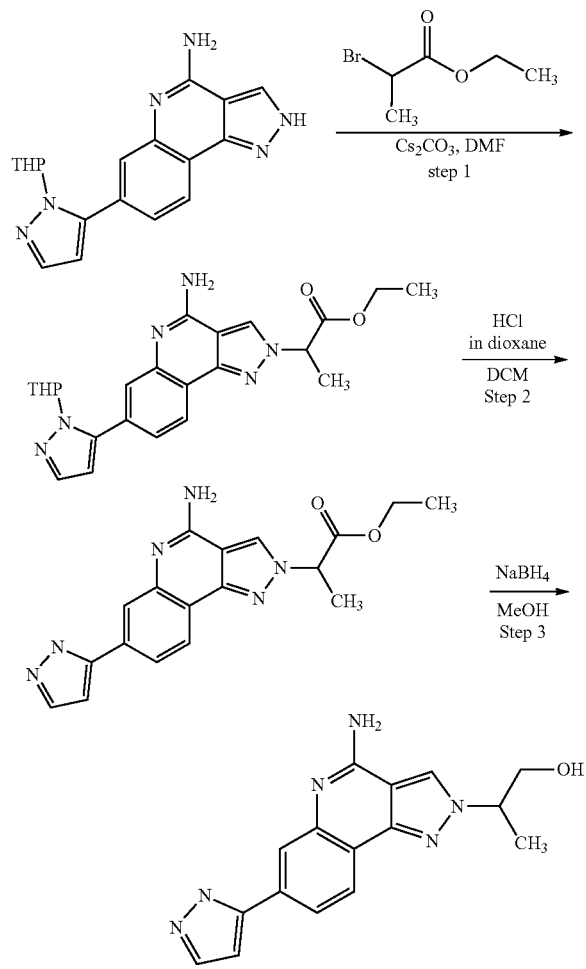

Step 1. Synthesis of ethyl 2-[4-amino-7-[1-(oxan-2-yl)-1H-pyrazol-5-yl]-2H-pyrazolo[4,3-c]quinolin-2-yl]propanoate Into a 25-mL round-bottom flask, was placed 7-[1-(oxan-2-yl)-1H-pyrazol-5-yl]-2H-pyrazolo[4,3-c]quinolin-4-amine (100 mg, 0.299 mmol, 1 equiv), Cs$_2$CO$_3$ (292 mg, 0.89 mmol, 3 equiv), DMF (5 mL), ethyl 2-bromopropanoate (64.9 mg, 0.36 mmol, 1.2 equiv). The resulting solution was stirred for 2 hr at 65° C. The residue was dissolved in 15 mL of H$_2$O. The resulting solution was extracted with 2×15 mL of ethyl acetate and concentrated. This resulted in 100 mg (77%) of ethyl 2-[4-amino-7-[1-(oxan-2-yl)-1H-pyrazol-5-yl]-2H-pyrazolo[4,3-c]quinolin-2-yl]propanoate as a yellow solid. LC-MS: (ES, m/z): [M+H]$^+$=435.5.

Step 2. Synthesis of ethyl 2-[4-amino-7-(1H-pyrazol-5-yl)-2H-pyrazolo[4,3-c]quinolin-2-yl]propanoate Into a 25-mL round-bottom flask, was placed ethyl 2-[4-amino-7-[1-(oxan-2-yl)-1H-pyrazol-5-yl]-2H-pyrazolo[4,3-c]quinolin-2-yl]propanoate (100 mg, 0.23 mmol, 1 equiv), DCM (10 mL), HCl in dioxane (0.5 mL, 16.4 mmol, 71.5 equiv). The resulting solution was stirred for 1 hr at rt. The resulting mixture was concentrated. This resulted in 60 mg (74%) of ethyl 2-[4-amino-7-(1H-pyrazol-5-yl)-2H-pyrazolo[4,3-c]quinolin-2-yl]propanoate as a yellow solid. LC-MS: (ES, m/z): [M+H]$^+$=351.4.

Step 3. Synthesis of 2-(4-amino-7-(1H-pyrazol-5-yl)-2H-pyrazolo[4,3-c]quinolin-2-yl)propan-1-ol Into a 25-mL round-bottom flask, was placed ethyl 2-[4-amino-7-(1H-pyrazol-5-yl)-2H-pyrazolo[4,3-c]quinolin-2-yl]propanoate (60 mg, 0.171 mmol, 1 equiv), MeOH (10 mL), NaBH$_4$ (16.20 mg, 0.428 mmol, 2.5 equiv). The resulting solution was stirred for 2 hr at 0 degrees C. The resulting mixture was concentrated. The crude product was purified by Prep-HPLC with the following conditions: Column, Sunfire Prep C18 OBD Column, 10 um, 19×250 mm; mobile phase, Water (0.05% TFA) and ACN (15% PhaseB up to 25% in 9 min); Detector, 254/210 nm. This resulted in 20 mg (27%) of 2-(4-amino-7-(1H-pyrazol-5-yl)-2H-pyrazolo[4,3-c]quinolin-2-yl)propan-1-ol as a white solid. LC-MS: (ES, m/z): [M+H]$^+$=309.2. $^1$H NMR (400 MHz, Methanol-$d_4$) δ 8.82 (s, 1H), 8.36-8.34 (d, J=8.0 Hz, 1H), 8.02-8.01 (m, 1H), 7.95-7.93 (m, 1H), 7.77-7.76 (d, J=2.4 Hz, 1H), 6.83-6.82 (d, J=2.4 Hz, 1H), 4.87-4.74 (m, 1H), 3.98-3.93 (m, 2H), 1.69-1.68 (d, J=6.8 Hz, 3H).

Examples 254 to 285 were prepared according to synthetic procedures similar to those described for Examples 150, 151, 209, or 253, from the appropriate starting materials.

Analytical LC/MS conditions:
A: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to 95% B over 2 min, then a 0.6 min hold at 95% B; Flow: 1 mL/min; Detection: MS and UV.

B: Column: Shim-pack XR-ODS, 3.0 mm×50 mm, 2.2 μm particles; Mobile Phase A: water with with 0.05% TFA; Mobile Phase B: acetonitrile with 0.05% TFA; Temperature: 40° C.; Gradient: 5% B to 95% B over 2 min, then a 0.7 min hold at 95% B; Flow: 1 mL/min; Detection: MS and UV.

C: Column: Kinetex EVO C18, 3.0 mm×50 mm, 2.2 μm particles; Mobile Phase A: water with with 5 mM ammonium bicarbonate; Mobile Phase B: acetonitrile; Temperature: 40° C.; Gradient: 10% B to 95% B over 2 min, then a 0.6 min hold at 95% B; Flow: 1 mL/min; Detection: MS and UV.

D: Column: Kinetex XB-C18, 2.1 mm×30 mm, 1.7 μm particles; Mobile Phase A: water with with 0.05% TFA; Mobile Phase B: acetonitrile with 0.05% TFA; Temperature: 40° C.; Gradient: 5% B to 35% B over 1.7 min, then to 100% over 0.5 min, then a 0.6 min hold at 100% B; Flow: 1 mL/min; Detection: MS and UV.

E: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 0% B to 30% B over 3 min, then to 95% over 0.2 min, then a 1.0 min hold at 95% B; Flow: 1 mL/min; Detection: MS and UV.

F: Column: XSelect HSS T3, 4.6 mm×100 mm, 3.7 μm particles; Mobile Phase A: water with with 0.05% TFA; Mobile Phase B: acetonitrile with 0.05% TFA; Temperature: 40° C.; Gradient: 10% B to 95% B over 6.0 min, then a 2.0 min hold at 100% B; Flow: 1.5 mL/min; Detection: UV.

G: Column: Ascentis Express C18, 3.0 mm×50 mm, 2.7 μm particles; Mobile Phase A: water with with 0.05% TFA; Mobile Phase B: acetonitrile with 0.05% TFA; Temperature: 40° C.; Gradient: 5% B to 95% B over 2.0 min, then a 0.7 min hold at 95% B; Flow: 1.5 mL/min; Detection: MS and UV.

H: Column: Shim-pack XR-ODS, 3.0 mm×50 mm, 2.2 μm particles; Mobile Phase A: water with with 0.05% TFA; Mobile Phase B: acetonitrile with 0.05% TFA; Temperature: 40° C.; Gradient: 5% B to 50% over 3 min, and then to 95% B over 0.3 min, then a 0.4 min hold at 95% B; Flow: 1 mL/min; Detection: MS and UV.

I: Column: Shim-pack XR-ODS, 3.0 mm×50 mm, 2.2 μm particles; Mobile Phase A: water with with 0.05% TFA; Mobile Phase B: acetonitrile with 0.05% TFA; Temperature: 40° C.; Gradient: 5% B to 40% over 3 min, and then to 100% B over 0.3 min, then a 0.4 min hold at 95% B; Flow: 1.2 mL/min; Detection: MS and UV.

J: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to 95% B over 3.2 min, then a 1.0 min hold at 95% B; Flow: 1 mL/min; Detection: MS and UV.

K: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to 40% B over 3.0 min, then to 95% B over 0.2 min, then a 1.0 min hold at 95% B; Flow: 1 mL/min; Detection: MS and UV.

L: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to to 95% B over 1.7 min, then a 1.0 min hold at 95% B; Flow: 1 mL/min; Detection: MS and UV.

M: Column: Titan C18, 2.1 mm×50 mm, 1.9 μm particles; Mobile Phase A: water with with 0.05% TFA; Mobile Phase B: acetonitrile with 0.05% TFA; Temperature: 40° C.; Gradient: 5% B to to 50% over 2.2 min, then to 100% B over 0.8 min, then a 0.8 min hold at 95% B; Flow: 0.7 mL/min; Detection: MS and UV.

N: Column: Ascentis Express C18, 3.0 mm×50 mm, 2.7 μm particles; Mobile Phase A: water with with 0.05% TFA; Mobile Phase B: acetonitrile with 0.05% TFA; Temperature: 40° C.; Gradient: 5% B to 100% B over 2.0 min, then a 0.8 min hold at 95% B; Flow: 1.5 mL/min; Detection: MS and UV.

O: Column: Kinetex XB-C18, 2.1 mm×30 mm, 1.7 μm particles; Mobile Phase A: water with with 0.05% TFA; Mobile Phase B: acetonitrile with 0.05% TFA; Temperature: 40° C.; Gradient: 5% B to 100% B over 0.8 min, then a 0.5 min hold at 100% B; Flow: 1 mL/min; Detection: MS and UV.

| Ex. No. | Structure | LC/MS [M + H]+ | RT (min)/ LC condition | $^1$H NMR, unless otherwise indicated, 400 MHz, Methanol-d$_4$ |
|---|---|---|---|---|
| 254 | 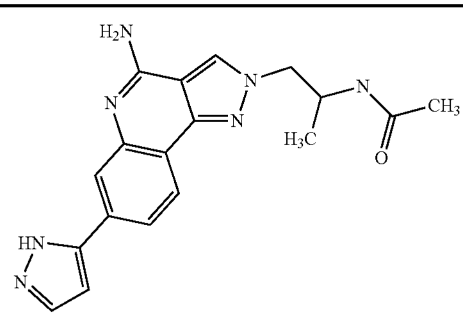 | 350.3 | 1.15/D | δ 8.41 (s, 1H), 8.26 (d, J = 8.1 Hz, 1H), 7.92 (s, 1H), 7.71 (s, 2H), 6.77 (d, J = 2.2 Hz, 1H), 4.61-4.45 (m, 2H), 1.93 (s, 3H), 1.26 (d, J = 6.2 Hz, 3H) |
| 255 | 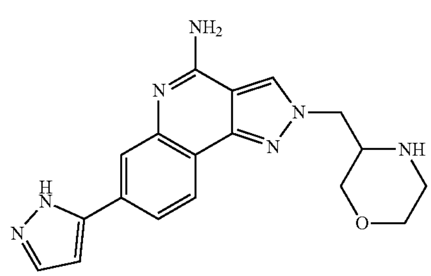 [SMILES: Nc1nc2cc(-c3ccn[nH]3)ccc2c2nn(CC3COCCN3)cc12] | 350.4 | 2.58/E | δ 8.45 (s, 1H), 8.25 (d, J = 8.2 Hz, 1H), 7.92 (s, 1H), 7.72 (s, 2H), 6.77 (d, J = 2.2 Hz, 1H), 4.49 (dd, J = 13.9, 5.5 Hz, 1H), 4.42 (dd, J = 13.9, 7.1 Hz, 1H), 3.87 (dd, J = 10.8, 2.6 Hz, 1H), 3.79 (dt, J = 11.4, 3.2 Hz, 1H), 3.64 – 3.52 (m, 1H), 3.48 – 3.34 (m, 2H), 2.95 (m, 2H) |

| Ex. No. | Structure | LC/MS [M + H]+ | RT (min)/ LC condition | 1H NMR, unless otherwise indicated, 400 MHz, Methanol-d4 |
|---|---|---|---|---|
| 256 | 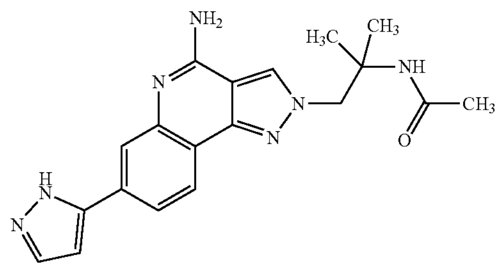 [SMILES: CC(=O)NC(C)(C)Cn1cc2c(N)nc3cc(-c4ccn[nH]4)ccc3c2n1] | 364.0 | 1.16/A | δ 8.31 (s, 1H), 8.27 (d, J = 8.2 Hz, 1H), 7.92 (s, 1H), 7.71 (s, 2H), 6.76 (s, 1H), 4.83 (s, 2H), 1.99 (s, 3H), 1.43 (s, 6H) |
| 257 | 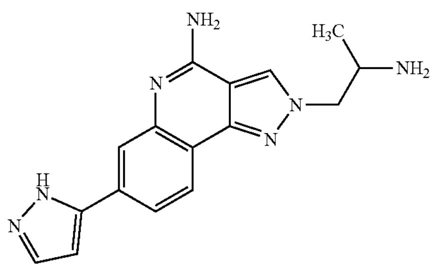 [SMILES: CC(N)Cn1cc2c(N)nc3cc(-c4ccn[nH]4)ccc3c2n1] | 308.2 | 2.20/F | 1H NMR (400 MHz, DMSO-d6) δ 8.97 (s, 1H), 8.28-8.13 (m, 2H), 7.98-7.87 (m, 2H), 6.85 (d, J = 2.4 Hz, 1H), 4.74-4.64 (m, 2H), 3.88 (s, 1H), 1.28 (d, J = 6.7 Hz, 3H) |
| 258 | 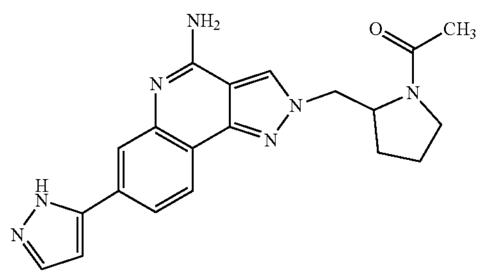 [SMILES: CC(=O)N1CCCC1Cn1cc2c(N)nc3cc(-c4ccn[nH]4)ccc3c2n1] | 376.2 | 0.88/G | 1H NMR (300 MHz, Methanol-d4) δ 8.70 (s, 1H), 8.34-8.32 (m, 1H), 8.01 (s, 1H), 7.96-7.93 (m, 1H), 7.77-7.76 (m, 1H), 6.83-6.82 (d, J = 2.3 Hz, 1H), 4.70-4.63 (m, 2H), 4.57-4.51 (m, 1H), 3.58-3.45 (m, 2H), 2.10 (s, 3H), 2.08-2.07 (m, 2H), 1.90-1.86 (m, 2H) |
| 259 | 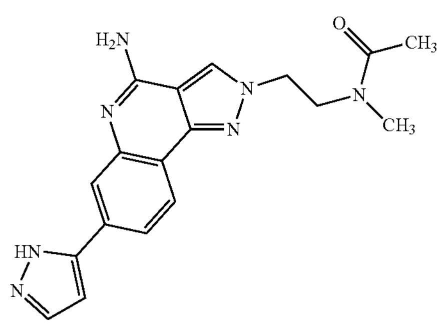 [SMILES: CC(=O)N(C)CCn1cc2c(N)nc3cc(-c4ccn[nH]4)ccc3c2n1] | 350.2 | 1.92/H | δ 8.74-8.72 (d, J = 8.5 Hz, 1H), 8.33-8.31 (d, J = 8.2 Hz, 1H), 8.01-8.00 (m, 1H), 7.99-7.96 (m, 1H), 7.77-7.76 (m, 1H), 6.83-6.82 (m, 1H), 4.78-4.67 (m, 2H), 4.07-3.94 (m, 2H), 3.01(s, 2H), 2.94 (s, 1H), 2.03-2.02 (d, J = 4.4 Hz, 2H), 1.73 (s, 1H) |
| 260 | 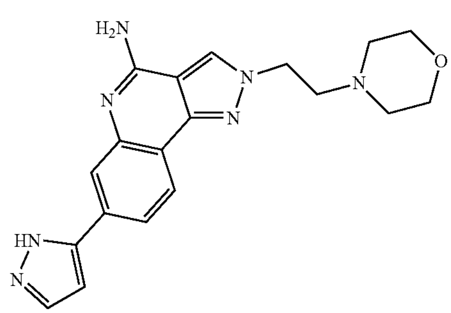 [SMILES: Nc1nc2cc(-c3ccn[nH]3)ccc2c2nn(CCN3CCOCC3)cc12] | 364.2 | 1.01/B | δ 8.86 (s, 1H), 8.34-8.32 (d, J = 8.3 Hz, 1H), 8.03-8.02 (m, 1H), 7.97-7.95 (m, 1H), 7.78-7.77 (d, J = 2.4 Hz, 1H), 6.83-6.82 (d, J = 2.4 Hz, 1H), 4.87 (m, 2H), 3.83 (s, 4H), 3.49-3.47 (m, 2H), 3.08 (s, 4H) |

| Ex. No. | Structure | LC/MS [M + H]+ | RT (min)/ LC condition | 1H NMR, unless otherwise indicated, 400 MHz, Methanol-d4 |
|---|---|---|---|---|
| 261 | 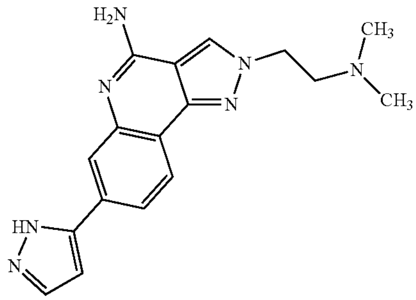 [SMILES: CN(C)CCn1cc2c(N)nc3cc(-c4ccn[nH]4)ccc3c2n1] | 322.2 | 1.71/I | δ 8.93 (s, 1H), 8.42-8.40 (d, J = 8.3 Hz, 1H), 8.06-8.05 (m, 1H), 8.00-7.97 (m, 1H), 7.80-7.79 (d, J = 2.4 Hz, 1H), 6.87-6.86 (d, J = 2.4 Hz, 1H), 5.04-5.02 (t, J = 5.8 Hz, 2H), 3.94-3.91 (t, J = 5.8 Hz, 2H), 3.10 (s, 6H) |
| 262 | 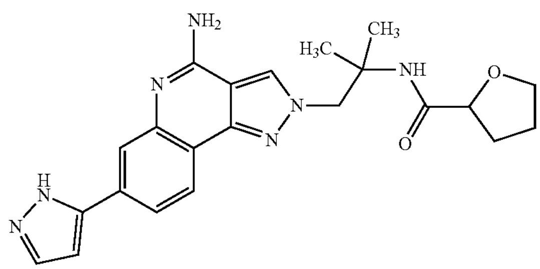 [SMILES: CC(C)(Cn1cc2c(N)nc3cc(-c4ccn[nH]4)ccc3c2n1)NC(=O)C1CCCO1] | 420.0 | 1.62/J | 1H NMR (400 MHz, DMSO-d6) δ 13.34 – 12.88 (s, 1H), 8.39 (s, 1H), 8.09 (d, J = 8.2 Hz, 1H), 7.88 – 7.55 (m, 3H), 7.49 (s, 1H), 6.97 – 6.94 (m, 2H), 6.76 (s, 1H), 4.70 (s, 2H), 4.19 – 4.15 (m, 1H), 3.80 – 3.70 (m, 2H), 2.12 – 2.08 (m, 1H), 2.08 – 1.90 (m, 1H), 1.81 – 1.64 (m, 2H), 1.38 (d, J = 10.5 Hz, 6H) |
| 263 | 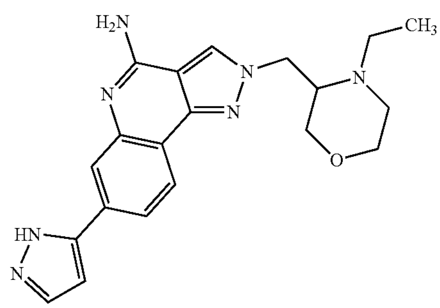 [SMILES: CCN1CCOCC1Cn1cc2c(N)nc3cc(-c4ccn[nH]4)ccc3c2n1] | 378.5 | 2.47/I | 1H NMR (300 MHz, Methanol-d4) δ 8.46 (s, 1H), 8.24 (d, J = 8.2 Hz, 1H), 7.92 (s, 1H), 7.70 (s, 2H), 6.76 (d, J = 2.2 Hz, 1H), 4.77 – 4.56 (m, 2H), 3.77 (t, J = 4.9 Hz, 2H), 3.63 (dd, J = 11.6, 3.0 Hz, 1H), 3.50 – 3.34 (m, 1H), 3.24 (s,1H), 2.99 – 2.84 (m, 2H), 2.81 – 2.66 (m, 1H), 2.57 (dd, J = 12.4, 4.6 Hz, 1H), 1.18 (t, J = 7.2 Hz, 3H) |
| 264 | 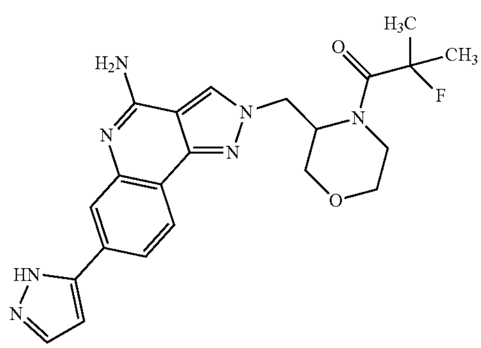 [SMILES: CC(C)(F)C(=O)N1CCOCC1Cn1cc2c(N)nc3cc(-c4ccn[nH]4)ccc3c2n1] | 438.0 | 1.28/A | 1H NMR (400 MHz, DMSO-d6) δ 13.28 (d, J = 200.7 Hz, 1H), 10.50 (s, 1H), 8.68 (s, 1H), 8.38 (d, J = 8.3 Hz, 1H), 8.28 (s, 1H), 8.08 (s, 1H), 7.86 (s, 1H), 6.89 (d, J = 2.2 Hz, 1H), 4.68 (d, J = 39.7 Hz, 2H), 3.95 (d, J = 12.0 Hz, 1H), 3.83 (d, J = 12.0 Hz, 1H), 3.74 (s, 1H), 3.54 (dt, J = 36.0, 10.7 Hz, 2H), 3.19 (d, J = 13.0 Hz, 1H), 3.01 (s, 1H), 1.70 (d, J = 21.8 Hz, 6H) |
| 265 | 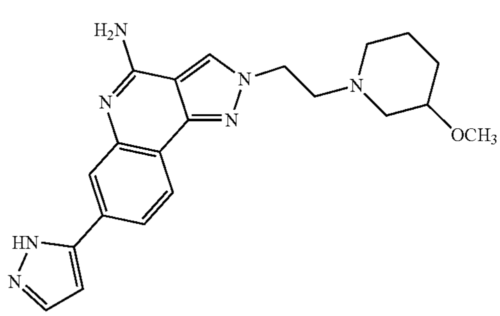 [SMILES: COC1CCCN(CCn2cc3c(N)nc4cc(-c5ccn[nH]5)ccc4c3n2)C1] | 392.3 | 1.94/K | δ 8.92 (s, 1H), 8.37-8.34 (d, J = 8.3 Hz, 1H), 8.01-7.97 (m, 2H), 7.78-7.77 (d, J = 2.4 Hz, 1H), 6.85-6.84 (d, J = 2.4 Hz, 1H), 5.03-4.93 (m, 2H), 3.93-3.59 (m, 5H), 3.50 (s, 3H), 3.48-3.36 (m, 2H), 2.24-2.14 (m,2H), 2.07-1.93 (m, 2H) |

-continued

| Ex. No. | Structure | LC/MS [M + H]+ | RT (min)/ LC condition | 1H NMR, unless otherwise indicated, 400 MHz, Methanol-d4 |
|---|---|---|---|---|
| 266 | 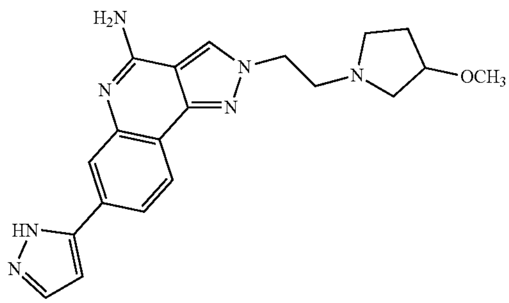 [SMILES: COC1CCN(CCn2cc3c(N)nc4cc(-c5ccn[nH]5)ccc4c3n2)C1] | 378.2 | 1.05/B | δ 8.89 (s, 1H), 8.36-8.34 (d, J = 8.2 Hz, 1H), 8.03-8.02 (m, 1H), 7.98-7.95 (m, 1H), 7.78-7.77 (d, J = 2.4 Hz, 1H), 6.84-6.83 (d, J = 2.4 Hz, 1H), 4.98-4.96 (m, 2H), 4.19 (s, 1H), 3.81 (s, 4H), 3.48 (s, 3H), 3.13-3.12 (m, 2H), 2.21 (s, 2H) |
| 267 | 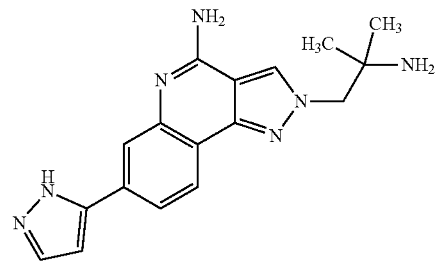 [SMILES: CC(C)(N)Cn1cc2c(N)nc3cc(-c4ccn[nH]4)ccc3c2n1] | 322.0 | 1.03/L | 1H NMR (300 MHz, Methanol-d4) δ 8.90 (s, 1H), 8.40 (d, J = 8.3 Hz, 1H), 8.04 − 7.94 (m, 2H), 7.77 (d, J = 2.4 Hz, 1H), 6.85 (d, J = 2.4 Hz, 1H), 4.75 (s, 2H), 1.45 (s, 6H) |
| 268 | 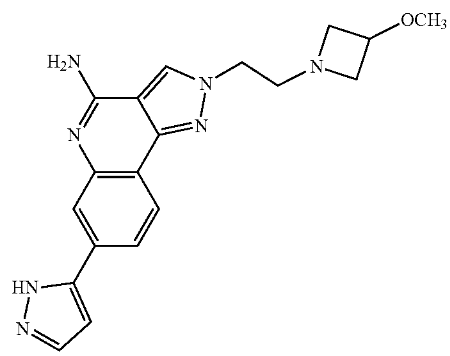 [SMILES: COC1CN(CCn2cc3c(N)nc4cc(-c5ccn[nH]5)ccc4c3n2)C1] | 364.2 | 1.02/B | δ 8.85 (s, 1H), 8.40-8.38 (d, J = 8.3 Hz, 1H), 8.05-8.04 (m, 1H), 7.98-7.96 (m, 1H), 7.78-7.77 (d, J = 2.4 Hz, 1H), 6.84-6.83 (d, J = 2.4 Hz, 1H), 4.96-4.84 (m, 2H), 4.66 −4.65 (m, 2H), 4.38-4.36 (m, 1H), 4.11-4.03 (m, 2H), 3.89-3.86 (m, 2H), 3.45 (s, 3H) |
| 269 | 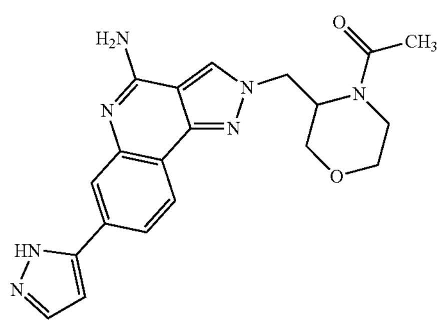 [SMILES: CC(=O)N1CCOCC1Cn1cc2c(N)nc3cc(-c4ccn[nH]4)ccc3c2n1] | 392.4 | 1.06/A | 1H NMR (400 MHz, DMSO-d6) δ 13.12 (d, J = 184.9 Hz, 1H), 8.45 (s, 1H), 8.07 (d, J = 7.9 Hz, 1H), 7.94 − 7.43 (m, 3H), 6.91 (s, 2H), 6.77 (s, 1H), 5.02 − 4.92 (m, 2H), 4.66 − 4.56 (m, 0.6H), 4.35 − 4.18 (m, 0.7H), 4.10 − 3.99 (m, 0.7H), 3.77 − 3.59 (m, 2H), 3.47 (d, J = 8.8 Hz, 2H), 3.39 (d, J = 12.6 Hz, 1H), 3.23 − 3.12 (m, 0.4H), 2.10 −1.51 (m, 3H) |
| 270 | 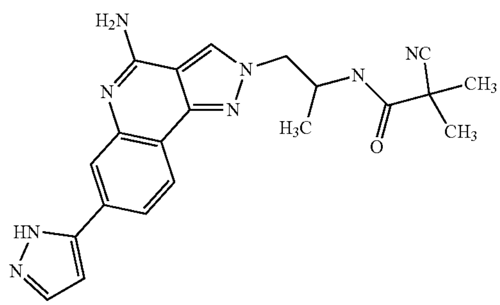 | 403.3 | 1.21/A | 1H NMR (400 MHz, DMSO-d6) 812.88 (s, 1H), 8.39 (s, 1H), 8.16 (d, J = 8.0 Hz, 1H), 8.06 (d, J = 8.5 Hz, 1H), 7.88 (s, 1H), 7.80 (s, 1H), 7.65 (d, J = 8.3 Hz, 1H), 7.54 (s, 1H), 6.95 (s, 1H), 6.87 (s, 2H), 6.77 (s, 1H), 4.56-4.42 (m, 2H), 4.38-4.28 (m, 1H), 1.43 (d, J = 15.1 Hz, 7H), 1.24 (s, 3H) |

-continued

| Ex. No. | Structure | LC/MS [M + H]+ | RT (min)/ LC condition | $^1$H NMR, unless otherwise indicated, 400 MHz, Methanol-d$_4$ |
|---|---|---|---|---|
| 271 | 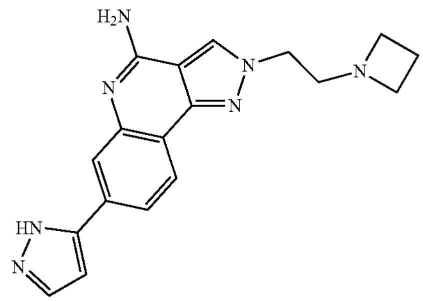 [SMILES: Nc1nc2cc(-c3ccn[nH]3)ccc2c2nn(CCN3CCC3)cc12] | 334.2 | 1.66/I | δ 8.85 (s, 1H), 8.41-8.39 (d, J = 8.4 Hz, 1H), 8.03 (s, 1H), 7.98-7.96 (m, 1H), 7.78-7.77 (d, J = 2.4 Hz, 1H), 6.84-6.83 (d, J = 2.4 Hz, 1H), 4.87-4.86 (m, 2H), 4.21 (t, J = 8.3 Hz, 4H), 3.87-3.86 (t, J = 5.5 Hz, 2H), 2.51 (s, 2H). |
| 272 | 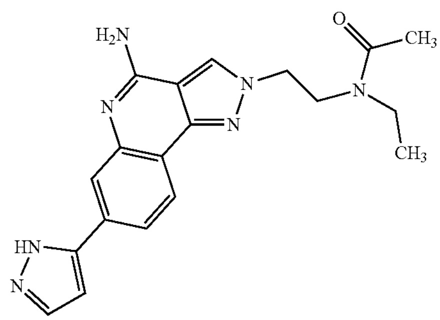 [SMILES: CCN(CCn1cc2c(N)nc3cc(-c4ccn[nH]4)ccc3c2n1)C(C)=O] | 364.3 | 0.94/B | $^1$H NMR (300 MHz, Methanol-d$_4$) δ 8.74-8.71 (d, J = 9.0 Hz, 1H), 8.35-8.32 (d, J = 8.2 Hz, 1H), 8.01-8.00 (m, 1H), 7.96-7.93 (m, 1H), 7.77-7.76 (m, 1H), 6.83-6.82 (d, J = 2.3 Hz, 1H), 4.74-4.70 (m, 2H), 4.03-3.90 (m, 2H), 3.43-3.36 (m, 2H), 2.08 (s, 2H), 1.75 (s, 1H), 1.16-1.10 (m, 3H) |
| 273 | 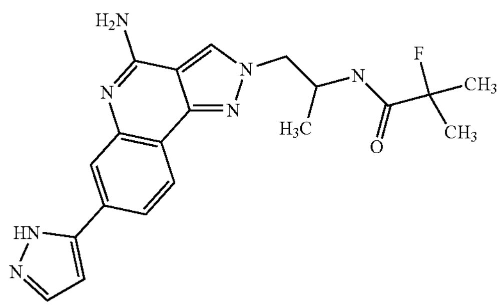 | 396.3 | 1.87/M | δ 8.44 (s, 1H), 8.24 (d, J = 8.2 Hz, 1H), 7.91 (s, 1H), 7.71 (s, 2H), 6.76 (d, J = 2.0 Hz, 1H), 4.64-4.46 (m, 3H), 1.48-1.37 (m, 9H) |
| 274 | 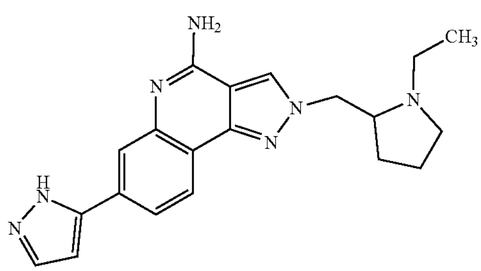 [SMILES: CCN1CCCC1Cn1cc2c(N)nc3cc(-c4ccn[nH]4)ccc3c2n1] | 362.2 | 0.71/N | $^1$H NMR (300 MHz, Methanol-d$_4$) δ 8.96 (s, 1H), 8.36-8.33 (d, J = 8.2 Hz, 1H), 8.04 (d, J = 1.5 Hz, 1H), 7.99-7.96 (m, 1H), 7.78-7.77 (d, J = 2.3 Hz, 1H), 6.85-6.84 (d, J = 2.4 Hz, 1H), 5.00-4.96 (m, 2H), 4.21-4.19 (m, 1H), 3.86-3.82 (m, 1H), 3.45-3.37 (m, 2H), 3.23-3.16 (m, 1H), 2.46-2.37 (m, 1H), 2.24-2.06 (m, 2H), 1.98-1.92 (m, 1H), 1.42-1.38 (t, J = 7.2 Hz, 3H). |
| 275 | 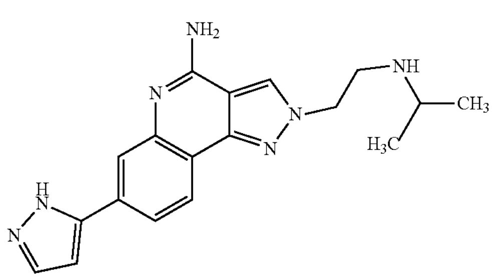 | 336.3 | 0.53/O | $^1$H NMR (300 MHz, Methanol-d$_4$) δ 8.89 (s, 1H), 8.36-8.33 (d, J = 8.1 Hz, 1H), 8.03 (s, 1H), 7.98-7.95 (m, 1H), 7.78-7.77 (d, J = 2.4 Hz, 1H), 6.84-6.83 (d, J = 2.4 Hz, 1H), 4.91-4.70 (m, 2H), 3.78-3.75 (t, J = 5.8 Hz, 2H), 3.60-3.51 (m, 1H), 1.41-1.38 (d, J = 6.5 Hz, 6H) |

-continued

| Ex. No. | Structure | LC/MS [M + H]⁺ | RT (min)/ LC condition | ¹H NMR, unless otherwise indicated, 400 MHz, Methanol-d₄ |
|---|---|---|---|---|
| 276 | 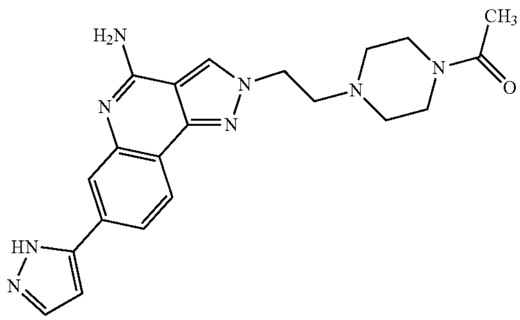 [SMILES: CC(=O)N1CCN(CCn2cc3c(N)nc4cc(-c5ccn[nH]5)ccc4c3n2)CC1] | 405.3 | 1.17/C | ¹H NMR (400 MHz, DMSO-d₆) δ 13.35 – 12.88 (m, 1H), 8.50 (s, 1H), 8.07 (d, J = 8.1 Hz, 1H), 7.87 (s, 1H), 7.79 – 7.63 (m, 2H), 6.89 (s, 2H), 6.75 (d, J = 2.1 Hz, 1H), 4.57 (t, J = 6.2 Hz, 2H), 3.43 (m, 4H), 2.88 (t, J = 6.2 Hz, 2H), 2.45 (m, 4H), 1.98 (s, 3H) |
| 277 | 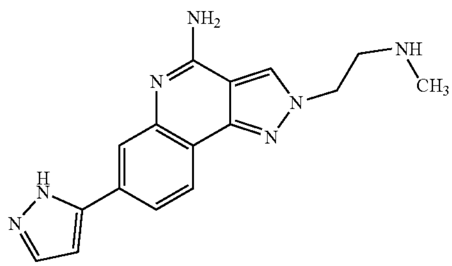 [SMILES: CNCCn1cc2c(N)nc3cc(-c4ccn[nH]4)ccc3c2n1] | 308.3 | 0.70/B | ¹H NMR (300 MHz, Methanol-d₄) δ 8.46 (s, 1), 8.27-8.24 (d, J = 8.2 Hz, 1H), 7.92 (s, 1H), 7.70 (s, 2H), 6.77-6.76 (d, J = 2.2 Hz, 1H), 4.62-4.58 (t, J = 6.0 Hz, 2H), 3.22-3.18 (t, J = 6.1 Hz, 2H), 2.44 (s, 3H) |
| 278 | 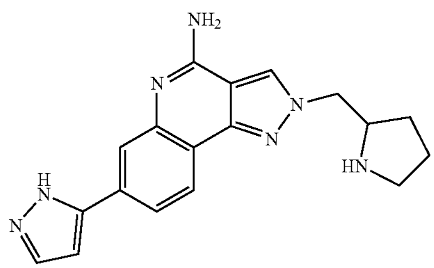 [SMILES: Nc1nc2cc(-c3ccn[nH]3)ccc2c2nn(CC3CCCN3)cc12] | 334.2 | 1.00/B | δ 8.87(s, 1H), 8.40-8.38 (d, J = 8.3 Hz, 1H), 8.04 (s, 1H), 7.97-7.96 (m, 1H), 7.78 (s, 1H), 6.84-6.83 (d, J = 2.4 Hz, 1H), 5.05-5.01 (m, 1H), 4.87-4.75 (m, 1H), 4.20-4.18 (m, 1H), 3.48-3.37 (m, 2H), 2.42 – 2.38 (m, 1H), 2.19 – 2.06 (m, 2H), 1.94-1.86 (m, 1H) |
| 279 | 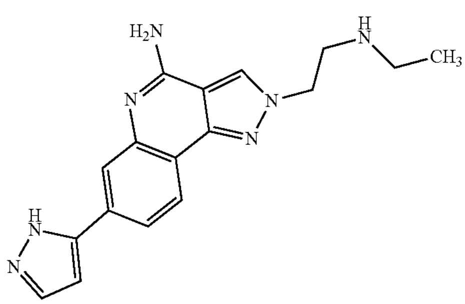 [SMILES: CCNCCn1cc2c(N)nc3cc(-c4ccn[nH]4)ccc3c2n1] | 322.1 | 0.64/N | ¹H NMR (300 MHz, Methanol-d₄) δ 8.89 (s, 1H), 8.38-8.35 (d, J = 8.4 Hz, 1H), 8.04 (s, 1H), 7.98-7.95 (d, J = 8.4 Hz, 1H), 7.77-7.76 (m, 1H), 6.84-6.83 (d, J = 2.4 Hz, 1H), 4.99-4.90 (m, 2H), 3.76-3.72 (t, J = 5.7 Hz, 2H), 3.25-3.17 (q, J = 7.2 Hz, 2H), 1.39-1.34 (t, J = 7.3 Hz, 3H) |
| 280 | 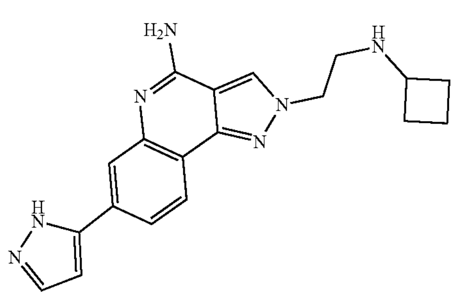 [SMILES: Nc1nc2cc(-c3ccn[nH]3)ccc2c2nn(CCNC3CCC3)cc12] | 348.3 | 1.06/A | ¹H NMR (300 MHz, Methanol-d₄) δ 8.88 (s, 1H), 8.35-8.32 (d, J = 8.3 Hz, 1H), 8.01-7.98 (m, 1H), 7.96-7.92 (m, 1H), 7.77-7.76 (d, J = 2.4 Hz, 1H), 6.84-6.83 (d, J = 2.4 Hz, 1H), 4.87 (s, 2H), 3.93-3.83 (m, 1H), 3.66-3.62 (t, J = 5.6 Hz, 2H), 2.37-2.15 (m, 4H), 1.96-1.84 (m, 2H) |

| Ex. No. | Structure | LC/MS [M + H]⁺ | RT (min)/ LC condition | ¹H NMR, unless otherwise indicated, 400 MHz, Methanol-d₄ |
|---|---|---|---|---|
| 281 | 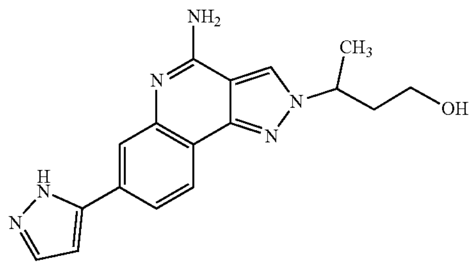 [SMILES: CC(CCO)n1cc2c(N)nc3cc(-c4ccn[nH]4)ccc3c2n1] | 323.2 | 1.22/B | δ 8.80 (s, 1H), 8.35-8.33 (d, J = 8.3 Hz, 1H), 8.04-8.03 (m, 1H), 7.95-7.93 (m, 1H), 7.77-7.76 (d, J = 2.3 Hz, 1H), 6.83-6.82 (d, J = 2.4 Hz, 1H), 4.99-4.88 (m, 1H), 3.62-3.57 (m, 1H), 3.35-3.33 (m, 1H), 2.36-2.34 (m, 1H), 2.20-2.10 (m, 1H), 1.72-1.70 (d, J = 6.8 Hz, 3H |
| 282 | 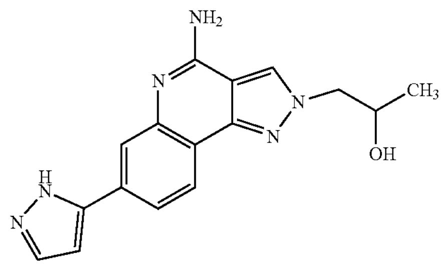 [SMILES: CC(O)Cn1cc2c(N)nc3cc(-c4ccn[nH]4)ccc3c2n1] | 309.2 | 1.19/B | δ 8.86 (s, 1H), 8.34-8.32 (d, J = 8.3 Hz, 1H), 8.12 (s, 1H), 8.02-7.94 (m, 1H), 7.79-7.78 (d, J = 2.4 Hz, 1H), 6.85-6.84 (d, J = 2.4 Hz, 1H), 4.57-4.57 (m, 1H), 4.43-4.31 (m, 2H), 1.39-1.38 (d, J = 5.8 Hz, 3H) |
| 283 | 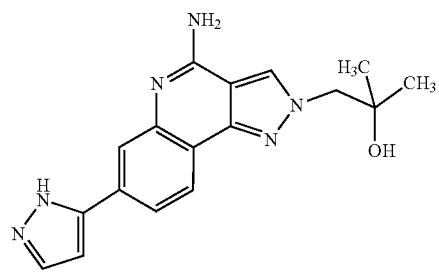 [SMILES: CC(C)(O)Cn1cc2c(N)nc3cc(-c4ccn[nH]4)ccc3c2n1] | 323.2 | 1.25/B | ¹H NMR (300 MHz, Methanol-d₄) δ 8.84 (s, 1H), 8.34-8.32 (d, J = 8.7 Hz, 1H), 8.02 (s, 1H), 7.96-7.93 (m, 1H), 7.79-7.78 (d, J = 2.4 Hz, 1H), 6.85-6.84 (d, J = 1.8 Hz, 1H), 4.48 (s, 2H), 1.30 (s, 6H) |
| 284 | 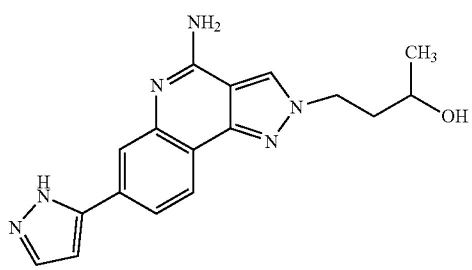 [SMILES: CC(O)CCn1cc2c(N)nc3cc(-c4ccn[nH]4)ccc3c2n1] | 323.2 | 2.03/H | δ 8.73(s, 1H), 8.29-8.29 (d, J = 8.3 Hz, 1H), 7.98-7.97 (m, 1H), 7.93-7.90 (m, 1H), 7.77-7.76 (d, J = 2.4 Hz, 1H), 6.83-6.82 (d, J = 2.3 Hz, 1H), 4.62-4.59 (m, 2H), 3.79-3.71 (m, 1H), 2.26-2.20 (m, 1H), 2.19-2.05 (m, 1H), 1.26-1.24 (d, J = 6.2 Hz, 3H) |
| 285 | 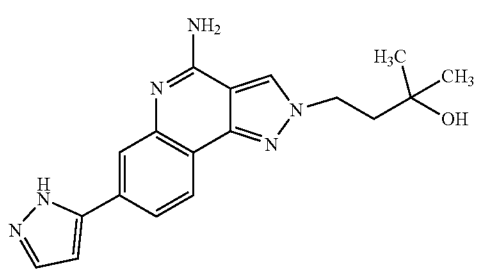 [SMILES: CC(C)(O)CCn1cc2c(N)nc3cc(-c4ccn[nH]4)ccc3c2n1] | 337.2 | 2.19/H | δ 8.75 (s, 1H), 8.32-8.30 (d, J = 8.3 Hz, 1H), 8.00 (s, 1H), 7.94-7.92 (m, 1H), 7.77-7.76 (d, J = 2.4 Hz, 1H), 6.83-6.82 (d, J = 2.4 Hz, 1H), 4.65-4.61 (m, 2H), 2.24-2.20 (m, 2H), 1.31 (s, 6H) |

Example 286

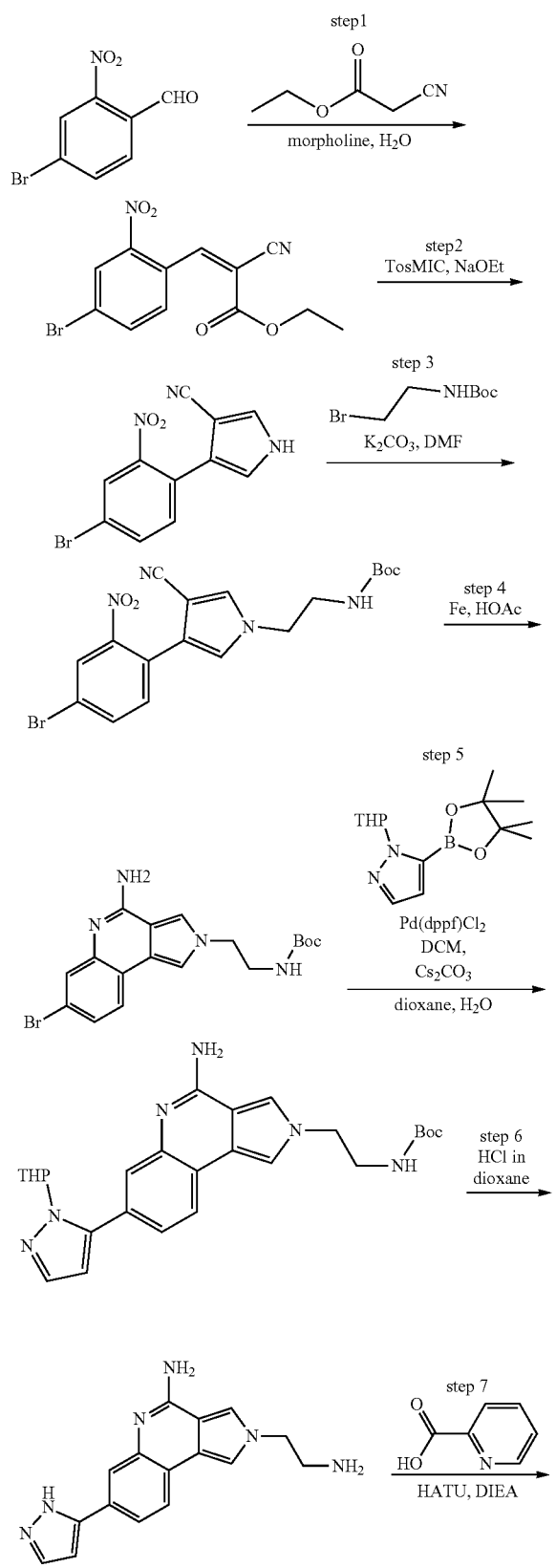

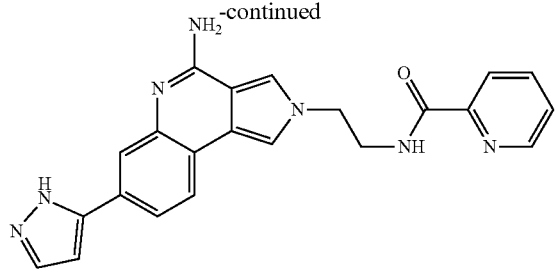

Step 1. Preparation of ethyl (2 Z)-3-(4-bromo-2-nitrophenyl)-2-cyanoprop-2-enoate Into a 100-mL round-bottom flask was added 4-bromo-2-nitrobenzaldehyde (8 g, 34.8 mmol, 1 equiv), H$_2$O (40 mL), ethyl 2-cyanoacetate (4.33 g, 38.2 mmol, 1.1 equiv), morpholine (0.30 g, 3.4 mmol, 0.1 equiv). The resulting solution was stirred at rt for 1 hr. The resulting solution was diluted with 50 mL of H$_2$O. The resulting solution was extracted with 2×200 mL of ethyl acetate. The organic layer was washed with 2×200 mL of brine. The resulting solution was dried over anhydrous sodium sulfate and concentrated. This resulted in 11 g (97.3%) of ethyl (2Z)-3-(4-bromo-2-nitrophenyl)-2-cyanoprop-2-enoate as a yellow solid.

Step 2. Preparation of 4-(4-bromo-2-nitrophenyl)-1H-pyrrole-3-carbonitrile

Into a 250-mL round-bottom flask was placed ethyl (2Z)-3-(4-bromo-2-nitrophenyl)-2-cyanoprop-2-enoate (12 g, 36.9 mmol, 1 equiv), EtOH (100 mL). This was followed by the addition of EtONa in EtOH (16.7 mL, 44.7 mmol, 1.2 equiv) dropwise with stirring at 5° C. in 30 min. To this was added a solution of TosMIC (8.65 g, 44.3 mmol, 1.2 equiv) in DCM (50 mL) dropwise with stirring at 5° C. in 20 min. The resulting solution was stirred for 2 hr at 25° C. The resulting solution was diluted with 500 mL of H$_2$O. The pH value of the solution was adjusted to 8 with conc. HCl. The resulting solution was extracted with 3×500 mL of DCM. The resulting mixture was washed with 2×500 mL of brine. The organic layer was dried over anhydrous sodium sulfate and concentrated. The residue was applied onto a silica gel column with ethyl acetate/petroleum ether (1:3). This resulted in 6.8 g (63.1%) of 4-(4-bromo-2-nitrophenyl)-1H-pyrrole-3-carbonitrile as a yellow solid. LC-MS (ES, m/z): [M+H]+=291.9. $^1$H NMR (300 MHz, DMSO-d$_6$) δ 8.41 (d, J=1.9 Hz, 1H), 8.15 (dd, J=8.3, 1.9 Hz, 1H), 7.78 (d, J=8.5 Hz, 1H), 7.74 (d, J=11.9 Hz, 1H), 6.19 (d, J=11.7 Hz, 1H).

Step 3. Preparation of tert-butyl N-[2-[3-(4-bromo-2-nitrophenyl)-4-cyano-1H-pyrrol-1-yl]ethyl]carbamate Into a 50-mL round-bottom flask was placed 4-(4-bromo-2-nitrophenyl)-1H-pyrrole-3-carbonitrile (1.8 g, 6.2 mmol, 1 equiv), DMF (15 mL), Cs$_2$CO$_3$ (6.02 g, 18.5 mmol, 3 equiv), tert-butyl N-(2-bromoethyl)carbamate (2.07 g, 9.2 mmol, 1.5 equiv). The resulting solution was stirred for 3 hr at 80° C. The resulting solution was diluted with 100 mL of H$_2$O. The resulting solution was extracted with 3×100 mL of ethyl acetate. The resulting mixture was washed with 3×100 ml of brine. The mixture was dried over anhydrous sodium sulfate and concentrated. This resulted in 2.1 g (78.3%) of tert-butyl N-[2-[3-(4-bromo-2-nitrophenyl)-4-cyano-1H-pyrrol-1-yl]

ethyl]carbamate as yellow oil. LC-MS: (ES, m/z): [M+H]⁺ =435.1 ¹H NMR (300 MHz, Methanol-d₄) δ 8.12 (d, J=2.0 Hz, 1H), 7.86 (dd, J=8.3, 2.0 Hz, 1H), 7.52-7.44 (m, 2H), 6.98-6.93 (m, 1H), 4.06 (t, J=6.1 Hz, 2H), 3.39 (t, J=5.9 Hz, 2H), 1.40 (s, 9H).

Step 4. Preparation of tert-butyl N-(2-[4-amino-7-bromo-2H-pyrrolo[3,4-c]quinolin-2-yl]ethyl)carbamate Into a 100-mL round-bottom flask was placed tert-butyl N-[2-[3-(4-bromo-2-nitrophenyl)-4-cyano-1H-pyrrol-1-yl] ethyl]carbamate (2.1 g, 4.8 mmol, 1 equiv), HOAc (20 mL). This was followed by the addition of Fe (1.35 g, 24.3 mmol, 5 equiv), in portions at 50° C. The resulting solution was stirred for 2 hr at 50° C. The resulting solution was diluted with 100 mL of MeOH. The solids were filtered out. The resulting mixture was concentrated. The residue was applied onto a silica gel column with dichloromethane/methanol (15:1). This resulted in 1.8 g (92.1%) of tert-butyl N-(2-[4-amino-7-bromo-2H-pyrrolo[3,4-c]quinolin-2-yl]ethyl)carbamate as a yellow solid. LC-MS (ES, m/z): [M+H]⁺=405.1 ¹H NMR (300 MHz, DMSO-d₆) δ 7.76 (d, J=8.2 Hz, 1H), 7.65 (s, 1H), 7.60 (s, 1H), 7.46 (d, J=1.7 Hz, 1H), 7.25-7.17 (m, 1H), 7.17-6.91 (m, 3H), 4.21 (t, J=5.6 Hz, 2H), 3.36 (q, J=5.7 Hz, 2H), 1.35 (s, 9H).

Step 5. tert-butyl N-(2-[4-amino-7-[1-(oxan-2-yl)-1H-pyrazol-5-yl]-2H-pyrrolo[3,4-c]quinolin-2-yl] ethyl)carbamate Into a 50-mL round-bottom flask purged and maintained with an inert atmosphere of nitrogen, was placed tert-butyl N-(2-[4-amino-7-bromo-2H-pyrrolo[3,4-c]quinolin-2-yl] ethyl)carbamate (1.8 g, 4.441 mmol, 1 equiv), 1-(oxan-2-yl)-5-(4,4,5,5-tetramethyl-1,3,2-dioxaborolan-2-yl)-1H-pyrazole (1.85 g, 6.662 mmol, 1.5 equiv), Cs₂CO₃ (4.34 g, 13.324 mmol, 3 equiv), dioxane (20 mL), Pd(dppf) Cl₂·CH₂Cl₂ (0.73 g, 0.888 mmol, 0.2 equiv), H₂O (0.5 mL). The resulting solution was stirred for 16 hr at 90 degrees C. The resulting mixture was concentrated. The residue was applied onto a silica gel column with dichloromethane/methanol (12:1). This resulted in 1.8 g (85%) of tert-butyl N-(2-[4-amino-7-[1-(oxan-2-yl)-1H-pyrazol-5-yl]-2H-pyrrolo[3,4-c]quinolin-2-yl]ethyl)carbamate as a yellow solid. LC-MS (ES, m/z): [M+H]⁺=477.2

Step 6. 2-(2-aminoethyl)-7-(1H-pyrazol-5-yl)-2H-pyrrolo[3,4-c]quinolin-4-amine

Into a 50-mL round-bottom flask, was placed tert-butyl N-(2-[4-amino-7-[1-(oxan-2-yl)-1H-pyrazol-5-yl]-2H-pyrrolo[3,4-c]quinolin-2-yl]ethyl)carbamate (1.6 g, 3.357 mmol, 1 equiv), HCl (gas) in 1,4-dioxane (20 mL). The resulting solution was stirred for 2 hr at rt. The resulting mixture was concentrated. This resulted in 1.4 g of 2-(2-aminoethyl)-7-(1H-pyrazol-5-yl)-2H-pyrrolo[3,4-c]quinolin-4-amine as a yellow solid. LC-MS-PH-BMS-L15-001-6: (ES, m/z): [M+H]⁺=293.1. ¹H NMR (400 MHz, Methanol-d₄) δ 8.13-8.04 (m, 2H), 7.92-7.83 (m, 2H), 7.83-7.86 (m, 1H), 7.80-7.75 (d, J=2.3 Hz, 1H), 6.80 (d, J=2.3 Hz, 1H), 4.65 (t, J=6.3 Hz, 2H), 3.58 (t, J=6.2 Hz, 2H).

Step 7. Preparation of N-[2-[4-amino-7-(1H-pyrazol-5-yl)-2H-pyrrolo[3,4-c]quinolin-2-yl]ethyl]pyridine-2-carboxamide Into a 50-mL round-bottom flask, was placed 2-(2-aminoethyl)-7-(1H-pyrazol-5-yl)-2H-pyrrolo[3,4-c]quinolin-4-amine (150 mg, 0.282 mmol, 1 equiv, 55%), DCM (5 mL), HATU (161 mg, 0.423 mmol, 1.50 equiv), DIEA (129 mg, 0.998 mmol, 3.54 equiv), pyridine-2-carboxylic acid (35 mg, 0.284 mmol, 1.01 equiv). The resulting solution was stirred for 2 h at rt. The resulting mixture was concentrated. The crude product was purified by Prep-HPLC with the following conditions: Column: XBridge Prep OBD C18 Column 30×150 mm 5 um; Mobile Phase A: Water (10 MMOL/L NH₄HCO₃), Mobile Phase B: ACN; Flow rate: 60 mL/min; Gradient: 15% B to 27% B in 7.5 min; 254/210 nm; RT: 6.87 min. This resulted in 14.9 mg (13.13%) of N-[2-[4-amino-7-(1H-pyrazol-5-yl)-2H-pyrrolo[3,4-c]quinolin-2-yl]ethyl]pyridine-2-carboxamide as a light yellow solid. LC-MS: (ES, m/z): [M+H]⁺=398.3 ¹H NMR (400 MHz, DMSO-d₆) δ 12.78-12.74 (m, 1H), 9.25 (s, 1H), 9.09 (t, J=6.0 Hz, 1H), 8.57-8.65 (m, 2H), 8.13 (d, J=1.9 Hz, 1H), 8.05-7.94 (m, 5H), 7.74-7.78 (m, 2H), 7.61-7.74 (m, 1H), 6.76 (d, J=2.3 Hz, 1H), 4.50 (t, J=6.0 Hz, 2H), 3.78-3.96 (m, 2H).

Examples 287 and 288

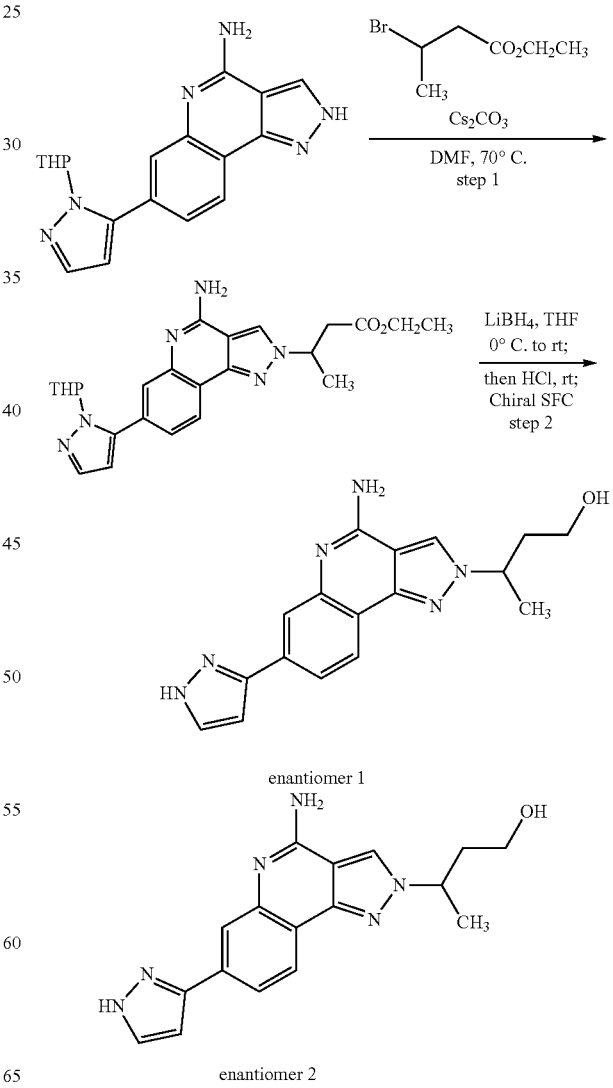

Step 1. Ethyl 3-(4-amino-7-(1-(tetrahydro-2H-pyran-2-yl)-1H-pyrazol-5-yl)-2H-pyrazolo[4,3-c]quinolin-2-yl)butanoate To a suspension of 7-(1-(tetrahydro-2H-pyran-2-yl)-1H-pyrazol-5-yl)-2H-pyrazolo[4,3-c]quinolin-4-amine (100 mg, 0.299 mmol) and cesium carbonate (292 mg, 0.897 mmol) in DMF (997 µl) was added ethyl 3-bromobutanoate (87 mg, 0.449 mmol). The suspension was stirred at 70° C. for 3 h. Additional ethyl 3-bromobutanoate (87 mg, 0.449 mmol) was added. The reaction was stirred at 70° C. for 2 h and then cooled to rt. The reaction was diluted with H$_2$O (20 mL) and extracted with EtOAc (3×20 mL). The combined organic layers were washed with sat. aq. NaCl (20 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide ethyl 3-(4-amino-7-(1-(tetrahydro-2H-pyran-2-yl)-1H-pyrazol-5-yl)-2H-pyrazolo[4,3-c]quinolin-2-yl)butanoate (85.8 mg, 0.191 mmol, 64.0% yield) as a white solid. LC-MS m/z 449 [M+H]$^+$; $^1$H NMR (400 MHz, DMSO-d$_6$) δ 8.56 (s, 1H), 8.15 (d, J=8.0 Hz, 1H), 7.59 (dd, J=5.1, 1.6 Hz, 2H), 7.31 (d, J=8.2 Hz, 1H), 6.99 (s, 2H), 6.50 (d, J=1.7 Hz, 1H), 5.29 (br d, J=9.7 Hz, 1H), 5.12-5.02 (m, 1H), 4.09-3.95 (m, 3H), 3.58 (br t, J=9.4 Hz, 1H), 3.15-3.06 (m, 1H), 3.05-2.97 (m, 1H), 2.47-2.37 (m, 1H), 1.99-1.92 (m, 1H), 1.83-1.74 (m, 1H), 1.63 (d, J=6.7 Hz, 3H), 1.55 (br t, J=8.6 Hz, 3H), 1.09 (t, J=7.1 Hz, 3H).

Step 2. 3-(4-amino-7-(1H-pyrazol-3-yl)-2H-pyrazolo[4,3-c]quinolin-2-yl)butan-1-ol To a 0° C. suspension of ethyl 3-(4-amino-7-(1-(tetrahydro-2H-pyran-2-yl)-1H-pyrazol-5-yl)-2H-pyrazolo[4,3-c]quinolin-2-yl)butanoate (85 mg, 0.190 mmol) in THF (1895 µl) was added lithium borohydride (2 M solution in THF) (284 µl, 0.569 mmol) dropwise. The reaction was stirred at rt for 2 h. Additional lithium borohydride (2 M solution in THF) (284 µl, 0.569 mmol) was added dropwise. The reaction was stirred at rt for 1.25 h before methanol (46.1 µl, 1.137 mmol) was added dropwise. The reaction was stirred at rt for 3 days. The reaction was diluted with H$_2$O (20 mL) and extracted with EtOAc (4×20 mL). The combined organic layers were washed with sat. aq. NaCl (20 mL), dried over Na$_2$SO$_4$, filtered, and concentrated in vacuo. The crude material was dissolved in MeOH (630 µL) and 4 M hydrogen chloride in dioxane (47.4 µl, 0.190 mmol) was added. The reaction was diluted with MeOH (1.5 mL) and CH$_2$Cl$_2$ (1.5 mL) (giving a clear solution), and silica-supported carbonate (SiliBond Carbonate, Silicycle, 0.51 mmol/g) (1.5 g, 0.765 mmol) was added. The suspension was stirred at rt for 1 h. The mixture was filtered and washed with 50% MeOH—CH$_2$Cl$_2$ (3×6 mL). Celite was added to the filtrate (enough to fill a 5 g load cartridge). The mixture was concentrated in vacuo. This material was dry loaded and purified by flash chromatography (12 g RediSep Gold silica gel with 5 g solid load cartridge; linear gradient 0-70% MeOH—CH$_2$Cl$_2$) to provide 3-(4-amino-7-(1H-pyrazol-3-yl)-2H-pyrazolo[4,3-c]quinolin-2-yl)butan-1-ol (38 mg, 55%). LCMS m/z 323.6 [M+H]$^+$.

The racemic compound was then purified via preparative chiral SFC with the following conditions to provide Example 287 and 288 as single unassigned isomers: Instrument: Berger SFC MGII: Column: ChiralCEL YMC SB, 30×250 mm. 5 micron; Mobile Phase: 85% CO$_2$/15% MeOH w/0.1% NH$_4$OH; Flow Conditions: 85 mL/min; Detector Wavelength: 220 nm. Example 287 (first-eluting isomer). Example 288 (second-eluting isomer).

Analytical Chiral SFC Conditions: Instrument: Agilent analytical SFC; Column: YMC SB, 4.6×250 mm, 5 micron; Mobile Phase: 85% CO$_2$/15% IPA w/0.1% NH$_4$OH; Flow Conditions: 2 mL/min; Detector Wavelength: 220 nm. Example 287 (first-eluting isomer) RT: 30.9 min. Example 288 (second-eluting isomer) RT: 33.4 min.

Example 287: LC-MS m/z 323 [M+H]$^+$; $^1$H NMR (400 MHz, DMSO-d$_6$) δ 13.47-12.74 (m, 1H), 8.61 (br s, 1H), 8.11 (d, J=8.1 Hz, 1H), 8.00-6.94 (m, 5H), 6.77 (br s, 1H), 4.88-4.77 (m, 1H), 4.61 (br t, J=4.7 Hz, 1H), 3.43-3.35 (m, 1H), 3.26-3.18 (m, 1H), 2.20-2.10 (m, 1H), 2.04-1.94 (m, 1H), 1.58 (br d, J=6.6 Hz, 3H).

Example 288: LC-MS m/z 323 [M+H]$^+$; $^1$H NMR (400 MHz, DMSO-d$_6$) δ 13.41-12.85 (m, 1H), 8.59 (br s, 1H), 8.10 (d, J=8.1 Hz, 1H), 7.99-6.91 (m, 5H), 6.76 (br s, 1H), 4.87-4.77 (m, 1H), 4.61 (t, J=4.9 Hz, 1H), 3.42-3.34 (m, 1H), 3.26-3.18 (m, 1H), 2.20-2.10 (m, 1H), 2.04-1.93 (m, 1H), 1.58 (d, J=6.6 Hz, 3H).

Example 289. Preparation of (2R)-3-[4-amino-7-(1H-pyrazol-3-yl)-2H-pyrazolo[4,3-c]quinolin-2-yl]-2-methoxypropan-1-ol, HCl

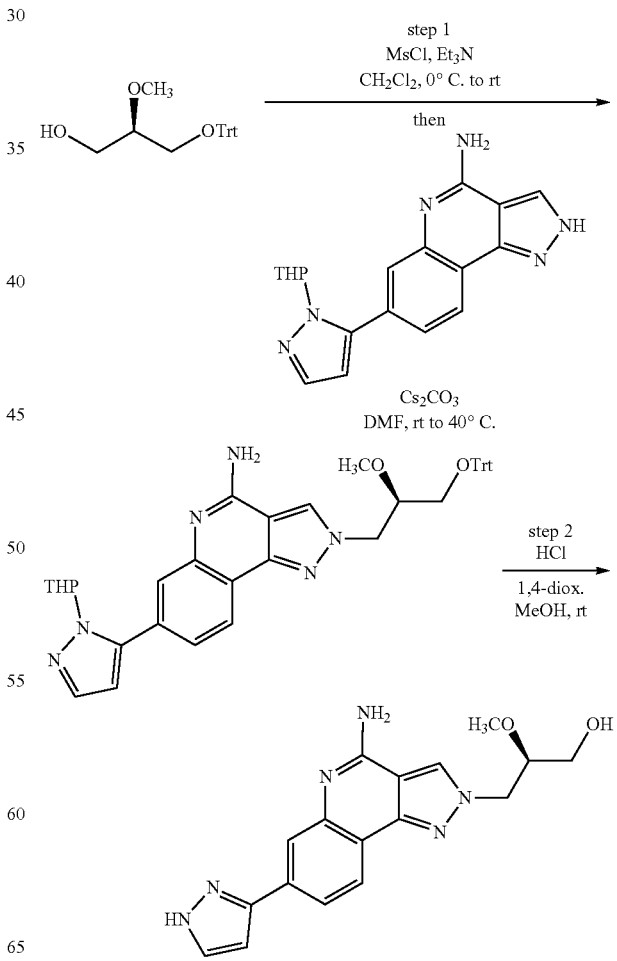

Step 1. 2-((R)-2-methoxy-3-(trityloxy)propyl)-7-(1-(tetrahydro-2H-pyran-2-yl)-1H-pyrazol-5-yl)-2H-pyrazolo[4,3-c]quinolin-4-amine To a 0° C. solution of (R)-2-methoxy-3-(trityloxy)propan-1-ol (156 mg, 0.449 mmol) in CH$_2$Cl$_2$ (997 µL) was added triethylamine (125 µl, 0.897 mmol), followed by methanesulfonyl chloride (34.7 µl, 0.449 mmol). The reaction was stirred at rt for 1 h. The reaction diluted with H$_2$O (2 mL) and extracted with CH$_2$Cl$_2$ (2×2 mL). The combined organic layers were dried over Na$_2$SO$_4$, filtered, and concentrated in vacuo.

The crude material was dissolved in DMF (997 µl) and added to a mixture of 7-(1-(tetrahydro-2H-pyran-2-yl)-1H-pyrazol-5-yl)-2H-pyrazolo[4,3-c]quinolin-4-amine (100 mg, 0.299 mmol) and cesium carbonate (292 mg, 0.897 mmol). The suspension was stirred at rt for 2 h, then at 40° C. for 3 h, and then at rt overnight. The reaction was diluted with H$_2$O (30 mL) and extracted with EtOAc (2×30 mL). The combined organic layers were washed with sat. aq. NaCl (30 mL), dried over Na$_2$SO$_4$, filtered, and concentrated in vacuo. The crude material was purified by flash chromatography (24 g RediSep Gold silica gel; linear gradient 0-10% MeOH—CH$_2$Cl$_2$) to provide 2-((R)-2-methoxy-3-(trityloxy)propyl)-7-(1-(tetrahydro-2H-pyran-2-yl)-1H-pyrazol-5-yl)-2H-pyrazolo[4,3-c]quinolin-4-amine (80 mg, 40%) as a white solid. The product was the second of the two observed regioisomeric peaks to elute from the column. LC-MS m/z 665 [M+H]$^+$; $^1$H NMR (400 MHz, DMSO-d$_6$) δ 8.48-8.44 (m, 1H), 8.13-8.08 (m, 1H), 7.61-7.57 (m, 2H), 7.45-7.40 (m, 6H), 7.36-7.29 (m, 7H), 7.28-7.22 (m, 3H), 7.01 (s, 2H), 6.52-6.47 (m, 1H), 5.34-5.28 (m, 1H), 4.68-4.53 (m, 2H), 4.09-4.00 (m, 1H), 3.92-3.84 (m, 1H), 3.63-3.51 (m, 1H), 3.22-3.19 (m, 3H), 3.25-3.15 (m, 1H), 3.05-2.97 (m, 1H), 2.44-2.36 (m, 1H), 1.98-1.91 (m, 1H), 1.84-1.76 (m, 1H), 1.63-1.48 (m, 3H).

Step 2. (R)-3-(4-amino-7-(1H-pyrazol-3-yl)-2H-pyrazolo[4,3-c]quinolin-2-yl)-2-methoxypropan-1-ol, HCl To a rt solution of 2-((R)-2-methoxy-3-(trityloxy)propyl)-7-(1-(tetrahydro-2H-pyran-2-yl)-1H-pyrazol-5-yl)-2H-pyrazolo[4,3-c]quinolin-4-amine (80 mg, 0.120 mmol) in MeOH (401 µl) was added 4 M hydrochloric acid in dioxane (90 µl, 0.361 mmol). The reaction was stirred at rt for 15 min. The reaction was added to Et$_2$O (6 mL) and the resulting solids were collected by vacuum filtration and washed with Et$_2$O (3×2 mL). The solids were dissolved in 1:1 MeCN—H$_2$O (2 mL), filtered, frozen at −78° C., and lyophilized to provide (R)-3-(4-amino-7-(1H-pyrazol-3-yl)-2H-pyrazolo[4,3-c]quinolin-2-yl)-2-methoxypropan-1-ol, HCl (34 mg, 75% yield) as a white solid. $^1$H NMR (400 MHz, DMSO-d$_6$) δ 13.16 (s, 1H), 9.81-9.66 (m, 1H), 8.97 (s, 1H), 8.68-8.53 (m, 1H), 8.20 (d, J=8.2 Hz, 1H), 8.12 (d, J=1.1 Hz, 1H), 7.92 (dd, J=8.2, 1.5 Hz, 1H), 7.84 (d, J=2.2 Hz, 1H), 6.82 (d, J=2.3 Hz, 1H), 4.67 (dd, J=14.1, 3.5 Hz, 1H), 4.52 (dd, J=14.1, 7.7 Hz, 1H), 3.71 (td, J=8.1, 5.0 Hz, 1H), 3.53 (d, J=5.1 Hz, 2H), 3.26 (s, 3H). Analytical LC/MS conditions: Column: Acquity UPLC BEH C18, 2.1 mm×50 mm, 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). m/z 339.2 [M+H]$^+$; RT: 0.52 min.

Example 290 to Example 302 were prepared according to synthetic procedures similar to those described for Examples 150 and 151 from the appropriate starting materials. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/mm; Detection: MS and UV (220 nm). Examples 300 and 299 were prepared as single unassigned isomers by purification of the racemic material via chiral SFC with the following conditions: Instrument: Waters 100 Prep SFC; Column: Chiral IC, 21×250 mm. 5 micron; Mobile Phase: 60% CO$_2$/40% MeOH w/0.1% DEA; Flow Conditions: 60 mL/min; Detector Wavelength: 220 nm. Example 300 (first-eluting isomer) RT: 7.50 min. Example 299 (second-eluting isomer) RT: 9.91 min. Analytical Chiral SFC Conditions: Instrument: Shimadzu Nexera UC SFC; Column: Chiral AD, 4.6×100 mm, 5 micron; Mobile Phase: 85% CO$_2$/15% MeOH w/0.1H)DEA; Flow Conditions: 2 mL/min; Detector Wavelength: 220 nm. Example 300 (first-eluting isomer) RT: 5.3 mi. Example 299 (second-eluting isomer) RT: 6.8 min.

| Ex. No. | Structure | LC/MS [M + H]$^+$ | RT (min) | $^1$H NMR (500 MHz, DMSO-d$_6$) |
|---|---|---|---|---|
| 290 | 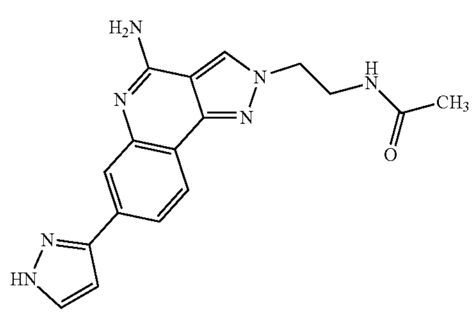 [SMILES: CC(=O)NCCn1cc2c(N)nc3cc(-c4cc[nH]n4)ccc3c2n1] | 336.2 | 1.0 | δ 8.43 (s, 1H), 8.09 (d, J = 8.2 Hz, 1H), 8.07 – 8.04 (m, 1H), 7.87 (s, 1H), 7.77 – 7.66 (m, 1H), 7.63 (br d, J = 6.4 Hz, 1H), 7.07 – 6.89 (m, 2H), 6.75 (d, J = 1.8 Hz, 1H), 4.45 (t, J = 6.0 Hz, 2H), 3.65 – 3.59 (m, 2H), 1.80 (s, 3H) |

| Ex. No. | Structure | LC/MS [M + H]+ | RT (min) | ¹H NMR (500 MHz, DMSO-d$_6$) |
|---|---|---|---|---|
| 291 | 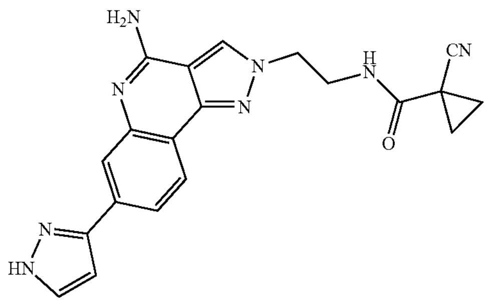 [SMILES: N#CC1(C(=O)NCCn2cc3c(N)nc4cc(-c5cc[nH]n5)ccc4c3n2)CC1] | 387.2 | 1.09 | δ 8.43 (s, 1H), 8.35 (br s, 1H), 8.10 (d, J = 8.2 Hz, 1H), 7.87 (br s, 1H), 7.78 – 7.59 (m, 2H), 7.06 – 6.90 (m, 2H), 6.76 (d, J = 1.4 Hz, 1H), 4.53 – 4.47 (m, 2H), 3.68 – 3.64 (m, 2H), 1.55 – 1.51 (m, 2H), 1.42 – 1.38 (m, 2H) |
| 292 | 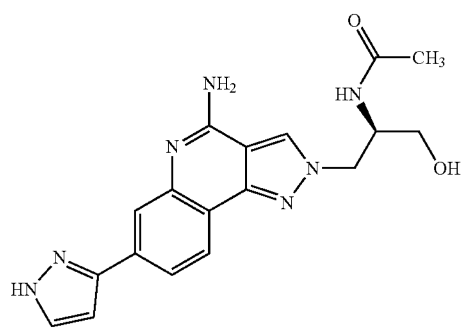 [SMILES: CC(=O)N[C@@H](CO)Cn1cc2c(N)nc3cc(-c4cc[nH]n4)ccc3c2n1] | 366.1 | 0.66 | δ 13.33 – 13.04 (m, 2H), 9.76 – 9.58 (m, 1H), 8.98 – 8.88 (m, 1H), 8.86 (s, 1H), 8.20 (d, J = 8.3 Hz, 1H), 8.14 – 8.06 (m, 1H), 7.97 (d, J = 8.5 Hz, 1H), 7.92 (br d, J = 7.7 Hz, 1H), 7.84 (br s, 1H), 6.82 (d, J = 1.9 Hz, 1H), 5.17 – 5.03 (m, 1H), 4.66 (dd, J = 13.8, 4.7 Hz, 1H), 4.45 (dd, J = 13.6, 8.1 Hz, 1H), 4.30 – 4.21 (m, 1H), 3.50 – 3.44 (m, 2H), 1.78 (s, 3H) |
| 293 | 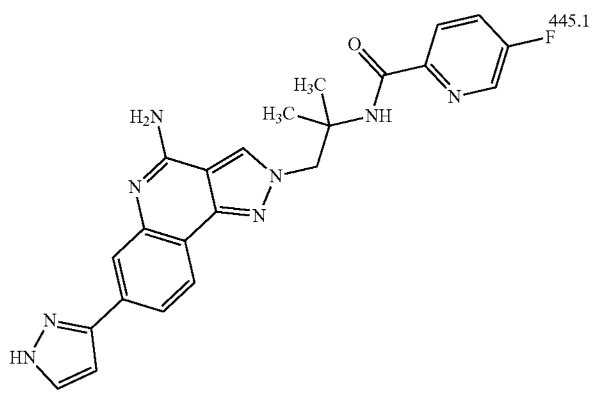 | 445.1 | 1.29 | δ 13.49 – 13.07 (m, 1H), 9.59 (br s, 1H), 9.06 (br s, 1H), 8.86 (s, 1H), 8.64 (d, J = 2.5 Hz, 1H), 8.58 (s, 1H), 8.17 (dd, J = 8.7, 4.5 Hz, 1H), 8.09 (br d, J = 8.3 Hz, 2H), 7.98 – 7.91 (m, 2H), 7.90 – 7.83 (m, 1H), 6.80 (br s, 1H), 4.89 (s, 2H), 1.48 (s, 6H) |
| 294 | 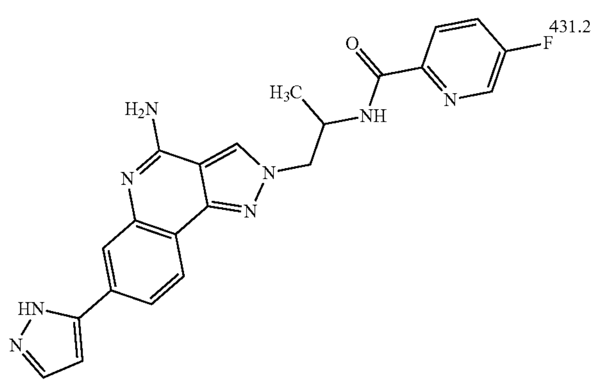 | 431.2 | 1.30 | δ 9.06 (br d, J = 7.6 Hz, 1H), 8.66 (d, J = 1.8 Hz, 1H), 8.47 (s, 1H), 8.08 (d, J = 8.2 Hz, 1H), 8.04 (dd, J = 8.5, 4.3 Hz, 1H), 7.93 – 7.82 (m, 2H), 7.71 (br s, 1H), 7.66 (br d, J = 7.3 Hz, 1H), 6.76 (s, 1H), 4.74 – 4.54 (m, 3H), 1.21 (br d, J = 5.8 Hz, 3H) |

-continued

| Ex. No. | Structure | LC/MS [M + H]+ | RT (min) | ¹H NMR (500 MHz, DMSO-d₆) |
|---|---|---|---|---|
| 295 | 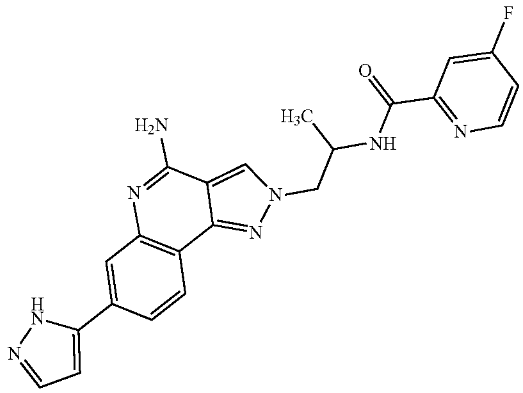 [SMILES: CC(Cn1cc2c(N)nc3cc(-c4ccn[nH]4)ccc3c2n1)NC(=O)c1cc(F)ccn1] | 431.18 | 1.29 | δ 9.22 (br d, J = 7.7 Hz, 1H), 8.79 – 8.66 (m, 1H), 8.48 (s, 1H), 8.08 (d, J = 8.2 Hz, 1H), 7.87 (s, 1H), 7.79 – 7.69 (m, 2H), 7.66 (br d, J = 8.2 Hz, 1H), 7.57 – 7.42 (m, 1H), 6.77 (d, J = 1.9 Hz, 1H), 4.73 – 4.50 (m, 3H), 1.22 (br d, J = 5.7 Hz, 3H) |
| 296 | 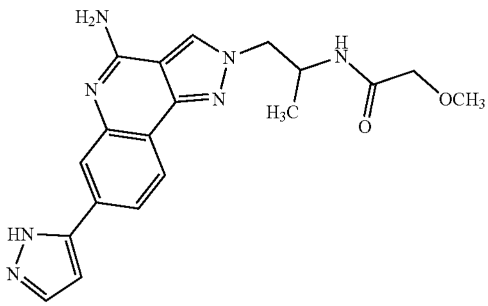 [SMILES: COCC(=O)NC(C)Cn1cc2c(N)nc3cc(-c4ccn[nH]4)ccc3c2n1] | 380.05 | 1.01 | δ 8.45 (s, 1H), 8.07 (d, J = 8.1 Hz, 1H), 8.02 (d, J = 8.3 Hz, 1H), 7.89 (s, 1H), 7.73 (br s, 1H), 7.64 (br d, J = 7.9 Hz, 1H), 6.77 (d, J = 1.8 Hz, 1H), 4.57 – 4.35 (m, 3H), 3.28 (s, 2H), 1.92 (s, 3H), 1.12 (d, J = 6.6 Hz, 3H |
| 297 | 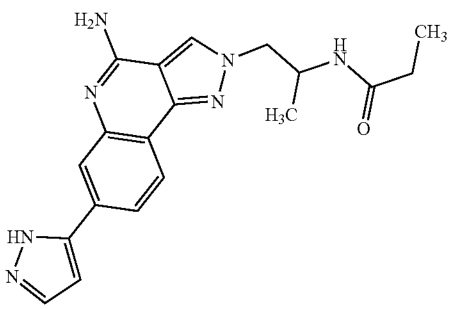 [SMILES: CCC(=O)NC(C)Cn1cc2c(N)nc3cc(-c4ccn[nH]4)ccc3c2n1] | 364.3 | 1.07 | δ 8.41 (s, 1H), 8.08 (d, J = 8.1 Hz, 1H), 7.90 – 7.82 (m, 2H), 7.72 (br s, 1H), 7.66 – 7.61 (m, 1H), 6.77 (d, J = 1.9 Hz, 1H), 4.49 – 4.34 (m, 2H), 4.31 – 4.21 (m, 1H), 2.05 (q, J = 7.5 Hz, 2H), 1.10 (d, J = 6.7 Hz, 3H), 0.94 (t, J = 7.6 Hz, 3H) |
| 298 | 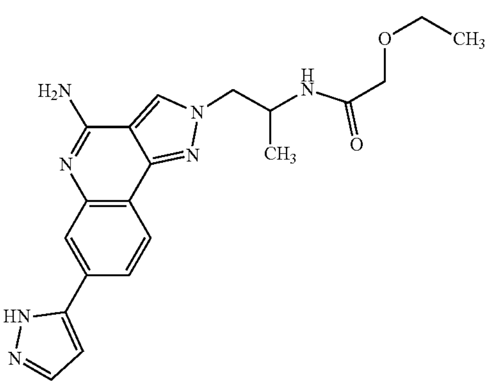 [SMILES: CCOCC(=O)NC(C)Cn1cc2c(N)nc3cc(-c4ccn[nH]4)ccc3c2n1] | 394.3 | 1.12 | δ 8.48 (s, 1H), 8.09 (br d, J = 7.9 Hz, 1H), 7.97 – 7.85 (m, 2H), 7.72 (br s, 1H), 7.66 (br d, J = 7.6 Hz, 1H), 6.77 (br d, J = 1.5 Hz, 1H), 4.50 (br d, J = 5.2 Hz, 2H), 4.44 – 4.37 (m, 1H), 3.84 – 3.72 (m, 2H), 3.47 – 3.33 (m, 2H), 1.17 – 1.07 (m, 6H) |

| Ex. No. | Structure | LC/MS [M + H]⁺ | RT (min) | ¹H NMR (500 MHz, DMSO-d₆) |
|---|---|---|---|---|
| 299 | enantiomer 1 | 350.18 | 0.98 | δ 8.42 (s, 1H), 8.09 (d, J = 7.9 Hz, 1H), 7.94 (d, J = 7.6 Hz, 1H), 7.88 (d, J = 1.2 Hz, 1H), 7.72 (br d, J = 1.5 Hz, 1H), 7.63 (br d, J = 7.3 Hz, 1H), 6.76 (d, J = 2.1 Hz, 1H), 4.41 (d, J = 6.1 Hz, 2H), 4.34 – 4.20 (m, 1H), 1.81 (s, 3H), 1.10 (d, J = 6.7 Hz, 3H) |
| 300 | enantiomer 2 | 350.19 | 0.99 | δ 8.42 (s, 1H), 8.09 (d, J = 7.9 Hz, 1H), 7.94 (d, J = 7.6 Hz, 1H), 7.88 (d, J = 1.2 Hz, 1H), 7.72 (br d, J = 1.5 Hz, 1H), 7.63 (br d, J = 7.3 Hz, 1H), 6.76 (d, J = 2.1 Hz, 1H), 4.41 (d, J = 6.1 Hz, 2H), 4.34 – 4.20 (m, 1H), 1.81 (s, 3H), 1.10 (d, J = 6.7 Hz, 3H) |
| 301 | 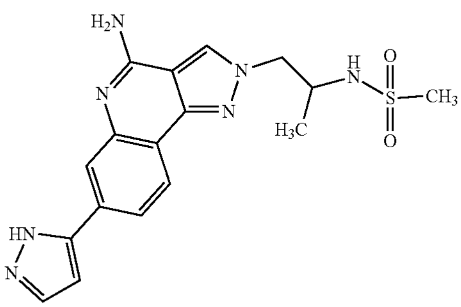 [SMILES: CC(Cn1cc2c(N)nc3cc(-c4ccn[nH]4)ccc3c2n1)NS(C)(=O)=O] | 385.9 | 1.04 | δ 8.81 (s, 1H), 8.20 (d, J = 8.2 Hz, 1H), 8.03 (br s, 1H), 7.88 (br d, J = 7.0 Hz, 1H), 7.84 – 7.68 (m, 1H), 6.82 (d, J = 2.1 Hz, 1H), 4.50 (dd, J = 13.6, 5.0 Hz, 1H), 4.38 (dd, J = 13.7, 7.9 Hz, 1H), 3.99 – 3.85 (m, 1H), 3.77 (br s, 1H), 1.22 (d, J = 6.4 Hz, 3H) |
| 302 | 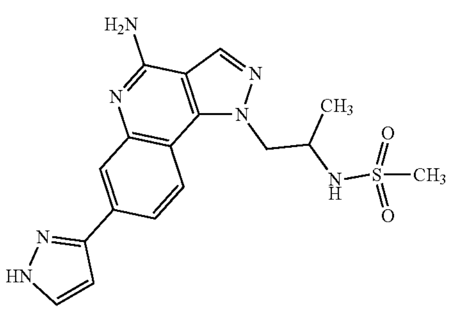 [SMILES: CC(Cn1ncc2c(N)nc3cc(-c4cc[nH]n4)ccc3c21)NS(C)(=O)=O] | 386.2 | 1.07 | δ 8.92 (s, 1H), 8.23 (br d, J = 8.5 Hz, 1H), 8.08 (br s, 1H), 7.93 (br d, J = 6.7 Hz, 1H), 7.83 (br d, J = 1.5 Hz, 1H), 7.25 (br s, 1H), 6.83 (s, 1H), 4.82 (br d, J = 6.4 Hz, 2H), 1.59 (br d, J = 6.7 Hz, 3H) |

Example 303 to Example 406 were prepared according to synthetic procedures similar to those described for Example 207 and Example 208, Example 209, Example 210, or Example 210 from the appropriate alkyl halide, mesylate, tosylate, epoxide, or alcohol starting materials, which, in some cases, may contain appropriate protecting groups. The temperature for the alkylation reactions ranged from rt to 90° C., and, in some cases, additional equivalents of the alkylating reagent were added. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% to 100% B over 3 min, then a 0.50 min hold at 100% B; Flow: 1 mL/min; Detection: MS and UV (220 nm).

The following Examples were prepared as single unassigned isomers by purification of the racemic material via chiral SFC with the following conditions:

Examples 315 and 316: Instrument: Waters 100 Prep SFC; Column: Chiral AD, 30×250 mm. 5 micron; Mobile Phase: 75% $CO_2$/25% MeOH w/0.1% DEA; Flow Conditions: 100 mL/min; Detector Wavelength: 220 nm. Example 315 (first-eluting isomer) RT: 10.61 min. Example 316 (second-eluting isomer) RT: 14.97 min. Analytical Chiral SFC Conditions: Instrument: Shimadzu Nexera UC SFC; Column: Chiralpak AD, 4.6×100 mm, 5 micron; Mobile Phase: 75% $CO_2$/25% MeOH w/0.1% DEA; Flow Conditions: 2 mL/min; Detector Wavelength: 220 nm. Example 315 (first-eluting isomer) RT: 5.2 min. Example 316 (second-eluting isomer) RT: 7.0 min.

Examples 318 and 319: Instrument: Waters 100 Prep SFC; Column: Chiral AD, 30×250 mm. 5 micron; Mobile Phase: 65% $CO_2$/35% MeOH w/0.1% DEA; Flow Conditions: 100 mL/min; Detector Wavelength: 220 nm. Example 318 (first-eluting isomer) RT: 5.47 min. Example 319 (second-eluting isomer) RT: 11.53 min. Analytical Chiral SFC Conditions: Instrument: Shimadzu Nexera UC SFC; Column: Chiralpak AD, 4.6×100 mm, 5 micron; Mobile Phase: 65% $CO_2$/35% MeOH w/0.1% DEA; Flow Conditions: 2 mL/min; Detector Wavelength: 220 nm. Example 318 (first-eluting isomer) RT: 2.6 min. Example 319 (second-eluting isomer) RT: 5.2 min.

Examples 324 and 325: Instrument: Berger SFC MGII; Column: CHIRALCEL AS SFC 30×250 mm ID, 5 μm; Mobile Phase: 78/18 $CO_2$/(MeOH with 0.5% DEA); Flow Conditions: 65 mL/min; Detector Wavelength: 270 nm. Example 324 (first-eluting isomer) RT: 60 min. Example 325 (second-eluting isomer) RT: 65 min. Analytical Chiral SFC Conditions: Instrument: Agilent analytical SFC; Column: AS Column 4.6×250 mm ID, 5 μm; Mobile Phase: 85/15 $CO_2$/(MeOH with 0.5% DEA); Flow Conditions: 2 mL/min. Example 324 (first-eluting isomer) RT: 44.0 min. Example 325 (second-eluting isomer) RT: 48.4 min.

Examples 327 and 328: Instrument: Berger SFC MGII; Column: CHIRALCEL YMC SB SFC 30×250 mm ID, 5 μm; Mobile Phase: 78/18 $CO_2$/(MeOH with 0.5% DEA); Flow Conditions: 85 mL/min; Detector Wavelength: 265 nm. Example 327 (first-eluting isomer) RT: 55 min. Example 328 (second-eluting isomer) RT: 61 min. Analytical Chiral SFC Conditions: Instrument: Agilent analytical SFC; Column: YMC SB Column 4.6×250 mm ID, 5 μm; Mobile Phase: 80/20 $CO_2$/(MeOH with 0.5% DEA); Flow Conditions: 2 mL/min. Example 327 (first-eluting isomer) RT: 22.3 min. Example 328 (second-eluting isomer) RT: 25.5 min.

Examples 337 and 338: Instrument: Waters 100 Prep SFC; Column: Chiral OJ, 30×250 mm. 5 micron; Mobile Phase: 90% $CO_2$/10% MeOH w/0.1% DEA; Flow Conditions: 100 mL/min; Detector Wavelength: 220 nm. Example 337 (first-eluting isomer) RT: 16.36 min. Example 338 (second-eluting isomer) RT: 26.8 min. Analytical Chiral SFC Conditions: Instrument: Shimadzu Nexera UC SFC; Column: Chiral OJ, 4.6×100 mm, 5 micron; Mobile Phase: 90% $CO_2$/10% MeOH w/0.1% DEA; Flow Conditions: 2 mL/min; Detector Wavelength: 220 nm. Example 337 (first-eluting isomer) RT: 9.9 min. Example 338 (second-eluting isomer) RT: 14.3 min.

Examples 341 and 342: Instrument: Waters 100 Prep SFC; Column: Chiral AD, 30×250 mm. 5 micron; Mobile Phase: 65% $CO_2$/35% IPA-ACN 50-50 w/0.1% DEA; Flow Conditions: 100 mL/min; Detector Wavelength: 220 nm. Example 341 (first-eluting isomer) RT: 17.91 min. Example 342 (second-eluting isomer) RT: 22.64 min. Analytical Chiral SFC Conditions: Instrument: Shimadzu Nexera UC SFC; Column: Chiral AD, 4.6×100 mm, 5 micron; Mobile Phase: 65% $CO_2$/35% IPA-ACN 50-50 w/0.1% DEA; Flow Conditions: 2 mL/min; Detector Wavelength: 220 nm. Example 341 (first-eluting isomer) RT: 7.2 min. Example 342 (second-eluting isomer) RT: 8.8 min.

Examples 344 and 345: Instrument: Waters 100 Prep SFC; Column: Chiral OD, 30×250 mm. 5 micron; Mobile Phase: 80% $CO_2$/20% MeOH w/0.1% DEA; Flow Conditions: 100 mL/min; Detector Wavelength: 220 nm. Example 344 (first-eluting isomer) RT: 23.91 min. Example 345 (second-eluting isomer) RT: 29.15 min. Analytical Chiral SFC Conditions: Instrument: Shimadzu Nexera UC SFC; Column: Chiral OD, 4.6×100 mm, 5 micron; Mobile Phase: 80% $CO_2$/20% MeOH w/0.1% DEA; Flow Conditions: 2 mL/min; Detector Wavelength: 220 nm. Example 344 (first-eluting isomer) RT: 8.0 min. Example 345 (second-eluting isomer) RT: 9.8 min.

Examples 346 and 347: Instrument: Waters 100 Prep SFC; Column: Chiral AD, 30×250 mm. 5 micron; Mobile Phase: 85% $CO_2$/15% MeOH w/0.1% DEA; Flow Conditions: 100 mL/min; Detector Wavelength: 220 nm. Example 346 (first-eluting isomer) RT: 21.99 min. Example 347 (second-eluting isomer) RT: 26.03 min. Analytical Chiral SFC Conditions: Instrument: Shimadzu Nexera UC SFC; Column: Chiral AD, 4.6×100 mm, 5 micron; Mobile Phase: 85% $CO_2$/15% MeOH w/0.1% DEA; Flow Conditions: 2 mL/min; Detector Wavelength: 220 nm. Example 346 (first-eluting isomer) RT: 10.8 min. Example 347 (second-eluting isomer) RT: 12.9 min.

Examples 376 and 377: Instrument: Waters 100 Prep SFC; Column: Chiral IC, 21×250 mm. 5 micron; Mobile Phase: 75% $CO_2$/25% MeOH w/0.1% DEA; Flow Conditions: 60 mL/min; Detector Wavelength: 220 nm. Example 376 (first-eluting isomer) RT: 26.43 min. Example 377 (second-eluting isomer) RT: 30.30 min. Analytical Chiral SFC Conditions: Instrument: Shimadzu Nexera UC SFC; Column: Chiral IC, 4.6×150 mm, 5 micron; Mobile Phase: 75% $CO_2$/25% MeOH w/0.1% DEA; Flow Conditions: 2 mL/min; Detector Wavelength: 220 nm. Example 376 (first-eluting isomer) RT: 19.6 min. Example 377 (second-eluting isomer) RT: 21.9 min.

Examples 378 and 379: Instrument: Waters 100 Prep SFC; Column: Chiral OD, 30×250 mm. 5 micron; Mobile Phase: 65% $CO_2$/35% IPA w/0.1% DEA; Flow Conditions: 100 mL/min; Detector Wavelength: 220 nm. Example 378 (first-eluting isomer) RT: 6.98 min. Example 379 (second-eluting isomer) RT: 10.17 min. Analytical Chiral SFC Conditions: Instrument: Shimadzu Nexera UC SFC; Column: Chiral OD, 4.6×100 mm, 5 micron; Mobile Phase: 65% $CO_2$/35% IPA w/0.1% DEA; Flow Conditions: 2 mL/min; Detector Wavelength: 220 nm. Example 378 (first-eluting isomer) RT: 2.4 min. Example 379 (second-eluting isomer) RT: 3.0 min.

| Ex. No. | Structure | LC/MS [M + H]+ | RT (min) | 1H NMR (500 MHz, DMSO-d6) |
|---|---|---|---|---|
| 303 | 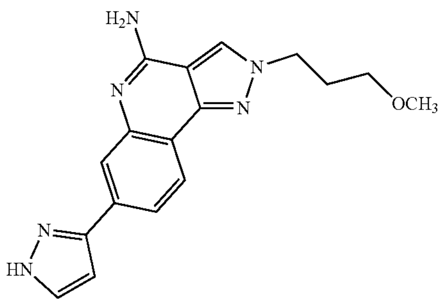 [SMILES: COCCCn1cc2c(N)nc3cc(-c4cc[nH]n4)ccc3c2n1] | 323.2 | 1.00 | δ 8.48 (s, 1H), 8.08 (d, J = 8.2 Hz, 1H), 7.88 (s, 1H), 7.71 (br s, 1H), 7.64 (br d, J = 8.3 Hz, 1H), 7.17 – 7.00 (m, 2H), 6.76 (d, J = 1.7 Hz, 1H), 4.45 (br t, J = 6.9 Hz, 2H), 3.31 (br t, J = 6.0 Hz, 2H), 3.24 (s, 3H), 2.14 (quin, J = 6.5 Hz, 2H) |
| 304 | 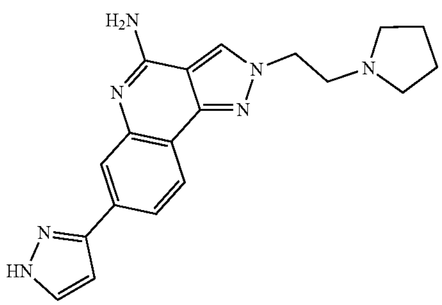 [SMILES: Nc1nc2cc(-c3cc[nH]n3)ccc2c2nn(CCN3CCCC3)cc12] | 348.2 | 0.88 | δ 9.01 (s, 1H), 8.21 (d, J = 8.3 Hz, 1H), 8.11 (br s, 1H), 7.94 (br d, J = 7.7 Hz, 1H), 7.85 (br s, 1H), 6.82 (d, J = 1.9 Hz, 1H), 4.91 (br t, J = 5.9 Hz, 2H), 3.85 – 3.79 (m, 2H), 2.05 – 1.83 (m, 4H); two CH protons are not visible, likely due to overlap with suppressed water peak. |
| 305 | 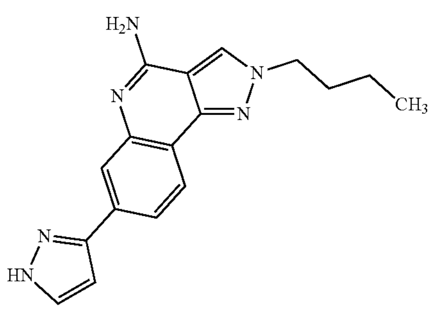 [SMILES: CCCCn1cc2c(N)nc3cc(-c4cc[nH]n4)ccc3c2n1] | 307.2 | 1.18 | δ 8.71 – 8.62 (m, 1H), 8.13 (d, J = 8.0 Hz, 1H), 7.97 (br s, 1H), 7.83 – 7.70 (m, 2H), 6.78 (s, 1H), 4.45 (br t, J = 6.9 Hz, 2H), 1.94 – 1.86 (m, 2H), 1.31 (sxt, J = 7.4 Hz, 2H), 0.92 (t, J = 7.4 Hz, 3H) |
| 306 | 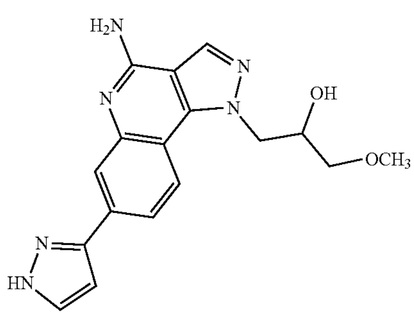 [SMILES: COCC(O)Cn1ncc2c(N)nc3cc(-c4cc[nH]n4)ccc3c21] | 339.3 | 1.00 | δ 8.64 (s, 1H), 8.49 (d, J = 8.9 Hz, 1H), 8.19 (br d, J = 2.4 Hz, 1H), 7.96 (br d, J = 7.6 Hz, 1H), 7.90 – 7.83 (m, 1H), 6.87 (s, 1H), 4.86 – 4.73 (m, 2H), 4.15 (br s, 1H), 3.42 (br s, 2H), 3.32 (s, 3H) |
| 307 | 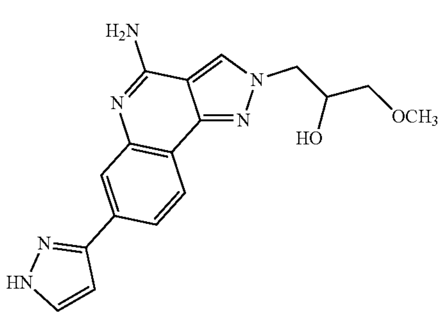 [SMILES: COCC(O)Cn1cc2c(N)nc3cc(-c4cc[nH]n4)ccc3c2n1] | 339.1 | 0.84 | δ 8.88 (s, 1H), 8.20 (d, J = 8.2 Hz, 1H), 8.06 (br d, J = 1.2 Hz, 1H), 7.91 (br d, J = 8.2 Hz, 1H), 7.81 (br s, 1H), 6.82 (s, 1H), 4.54 (dd, J = 13.7, 3.1 Hz, 1H), 4.37 (dd, J = 13.7, 8.5 Hz, 1H), 4.09 (br s, 1H), 3.40 – 3.34 (m, 2H), 3.31 (s, 3H) |

| Ex. No. | Structure | LC/MS [M + H]+ | RT (min) | 1H NMR (500 MHz, DMSO-d6) |
|---|---|---|---|---|
| 308 | 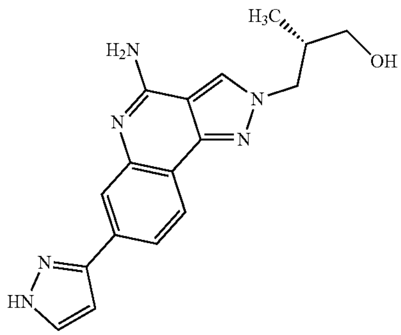 [SMILES: C[C@H](CO)Cn1cc2c(N)nc3cc(-c4cc[nH]n4)ccc3c2n1] | 323.2 | 1.00 | δ 8.87 (s, 1H), 8.19 (d, J = 8.0 Hz, 1H), 8.12 – 8.03 (m, 1H), 7.91 (br d, J = 8.3 Hz, 1H), 7.87 – 7.79 (m, 1H), 6.82 (s, 1H), 4.96 – 4.83 (m, 1H), 4.52 (dd, J = 13.6, 5.9 Hz, 1H), 4.30 (dd, J = 13.2, 8.0 Hz, 1H), 3.34 (br t, J = 5.6 Hz, 2H), 2.30 – 2.20 (m, 1H), 0.85 (d, J = 6.9 Hz, 3H) |
| 309 | 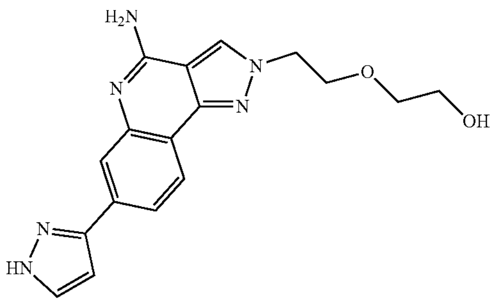 [SMILES: Nc1nc2cc(-c3cc[nH]n3)ccc2c2nn(CCOCCO)cc12] | 339.2 | 0.74 | δ 8.93 (s, 1H), 8.19 (br d, J = 8.3 Hz, 1H), 8.10 (br s, 1H), 7.91 (br d, J = 8.0 Hz, 1H), 7.87 – 7.80 (m, 1H), 6.81 (s, 1H), 4.66 (br t, J = 4.4 Hz, 2H), 4.29 – 3.97 (m, 4H), 3.92 (br t, J = 4.4 Hz, 2H) |
| 310 | 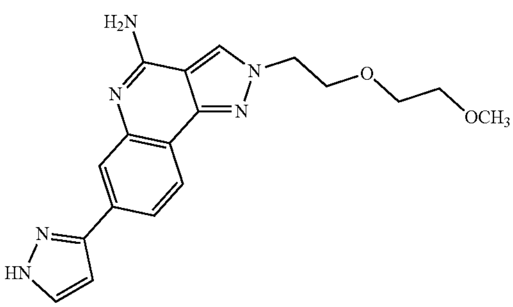 [SMILES: COCCOCCn1cc2c(N)nc3cc(-c4cc[nH]n4)ccc3c2n1] | 353.2 | 0.93 | δ 8.92 – 8.88 (m, 1H), 8.19 (br d, J = 8.1 Hz, 1H), 8.10 (br s, 1H), 7.92 (br d, J = 8.1 Hz, 1H), 7.88 – 7.82 (m, 1H), 6.82 (s, 1H), 4.65 (br d, J = 4.3 Hz, 2H), 3.91 (br s, 2H), 3.41 – 3.38 (m, 2H), 3.18 – 3.16 (m, 3H); two CH protons are not visible, likely due to overlap with suppressed water peak. |
| 311 | 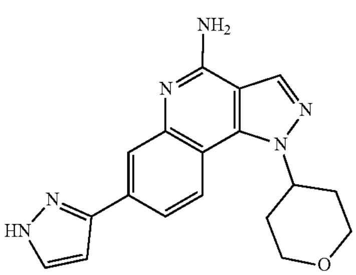 [SMILES: Nc1nc2cc(-c3cc[nH]n3)ccc2c2c1cnn2C1CCOCC1] | 335.2 | 0.92 | δ 8.38 (s, 1H), 8.27 (d, J = 8.5 Hz, 1H), 8.03 (s, 1H), 7.81 – 7.73 (m, 2H), 7.34 – 7.15 (m, 2H), 6.81 (d, J = 1.9 Hz, 1H), 5.34 – 5.26 (m, 1H), 4.02 (br d, J = 9.9 Hz, 2H), 3.71 (br t, J = 11.3 Hz, 2H), 2.24 – 2.14 (m, 2H), 2.11 – 2.04 (m, 2H) |
| 312 | 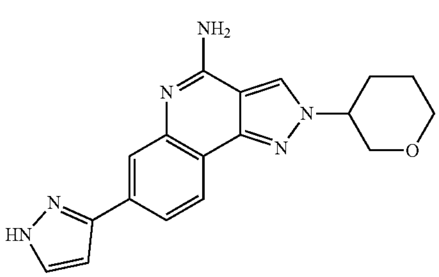 [SMILES: Nc1nc2cc(-c3cc[nH]n3)ccc2c2nn(C3CCCOC3)cc12] | 335.1 | 1.18 | δ 13.12 (br s, 1H), 9.09 (br s, 1H), 8.19 (d, J = 8.2 Hz, 1H), 8.10 (br s, 1H), 7.94 – 7.83 (m, 2H), 6.82 (br s, 1H), 4.78 – 4.67 (m, 1H), 4.11 (br dd, J = 11.5, 3.5 Hz, 1H), 3.94 (br dd, J = 11.4, 7.2 Hz, 1H), 3.82 – 3.76 (m, 1H), 3.64 (ddd, J = 11.3, 8.0, 3.4 Hz, 1H), 2.31 – 2.20 (m, 2H), 1.77 – 1.64 (m, 2H) |

| Ex. No. | Structure | LC/MS [M + H]⁺ | RT (min) | ¹H NMR (500 MHz, DMSO-d₆) |
|---|---|---|---|---|
| 313 | 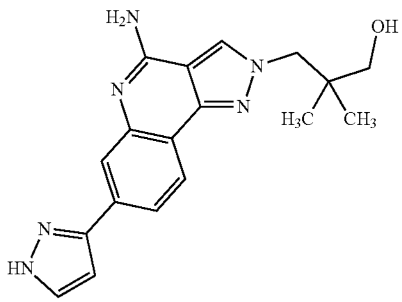 [SMILES: CC(C)(CO)Cn1cc2c(N)nc3cc(-c4cc[nH]n4)ccc3c2n1] | 337.1 | 0.99 | δ 13.23 – 13.03 (m, 1H), 8.83 (s, 1H), 8.19 (d, J = 8.0 Hz, 1H), 8.11 – 8.02 (m, 1H), 7.94 – 7.87 (m, 1H), 7.83 (dt, J = 4.3, 2.3 Hz, 1H), 6.82 (s, 1H), 5.04 (br s, 1H), 4.34 (s, 2H), 3.20 (br d, J = 2.5 Hz, 2H), 0.90 (s, 6H) |
| 314 | diastereomer 1 | 335.1 | 1.00 | δ 8.55 (s, 1H), 8.09 (br d, J = 8.0 Hz, 1H), 7.88 (s, 1H), 7.71 (br s, 1H), 7.64 (br d, J = 8.3 Hz, 1H), 7.21 – 7.01 (m, 2H), 6.75 (d, J = 1.9 Hz, 1H), 5.43 – 5.24 (m, 1H), 4.65 – 4.58 (m, 1H), 4.34 (q, J = 6.9 Hz, 1H), 2.34 – 2.25 (m, 1H), 2.20 – 2.10 (m, 1H), 2.09 – 2.00 (m, 1H), 1.89 – 1.81 (m, 2H), 1.69 – 1.58 (m, 1H) |
| 315 | enantiomer 1 | 335.2 | 1.01 | δ 8.52 (s, 1H), 8.09 (d, J = 8.3 Hz, 1H), 7.86 (s, 1H), 7.75 – 7.67 (m, 1H), 7.62 (br d, J = 8.0 Hz, 1H), 6.81 (br s, 2H), 6.74 (d, J = 1.7 Hz, 1H), 5.37 (br s, 1H), 4.65 – 4.56 (m, 1H), 4.37 – 4.31 (m, 1H), 2.34 – 2.24 (m, 1H), 2.18 – 2.09 (m, 1H), 2.08 – 2.00 (m, 1H), 1.89 – 1.80 (m, 2H), 1.67 – 1.58 (m, 1H) |
| 316 | enantiomer 2 | 335.2 | 1.01 | δ 8.52 (s, 1H), 8.09 (d, J = 8.3 Hz, 1H), 7.86 (s, 1H), 7.75 – 7.66 (m, 1H), 7.62 (br d, J = 9.1 Hz, 1H), 6.82 (br s, 2H), 6.74 (d, J = 1.7 Hz, 1H), 5.35 (br s, 1H), 4.64 – 4.58 (m, 1H), 4.37 – 4.31 (m, 1H), 2.33 – 2.25 (m, 1H), 2.18 – 2.08 (m, 1H), 2.08 – 2.00 (m, 1H), 1.89 – 1.80 (m, 2H), 1.67 – 1.59 (m, 1H) |
| 317 | 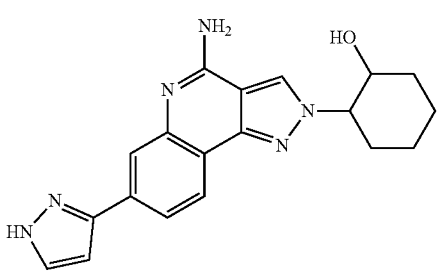 [SMILES: Nc1nc2cc(-c3cc[nH]n3)ccc2c2nn(C3CCCCC3O)cc12] | 349.1 | 1.09 | δ 8.48 (s, 1H), 8.09 (d, J = 8.2 Hz, 1H), 7.87 (s, 1H), 7.71 (br s, 1H), 7.63 (br d, J = 8.0 Hz, 1H), 7.11 – 6.94 (m, 2H), 6.75 (d, J = 2.1 Hz, 1H), 5.00 (ddd, J = 6.0, 4.1, 1.6 Hz, 1H), 4.18 – 4.11 (m, 1H), 3.86 – 3.78 (m, 1H), 2.09 – 1.97 (m, 3H), 1.82 – 1.71 (m, 2H), 1.44 – 1.34 (m, 3H |

| Ex. No. | Structure | LC/MS [M + H]+ | RT (min) | ¹H NMR (500 MHz, DMSO-d₆) |
|---|---|---|---|---|
| 318 | enantiomer 1 | 349.3 | 1.10 | δ 8.45 (s, 1H), 8.08 (d, J = 8.0 Hz, 1H), 7.87 (s, 1H), 7.75 – 7.66 (m, 1H), 7.61 (br d, J = 6.3 Hz, 1H), 6.86 (br s, 2H), 6.74 (d, J = 1.1 Hz, 1H), 4.96 (br d, J = 3.6 Hz, 1H), 4.18 – 4.10 (m, 1H), 3.85 – 3.79 (m, 1H), 2.09 – 1.97 (m, 3H), 1.81 – 1.72 (m, 2H), 1.44 – 1.34 (m, 3H) |
| 319 | enantiomer 2 | 349.2 | 1.10 | δ 8.45 (s, 1H), 8.08 (d, J = 8.0 Hz, 1H), 7.86 (s, 1H), 7.75 – 7.65 (m, 1H), 7.63 – 7.58 (m, 1H), 6.83 (br s, 2H), 6.74 (s, 1H), 4.96 (br d, J = 1.7 Hz, 1H), 4.17 – 4.10 (m, 1H), 3.86 – 3.78 (m, 1H), 2.09 – 1.94 (m, 3H), 1.83 – 1.70 (m, 2H), 1.44 – 1.34 (m, 3H) |
| 320 | 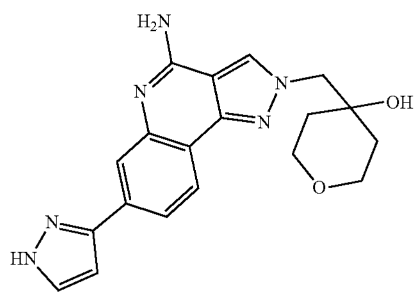 [SMILES: Nc1nc2cc(-c3cc[nH]n3)ccc2c2nn(CC3(O)CCOCC3)cc12] | 365.2 | 1.00 | δ 13.20 – 13.03 (m, 1H), 8.91 (s, 1H), 8.18 (d, J = 8.0 Hz, 1H), 8.12 – 8.05 (m, 1H), 7.94 – 7.88 (m, 1H), 7.88 – 7.80 (m, 1H), 6.81 (s, 1H), 5.10 (s, 1H), 4.46 (s, 2H), 3.68 – 3.56 (m, 4H), 1.70 – 1.62 (m, 2H), 1.36 (br d, J = 13.2 Hz, 2H) |
| 321 | 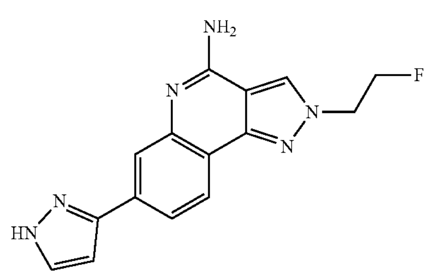 [SMILES: Nc1nc2cc(-c3cc[nH]n3)ccc2c2nn(CCF)cc12] | 297.1 | 1.03 | δ 13.22 – 13.05 (m, 1H), 8.95 (s, 1H), 8.20 (d, J = 8.2 Hz, 1H), 8.10 (br s, 1H), 7.92 (br d, J = 7.2 Hz, 1H), 7.85 (br s, 1H), 6.82 (d, J = 1.8 Hz, 1H), 4.99 – 4.81 (m, 4H) |
| 322 | 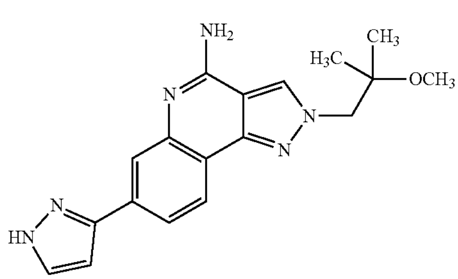 [SMILES: COC(C)(C)Cn1cc2c(N)nc3cc(-c4cc[nH]n4)ccc3c2n1] | 337.1 | 1.09 | δ 13.27 – 13.00 (m, 1H), 8.85 (s, 1H), 8.18 (d, J = 8.2 Hz, 1H), 8.07 (br s, 1H), 7.91 (br d, J = 8.3 Hz, 1H), 7.82 (br s, 1H), 6.82 (d, J = 1.9 Hz, 1H), 4.51 (s, 2H), 3.23 (s, 3H), 1.14 (s, 6H) |

| Ex. No. | Structure | LC/MS [M + H]+ | RT (min) | ¹H NMR (500 MHz, DMSO-d₆) |
|---|---|---|---|---|
| 323 | 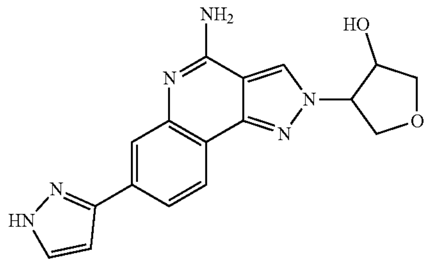 [SMILES: Nc1nc2cc(-c3cc[nH]n3)ccc2c2nn(C3COCC3O)cc12] | 337.1 | 0.78 | δ 8.58 (s, 1H), 8.08 (d, J = 8.2 Hz, 1H), 7.87 (s, 1H), 7.71 (br s, 1H), 7.65 (br d, J = 7.8 Hz, 1H), 7.14 – 6.97 (m, 2H), 6.76 (d, J = 2.1 Hz, 1H), 5.89 (br d, J = 3.7 Hz, 1H), 5.04 – 4.98 (m, 1H), 4.54 (br s, 1H), 4.29 (dd, J = 9.9, 6.2 Hz, 1H), 4.18 – 4.13 (m, 2H), 3.70 – 3.65 (m, 1H) |
| 324 | HN enantiomer 1 | 337.2 | 0.74 | δ 8.66 (br s, 1H), 8.11 (d, J = 8.2 Hz, 1H), 7.91 (br s, 1H), 7.76 – 7.65 (m, 2H), 6.77 (s, 1H), 5.03 (br s, 1H), 4.55 (br s, 1H), 4.31 – 4.26 (m, 1H), 4.18 – 4.13 (m, 2H), 3.70 – 3.65 (m, 1H) |
| 325 | HN enantiomer 2 | 337.1 | 0.75 | δ 8.71 – 8.60 (m, 1H), 8.15 – 8.05 (m, 1H), 7.91 (br s, 1H), 7.82 – 7.60 (m, 2H), 6.78 (s, 1H), 5.03 (br s, 1H), 4.56 – 4.50 (m, 1H), 4.31 – 4.26 (m, 1H), 4.21 – 4.13 (m, 2H), 3.72 – 3.65 (m, 1H) |
| 326 | 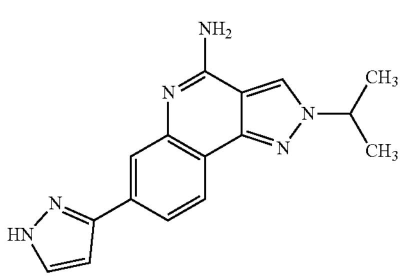 [SMILES: CC(C)n1cc2c(N)nc3cc(-c4cc[nH]n4)ccc3c2n1] | 293.2 | 1.06 | δ 8.55 (s, 1H), 8.10 (d, J = 8.1 Hz, 1H), 7.88 (d, J = 1.1 Hz, 1H), 7.71 (br s, 1H), 7.64 (br d, J = 8.1 Hz, 1H), 7.16 – 6.95 (m, 2H), 6.76 (d, J = 1.9 Hz, 1H), 4.84 – 4.76 (m, 1H), 1.56 (d, J = 6.6 Hz, 6H) |

| Ex. No. | Structure | LC/MS [M + H]+ | RT (min) | ¹H NMR (500 MHz, DMSO-d₆) |
|---|---|---|---|---|
| 327 | 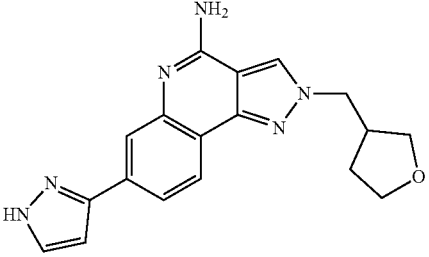 [SMILES: Nc1nc2cc(-c3cc[nH]n3)ccc2c2nn(CC3CCOC3)cc12]<br>enantiomer 1 | 335.0 | 0.92 | δ 8.49 (s, 1H), 8.07 (d, J = 8.3 Hz, 1H), 7.87 (s, 1H), 7.71 (br s, 1H), 7.62 (br d, J = 8.0 Hz, 1H), 6.97 – 6.84 (m, 2H), 6.75 (d, J = 1.7 Hz, 1H), 4.43 (br d, J = 7.4 Hz, 2H), 3.84 – 3.78 (m, 1H), 3.75 – 3.70 (m, 1H), 3.70 – 3.63 (m, 1H), 3.54 (br dd, J = 8.5, 5.5 Hz, 1H), 2.88 – 2.79 (m, 1H), 2.03 – 1.94 (m, 1H), 1.73 – 1.63 (m, 1H) |
| 328 | 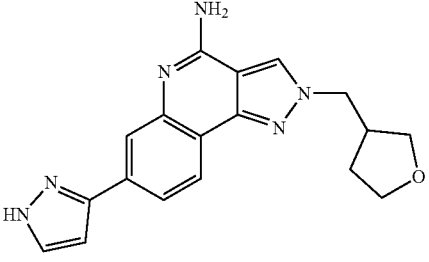 [SMILES: Nc1nc2cc(-c3cc[nH]n3)ccc2c2nn(CC3CCOC3)cc12]<br>enantiomer 2 | 335.2 | 0.92 | δ 8.49 (s, 1H), 8.07 (d, J = 8.3 Hz, 1H), 7.87 (s, 1H), 7.71 (br s, 1H), 7.62 (br d, J = 9.1 Hz, 1H), 6.96 – 6.84 (m, 2H), 6.75 (d, J = 1.7 Hz, 1H), 4.42 (br d, J = 7.7 Hz, 2H), 3.83 – 3.78 (m, 1H), 3.74 – 3.70 (m, 1H), 3.69 – 3.63 (m, 1H), 3.56 – 3.52 (m, 1H), 2.92 – 2.80 (m, 1H), 2.02 – 1.94 (m, 1H), 1.73 – 1.63 (m, 1H) |
| 329 | 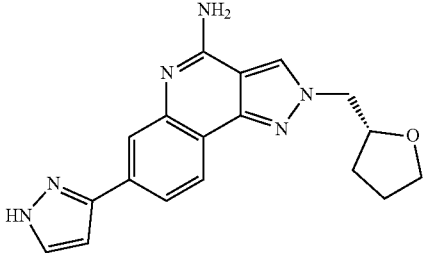 [SMILES: Nc1nc2cc(-c3cc[nH]n3)ccc2c2nn(C[C@H]3CCCO3)cc12] | 335.3 | 0.97 | δ 8.49 (s, 1H), 8.06 (d, J = 8.2 Hz, 1H), 7.86 (s, 1H), 7.74 – 7.68 (m, 1H), 7.61 (br d, J = 7.6 Hz, 1H), 6.92 (br s, 2H), 6.75 (d, J = 1.4 Hz, 1H), 4.55 – 4.49 (m, 1H), 4.44 – 4.37 (m, 1H), 4.32 – 4.25 (m, 1H), 3.77 (q, J = 7.0 Hz, 1H), 3.69 – 3.63 (m, 1H), 2.07 – 1.98 (m, 1H), 1.85 – 1.73 (m, 2H), 1.69 – 1.60 (m, 1H) |
| 330 | 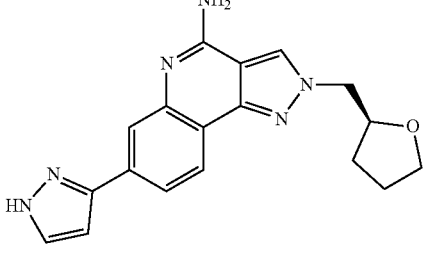 | 335.2 | 0.96 | δ 8.89 (s, 1H), 8.19 (d, J = 8.2 Hz, 1H), 8.05 (s, 1H), 7.91 (br d, J = 7.9 Hz, 1H), 7.81 (br s, 1H), 6.82 (s, 1H), 4.58 (br dd, J = 14.0, 2.7 Hz, 1H), 4.50 – 4.41 (m, 1H), 4.33 – 4.26 (m, 1H), 3.80 – 3.68 (m, 2H), 2.09 – 2.01 (m, 1H), 1.86 – 1.75 (m, 2H), 1.69 – 1.60 (m, 1H) |
| 331 | 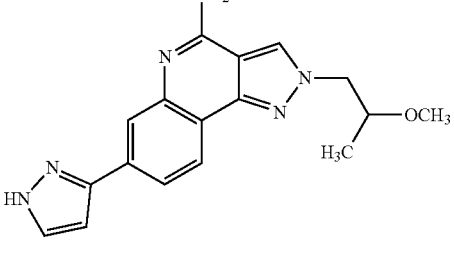 | 323.3 | 0.95 | δ 13.18 – 13.05 (m, 1H), 8.86 (br s, 1H), 8.18 (br d, J = 8.3 Hz, 1H), 8.10 (br d, J = 1.1 Hz, 1H), 7.94 – 7.83 (m, 2H), 6.81 (br s, 1H), 4.59 (br dd, J = 14.0, 2.5 Hz, 1H), 4.46 (br dd, J = 14.3, 7.2 Hz, 1H), 3.89 – 3.83 (m, 1H), 3.23 (s, 3H), 1.15 (br d, J = 6.3 Hz, 3H) |

| Ex. No. | Structure | LC/MS [M + H]+ | RT (min) | ¹H NMR (500 MHz, DMSO-d₆) |
|---|---|---|---|---|
| 332 | 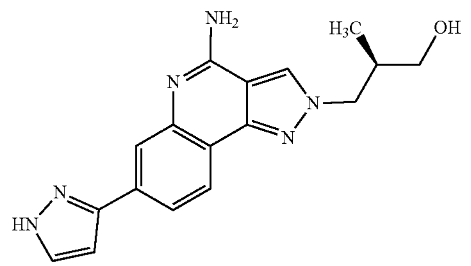 [SMILES: C[C@@H](CO)Cn1cc2c(N)nc3cc(-c4cc[nH]n4)ccc3c2n1] | 322.9 | 1.07 | δ 13.23 – 13.01 (m, 1H), 8.88 (s, 1H), 8.19 (d, J = 8.0 Hz, 1H), 8.10 (br s, 1H), 7.92 (br d, J = 7.4 Hz, 1H), 7.84 (br s, 1H), 6.82 (s, 1H), 4.90 – 4.82 (m, 1H), 4.52 (dd, J = 13.6, 6.2 Hz, 1H), 4.30 (dd, J = 13.6, 7.8 Hz, 1H), 3.38 – 3.31 (m, 2H), 2.30 – 2.22 (m, 1H), 0.86 (d, J = 6.6 Hz, 3H) |
| 333 | 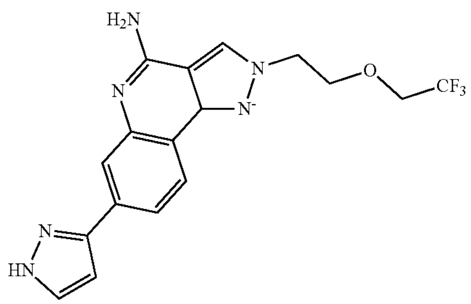 [SMILES: NC1=Nc2cc(-c3cc[nH]n3)ccc2C2[N-]N(CCOCC(F)(F)F)C=C12] | 377.1 | 1.32 | δ 13.25 – 13.02 (m, 1H), 8.91 (s, 1H), 8.20 (d, J = 8.3 Hz, 1H), 8.08 (br s, 1H), 7.92 (br d, J = 8.3 Hz, 1H), 7.83 (br s, 1H), 6.82 (d, J = 1.9 Hz, 1H), 4.71 (t, J = 4.8 Hz, 2H), 4.13 – 4.06 (m, 4H) |
| 334 | 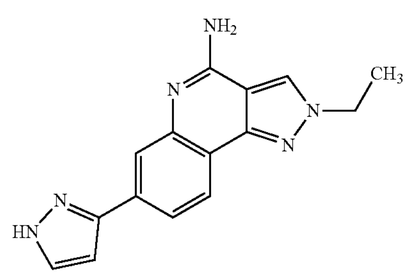 [SMILES: CCn1cc2c(N)nc3cc(-c4cc[nH]n4)ccc3c2n1] | 279.1 | 0.90 | δ 8.50 (s, 1H), 8.13 – 8.05 (m, 1H), 7.87 (s, 1H), 7.71 (br d, J = 1.0 Hz, 1H), 7.64 (br dd, J = 5.3, 1.6 Hz, 1H), 7.11 – 6.92 (m, 2H), 6.75 (br d, J = 2.1 Hz, 1H), 4.43 (q, J = 7.2 Hz, 2H), 1.51 (t, J = 7.3 Hz, 3H) |
| 335 | 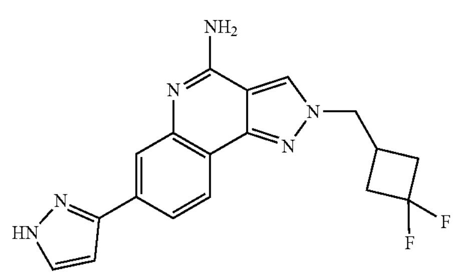 [SMILES: Nc1nc2cc(-c3cc[nH]n3)ccc2c2nn(CC3CC(F)(F)C3)cc12] | 355.0 | 1.17 | δ 13.19 – 13.04 (m, 1H), 8.88 (br s, 1H), 8.18 (d, J = 8.2 Hz, 1H), 8.09 (br s, 1H), 7.95 – 7.83 (m, 2H), 6.81 (s, 1H), 4.65 (br d, J = 6.8 Hz, 2H), 2.83 – 2.67 (m, 3H), 2.60 – 2.52 (m, 2H) |
| 336 | 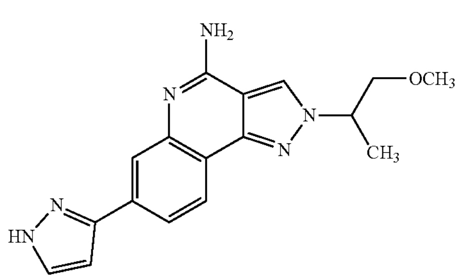 [SMILES: COCC(C)n1cc2c(N)nc3cc(-c4cc[nH]n4)ccc3c2n1] | 323.2 | 0.98 | δ 8.54 (s, 1H), 8.11 (d, J = 8.2 Hz, 1H), 7.88 (s, 1H), 7.71 (s, 1H), 7.65 (br d, J = 8.2 Hz, 1H), 6.76 (d, J = 2.1 Hz, 1H), 4.87 – 4.79 (m, 1H), 3.80 – 3.74 (m, 1H), 3.69 – 3.65 (m, 1H), 3.20 (s, 3H), 1.53 (d, J = 6.7 Hz, 3H) |

-continued

| Ex. No. | Structure | LC/MS [M + H]⁺ | RT (min) | ¹H NMR (500 MHz, DMSO-d₆) |
|---|---|---|---|---|
| 337 | enantiomer 1 | 323.3 | 1.13 | δ 8.51 (s, 1H), 8.08 (d, J = 8.0 Hz, 1H), 7.86 (s, 1H), 7.70 (br s, 1H), 7.62 (br d, J = 8.0 Hz, 1H), 6.97 – 6.81 (m, 2H), 6.75 (s, 1H), 4.87 – 4.80 (m, 1H), 3.80 – 3.74 (m, 1H), 3.69 (br dd, J = 10.5, 3.9 Hz, 1H), 3.22 (s, 3H), 1.54 (d, J = 6.9 Hz, 3H) |
| 338 | enantiomer 2 | 323.1 | 1.15 | δ 8.51 (s, 1H), 8.08 (d, J = 8.0 Hz, 1H), 7.86 (s, 1H), 7.70 (br s, 1H), 7.62 (br d, J = 8.5 Hz, 1H), 6.89 (br s, 2H), 6.75 (d, J = 1.8 Hz, 1H), 4.88 – 4.80 (m, 1H), 3.79 – 3.74 (m, 1H), 3.68 (br dd, J = 10.3, 4.1 Hz, 1H), 3.22 (s, 3H), 1.54 (br d, J = 6.8 Hz, 3H) |
| 339 | 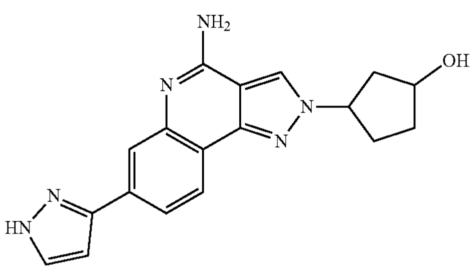 [SMILES: Nc1nc2cc(-c3cc[nH]n3)ccc2c2nn(C3CCC(O)C3)cc12] | 335.3 | 1.04 | δ 13.49 – 13.01 (m, 1H), 9.69 – 9.40 (m, 1H), 8.96 – 8.92 (m, 1H), 8.90 – 8.71 (m, 1H), 8.19 (d, J = 8.2 Hz, 1H), 8.06 (br s, 1H), 7.91 (br d, J = 8.2 Hz, 1H), 7.83 (br s, 1H), 6.81 (d, J = 1.7 Hz, 1H), 5.28 – 5.20 (m, 1H), 5.10 – 4.89 (m, 1H), 4.44 (br s, 1H), 2.47 – 2.38 (m, 1H), 2.28 – 2.10 (m, 3H), 2.04 – 1.96 (m, 1H), 1.72 – 1.64 (m, 1H) |
| 340 | diastereomer 2 | 335.2 | 0.96 | δ 8.65 (s, 1H), 8.10 (d, J = 8.1 Hz, 1H), 7.90 (br s, 1H), 7.77 – 7.63 (m, 2H), 7.31 – 7.05 (m, 2H), 6.77 (d, J = 1.8 Hz, 1H), 5.03 (br s, 1H), 4.86 – 4.76 (m, 1H), 4.29 (br s, 1H), 2.31 – 2.20 (m, 2H), 2.04 – 1.95 (m, 2H), 1.80 – 1.67 (m, 2H) |
| 341 | enantiomer 1 | 335.1 | 0.91 | δ 8.61 (s, 1H), 8.06 (d, J = 8.3 Hz, 1H), 7.87 (s, 1H), 7.73 – 7.67 (m, 1H), 7.62 (br d, J = 8.8 Hz, 1H), 6.96 – 6.87 (m, 2H), 6.75 (d, J = 1.7 Hz, 1H), 5.04 – 4.95 (m, 1H), 4.29 – 4.23 (m, 1H), 2.32 – 2.15 (m, 3H), 1.98 (dt, J = 13.1, 6.4 Hz, 1H), 1.89 – 1.77 (m, 2H) |

-continued

| Ex. No. | Structure | LC/MS [M + H]+ | RT (min) | ¹H NMR (500 MHz, DMSO-d₆) |
|---|---|---|---|---|
| 342 | enantiomer 2 | 335.3 | 0.91 | δ 8.61 (s, 1H), 8.07 (d, J = 8.0 Hz, 1H), 7.86 (s, 1H), 7.70 (br s, 1H), 7.62 (d, J = 8.3 Hz, 1H), 6.97 – 6.86 (m, 2H), 6.75 (s, 1H), 5.02 – 4.94 (m, 1H), 4.29 – 4.23 (m, 1H), 2.30 – 2.13 (m, 3H), 1.97 (dt, J = 12.7, 6.2 Hz, 1H), 1.88 – 1.74 (m, 2H) |
| 343 | 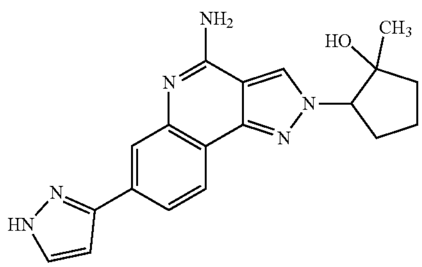 [SMILES: CC1(O)CCCC1n1cc2c(N)nc3cc(-c4cc[nH]n4)ccc3c2n1] | 349.3 | 1.16 | δ 8.93 (s, 1H), 8.20 (d, J = 8.3 Hz, 1H), 8.09 (br s, 1H), 7.92 (br d, J = 8.3 Hz, 1H), 7.87 – 7.80 (m, 1H), 6.81 (s, 1H), 5.18 (br s, 1H), 4.74 (t, J = 7.3 Hz, 1H), 2.47 – 2.32 (m, 2H), 1.98 – 1.78 (m, 4H), 0.82 (s, 3H) |
| 344 | enantiomer 1 | 349.1 | 1.10 | δ 8.75 (br s, 1H), 8.15 (d, J = 8.2 Hz, 1H), 7.98 (br d, J = 1.5 Hz, 1H), 7.79 (br d, J = 8.5 Hz, 2H), 6.79 (d, J = 1.7 Hz, 1H), 5.17 (br s, 1H), 4.70 (br t, J = 7.2 Hz, 1H), 2.46 – 2.30 (m, 2H), 1.97 – 1.77 (m, 4H), 0.80 (s, 3H) |
| 345 | enantiomer 2 | 349.2 | 1.10 | δ 8.64 (s, 1H), 8.11 (d, J = 8.1 Hz, 1H), 7.93 (s, 1H), 7.77 – 7.68 (m, 2H), 6.77 (d, J = 1.8 Hz, 1H), 5.10 (br s, 1H), 4.68 (br t, J = 7.1 Hz, 1H), 2.47 – 2.31 (m, 2H), 1.98 – 1.76 (m, 4H), 0.79 (s, 3H) |
| 346 | enantiomer 1 | 323.1 | 1.02 | δ 8.54 (br s, 1H), 8.09 (d, J = 8.2 Hz, 1H), 7.92 (br s, 1H), 7.81 – 7.62 (m, 2H), 6.77 (s, 1H), 4.52 (br dd, J = 14.2, 3.6 Hz, 1H), 4.41 (dd, J = 14.0, 7.1 Hz, 1H), 3.84 (br dd, J = 10.3, 6.4 Hz, 1H), 3.21 (s, 3H), 1.14 (d, J = 6.3 Hz, 3H) |

| Ex. No. | Structure | LC/MS [M + H]+ | RT (min) | ¹H NMR (500 MHz, DMSO-d₆) |
|---|---|---|---|---|
| 347 | *enantiomer 2* | 323.1 | 1.02 | δ 8.45 (s, 1H), 8.07 (d, J = 8.0 Hz, 1H), 7.87 (s, 1H), 7.75 – 7.68 (m, 1H), 7.61 (br d, J = 7.2 Hz, 1H), 6.89 (br s, 2H), 6.75 (s, 1H), 4.53 – 4.46 (m, 1H), 4.39 (br dd, J = 13.9, 6.7 Hz, 1H), 3.87 – 3.79 (m, 1H), 3.21 (s, 3H), 1.14 (br d, J = 6.3 Hz, 3H) |
| 348 | 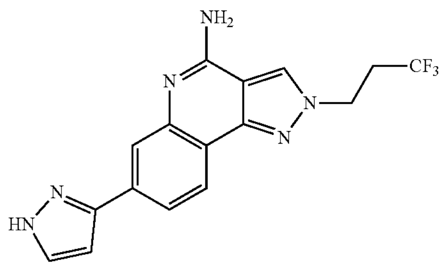 [SMILES: Nc1nc2cc(-c3cc[nH]n3)ccc2c2nn(CCC(F)(F)F)cc12] | 347.2 | 1.22 | δ 13.54 – 13.02 (m, 1H), 9.00 (s, 1H), 8.21 (br d, J = 8.3 Hz, 1H), 8.16 – 8.08 (m, 1H), 7.93 (br d, J = 8.0 Hz, 1H), 7.90 – 7.83 (m, 1H), 6.82 (br s, 1H), 4.83 (br t, J = 6.5 Hz, 2H), 3.15 – 3.05 (m, 2H) |
| 349 | 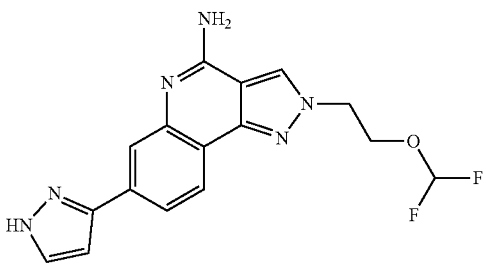 [SMILES: Nc1nc2cc(-c3cc[nH]n3)ccc2c2nn(CCOC(F)F)cc12] | 345.2 | 1.04 | δ 13.52 – 12.80 (m, 1H), 8.52 (s, 1H), 8.08 (d, J = 8.1 Hz, 1H), 7.88 (br s, 1H), 7.83 – 7.60 (m, 2H), 7.12 – 6.95 (m, 2H), 6.78 – 6.74 (m, 1H), 6.66 (t, J = 75.2 Hz, 1H), 4.69 (br t, J = 4.6 Hz, 2H), 4.33 (t, J = 4.8 Hz, 2H) |
| 350 | 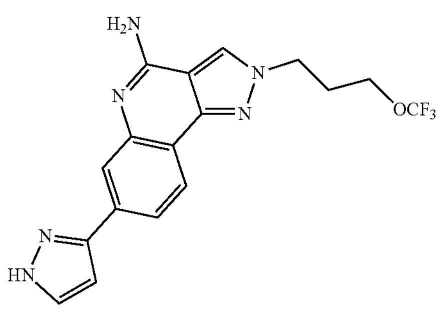 [SMILES: Nc1nc2cc(-c3cc[nH]n3)ccc2c2nn(CCCOC(F)(F)F)cc12] | 377.3 | 1.35 | δ 13.09 – 12.78 (m, 1H), 8.53 (s, 1H), 8.08 (d, J = 8.0 Hz, 1H), 7.90 (br s, 1H), 7.83 – 7.60 (m, 2H), 7.25 – 6.98 (m, 2H), 6.75 (s, 1H), 4.54 (br t, J = 6.9 Hz, 2H), 4.14 (br t, J = 6.1 Hz, 2H), 2.34 (br t, J = 6.5 Hz, 2H) |
| 351 | 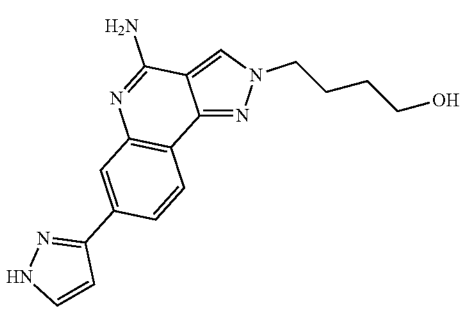 [SMILES: Nc1nc2cc(-c3cc[nH]n3)ccc2c2nn(CCCCO)cc12] | 323.3 | 0.97 | δ 8.49 (s, 1H), 8.08 (d, J = 8.3 Hz, 1H), 7.88 (s, 1H), 7.73 – 7.69 (m, 1H), 7.63 (br d, J = 8.0 Hz, 1H), 7.05 – 6.94 (m, 2H), 6.75 (d, J = 1.7 Hz, 1H), 4.56 – 4.47 (m, 1H), 4.43 (br t, J = 6.9 Hz, 2H), 1.99 – 1.92 (m, 2H), 1.47 – 1.39 (m, 2H) |

-continued

| Ex. No. | Structure | LC/MS [M + H]+ | RT (min) | 1H NMR (500 MHz, DMSO-d6) |
|---|---|---|---|---|
| 352 | 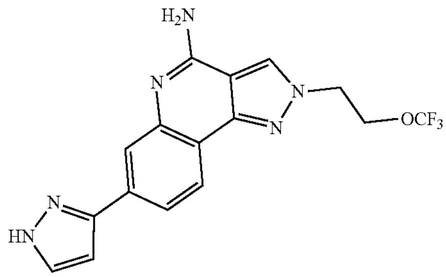 [SMILES: Nc1nc2cc(-c3cc[nH]n3)ccc2c2nn(CCOC(F)(F)F)cc12] | 363.2 | 1.23 | δ 13.18 – 12.83 (m, 1H), 8.59 (s, 1H), 8.10 (br d, J = 8.3 Hz, 1H), 7.90 (br s, 1H), 7.83 – 7.62 (m, 2H), 7.39 – 7.05 (m, 2H), 6.76 (s, 1H), 4.79 (br d, J = 4.1 Hz, 2H), 4.59 (br t, J = 4.4 Hz, 2H) |
| 353 | 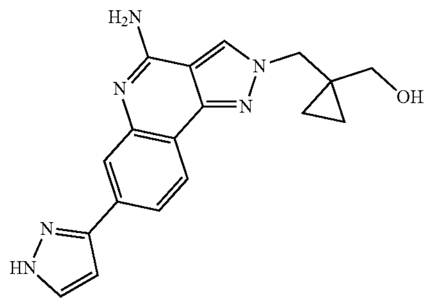 [SMILES: Nc1nc2cc(-c3cc[nH]n3)ccc2c2nn(CC3(CO)CC3)cc12] | 335.2 | 0.88 | δ 13.19 – 13.05 (m, 1H), 8.94 (s, 1H), 8.19 (br d, J = 8.3 Hz, 1H), 8.11 – 8.02 (m, 1H), 7.95 – 7.88 (m, 1H), 7.87 – 7.77 (m, 1H), 6.81 (br s, 1H), 4.93 (s, 1H), 4.45 (s, 2H), 3.21 (br s, 2H), 0.74 (br s, 2H), 0.58 (br s, 2H) |
| 354 | 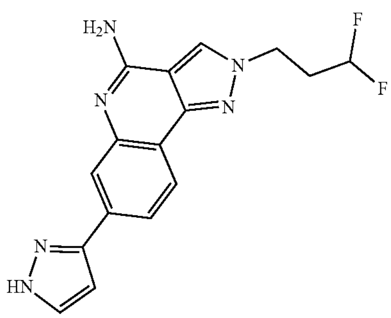 [SMILES: Nc1nc2cc(-c3cc[nH]n3)ccc2c2nn(CCC(F)F)cc12] | 329.3 | 1.13 | δ 13.19 – 13.07 (m, 1H), 8.94 (s, 1H), 8.20 (br d, J = 8.0 Hz, 1H), 8.14 – 8.04 (m, 1H), 7.92 (br d, J = 8.3 Hz, 1H), 7.88 – 7.79 (m, 1H), 6.81 (s, 1H), 6.39 – 6.14 (m, 1H), 4.68 (br t, J = 6.7 Hz, 2H), 2.64 – 2.55 (m, 2H) |
| 355 | 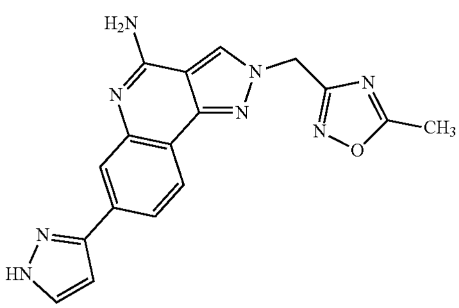 [SMILES: Cc1nc(Cn2cc3c(N)nc4cc(-c5cc[nH]n5)ccc4c3n2)no1] | 347.0 | 1.04 | δ 13.33 – 13.02 (m, 1H), 9.12 (s, 1H), 8.15 (br d, J = 8.0 Hz, 1H), 8.12 – 8.07 (m, 1H), 7.90 (br d, J = 7.2 Hz, 1H), 7.87 – 7.81 (m, 1H), 6.81 (s, 1H), 5.99 (s, 2H), 2.58 (s, 3H) |
| 356 | 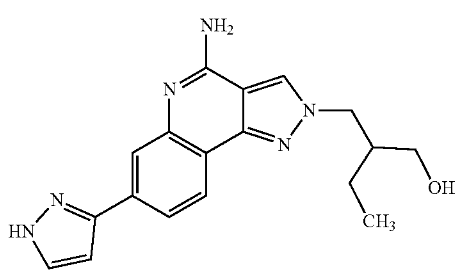 [SMILES: CCC(CO)Cn1cc2c(N)nc3cc(-c4cc[nH]n4)ccc3c2n1] | 337.2 | 1.19 | δ 13.19 – 12.72 (m, 1H), 8.57 – 8.48 (m, 1H), 8.09 (br d, J = 8.0 Hz, 1H), 7.91 (br s, 1H), 7.82 – 7.59 (m, 2H), 7.38 – 7.01 (m, 2H), 6.76 (s, 1H), 4.70 (br s, 1H), 4.45 (br dd, J = 12.9, 6.6 Hz, 1H), 4.33 (br dd, J = 13.9, 7.3 Hz, 1H), 2.08 – 1.98 (m, 1H), 1.41 – 1.32 (m, 1H), 1.30 – 1.20 (m, 1H), 0.90 (br t, J = 7.4 Hz, 3H); two CH protons are not visible, likely due to overlap with suppressed water peak. |

| Ex. No. | Structure | LC/MS [M + H]+ | RT (min) | ¹H NMR (500 MHz, DMSO-d₆) |
|---|---|---|---|---|
| 357 | 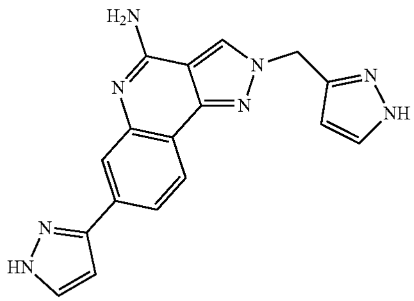 | 331.2 | 1.00 | δ 13.31 – 12.92 (m, 2H), 8.89 (s, 1H), 8.19 (br d, J = 8.0 Hz, 1H), 8.14 – 8.05 (m, 1H), 7.91 (br d, J = 8.0 Hz, 1H), 7.84 (br d, J = 1.7 Hz, 1H), 7.76 (br d, J = 1.9 Hz, 1H), 6.81 (s, 1H), 6.38 (s, 1H), 5.70 (br s, 2H) |
| 358 | 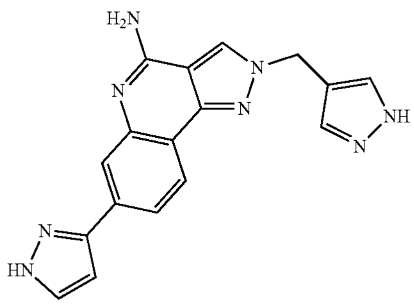 [SMILES: Nc1nc2cc(-c3cc[nH]n3)ccc2c2nn(Cc3cn[nH]c3)cc12] | 330.9 | 1.04 | δ 8.40 (s, 1H), 8.08 (d, J = 8.1 Hz, 1H), 7.86 (d, J = 1.1 Hz, 1H), 7.76 (br s, 2H), 7.70 (br s, 1H), 7.62 (br d, J = 7.9 Hz, 1H), 7.04 – 6.86 (m, 2H), 6.75 (d, J = 2.0 Hz, 1H), 5.52 (s, 2H) |
| 359 | 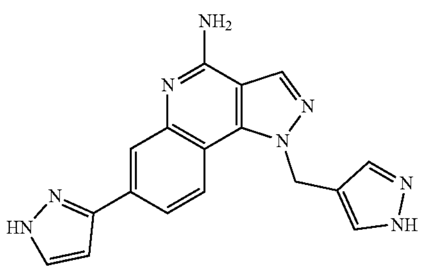 [SMILES: Nc1nc2cc(-c3cc[nH]n3)ccc2c2c1cnn2Cc1cn[nH]c1] | 331.2 | 0.99 | δ 8.66 – 8.62 (m, 1H), 8.36 (br d, J = 8.5 Hz, 1H), 8.16 (br s, 1H), 7.96 (br d, J = 8.6 Hz, 1H), 7.84 (br s, 1H), 7.56 (br s, 2H), 6.85 (d, J = 1.8 Hz, 1H), 5.93 (s, 2H) |
| 360 | 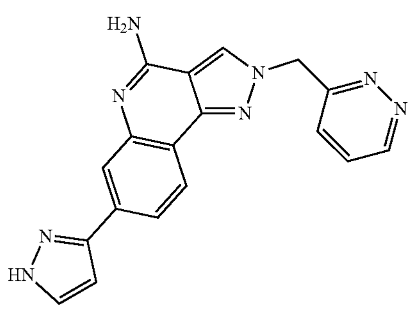 [SMILES: Nc1nc2cc(-c3cc[nH]n3)ccc2c2nn(Cc3cccnn3)cc12] | 343.2 | 1.00 | δ 13.37 – 12.95 (m, 1H), 9.85 – 9.60 (m, 1H), 9.22 (dd, J = 4.3, 1.9 Hz, 1H), 9.13 – 9.10 (m, 1H), 9.00 – 8.80 (m, 1H), 8.14 (d, J = 8.3 Hz, 1H), 8.07 (br s, 1H), 7.89 (br d, J = 8.5 Hz, 1H), 7.82 (br s, 1H), 7.79 – 7.72 (m, 2H), 6.81 (d, J = 1.9 Hz, 1H), 6.10 – 6.04 (m, 2H) |
| 361 | 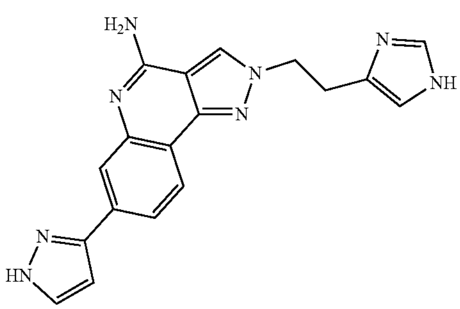 [SMILES: Nc1nc2cc(-c3cc[nH]n3)ccc2c2nn(CCc3c[nH]cn3)cc12] | 344.9 | 0.87 | δ 8.95 – 8.91 (m, 1H), 8.85 – 8.82 (m, 1H), 8.16 (d, J = 8.2 Hz, 1H), 8.09 (br s, 1H), 7.92 (br d, J = 8.2 Hz, 1H), 7.84 (br s, 1H), 7.38 (br s, 1H), 6.81 (d, J = 2.1 Hz, 1H), 4.82 (br t, J = 6.4 Hz, 2H), 3.39 – 3.34 (m, 2H |

| Ex. No. | Structure | LC/MS [M + H]+ | RT (min) | 1H NMR (500 MHz, DMSO-d6) |
|---|---|---|---|---|
| 362 | 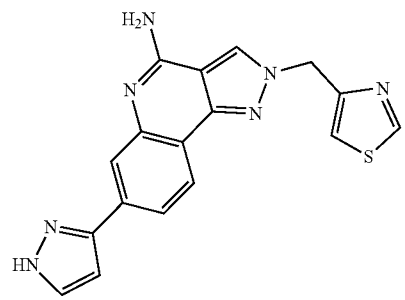 [SMILES: Nc1nc2cc(-c3cc[nH]n3)ccc2c2nn(Cc3cscn3)cc12] | 348.1 | 1.08 | δ 13.28 – 13.04 (m, 1H), 9.77 – 9.54 (m, 1H), 9.14 (br d, J = 1.6 Hz, 1H), 8.99 (s, 1H), 8.95 – 8.80 (m, 1H), 8.17 (d, J = 8.2 Hz, 1H), 8.08 (br s, 1H), 7.93 – 7.87 (m, 2H), 7.84 (br s, 1H), 6.82 (d, J = 1.9 Hz, 1H), 5.87 (br s, 2H) |
| 363 | 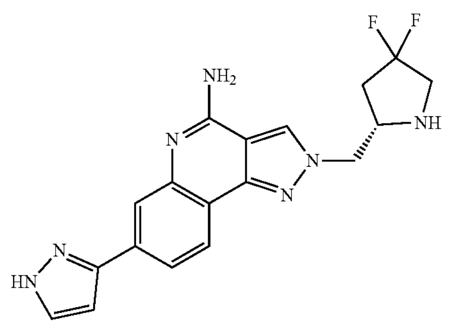 [SMILES: Nc1nc2cc(-c3cc[nH]n3)ccc2c2nn(C[C@@H]3CC(F)(F)CN3)cc12] | 370.2 | 0.89 | δ 8.95 (s, 1H), 8.24 (d, J = 8.3 Hz, 1H), 8.08 (s, 1H), 7.93 (dd, J = 8.3, 1.1 Hz, 1H), 7.83 (d, J = 2.2 Hz, 1H), 6.83 (d, J = 2.2 Hz, 1H), 4.88 – 4.80 (m, 1H), 4.73 (dd, J = 14.3, 8.5 Hz, 1H), 4.29 – 4.21 (m, 1H), 2.79 – 2.69 (m, 1H), 2.44 – 2.33 (m, 1H); two CH protons are not visible, likely due to overlap with suppressed water peak. |
| 364 | 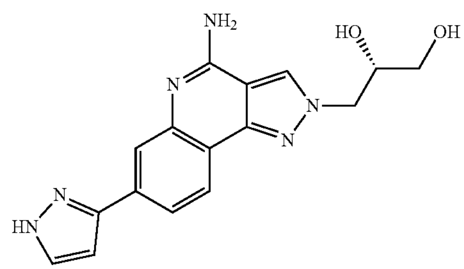 | 325.1 | 0.91 | δ 13.38 – 13.04 (m, 1H), 8.92 (s, 1H), 8.19 (br d, J = 8.2 Hz, 1H), 8.12 (br s, 1H), 7.92 (br d, J = 8.1 Hz, 1H), 7.87 (br s, 1H), 6.82 (br s, 1H), 5.29 (br d, J = 5.2 Hz, 1H), 4.96 (br t, J = 5.1 Hz, 1H), 4.61 (dd, J = 13.8, 2.6 Hz, 1H), 4.35 (dd, J = 13.7, 8.6 Hz, 1H), 3.94 (br s, 1H), 3.51 – 3.46 (m, 2H) |
| 365 | 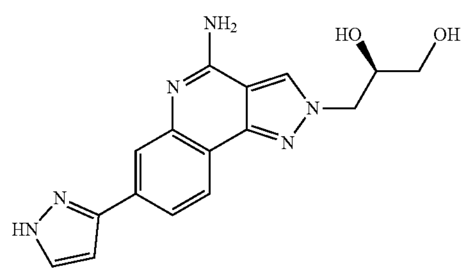 [SMILES: Nc1nc2cc(-c3cc[nH]n3)ccc2c2nn(C[C@@H](O)CO)cc12] | 324.9 | 0.92 | δ 13.27 – 13.06 (m, 1H), 8.94 (s, 1H), 8.20 (d, J = 8.3 Hz, 1H), 8.12 (br s, 1H), 7.92 (br d, J = 7.7 Hz, 1H), 7.85 (br d, J = 6.6 Hz, 1H), 6.81 (d, J = 1.4 Hz, 1H), 5.27 (br d, J = 3.6 Hz, 1H), 4.93 (br d, J = 4.4 Hz, 1H), 4.61 (dd, J = 13.8, 3.0 Hz, 1H), 4.36 (dd, J = 13.8, 8.5 Hz, 1H), 3.94 (br d, J = 5.0 Hz, 1H), 3.52 – 3.46 (m, 1H), 3.43 – 3.38 (m, 1H) |
| 366 | 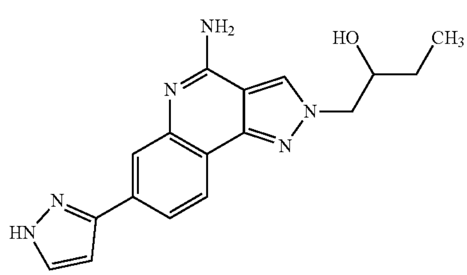 [SMILES: CCC(O)Cn1cc2c(N)nc3cc(-c4cc[nH]n4)ccc3c2n1] | 323.3 | 0.92 | δ 8.89 (s, 1H), 8.21 (d, J = 8.2 Hz, 1H), 8.07 (br s, 1H), 7.92 (br d, J = 8.5 Hz, 1H), 7.83 (br s, 1H), 6.83 (s, 1H), 4.49 (dd, J = 13.7, 2.7 Hz, 1H), 4.32 (dd, J = 13.7, 8.2 Hz, 1H), 3.86 (br d, J = 1.8 Hz, 1H), 1.61 – 1.47 (m, 1H), 1.42 (dt, J = 13.9, 7.1 Hz, 1H), 0.95 (t, J = 7.5 Hz, 3H) |

| Ex. No. | Structure | LC/MS [M + H]+ | RT (min) | ¹H NMR (500 MHz, DMSO-d$_6$) |
|---|---|---|---|---|
| 367 | 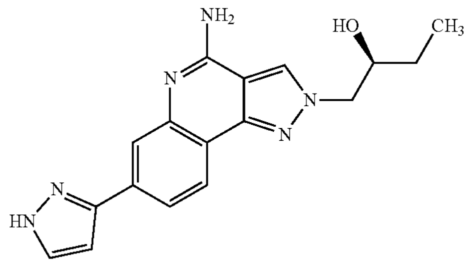 [SMILES: CC[C@H](O)Cn1cc2c(N)nc3cc(-c4cc[nH]n4)ccc3c2n1] | 323.1 | 0.98 | δ 8.90 (br d, J = 2.4 Hz, 1H), 8.21 (d, J = 8.2 Hz, 1H), 8.08 (br s, 1H), 7.93 (d, J = 7.9 Hz, 1H), 7.84 (s, 1H), 6.84 (d, J = 2.3 Hz, 1H), 4.57 – 4.45 (m, 1H), 4.32 (br dd, J = 13.6, 8.1 Hz, 1H), 3.95 – 3.82 (m, 1H), 1.51 (br dd, J = 13.3, 6.2 Hz, 1H), 1.44 – 1.33 (m, 1H), 0.96 (t, J = 7.3 Hz, 3H) |
| 368 | 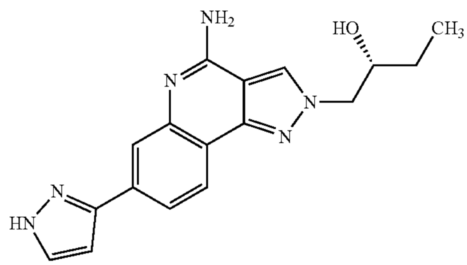 [SMILES: CC[C@@H](O)Cn1cc2c(N)nc3cc(-c4cc[nH]n4)ccc3c2n1] | 323.1 | 0.98 | δ 8.90 (br d, J = 2.4 Hz, 1H), 8.21 (d, J = 8.2 Hz, 1H), 8.08 (br s, 1H), 7.93 (d, J = 7.9 Hz, 1H), 7.84 (s, 1H), 6.84 (d, J = 2.3 Hz, 1H), 4.57 – 4.45 (m, 1H), 4.32 (br dd, J = 13.6, 8.1 Hz, 1H), 3.95 – 3.82 (m, 1H), 1.51 (br dd, J = 13.3, 6.2 Hz, 1H), 1.44 – 1.33 (m, 1H), 0.96 (t, J = 7.3 Hz, 3H) |
| 369 | 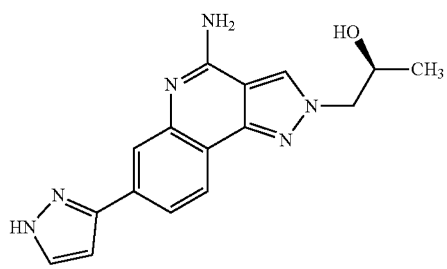 [SMILES: C[C@H](O)Cn1cc2c(N)nc3cc(-c4cc[nH]n4)ccc3c2n1] | 309.3 | 0.98 | ¹H NMR (400 MHz, DMSO-d$_6$) δ 8.98 (s, 1H), 8.21 (d, J = 8.2 Hz, 1H), 8.13 (s, 1H), 7.93 (dd, J = 8.2, 1.4 Hz, 1H), 7.86 (d, J = 2.1 Hz, 1H), 6.83 (d, J = 2.2 Hz, 1H), 4.49 (dd, J = 13.6, 3.4 Hz, 1H), 4.34 (dd, J = 13.7, 7.8 Hz, 1H), 4.22 – 4.06 (m, 1H), 1.20 – 1.17 (m, 3H) |
| 370 | 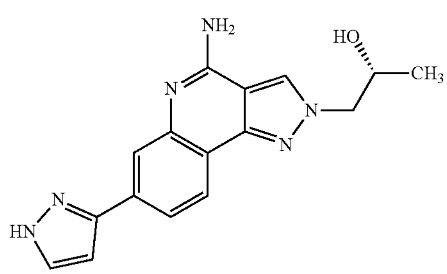 [SMILES: C[C@@H](O)Cn1cc2c(N)nc3cc(-c4cc[nH]n4)ccc3c2n1] | 309.1 | 0.98 | δ 9.76 – 9.55 (m, 1H), 8.97 – 8.89 (m, 1H), 8.21 (d, J = 8.2 Hz, 1H), 8.10 (br s, 1H), 7.93 (br d, J = 8.3 Hz, 1H), 7.85 (br s, 1H), 6.83 (d, J = 2.0 Hz, 1H), 4.48 (br dd, J = 13.3, 3.1 Hz, 1H), 4.32 (br dd, J = 13.7, 8.1 Hz, 1H), 4.20 – 4.06 (m, 1H), 1.18 (d, J = 6.2 Hz, 3H) |
| 371 | 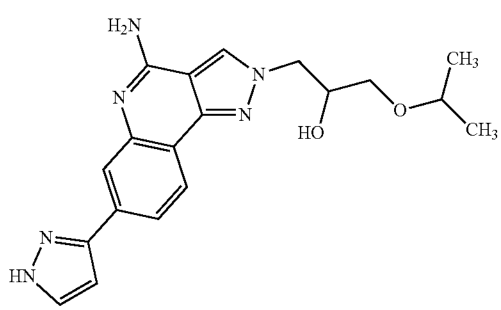 [SMILES: CC(C)OCC(O)Cn1cc2c(N)nc3cc(-c4cc[nH]n4)ccc3c2n1] | 367.4 | 1.33 | δ 9.80 – 9.56 (m, 1H), 8.97 – 8.87 (m, 1H), 8.21 (d, J = 8.2 Hz, 1H), 8.09 (br s, 1H), 7.93 (br d, J = 7.9 Hz, 1H), 7.84 (br s, 1H), 6.83 (d, J = 2.1 Hz, 1H), 4.63 – 4.54 (m, 1H), 4.39 (br dd, J = 13.8, 8.0 Hz, 1H), 4.13 – 3.98 (m, 1H), 3.51 – 3.30 (m, 2H), 1.12 (br t, J = 5.6 Hz, 6H) |

| Ex. No. | Structure | LC/MS [M + H]⁺ | RT (min) | ¹H NMR (500 MHz, DMSO-d₆) |
|---|---|---|---|---|
| 372 | 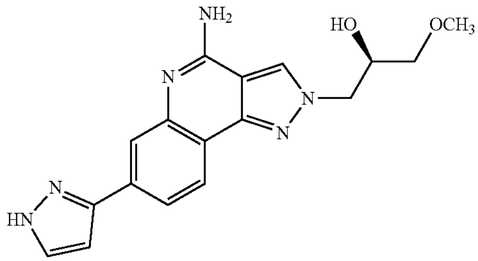 [SMILES: COC[C@H](O)Cn1cc2c(N)nc3cc(-c4cc[nH]n4)ccc3c2n1] | 339.0 | 1.27 | δ 8.87 (s, 1H), 8.20 (d, J = 8.2 Hz, 1H), 8.13 – 8.03 (m, 1H), 7.90 (br d, J = 5.8 Hz, 1H), 7.88 – 7.80 (m, 1H), 6.82 (d, J = 1.4 Hz, 1H), 4.56 (dd, J = 13.8, 3.2 Hz, 1H), 4.39 (dd, J = 13.8, 8.2 Hz, 1H), 4.16 – 4.04 (m, 1H), 3.45 – 3.36 (m, 2H), 3.33 (s, 3H) |
| 373 | 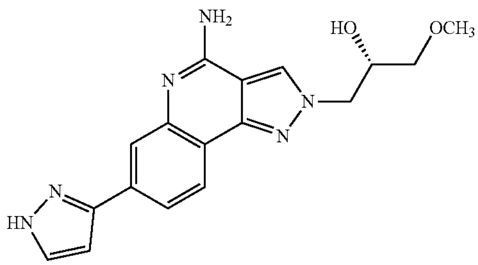 [SMILES: COC[C@@H](O)Cn1cc2c(N)nc3cc(-c4cc[nH]n4)ccc3c2n1] | 339.2 | 1.22 | δ 8.85 (br s, 1H), 8.19 (d, J = 8.2 Hz, 1H), 8.07 (br s, 1H), 7.95 – 7.72 (m, 2H), 6.81 (s, 1H), 4.56 (dd, J = 13.9, 3.2 Hz, 1H), 4.39 (dd, J = 13.7, 8.2 Hz, 1H), 4.11 (br s, 1H), 3.49 – 3.35 (m, 2H), 3.31 (s, 3H)) |
| 374 | 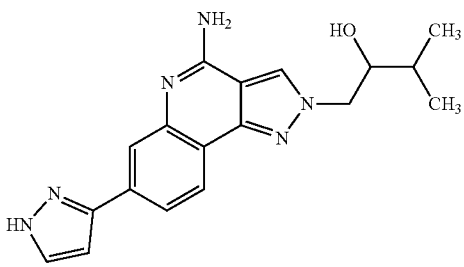 [SMILES: CC(C)C(O)Cn1cc2c(N)nc3cc(-c4cc[nH]n4)ccc3c2n1] | 337.1 | 1.37 | δ 9.74 – 9.55 (m, 1H), 8.99 – 8.81 (m, 2H), 8.21 (d, J = 8.3 Hz, 1H), 8.10 (br s, 1H), 7.93 (d, J = 8.6 Hz, 1H), 7.84 (br s, 1H), 6.83 (d, J = 2.2 Hz, 1H), 4.53 (br d, J = 13.3 Hz, 1H), 4.40 – 4.28 (m, 1H), 3.79 – 3.67 (m, 1H), 1.77 – 1.64 (m, 1H), 0.97 (br dd, J = 12.6, 6.8 Hz, 6H) |
| 375 | 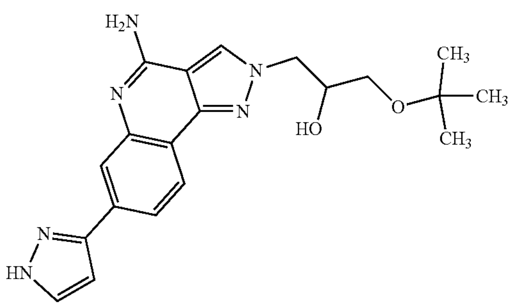 [SMILES: CC(C)(C)OCC(O)Cn1cc2c(N)nc3cc(-c4cc[nH]n4)ccc3c2n1] | 381.3 | 1.46 | δ 8.89 (s, 1H), 8.20 (d, J = 8.5 Hz, 1H), 8.08 (br d, J = 4.3 Hz, 1H), 7.98 – 7.89 (m, 1H), 7.88 – 7.78 (m, 1H), 6.83 (s, 1H), 4.62 – 4.53 (m, 1H), 4.37 (dd, J = 13.9, 8.1 Hz, 1H), 4.01 (br d, J = 3.4 Hz, 1H), 3.61 (br d, J = 6.7 Hz, 1H), 3.39 (br dd, J = 8.7, 4.7 Hz, 1H), 3.33 – 3.24 (m, 1H), 1.17 (s, 9H) |
| 376 | | 327.3 | 0.78 | δ 13.45 – 12.78 (m, 1H), 8.48 (s, 1H), 8.07 (d, J = 8.2 Hz, 1H), 7.87 (s, 1H), 7.72 (br d, J = 6.6 Hz, 1H), 7.62 (br d, J = 7.7 Hz, 1H), 6.91 (br s, 2H), 6.75 (d, J = 1.6 Hz, 1H), 5.76 – 5.59 (m, 1H), 4.58 – 4.32 (m, 4H), 4.26 – 4.16 (m, 1H) | enantiomer 1

-continued

| Ex. No. | Structure | LC/MS [M + H]⁺ | RT (min) | ¹H NMR (500 MHz, DMSO-d₆) |
|---|---|---|---|---|
| 377 | enantiomer 2 | 327.3 | 0.78 | δ 13.35 – 12.64 (m, 1H), 8.48 (s, 1H), 8.07 (d, J = 8.2 Hz, 1H), 7.86 (d, J = 1.3 Hz, 1H), 7.71 (br s, 1H), 7.62 (br d, J = 8.5 Hz, 1H), 6.90 (br s, 2H), 6.75 (d, J = 2.1 Hz, 1H), 5.85 – 5.54 (m, 1H), 4.57 – 4.33 (m, 4H), 4.26 – 4.16 (m, 1H) |
| 378 | enantiomer 1 | 377.1 | 1.21 | δ 8.51 (s, 1H), 8.09 (d, J = 8.0 Hz, 1H), 7.88 (s, 1H), 7.76 – 7.68 (m, 1H), 7.67 – 7.63 (m, 1H), 7.18 – 7.00 (m, 2H), 6.75 (d, J = 1.9 Hz, 1H), 5.73 – 5.62 (m, 1H), 4.50 (br dd, J = 12.9, 2.8 Hz, 1H), 4.39 – 4.28 (m, 2H), 2.66 – 2.55 (m, 1H), 2.45 – 2.34 (m, 1H) |
| 379 | enantiomer 2 | 377.1 | 1.26 | δ 8.49 (s, 1H), 8.08 (d, J = 8.0 Hz, 1H), 7.87 (s, 1H), 7.75 – 7.66 (m, 1H), 7.63 (br d, J = 7.2 Hz, 1H), 6.95 (br s, 2H), 6.75 (d, J = 1.9 Hz, 1H), 5.62 (br d, J = 5.8 Hz, 1H), 4.51 (dd, J = 13.2, 3.0 Hz, 1H), 4.40 – 4.27 (m, 2H), 2.68 – 2.55 (m, 1H), 2.47 – 2.34 (m, 1H) |
| 380 | 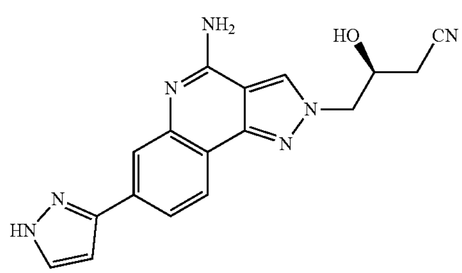 | 334.1 | 0.71 | δ 9.01 (s, 1H), 8.19 (d, J = 8.3 Hz, 1H), 8.08 (br s, 1H), 7.90 (br d, J = 6.1 Hz, 1H), 7.86 – 7.80 (m, 1H), 6.81 (d, J = 2.2 Hz, 1H), 5.46 (br t, J = 5.1 Hz, 1H), 5.08 (quin, J = 6.4 Hz, 1H), 3.89 – 3.86 (m, 2H), 3.30 (br d, J = 6.9 Hz, 2H) |
| 381 | 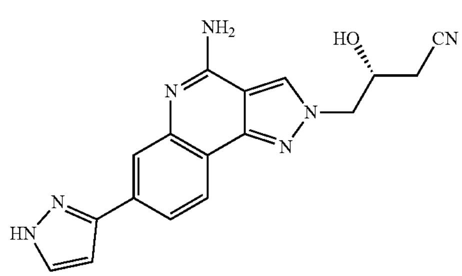 | 333.9 | 1.05 | δ 9.06 (s, 1H), 8.21 (d, J = 8.3 Hz, 1H), 8.11 (br s, 1H), 7.94 (br d, J = 8.3 Hz, 1H), 7.87 – 7.80 (m, 1H), 6.82 (d, J = 2.2 Hz, 1H), 5.49 (br s, 1H), 5.12 – 5.05 (m, 1H), 3.91 – 3.82 (m, 2H), 3.30 (d, J = 7.2 Hz, 2H) |

| Ex. No. | Structure | LC/MS [M + H]+ | RT (min) | ¹H NMR (500 MHz, DMSO-d₆) |
|---|---|---|---|---|
| 382 | 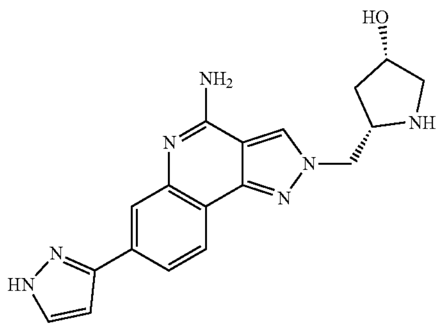 [SMILES: Nc1nc2cc(-c3cc[nH]n3)ccc2c2nn(C[C@@H]3C[C@H](O)CN3)cc12] | 349.9 | 0.48 | δ 8.51 (s, 1H), 8.07 (d, J = 8.3 Hz, 1H), 7.87 (d, J = 1.4 Hz, 1H), 7.71 (s, 1H), 7.62 (dd, J = 8.1, 1.2 Hz, 1H), 7.10 – 6.94 (m, 2H), 6.75 (d, J = 2.2 Hz, 1H), 4.46 – 4.35 (m, 2H), 4.22 – 4.18 (m, 1H), 2.94 (dd, J = 11.0, 5.8 Hz, 1H), 2.70 (dd, J = 11.1, 4.0 Hz, 1H), 2.10 – 2.02 (m, 1H), 1.41 (dt, J = 12.9, 5.4 Hz, 1H) |
| 383 | 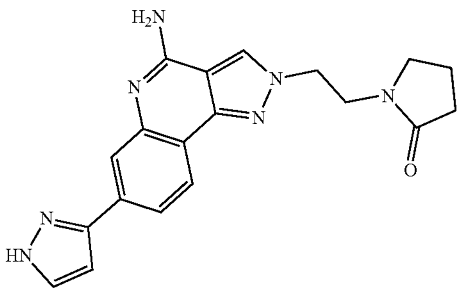 [SMILES: Nc1nc2cc(-c3cc[nH]n3)ccc2c2nn(CCN3CCCC3=O)cc12] | 362.0 | 0.95 | δ 13.29 – 13.10 (m, 1H), 9.73 – 9.50 (m, 1H), 8.88 (s, 1H), 9.02 – 8.84 (m, 1H), 8.20 (d, J = 8.3 Hz, 1H), 8.11 (br s, 1H), 7.92 (br d, J = 8.0 Hz, 1H), 7.89 – 7.82 (m, 1H), 6.81 (d, J = 1.7 Hz, 1H), 4.66 (t, J = 5.8 Hz, 2H), 3.70 (t, J = 5.8 Hz, 2H), 3.33 – 3.29 (m, 2H), 2.15 – 2.10 (m, 2H), 1.91 (quin, J = 7.5 Hz, 2H) |
| 384 | 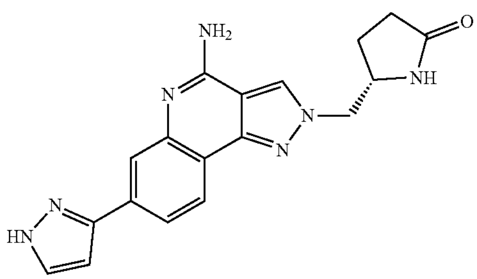 [SMILES: Nc1nc2cc(-c3cc[nH]n3)ccc2c2nn(C[C@@H]3CCC(=O)N3)cc12] | 348.1 | 0.96 | δ 8.45 (s, 1H), 8.08 (d, J = 8.3 Hz, 1H), 7.88 (br s, 1H), 7.80 (s, 1H), 7.71 (br s, 1H), 7.62 (br d, J = 8.3 Hz, 1H), 7.03 – 6.90 (m, 2H), 6.75 (d, J = 1.1 Hz, 1H), 4.50 – 4.42 (m, 2H), 4.12 – 4.05 (m, 1H), 2.18 – 2.10 (m, 1H), 2.09 – 2.03 (m, 2H), 2.02 – 1.84 (m, 1H). |
| 385 | 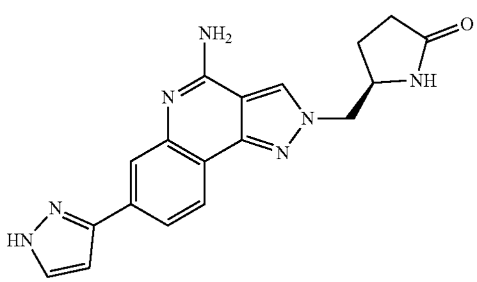 [SMILES: Nc1nc2cc(-c3cc[nH]n3)ccc2c2nn(C[C@H]3CCC(=O)N3)cc12] | 348.0 | 0.92 | δ 8.45 (s, 1H), 8.08 (d, J = 8.0 Hz, 1H), 7.86 (s, 1H), 7.81 (s, 1H), 7.74 – 7.66 (m, 1H), 7.65 – 7.59 (m, 1H), 6.88 (br s, 2H), 6.75 (d, J = 1.9 Hz, 1H), 4.49 – 4.41 (m, 2H), 4.12 – 4.06 (m, 1H), 2.19 – 2.09 (m, 1H), 2.08 – 2.03 (m, 2H), 1.93 – 1.84 (m, 1H) |
| 386 | 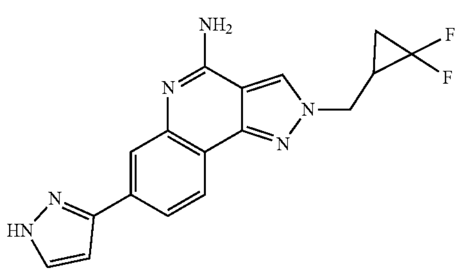 [SMILES: Nc1nc2cc(-c3cc[nH]n3)ccc2c2nn(CC3CC3(F)F)cc12] | 341.0 | 1.09 | δ 13.12 – 12.81 (m, 1H), 8.62 (br s, 1H), 8.10 (d, J = 8.2 Hz, 1H), 7.92 (br s, 1H), 7.85 – 7.62 (m, 2H), 7.57 – 7.12 (m, 2H), 6.77 (d, J = 1.3 Hz, 1H), 4.66 – 4.60 (m, 1H), 4.59 – 4.53 (m, 1H), 2.47 – 2.38 (m, 1H), 1.84 – 1.73 (m, 1H), 1.67 – 1.57 (m, 1H) |

| Ex. No. | Structure | LC/MS [M + H]+ | RT (min) | ¹H NMR (500 MHz, DMSO-d₆) |
|---|---|---|---|---|
| 387 | 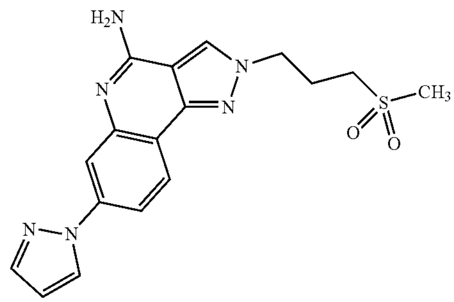 [SMILES: CS(=O)(=O)CCCn1cc2c(N)nc3cc(-n4cccn4)ccc3c2n1] | 371.2 | 1.09 | δ 8.93 (s, 1H), 8.62 (d, J = 2.5 Hz, 1H), 8.28 (d, J = 8.5 Hz, 1H), 8.16 (d, J = 1.9 Hz, 1H), 7.96 (dd, J = 8.7, 2.1 Hz, 1H), 7.85 (d, J = 1.4 Hz, 1H), 6.65 – 6.62 (m, 1H), 4.64 (t, J = 6.9 Hz, 2H), 3.24 – 3.17 (m, 2H), 3.01 (s, 3H), 2.39 (quin, J = 7.3 Hz, 2H) |
| 389 | | 339.3 | 0.86 | δ 8.88 (s, 1H), 8.58 (d, J = 2.2 Hz, 1H), 8.26 (d, J = 8.6 Hz, 1H), 8.11 (s, 1H), 7.93 (br d, J = 8.6 Hz, 1H), 7.84 (s, 1H), 6.63 (t, J = 1.9 Hz, 1H), 5.15 – 4.99 (m, 1H), 4.64 (dd, J = 13.9, 3.1 Hz, 1H), 4.50 (dd, J = 14.2, 7.6 Hz, 1H), 3.72 – 3.65 (m, 1H), 3.54 – 3.50 (m, 2H), 3.24 (s, 3H) |
| 389 | | 325.2 | 0.95 | δ 8.56 (d, J = 2.2 Hz, 1H), 8.52 (s, 1H), 8.14 (d, J = 8.5 Hz, 1H), 7.87 (d, J = 2.2 Hz, 1H), 7.76 (d, J = 1.4 Hz, 1H), 7.68 (dd, J = 8.5, 2.2 Hz, 1H), 7.20 – 7.10 (m, 2H), 6.56 – 6.55 (m, 1H), 5.17 (d, J = 5.2 Hz, 1H), 4.90 – 4.83 (m, 1H), 4.56 (dd, J = 13.5, 3.3 Hz, 1H), 4.26 (dd, J = 13.6, 8.4 Hz, 1H), 3.95 (br d, J = 2.8 Hz, 1H), 3.49 – 3.43 (m, 2H) |
| 390 | 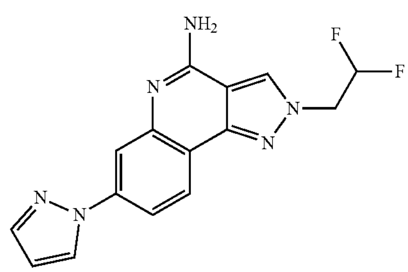 [SMILES: Nc1nc2cc(-n3cccn3)ccc2c2nn(CC(F)F)cc12] | 315.2 | 1.11 | δ 8.59 (s, 1H), 8.56 (d, J = 2.2 Hz, 1H), 8.14 (d, J = 8.3 Hz, 1H), 7.87 (d, J = 1.9 Hz, 1H), 7.77 (s, 1H), 7.69 (dd, J = 8.5, 1.9 Hz, 1H), 7.24 – 7.08 (m, 2H), 6.55 (d, J = 1.7 Hz, 1H), 6.66 – 6.41 (m, 1H), 5.01 (td, J = 15.2, 3.2 Hz, 2H) |
| 391 | 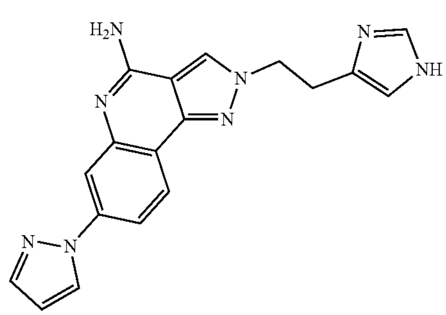 [SMILES: Nc1nc2cc(-n3cccn3)ccc2c2nn(CCc3c[nH]cn3)cc12] | 345.3 | 0.70 | δ 8.91 (br d, J = 1.1 Hz, 1H), 8.83 (d, J = 2.7 Hz, 1H), 8.60 (br d, J = 1.8 Hz, 1H), 8.23 (d, J = 8.6 Hz, 1H), 8.14 (br d, J = 1.4 Hz, 1H), 7.96 (br d, J = 8.8 Hz, 1H), 7.85 (s, 1H), 7.37 (br s, 1H), 6.67 – 6.60 (m, 1H), 4.81 (br t, J = 5.9 Hz, 2H), 3.39 – 3.35 (m, 2H) |

| Ex. No. | Structure | LC/MS [M + H]+ | RT (min) | ¹H NMR (500 MHz, DMSO-d₆) |
|---|---|---|---|---|
| 392 | 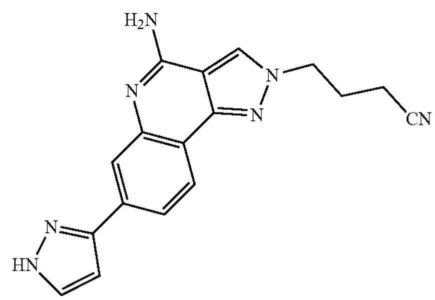 [SMILES: N#CCCCn1cc2c(N)nc3cc(-c4cc[nH]n4)ccc3c2n1] | 318.2 | 1.10 | δ 8.52 (s, 1H), 8.09 (d, J = 8.1 Hz, 1H), 7.89 (s, 1H), 7.72 (br s, 1H), 7.65 (br d, J = 8.5 Hz, 1H), 7.27 – 6.97 (m, 2H), 6.78 – 6.74 (m, 1H), 4.50 (br t, J = 6.7 Hz, 2H), 2.58 – 2.53 (m, 2H), 2.24 (quin, J = 6.8 Hz, 2H) |
| 393 | 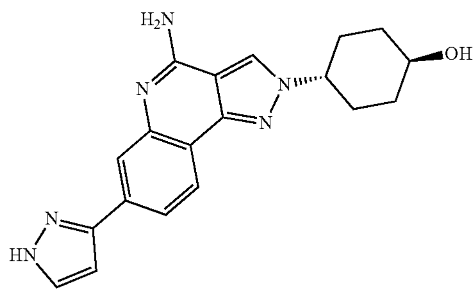 [SMILES: Nc1nc2cc(-c3cc[nH]n3)ccc2c2nn([C@H]3CC[C@H](O)CC3)cc12] | 349.2 | 0.86 | δ 8.51 (s, 1H), 8.06 (d, J = 8.3 Hz, 1H), 7.86 (s, 1H), 7.78 – 7.65 (m, 1H), 7.61 (br d, J = 7.4 Hz, 1H), 6.83 (br s, 2H), 6.74 (d, J = 1.9 Hz, 1H), 4.86 – 4.62 (m, 1H), 4.51 – 4.40 (m, 1H), 3.62 – 3.53 (m, 1H), 2.20 – 2.13 (m, 2H), 2.03 – 1.96 (m, 2H), 1.96 – 1.85 (m, 2H), 1.49 – 1.39 (m, 2H) |
| 394 | 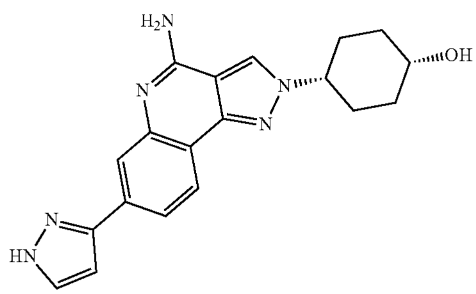 [SMILES: Nc1nc2cc(-c3cc[nH]n3)ccc2c2nn([C@H]3CC[C@@H](O)CC3)cc12] | 349.3 | 1.14 | δ 8.94 (s, 1H), 8.20 (d, J = 8.3 Hz, 1H), 8.12 – 8.06 (m, 1H), 7.94 – 7.88 (m, 1H), 7.87 – 7.81 (m, 1H), 6.82 (s, 1H), 4.70 (br s, 1H), 4.60 – 4.52 (m, 1H), 3.60 – 3.56 (m, 1H), 2.31 – 2.19 (m, 2H), 1.98 – 1.91 (m, 2H), 1.82 – 1.75 (m, 2H), 1.73 – 1.63 (m, 2H) |
| 395 | 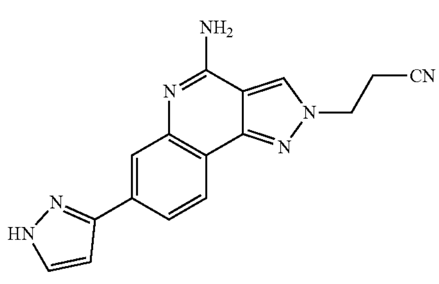 [SMILES: N#CCCn1cc2c(N)nc3cc(-c4cc[nH]n4)ccc3c2n1] | 304.2 | 0.83 | δ 13.24 – 13.05 (m, 1H), 9.01 – 8.97 (m, 1H), 8.21 – 8.17 (m, 1H), 8.10 (br s, 1H), 7.93 (br d, J = 7.3 Hz, 1H), 7.85 (br s, 1H), 6.82 (br s, 1H), 4.85 – 4.79 (m, 2H), 3.30 – 3.25 (m, 2H) |
| 396 | 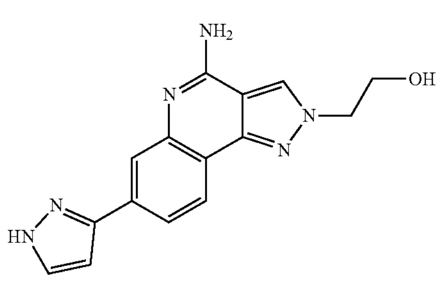 | 295.2 | 0.96 | δ 8.71 (s, 1H), 7.96 (d, J = 8.3 Hz, 1H), 7.91 (s, 1H), 7.77 – 7.59 (m, 2H), 7.12 – 6.89 (m, 2H), 6.74 (s, 1H), 5.10 – 5.07 (m, 1H), 4.48 (t, J = 5.2 Hz, 2H), 3.93 – 3.88 (m, 2H) |

| Ex. No. | Structure | LC/MS [M + H]⁺ | RT (min) | ¹H NMR (500 MHz, DMSO-d₆) |
|---|---|---|---|---|
| 397 | 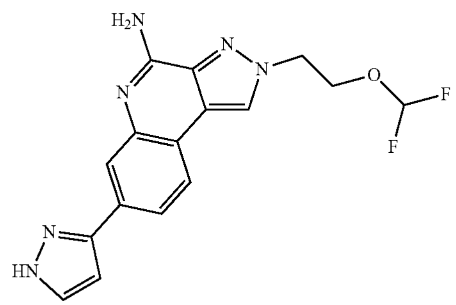 [SMILES: Nc1nc2cc(-c3cc[nH]n3)ccc2c2cn(CCOC(F)F)nc12] | 345.2 | 0.92 | δ 13.52 – 12.76 (m, 1H), 8.74 (s, 1H), 7.94 (br d, J = 7.9 Hz, 1H), 7.90 (br s, 1H), 7.81 – 7.58 (m, 2H), 6.94 – 6.83 (m, 2H), 6.83 – 6.50 (m, 2H), 4.71 (t, J = 5.0 Hz, 2H), 4.37 (t, J = 5.0 Hz, 2H) |
| 398 | 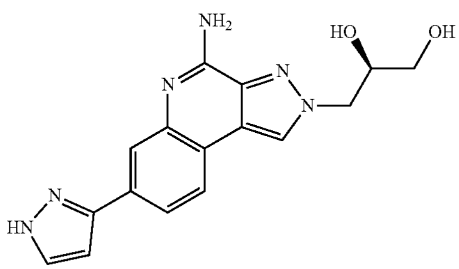 [SMILES: Nc1nc2cc(-c3cc[nH]n3)ccc2c2cn(C[C@@H](O)CO)nc12] | 325.1 | 0.67 | δ 8.66 (s, 1H), 7.96 (d, J = 8.0 Hz, 1H), 7.90 (s, 1H), 7.69 (br s, 1H), 7.63 (br d, J = 7.7 Hz, 1H), 6.94 – 6.79 (m, 2H), 6.74 (d, J = 1.9 Hz, 1H), 5.16 (br s, 1H), 4.93 – 4.81 (m, 1H), 4.57 (dd, J = 13.8, 3.6 Hz, 1H), 4.30 (dd, J = 13.8, 8.3 Hz, 1H), 3.98 (br s, 1H), 3.51 – 3.43 (m, 2H) |
| 399 | 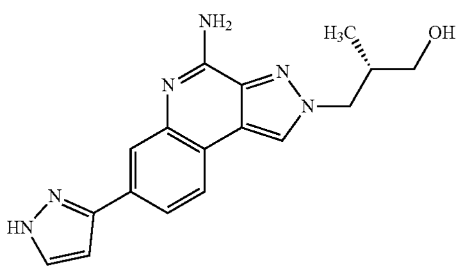 [SMILES: C[C@H](CO)Cn1cc2c(n1)c(N)nc1cc(-c3cc[nH]n3)ccc12] | 323.3 | 1.06 | δ 13.28 – 12.91 (m, 1H), 9.85 – 9.04 (m, 2H), 8.96 (s, 1H), 8.11 (br d, J = 8.0 Hz, 2H), 7.89 (br d, J = 8.5 Hz, 1H), 7.82 (br s, 1H), 6.79 (d, J = 1.7 Hz, 1H), 4.95 – 4.77 (m, 1H), 4.58 (dd, J = 13.3, 6.2 Hz, 1H), 4.31 (dd, J = 13.5, 8.0 Hz, 1H), 3.41 – 3.33 (m, 2H), 2.34 – 2.24 (m, 1H), 0.87 (d, J = 6.9 Hz, 3H) |
| 400 | 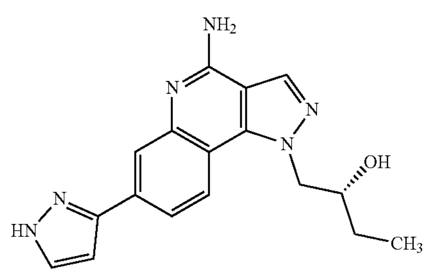 [SMILES: CC[C@@H](O)Cn1ncc2c(N)nc3cc(-c4cc[nH]n4)ccc3c21] | 323.1 | 1.21 | δ 8.64 (s, 1H), 8.48 (br d, J = 8.9 Hz, 1H), 8.19 (br s, 1H), 7.97 (br d, J = 7.3 Hz, 1H), 7.87 (br d, J = 2.4 Hz, 1H), 6.87 (s, 1H), 4.85 – 4.65 (m, 2H), 3.92 (br s, 1H), 1.58 (br d, J = 7.3 Hz, 1H), 1.49 (br d, J = 7.3 Hz, 1H), 0.96 (t, J = 7.2 Hz, 3H) |
| 401 | 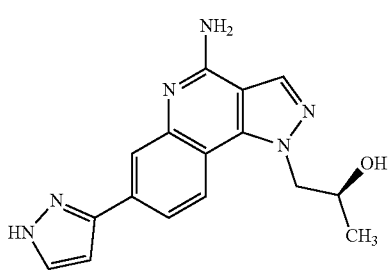 [SMILES: C[C@H](O)Cn1ncc2c(N)nc3cc(-c4cc[nH]n4)ccc3c21] | 309.2 | 0.97 | δ 8.34 (s, 1H), 8.31 (d, J = 8.6 Hz, 1H), 8.01 (s, 1H), 7.79 – 7.71 (m, 2H), 6.82 (d, J = 2.1 Hz, 1H), 4.78 – 4.69 (m, 1H), 4.58 (dd, J = 14.3, 5.6 Hz, 1H), 4.22 – 4.12 (m, 1H), 1.15 (d, J = 6.2 Hz, 3H) |

-continued

| Ex. No. | Structure | LC/MS [M + H]+ | RT (min) | 1H NMR (500 MHz, DMSO-d6) |
|---|---|---|---|---|
| 402 | 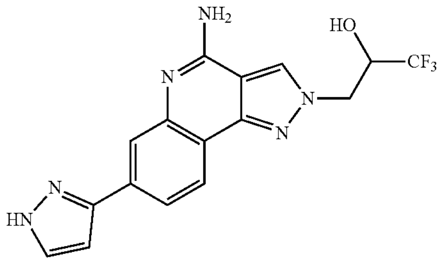 [SMILES: Nc1nc2cc(-c3cc[nH]n3)ccc2c2nn(CC(O)C(F)(F)F)cc12] | 377.2 | 1.23 | δ 8.90 (s, 1H), 8.22 (d, J = 7.9 Hz, 1H), 8.09 (br s, 1H), 7.93 (br d, J = 8.2 Hz, 1H), 7.84 (br s, 1H), 6.83 (d, J = 1.5 Hz, 1H), 4.59 (dd, J = 13.4, 3.1 Hz, 1H), 4.45 (dd, J = 13.7, 8.2 Hz, 1H), 4.33 (br d, J = 3.4 Hz, 1H), 2.77 – 2.60 (m, 1H), 2.47 – 2.35 (m, 1H) |
| 403 | 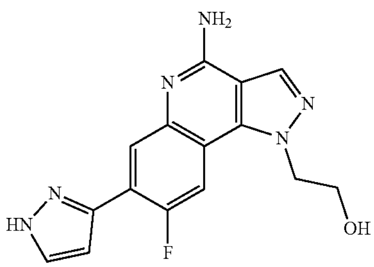 [SMILES: Nc1nc2cc(-c3cc[nH]n3)c(F)cc2c2c1cnn2CCO] | 312.9 | 1.04 | δ 8.92 (s, 1H), 8.27 (br d, J = 1.5 Hz, 1H), 7.98 (br d, J = 10.7 Hz, 1H), 7.89 (br s, 1H), 6.77 (br s, 1H), 4.52 (t, J = 4.3 Hz, 2H), 3.90 (t, J = 4.3 Hz, 2H) |
| 404 | 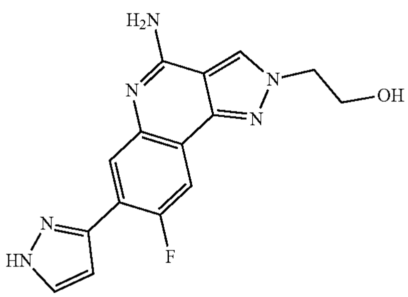 [SMILES: Nc1nc2cc(-c3cc[nH]n3)c(F)cc2c2nn(CCO)cc12] | 312.9 | 1.10 | δ 8.91 (s, 1H), 8.42 – 8.17 (m, 1H), 7.98 (br d, J = 10.7 Hz, 1H), 7.88 (br s, 1H), 6.76 (br s, 1H), 4.52 (br t, J = 4.6 Hz, 2H), 3.89 (br s, 2H) |
| 405 | 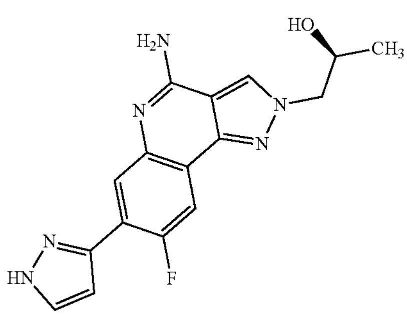 [SMILES: C[C@H](O)Cn1cc2c(N)nc3cc(-c4cc[nH]n4)c(F)cc3c2n1] | 327.1 | 1.00 | δ 8.92 (s, 1H), 8.33 (br d, J = 1.1 Hz, 1H), 7.97 (br d, J = 10.9 Hz, 1H), 7.93 (br s, 1H), 6.84 – 6.70 (m, 1H), 4.49 (dd, J = 13.6, 2.9 Hz, 1H), 4.33 (br dd, J = 13.7, 8.0 Hz, 1H), 4.12 (br s, 1H), 1.18 (d, J = 6.3 Hz, 3H) |
| 406 | 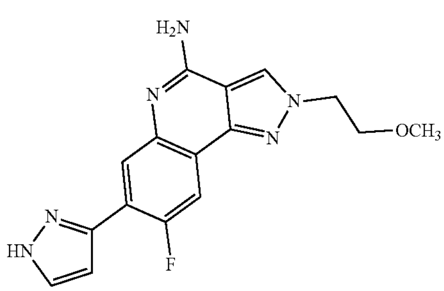 [SMILES: COCCn1cc2c(N)nc3cc(-c4cc[nH]n4)c(F)cc3c2n1] | 327.1 | 1.17 | δ 8.94 (s, 1H), 8.42 – 8.24 (m, 1H), 7.98 (br d, J = 10.9 Hz, 1H), 7.93 (br s, 1H), 6.77 (dd, J = 4.0, 2.2 Hz, 1H), 4.69 (br t, J = 4.8 Hz, 2H), 3.84 (t, J = 4.9 Hz, 2H), 3.29 (s, 3H) |

Example 407. Preparation of 2-(4-amino-7-(1H-pyrazol-3-yl)-2H-pyrazolo[4,3-c]quinolin-2-yl)-2-methylpropan-1-ol, TFA

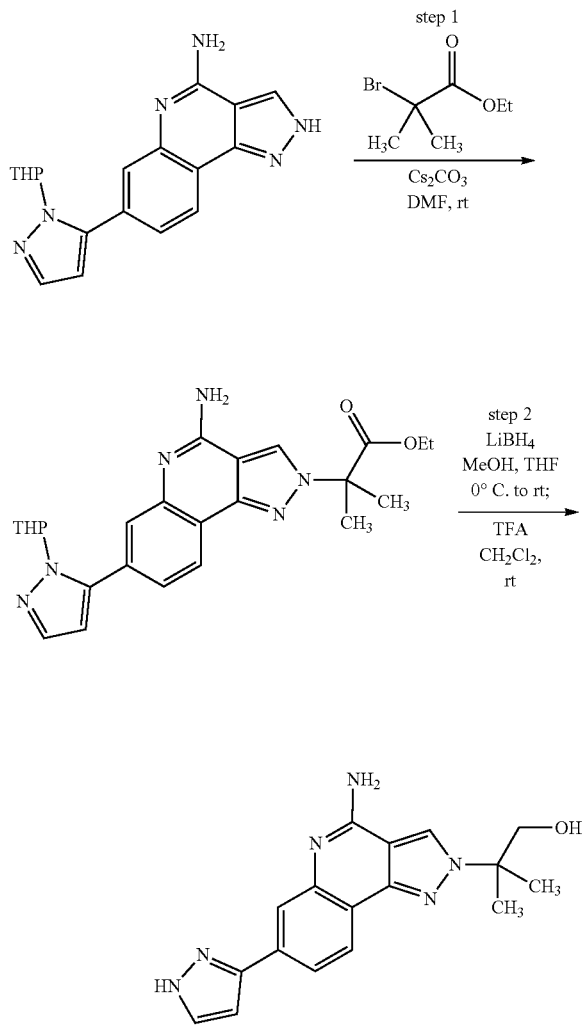

Step 1. ethyl 2-(4-amino-7-(1-(tetrahydro-2H-pyran-2-yl)-1H-pyrazol-5-yl)-2H-pyrazolo[4,3-c]quinolin-2-yl)-2-methylpropanoate To a rt suspension of 7-(1-(tetrahydro-2H-pyran-2-yl)-1H-pyrazol-5-yl)-2H-pyrazolo[4,3-c]quinolin-4-amine (50 mg, 0.150 mmol) in DMF (498 µl) was added cesium carbonate (146 mg, 0.449 mmol) followed by ethyl 2-bromo-2-methylpropanoate (24.14 µl, 0.164 mmol). The suspension was stirred at rt for 20 h. The reaction was diluted with EtOAc (20 mL) and H$_2$O (20 mL). The layers were separated and the aqueous layer was extracted with EtOAc (10 mL). The combined organic layers were washed with sat. aq. NaCl (20 mL), dried over Na$_2$SO$_4$, filtered, and concentrated in vacuo. The crude material was purified by flash chromatography (12 g silica gel; linear gradient 0-10% MeOH—CH$_2$Cl$_2$) to provide ethyl 2-(4-amino-7-(1-(tetrahydro-2H-pyran-2-yl)-1H-pyrazol-5-yl)-2H-pyrazolo[4,3-c]quinolin-2-yl)-2-methylpropanoate (50.1 mg, 75% yield) as a white solid. LC-MS m/z 449 [M+H]$^+$; $^1$H NMR (400 MHz, DMSO-d$_6$) δ 8.79 (s, 1H), 8.14 (d, J=8.1 Hz, 1H), 7.61 (d, J=1.5 Hz, 1H), 7.59 (d, J=1.8 Hz, 1H), 7.32 (dd, J=8.0, 1.5 Hz, 1H), 7.16-6.99 (m, 2H), 6.50 (d, J=1.8 Hz, 1H), 5.29 (dd, J=10.0, 2.0 Hz, 1H), 4.13 (q, J=7.1 Hz, 2H), 4.07-3.99 (m, 1H), 3.63-3.54 (m, 1H), 2.49-2.36 (m, 2H), 1.95 (s, 6H), 1.79 (br d, J=12.0 Hz, 1H), 1.62-1.49 (m, 3H), 1.12 (t, J=7.1 Hz, 3H).

Step 2. 2-(4-amino-7-(1H-pyrazol-3-yl)-2H-pyrazolo[4,3-c]quinolin-2-yl)-2-methylpropan-1-ol, TFA To a suspension of ethyl 2-(4-amino-7-(1-(tetrahydro-2H-pyran-2-yl)-1H-pyrazol-5-yl)-2H-pyrazolo[4,3-c]quinolin-2-yl)-2-methylpropanoate (50.1 mg, 0.112 mmol) in THF (1005 µl) was added MeOH (112 µl), giving a clear colorless solution. The solution was cooled to 0° C. and lithium borohydride (2 M solution in THF) (168 µl, 0.335 mmol) was added dropwise. The reaction was stirred at 0° C. for 15 min, then at rt for 1 h. The reaction was diluted with H$_2$O (20 mL) and extracted with EtOAc (3×10 mL). The combined organic layers were washed with sat. aq. NaCl (20 mL), dried over Na$_2$SO$_4$, filtered, and concentrated in vacuo.

The crude material was mixed with CH$_2$Cl$_2$ (200 µL) and TFA (200 µL) and the stirred at rt for 1 h. The reaction was concentrated in vacuo. The crude material was dissolved in CH$_2$Cl$_2$ (300 µL) and concentrated in vacuo. The crude material was dissolved in DMF (2 mL), filtered (Acrodisc 0.45 µm nylon syringe filter), and purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-30% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to provide 2-(4-amino-7-(1H-pyrazol-3-yl)-2H-pyrazolo[4,3-c]quinolin-2-yl)-2-methylpropan-1-ol, TFA (30.8 mg, 63%). $^1$H NMR (500 MHz, DMSO-d$_6$) δ 13.22 (br s, 1H), 9.60-9.42 (m, 1H), 9.03-8.99 (m, 1H), 8.83-8.61 (m, 1H), 8.22 (d, J=8.2 Hz, 1H), 8.06 (br s, 1H), 7.92 (br d, J=7.9 Hz, 1H), 7.83 (br s, 1H), 6.82 (d, J=2.2 Hz, 1H), 5.32 (br s, 1H), 1.64 (s, 6H); two CH protons are not visible, likely due to overlap with suppressed water peak. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 323.0 [M+H]$^+$; RT: 0.9 min.

Example 408 to Example 409 were prepared according to synthetic procedures similar to those described for Example 407 from the appropriate alkyl chloride or mesylate starting materials. The temperature for the alkylation reaction ranged from rt to 50° C. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

| Ex. No. | Structure | LC/MS [M + H]+ | RT (min) | 1H NMR (500 MHz, DMSO-d6) |
|---|---|---|---|---|
| 408 | 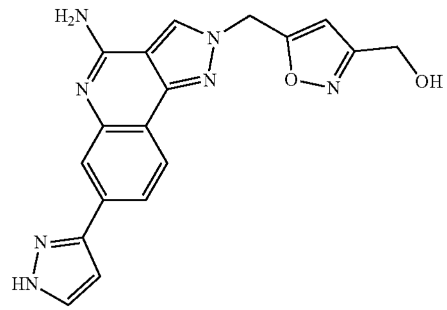 [SMILES: Nc1nc2cc(-c3cc[nH]n3)ccc2c2nn(Cc3cc(CO)no3)cc12] | 362.1 | 0.72 | δ 13.19-12.98 (m, 1H), 9.01-8.83 (m, 1H), 8.92-8.31 (m, 2H), 8.13 (d, J = 8.2 Hz, 1H), 8.02 (br d, J = 2.8 Hz, 1H), 7.91-7.72 (m, 2H), 6.80 (s, 1H), 6.59 (s, 1H), 5.99 (s, 2H), 5.68-5.55 (m, 1H), 4.49 (d, J = 5.6 Hz, 2H) |
| 409 | 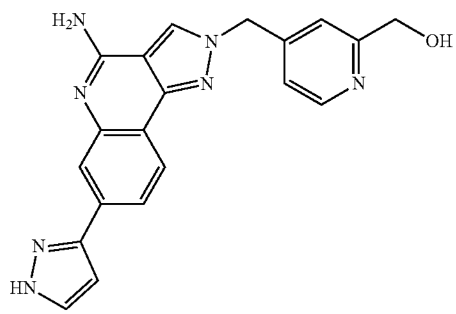 [SMILES: Nc1nc2cc(-c3cc[nH]n3)ccc2c2nn(Cc3ccnc(CO)c3)cc12] | 372.2 | 0.93 | δ 8.60 (s, 1H), 8.45 (d, J = 5.0 Hz, 1H), 8.06 (d, J = 8.0 Hz, 1H), 7.88 (d, J = 1.4 Hz, 1H), 7.71 (br s, 1H), 7.62 (dd, J = 8.1, 1.2 Hz, 1H), 7.30 (s, 1H), 7.11 (br d, J = 4.7 Hz, 1H), 7.08-6.94 (m, 2H), 6.75 (d, J = 2.2 Hz, 1H), 5.76 (s, 2H), 5.64-5.36 (m, 1H), 4.53 (s, 2H) |

Example 410. Preparation of 3-(4-amino-7-(1H-pyrazol-3-yl)-2H-pyrazolo[4,3-c]quinolin-2-yl)-3-methylbutan-1-ol, TFA

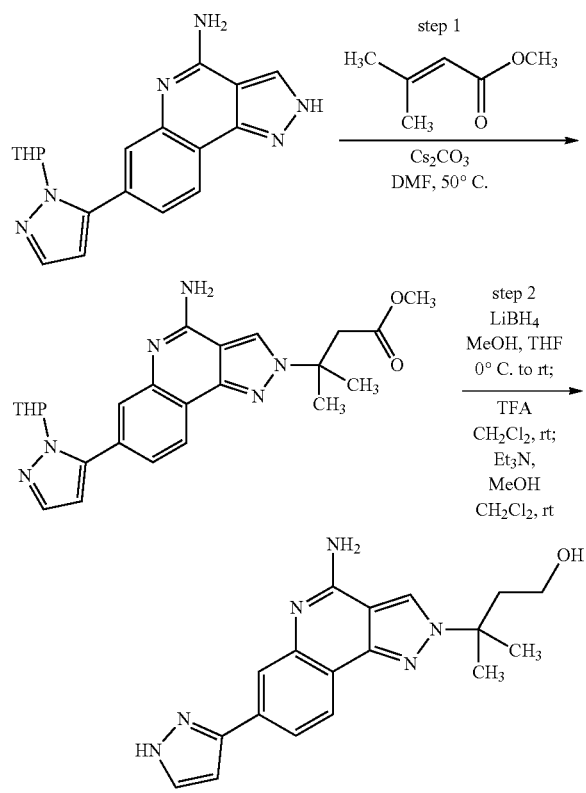

Step 1. methyl 3-(4-amino-7-(1-(tetrahydro-2H-pyran-2-yl)-1H-pyrazol-5-yl)-2H-pyrazolo[4,3-c]quinolin-2-yl)-3-methylbutanoate To a rt suspension of 7-(1-(tetrahydro-2H-pyran-2-yl)-1H-pyrazol-5-yl)-2H-pyrazolo[4,3-c]quinolin-4-amine (30 mg, 0.090 mmol) in DMF (299 μl) was added cesium carbonate (88 mg, 0.269 mmol) followed by methyl 3-methylbut-2-enoate (12.90 μl, 0.099 mmol). The reaction was stirred at rt for 19 h. The reaction was stirred at 50° C. for 2 h. Additional methyl 3-methylbut-2-enoate (25.8 μL, 0.198 mmol) was added. The reaction was stirred at 50° C. for 22 h. Additional methyl 3-methylbut-2-enoate (50 μL) was added. The reaction was stirred at rt for 16 h. Additional methyl 3-methylbut-2-enoate (50 μL) was added. The reaction was stirred at rt for 4 h. The reaction was diluted with EtOAc (20 mL) and H2O (20 mL). The layers were separated and the aqueous layer was extracted with EtOAc (10 mL). The combined organic layers were washed with sat. aq. NaCl (20 mL), dried over Na2SO4, filtered, and concentrated in vacuo. The crude material was purified by flash chromatography (12 g silica gel; linear gradient 0-10% MeOH—CH2Cl2) to provide methyl 3-(4-amino-7-(1-(tetrahydro-2H-pyran-2-yl)-1H-pyrazol-5-yl)-2H-pyrazolo[4,3-c]quinolin-2-yl)-3-methylbutanoate as a mixture with unreacted starting material (20 mg). This material was used without further purification.

Step 2. 3-(4-amino-7-(1H-pyrazol-3-yl)-2H-pyrazolo[4,3-c]quinolin-2-yl)-3-methylbutan-1-ol, TFA The material from the previous step was suspended in THF (401 μl) and then MeOH (44.6 μl) was added. The mixture was cooled to 0° C. and lithium borohydride (2 M solution in THF) (66.9 μl, 0.134 mmol) was added, dropwise. The reaction was stirred at rt for 5 h. Additional LiBH4 (67 μL) was added. The reaction was stirred at rt 30 min.

Additional LiBH₄ (134 μL) was added. The reaction was stirred at rt for 18 h. The reaction was diluted with H₂O (20 mL) and extracted with EtOAc (3×10 mL). The combined organic layers were washed with sat. aq. NaCl (20 mL), dried over Na₂SO₄, filtered, and concentrated in vacuo.

The crude material was mixed with CH₂Cl₂ (150 μL) and TFA (150 μL) and the reaction was stirred at rt for 1 h. The reaction was concentrated in vacuo. The crude material was dissolved in CH₂Cl₂ (300 μL) and concentrated in vacuo.

The crude material was mixed with CH₂Cl₂ (150 μL) and MeOH (150 μL), and triethylamine (31.1 μl, 0.223 mmol) was added. The reaction was stirred at rt for 15 min. The reaction was concentrated in vacuo. The crude material was dissolved in CH₂Cl₂ (300 μL) and concentrated in vacuo. The crude material was dissolved in DMF (2 mL), filtered (Acrodisc 0.45 μm nylon syringe filter), and purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.10% trifluoroacetic acid; Gradient: a 0-minute hold at 1% B, 1-41% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to provide 3-(4-amino-7-(1H-pyrazol-3-yl)-2H-pyrazolo[4,3-c]quinolin-2-yl)-3-methylbutan-1-ol, TFA (10.2 mg, 50%). ¹H NMR (500 MHz, DMSO-d₆) δ 13.22-13.01 (m, 1H), 9.59-9.35 (m, 1H), 9.04 (s, 1H), 8.91-8.72 (m, 1H), 8.21 (d, J=8.3 Hz, 1H), 8.10 (br s, 1H), 7.92 (br d, J=7.9 Hz, 1H), 7.85 (br s, 1H), 6.82 (d, J=1.9 Hz, 1H), 4.58 (br s, 1H), 3.29 (br t, J=6.8 Hz, 2H), 2.19 (t, J=6.9 Hz, 2H), 1.72 (s, 6H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 337.2 [M+H]⁺; RT: 1.1 min.

Example 411. Preparation of 2-[(morpholin-4-yl)methyl]-7-(1H-pyrazol-5-yl)-1H-pyrrolo[3,2-c]quinolin-4-amine

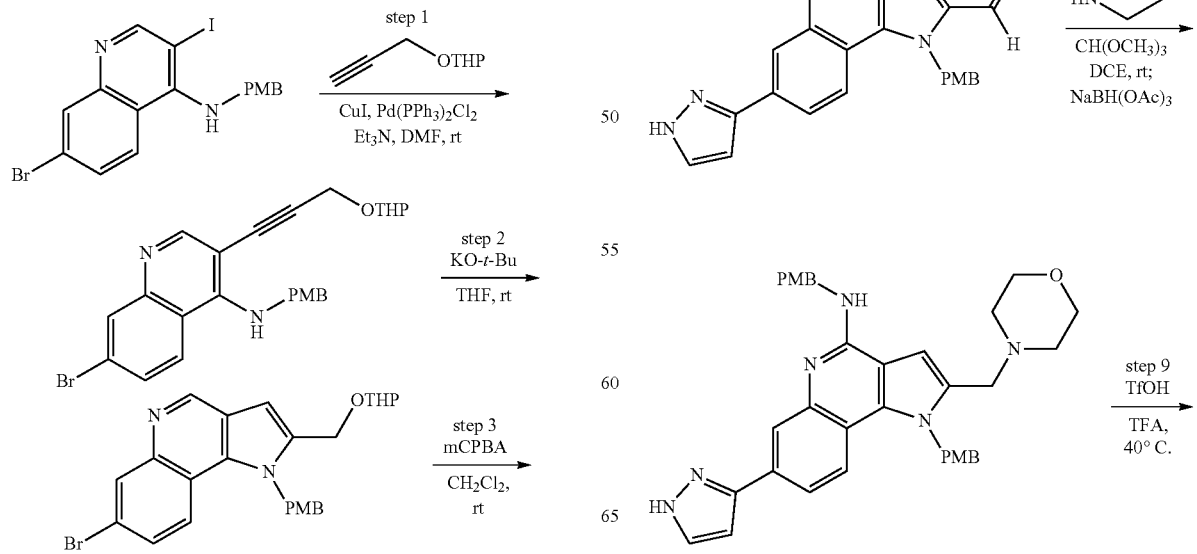

-continued

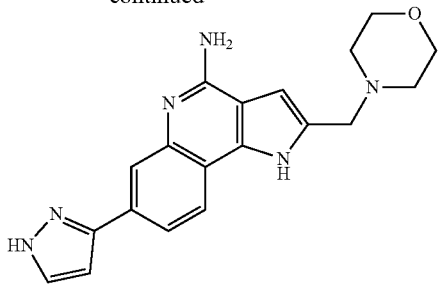

Step 1. 7-bromo-N-(4-methoxybenzyl)-3-(3-((tetrahydro-2H-pyran-2-yl)oxy)prop-1-yn-1-yl)quinolin-4-amine To a rt suspension of 7-bromo-3-iodo-N-(4-methoxybenzyl)quinolin-4-amine (4.89 g, 10.42 mmol) in DMF (34.7 ml) was added triethylamine (5.81 ml, 41.7 mmol). The mixture was sparged with $N_2$ for 15 min, then bis(triphenylphosphine)palladium(II) dichloride (0.146 g, 0.208 mmol) and copper(I) iodide (0.099 g, 0.521 mmol) were added. The mixture was sparged with $N_2$ for 2 min, then 2-(prop-2-yn-1-yloxy)tetrahydro-2H-pyran (1.753 g, 12.51 mmol) was added dropwise. The reaction was stirred at rt for 19 h. The reaction was diluted with EtOAc (300 mL), washed with aq. LiCl (3×200 mL) and sat. aq. NaCl (200 mL), dried over $Na_2SO_4$, filtered, and concentrated in vacuo. The crude material was mixed with $Et_2O$ (50 mL), and the solids were collected by vacuum filtration and washed with $Et_2O$ (4×10 mL). The filtrate was concentrated in vacuo and the residue was purified by flash chromatography (40 g silica gel; linear gradient 0-100% EtOAc-hexanes). The product from the chromatography was combined with the solids from the filtration to provide 7-bromo-N-(4-methoxybenzyl)-3-(3-((tetrahydro-2H-pyran-2-yl)oxy)prop-1-yn-1-yl)quinolin-4-amine (4.62 g, 92%) as a yellow solid. LC-MS m/z 481/483 [M+H]$^+$; $^1$H NMR (400 MHz, DMSO-d$_6$) δ 8.36-8.30 (m, 2H), 8.00-7.95 (m, 2H), 7.66 (dd, J=9.0, 2.1 Hz, 1H), 7.26 (d, J=8.7 Hz, 2H), 6.89-6.84 (m, 2H), 5.09 (d, J=6.7 Hz, 2H), 4.74-4.71 (m, 1H), 4.48-4.42 (m, 1H), 4.39-4.32 (m, 1H), 3.78-3.71 (m, 1H), 3.70 (s, 3H), 3.50-3.41 (m, 1H), 1.76-1.57 (m, 2H), 1.54-1.42 (m, 4H).

Step 2. 7-bromo-1-(4-methoxybenzyl)-2-(((tetrahydro-2H-pyran-2-yl)oxy)methyl)-1H-pyrrolo[3,2-c]quinoline A mixture of 7-bromo-N-(4-methoxybenzyl)-3-(3-((tetrahydro-2H-pyran-2-yl)oxy)prop-1-yn-1-yl)quinolin-4-amine (3.540 g, 7.35 mmol) and potassium tert-butoxide (1.650 g, 14.71 mmol) in THF (36.8 ml) was stirred at rt for 24 h. The reaction was quenched by addition to sat. aq. $NH_4Cl$ (200 mL) and extracted with EtOAc (2×200 mL). The combined organic layers were washed with sat. aq. NaCl (200 mL), dried over $Na_2SO_4$, filtered, and concentrated in vacuo. The crude material was purified by flash chromatography (80 g silica gel; linear gradient 0-100% EtOAc-hexanes) to provide 7-bromo-1-(4-methoxybenzyl)-2-(((tetrahydro-2H-pyran-2-yl)oxy)methyl)-1H-pyrrolo[3,2-c]quinoline (2.87 g, 81%) as an off-white solid. LC-MS m/z 481/483 [M+H]$^+$; $^1$H NMR (400 MHz, DMSO-d$_6$) δ 9.16 (s, 1H), 8.23 (d, J=2.2 Hz, 1H), 8.08 (d, J=9.0 Hz, 1H), 7.57 (dd, J=9.0, 2.1 Hz, 1H), 7.00 (s, 1H), 6.90-6.86 (m, 2H), 6.85-6.81 (m, 2H), 5.87 (s, 2H), 4.90 (d, J=12.8 Hz, 1H), 4.73-4.67 (m, 2H), 3.74 (ddd, J=11.2, 8.4, 2.3 Hz, 1H), 3.66 (s, 3H), 3.50-3.44 (m, 1H), 1.58-1.33 (m, 5H), 1.28-1.19 (m, 1H).

Step 3. 7-bromo-1-(4-methoxybenzyl)-2-(((tetrahydro-2H-pyran-2-yl)oxy)methyl)-1H-pyrrolo[3,2-c]quinoline 5-oxide To a rt solution of 7-bromo-1-(4-methoxybenzyl)-2-(((tetrahydro-2H-pyran-2-yl)oxy)methyl)-1H-pyrrolo[3,2-c]quinoline (2.87 g, 5.96 mmol) in $CH_2Cl_2$ (29.8 ml) was added 3-chloroperoxybenzoic acid (<77%) (1.737 g, 7.75 mmol), portionwise. The clear orange solution was stirred at rt for 2 h. The reaction was diluted with $CH_2Cl_2$ (200 mL), washed with a 1:1 mixture of 10% w/w aq. $Na_2S_2O_3$ and sat. aq. $NaHCO_3$ (2×200 mL) and then with $H_2O$ (200 mL), dried over $Na_2SO_4$, filtered, and concentrated in vacuo. The crude material was purified by flash chromatography (40 g silica gel; linear gradient 0-10% MeOH—$CH_2Cl_2$). The mixed fractions were re-purified by flash chromatography (40 g silica gel; linear gradient 0-10% MeOH—$CH_2Cl_2$). The product-containing fractions from both columns were combined to provide 7-bromo-1-(4-methoxybenzyl)-2-(((tetrahydro-2H-pyran-2-yl)oxy)methyl)-1H-pyrrolo[3,2-c]quinoline 5-oxide (2.591 g, 87%) as an orange foam. LC-MS m/z 497/499 [M+H]$^+$; $^1$H NMR (400 MHz, DMSO-d$_6$) δ 9.04 (s, 1H), 8.90 (d, J=2.1 Hz, 1H), 8.12 (d, J=9.1 Hz, 1H), 7.76 (dd, J=9.0, 2.2 Hz, 1H), 6.92-6.88 (m, 3H), 6.86-6.82 (m, 2H), 5.85 (s, 2H), 4.88 (d, J=12.8 Hz, 1H), 4.71-4.66 (m, 2H), 3.76-3.69 (m, 1H), 3.66 (s, 3H), 3.50-3.43 (m, 1H), 1.58-1.33 (m, 5H), 1.28-1.20 (m, 1H)

Step 4. 7-bromo-N,1-bis(4-methoxybenzyl)-2-(((tetrahydro-2H-pyran-2-yl)oxy)methyl)-1H-pyrrolo[3,2-c]quinolin-4-amine To a rt solution of 7-bromo-1-(4-methoxybenzyl)-2-(((tetrahydro-2H-pyran-2-yl)oxy)methyl)-1H-pyrrolo[3,2-c]quinoline 5-oxide (2.590 g, 5.21 mmol) in $CH_2Cl_2$ (26.0 ml) was added N,N-diisopropylethylamine (2.72 ml, 15.62 mmol), 4-methoxybenzylamine (0.816 ml, 6.25 mmol), and PyBroP (2.91 g, 6.25 mmol). The reaction was stirred at rt for 5 h. The reaction was diluted with $CH_2Cl_2$ (200 mL), washed with $H_2O$ (200 mL), dried over $Na_2SO_4$, filtered, and concentrated in vacuo. The crude material was purified by flash chromatography (80 g silica gel; linear gradient 0-100% EtOAc-hexanes) to provide 7-bromo-N,1-bis(4-methoxybenzyl)-2-(((tetrahydro-2H-pyran-2-yl)oxy)methyl)-1H-pyrrolo[3,2-c]quinolin-4-amine (2.414 g, 75%) as a yellow solid. LC-MS m/z 616/618 [M+H]$^+$; $^1$H NMR (400 MHz, DMSO-d$_6$) δ 7.80 (t, J=6.0 Hz, 1H), 7.75 (d, J=8.9 Hz, 1H), 7.69 (d, J=2.1 Hz, 1H), 7.37 (d, J=8.7 Hz, 2H), 7.10 (dd, J=8.8, 2.2 Hz, 1H), 7.06 (s, 1H), 6.90-6.86 (m, 4H), 6.85-6.82 (m, 2H), 5.75 (s, 2H), 4.80 (d, J=12.8 Hz, 1H), 4.72 (d, J=6.0 Hz, 2H), 4.67 (t, J=3.4 Hz, 1H), 4.61 (d, J=12.8 Hz, 1H), 3.72 (s, 3H), 3.76-3.70 (m, 1H), 3.67 (s, 3H), 3.49-3.42 (m, 1H), 1.60-1.33 (m, 5H), 1.29-1.21 (m, 1H).

Step 5. N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine A mixture of 7-bromo-N,1-bis(4-methoxybenzyl)-2-(((tetrahydro-2H-pyran-2-yl)oxy)methyl)-1H-pyrrolo[3,2-c]quinolin-4-amine (2.414 g, 3.92 mmol), 1-(tetrahydro-2H-pyran-2-yl)-5-(4,4,5,5-tetramethyl-1,3,2-dioxaborolan-2- yl)-1H-pyrazole (1.416 g, 5.09 mmol), and potassium phosphate tribasic (2.493 g, 11.75 mmol) was evacuated and back-filled with $N_2$, then it was mixed with 1,4-dioxane (16.31 ml) and $H_2O$ (3.26 ml). The resulting mixture was sparged with $N_2$ for 15 min, then chloro(2-dicyclohexylphosphino-2',4',6'-triisopropyl-1,1'-biphenyl)[2-(2'-amino-1,1'-biphenyl)]palladium(II) (0.062 g, 0.078 mmol) was added. The reaction was stirred at 100° C. for 1 h. The reaction was cooled to rt, diluted with EtOAc (200 mL), washed with $H_2O$ (3×200 mL) and sat. aq. NaCl (200 mL), dried over $Na_2SO_4$, filtered, and concentrated in vacuo. The crude material was purified by flash chromatography (80 g silica gel; linear gradient 0-100% EtOAc-hexanes) to provide N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (2.644 g, 98%) as an orange foam. LC-MS m/z 688 [M+H]$^+$; $^1$H NMR (400 MHz, DMSO-d$_6$) δ 7.91 (d, J=8.6 Hz, 1H), 7.78-7.72 (m, 2H), 7.54 (d, J=1.8 Hz, 1H), 7.40 (d, J=8.7 Hz, 2H), 7.12 (dd, J=8.5, 1.9 Hz, 1H), 7.06 (s, 1H), 6.93-6.89 (m, 2H), 6.88-6.81 (m, 4H), 6.47 (d, J=1.8 Hz, 1H), 5.79 (s, 2H), 5.20 (br d, J=9.8 Hz, 1H), 4.83 (d, J=12.5 Hz, 1H), 4.79-4.72 (m, 1H), 4.71-4.66 (m, 2H), 4.66-4.60 (m, 1H), 4.07-3.99 (m, 1H), 3.70 (s, 3H), 3.77-3.69 (m, 1H), 3.66 (s, 3H), 3.55-3.44 (m, 2H), 2.45-2.34 (m, 1H), 1.97-1.89 (m, 1H), 1.74 (br d, J=12.2 Hz, 1H), 1.61-1.34 (m, 8H), 1.30-1.21 (m, 1H).

Step 6. (1-(4-methoxybenzyl)-4-((4-methoxybenzyl)amino)-7-(1H-pyrazol-3-yl)-1H-pyrrolo[3,2-c]quinolin-2-yl)methanol To a rt suspension of N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (500 mg, 0.727 mmol) in MeOH (7269 μl) was added 4 M hydrochloric acid in 1,4-dioxane (363 μl, 1.454 mmol). The mixture was sonicated until it became a clear yellow solution. The reaction was stirred at rt for 45 min, becoming a suspension. The reaction was added to $Et_2O$ (70 mL), and the solids were collected by vacuum filtration and washed with $Et_2O$ (2×4 mL). The solids were mixed with 20% MeOH—$CH_2Cl_2$ (200 mL) and sat. aq. $NaHCO_3$ (200 mL). The layers were separated and the organic layer was dried over $Na_2SO_4$, filtered, and concentrated in vacuo to provide (1-(4-methoxybenzyl)-4-((4-methoxybenzyl)amino)-7-(1H-pyrazol-3-yl)-1H-pyrrolo[3,2-c]quinolin-2-yl)methanol (361 mg, 96%) as a white solid. LC-MS m/z 520 [M+H]$^+$; $^1$H NMR (400 MHz, DMSO-d$_6$) δ 13.26-12.80 (m, 1H), 7.95 (d, J=1.9 Hz, 1H), 7.87-7.82 (m, 1H), 7.75 (s, 1H), 7.70-7.53 (m, 1H), 7.51-7.43 (m, 1H), 7.41-7.32 (m, 2H), 6.97-6.91 (m, 3H), 6.90-6.82 (m, 4H), 6.76-6.67 (m, 1H), 5.79 (br s, 2H), 5.40-5.33 (m, 1H), 4.80-4.71 (m, 2H), 4.63-4.55 (m, 2H), 3.70 (s, 3H), 3.66 (s, 3H).

Step 7. 1-(4-methoxybenzyl)-4-((4-methoxybenzyl)amino)-7-(1H-pyrazol-3-yl)-1H-pyrrolo[3,2-c]quinoline-2-carbaldehyde To a rt suspension of (1-(4-methoxybenzyl)-4-((4-methoxybenzyl)amino)-7-(1H-pyrazol-3-yl)-1H-pyrrolo[3,2-c]quinolin-2-yl)methanol (0.361 g, 0.695 mmol) in $CH_2Cl_2$ (19.85 ml) was added Dess-Martin periodinane (0.589 g, 1.390 mmol). The reaction was stirred at rt for 10 min. The reaction was quenched by addition of a mixture of 10% aq. $Na_2S_2O_3$ (10 mL) and sat. aq. $NaHCO_3$ (10 mL), and it was stirred vigorously for 30 min, then it was extracted with 10% MeOH—$CH_2Cl_2$ (2×20 mL). The combined organic layers were dried over $Na_2SO_4$, filtered, and concentrated in vacuo. The crude material was purified by flash chromatography (40 g silica gel; linear gradient 0-10% MeOH—$CH_2Cl_2$) to provide 1-(4-methoxybenzyl)-4-((4-methoxybenzyl)amino)-7-(1H-pyrazol-3-yl)-1H-pyrrolo[3,2-c]quinoline-2-carbaldehyde mixed with a minor amount of the corresponding material without one of the 4-methoxybenzylamino groups (309 mg, 86%) as a yellow solid that was used without further purification. LC-MS m/z 518 [M+H]$^+$.

Steps 8 and 9. 2-(morpholinomethyl)-7-(1H-pyrazol-3-yl)-1H-pyrrolo[3,2-c]quinolin-4-amine, 2 AcOH To a rt suspension of 1-(4-methoxybenzyl)-4-((4-methoxybenzyl)amino)-7-(1H-pyrazol-3-yl)-1H-pyrrolo[3,2-c]quinoline-2-carbaldehyde (47.7 mg, 0.092 mmol) in DCE (461 μl) was added morpholine (11.92 μl, 0.138 mmol) and trimethyl orthoformate (81 μl, 0.737 mmol). The reaction was stirred at rt for 1 h, then sodium triacetoxyborohydride (39.1 mg, 0.184 mmol) was added. The reaction was stirred at rt for 2 h. Additional sodium triacetoxyborohydride (20 mg, 0.094 mmol) was added. The reaction was stirred at rt for 1 h. The reaction was diluted with sat. aq. $NaHCO_3$ (4 mL) and extracted with $CH_2Cl_2$ (2×4 mL). The combined organic layers were dried over $Na_2SO_4$, filtered, and concentrated in vacuo.

The crude material was dissolved in TFA (415 μL) and TfOH (46 μL) was added. The reaction was sealed and stirred at 40° C. for 2.5 h. The reaction was cooled to rt and added, dropwise, to $Et_2O$ (15 mL). The resulting solids were collected by vacuum filtration. This material was purified by preparative HPLC (three 1-mL injections) (column: Waters XBridge 19×100 mm; linear gradient 10-90% B-A over 10 min; solvent A=5% MeCN—$H_2O$ with 10 mM $NH_4OAc$; solvent B=95% MeCN—$H_2O$ with 10 mM $NH_4OAc$; flow rate: 30 mL/min; detector wavelength: 220 nm). The product-containing fractions were frozen at −78° C. and lyophilized to provide 2-(morpholinomethyl)-7-(1H-pyrazol-3-yl)-1H-pyrrolo[3,2-c]quinolin-4-amine, 2 AcOH (21.6 mg, 50%) as a white solid. $^1$H NMR (400 MHz, DMSO-d$_6$) δ 12.05-11.95 (m, 1H), 8.15 (d, J=8.3 Hz, 1H), 7.90 (d, J=1.6 Hz, 1H), 7.68 (br s, 1H), 7.59 (br d, J=8.6 Hz, 1H), 6.73 (d, J=2.0 Hz, 1H), 6.64 (s, 1H), 6.52 (s, 2H), 3.63 (s, 2H), 3.62-3.59 (m, 4H), 2.44 (br s, 4H), 1.88 (s, 6H). Analytical LC/MS conditions: Column: Acquity UPLC BEH C18, 2.1 mm×50 mm, 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). m/z 349.2 [M+H]$^+$; RT: 0.45 min.

Example 412 to Example 422 were prepared according to synthetic procedures similar to those described for Example 150, Example 151, and Example 411 from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% over 3 min, then a 0.50 min hold at 100% B; Flow: 1 mL/min; Detection: MS and UV (220 nm).

| Ex. No. | Structure | LC/MS [M + H]+ | RT (min) | $^1$H NMR (500 MHz, DMSO-$d_6$) |
|---|---|---|---|---|
| 412 | 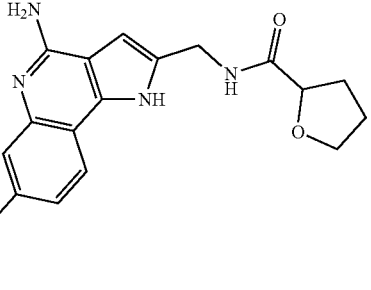 | 377.0 | 0.84 | δ 8.31 (br t, J = 5.6 Hz, 1H), 8.07 (d, J = 8.2 Hz, 1H), 7.95 (s, 1H), 7.77-7.62 (m, 2H), 6.76 (s, 1H), 6.64 (s, 1H), 4.55-4.37 (m, 2H), 4.29 (dd, J = 8.1, 5.6 Hz, 1H), 3.98-3.88 (m, 1H), 3.79 (q, J = 6.9 Hz, 1H), 2.17 (br dd, J = 12.2, 7.6 Hz, 1H), 1.84 (quin, J = 6.7 Hz, 2H) |
| 413 | 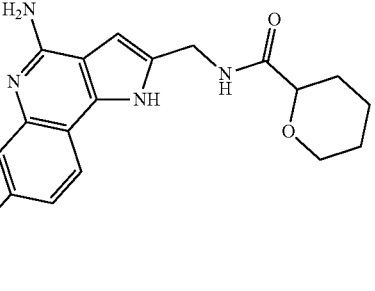 | 391.2 | 1.05 | δ 8.12-8.00 (m, 2H), 7.93 (s, 1H), 7.70 (br s, 1H), 7.65 (br d, J = 7.9 Hz, 1H), 6.74 (s, 1H), 6.61 (s, 1H), 4.47 (br t, J = 6.0 Hz, 2H), 3.97 (br d, J = 10.7 Hz, 1H), 3.80 (br d, J = 11.3 Hz, 1H), 1.93 (br s, 1H), 1.85-1.74 (m, 1H), 1.60-1.30 (m, 4H) |
| 414 | 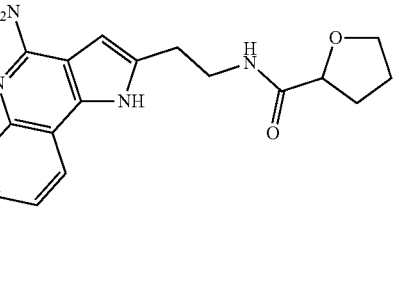 | 391.2 | 0.86 | δ 8.22 (br d, J = 8.5 Hz, 1H), 8.13 (br s, 1H), 8.00-7.75 (m, 4H), 6.84 (br s, 2H), 4.18 (dd, J = 8.2, 5.2 Hz, 1H), 3.89-3.78 (m, 1H), 3.77-3.68 (m, 1H), 3.62 (br d, J = 7.0 Hz, 1H), 3.47 (dt, J = 13.0, 6.8 Hz, 1H), 2.96 (br t, J = 7.0 Hz, 2H), 2.17-2.00 (m, 2H), 1.85-1.60 (m, 4H) |
| 415 | 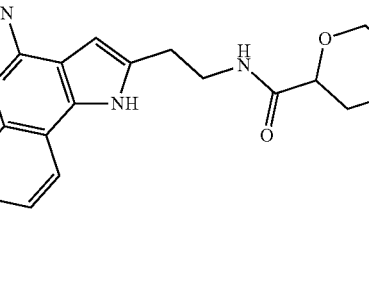 | 405.1 | 0.99 | δ 8.28-8.17 (m, 1H), 8.12 (br s, 1H), 7.98-7.89 (m, 2H), 7.86-7.75 (m, 2H), 6.84 (br s, 2H), 3.92 (br d, J = 10.4 Hz, 1H), 3.75-3.64 (m, 1H), 3.50-3.33 (m, 2H), 2.96 (br t, J = 7.0 Hz, 2H), 1.87-1.70 (m, 2H), 1.57-1.36 (m, 4H), 1.31-1.16 (m, 1H) |
| 416 | 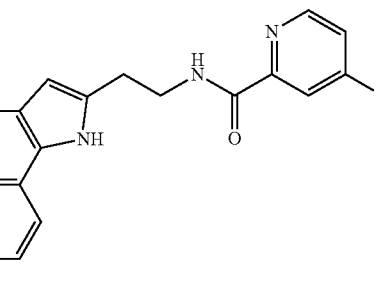 | 416.2 | 1.62 | δ 9.09 (br t, J = 6.0 Hz, 1H), 8.75-8.62 (m, 1H), 8.22 (br d, J = 8.5 Hz, 1H), 8.13 (br s, 1H), 7.99-7.90 (m, 1H), 7.86-7.73 (m, 2H), 7.53 (br t, J = 5.8 Hz, 1H), 6.93-6.73 (m, 2H), 3.72 (br d, J = 6.7 Hz, 2H), 3.10 (br t, J = 7.0 Hz, 2H) |

| Ex. No. | Structure | LC/MS [M + H]+ | RT (min) | ¹H NMR (500 MHz, DMSO-d$_6$) |
|---|---|---|---|---|
| 417 | 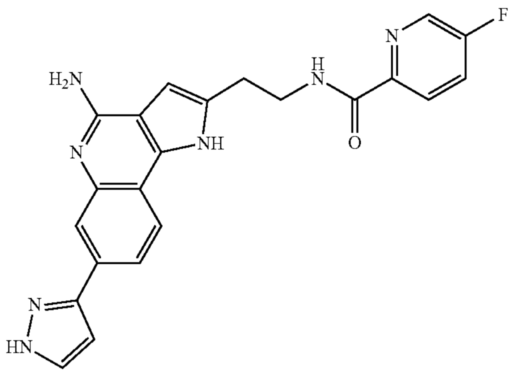 [SMILES: Nc1nc2cc(-c3cc[nH]n3)ccc2c2[nH]c(CCNC(=O)c3ccc(F)cn3)cc12] | 416.1 | 1.62 | ¹H NMR (500 MHz, DMSO-d$_6$) δ 8.91 (br t, J = 5.3 Hz, 1H), 8.62 (br s, 1H), 8.13 (br dd, J = 8.5, 4.6 Hz, 1H), 8.07 (br d, J = 8.2 Hz, 1H), 7.97-7.85 (m, 2H), 7.70 (br s, 1H), 7.65 (br d, J = 7.6 Hz, 1H), 6.75 (s, 1H), 6.59 (s, 1H), 3.71 (br d, J = 5.8 Hz, 2H), 3.07 (br t, J = 7.0 Hz, 2H) |
| 418 | 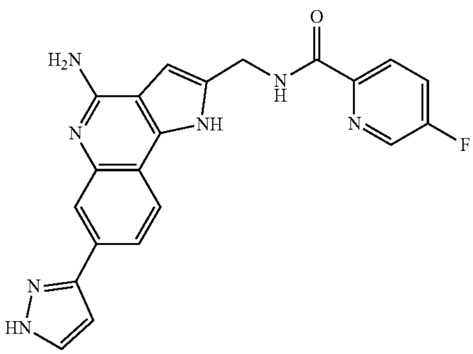 [SMILES: Nc1nc2cc(-c3cc[nH]n3)ccc2c2[nH]c(CNC(=O)c3ccc(F)cn3)cc12] | 402.0 | 1.21 | δ 9.42 (t, J = 6.1 Hz, 1H), 8.70 (br s, 2H), 8.25 (br d, J = 8.2 Hz, 1H), 8.20-8.04 (m, 2H), 8.03-7.88 (m, 2H), 7.85 (br s, 1H), 6.98 (s, 1H), 6.83 (d, J = 2.0 Hz, 1H), 4.71 (br d, J = 6.0 Hz, 2H) |
| 419 | 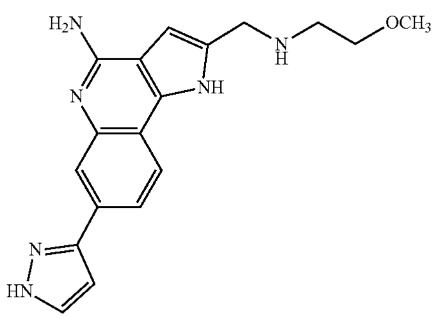 [SMILES: COCCNCc1cc2c(N)nc3cc(-c4cc[nH]n4)ccc3c2[nH]1] | 337.2 | 0.88 | δ 8.24 (d, J = 8.5 Hz, 1H), 8.18 (br s, 1H), 8.00 (br d, J = 7.9 Hz, 1H), 7.85 (br s, 1H), 7.27 (s, 1H), 6.86 (d, J = 2.1 Hz, 1H), 4.43 (s, 2H), 3.63 (br t, J = 4.9 Hz, 2H), 3.33 (s, 3H), 3.22 (br t, J = 4.9 Hz, 2H) |
| 420 | 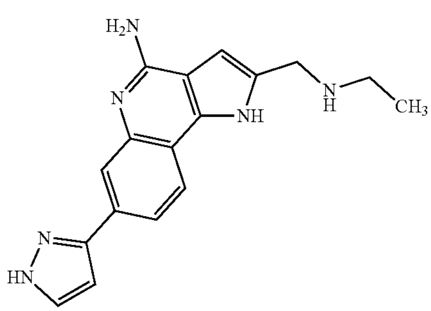 [SMILES: CCNCc1cc2c(N)nc3cc(-c4cc[nH]n4)ccc3c2[nH]1] | 306.9 | 0.83 | δ 8.25 (d, J = 8.2 Hz, 1H), 8.19 (br s, 1H), 8.00 (br d, J = 8.5 Hz, 1H), 7.87 (br s, 1H), 7.26 (s, 1H), 6.85 (d, J = 1.8 Hz, 1H), 4.41 (s, 2H), 3.08 (q, J = 7.5 Hz, 2H), 1.26 (t, J = 7.3 Hz, 3H) |

| Ex. No. | Structure | LC/MS [M + H]+ | RT (min) | 1H NMR (500 MHz, DMSO-d6) |
|---|---|---|---|---|
| 421 | 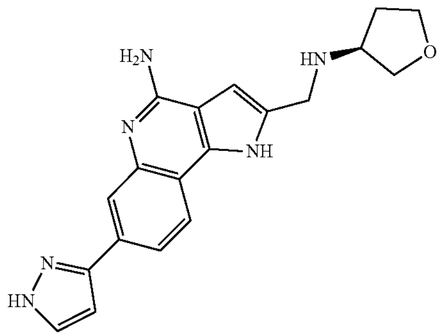 [SMILES: Nc1nc2cc(-c3cc[nH]n3)ccc2c2[nH]c(CN[C@H]3CCOC3)cc12] | 349.3 | 0.83 | δ 8.24 (d, J = 8.2 Hz, 1H), 8.18 (br s, 1H), 8.00 (br d, J = 8.5 Hz, 1H), 7.85 (br d, J = 2.1 Hz, 1H), 7.25 (s, 1H), 6.85 (d, J = 2.1 Hz, 1H), 4.39 (br s, 2H), 4.01-3.86 (m, 2H), 3.85-3.78 (m, 1H), 3.74-3.64 (m, 1H), 2.29 (m 1H), 2.13-1.96 (m, 1H) |
| 422 | 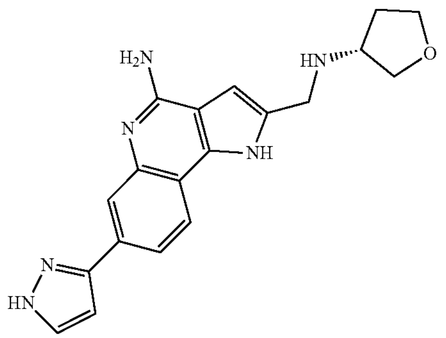 [SMILES: Nc1nc2cc(-c3cc[nH]n3)ccc2c2[nH]c(CN[C@@H]3CCOC3)cc12] | 349.1 | 0.84 | δ 8.24 (d, J = 8.5 Hz, 1H), 8.17 (s, 1H), 8.00 (d, J = 8.5 Hz, 1H), 7.85 (s, 1H), 7.27 (s, 1H), 6.86 (d, J = 2.1 Hz, 1H), 4.42 (s, 2H), 4.00-3.90 (m, 3H), 3.86-3.79 (m, 1H), 3.74-3.64 (m, 1H), 2.31 (m Hz, 1H), 2.06 (m1H) |
Example 423. Preparation of 2,3-dimethyl-7-(1H-pyrazol-3-yl)-1H-pyrrolo[3,2-c]quinolin-4-amine
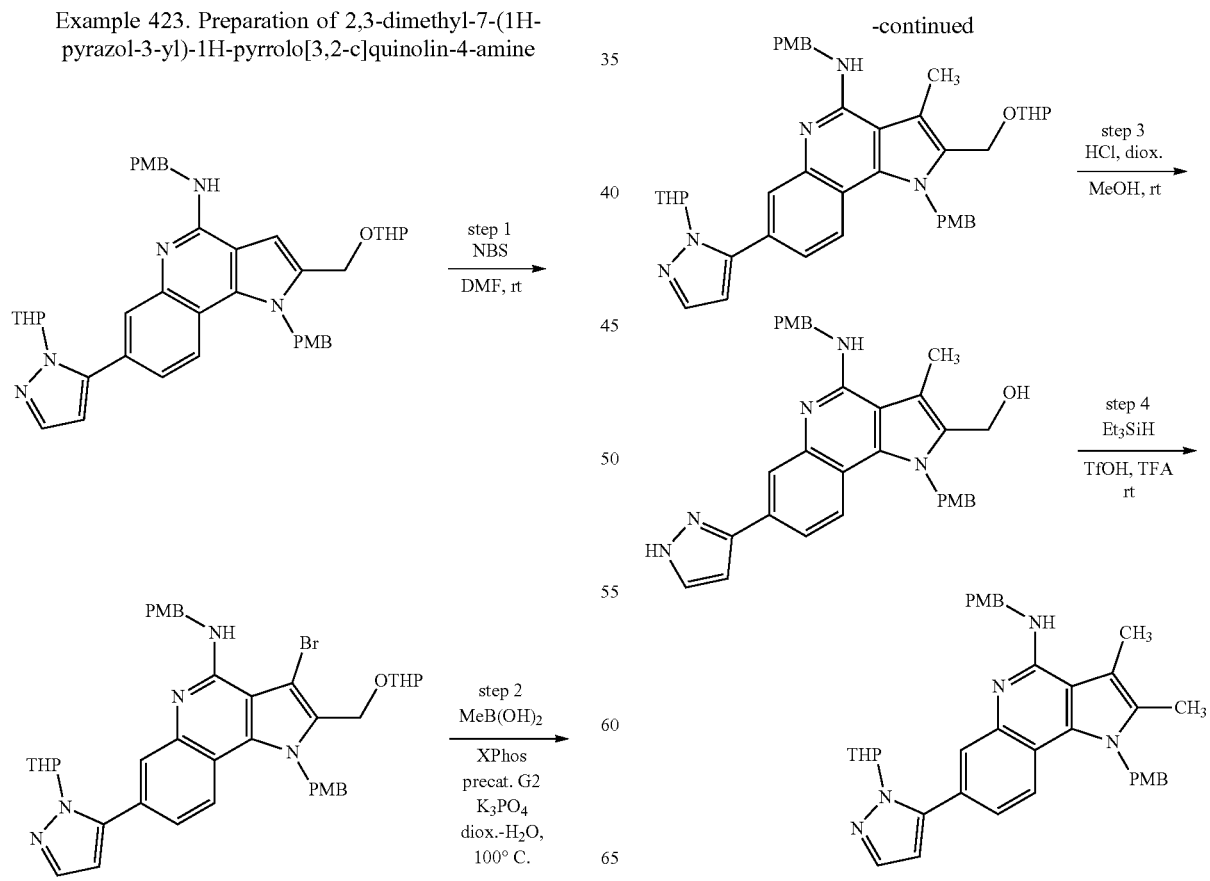

Step 1. 3-bromo-N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine To a solution of N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (510 mg, 0.741 mmol) in DMF (4943 μL) was added N-bromosuccinimide (139 mg, 0.779 mmol). The reaction was stirred at rt for 30 min. The mixture was diluted with EtOAc (100 mL), washed with $H_2O$ (2×100 mL) and sat. aq. NaCl (100 mL), dried over $Na_2SO_4$, filtered, and concentrated in vacuo. The crude material was purified by flash chromatography (24 g silica gel; linear gradient 0-100% EtOAc-hexanes) to provide 3-bromo-N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (506 mg, 89%) as a yellow foam. LC-MS m/z 766/768 [M+H]$^+$; $^1$H NMR (400 MHz, DMSO-d$_6$) δ 7.96 (d, J=8.6 Hz, 1H), 7.78 (d, J=1.8 Hz, 1H), 7.55 (d, J=1.7 Hz, 1H), 7.45-7.41 (m, 2H), 7.18 (dd, J=8.6, 1.9 Hz, 1H), 6.98-6.92 (m, 3H), 6.90-6.83 (m, 4H), 6.50 (d, J=1.8 Hz, 1H), 5.87 (s, 2H), 5.20 (br d, J=9.7 Hz, 1H), 4.88 (dd, J=12.8, 1.8 Hz, 1H), 4.85-4.79 (m, 1H), 4.79-4.73 (m, 1H), 4.73-4.66 (m, 2H), 4.06-3.99 (m, 1H), 3.79-3.71 (m, 1H), 3.71 (s, 3H), 3.66 (s, 3H), 3.55-3.43 (m, 2H), 2.46-2.34 (m, 1H), 1.97-1.88 (m, 1H), 1.75 (br d, J=12.5 Hz, 1H), 1.62-1.32 (m, 8H), 1.25-1.18 (m, 1H).

Step 2. N,1-bis(4-methoxybenzyl)-3-methyl-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine A mixture of 3-bromo-N,1-bis(4-methoxybenzyl)-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (268 mg, 0.350 mmol), methylboronic acid (27.2 mg, 0.454 mmol), and potassium phosphate tribasic (223 mg, 1.049 mmol) was evacuated and back-filled with $N_2$, then it was mixed with 1,4-dioxane (1942 μl) and $H_2O$ (388 μl). The mixture was sparged with $N_2$ for 25 min, then chloro(2-dicyclohexylphosphino-2',4',6'-triisopropyl-1,1'-biphenyl)[2-(2'-amino-1,1'-biphenyl)]palladium(II) (13.75 mg, 0.017 mmol) was added. The reaction was sealed and stirred at 100° C. for 30 min. Additional methylboronic acid (27.2 mg, 0.454 mmol) and chloro(2-dicyclohexylphosphino-2',4',6'-triisopropyl-1,1'-biphenyl)[2-(2'-amino-1,1'-biphenyl)]palladium(II) (13.75 mg, 0.017 mmol) were added. The reaction was stirred at 100° C. for 30 min. The reaction was cooled to rt, diluted with EtOAc (100 mL), washed with $H_2O$ (100 mL) and sat. aq. NaCl (100 mL), dried over $Na_2SO_4$, filtered, and concentrated in vacuo. The crude material was purified by flash chromatography (40 g RediSep Gold silica gel; linear gradient 0-75% EtOAc-$CH_2Cl_2$) to provide N,1-bis(4-methoxybenzyl)-3-methyl-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (173 mg, 71%) as a yellow foam. LC-MS m/z 702 [M+H]$^+$; $^1$H NMR (400 MHz, DMSO-d$_6$) δ 7.91 (d, J=8.7 Hz, 1H), 7.72 (d, J=1.7 Hz, 1H), 7.54 (d, J=1.8 Hz, 1H), 7.44 (d, J=8.6 Hz, 2H), 7.11 (dd, J=8.5, 1.8 Hz, 1H), 6.93-6.87 (m, 2H), 6.87-6.81 (m, 4H), 6.73 (t, J=6.0 Hz, 1H), 6.47 (d, J=1.8 Hz, 1H), 5.79 (s, 2H), 5.19 (br d, J=9.9 Hz, 1H), 4.81-4.60 (m, 5H), 4.06-3.99 (m, 1H), 3.79-3.71 (m, 1H), 3.70 (s, 3H), 3.66 (s, 3H), 3.53-3.44 (m, 2H), 2.60 (s, 3H), 2.45-2.35 (m, 1H), 1.98-1.88 (m, 1H), 1.74 (br d, J=11.9 Hz, 1H), 1.64-1.34 (m, 8H), 1.27-1.20 (m, 1H)

Step 3. (1-(4-methoxybenzyl)-4-((4-methoxybenzyl)amino)-3-methyl-7-(1H-pyrazol-3-yl)-1H-pyrrolo[3,2-c]quinolin-2-yl)methanol To a rt suspension of N,1-bis(4-methoxybenzyl)-3-methyl-7-(1-(tetrahydro-2H-pyran-2-yl)-1H-pyrazol-5-yl)-2-(((tetrahydro-2H-pyran-2-yl)oxy)methyl)-1H-pyrrolo[3,2-c]quinolin-4-amine (172 mg, 0.245 mmol) in MeOH (2451 μL) was added 4 M hydrochloric acid in 1,4-dioxane (123 μL, 0.490 mmol. The reaction was stirred at rt for 30 min. The reaction was added to $Et_2O$ (20 mL), and the solids were collected by vacuum filtration and washed with $Et_2O$ (2×3 mL). The solids were mixed with 10% MeOH—$CH_2Cl_2$ (100 mL) and sat. aq. $NaHCO_3$ (100 mL). The layers were separated and the organic layer was dried over $Na_2SO_4$, filtered, and concentrated in vacuo to provide (1-(4-methoxybenzyl)-4-((4-methoxybenzyl)amino)-3-methyl-7-(1H-pyrazol-3-yl)-1H-pyrrolo[3,2-c]quinolin-2-yl)methanol (104 mg, 80%) as a white solid. LC-MS m/z 534 [M+H]$^+$; $^1$H NMR (400 MHz, DMSO-d$_6$) δ 13.25-12.80 (m, 1H), 7.95-7.92 (m, 1H), 7.88-7.71 (m, 1H), 7.51-7.31 (m, 3H), 6.94-6.89 (m, 4H), 6.88-6.82 (m, 3H), 6.75-6.68 (m, 1H), 6.58-6.46 (m, 1H), 5.81 (br s, 2H), 5.19-5.12 (m, 1H), 4.82-4.75 (m, 2H), 4.57-4.53 (m, 2H), 3.71 (s, 3H), 3.67 (s, 3H), 2.57 (s, 3H).

Step 4. 2,3-dimethyl-7-(1H-pyrazol-3-yl)-1H-pyrrolo[3,2-c]quinolin-4-amine

To a rt solution of (1-(4-methoxybenzyl)-4-((4-methoxybenzyl)amino)-3-methyl-7-(1H-pyrazol-3-yl)-1H-pyrrolo[3,2-c]quinolin-2-yl)methanol (24 mg, 0.045 mmol) in TFA (202 μl) was added triethylsilane (35.9 μl, 0.225 mmol) and TfOH (22.49 μl). The reaction was stirred at rt for 30 min. The reaction was concentrated in vacuo. The crude material was taken up in MeOH (300 μL) and concentrated in vacuo. The crude material was dissolved in DMF (2 mL), filtered (syringe filter), and purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 2% B, 2-42% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to provide 2,3-dimethyl-7-(1H-pyrazol-3-yl)-1H-pyrrolo[3,2-c]quinolin-4-amine (5.8 mg, 47%). $^1$H NMR (500 MHz, DMSO-d$_6$) δ 11.84 (br s, 1H), 8.02 (d, J=8.3 Hz, 1H), 7.91 (s, 1H), 7.69 (br s, 1H), 7.63 (br d, J=8.3 Hz, 1H), 6.73 (d, J=1.7 Hz, 1H), 6.49-6.36 (m, 2H), 2.36 (s, 3H), 2.34 (s, 3H). Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 278.2 [M+H]$^+$; RT: 1.12 min.

Example 424 to Example 456 were prepared according to synthetic procedures similar to those described for Examples 150, 151, 209, 253, or 286, from the appropriate starting materials. Analytical LC/MS conditions:

A: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to 95% B over 2 min, then a 0.7 min hold at 95% B; Flow: 1 mL/min; Detection: MS and UV.

B: Column: CORTECS C18, 2.1 mm×50 mm, 2.7 μm particles; Mobile Phase A: water with with 0.09% FA; Mobile Phase B: acetonitrile with 0.1% FA; Temperature: 40° C.; Gradient: 5% B to 95% B over 2 min, then a 0.6 min hold at 95% B; Flow: 1 mL/min; Detection: MS and UV.

C: Column: Shim-pack XR-ODS, 3.0 mm×50 mm, 2.2 μm particles; Mobile Phase A: water with with 0.05% TFA; Mobile Phase B: acetonitrile with 0.05% TFA; Temperature: 40° C.; Gradient: 5% B to 95% B over 2 min, then a 0.7 min hold at 95% B; Flow: 1 mL/min; Detection: MS and UV.

D: Column: Kinetex XB-C18, 2.1 mm×30 mm, 1.7 μm particles; Mobile Phase A: water with with 0.05% TFA; Mobile Phase B: acetonitrile with 0.05% TFA; Temperature: 40° C.; Gradient: 5% B to 100% B over 1.2 min, then a 0.6 min hold at 100% B; Flow: 1 mL/min; Detection: MS and UV.

E: Column: Kinetex EVO C18, 3.0 mm×50 mm, 2.2 μm particles; Mobile Phase A: water with with 5 mM ammonium bicarbonate; Mobile Phase B: acetonitrile; Temperature: 40° C.; Gradient: 10% B to 95% B over 2 min, then a 0.6 min hold at 95% B; Flow: 1 mE/min; Detection: MS and UV.

F: Column: PoroShell HPH C18, 3.0 mm×50 mm, 2.7 μm particles; Mobile Phase A: water with 5 mM ammonium bicarbonate; Mobile Phase B: acetonitrile; Temperature: 40° C.; Gradient: 5% B to 60% B over 3 min, then to 95% over 0.2 min, then a 1.0 min hold at 95% B; Flow: 1 mL/min; Detection: MS and UV.

G: Column: Xbridge BEH Shield RP18, 2.1 mm×50 mm, 2.5 μm particles; Mobile Phase A: 0.1 $NH_3·H_2O$; Mobile Phase B: acetonitrile; Temperature: 40° C.; Gradient: 10% B to 50% B over 2.2 min, then to 95% over 0.6 min, then a 0.7 min hold at 95% B; Flow: 1 mL/min; Detection: MS and UV.

H: Column: Ascentis Express C18, 3.0 mm×50 mm, 2.7 μm particles; Mobile Phase A: water with with 0.05% TFA; Mobile Phase B: acetonitrile with 0.05% TFA; Temperature: 40° C.; Gradient: 5% B to 95% B over 2.0 min, then a 0.7 min hold at 95% B; Flow: 1.5 mL/min; Detection: MS and UV.

I: Column: Titan C18, 2.1 mm×50 mm, 1.9 μm particles; Mobile Phase A: water with with 0.05% TFA; Mobile Phase B: acetonitrile with 0.05% TFA; Temperature: 40° C.; Gradient: 10% B to to 95% over 2.0 min, then a 0.65 min hold at 95% B; Flow: 0.7 mL/min; Detection: MS and UV.

J: Column: Shim-pack XR-ODS, 3.0 mm×50 mm, 2.2 μm particles; Mobile Phase A: water with with 0.05% TFA; Mobile Phase B: acetonitrile with 0.05% TFA; Temperature: 40° C.; Gradient: 5% B to 30% over 2.5 min, and then to 95% B over 0.7 min, then a 1.0 min hold at 95% B; Flow: 1.2 mL/min; Detection: MS and UV.

| Ex. No. | Structure | LC/MS [M + H]+ | RT (min) | $^1$H NMR, 400 MHz, Methanol-$d_4$ unless otherwise noted |
|---|---|---|---|---|
| 424 | 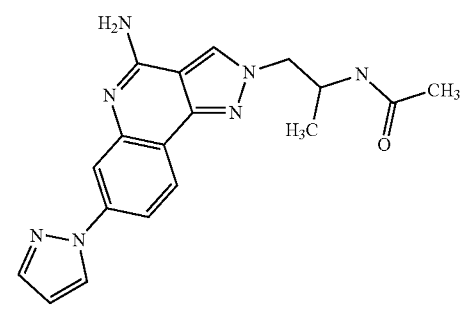 [SMILES: CC(=O)NC(C)Cn1cc2c(N)nc3cc(-n4cccn4)ccc3c2n1] | 350.0 | 1.16/ A | δ 8.72 (s, 1H), 8.39-8.35 (m, 2H), 8.04 (t, J = 1.6 Hz, 1H), 7.91-7.89 (m, 1H), 7.81 (d, J = 1.8 Hz, 1H), 6.61-6.60 (m, 1H), 4.60 (t, J = 8.4 Hz, 1H), 4.50-4.42 (m, 2H), 1.88 (s, 3H), 1.28 (d, J = 6.5 Hz, 3H) |
| 425 | 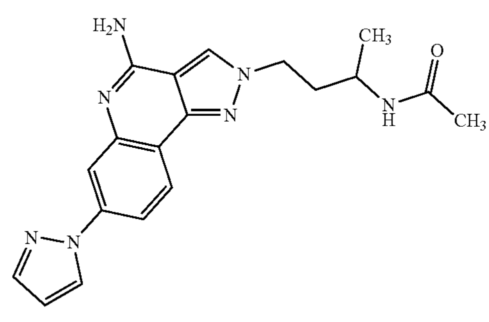 [SMILES: CC(=O)NC(C)CCn1cc2c(N)nc3cc(-n4cccn4)ccc3c2n1] | 364.4 | 0.95/ B | δ 8.72-8.71 (m, 1H), 8.38 (d, J = 2.7 Hz, 1H), 8.35 (t, J = 8.6 Hz, 1H), 8.02 (d, J = 8.4 Hz, 1H), 7.90 (d, J = 7.5 Hz, 1H), 7.80 (d, J = 1.7 Hz, 1H), 6.60 (m, 1H), 4.53 (d, J = 6.3 Hz, 2H), 3.93-3.88 (m, 1H), 2.28-2.22 (m, 1H), 2.15-2.06 (m, 1H), 1.98 (s, 3H), 1.21 (d, J = 6.7 Hz, 3H) |

-continued

| Ex. No. | Structure | LC/MS [M + H]+ | RT (min) | ¹H NMR, 400 MHz, Methanol-d₄ unless otherwise noted |
|---|---|---|---|---|
| 426 | 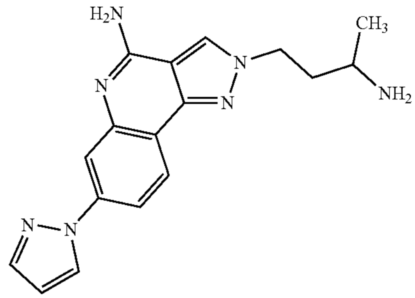 [SMILES: CC(N)CCn1cc2c(N)nc3cc(-n4cccn4)ccc3c2n1] | 322.1 | 1.1/I | δ 8.86 (s, 1H), 8.41-8.35 (m, 2H), 8.06-8.04 (m, 1H), 7.98-7.92 (m, 1H), 7.81 (d, J = 1.8 Hz, 1H), 6.62-6.61 (m, 1H), 4.87-4.62 (m, 2H), 3.49-3.42 (m, 1H), 2.50-2.41 (m, 1H), 2.33-2.24 (m, 1H), 1.43 (d, J = 6.6 Hz, 3H) |
| 427 | 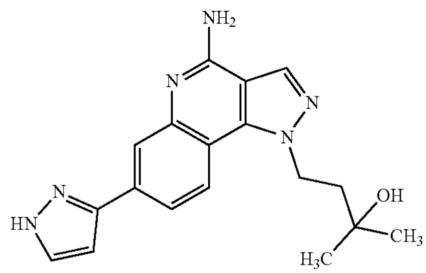 [SMILES: CC(C)(O)CCn1ncc2c(N)nc3cc(-c4cc[nH]n4)ccc3c21] | 337.2 | 0.92/C | δ 8.49-8.46 (m, 2H), 8.14 (s, 1H), 8.07-8.05 (m, 1H), 7.79-7.78 (d, J = 2.4 Hz, 1H), 6.87-6.86 (d, J = 2.4 Hz, 1H), 4.99-4.95 (m, 2H), 2.17-2.13 (m, 2H), 1.36 (s, 3H) |
| 428 | 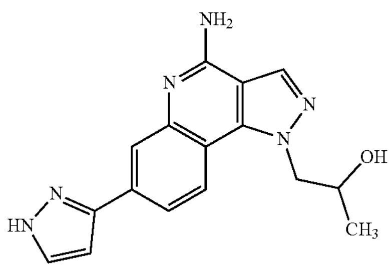 [SMILES: CC(O)Cn1ncc2c(N)nc3cc(-c4cc[nH]n4)ccc3c21] | 309.2 | 1.15/C | δ 8.58-8.55 (m, 2H), 8.13 (s, 1H), 8.09-8.06 (m, 1H), 7.81-7.80 (d, J = 2.4 Hz, 1H), 6.89-6.88 (d, J = 2.4 Hz, 1H), 4.89-4.75 (m, 2H), 4.42-4.37 (m, 1H), 1.39-1.38 (d, J = 6.4 Hz, 3H) |
| 429 | 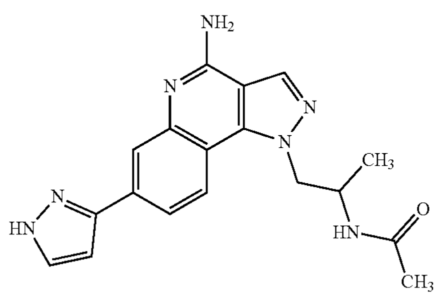 [SMILES: CC(=O)NC(C)Cn1ncc2c(N)nc3cc(-c4cc[nH]n4)ccc3c21] | 350.3 | 0.54/D | δ 12.96 (s, 1H), 8.49 (s, 1H), 8.44 (d, J = 8.5 Hz, 1H), 8.28 (s, 1H), 8.02 (d, J = 8.5 Hz, 2H), 7.84 (s, 2H), 7.00 (s, 1H), 6.93 (s, 1H), 6.84 (s, 1H), 4.85-4.76 (m, 1H), 4.34-4.58 (m, J = 14.3, 7.8 Hz, 1H), 4.36 (s, 1H), 1.77 (s, 3H), 1.05 (d, J = 6.7 Hz, 3H) |
| 430 | 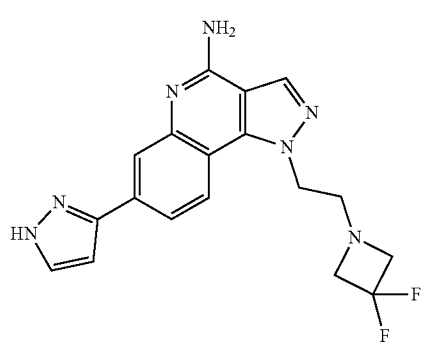 [SMILES: Nc1nc2cc(-c3cc[nH]n3)ccc2c2c1cnn2CCN1CC(F)(F)C1] | 370.2 | 1.23/E | δ 8.61 (s, 1H), 8.43-8.40 (d, J = 8.6 Hz, 1H), 8.15 (s, 1H), 8.10-8.04 (m, 1H), 7.80-7.79 (d, J = 2.4 Hz, 1H), 6.88-6.87 (d, J = 2.4 Hz, 1H), 5.01-4.98 (t, J = 5.9 Hz, 2H), 4.99-4.88 (t, J = 5.9 Hz, 4H), 3.47-3.43 (m, 2H) |

| Ex. No. | Structure | LC/MS [M + H]⁺ | RT (min) | ¹H NMR, 400 MHz, Methanol-d₄ unless otherwise noted |
|---|---|---|---|---|
| 431 | 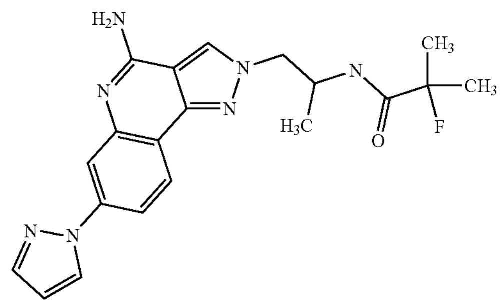 [SMILES: CC(Cn1cc2c(N)nc3cc(-n4cccn4)ccc3c2n1)NC(=O)C(C)(C)F] | 396.0 | 1.34/ A | δ 8.74 (s, 1H), 8.39-8.34 (m, 2H), 8.05 (d, J = 2.1 Hz, 1H), 7.92-7.90 (m, 1H), 7.81 (d, J = 1.8 Hz, 1H), 6.61-6.60 (m, 1H), 4.69-4.65 (m, 1H), 4.59-4.47 (m, 2H), 1.45 (d, J = 21.7 Hz, 3H), 1.40-1.34 (m, 6H) |
| 432 | 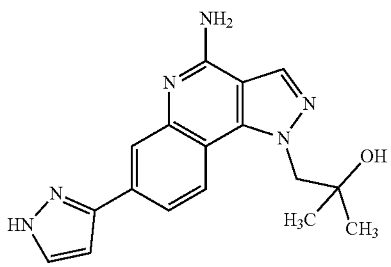 [SMILES: CC(C)(O)Cn1ncc2c(N)nc3cc(-c4cc[nH]n4)ccc3c21] | 323.2 | 1.21/ C | δ 8.75-8.73 (d, J = 8.7 Hz, 1H), 8.56 (s, 1H), 8.12 (s, 1H), 8.03-8.01 (m, 1H), 7.81-7.80 (d, J = 2.4 Hz, 1H), 6.89-6.88 (d, J = 2.4 Hz, 1H), 4.89-4.85 (m, 2H), 1.31 (s, 6H) |
| 433 | 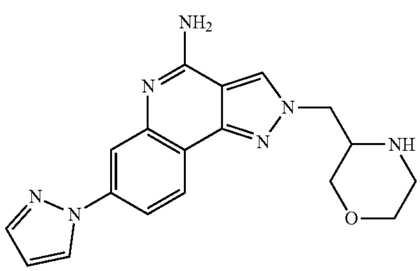 [SMILES: Nc1nc2cc(-n3cccn3)ccc2c2nn(CC3COCCN3)cc12] | 350.4 | 1.73/ F | δ 8.64-8.55 (m, 2H), 8.18 (d, J = 8.5 Hz, 1H), 7.94 (s, 1H), 7.84-7.69 (m, 2H), 7.51 (s, 1H), 6.59 (t, J = 2.1 Hz, 1H), 4.51-4.37 (m, 1H), 4.31-4.01 (m, 1H), 3.75 (dd, J = 39.3, 10.8 Hz, 2H), 3.56-3.38 (m, 2H), 3.06 (s, 0.4H), 2.92 (d, J = 13.0 Hz, 1H), 2.79 (s, 1H) |
| 434 | 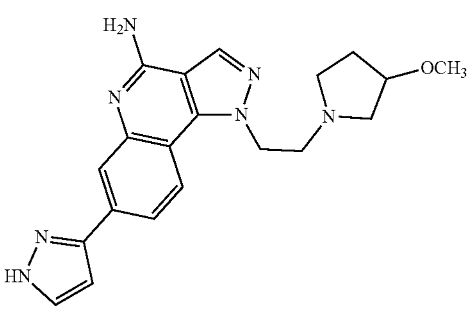 [SMILES: COC1CCN(CCn2ncc3c(N)nc4cc(-c5cc[nH]n5)ccc4c32)C1] | 378.2 | 1.88/ G | δ 8.61 (s, 1H), 8.40-8.38 (d, J = 8.6 Hz, 1H), 8.17 (s, 1H), 8.10-8.08 (m, 1H), 7.81-7.80 (d, J = 2.4 Hz, 1H), 6.89-6.88 (d, J = 2.4 Hz, 1H), 5.39 (s, 2H), 4.20 (s, 1H), 4.00-3.90 (m, 2H), 3.85-3.54 (m, 4H), 3.40 (s, 3H), 2.33-2.28 (m, 2H) |
| 435 | 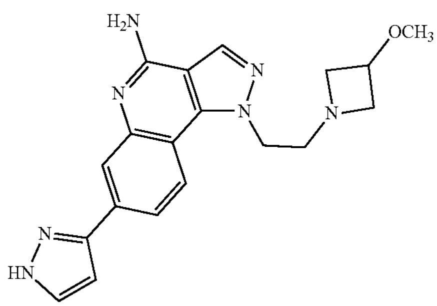 [SMILES: COC1CN(CCn2ncc3c(N)nc4cc(-c5cc[nH]n5)ccc4c32)C1] | 364.3 | 0.63/ H | δ 8.60 (s, 1H), 8.38-8.36 (d, J = 8.6 Hz, 1H), 8.17 (s, 1H), 8.10-8.07 (m, 1H), 7.81-7.80 (d, J = 2.4 Hz, 1H), 6.89-6.88 (d, J = 2.4 Hz, 1H), 5.19-5.19 (m, 2H), 4.50-4.44 (m, 2H), 4.30-4.27 (m, 1H), 4.10-4.08 (m, 2H), 4.02-3.98 (m, 2H), 3.48 (s, 3H) |

| Ex. No. | Structure | LC/MS [M + H]+ | RT (min) | ¹H NMR, 400 MHz, Methanol-d₄ unless otherwise noted |
|---|---|---|---|---|
| 436 | 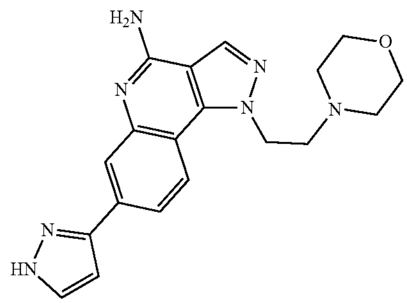 [SMILES: Nc1nc2cc(-c3cc[nH]n3)ccc2c2c1cnn2CCN1CCOCC1] | 364.2 | 1.07/ H | δ 8.58 (s, 1H), 8.42-8.40 (d, J = 8.5 Hz, 1H), 8.17 (s, 1H), 8.12-8.08 (m, 1H), 7.81-7.80 (d, J = 2.4 Hz, 1H), 6.90-6.89 (d, J = 2.4 Hz, 1H), 5.27-5.25 (t, J = 6.1 Hz, 2H), 4.90-4.84 (m, 4H), 4.84 (s, 4H), 3.75 (s, 2H) |
| 437 | 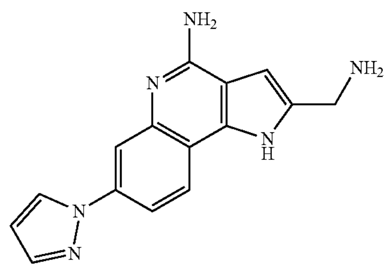 [SMILES: NCc1cc2c(N)nc3cc(-n4cccn4)ccc3c2[nH]1] | 279.3 | 0.75/ C | δ 8.41 (d, J = 2.6 Hz, 1H), 8.26 (d, J = 8.8 Hz, 1H), 8.11 (d, J = 2.0 Hz, 1H), 7.97 (dd, J = 8.7, 1.9 Hz, 1H), 7.81 (d, J = 1.8 Hz, 1H), 7.20 (s, 1H), 6.64-6.59 (m, 1H), 4.40 (s, 2H). |
| 438 | 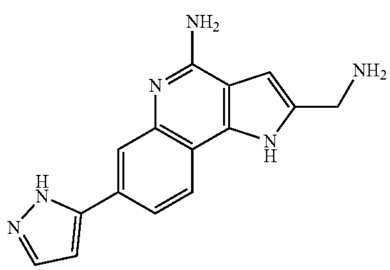 [SMILES: NCc1cc2c(N)nc3cc(-c4ccn[nH]4)ccc3c2[nH]1] | 279.3 | 1.30/ J | δ 8.19 (d, J = 8.4 Hz, 1H), 8.09 (d, J = 1.5 Hz, 1H), 7.99 (dd, J = 8.4, 1.6 Hz, 1H), 7.78 (d, J = 2.4 Hz, 1H), 7.20 (s, 1H), 6.85 (d, J = 2.3 Hz, 1H), 4.40 (s, 2H) |
| 439 | 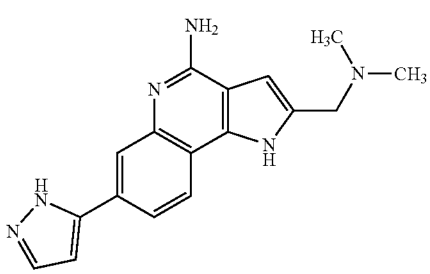 [SMILES: CN(C)Cc1cc2c(N)nc3cc(-c4ccn[nH]4)ccc3c2[nH]1] | 307.4 | 0.73/ C | δ 8.24 (d, J = 8.4 Hz, 1H), 8.10 (d, J = 1.7 Hz, 1H), 8.00 (d, J = 8.4 Hz, 1H), 7.78 (dd, J = 2.4, 1.1 Hz, 1H), 7.33 (s, 1H), 6.85 (d, J = 2.4 Hz, 1H), 4.60 (s, 2H), 2.97 (s, 6H) |
| 440 | 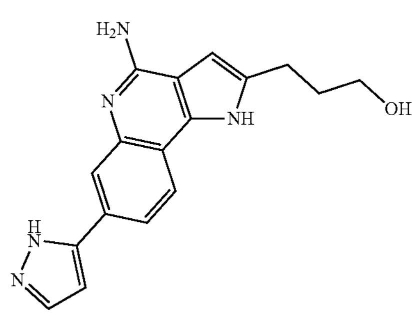 [SMILES: Nc1nc2cc(-c3ccn[nH]3)ccc2c2[nH]c(CCCO)cc12] | 308.1 | 0.82/ H | δ 8.07 (d, J = 8.4 Hz, 1H), 7.97 (s, 1H), 7.75-7.66 (m, 2H), 6.76 (d, J = 2.3 Hz, 1H), 6.56 (d, J = 1.0 Hz, 1H), 3.70 (t, J = 6.4 Hz, 2H), 3.00-2.90 (m, 2H), 2.08-2.00 (m, 2H) |

-continued

| Ex. No. | Structure | LC/MS [M + H]+ | RT (min) | 1H NMR, 400 MHz, Methanol-d4 unless otherwise noted |
|---|---|---|---|---|
| 441 | 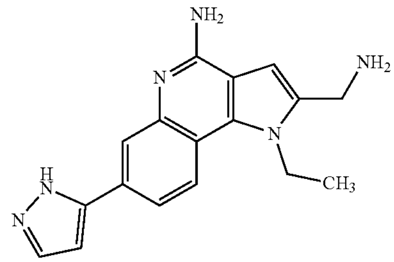 [SMILES: CCn1c(CN)cc2c(N)nc3cc(-c4ccn[nH]4)ccc3c21] | 307.4 | 0.71/ H | δ 8.38 (d, J = 8.8 Hz, 1H), 8.20 (d, J = 1.6 Hz, 1H), 8.03 (dd, J = 8.7, 1.6 Hz, 1H), 7.87 (d, J = 2.3 Hz, 1H), 7.27 (s, 1H), 6.89 (d, J = 2.3 Hz, 1H), 4.64 (d, J = 7.4 Hz, 2H), 4.39 (s, 2H), 1.47 (t, J = 7.1 Hz, 3H) |
| 442 | 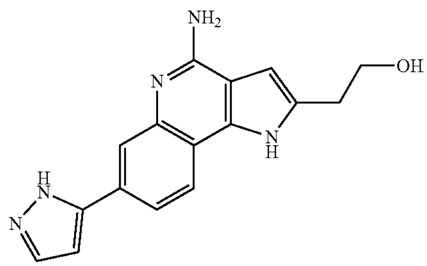 [SMILES: Nc1nc2cc(-c3ccn[nH]3)ccc2c2[nH]c(CCO)cc12] | 294.1 | 0.85/ E | δ 8.26 (d, J = 8.4 Hz, 1H), 8.05 (d, J = 1.5 Hz, 1H), 7.96 (dd, J = 8.4, 1.6 Hz, 1H), 7.79 (d, J = 2.4 Hz, 1H), 6.86-6.84 (m, 2H), 3.96 (t, J = 6.6 Hz, 2H), 3.10-3.07 (m, 2H) |
| 443 | 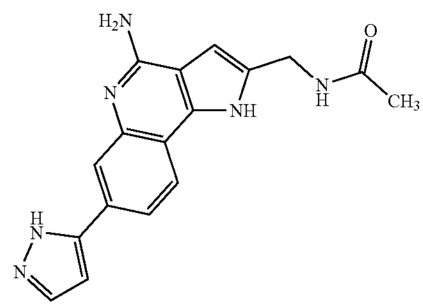 [SMILES: CC(=O)NCc1cc2c(N)nc3cc(-c4ccn[nH]4)ccc3c2[nH]1] | 321.3 | 0.83/ C | δ 8.20 (d, J = 8.4 Hz, 1H), 8.05 (d, J = 1.5 Hz, 1H), 7.95 (dd, J = 8.5, 1.6 Hz, 1H), 7.77 (d, J = 2.4 Hz, 1H), 6.93 (s, 1H), 6.82 (d, J = 2.4 Hz, 1H), 4.58 (s, 2H), 3.66 (s, 3H) |
| 444 | 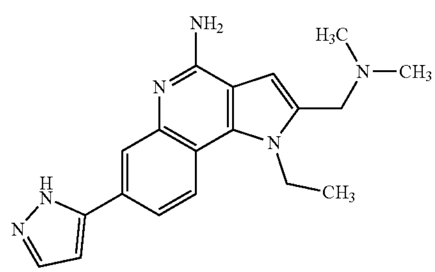 [SMILES: CCn1c(CN(C)C)cc2c(N)nc3cc(-c4ccn[nH]4)ccc3c21] | 335.4 | 1.06/ C | δ 8.41 (d, J = 8.8 Hz, 1H), 8.13 (d, J = 1.5 Hz, 1H), 8.04 (dd, J = 8.7, 1.6 Hz, 1H), 7.78 (d, J = 2.3 Hz, 1H), 7.44 (s, 1H), 6.87 (d, J = 2.3 Hz, 1H), 4.83-4.67 (m, 4H), 3.02 (s, 6H), 1.54 (t, J = 7.1 Hz, 3H) |
| 445 | 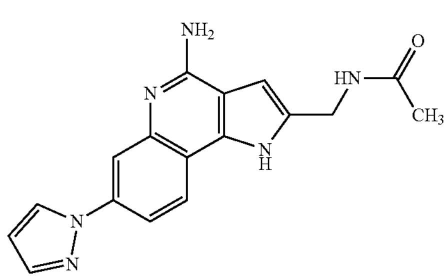 [SMILES: CC(=O)NCc1cc2c(N)nc3cc(-n4cccn4)ccc3c2[nH]1] | 321.1 | 1.56/ F | δ 8.38 (d, J = 2.5 Hz, 1H), 8.23 (d, J = 8.7 Hz, 1H), 8.06 (s, 1H), 7.90 (d, J = 8.7 Hz, 1H), 7.80 (d, J = 1.9 Hz, 1H), 6.90 (s, 1H), 6.63-6.57 (m, 1H), 4.57 (s, 2H), 2.04 (s, 3H) |

| Ex. No. | Structure | LC/MS [M + H]+ | RT (min) | 1H NMR, 400 MHz, Methanol-d4 unless otherwise noted |
|---|---|---|---|---|
| 446 | 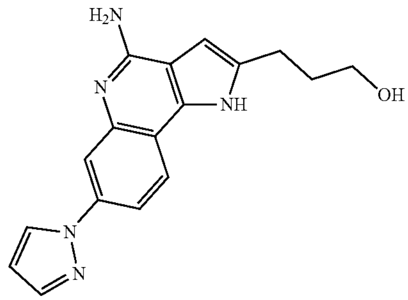 [SMILES: Nc1nc2cc(-n3cccn3)ccc2c2[nH]c(CCCO)cc12] | 308.1 | 0.95/ A | δ 8.30 (dd, J = 2.6, 0.7 Hz, 1H), 8.13 (d, J = 8.7 Hz, 1H), 7.90 (d, J = 2.2 Hz, 1H), 7.78 (dd, J = 1.8, 0.6 Hz, 1H), 7.69 (dd, J = 8.7, 2.2 Hz, 1H), 6.62-6.53 (m, 2H), 3.70 (t, J = 6.4 Hz, 2H), 2.98-2.89 (m, 2H), 2.06-1.98 (m, 2H) |
| 447 | 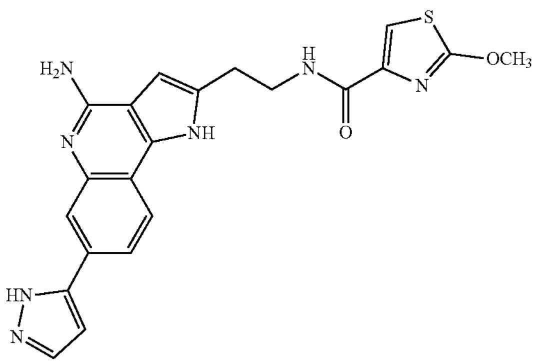 [SMILES: COc1nc(C(=O)NCCc2cc3c(N)nc4cc(-c5ccn[nH]5)ccc4c3[nH]2)cs1] | 434.1 | 0.99/ H | δ 8.14 (d, J = 8.4 Hz, 1H), 8.01 (d, J = 1.5 Hz, 1H), 7.93 (dd, J = 8.4, 1.6 Hz, 1H), 7.77 (d, J = 2.3 Hz, 1H), 7.55 (s, 1H), 6.81 (s, 2H), 4.08 (d, J = 2.0 Hz, 3H), 3.77 (td, J = 7.1, 3.8 Hz, 2H), 3.15 (t, J = 7.0 Hz, 2H) |
| 448 | 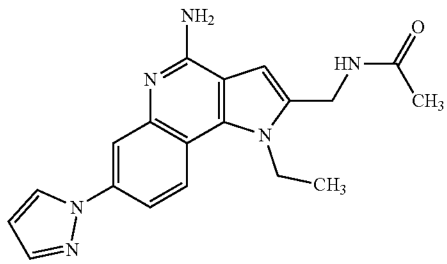 [SMILES: CCn1c(CNC(C)=O)cc2c(N)nc3cc(-n4cccn4)ccc3c21] | 349.4 | 0.89/ H | δ 8.44-8.25 (m, 2H), 8.09 (d, J = 1.8 Hz, 1H), 7.95 (dd, J = 9.0, 1.8 Hz, 1H), 7.81 (d, J = 1.6 Hz, 1H), 7.03 (s, 1H), 6.65-6.58 (m, 1H), 4.63 (d, J = 7.3 Hz, 4H), 2.05 (s, 3H), 1.54 (s, 3H) |
| 449 | 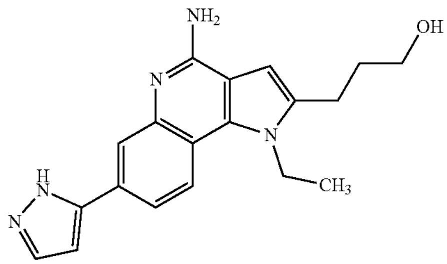 [SMILES: CCn1c(CCCO)cc2c(N)nc3cc(-c4ccn[nH]4)ccc3c21] | 336.2 | 0.93/ H | δ 8.34-8.31 (d, J = 8.7 Hz, 1H), 8.06-7.98 (m, 1H), 7.98-7.95 (d, J = 8.4 Hz, 1H), 7.76-7.70 (d, J = 18.3 Hz, 1H), 6.87-6.83 (m, 2H), 4.67-4.59 (m, 2H), 3.77-3.73 (t, J = 12.3 Hz, 2H), 2.97-2.92 (t, J = 15.3 Hz, 2H), 2.08-1.99 (m, 2H), 1.56-1.52 (t, J = 14.4 Hz, 3H) |
| 450 | 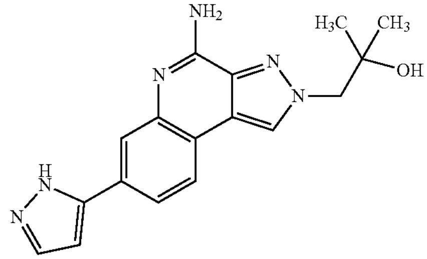 [SMILES: CC(C)(O)Cn1cc2c(n1)c(N)nc1cc(-c3ccn[nH]3)ccc12] | 323.2 | 2.01/ J | δ 8.76 (s, 1H), 8.18-8.03 (m, 2H), 7.86 (dd, J = 59.7, 1.9 Hz, 2H), 6.82 (d, J = 2.3 Hz, 1H), 4.54 (s, 2H), 1.30 (s, 6H) |

| Ex. No. | Structure | LC/MS [M + H]+ | RT (min) | ¹H NMR, 400 MHz, Methanol-d₄ unless otherwise noted |
|---|---|---|---|---|
| 451 | 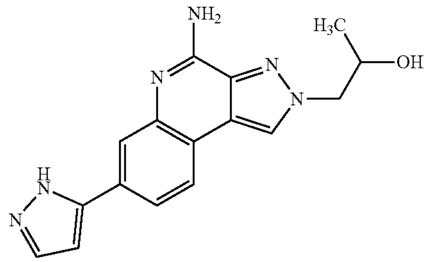 [SMILES: CC(O)Cn1cc2c(n1)c(N)nc1cc(-c3ccn[nH]3)ccc12] | 309.1 | 0.48/ D | δ 8.74 (s, 1H), 8.09 (d, J = 8.2 Hz, 1H), 8.02 (s, 1H), 7.90 (d, J = 8.3 Hz, 1H), 7.81-7.72 (m, 1H), 6.82 (d, J = 2.4 Hz, 1H), 4.58 (dd, J = 13.4, 3.5 Hz, 1H), 4.48-4.28 (m, 2H), 1.31 (d, J = 6.2 Hz, 3H) |
| 452 | 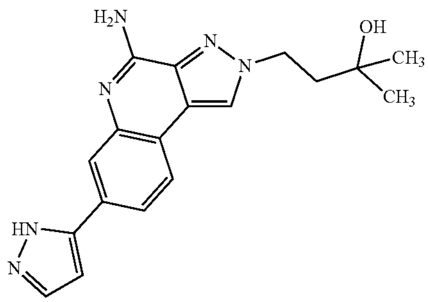 [SMILES: CC(C)(O)CCn1cc2c(n1)c(N)nc1cc(-c3ccn[nH]3)ccc12] | 337.4 | 2.16/ F | δ 8.60 (s, 1H), 7.97 (t, J = 11.7 Hz, 2H), 7.70 (s, 2H), 6.74 (s, 1H), 4.68-4.58 (m, 2H), 2.32-2.20 (m, 2H), 1.32 (s, 6H) |
| 453 | 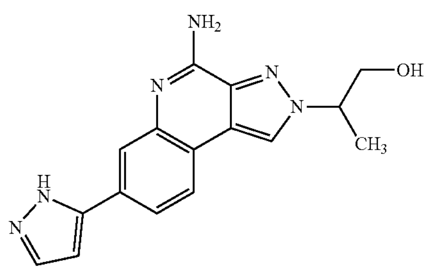 [SMILES: CC(CO)n1cc2c(n1)c(N)nc1cc(-c3ccn[nH]3)ccc12] | 309.4 | 1.14/ A | δ 8.63 (s, 1H), 7.98 (t, J = 14.7 Hz, 2H), 7.71 (s, 2H), 6.74 (s, 1H), 4.78 (qd, J = 7.0, 4.5 Hz, 1H), 4.17-3.89 (m, 2H), 1.68 (d, J = 6.9 Hz, 3H). |
| 454 | 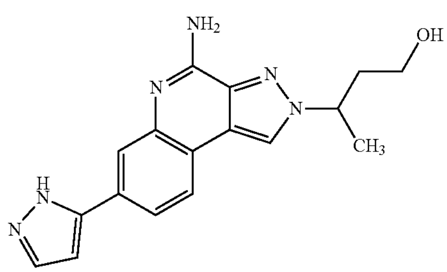 [SMILES: CC(CCO)n1cc2c(n1)c(N)nc1cc(-c3ccn[nH]3)ccc12] | 323.4 | 1.17/ A | δ 8.73 (s, 1H), 8.04 (t, J = 10.8 Hz, 2H), 7.80 (d, J = 29.6 Hz, 2H), 6.78 (s, 1H), 5.05-4.95 (m, 1H), 3.58 (dt, J = 11.1, 5.5 Hz, 1H), 3.39-3.34 (m, 1H), 2.42-2.24 (m, 1H), 2.19-2.03 (m, 1H), 1.72 (d, J = 6.7 Hz, 3H) |
| 455 | 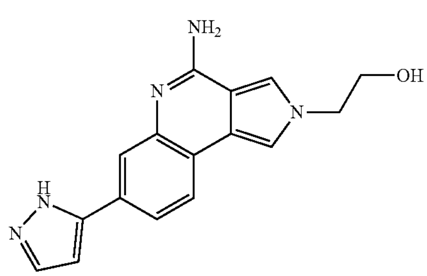 [SMILES: Nc1nc2cc(-c3ccn[nH]3)ccc2c2cn(CCO)cc12] | 294.2 | 0.57/ D | δ 12.78 (s, 1H), 7.84 (d, J = 8.0 Hz, 2H), 7.77 (s, 1H), 7.61-7.64 (m, J = 12.4, 1.8 Hz, 1H), 7.52 (s, 2H), 6.69 (s, 1H), 6.60 (s, 2H), 5.05 (t, J = 5.2 Hz, 1H), 4.22 (t, J = 5.4 Hz, 2H), 3.76-3.80 (m, 2H) |

| Ex. No. | Structure | LC/MS [M + H]+ | RT (min) | 1H NMR, 400 MHz, Methanol-d4 unless otherwise noted |
|---|---|---|---|---|
| 456 | 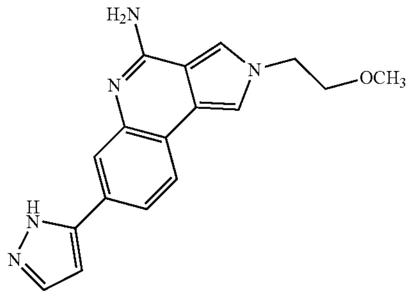 [SMILES: COCCn1cc2c(N)nc3cc(-c4ccn[nH]4)ccc3c2c1] | 308.3 | 0.92/H | δ 13.24-12.80 (m, 1H), 7.84-7.52 (m, 6H), 6.68 (s, 1H), 6.59 (s, 2H), 4.36 (t, J = 5.1 Hz, 2H), 3.74 (t, J = 5.1 Hz, 2H), 3.27 (s, 3H) |

Example 457. Preparation of 7-(1H-pyrazol-3-yl)-2H-pyrazolo[4,3-c]quinolin-4-amine Example 458. Preparation of 2-(4-amino-7-(1H-pyrazol-5-yl)-2H-pyrazolo[4,3-c]quinolin-2-yl)-N,N-dimethylacetamide.TFA

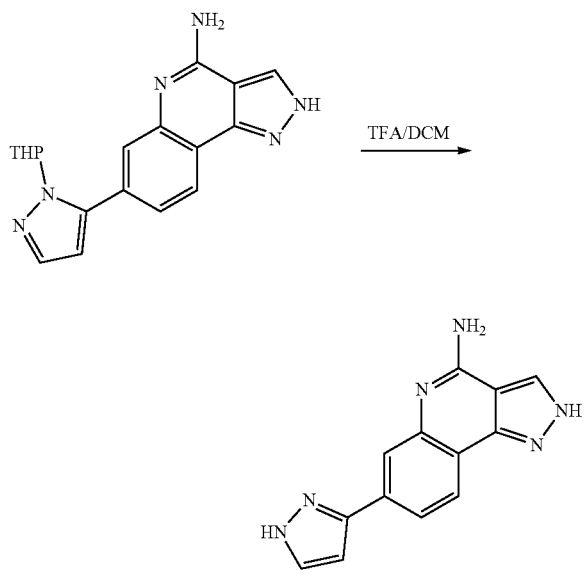

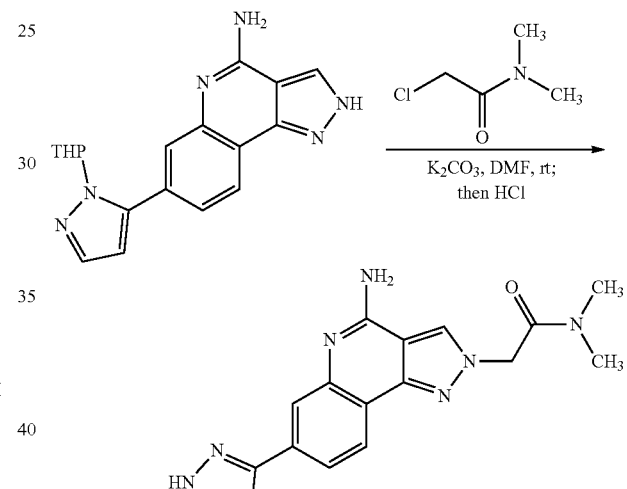

To a rt suspension of 7-(1-(tetrahydro-2H-pyran-2-yl)-1H-pyrazol-5-yl)-2H-pyrazolo[4,3-c]quinolin-4-amine (30 mg, 0.09 mmol) in DCM (150 µl) was added TFA (150 µl). The reaction was stirred at rt for 2 h. The reaction was concentrated in vacuo. The crude material was taken up in DCM (300 µL) and concentrated, then it was dissolved in DMF (2 mL), filtered (Acrodisc 0.45 µm nylon syringe filter), and purified by preparative HPLC to provide 7-(1H-pyrazol-3-yl)-2H-pyrazolo[4,3-c]quinolin-4-amine (13.6 mg, 60.6%). 1H NMR (500 MHz, DMSO-d6) δ 14.35-13.89 (m, 1H), 13.24-12.82 (m, 1H), 8.37 (br s, 1H), 8.13 (d, J=8.3 Hz, 1H), 8.04-7.94 (m, 1H), 7.86-7.68 (m, 2H), 7.52-7.03 (m, 2H), 6.80 (br s, 1H). Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). m/z 250.9 [M+H]+; RT: 0.89 min.

A suspension of 7-(1-(tetrahydro-2H-pyran-2-yl)-1H-pyrazol-5-yl)-1H-pyrazolo[4,3-c]quinolin-4-amine (34 mg, 0.102 mmol), cesium carbonate (83 mg, 0.254 mmol), and 2-chloro-N,N-dimethylacetamide (24.72 mg, 0.203 mmol) in DMF (1 mL) were stirred at rt for 3 h. The reaction was diluted with EtOAc (10 mL) and washed with water. The organic layer was dried over sodium sulfate and concentrated. The residue was then taken up with EtOAc (1 mL). 4 N HCL in dioxane (0.5 mL) was added. The resulting mixture was stirred at rt for 30 min and concentrated in vacuo. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-28% B over 25 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). LCMS M+H: 336.26; Retention Time: 1.04 min. $^1$H NMR (500 MHz, DMSO-d$_6$) δ 8.91 (s, 1H), 8.18 (m, 2H), 7.94 (br d, J=7.9 Hz, 1H), 7.88 (br s, 1H), 6.84 (s, 1H), 5.63 (s, 2H), 3.13 (s, 3H), 2.92 (s, 3H).

Alternative Method to Prepare 2-(4-amino-7-(1H-pyrazol-5-yl)-2H-pyrazolo[4,3-c]quinolin-2-yl)-N,N-dimethylacetamide

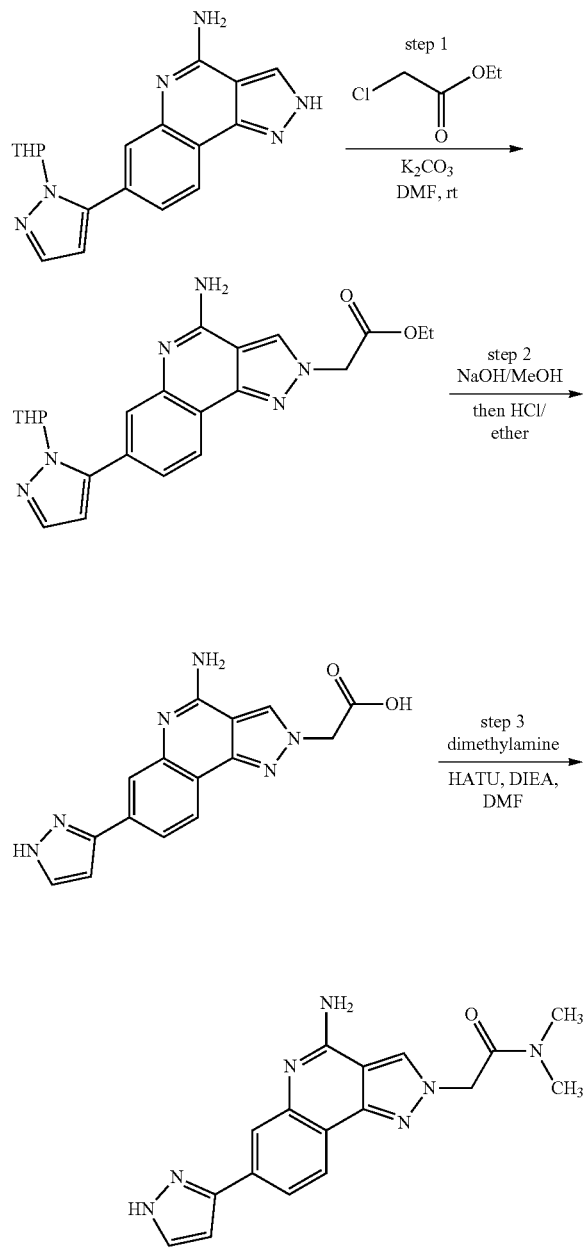

Step 1. ethyl 2-(4-amino-7-(1-(tetrahydro-2H-pyran-2-yl)-1H-pyrazol-5-yl)-2H-pyrazolo[4,3-c]quinolin-2-yl)acetate A suspension of 7-(1-(tetrahydro-2H-pyran-2-yl)-1H-pyrazol-5-yl)-1H-pyrazolo[4,3-c]quinolin-4-amine (700 mg, 2.093 mmol), cesium carbonate (1705 mg, 5.23 mmol), and ethyl 2-chloroacetate (513 mg, 4.19 mmol) in DMF (6 mL) were stirred at rt for 3 h at which point LCMS showed full conversion. The reaction was quenched with water (10 mL), extracted with 5% MeOH/DCM (3×). The combined organic layers were dried over Na$_2$SO$_4$, concentrated in vacuo, and purified by flash chromatography (0-20% MeOH/DCM, 2N NH$_3$) to give the desired isomer (550 mg, 62.5%). LCMS M+=393.3.

Step 2. 2-(4-amino-7-(1H-pyrazol-5-yl)-2H-pyrazolo[4,3-c]quinolin-2-yl)acetic acid To a suspension of the acid from step 1 in THF/MeOH (1:1, 12 mL) was added aq. NaOH (2N, 2 mL). The mixture was stirred at rt for 3 h before it was concentrated in vacuo. A solution of HCl in Et$_2$O (2N, 8 mL) was then added. The resulting suspension was stirred at rt for 30 min before it was concentrated and neutralized to pH=6 with aq. NaHCO$_3$. The product was collected by vaccum filtration, washing with Et$_2$O and water, and dried under vaccum to give 2-(4-amino-7-(1H-pyrazol-5-yl)-2H-pyrazolo[4,3-c]quinolin-2-yl)acetic acid as a white solid (350 mg, 85%). LCMS M+=309.2. 1H NMR (400 MHz, DMSO-d$_6$) Shift 9.06-8.68 (m, 2H), 8.28-7.59 (m, 4H), 6.77 (s, 1H), 5.36 (s, 2H).

Step 3. 2-(4-amino-7-(1H-pyrazol-5-yl)-2H-pyrazolo[4,3-c]quinolin-2-yl)-N,N-dimethylacetamide A suspension of 2-(4-amino-7-(1H-pyrazol-5-yl)-2H-pyrazolo[4,3-c]quinolin-2-yl)acetic acid (20 mg, 0.065 mmol), Hunig's base (68.0 µl, 0.389 mmol) in DMF (0.8 mL) was sonicated for 2 min before a solution of dimethylamine (97 µl, 0.195 mmol, 2M in THF) and HATU (24.67 mg, 0.065 mmol) was added. The mixture was stirred at rt for 1 h before additional HATU (24.67 mg, 0.065 mmol) was added. The reaction stirred at rt for 30 min and then concentrated in vacuo. The crude product was purified by preparative HPLC to give 2-(4-amino-7-(1H-pyrazol-5-yl)-2H-pyrazolo[4,3-c]quinolin-2-yl)-N,N-dimethylacetamid. LC/MS M+=336.1.

Example 459 to Example 487 were prepared according to synthetic procedures similar to those described for earlier examples from the appropriate starting materials. Analytical LC/MS conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

| Ex. No. | Structure | LC/MS [M + H]+ | RT (min) | 1H NMR, 400 MHz, Methanol-d4 unless otherwise noted |
|---|---|---|---|---|
| 459 | 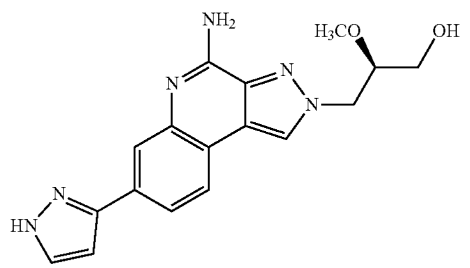 [SMILES: CO[C@@H](CO)Cn1cc2c(n1)c(N)nc1cc(-c3cc[nH]n3)ccc12] | 338.9 | 1.01 | δ 8.67 (s, 1H), 7.95 (d, J = 8.1 Hz, 1H), 7.89 (s, 1H), 7.74-7.65 (m, 1H), 7.62 (br d, J = 7.2 Hz, 1H), 6.74 (s, 1H), 6.77 (br s, 2H), 5.03-4.89 (m, 1H), 4.59 (dd, J = 14.1, 3.4 Hz, 1H), 4.44 (dd, J = 13.8, 7.7 Hz, 1H), 3.73 (dq, J = 8.0, 4.2 Hz, 1H), 3.56-3.48 (m, 2H), 3.22 (s, 3H) |
| 460 | 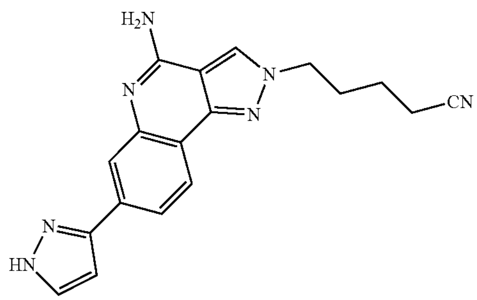 [SMILES: N#CCCCCn1cc2c(N)nc3cc(-c4cc[nH]n4)ccc3c2n1] | 332.3 | 0.99 | δ 8.93 (s, 1H), 8.20 (d, J = 8.2 Hz, 1H), 8.11 (br s, 1H), 7.92 (br d, J = 8.0 Hz, 1H), 7.86 (br s, 1H), 6.82 (d, J = 2.0 Hz, 1H), 4.56 (t, J = 6.9 Hz, 2H), 2.59 (t, J = 7.1 Hz, 2H), 2.16-1.97 (m, 2H), 1.70-1.54 (m, 2H) |
| 461 | 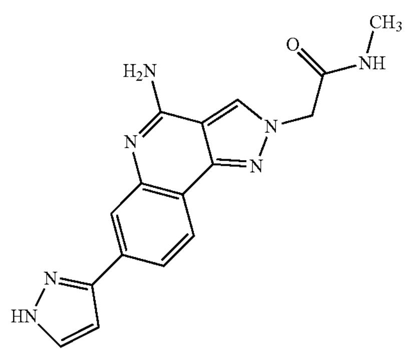 [SMILES: CNC(=O)Cn1cc2c(N)nc3cc(-c4cc[nH]n4)ccc3c2n1] | 322.2 | 0.95 | δ 8.98 (s, 1H), 8.37 (br d, J = 4.3 Hz, 1H), 8.19 (br d, J = 7.9 Hz, 1H), 8.14 (br s, 1H), 7.93 (br d, J = 7.3 Hz, 1H), 7.88 (br d, J = 1.2 Hz, 1H), 6.83 (s, 1H), 5.26 (s, 2H), 2.70 (d, J = 4.3 Hz, 3H) |
| 462 | 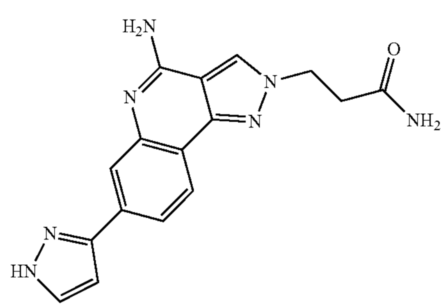 [SMILES: NC(=O)CCn1cc2c(N)nc3cc(-c4cc[nH]n4)ccc3c2n1] | 322.3 | 0.94 | δ 8.92 (s, 1H), 8.19 (br d, J = 8.2 Hz, 1H), 8.12 (br s, 1H), 7.93 (br d, J = 7.9 Hz, 1H), 7.87 (br s, 1H), 7.50 (br s, 1H), 6.98 (br s, 1H), 6.82 (br s, 1H), 4.68 (br t, J = 6.3 Hz, 2H), 2.83 (br t, J = 6.3 Hz, 2H) |
| 463 | 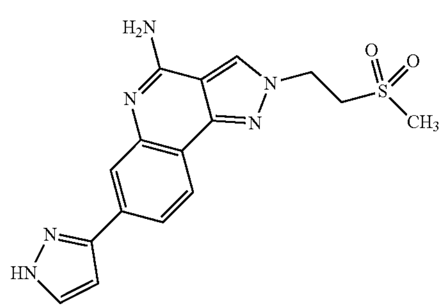 [SMILES: CS(=O)(=O)CCn1cc2c(N)nc3cc(-c4cc[nH]n4)ccc3c2n1] | 357.2 | 1.0 | δ 9.01 (s, 1H), 8.21 (br d, J = 8.2 Hz, 1H), 8.13 (br s, 1H), 7.94 (br d, J = 7.6 Hz, 1H), 7.87 (br s, 1H), 6.83 (s, 1H), 4.99 (br t, J = 6.6 Hz, 2H), 3.97-3.83 (m, 2H), 3.07 (s, 2H) |

-continued

| Ex. No. | Structure | LC/MS [M + H]+ | RT (min) | 1H NMR, 400 MHz, Methanol-d4 unless otherwise noted |
|---|---|---|---|---|
| 464 | 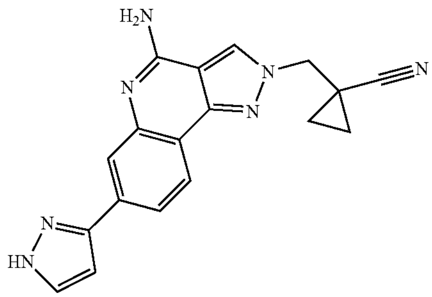 [SMILES: N#CC1(Cn2cc3c(N)nc4cc(-c5cc[nH]n5)ccc4c3n2)CC1] | 330.3 | 0.97 | δ 8.65 (s, 1H), 8.11 (d, J = 8.2 Hz, 1H), 7.90 (s, 1H), 7.82-7.71 (m, 1H), 7.67 (br d, J = 7.2 Hz, 1H), 6.78 (d, J = 1.9 Hz, 1H), 4.64 (s, 2H), 1.52-1.36 (m, 4H) |
| 465 | 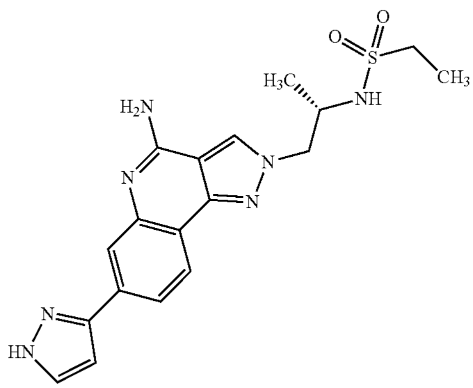 [SMILES: CCS(=O)(=O)N[C@@H](C)Cn1cc2c(N)nc3cc(-c4cc[nH]n4)ccc3c2n1] | 400.1 | 1.08 | δ 8.93 (s, 1H), 8.21 (d, J = 8.2 Hz, 1H), 8.11 (br s, 1H), 7.93 (br d, J = 8.4 Hz, 1H), 7.85 (br s, 1H), 7.37 (d, J = 8.5 Hz, 1H), 6.83 (d, J = 2.1 Hz, 1H), 4.53 (br dd, J = 13.6, 4.9 Hz, 1H), 4.41 (br dd, J = 13.8, 7.9 Hz, 1H), 3.97-3.84 (m, 1H), 2.97-2.84 (m, 1H), 2.84-2.72 (m, 1H), 1.23 (br d, J = 6.6 Hz, 3H), 0.99 (t, J = 7.3 Hz, 3H) |
| 466 | 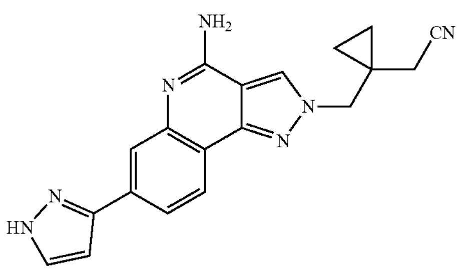 [SMILES: N#CCC1(Cn2cc3c(N)nc4cc(-c5cc[nH]n5)ccc4c3n2)CC1] | 344.1 | 1.03 | δ 13.19-12.78 (m, 1H), 8.60 (s, 1H), 8.11 (d, J = 8.0 Hz, 1H), 7.91 (br s, 1H), 7.81-7.61 (m, 2H), 7.38-7.04 (m, 2H), 6.76 (s, 1H), 4.45 (s, 2H), 2.65 (s, 2H), 0.93-0.89 (m, 2H), 0.75-0.70 (m, 2H) |
| 467 | 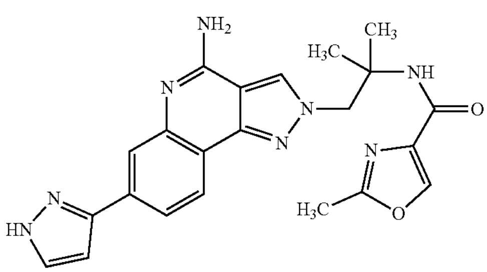 [SMILES: Cc1nc(C(=O)NC(C)(C)Cn2cc3c(N)nc4cc(-c5cc[nH]n5)ccc4c3n2)co1] | 431.0 | 1.33 | δ 8.48 (s, 1H), 8.43 (s, 1H), 8.32 (s, 1H), 8.19 (d, J = 8.0 Hz, 1H), 7.88 (br s, 1H), 7.80-7.59 (m, 2H), 7.17-6.95 (m, 2H), 6.77 (d, J = 1.7 Hz, 1H), 4.70 (s, 2H), 2.49 (br s, 3H), 1.42 (s, 6H) |
| 468 | 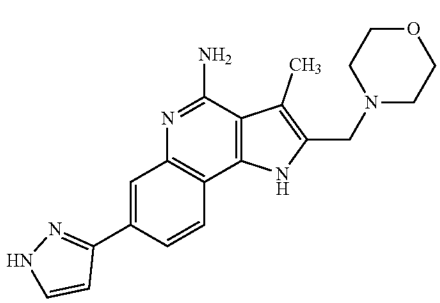 [SMILES: Cc1c(CN2CCOCC2)[nH]c2c1c(N)nc1cc(-c3cc[nH]n3)ccc12] | 363.0 | 0.85 | δ 13.37-13.14 (m, 2H), 8.31-8.21 (m, 3H), 8.12 (s, 1H), 7.96 (br d, J = 8.0 Hz, 1H), 7.83 (s, 1H), 6.84 (d, J = 1.9 Hz, 1H), 4.41 (br s, 2H), 3.84-3.74 (m, 4H), 3.21-3.13 (m, 4H), 2.53 (br s, 3H) |

| Ex. No. | Structure | LC/MS [M + H]+ | RT (min) | 1H NMR, 400 MHz, Methanol-d4 unless otherwise noted |
|---|---|---|---|---|
| 469 | 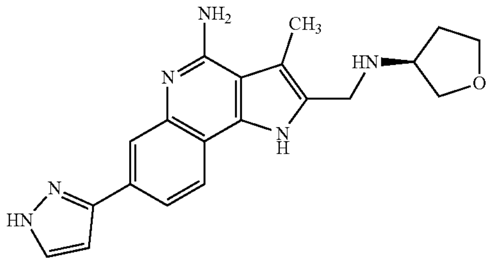 [SMILES: Cc1c(CN[C@H]2CCOC2)[nH]c2c1c(N)nc1cc(-c3cc[nH]n3)ccc12] | 363.2 | 0.89 | 8.10 (d, J = 8.3 Hz, 1H), 7.94 (s, 1H), 7.71 (br s, 1H), 7.68 (br d, J = 8.0 Hz, 1H), 6.76 (d, J = 1.9 Hz, 1H), 6.74-6.63 (m, 2H), 3.84-3.77 (m, 2H), 3.78-3.67 (m, 3H), 3.44 (br dd, J = 8.7, 4.3 Hz, 1H), 3.30-3.26 (m, 1H), 2.41 (s, 3H), 1.98-1.92 (m, 1H), 1.74-1.65 (m, 1H) |
| 470 | 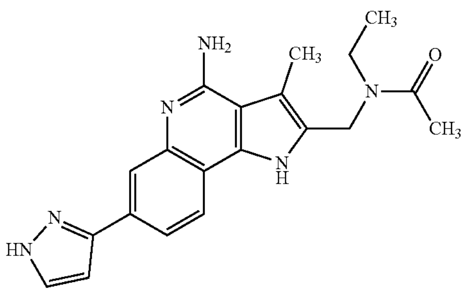 [SMILES: CCN(Cc1[nH]c2c(c(N)nc3cc(-c4cc[nH]n4)ccc32)c1C)C(C)=O] | 363.1 | 1.13 | δ 11.90-11.67 (m, 1H), 8.20-8.11 (m, 1H), 7.90 (br s, 1H), 7.69 (br s, 1H), 7.66-7.60 (m, 1H), 6.74 (s, 1H), 6.21 (br s, 2H), 4.70-4.62 (m, 2H), 3.28-3.17 (m, 2H), 2.46-2.40 (m, 3H), 2.25-2.04 (m, 3H), 1.09-0.85 (m, 3H) |
| 471 | 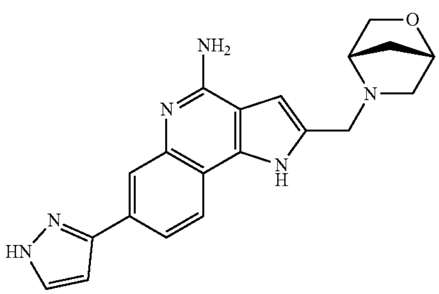 [SMILES: Nc1nc2cc(-c3cc[nH]n3)ccc2c2[nH]c(CN3C[C@@H]4C[C@H]3CO4)cc12] | 361.1 | 1.03 | δ 8.18 (d, J = 8.3 Hz, 1H), 7.94 (s, 1H), 7.71 (s, 1H), 7.65 (br d, J = 7.5 Hz, 1H), 7.26-7.11 (m, 2H), 6.75 (s, 1H), 6.70 (s, 1H), 4.38 (s, 1H), 3.95 (br d, J = 7.6 Hz, 1H), 3.90-3.81 (m, 2H), 3.16 (s, 1H), 2.80 (br d, J = 9.3 Hz, 1H), 1.82 (br d, J = 9.0 Hz, 1H), 1.62 (br d, J = 9.3 Hz, 1H); two CH protons are not visible, likely due to overlap with suppressed water peak. |
| 472 | 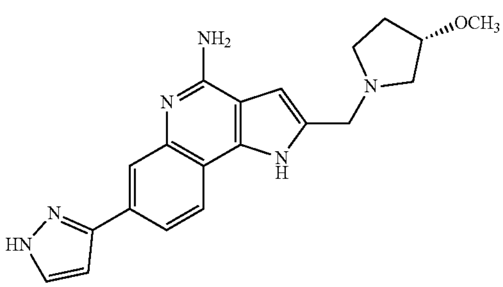 [SMILES: CO[C@H]1CCN(Cc2cc3c(N)nc4cc(-c5cc[nH]n5)ccc4c3[nH]2)C1] | 362.9 | 0.95 | δ 12.25-11.99 (m, 1H), 8.17 (d, J = 8.3 Hz, 1H), 7.93 (s, 1H), 7.70 (br s, 1H), 7.62 (br d, J = 8.1 Hz, 1H), 6.99-6.89 (m, 2H), 6.74 (d, J = 1.8 Hz, 1H), 6.66 (s, 1H), 3.94-3.86 (m, 1H), 3.72 (s, 2H), 3.19-3.12 (m, 4H), 2.72 (dd, J = 10.0, 6.1 Hz, 1H), 2.62 (q, J = 7.6 Hz, 1H), 2.49-2.43 (m, 1H), 2.06-1.97 (m, 1H), 1.72-1.62 (m, 1H) |
| 473 | 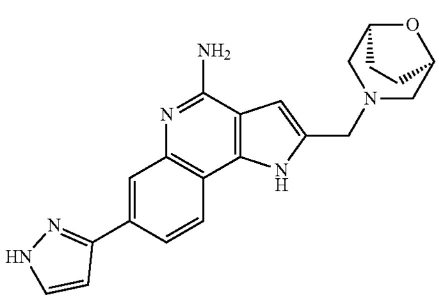 [SMILES: Nc1nc2cc(-c3cc[nH]n3)ccc2c2[nH]c(CN3C[C@H]4CC[C@@H](C3)O4)cc12] | 375.1 | 0.67 | 1H NMR (500 MHz, DMSO-d6) δ 11.99-11.91 (m, 1H), 8.14 (d, J = 8.3 Hz, 1H), 7.92 (s, 1H), 7.70 (br d, J = 2.2 Hz, 1H), 7.63 (br d, J = 7.9 Hz, 1H), 6.74 (d, J = 2.0 Hz, 1H), 6.72-6.67 (m, 2H), 6.66 (s, 1H), 4.22 (br s, 2H), 3.61 (s, 2H), 2.59 (br d, J = 10.6 Hz, 2H), 2.26 (br d, J = 9.8 Hz, 2H), 1.93 (q, J = 5.9 Hz, 2H), 1.75-1.69 (m, 2H) |

-continued

| Ex. No. | Structure | LC/MS [M + H]+ | RT (min) | 1H NMR, 400 MHz, Methanol-d4 unless otherwise noted |
|---|---|---|---|---|
| 474 | 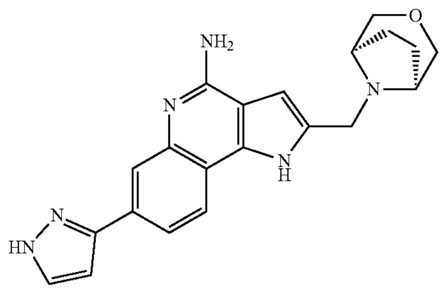 [SMILES: Nc1nc2cc(-c3cc[nH]n3)ccc2c2[nH]c(CN3[C@@H]4CC[C@H]3COC4)cc12] | 375.1 | 0.66 | δ 12.36-11.99 (m, 1H), 8.19 (d, J = 8.3 Hz, 1H), 7.94 (s, 1H), 7.70 (br s, 1H), 7.65 (br d, J = 7.4 Hz, 1H), 7.10-7.00 (m, 2H), 6.75 (d, J = 1.9 Hz, 1H), 6.72 (s, 1H), 3.60-3.56 (m, 2H), 3.09 (br s, 2H), 2.03-1.96 (m, 2H), 1.78 (br d, J = 7.2 Hz, 2H); four CH protons are not visible, likely due to overlap with suppressed water peak. |
| 475 | 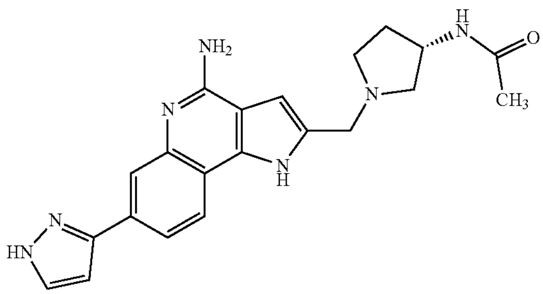 [SMILES: CC(=O)N[C@H]1CCN(Cc2cc3c(N)nc4cc(-c5cc[nH]n5)ccc4c3[nH]2)C1] | 390.2 | 0.59 | δ 12.32-12.11 (m, 1H), 8.18 (d, J = 8.3 Hz, 1H), 7.96 (br d, J = 6.1 Hz, 2H), 7.76-7.59 (m, 2H), 7.21-6.84 (m, 2H), 6.75 (br d, J = 1.4 Hz, 1H), 6.70 (s, 1H), 4.15 (br dd, J = 8.8, 4.7 Hz, 1H), 3.80-3.68 (m, 2H), 2.84-2.76 (m, 1H), 2.67-2.60 (m, 1H), 2.32 (br dd, J = 9.4, 5.0 Hz, 1H), 2.16-2.06 (m, 1H), 1.76 (s, 3H), 1.64-1.52 (m, 1H); one CH proton are not visible, likely due to overlap with suppressed water peak. |
| 476 | 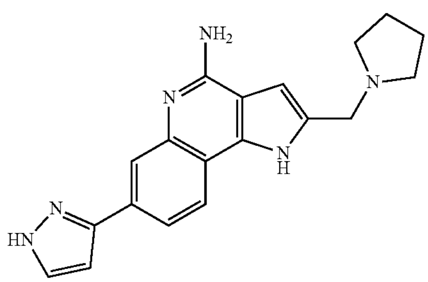 [SMILES: Nc1nc2cc(-c3cc[nH]n3)ccc2c2[nH]c(CN3CCCC3)cc12] | 333.2 | 0.92 | δ 8.18 (d, J = 8.3 Hz, 1H), 7.95 (s, 1H), 7.70 (br s, 1H), 7.64 (br d, J = 8.3 Hz, 1H), 7.14 (br d, J = 2.8 Hz, 2H), 6.75 (d, J = 1.9 Hz, 1H), 6.68 (s, 1H), 3.75 (s, 2H), 2.53-2.50 (m, 4H), 1.73 (br s, 4H) |
| 477 | 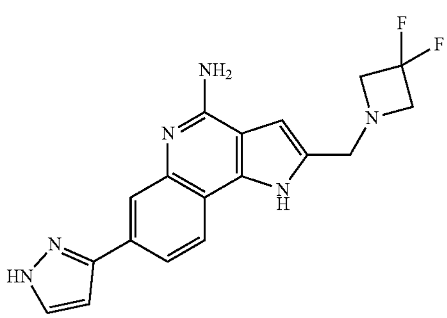 [SMILES: Nc1nc2cc(-c3cc[nH]n3)ccc2c2[nH]c(CN3CC(F)(F)C3)cc12] | 354.9 | 0.96 | δ 12.25-12.13 (m, 1H), 8.14 (d, J = 8.5 Hz, 1H), 7.93 (s, 1H), 7.70 (br s, 1H), 7.63 (br d, J = 8.3 Hz, 1H), 6.95 (br s, 2H), 6.74 (d, J = 1.7 Hz, 1H), 6.70 (s, 1H), 3.89 (s, 2H), 3.70-3.62 (m, 4H) |
| 478 | 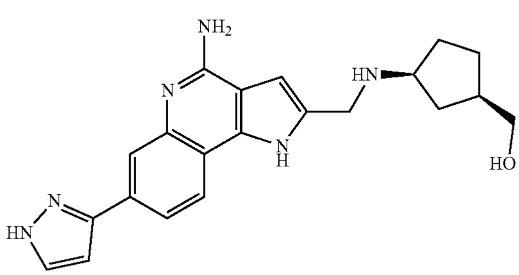 [SMILES: Nc1nc2cc(-c3cc[nH]n3)ccc2c2[nH]c(CN[C@H]3CC[C@@H](CO)C3)cc12] | 377.3 | 0.64 | δ 13.69-13.39 (m, 2H), 13.23-13.03 (m, 1H), 9.35-9.19 (m, 1H), 9.16-8.82 (m, 2H), 8.25 (br d, J = 8.5 Hz, 1H), 8.19 (br s, 1H), 7.99 (br d, J = 8.0 Hz, 1H), 7.86 (br s, 1H), 7.26 (s, 1H), 6.84 (s, 1H), 4.85-4.68 (m, 1H), 4.40 (br s, 2H), 3.63-3.55 (m, 1H), 3.41-3.37 (m, 1H), 2.26-2.17 (m, 1H), 2.11-1.97 (m, 2H), 1.78-1.63 (m, 2H), 1.55-1.47 (m, 1H), 1.43-1.34 (m, 1H) |

-continued

| Ex. No. | Structure | LC/MS [M + H]+ | RT (min) | 1H NMR, 400 MHz, Methanol-d4 unless otherwise noted |
|---|---|---|---|---|
| 479 | 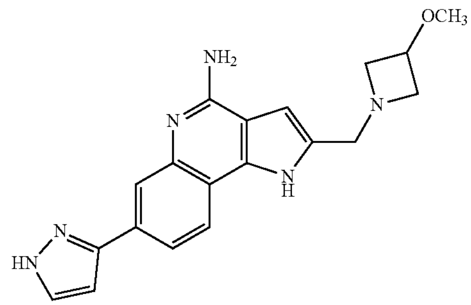 [SMILES: COC1CN(Cc2cc3c(N)nc4cc(-c5cc[nH]n5)ccc4c3[nH]2)C1] | 349.1 | 1.07 | δ 13.66-13.42 (m, 2H), 13.31-12.94 (m, 1H), 9.26-8.78 (m, 2H), 8.26 (d, J = 8.3 Hz, 1H), 8.17 (br s, 1H), 7.98 (br d, J = 8.3 Hz, 1H), 7.84 (br s, 1H), 7.26 (s, 1H), 6.83 (d, J = 2.2 Hz, 1H), 4.60 (br s, 2H), 4.34 (br d, J = 1.9 Hz, 2H), 4.28-4.18 (m, 2H), 4.07-3.96 (m, 1H), 3.27-3.22 (m, 3H) |
| 480 | 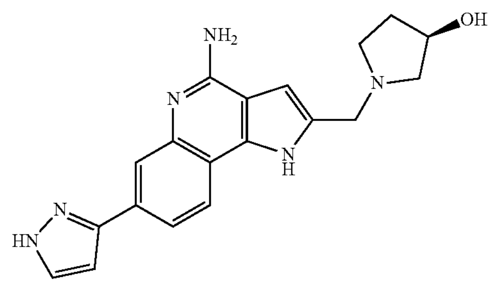 [SMILES: Nc1nc2cc(-c3cc[nH]n3)ccc2c2[nH]c(CN3CC[C@@H](O)C3)cc12] | 349.1 | 0.56 | δ 8.16 (d, J = 8.3 Hz, 1H), 7.93 (s, 1H), 7.70 (br s, 1H), 7.62 (br d, J = 8.4 Hz, 1H), 7.04-6.91 (m, 2H), 6.74 (d, J = 1.7 Hz, 1H), 6.65 (s, 1H), 4.22 (tt, J = 6.7, 3.4 Hz, 1H), 3.77-3.67 (m, 2H), 2.75 (br dd, J = 9.5, 6.3 Hz, 1H), 2.68-2.55 (m, 2H), 2.37 (dd, J = 9.7, 3.8 Hz, 1H), 2.08-1.97 (m, 1H), 1.58 (td, J = 8.0, 4.6 Hz, 1H) |
| 481 | 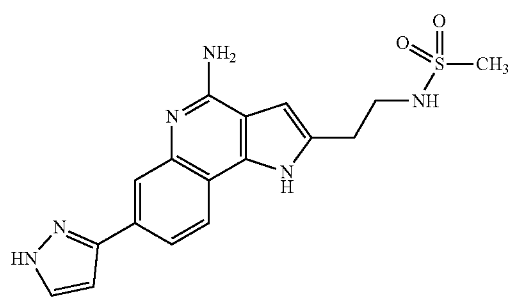 [SMILES: CS(=O)(=O)NCCc1cc2c(N)nc3cc(-c4cc[nH]n4)ccc3c2[nH]1] | 371.2 | 0.81 | δ 13.10 (br d, J = 4.2 Hz, 1H), 12.83 (br s, 1H), 8.60 (td, J = 5.5, 2.8 Hz, 2H), 8.25-8.18 (m, 1H), 8.14 (br s, 1H), 7.94 (br d, J = 7.3 Hz, 1H), 7.84 (br s, 1H), 7.22 (t, J = 5.7 Hz, 1H), 6.90 (s, 1H), 6.82 (s, 1H), 3.37-3.31 (m, 2H), 3.00 (br t, J = 7.3 Hz, 2H), 2.91 (s, 3H) |
| 482 | 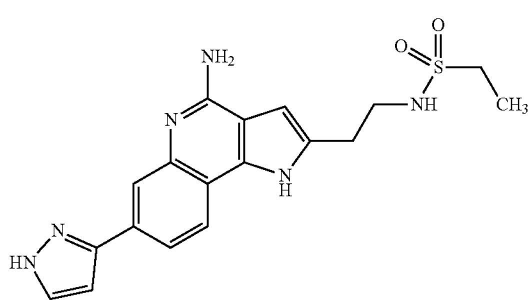 [SMILES: CCS(=O)(=O)NCCc1cc2c(N)nc3cc(-c4cc[nH]n4)ccc3c2[nH]1] | 385.3 | 0.87 | δ 13.20-13.01 (m, 1H), 12.85 (br s, 1H), 8.84-8.34 (m, 2H), 8.21 (d, J = 8.3 Hz, 1H), 8.17-8.09 (m, 1H), 7.94 (br d, J = 8.9 Hz, 1H), 7.84 (br s, 1H), 7.24 (br t, J = 5.8 Hz, 1H), 6.89 (s, 1H), 6.82 (s, 1H), 3.32 (q, J = 6.9 Hz, 2H), 3.03-2.95 (m, 4H), 1.15 (t, J = 7.4 Hz, 3H) |
| 483 | 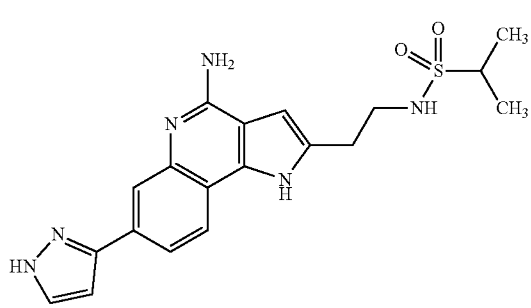 [SMILES: CC(C)S(=O)(=O)NCCc1cc2c(N)nc3cc(-c4cc[nH]n4)ccc3c2[nH]1] | 399.2 | 0.95 | δ 13.17 (br s, 1H), 13.09 (br d, J = 0.8 Hz, 1H), 12.81 (br s, 1H), 8.82-8.42 (m, 2H), 8.26-8.20 (m, 1H), 8.16 (br s, 1H), 7.96 (br d, J = 7.4 Hz, 1H), 7.86 (br s, 1H), 7.23 (t, J = 5.8 Hz, 1H), 6.91 (s, 1H), 6.82 (br s, 1H), 3.32-3.24 (m, 1H), 3.21-3.14 (m, 2H), 2.99 (br t, J = 7.2 Hz, 2H), 1.21 (d, J = 6.6 Hz, 6H) |

-continued

| Ex. No. | Structure | LC/MS [M + H]+ | RT (min) | 1H NMR, 400 MHz, Methanol-d4 unless otherwise noted |
|---|---|---|---|---|
| 484 | 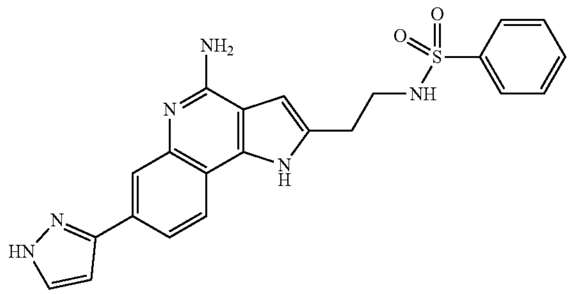 [SMILES: Nc1nc2cc(-c3cc[nH]n3)ccc2c2[nH]c(CCNS(=O)(=O)c3ccccc3)cc12] | 432.9 | 1.23 | δ 13.17 (br s, 1H), 13.12-13.05 (m, 1H), 12.74 (br s, 1H), 8.73-8.48 (m, 2H), 8.22-8.13 (m, 2H), 7.94 (br d, J = 9.4 Hz, 1H), 7.90-7.83 (m, 2H), 7.78 (br d, J = 7.2 Hz, 2H), 7.60-7.51 (m, 3H), 6.84 (s, 1H), 6.81 (s, 1H), 3.15 (q, J = 6.8 Hz, 2H), 2.93 (br t, J = 7.3 Hz, 2H) |
| 485 | 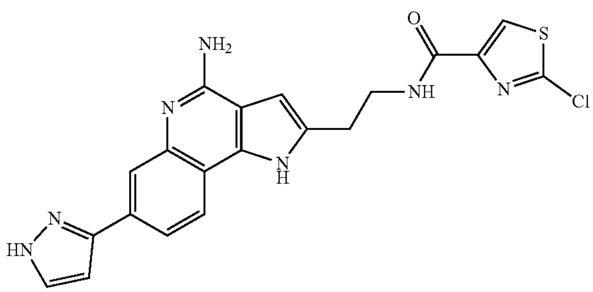 [SMILES: Nc1nc2cc(-c3cc[nH]n3)ccc2c2[nH]c(CCNC(=O)c3csc(Cl)n3)cc12] | 438.3 | 1.1 | δ 13.28 (br s, 1H), 13.15-13.02 (m, 1H), 12.87 (br s, 1H), 8.73 (br t, J = 5.8 Hz, 1H), 8.79-8.54 (m, 2H), 8.28-8.23 (m, 2H), 8.15 (br s, 1H), 7.95 (br d, J = 8.4 Hz, 1H), 7.85 (br s, 1H), 6.88 (s, 1H), 6.82 (d, J = 1.9 Hz, 1H), 3.65 (q, J = 7.1 Hz, 2H), 3.07 (br t, J = 7.2 Hz, 2H) |
| 486 | 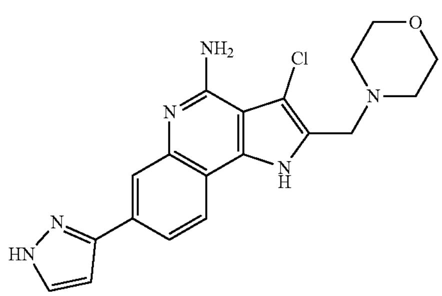 [SMILES: Nc1nc2cc(-c3cc[nH]n3)ccc2c2[nH]c(CN3CCOCC3)c(Cl)c12] | 383.0 | 0.95 | δ 8.20 (d, J = 8.4 Hz, 1H), 7.92 (s, 1H), 7.74-7.62 (m, 2H), 6.77 (d, J = 1.8 Hz, 1H), 6.35-6.25 (m, 2H), 3.65 (s, 2H), 3.60-3.57 (m, 4H), 2.45 (br s, 4H) |
| 487 | 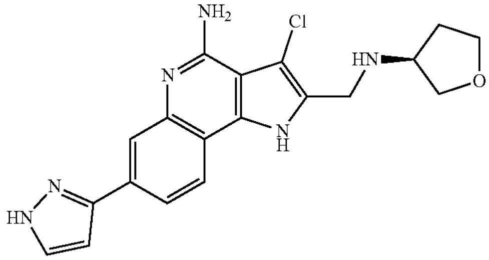 [SMILES: Nc1nc2cc(-c3cc[nH]n3)ccc2c2[nH]c(CN[C@H]3CCOC3)c(Cl)c12] | 383.3 | 0.61 | δ 8.81-8.39 (m, 2H), 8.26 (d, J = 8.3 Hz, 1H), 8.18 (s, 1H), 8.01 (d, J = 8.5 Hz, 1H), 7.85 (br s, 1H), 6.86 (d, J = 2.2 Hz, 1H), 4.40 (s, 2H), 3.98-3.88 (m, 3H), 3.82 (dd, J = 10.3, 5.9 Hz, 1H), 3.71-3.65 (m, 1H), 2.37-2.25 (m, 1H), 2.11-2.02 (m, 1H) |

Example 488. Preparation of 3-(4-amino-7-(1H-pyrazol-5-yl)-2H-pyrazolo[4,3-c]quinolin-2-yl)-N,N,2-trimethylpropanamide.TFA

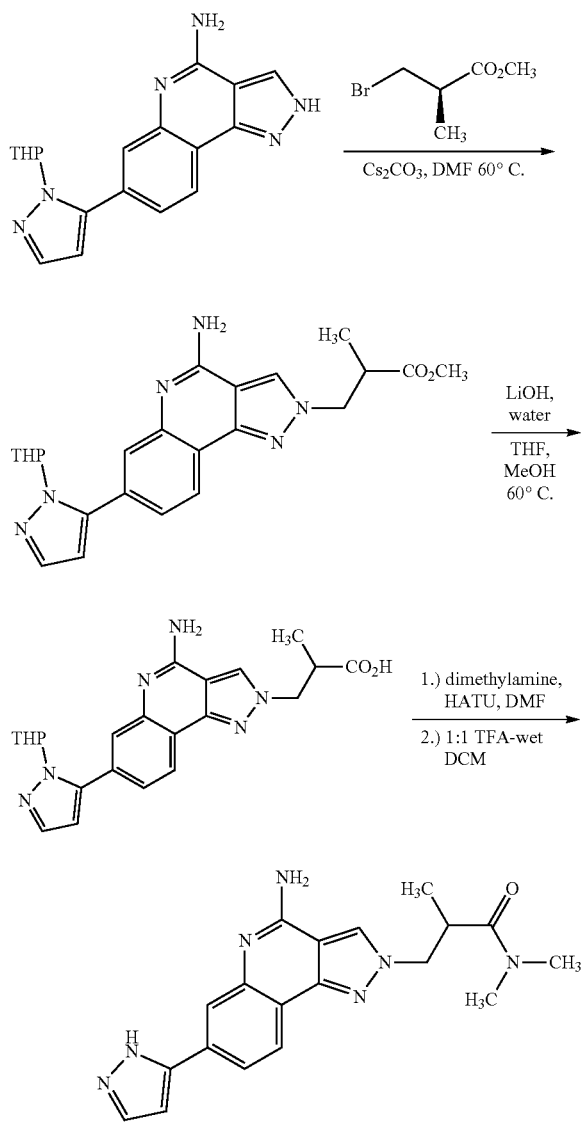

Step 1. Preparation of methyl 3-(4-amino-7-(1-(tetrahydro-2H-pyran-2-yl)-1H-pyrazol-5-yl)-2H-pyrazolo[4,3-c]quinolin-2-yl)-2-methylpropanoate A suspension of 7-(1-(tetrahydro-2H-pyran-2-yl)-1H-pyrazol-5-yl)-2H-pyrazolo[4,3-c]quinolin-4-amine (0.2 g, 0.598 mmol) and cesium carbonate (0.585 g, 1.794 mmol) in DMF (1.994 ml) was stirred briefly (~2 min.) then treated with methyl (R)-3-bromo-2-methylpropanoate (0.178 g, 0.96 mol). The reaction was then warmed to 60° C. and stirred. After 5 h, the reaction was treated with 0.1 g more cesium carbonate and 0.1 g more methyl (R)-3-bromo-2-methylpropanoate. Stirring at 60° C. was continued ON, after which time the reaction was poured into water, and the pH was adjusted to ~6. The resulting mixture was extracted twice with EtOAc, and the combined organic extract was dried, concentrated, and purified by silica gel chromatography (50-100% THF-hexane) to afford methyl 3-(4-amino-7-(1-(tetrahydro-2H-pyran-2-yl)-1H-pyrazol-5-yl)-2H-pyrazolo[4,3-c]quinolin-2-yl)-2-methylpropanoate (195 mg, 0.449 mmol, 75% yield) as a colorless glass. Analytical LC/MS conditions: Column: Acquity UPLC BEH C18, 2.1 mm×50 mm, 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). RT: 0.69 min. m/z 435.3 [M+H]$^+$.

Step 2. Preparation of 3-(4-amino-7-(1-(tetrahydro-2H-pyran-2-yl)-1H-pyrazol-5-yl)-2H-pyrazolo[4,3-c]quinolin-2-yl)-2-methylpropanoic acid A solution of methyl 3-(4-amino-7-(1-(tetrahydro-2H-pyran-2-yl)-1H-pyrazol-5-yl)-2H-pyrazolo[4,3-c]quinolin-2-yl)-2-methylpropanoate (190 mg, 0.437 mmol) in THF (2.2 mL) was treated with aq. lithium hydroxide (2.186 mL, 2.186 mmol) followed by 0.6 mL of MeOH. The reaction was warmed to 60° C. and stirred for 3 h. Most of the organic solvent was removed under a stream of nitrogen, and the residue was diluted with 2 mL of water and filtered. The filtrate was brought to pH-5.5 with glacial HOAc, and the resulting precipitate was filtered, rinsed with water, and air-dried to afford 3-(4-amino-7-(1-(tetrahydro-2H-pyran-2-yl)-1H-pyrazol-5-yl)-2H-pyrazolo[4,3-c]quinolin-2-yl)-2-methylpropanoic acid (135 mg, 0.321 mmol, 73.4% yield) as a white powder. Analytical LC/MS conditions: Column: Acquity UPLC BEH C18, 2.1 mm×50 mm, 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). RT: 0.63 min. m/z 421.2 [M+H]$^+$.

Step 3. Preparation of 3-(4-amino-7-(1H-pyrazol-5-yl)-2H-pyrazolo[4,3-c]quinolin-2-yl)-N,N,2-trimethylpropanamide, TFA A solution of 3-(4-amino-7-(1-(tetrahydro-2H-pyran-2-yl)-1H-pyrazol-5-yl)-2H-pyrazolo[4,3-c]quinolin-2-yl)-2-methylpropanoic acid (18 mg, 0.043 mmol) and dimethylamine ((2M in THF), 86 μl, 0.171 mmol) in DMF (214 μl) was treated with BOP (22.72 mg, 0.051 mmol), and the resulting solution was stirred 1 h at rt. The reaction was then treated with 0.8 mL of 1:1 TFA-DCM and stirred for 2 h at rt. The reaction was concentrated under vaccum. The crude product was purified by prep. HPLC. Concentration of the appropriate fractions afforded 3-(4-amino-7-(1H-pyrazol-5-yl)-2H-pyrazolo[4,3-c]quinolin-2-yl)-N,N,2-trimethylpropanamide, TFA (10 mg, 49%) as a colorless solid. Analytical LC/MS conditions: Column: Acquity UPLC BEH C18, 2.1 mm×50 mm, 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm). RT: 0.56 min. m/z 364.1[M+H]$^+$. $^1$H NMR (400 MHz, MeOH-d$_4$) δ 8.70 (s, 1H), 8.30 (d, J=8.3 Hz, 1H), 8.01 (s, 1H), 7.95

(d, J=8.2 Hz, 1H), 7.79 (d, J=2.2 Hz, 1H), 6.85 (d, J=2.2 Hz, 1H), 4.63 (ABq, $J_{AB}$=13.3 Hz, $J_{AX}$=9.4 Hz, $J_{BX}$=4.9 Hz, Δv=109 Hz, 2H), 3.77-3.87 (m, 1H), 3.07 (s, 3H), 2.89 (s, 3H), 1.28 (d, J=6.9 Hz, 3H).

Example 489 to Example 624 were prepared according to synthetic procedures similar to those described for earlier examples from the appropriate starting materials. Analytical LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Analytical LC/MS conditions for Example 489 and 612: Column: Acquity UPLC BEH C18, 2.1 mm×50 mm, 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.50 min hold at 98% B; Flow: 0.8 mL/min; Detection: MS and UV (254 nm).

| Ex. No. | Structure | LC/MS [M + H]+ | RT (min) | 1H NMR (500 MHz, DMSO-$d_6$) |
|---|---|---|---|---|
| 489 | 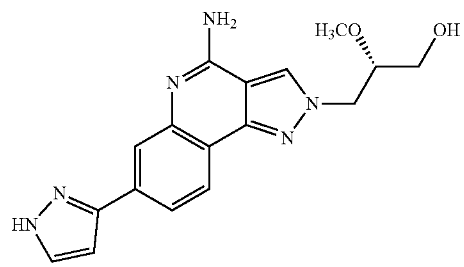 [SMILES: CO[C@H](CO)Cn1cc2c(N)nc3cc(-c4cc[nH]n4)ccc3c2n1] | 339.1 | 0.51 | δ 13.05 (s, 1H), 9.78-9.61 (m, 1H), 8.96 (s, 1H), 8.65-8.51 (m, 1H), 8.21 (d, J = 8.2 Hz, 1H), 8.12 (s, 1H), 7.93 (dd, J = 8.2, 1.4 Hz, 1H), 7.85 (d, J = 1.8 Hz, 1H), 6.82 (d, J = 2.2 Hz, 1H), 4.67 (dd, J = 14.0, 3.5 Hz, 1H), 4.53 (dd, J = 14.1, 7.7 Hz, 1H), 3.75-3.68 (m, 1H), 3.53 (d, J = 5.0 Hz, 2H), 3.26 (s, 3H) |
| 490 | 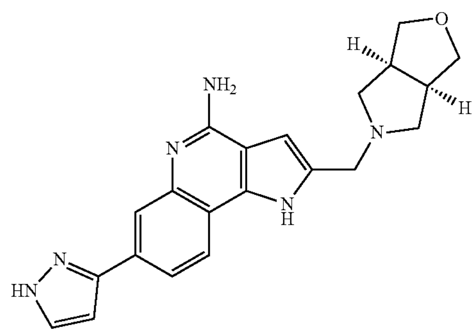 [SMILES: Nc1nc2cc(-c3cc[nH]n3)ccc2c2[nH]c(CN3C[C@H]4COC[C@H]4C3)cc12] | 375.1 | 0.63 | δ 12.19-11.97 (m, 1H), 8.14 (d, J = 8.2 Hz, 1H), 7.91 (s, 1H), 7.69 (br s, 1H), 7.60 (br d, J = 7.6 Hz, 1H), 6.73 (s, 1H), 6.73-6.67 (m, 2H), 6.63 (s, 1H), 3.71-3.63 (m, 6H), 2.72 (br s, 2H), 2.69-2.63 (m, 2H), 2.31 (br d, J = 7.9 Hz, 2H) |
| 491 | 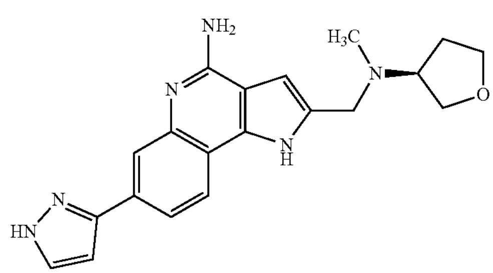 [SMILES: CN(Cc1cc2c(N)nc3cc(-c4cc[nH]n4)ccc3c2[nH]1)[C@H]1CCOC1] | 363.1 | 0.97 | δ 8.21 (d, J = 8.0 Hz, 1H), 7.97 (br d, J = 2.8 Hz, 1H), 7.88-7.57 (m, 2H), 7.28-6.90 (m, 2H), 6.74 (br d, J = 9.1 Hz, 2H), 3.86 (td, J = 8.4, 4.4 Hz, 1H), 3.82-3.77 (m, 1H), 3.72-3.58 (m, 4H), 3.23-3.15 (m, 1H), 2.14 (s, 3H), 2.08-1.99 (m, 1H), 1.88 (dq, J = 12.6, 7.6 Hz, 1H) |
| 492 | 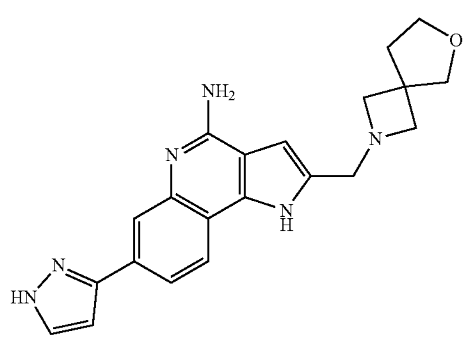 [SMILES: Nc1nc2cc(-c3cc[nH]n3)ccc2c2[nH]c(CN3CC4(CCOC4)C3)cc12] | 375.1 | 0.95 | δ 8.16 (br d, J = 8.3 Hz, 1H), 7.95 (br s, 1H), 7.71 (br s, 1H), 7.66 (br d, J = 8.3 Hz, 1H), 7.34-7.15 (m, 2H), 6.76 (s, 1H), 6.69 (s, 1H), 3.71 (s, 2H), 3.65-3.61 (m, 2H), 3.24-3.19 (m, 2H), 2.01 (br t, J = 6.9 Hz, 2H); four CH protons are not visible, likely due to overlap with suppressed water peak. |

-continued

| Ex. No. | Structure | LC/MS [M + H]⁺ | RT (min) | ¹H NMR (500 MHz, DMSO-d₆) |
|---|---|---|---|---|
| 493 | 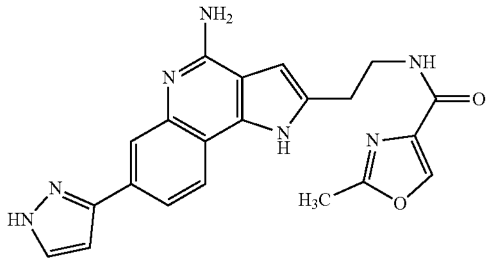 [SMILES: Cc1nc(C(=O)NCCc2cc3c(N)nc4cc(-c5cc[nH]n5)ccc4c3[nH]2)co1] | 402.3 | 1.11 | δ 11.95 (br s, 1H), 8.44 (s, 1H), 8.35 (br t, J = 5.6 Hz, 1H), 8.06 (d, J = 8.3 Hz, 1H), 7.91 (s, 1H), 7.75-7.65 (m, 1H), 7.64-7.55 (m, 1H), 6.73 (s, 1H), 6.57-6.51 (m, 3H), 3.65-3.58 (m, 2H), 3.03-2.98 (m, 2H), 2.44 (s, 3H) |
| 494 | 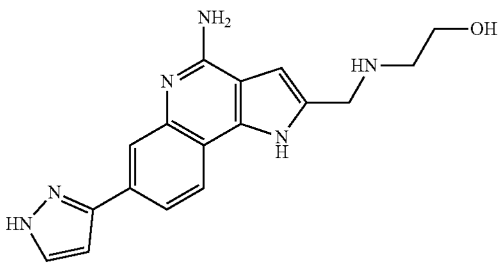 [SMILES: Nc1nc2cc(-c3cc[nH]n3)ccc2c2[nH]c(CNCCO)cc12] | 323.2 | 0.87 | δ 8.18 (br d, J = 8.3 Hz, 1H), 8.06-7.98 (m, 1H), 7.85-7.69 (m, 2H), 6.84 (br s, 1H), 6.77 (br s, 1H), 4.81-4.62 (m, 1H), 4.00 (br s, 2H), 3.57-3.51 (m, 2H), 2.74 (br s, 2H) |
| 495 | 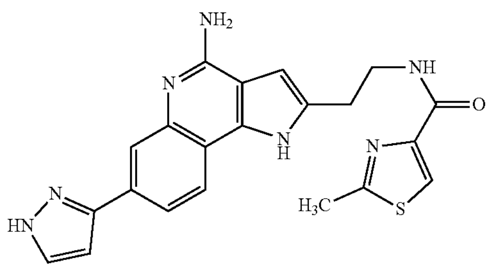 [SMILES: Cc1nc(C(=O)NCCc2cc3c(N)nc4cc(-c5cc[nH]n5)ccc4c3[nH]2)cs1] | 418.2 | 0.99 | δ 12.12-12.00 (m, 1H), 8.49 (br t, J = 5.6 Hz, 1H), 8.10-8.06 (m, 2H), 7.92 (s, 1H), 7.69 (br s, 1H), 7.63 (br d, J = 8.5 Hz, 1H), 6.82 (br s, 2H), 6.73 (d, J = 1.7 Hz, 1H), 6.56 (s, 1H), 3.69-3.62 (m, 2H), 3.04 (br t, J = 7.6 Hz, 2H), 2.69 (s, 3H) |
| 496 | 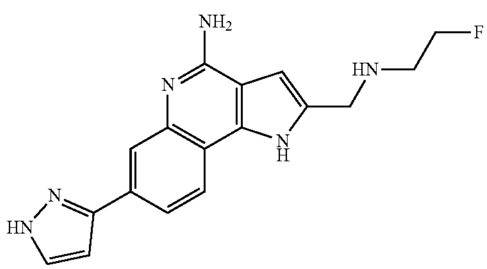 [SMILES: Nc1nc2cc(-c3cc[nH]n3)ccc2c2[nH]c(CNCCF)cc12] | 325.3 | 0.55 | δ 8.22 (d, J = 8.3 Hz, 1H), 8.15 (s, 1H), 7.98 (d, J = 8.5 Hz, 1H), 7.83 (br s, 1H), 7.25 (s, 1H), 6.84 (d, J = 2.2 Hz, 1H), 4.75 (dt, J = 46.8, 4.4 Hz, 2H), 4.44 (s, 2H), 3.43-3.34 (m, 2H) |
| 497 | 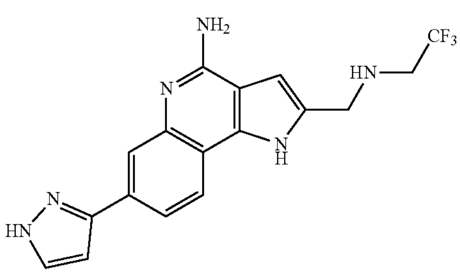 [SMILES: Nc1nc2cc(-c3cc[nH]n3)ccc2c2[nH]c(CNCC(F)(F)F)cc12] | 361.1 | 1.18 | δ 13.24 (s, 1H), 12.95 (br s, 1H), 8.93-8.52 (m, 2H), 8.28 (d, J = 8.3 Hz, 1H), 8.15 (s, 1H), 7.95 (d, J = 8.3 Hz, 1H), 7.83 (d, J = 1.9 Hz, 1H), 7.04 (s, 1H), 6.82 (d, J = 2.2 Hz, 1H), 4.05 (s, 2H), 3.44-3.35 (m, 2H) |

| Ex. No. | Structure | LC/MS [M + H]+ | RT (min) | 1H NMR (500 MHz, DMSO-d6) |
|---|---|---|---|---|
| 498 | 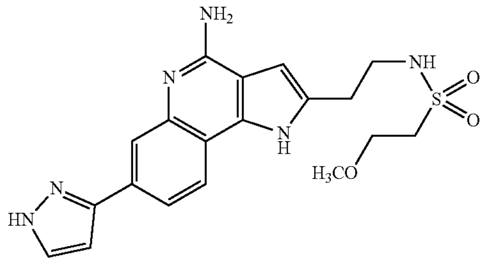 [SMILES: COCCS(=O)(=O)NCCc1cc2c(N)nc3cc(-c4cc[nH]n4)ccc3c2[nH]1] | 415.0 | 1.09 | δ 13.15 (br s, 1H), 12.85 (s, 1H), 8.22 (d, J = 8.5 Hz, 1H), 8.12 (s, 1H), 7.94 (d, J = 8.5 Hz, 1H), 7.82 (s, 1H), 7.26 (br d, J = 5.5 Hz, 1H), 6.90 (s, 1H), 6.82 (d, J = 2.1 Hz, 1H), 3.62-3.59 (m, 2H), 3.36-3.31 (m, 2H), 3.27 (br t, J = 6.1 Hz, 2H), 3.20 (s, 3H), 2.98 (br t, J = 7.2 Hz, 2H) |
| 499 | 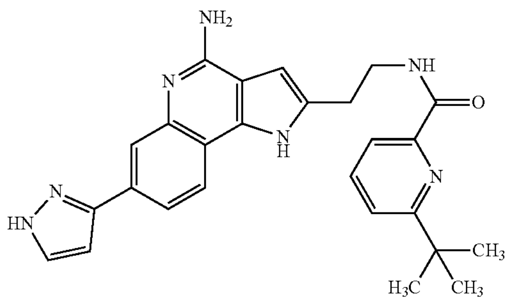 [SMILES: CC(C)(C)c1cccc(C(=O)NCCc2cc3c(N)nc4cc(-c5cc[nH]n5)ccc4c3[nH]2)n1] | 454.0 | 1.50 | δ 13.25 (br d, J = 4.7 Hz, 1H), 12.93 (s, 1H), 8.66 (br t, J = 5.9 Hz, 1H), 8.86-8.48 (m, 2H), 8.26 (br d, J = 8.3 Hz, 1H), 8.15 (s, 1H), 7.95 (br d, J = 8.2 Hz, 1H), 7.92-7.88 (m, 1H), 7.86-7.82 (m, 2H), 7.61 (d, J = 7.9 Hz, 1H), 6.94 (s, 1H), 6.82 (d, J = 1.8 Hz, 1H), 3.75 (q, J = 7.0 Hz, 2H), 3.12 (br t, J = 7.1 Hz, 2H), 1.27 (s, 9H) |
| 500 | 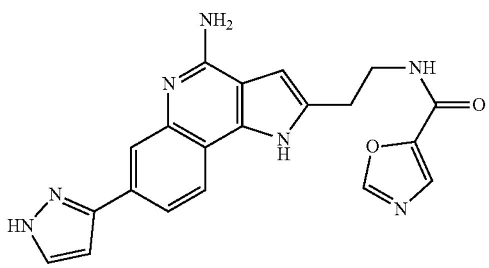 [SMILES: Nc1nc2cc(-c3cc[nH]n3)ccc2c2[nH]c(CCNC(=O)c3cnco3)cc12] | 388.0 | 1.04 | δ 8.85 (br t, J = 5.7 Hz, 1H), 8.52-8.46 (m, 1H), 8.07 (d, J = 8.3 Hz, 1H), 7.94 (s, 1H), 7.75 (s, 1H), 7.70 (br s, 1H), 7.66 (br d, J = 8.2 Hz, 1H), 6.76 (s, 1H), 6.59 (s, 1H), 3.73-3.57 (m, 2H), 3.02 (br t, J = 7.3 Hz, 2H) |
| 501 | 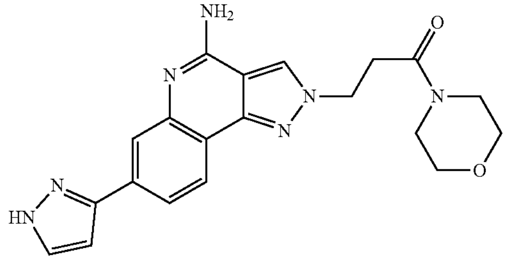 [SMILES: Nc1nc2cc(-c3cc[nH]n3)ccc2c2nn(CCC(=O)N3CCOCC3)cc12] | 392.3 | 1.05 | δ 8.51 (s, 1H), 8.06 (d, J = 8.2 Hz, 1H), 7.87 (s, 1H), 7.75-7.68 (m, 1H), 7.65-7.58 (m, 1H), 6.75 (d, J = 1.8 Hz, 1H), 4.64 (br t, J = 6.3 Hz, 2H), 3.05 (br t, J = 6.4 Hz, 2H); eight CH protons are not visible, likely due to overlap with suppressed water peak. |
| 502 | 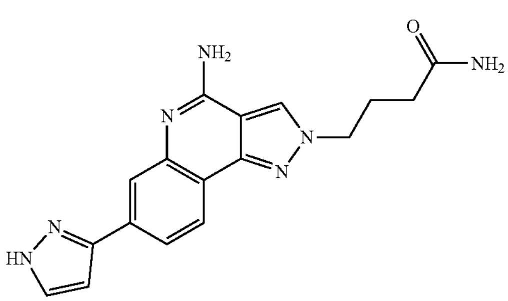 [SMILES: NC(=O)CCCn1cc2c(N)nc3cc(-c4cc[nH]n4)ccc3c2n1] | 336.2 | 0.97 | δ 8.47 (s, 1H), 8.08 (d, J = 8.0 Hz, 1H), 7.87 (s, 1H), 7.70 (br s, 1H), 7.62 (br d, J = 8.3 Hz, 1H), 7.35 (br s, 1H), 6.96-6.84 (m, 2H), 6.80 (br s, 1H), 6.75 (d, J = 1.9 Hz, 1H), 4.41 (br t, J = 6.5 Hz, 2H), 2.16-2.07 (m, 4H) |

-continued

| Ex. No. | Structure | LC/MS [M + H]+ | RT (min) | 1H NMR (500 MHz, DMSO-d6) |
|---|---|---|---|---|
| 503 | 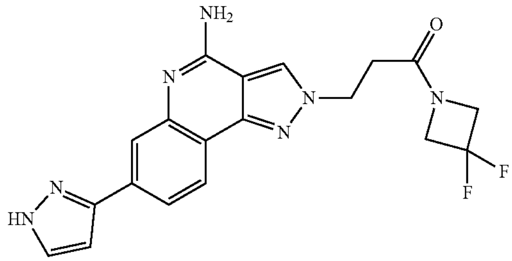 [SMILES: Nc1nc2cc(-c3cc[nH]n3)ccc2c2nn(CCC(=O)N3CC(F)(F)C3)cc12] | 398.3 | 0.92 | δ 8.48 (s, 1H), 8.06 (d, J = 8.0 Hz, 1H), 7.86 (s, 1H), 7.70 (br s, 1H), 7.61 (br d, J = 8.0 Hz, 1H), 6.91 (br s, 2H), 6.75 (d, J = 1.7 Hz, 1H), 4.63 (t, J = 6.5 Hz, 2H), 4.57 (br t, J = 12.2 Hz, 2H), 4.27 (br t, J = 12.5 Hz, 2H), 2.89 (t, J = 6.5 Hz, 2H) |
| 504 | 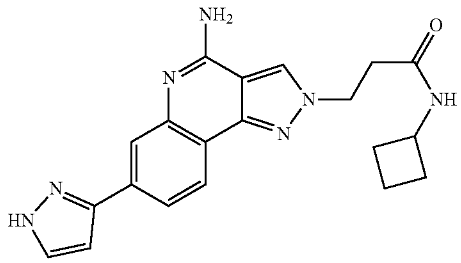 [SMILES: Nc1nc2cc(-c3cc[nH]n3)ccc2c2nn(CCC(=O)NC3CCC3)cc12] | 376.3 | 1.13 | δ 13.37-13.01 (m, 1H), 9.73-9.58 (m, 1H), 9.04-8.94 (m, 1H), 8.90 (s, 1H), 8.25 (br d, J = 7.7 Hz, 1H), 8.17 (br d, J = 8.2 Hz, 1H), 8.10 (br s, 1H), 7.92 (br d, J = 8.2 Hz, 1H), 7.84 (br s, 1H), 6.81 (s, 1H), 4.72-4.65 (m, 2H), 4.21-4.10 (m, 1H), 2.77 (br t, J = 6.3 Hz, 2H), 2.14-2.05 (m, 2H), 1.87-1.69 (m, 2H), 1.62-1.55 (m, 2H) |
| 505 | 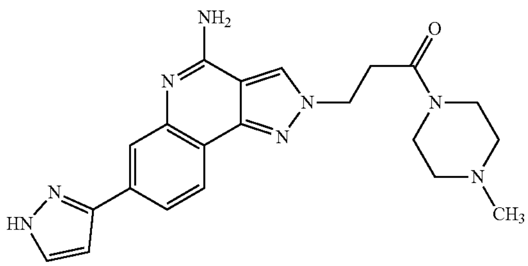 [SMILES: CN1CCN(C(=O)CCn2cc3c(N)nc4cc(-c5cc[nH]n5)ccc4c3n2)CC1] | 405.3 | 0.92 | δ 8.50 (s, 1H), 8.07 (d, J = 8.0 Hz, 1H), 7.86 (s, 1H), 7.70 (s, 1H), 7.62 (br d, J = 8.0 Hz, 1H), 7.07-6.88 (m, 2H), 6.74 (d, J = 1.9 Hz, 1H), 4.63 (br t, J = 6.3 Hz, 2H), 3.44-3.40 (m, 2H), 3.40-3.36 (m, J = 4.7 Hz, 2H), 3.03 (br t, J = 6.5 Hz, 2H), 2.20-2.16 (m, 4H), 2.09 (s, 3H) |
| 506 | 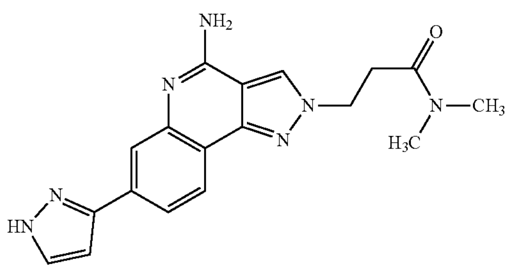 [SMILES: CN(C)C(=O)CCn1cc2c(N)nc3cc(-c4cc[nH]n4)ccc3c2n1] | 350.0 | 1.07 | δ 8.63 (br s, 1H), 8.09 (d, J = 8.3 Hz, 1H), 7.95-7.89 (m, 1H), 7.82-7.62 (m, 2H), 6.76 (s, 1H), 4.64 (br t, J = 6.3 Hz, 2H), 3.04 (br t, J = 6.3 Hz, 2H), 2.94 (s, 3H), 2.81 (s, 3H) |
| 507 | 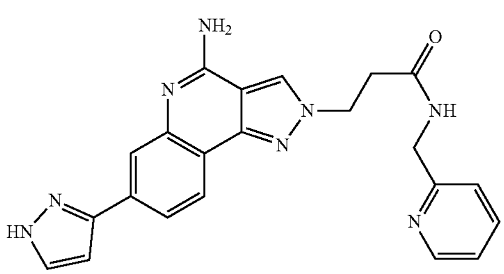 [SMILES: Nc1nc2cc(-c3cc[nH]n3)ccc2c2nn(CCC(=O)NCc3ccccn3)cc12] | 413.3 | 0.95 | δ 8.61 (br t, J = 6.1 Hz, 1H), 8.45 (s, 1H), 8.40 (br d, J = 4.4 Hz, 1H), 8.08 (d, J = 8.1 Hz, 1H), 7.89 (s, 1H), 7.71 (br s, 1H), 7.62 (br d, J = 8.4 Hz, 1H), 7.39 (td, J = 7.6, 1.6 Hz, 1H), 7.18-7.12 (m, 1H), 7.01-6.92 (m, 2H), 6.89 (br d, J = 7.8 Hz, 1H), 6.76 (d, J = 1.7 Hz, 1H), 4.68 (br t, J = 6.3 Hz, 2H), 4.32 (d, J = 6.0 Hz, 2H), 2.93 (br t, J = 6.4 Hz, 2H) |

| Ex. No. | Structure | LC/MS [M + H]+ | RT (min) | ¹H NMR (500 MHz, DMSO-d$_6$) |
|---|---|---|---|---|
| 508 | 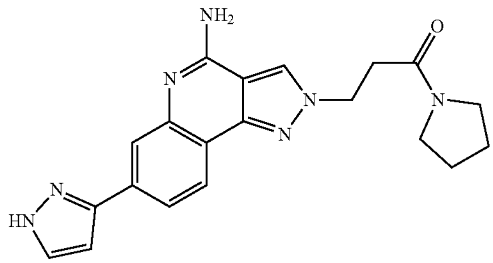 [SMILES: Nc1nc2cc(-c3cc[nH]n3)ccc2c2nn(CCC(=O)N3CCCC3)cc12] | 376.1 | 1.18 | δ 8.51 (s, 1H), 8.06 (d, J = 8.0 Hz, 1H), 7.86 (s, 1H), 7.78-7.57 (m, 2H), 6.92 (br s, 2H), 6.75 (s, 1H), 4.64 (t, J = 6.5 Hz, 2H), 3.28 (br t, J = 6.7 Hz, 2H), 2.96 (br t, J = 6.3 Hz, 2H), 1.81 (quin, J = 6.7 Hz, 2H), 1.76-1.66 (m, 2H); two CH protons are not visible, likely due to overlap with suppressed water peak. |
| 509 | 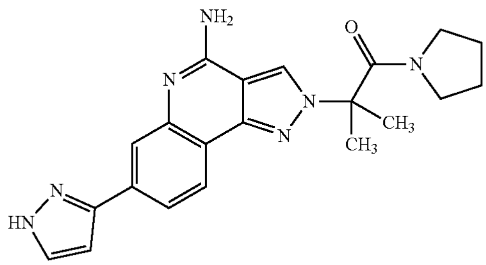 [SMILES: CC(C)(C(=O)N1CCCC1)n1cc2c(N)nc3cc(-c4cc[nH]n4)ccc3c2n1] | 390.3 | 1.03 | δ 8.72 (s, 1H), 8.07 (d, J = 8.3 Hz, 1H), 7.88 (s, 1H), 7.71 (br s, 1H), 7.63 (br d, J = 8.0 Hz, 1H), 7.04-6.87 (m, 2H), 6.75 (d, J = 1.9 Hz, 1H), 3.39 (br s, 2H), 2.34 (br s, 2H), 1.84 (s, 6H), 1.57 (br s, 4H) |
| 510 | 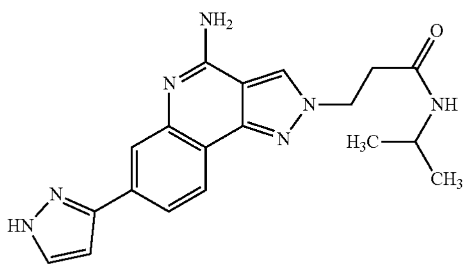 [SMILES: CC(C)NC(=O)CCn1cc2c(N)nc3cc(-c4cc[nH]n4)ccc3c2n1] | 364.2 | 1.08 | δ 8.45 (s, 1H), 8.07 (d, J = 8.1 Hz, 1H), 7.89-7.82 (m, 2H), 7.71 (br s, 1H), 7.64 (br d, J = 8.2 Hz, 1H), 7.17-6.94 (m, 2H), 6.75 (d, J = 2.0 Hz, 1H), 4.61 (br t, J = 6.5 Hz, 2H), 3.85-3.75 (m, 1H), 2.72 (t, J = 6.5 Hz, 2H), 0.95 (d, J = 6.6 Hz, 6H) |
| 511 | 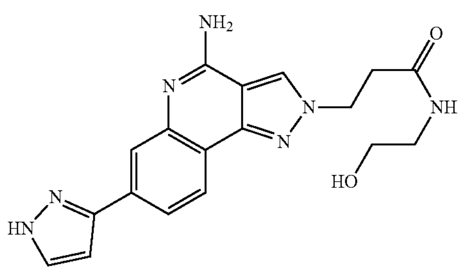 [SMILES: Nc1nc2cc(-c3cc[nH]n3)ccc2c2nn(CCC(=O)NCCO)cc12] | 366.3 | 0.94 | δ 13.29-13.05 (m, 1H), 9.74-9.52 (m, 1H), 8.89 (s, 1H), 9.03-8.79 (m, 1H), 8.18 (d, J = 8.2 Hz, 1H), 8.09 (br s, 1H), 8.03 (br t, J = 5.6 Hz, 1H), 7.91 (br d, J = 8.2 Hz, 1H), 7.84 (br s, 1H), 6.81 (d, J = 2.1 Hz, 1H), 4.68 (br t, J = 6.4 Hz, 2H), 3.34 (br t, J = 6.0 Hz, 2H), 3.10 (q, J = 6.0 Hz, 2H), 2.82 (t, J = 6.4 Hz, 2H) |
| 512 | 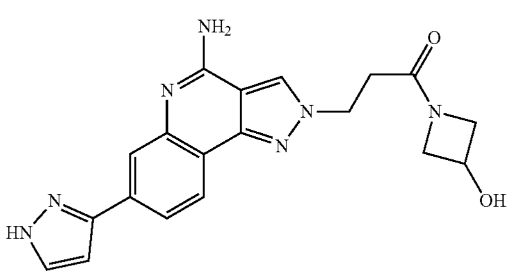 [SMILES: Nc1nc2cc(-c3cc[nH]n3)ccc2c2nn(CCC(=O)N3CC(O)C3)cc12] | 377.9 | 0.96 | δ 8.52 (s, 1H), 8.09 (d, J = 8.2 Hz, 1H), 7.88 (s, 1H), 7.76-7.61 (m, 2H), 6.76 (d, J = 1.9 Hz, 1H), 4.60 (br t, J = 6.4 Hz, 2H), 4.36 (br s, 1H), 4.20 (br t, J = 7.9 Hz, 1H), 4.01 (dd, J = 9.7, 7.6 Hz, 1H), 3.79 (br dd, J = 9.1, 4.1 Hz, 1H), 2.77 (br t, J = 6.4 Hz, 2H); one CH proton is not visible, likely due to overlap with suppressed water peak. |

| Ex. No. | Structure | LC/MS [M + H]+ | RT (min) | ¹H NMR (500 MHz, DMSO-d₆) |
|---|---|---|---|---|
| 513 | 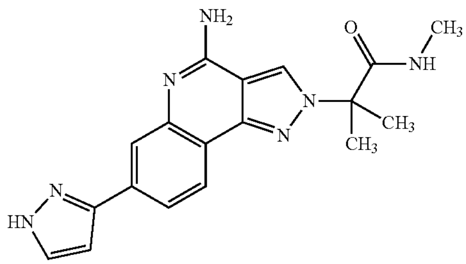 [SMILES: CNC(=O)C(C)(C)n1cc2c(N)nc3cc(-c4cc[nH]n4)ccc3c2n1] | 349.9 | 1.08 | δ 8.70 (s, 1H), 8.07 (d, J = 8.0 Hz, 1H), 7.87 (s, 1H), 7.78-7.56 (m, 3H), 6.96 (br s, 2H), 6.75 (d, J = 1.7 Hz, 1H), 2.59 (d, J = 4.7 Hz, 3H), 1.86 (s, 6H) |
| 514 | 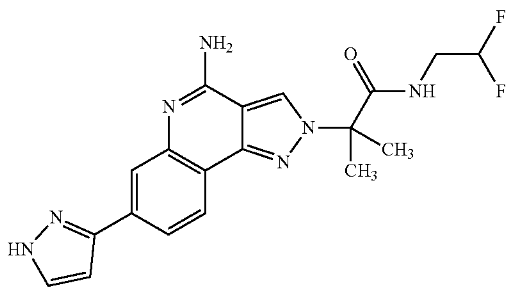 [SMILES: CC(C)(C(=O)NCC(F)F)n1cc2c(N)nc3cc(-c4cc[nH]n4)ccc3c2n1] | 400.2 | 1.19 | δ 8.76 (s, 1H), 8.09 (d, J = 7.9 Hz, 1H), 8.02 (t, J = 5.8 Hz, 1H), 7.90 (s, 1H), 7.72 (br s, 1H), 7.66 (br d, J = 7.6 Hz, 1H), 6.76 (d, J = 1.5 Hz, 1H), 5.97 (tt, J = 56.2, 4.0 Hz, 1H), 1.89 (s, 6H); two CH protons are not visible, likely due to overlap with suppressed water peak. |
| 515 | 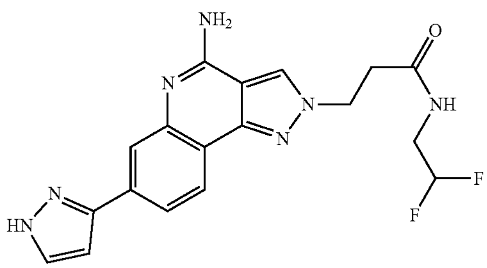 [SMILES: Nc1nc2cc(-c3cc[nH]n3)ccc2c2nn(CCC(=O)NCC(F)F)cc12] | 386.3 | 1.09 | δ 8.46 (s, 1H), 8.41 (br t, J = 5.8 Hz, 1H), 8.06 (d, J = 8.2 Hz, 1H), 7.87 (s, 1H), 7.79-7.56 (m, 2H), 6.75 (d, J = 1.5 Hz, 1H), 5.95 (tt, J = 55.8, 3.7 Hz, 1H), 4.64 (t, J = 6.4 Hz, 2H), 2.86 (t, J = 6.6 Hz, 2H); two CH protons are not visible, likely due to overlap with suppressed water peak. |
| 516 | 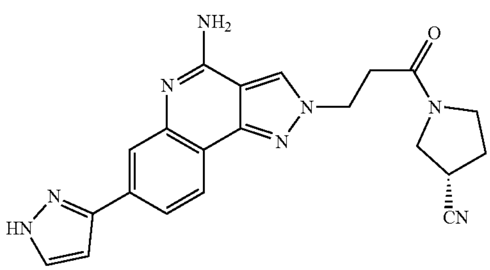 [SMILES: N#C[C@H]1CCN(C(=O)CCn2cc3c(N)nc4cc(-c5cc[nH]n5)ccc4c3n2)C1] | 401.3 | 1.07 | δ 8.54 (s, 1H), 8.07 (d, J = 8.1 Hz, 1H), 7.88 (br s, 1H), 7.82-7.58 (m, 2H), 7.18-6.96 (m, 2H), 6.75 (s, 1H), 4.64 (br t, J = 6.4 Hz, 2H), 3.76 (br dd, J = 10.3, 7.4 Hz, 1H), 3.68-3.53 (m, 3H), 3.40-3.34 (m, 1H), 3.07-2.94 (m, 2H), 2.29-2.00 (m, 2H) |
| 517 | 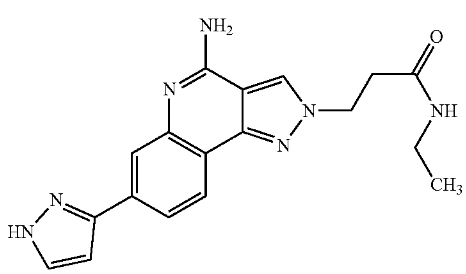 [SMILES: CCNC(=O)CCn1cc2c(N)nc3cc(-c4cc[nH]n4)ccc3c2n1] | 349.9 | 1.01 | δ 8.50 (s, 1H), 8.08 (d, J = 8.2 Hz, 1H), 7.96 (br t, J = 5.2 Hz, 1H), 7.90 (br s, 1H), 7.83-7.60 (m, 2H), 7.48-7.14 (m, 2H), 6.76 (s, 1H), 4.62 (t, J = 6.5 Hz, 2H), 3.08-2.99 (m, 2H), 2.76 (t, J = 6.5 Hz, 2H), 0.93 (t, J = 7.2 Hz, 3H) |

-continued

| Ex. No. | Structure | LC/MS [M + H]⁺ | RT (min) | ¹H NMR (500 MHz, DMSO-d₆) |
|---|---|---|---|---|
| 518 | 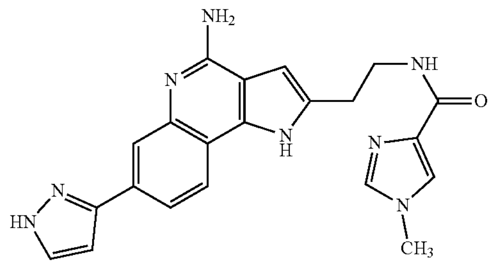 [SMILES: Cn1cnc(C(=O)NCCc2cc3c(N)nc4cc(-c5cc[nH]n5)ccc4c3[nH]2)c1] | 401.1 | 1.02 | δ 13.32 (br s, 1H), 12.86 (s, 1H), 8.79-8.57 (m, 2H), 8.26 (d, J = 8.3 Hz, 1H), 8.17-8.10 (m, 2H), 7.95 (d, J = 8.5 Hz, 1H), 7.83 (br s, 1H), 7.69 (s, 1H), 7.63 (s, 1H), 6.89 (s, 1H), 6.81 (d, J = 2.2 Hz, 1H), 3.68 (s, 3H), 3.63 (q, J = 6.9 Hz, 2H), 3.05 (br t, J = 7.3 Hz, 2H) |
| 519 | 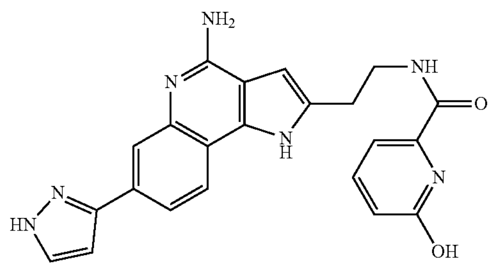 [SMILES: Nc1nc2cc(-c3cc[nH]n3)ccc2c2[nH]c(CCNC(=O)c3cccc(O)n3)cc12] | 413.9 | 1.00 | δ 13.31-13.12 (m, 1H), 12.88 (s, 1H), 8.75-8.48 (m, 3H), 8.26 (d, J = 8.5 Hz, 1H), 8.14 (br s, 1H), 7.95 (br d, J = 8.3 Hz, 1H), 7.83 (br s, 1H), 7.70 (br t, J = 6.1 Hz, 1H), 7.38-7.14 (m, 1H), 6.90 (s, 1H), 6.81 (d, J = 1.9 Hz, 1H), 6.74 (br d, J = 6.6 Hz, 1H), 3.69 (q, J = 6.9 Hz, 2H), 3.08 (br t, J = 7.0 Hz, 2H) |
| 520 | 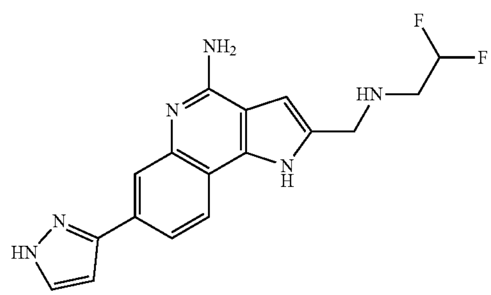 [SMILES: Nc1nc2cc(-c3cc[nH]n3)ccc2c2[nH]c(CNCC(F)F)cc12] | 343.2 | 0.91 | δ 11.98 (br s, 1H), 8.08 (d, J = 8.3 Hz, 1H), 7.92 (s, 1H), 7.69 (br s, 1H), 7.61 (br d, J = 8.0 Hz, 1H), 6.73 (d, J = 1.9 Hz, 1H), 6.68-6.61 (m, 3H), 6.03 (tt, J = 56.4, 4.1 Hz, 1H), 3.92 (s, 2H), 2.93 (td, J = 16.0, 4.1 Hz, 2H) |
| 521 | 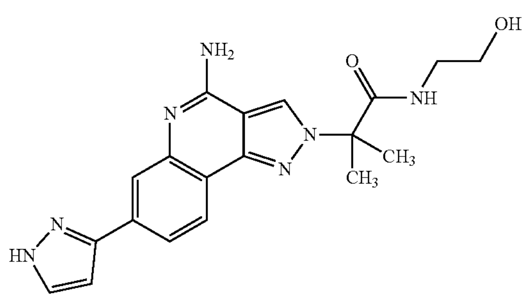 [SMILES: CC(C)(C(=O)NCCO)n1cc2c(N)nc3cc(-c4cc[nH]n4)ccc3c2n1] | 379.9 | 1.02 | δ 9.12 (s, 1H), 8.19 (d, J = 8.2 Hz, 1H), 8.11 (br s, 1H), 7.91 (br d, J = 8.5 Hz, 1H), 7.85 (br s, 1H), 7.81 (br t, J = 5.6 Hz, 1H), 6.81 (s, 1H), 3.15 (q, J = 6.3 Hz, 2H), 1.91 (s, 6H); two CH protons are not visible, likely due to overlap with suppressed water peak. |
| 522 | 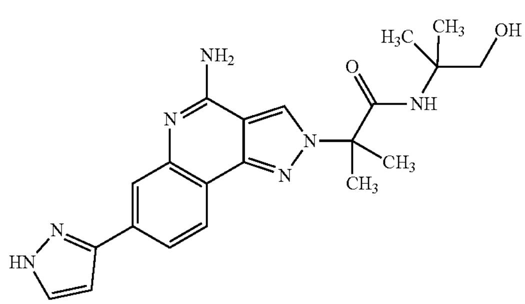 [SMILES: CC(C)(CO)NC(=O)C(C)(C)n1cc2c(N)nc3cc(-c4cc[nH]n4)ccc3c2n1] | 408.1 | 1.19 | δ 8.72 (s, 1H), 8.09 (d, J = 8.0 Hz, 1H), 7.87 (s, 1H), 7.71 (br s, 1H), 7.62 (br d, J = 8.0 Hz, 1H), 6.99-6.90 (m, 3H), 6.75 (s, 1H), 3.28 (s, 2H), 1.87 (s, 6H), 1.17 (s, 6H) |

| Ex. No. | Structure | LC/MS [M + H]+ | RT (min) | ¹H NMR (500 MHz, DMSO-d₆) |
|---|---|---|---|---|
| 523 | 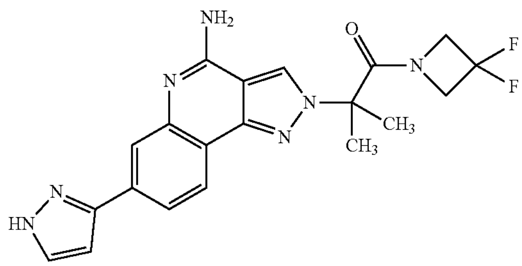 [SMILES: CC(C)(C(=O)N1CC(F)(F)C1)n1cc2c(N)nc3cc(-c4cc[nH]n4)ccc3c2n1] | 412.0 | 1.23 | δ 8.77 (s, 1H), 8.10 (d, J = 8.3 Hz, 1H), 7.89 (br s, 1H), 7.81-7.59 (m, 2H), 7.14-6.99 (m, 2H), 6.76 (s, 1H), 4.46-4.25 (m, 2H), 3.71-3.55 (m, 2H), 1.86 (s, 6H) |
| 524 | 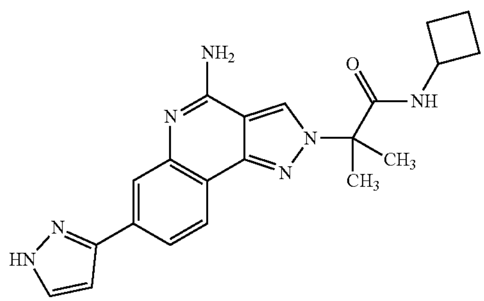 [SMILES: CC(C)(C(=O)NC1CCC1)n1cc2c(N)nc3cc(-c4cc[nH]n4)ccc3c2n1] | 390.1 | 1.33 | δ 8.66 (s, 1H), 8.06 (d, J = 8.2 Hz, 1H), 7.89-7.85 (m, 2H), 7.71 (br s, 1H), 7.63 (br d, J = 8.2 Hz, 1H), 7.11-6.92 (m, 2H), 6.75 (d, J = 2.1 Hz, 1H), 4.24-4.15 (m, 1H), 2.15-2.06 (m, 2H), 1.98-1.89 (m, 2H), 1.85 (s, 6H), 1.63-1.54 (m, 2H) |
| 525 | 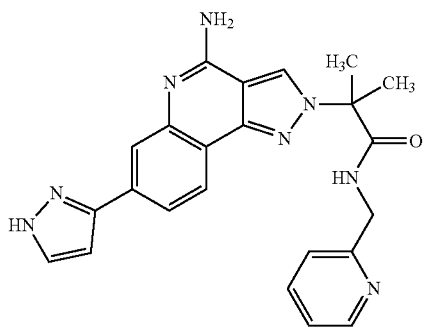 [SMILES: CC(C)(C(=O)NCc1ccccn1)n1cc2c(N)nc3cc(-c4cc[nH]n4)ccc3c2n1] | 427.1 | 1.05 | δ 8.76 (s, 1H), 8.42 (br d, J = 4.4 Hz, 1H), 8.27 (br t, J = 5.8 Hz, 1H), 8.14 (d, J = 8.3 Hz, 1H), 7.88 (s, 1H), 7.72 (br s, 1H), 7.68-7.64 (m, 2H), 7.37 (d, J = 8.0 Hz, 1H), 7.24-7.18 (m, 1H), 6.92 (br s, 2H), 6.76 (d, J = 1.9 Hz, 1H), 4.36 (d, J = 6.1 Hz, 2H), 1.93 (s, 6H) |
| 526 | 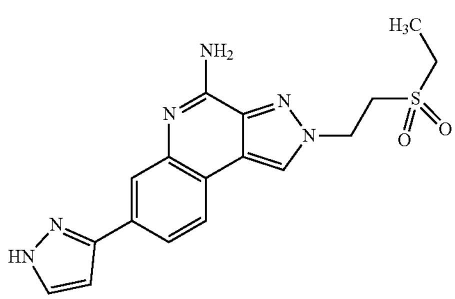 [SMILES: CCS(=O)(=O)CCn1cc2c(n1)c(N)nc1cc(-c3cc[nH]n3)ccc12] | 371.0 | 1.07 | δ 9.01 (s, 1H), 8.21 (d, J = 8.1 Hz, 1H), 8.13 (br s, 1H), 7.94 (br d, J = 7.3 Hz, 1H), 7.87 (br d, J = 1.9 Hz, 1H), 6.83 (s, 1H), 4.98 (br t, J = 6.4 Hz, 2H), 3.88 (t, J = 6.6 Hz, 2H), 3.17 (q, J = 7.3 Hz, 2H), 1.23 (t, J = 7.4 Hz, 3H) |
| 527 | 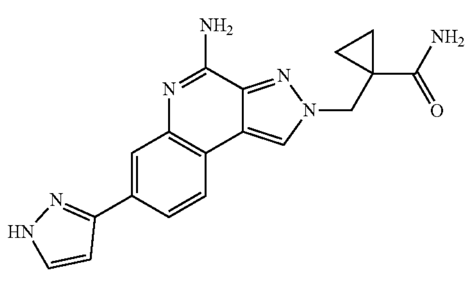 [SMILES: NC(=O)C1(Cn2cc3c(n2)c(N)nc2cc(-c4cc[nH]n4)ccc23)CC1] | 348.1 | 1.08 | δ 9.06 (s, 1H), 8.19 (d, J = 8.2 Hz, 1H), 8.08 (br s, 1H), 7.92 (br d, J = 8.3 Hz, 1H), 7.85 (br d, J = 1.0 Hz, 1H), 7.17 (br s, 1H), 7.00 (br s, 1H), 6.83 (d, J = 2.1 Hz, 1H), 4.67 (s, 2H), 1.30-1.26 (m, 2H), 1.21-1.10 (m, 2H); two protons not visible, likely due to overlap with water/water suppression. |

| Ex. No. | Structure | LC/MS [M + H]+ | RT (min) | ¹H NMR (500 MHz, DMSO-d₆) |
|---|---|---|---|---|
| 528 | 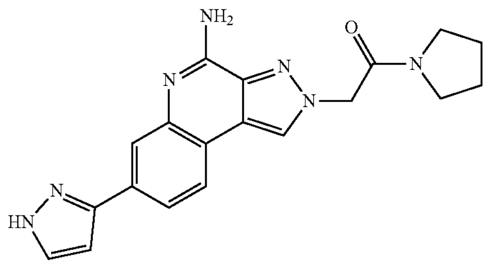 [SMILES: Nc1nc2cc(-c3cc[nH]n3)ccc2c2cn(CC(=O)N3CCCC3)nc12] | 362.2 | 1.09 | δ 8.47 (s, 1H), 8.06 (d, J = 8.2 Hz, 1H), 7.90 (s, 1H), 7.72 (br d, J = 3.7 Hz, 1H), 7.64 (br d, J = 7.6 Hz, 1H), 6.77 (d, J = 1.8 Hz, 1H), 5.42 (s, 2H), 3.59 (t, J = 6.7 Hz, 1H), 2.03-1.94 (m, 2H), 1.84 (m, 2H); four protons not visible, likely due to overlap with water/water suppression. |
| 529 | 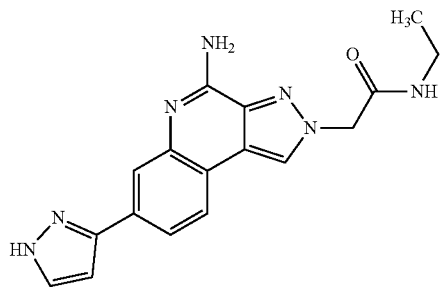 [SMILES: CCNC(=O)Cn1cc2c(n1)c(N)nc1cc(-c3cc[nH]n3)ccc12] | 336.1 | 1.07 | δ 8.50 (s, 1H), 8.05 (d, J = 8.2 Hz, 1H), 7.88 (s, 1H), 7.72 (br dd, J = 5.0, 3.4 Hz, 1H), 7.64-7.58 (m, 1H), 6.77 (s, 1H), 5.12 (s, 2H), 3.24-3.10 (m, 2H), 1.08 (t, J = 7.2 Hz, 3H) |
| 530 | 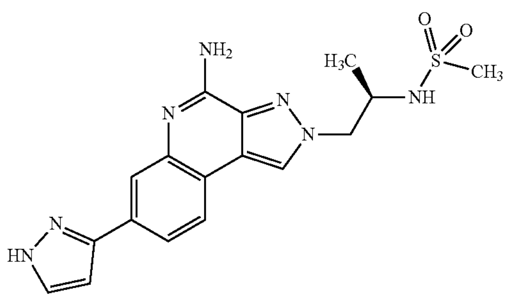 [SMILES: C[C@H](Cn1cc2c(n1)c(N)nc1cc(-c3cc[nH]n3)ccc12)NS(C)(=O)=O] | 386.3 | 0.88 | δ 8.50 (s, 1H), 8.10 (d, J = 8.2 Hz, 1H), 7.88 (s, 1H), 7.72 (br s, 1H), 7.63 (br d, J = 7.3 Hz, 1H), 6.76 (d, J = 2.1 Hz, 1H), 4.50-4.35 (m, 2H), 4.02-3.92 (m, 1H), 2.66 (s, 3H), 1.19 (d, J = 6.7 Hz, 3H) |
| 531 | 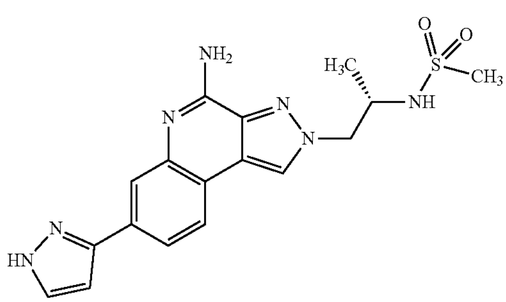 [SMILES: C[C@@H](Cn1cc2c(n1)c(N)nc1cc(-c3cc[nH]n3)ccc12)NS(C)(=O)=O] | 386.0 | 0.87 | δ 8.50 (s, 1H), 8.10 (d, J = 8.2 Hz, 1H), 7.88 (s, 1H), 7.72 (br s, 1H), 7.63 (br d, J = 7.3 Hz, 1H), 6.76 (d, J = 2.1 Hz, 1H), 4.50-4.35 (m, 2H), 4.02-3.92 (m, 1H), 2.66 (s, 3H), 1.19 (d, J = 6.7 Hz, 3H) |
| 532 | 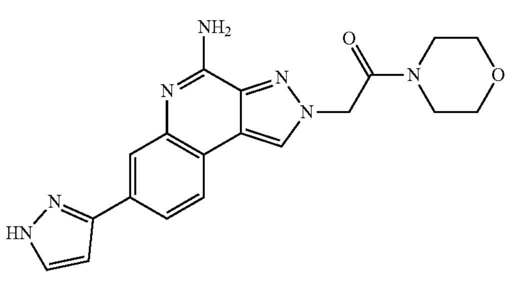 [SMILES: Nc1nc2cc(-c3cc[nH]n3)ccc2c2cn(CC(=O)N3CCOCC3)nc12] | 377.9 | 1.09 | δ 8.92 (s, 1H), 8.18 (d, J = 8.2 Hz, 1H), 8.15 (br d, J = 4.0 Hz, 1H), 7.93 (d, J = 8.2 Hz, 1H), 7.88 (br s, 1H), 6.83 (br d, J = 0.6 Hz, 1H), 5.68 (s, 2H), 3.72 (br d, J = 4.6 Hz, 2H), 3.67-3.62 (m, 2H), 3.60 (m, 2H), 3.51 (m, 2H) |

| Ex. No. | Structure | LC/MS [M + H]+ | RT (min) | 1H NMR (500 MHz, DMSO-d6) |
|---|---|---|---|---|
| 533 | 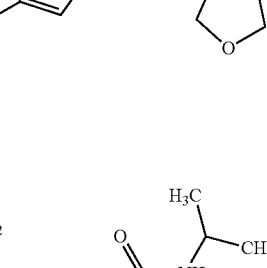 | 377.9 | 1.02 | δ 8.71 (br d, J = 6.7 Hz, 1H), 8.50 (s, 1H), 8.06 (d, J = 8.2 Hz, 1H), 7.88 (s, 1H), 7.64 (br d, J = 4.6 Hz, 1H), 6.77 (s, 1H), 5.14 (s, 2H), 4.29 (br s, 1H), 3.89-3.81 (m, 1H), 3.77 (dd, J = 9.0, 6.0 Hz, 1H), 2.14 (m, 1H), 1.80 (br d, J = 4.9 Hz, 1H); two protons not visible, likely due to overlap with water/water suppression. |
| 534 | 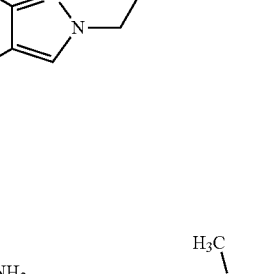 | 350.2 | 1.12 | δ 8.52 (s, 1H), 8.31 (br d, J = 7.3 Hz, 1H), 8.06 (d, J = 7.9 Hz, 1H), 7.89 (s, 1H), 7.64 (br d, J = 1.2 Hz, 1H), 6.77 (s, 1H), 5.11 (s, 2H), 3.94-3.83 (m, 1H), 1.14 (s, 3H), 1.12 (s, 3H) |
| 535 | 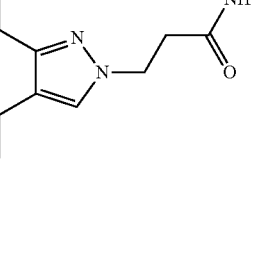 | 336.1 | 0.99 | δ 8.88 (s, 1H), 8.19 (d, J = 8.2 Hz, 1H), 8.07 (s, 1H), 7.97 (br d, J = 4.3 Hz, 1H), 7.94-7.89 (m, 1H), 7.83 (d, J = 1.5 Hz, 1H), 6.83 (d, J = 2.1 Hz, 1H), 4.68 (br t, J = 6.4 Hz, 2H), 2.83 (br t, J = 6.4 Hz, 2H), 2.56 (s, 3H) |
| 536 | 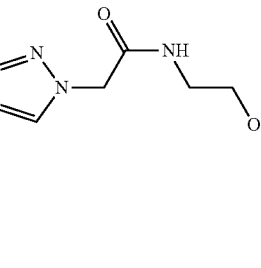 | 366.3 | 1.08 | δ 8.96 (s, 1H), 8.57 (br t, J = 5.5 Hz, 1H), 8.19 (br d, J = 8.2 Hz, 1H), 8.13 (br s, 1H), 7.93 (br d, J = 7.0 Hz, 1H), 7.88 (br d, J = 2.1 Hz, 1H), 6.83 (s, 1H), 5.29 (s, 2H); seven protons not visible, likely due to overlap with water/water suppression. |
| 537 | 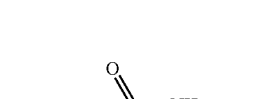 | 380.0 | 1.01 | δ 8.94 (s, 1H), 8.20 (d, J = 8.2 Hz, 1H), 8.13 (br s, 1H), 7.99 (s, 1H), 7.93 (br d, J = 8.2 Hz, 1H), 7.87 (br s, 1H), 6.83 (s, 1H), 5.24 (s, 2H), 1.24 (s, 6H); two protons not visible, likely due to overlap with water/water suppression. |

| Ex. No. | Structure | LC/MS [M + H]+ | RT (min) | ¹H NMR (500 MHz, DMSO-d₆) |
|---|---|---|---|---|
| 538 | 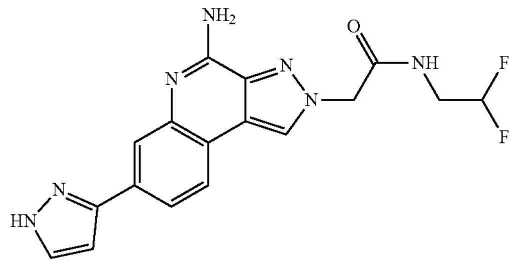 [SMILES: Nc1nc2cc(-c3cc[nH]n3)ccc2c2cn(CC(=O)NCC(F)F)nc12] | 372.0 | 1.04 | δ 8.77 (br t, J = 5.6 Hz, 1H), 8.55 (s, 1H), 8.07 (d, J = 8.1 Hz, 1H), 7.90 (s, 1H), 7.73 (br s, 1H), 7.65 (br d, J = 7.3 Hz, 1H), 6.77 (d, J = 1.8 Hz, 1H), 6.28-5.92 (m, 1H), 5.26 (s, 2H), 3.69-3.50 (m, 2H) |
| 539 | 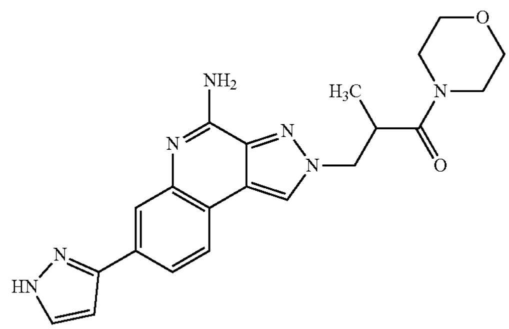 [SMILES: CC(Cn1cc2c(n1)c(N)nc1cc(-c3cc[nH]n3)ccc12)C(=O)N1CCOCC1] | 406.3 | 0.89 | δ 8.43 (s, 1H), 8.07 (d, J = 8.2 Hz, 1H), 7.87 (s, 1H), 7.72 (br s, 1H), 7.63 (br d, J = 7.8 Hz, 1H), 6.76 (s, 1H), 4.68-4.55 (m, 1H), 4.41 (br dd, J = 13.0, 5.7 Hz, 1H), 3.66-3.54 (m, 1H), 1.12 (br d, J = 6.7 Hz, 3H); eight protons not visible, likely due to overlap with water/water suppression. |
| 540 | 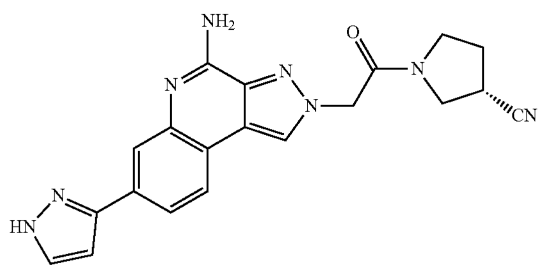 [SMILES: N#C[C@H]1CCN(C(=O)Cn2cc3c(n2)c(N)nc2cc(-c4cc[nH]n4)ccc23)C1] | 387.0 | 1.07 | δ 8.93 (s, 1H), 8.17 (d, J = 8.3 Hz, 1H), 8.13 (br d, J = 1.3 Hz, 1H), 7.93 (br d, J = 8.5 Hz, 1H), 7.87 (br s, 1H), 6.83 (s, 1H), 5.73-5.43 (m, 2H), 4.06-3.87 (m, 1H), 3.83-3.59 (m, 2H), 3.55-3.43 (m, 1H), 2.44-2.07 (m, 3H) |
| 541 | 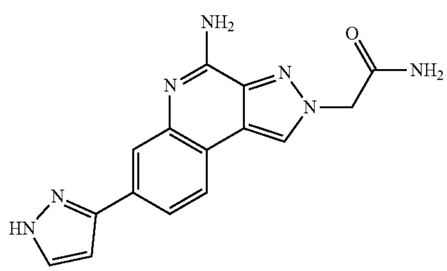 [SMILES: NC(=O)Cn1cc2c(n1)c(N)nc1cc(-c3cc[nH]n3)ccc12] | 308.0 | 0.95 | δ 8.93 (br d, J = 1.3 Hz, 1H), 8.19 (dd, J = 8.1, 1.9 Hz, 1H), 8.11 (br d, J = 1.0 Hz, 1H), 7.93 (br d, J = 7.0 Hz, 1H), 7.90-7.79 (m, 2H), 7.51 (br s, 1H), 6.84 (br s, 1H), 5.24 (br s, 2H) |
| 542 | 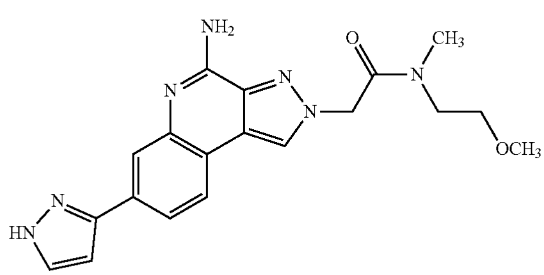 [SMILES: COCCN(C)C(=O)Cn1cc2c(n1)c(N)nc1cc(-c3cc[nH]n3)ccc12] | 380.3 | 1.06 | δ 8.91 (s, 1H), 8.18 (br d, J = 8.2 Hz, 1H), 8.14 (br s, 1H), 7.93 (br d, J = 7.9 Hz, 1H), 7.88 (br s, 1H), 6.83 (s, 1H), 5.64 (d, J = 13.7 Hz, 2H), 3.62 (br dd, J = 15.7, 4.7 Hz, 2H), 3.54-3.42 (m, 2H), 3.15 (s, 3H), 2.93 (s, 3H) |

| Ex. No. | Structure | LC/MS [M + H]+ | RT (min) | 1H NMR (500 MHz, DMSO-d6) |
|---|---|---|---|---|
| 543 | 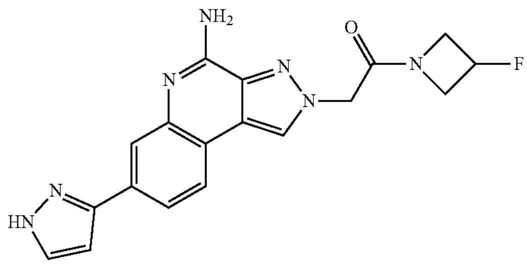 [SMILES: Nc1nc2cc(-c3cc[nH]n3)ccc2c2cn(CC(=O)N3CC(F)C3)nc12] | 366.3 | 0.83 | δ 8.52 (s, 1H), 8.07 (d, J = 8.1 Hz, 1H), 7.91 (s, 1H), 7.73 (br s, 1H), 7.66 (br d, J = 8.1 Hz, 1H), 6.77 (d, J = 1.8 Hz, 1H), 5.60-5.37 (m, 1H), 5.33-5.19 (m, 2H), 4.72-4.52 (m, 1H), 4.46-4.21 (m, 2H), 4.12-3.94 (m, 1H) |
| 544 | 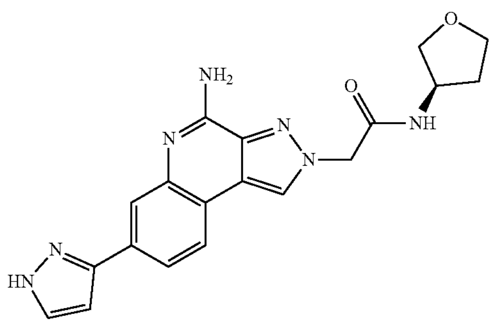 [SMILES: Nc1nc2cc(-c3cc[nH]n3)ccc2c2cn(CC(=O)N[C@@H]3CCOC3)nc12] | 378.1 | 1.01 | δ 8.71 (d, J = 6.7 Hz, 1H), 8.53 (s, 1H), 8.07 (d, J = 8.2 Hz, 1H), 7.89 (s, 1H), 7.72 (br s, 1H), 7.65 (br d, J = 7.9 Hz, 1H), 6.77 (d, J = 2.1 Hz, 1H), 5.14 (s, 2H), 4.29 (br d, J = 3.1 Hz, 1H), 3.84 (d, J = 7.9 Hz, 1H), 2.24-2.07 (m, 1H), 1.80 (br dd, J = 8.1, 3.5 Hz, 1H)); two protons not visible, likely due to overlap with water/water suppression. |
| 545 | 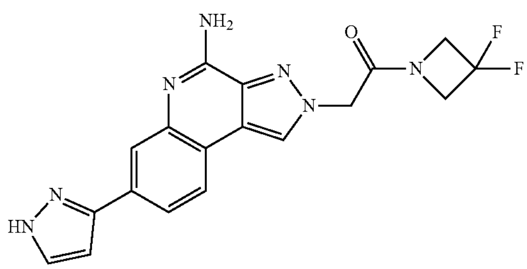 [SMILES: Nc1nc2cc(-c3cc[nH]n3)ccc2c2cn(CC(=O)N3CC(F)(F)C3)nc12] | 384.3 | 0.91 | δ 8.48 (s, 1H), 8.06 (d, J = 8.2 Hz, 1H), 7.89 (s, 1H), 7.81-7.69 (m, 1H), 7.63 (br d, J = 7.3 Hz, 1H), 6.77 (d, J = 1.8 Hz, 1H), 5.37 (s, 2H), 4.78 (br t, J = 12.7 Hz, 2H), 4.43 (br t, J = 12.5 Hz, 2H) |
| 546 | 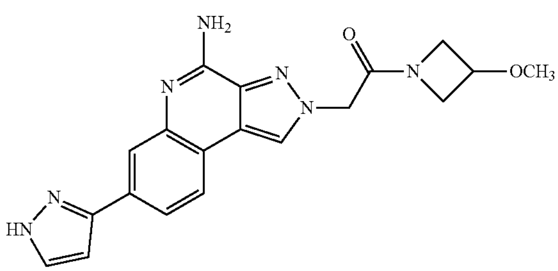 [SMILES: COC1CN(C(=O)Cn2cc3c(n2)c(N)nc2cc(-c4cc[nH]n4)ccc23)C1] | 378.3 | 0.86 | δ 8.92 (s, 1H), 8.18 (d, J = 8.2 Hz, 1H), 8.10 (br s, 1H), 7.93 (d, J = 8.1 Hz, 1H), 7.85 (br s, 1H), 6.84 (d, J = 2.3 Hz, 1H), 5.46-5.27 (m, 2H), 4.48 (br dd, J = 9.1, 6.6 Hz, 1H), 4.36-4.26 (m, 1H), 4.21-4.08 (m, 2H), 3.76 (br dd, J = 10.8, 3.5 Hz, 2H), 3.25 (s, 3H) |
| 547 | 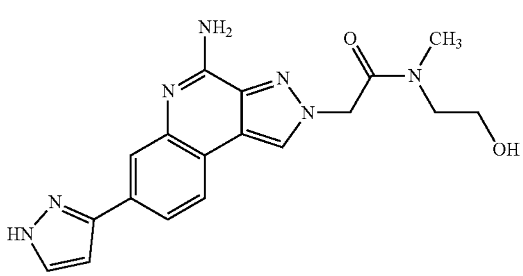 [SMILES: CN(CCO)C(=O)Cn1cc2c(n1)c(N)nc1cc(-c3cc[nH]n3)ccc12] | 366.1 | 1.02 | ) δ 8.50 (s, 1H), 8.07 (d, J = 7.9 Hz, 1H), 7.92 (br s, 1H), 7.79-7.60 (m, 2H), 6.78 (s, 1H), 5.63-5.46 (m, 2H), 3.67 (m, 1H), 3.53 (m, 1H), 3.16 (s, 3H), 2.91 (s, 3H); two protons not visible, likely due to overlap with water/water suppression. |

| Ex. No. | Structure | LC/MS [M + H]+ | RT (min) | ¹H NMR (500 MHz, DMSO-d₆) |
|---|---|---|---|---|
| 548 | 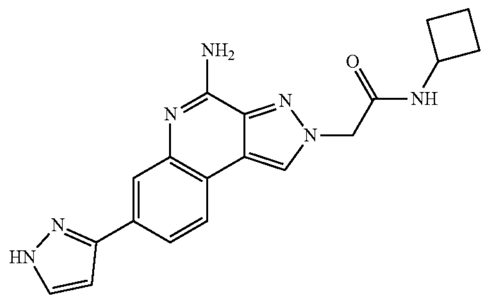 [SMILES: Nc1nc2cc(-c3cc[nH]n3)ccc2c2cn(CC(=O)NC3CCC3)nc12] | 362.1 | 0.97 | δ 8.69 (br d, J = 7.6 Hz, 1H), 8.49 (s, 1H), 8.05 (d, J = 8.1 Hz, 1H), 7.88 (s, 1H), 7.72 (br s, 1H), 7.63 (br d, J = 8.2 Hz, 1H), 6.76 (d, J = 1.9 Hz, 1H), 5.09 (s, 2H), 4.22 (br d, J = 7.8 Hz, 1H), 2.26-2.14 (m, 2H), 2.02-1.92 (m, 2H), 1.74-1.56 (m, 2H |
| 549 | 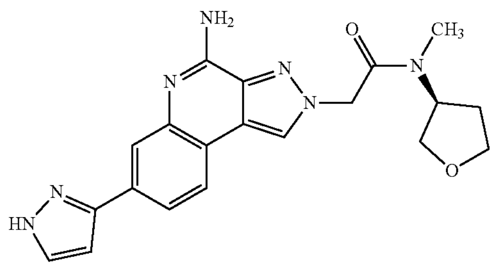 [SMILES: CN(C(=O)Cn1cc2c(n1)c(N)nc1cc(-c3cc[nH]n3)ccc12)[C@H]1CCOC1] | 392.1 | 1.08 | δ 8.90 (s, 1H), 8.18 (d, J = 8.2 Hz, 1H), 8.13 (br s, 1H), 7.93 (br d, J = 7.6 Hz, 1H), 7.86 (br s, 1H), 6.83 (d, J = 1.8 Hz, 1H), 5.74 (br d, J = 5.2 Hz, 1H), 5.61 (s, 2H), 5.16-5.01 (m, 1H), 4.80-4.66 (m, 1H), 4.08-3.92 (m, 1H), 3.86-3.52 (m, 3H), 3.03 (s, 3H), 2.41-2.27 (m, 1H), 2.15 (br dd, J = 7.9, 4.6 Hz, 1H), 2.03-1.75 (m, 2H) |
| 550 | 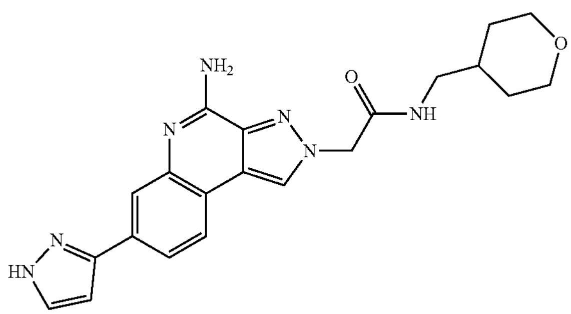 [SMILES: Nc1nc2cc(-c3cc[nH]n3)ccc2c2cn(CC(=O)NCC3CCOCC3)nc12] | 406.1 | 1.09 | δ 8.53 (s, 1H), 8.39 (t, J = 6.0 Hz, 1H), 8.06 (d, J = 8.2 Hz, 1H), 7.89 (s, 1H), 7.72 (br d, J = 0.6 Hz, 1H), 7.65 (d, J = 7.6 Hz, 1H), 6.77 (d, J = 1.8 Hz, 1H), 5.15 (s, 2H), 3.84 (br dd, J = 11.3, 3.1 Hz, 2H), 3.26 (br t, J = 11.0 Hz, 2H), 3.04 (t, J = 6.3 Hz, 2H), 1.69 (br s, 1H), 1.58 (br d, J = 12.8 Hz, 2H), 1.17 (qd, J = 12.3, 4.3 Hz, 2H) |
| 551 | 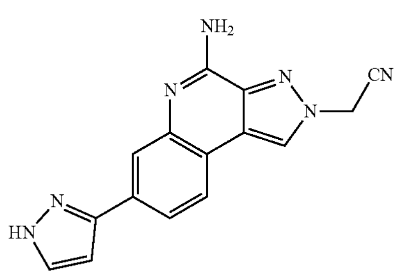 [SMILES: N#CCn1cc2c(n1)c(N)nc1cc(-c3cc[nH]n3)ccc12] | 290.3 | 1.11 | δ 9.11-9.02 (m, 1H), 8.22 (d, J = 8.2 Hz, 1H), 8.11 (br s, 1H), 7.94 (br d, J = 8.2 Hz, 1H), 7.86 (br s, 1H), 6.84 (d, J = 1.9 Hz, 1H), 5.95 (s, 2H) |
| 552 | 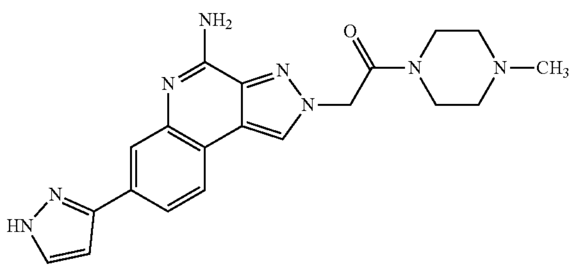 [SMILES: CN1CCN(C(=O)Cn2cc3c(n2)c(N)nc2cc(-c4cc[nH]n4)ccc23)CC1] | 391.1 | 0.85 | δ 8.44 (s, 1H), 8.05 (d, J = 8.2 Hz, 1H), 7.89 (s, 1H), 7.72 (br s, 1H), 7.63 (br d, J = 7.9 Hz, 1H), 6.77 (s, 1H), 5.54 (s, 2H), 2.42 (br s, 2H), 2.32 (br s, 2H), 1.92 (s, 3H); four protons not visible, likely due to overlap with water/water suppression. |

| Ex. No. | Structure | LC/MS [M + H]+ | RT (min) | 1H NMR (500 MHz, DMSO-d6) |
|---|---|---|---|---|
| 553 | 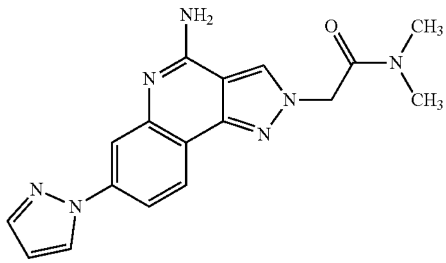 [SMILES: CN(C)C(=O)Cn1cc2c(N)nc3cc(-n4cccn4)ccc3c2n1] | 336.3 | 1.07 | δ 8.56 (d, J = 2.4 Hz, 1H), 8.44 (s, 1H), 8.09 (d, J = 8.5 Hz, 1H), 7.85 (d, J = 2.1 Hz, 1H), 7.78-7.73 (m, 1H), 7.66 (dd, J = 8.5, 2.1 Hz, 1H), 6.55 (d, J = 2.1 Hz, 1H), 5.49 (s, 2H), 3.11 (s, 3H), 2.92-2.88 (m, 3H) |
| 554 | 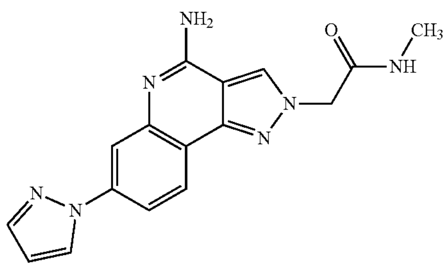 [SMILES: CNC(=O)Cn1cc2c(N)nc3cc(-n4cccn4)ccc3c2n1] | 322.2 | 0.99 | δ 8.95 (s, 1H), 8.62 (br d, J = 2.4 Hz, 1H), 8.39-8.33 (m, 1H), 8.24 (d, J = 8.6 Hz, 1H), 8.16 (d, J = 1.3 Hz, 1H), 7.95 (dd, J = 8.7, 1.9 Hz, 1H), 7.85 (d, J = 1.5 Hz, 1H), 6.68-6.61 (m, 1H), 5.24 (s, 2H), 2.67 (d, J = 4.6 Hz, 3H) |
| 555 | 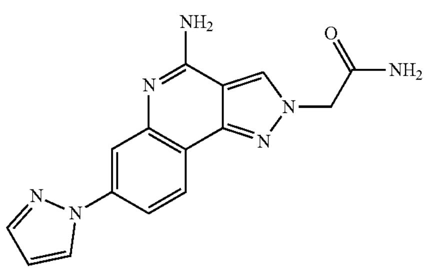 [SMILES: NC(=O)Cn1cc2c(N)nc3cc(-n4cccn4)ccc3c2n1] | 308.2 | 0.94 | δ 8.93 (s, 1H), 8.61 (br s, 1H), 8.24 (d, J = 8.6 Hz, 1H), 8.15 (s, 1H), 7.95 (dd, J = 8.7, 1.7 Hz, 1H), 7.89-7.81 (m, 2H), 7.50 (br s, 1H), 6.68-6.59 (m, 1H), 5.24 (s, 2H) |
| 556 | 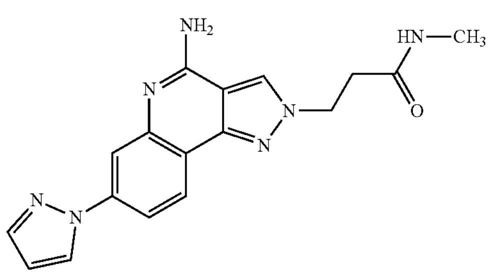 [SMILES: CNC(=O)CCn1cc2c(N)nc3cc(-n4cccn4)ccc3c2n1] | 336.2 | 0.81 | δ 8.91 (s, 1H), 8.62 (d, J = 2.3 Hz, 1H), 8.24 (d, J = 8.6 Hz, 1H), 8.15 (d, J = 1.7 Hz, 1H), 7.96 (br d, J = 8.7 Hz, 2H), 7.85 (d, J = 0.9 Hz, 1H), 6.64 (s, 1H), 4.70 (br t, J = 6.3 Hz, 2H), 2.82 (br t, J = 6.3 Hz, 2H), 2.57-2.55 (m, 3H) |
| 557 | 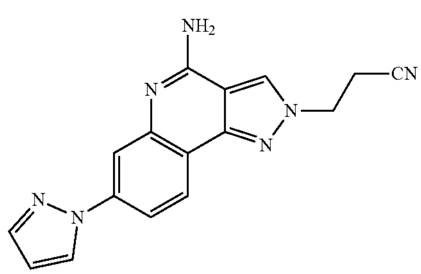 [SMILES: N#CCCn1cc2c(N)nc3cc(-n4cccn4)ccc3c2n1] | 304.1 | 1.13 | δ 9.01 (s, 1H), 8.63 (d, J = 2.4 Hz, 1H), 8.26 (d, J = 8.5 Hz, 1H), 8.16 (d, J = 1.5 Hz, 1H), 7.97 (dd, J = 8.7, 1.7 Hz, 1H), 7.86 (d, J = 1.5 Hz, 1H), 6.64 (t, J = 1.8 Hz, 1H), 4.84 (t, J = 6.3 Hz, 2H); two protons are not visible, likely due to overlap with suppressed water peak. |

| Ex. No. | Structure | LC/MS [M + H]+ | RT (min) | ¹H NMR (500 MHz, DMSO-d₆) |
|---|---|---|---|---|
| 558 | 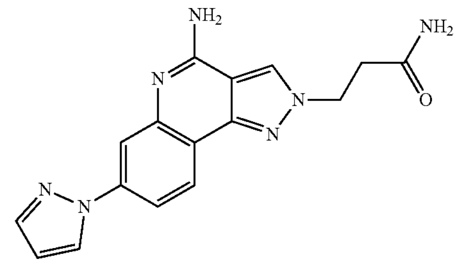 [SMILES: NC(=O)CCn1cc2c(N)nc3cc(-n4cccn4)ccc3c2n1] | 322.0 | 0.99 | δ 8.91 (s, 1H), 8.62 (d, J = 2.3 Hz, 1H), 8.26-8.22 (m, 1H), 8.14 (d, J = 1.7 Hz, 1H), 7.95 (dd, J = 8.7, 1.8 Hz, 1H), 7.85 (d, J = 1.3 Hz, 1H), 7.49 (br s, 1H), 6.98 (br s, 1H), 6.65-6.61 (m, 1H), 4.67 (br t, J = 6.4 Hz, 2H), 2.82 (br t, J = 6.4 Hz, 2H) |
| 559 | 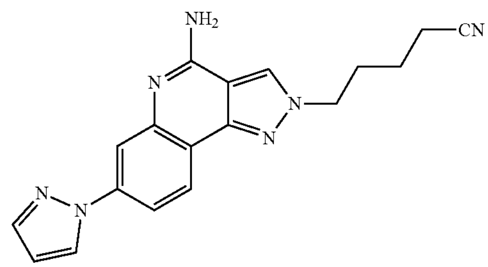 [SMILES: N#CCCCCn1cc2c(N)nc3cc(-n4cccn4)ccc3c2n1] | 332.2 | 1.19 | δ 8.94-8.89 (m, 1H), 8.64-8.59 (m, 1H), 8.26 (d, J = 8.6 Hz, 1H), 8.15 (br s, 1H), 7.95 (br d, J = 8.7 Hz, 1H), 7.87-7.83 (m, 1H), 6.67-6.60 (m, 1H), 4.55 (br t, J = 6.5 Hz, 2H), 2.62-2.55 (m, 2H), 2.03 (quin, J = 7.3 Hz, 2H), 1.66-1.55 (m, 2H) |
| 560 | 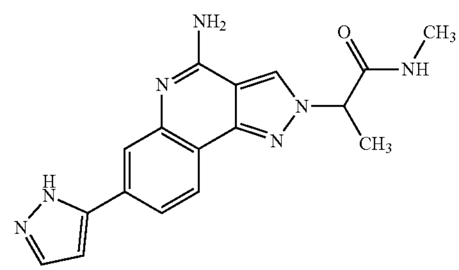 [SMILES: CNC(=O)C(C)n1cc2c(N)nc3cc(-c4ccn[nH]4)ccc3c2n1] | 336.1 | 1.03 | δ 9.09 (s, 1H), 8.45-8.37 (m, 1H), 8.17 (d, J = 8.2 Hz, 1H), 8.13-8.05 (m, 1H), 7.91 (br d, J = 8.9 Hz, 1H), 7.88-7.79 (m, 1H), 6.81 (d, J = 1.8 Hz, 1H), 5.40 (q, J = 7.2 Hz, 1H), 2.65 (d, J = 4.6 Hz, 2H), 1.76 (d, J = 7.0 Hz, 3H) |
| 561 | 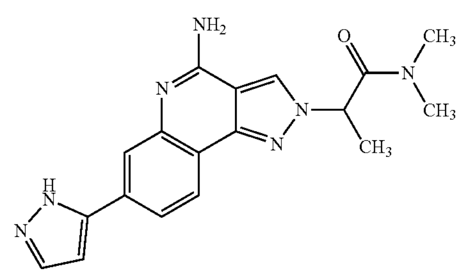 [SMILES: CC(C(=O)N(C)C)n1cc2c(N)nc3cc(-c4ccn[nH]4)ccc3c2n1] | 350.1 | 1.11 | δ 8.70 (s, 1H), 8.07 (d, J = 8.2 Hz, 1H), 7.90 (br s, 1H), 7.80-7.69 (m, 1H), 7.68-7.61 (m, 1H), 6.76 (d, J = 1.8 Hz, 1H), 5.97-5.89 (m, 1H), 3.14 (s, 3H), 2.88 (s, 3H), 1.70 (d, J = 7.0 Hz, 3H) |
| 562 | 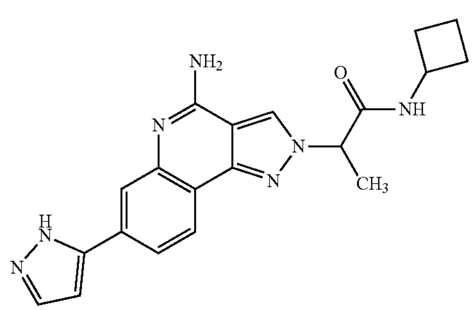 [SMILES: CC(C(=O)NC1CCC1)n1cc2c(N)nc3cc(-c4ccn[nH]4)ccc3c2n1] | 376.1 | 1.25 | δ 9.08 (s, 1H), 8.82 (br d, J = 7.5 Hz, 1H), 8.17 (d, J = 8.2 Hz, 1H), 8.10 (br s, 1H), 7.91 (br d, J = 8.4 Hz, 1H), 7.84 (br s, 1H), 6.81 (s, 1H), 5.35 (q, J = 7.3 Hz, 1H), 4.24-4.12 (m, 1H), 2.25-2.11 (m, 2H), 2.00-1.86 (m, 2H), 1.75 (d, J = 7.1 Hz, 3H), 1.70-1.57 (m, 2H) |

| Ex. No. | Structure | LC/MS [M + H]+ | RT (min) | ¹H NMR (500 MHz, DMSO-d₆) |
|---|---|---|---|---|
| 563 | 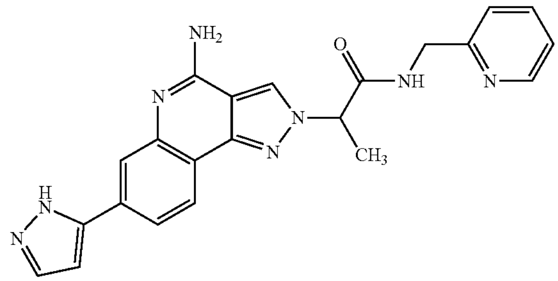 [SMILES: CC(C(=O)NCc1ccccn1)n1cc2c(N)nc3cc(-c4ccn[nH]4)ccc3c2n1] | 413.3 | 1.01 | δ 9.71-9.59 (m, 1H), 9.19-9.05 (m, 2H), 9.00-8.85 (m, 1H), 8.53 (br d, J = 4.7 Hz, 1H), 8.20 (d, J = 8.2 Hz, 1H), 8.09 (s, 1H), 7.94 (dd, J = 8.2, 1.1 Hz, 1H), 7.86-7.76 (m, 2H), 7.38 (d, J = 7.6 Hz, 1H), 7.35-7.30 (m, 1H), 6.82 (d, J = 2.1 Hz, 1H), 5.62-5.52 (m, 1H), 4.45 (d, J = 5.9 Hz, 2H), 1.83 (d, J = 7.0 Hz, 3H) |
| 564 | 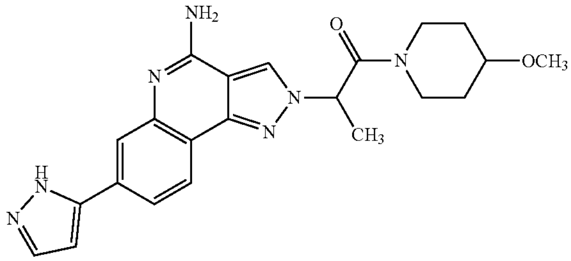 [SMILES: COC1CCN(C(=O)C(C)n2cc3c(N)nc4cc(-c5ccn[nH]5)ccc4c3n2)CC1] | 420.1 | 1.21 | δ 8.67 (br d, J = 4.2 Hz, 1H), 8.06 (d, J = 8.1 Hz, 1H), 7.89 (s, 1H), 7.72 (br s, 1H), 7.65 (br d, J = 7.6 Hz, 1H), 6.76 (d, J = 1.9 Hz, 1H), 5.98 (q, J = 6.8 Hz, 1H), 3.91-3.72 (m, 2H), 3.69-3.53 (m, 1H), 3.43-3.31 (m, 1H), 3.28-3.18 (m, 3H), 3.15-3.06 (m, 1H), 1.86-1.78 (m, 1H), 1.77-1.71 (m, 1H), 1.69 (br dd, J = 6.4, 3.9 Hz, 3H), 1.52-1.11 (m, 2H) |
| 565 | 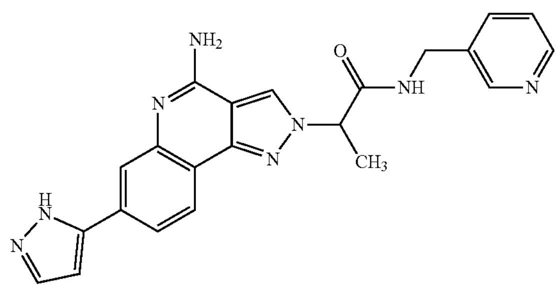 [SMILES: CC(C(=O)NCc1cccnc1)n1cc2c(N)nc3cc(-c4ccn[nH]4)ccc3c2n1] | 413.3 | 0.95 | ¹H NMR (500 MHz, DMSO-d₆) δ 9.02-8.91 (m, 1H), 8.72 (s, 1H), 8.56-8.39 (m, 2H), 8.08 (d, J = 8.2 Hz, 1H), 7.98-7.83 (m, 1H), 7.80-7.57 (m, 3H), 7.34 (dd, J = 7.7, 4.9 Hz, 1H), 6.77 (s, 1H), 5.42 (q, J = 7.1 Hz, 1H), 4.36 (br d, J = 5.7 Hz, 2H), 1.78 (br d, J = 7.0 Hz, 3H) |
| 566 | 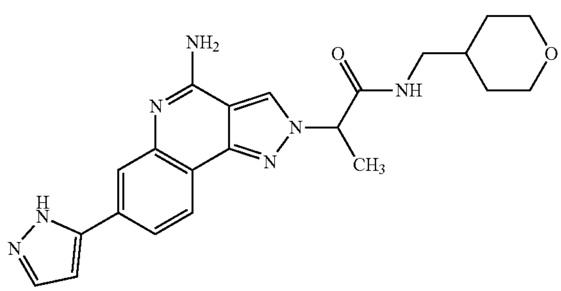 [SMILES: CC(C(=O)NCC1CCOCC1)n1cc2c(N)nc3cc(-c4ccn[nH]4)ccc3c2n1] | 419.9 | 1.12 | δ 9.01 (br s, 1H), 8.50 (br t, J = 5.6 Hz, 1H), 8.13 (d, J = 8.2 Hz, 1H), 8.06 (br d, J = 1.8 Hz, 1H), 7.93-7.77 (m, 2H), 6.80 (s, 1H), 5.42 (q, J = 7.0 Hz, 1H), 3.82 (br d, J = 10.7 Hz, 2H), 3.24 (br t, J = 11.3 Hz, 1H), 3.10-2.97 (m, 2H), 1.76 (d, J = 7.0 Hz, 3H), 1.72-1.61 (m, 1H), 1.55 (br d, J = 13.1 Hz, 2H), 1.21-1.09 (m, 2H); one proton from sidechain is not visible, likely due to overlap with suppressed water peak. |
| 567 | 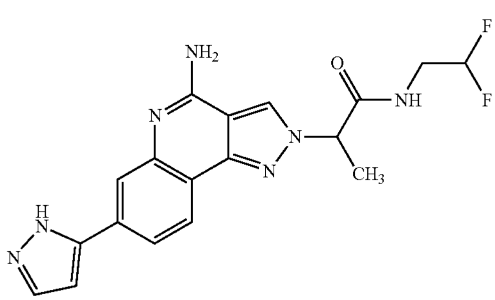 [SMILES: CC(C(=O)NCC(F)F)n1cc2c(N)nc3cc(-c4ccn[nH]4)ccc3c2n1] | 386.0 | 1.15 | δ 9.10 (s, 1H), 8.92 (br t, J = 6.0 Hz, 1H), 8.17 (d, J = 8.1 Hz, 1H), 8.10 (br s, 1H), 7.91 (br d, J = 7.7 Hz, 1H), 7.88-7.81 (m, 1H), 6.81 (s, 1H), 6.20-5.91 (m, 1H), 5.52 (q, J = 7.2 Hz, 1H), 3.64-3.39 (m, 2H), 1.79 (d, J = 7.1 Hz, 3H) |

| Ex. No. | Structure | LC/MS [M + H]+ | RT (min) | 1H NMR (500 MHz, DMSO-d6) |
|---|---|---|---|---|
| 568 | 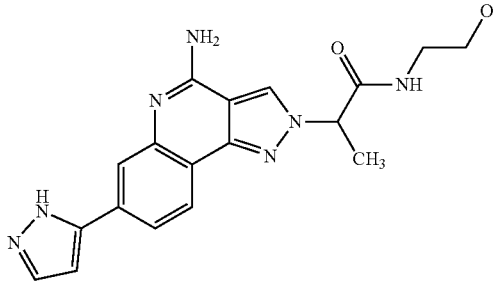 | 366.3 | 1.01 | δ 8.67 (s, 1H), 8.42 (t, J = 5.6 Hz, 1H), 8.05 (d, J = 8.2 Hz, 1H), 7.87 (s, 1H), 7.77-7.67 (m, 1H), 7.66-7.58 (m, 1H), 6.75 (d, J = 1.8 Hz, 1H), 5.37 (q, J = 7.2 Hz, 1H), 3.23-3.11 (m, 2H), 1.73 (d, J = 7.0 Hz, 3H); two protons are not visible, likely due to overlap with suppressed water peak. |
| 569 | 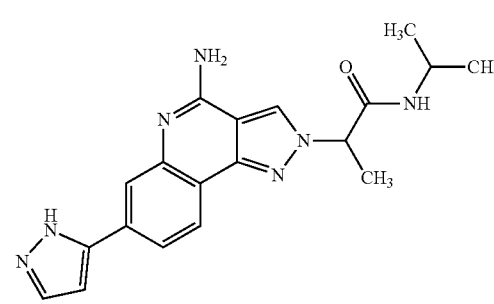 [SMILES: CC(C)NC(=O)C(C)n1cc2c(N)nc3cc(-c4ccn[nH]4)ccc3c2n1] | 364.1 | 1.19 | δ 8.82 (br s, 1H), 8.40 (br d, J = 7.5 Hz, 1H), 8.09 (d, J = 8.2 Hz, 1H), 7.95 (br s, 1H), 7.80-7.67 (m, 2H), 6.77 (d, J = 1.7 Hz, 1H), 5.32 (q, J = 7.2 Hz, 1H), 3.84 (dq, J = 13.5, 6.5 Hz, 1H), 1.73 (d, J = 7.1 Hz, 3H), 1.10 (dd, J = 12.2, 6.6 Hz, 6H) |
| 570 | 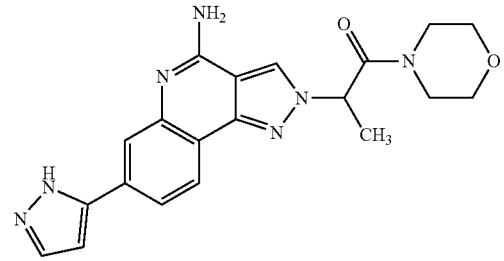 [SMILES: CC(C(=O)N1CCOCC1)n1cc2c(N)nc3cc(-c4ccn[nH]4)ccc3c2n1] | 392.3 | 1.11 | δ 9.10 (s, 1H), 8.17 (d, J = 8.2 Hz, 1H), 8.10 (br s, 1H), 7.91 (q, J = 7.9 Hz, 1H), 7.85 (br s, 1H), 6.81 (d, J = 1.8 Hz, 1H), 6.09-6.01 (m, 1H), 3.78-3.44 (m, 5H), 1.75 (d, J = 7.0 Hz, 3H); three protons are not visible, likely due to overlap with suppressed water peak. |
| 571 | 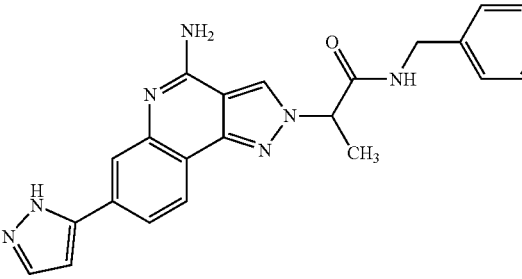 | 412.1 | 1.31 | δ 8.90 (br t, J = 6.0 Hz, 1H), 8.74 (s, 1H), 8.09 (d, J = 8.2 Hz, 1H), 7.91 (s, 1H), 7.73 (br d, J = 2.1 Hz, 1H), 7.67 (br d, J = 6.4 Hz, 1H), 7.36-7.21 (m, 5H), 6.77 (d, J = 1.8 Hz, 1H), 5.43 (q, J = 6.9 Hz, 1H), 4.34 (br d, J = 6.1 Hz, 2H), 1.79 (d, J = 7.0 Hz, 3H) |
| 572 | 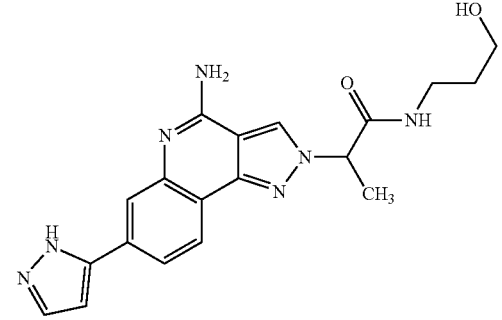 [SMILES: CC(C(=O)NCCCO)n1cc2c(N)nc3cc(-c4ccn[nH]4)ccc3c2n1] | 380.1 | 1.03 | δ 8.65 (s, 1H), 8.38 (br t, J = 5.5 Hz, 1H), 8.05 (d, J = 8.2 Hz, 1H), 7.86 (s, 1H), 7.74-7.67 (m, 1H), 7.63 (br d, J = 8.2 Hz, 1H), 6.75 (d, J = 2.1 Hz, 1H), 5.30 (q, J = 6.8 Hz, 1H), 3.41 (t, J = 6.3 Hz, 2H), 3.14 (qt, J = 13.7, 6.5 Hz, 2H), 1.73 (d, J = 7.0 Hz, 3H), 1.63-1.49 (m, 2H) |

| Ex. No. | Structure | LC/MS [M + H]+ | RT (min) | 1H NMR (500 MHz, DMSO-d6) |
|---|---|---|---|---|
| 573 | 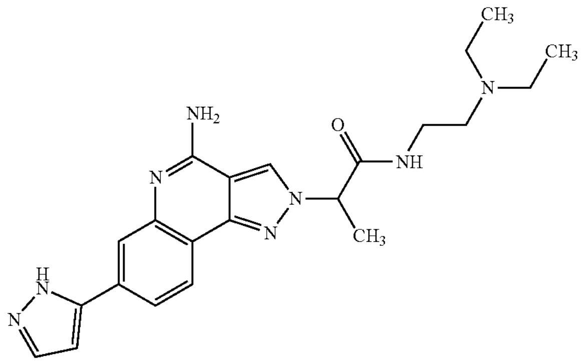 [SMILES: CCN(CC)CCNC(=O)C(C)n1cc2c(N)nc3cc(-c4ccn[nH]4)ccc3c2n1] | 421.1 | 1.00 | δ 8.75 (s, 1H), 8.47-8.33 (m, 1H), 8.07 (d, J = 7.9 Hz, 1H), 7.92 (s, 1H), 7.78-7.63 (m, 2H), 6.76 (d, J = 1.8 Hz, 1H), 5.43-5.31 (m, 1H), 2.75 (br s, 4H), 1.75 (br d, J = 7.0 Hz, 3H), 1.01 (br t, J = 7.0 Hz, 6H); four protons are not visible, likely due to overlap with suppressed water peak. |
| 574 | 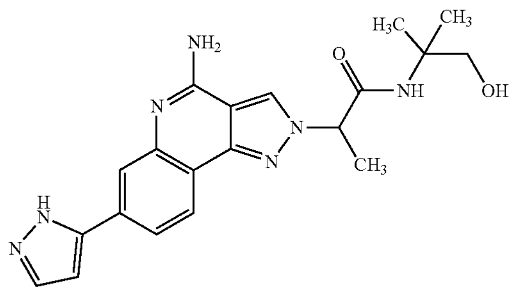 [SMILES: CC(C(=O)NC(C)(C)CO)n1cc2c(N)nc3cc(-c4ccn[nH]4)ccc3c2n1] | 394.3 | 0.90 | δ 9.08 (s, 1H), 8.17 (d, J = 7.9 Hz, 1H), 8.13-8.07 (m, 1H), 8.05 (s, 1H), 7.96-7.78 (m, 2H), 6.81 (br d, J = 0.6 Hz, 1H), 5.45 (q, J = 7.2 Hz, 1H), 1.73 (d, J = 7.0 Hz, 3H), 1.21 (s, 6H); two protons are not visible, likely due to overlap with suppressed water peak. |
| 575 | 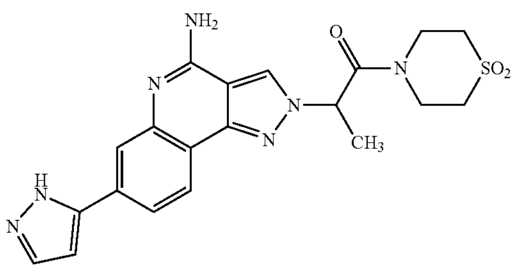 [SMILES: CC(C(=O)N1CCS(=O)(=O)CC1)n1cc2c(N)nc3cc(-c4ccn[nH]4)ccc3c2n1] | 440.1 | 1.05 | δ 8.73 (s, 1H), 8.07 (d, J = 7.9 Hz, 1H), 7.92 (s, 1H), 7.73 (br s, 1H), 7.70-7.64 (m, 1H), 6.77 (d, J = 2.1 Hz, 1H), 6.14-6.05 (m, 1H), 3.45-3.32 (m, 2H), 3.25-3.03 (m, 4H), 2.90-2.86 (m, 1H), 2.82-2.77 (m, 1H), 1.74 (d, J = 7.0 Hz, 3H) |
| 576 | 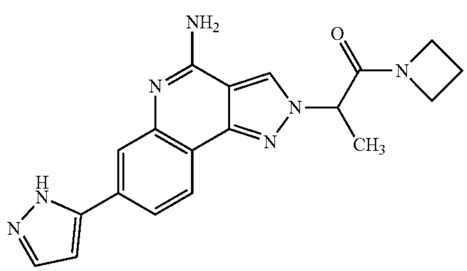 [SMILES: CC(C(=O)N1CCC1)n1cc2c(N)nc3cc(-c4ccn[nH]4)ccc3c2n1] | 362.2 | 1.08 | δ 8.69 (s, 1H), 8.08 (d, J = 8.2 Hz, 1H), 7.89 (s, 1H), 7.72 (br s, 1H), 7.66 (br d, J = 7.9 Hz, 1H), 6.76 (d, J = 1.8 Hz, 1H), 5.46 (q, J = 7.1 Hz, 1H), 4.35-4.25 (m, 1H), 4.21-4.09 (m, 1H), 3.96-3.86 (m, 2H), 2.26-2.17 (m, 2H), 1.69 (d, J = 7.0 Hz, 3H) |
| 577 | 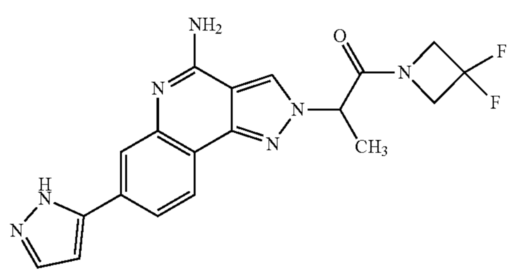 [SMILES: CC(C(=O)N1CC(F)(F)C1)n1cc2c(N)nc3cc(-c4ccn[nH]4)ccc3c2n1] | 397.9 | 1.17 | δ 9.06 (s, 1H), 8.18 (d, J = 8.2 Hz, 1H), 8.09 (br s, 1H), 7.96-7.87 (m, 1H), 7.87-7.77 (m, 1H), 6.86-6.80 (m, 1H), 5.65 (q, J = 7.0 Hz, 1H), 4.92-4.78 (m, 1H), 4.73-4.62 (m, 1H), 4.50-4.33 (m, 2H), 1.76 (d, J = 7.0 Hz, 3H) |

| Ex. No. | Structure | LC/MS [M + H]+ | RT (min) | ¹H NMR (500 MHz, DMSO-d₆) |
|---|---|---|---|---|
| 578 | 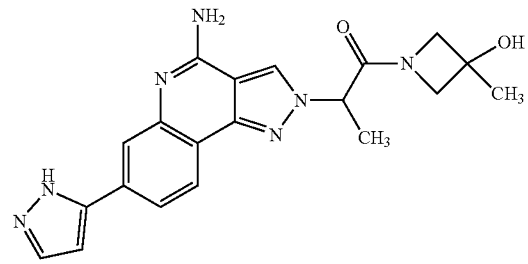 [SMILES: CC(C(=O)N1CC(C)(O)C1)n1cc2c(N)nc3cc(-c4ccn[nH]4)ccc3c2n1] | 392.1 | 1.06 | δ 9.09 (s, 1H), 8.18 (t, J = 7.8 Hz, 1H), 8.14-8.06 (m, 1H), 7.92 (br d, J = 8.2 Hz, 1H), 7.86 (br s, 1H), 6.82 (d, J = 1.5 Hz, 1H), 5.63-5.55 (m, 1H), 4.22-4.17 (m, 1H), 4.15 (s, 1H), 4.01 (br d, J = 8.9 Hz, 1H), 3.83-3.71 (m, 2H), 1.73 (t, J = 6.7 Hz, 3H), 1.39 (d, J = 16.5 Hz, 3H) |
| 579 | 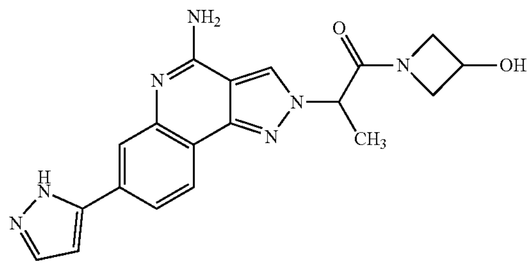 [SMILES: CC(C(=O)N1CC(O)C1)n1cc2c(N)nc3cc(-c4ccn[nH]4)ccc3c2n1] | 378.1 | 1.02 | δ 9.10 (d, J = 1.8 Hz, 1H), 8.24-8.16 (m, 1H), 8.12 (br s, 1H), 7.92 (br d, J = 7.6 Hz, 1H), 7.90-7.79 (m, 1H), 6.81 (s, 1H), 5.64-5.51 (m, 1H), 4.58-4.40 (m, 2H), 4.17-4.10 (m, 1H), 4.10-3.89 (m, 1H), 3.72-3.59 (m, 1H), 1.72 (t, J = 6.9 Hz, 3H) |
| 580 | 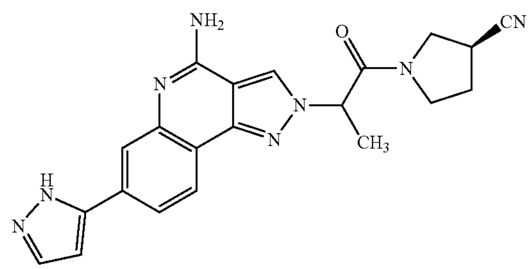 [SMILES: CC(C(=O)N1CC[C@H](C#N)C1)n1cc2c(N)nc3cc(-c4ccn[nH]4)ccc3c2n1] | 401.0 | 1.12 | δ 9.08 (br s, 1H), 8.22-8.14 (m, 1H), 8.10 (br s, 1H), 7.95-7.78 (m, 2H), 6.81 (br s, 1H), 5.82 (br t, J = 6.5 Hz, 1H), 4.07-3.37 (m, 4H), 2.41-2.33 (m, 1H), 2.31-2.19 (m, 1H), 2.18-2.07 (m, 1H), 1.80-1.71 (m, 3H) |
| 581 | 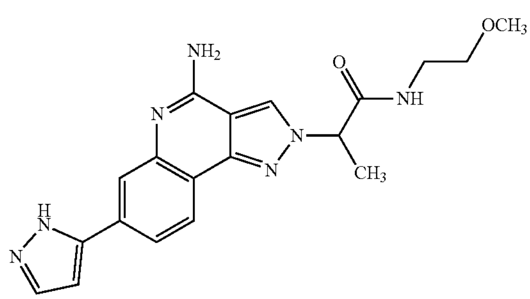 [SMILES: COCCNC(=O)C(C)n1cc2c(N)nc3cc(-c4ccn[nH]4)ccc3c2n1] | 380.2 | 1.05 | δ 8.78 (s, 1H), 8.52 (br t, J = 5.3 Hz, 1H), 8.09 (d, J = 8.2 Hz, 1H), 7.93 (br s, 1H), 7.76-7.68 (m, 2H), 6.77 (d, J = 1.8 Hz, 1H), 5.42-5.33 (m, 1H), 3.41-3.33 (m, 2H), 3.29-3.24 (m, 2H), 3.24-3.20 (m, 3H), 1.73 (d, J = 7.3 Hz, 3H) |
| 582 | 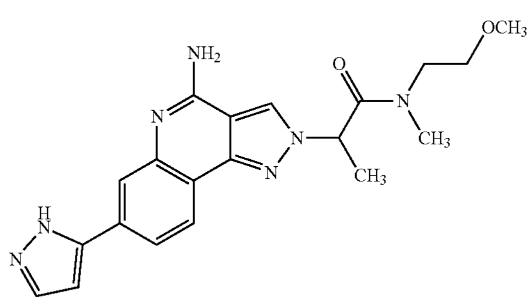 [SMILES: COCCN(C)C(=O)C(C)n1cc2c(N)nc3cc(-c4ccn[nH]4)ccc3c2n1] | 394.3 | 1.17 | ¹H NMR (500 MHz, DMSO-d₆) δ 8.69 (br d, J = 5.9 Hz, 1H), 8.06 (d, J = 8.2 Hz, 1H), 7.89 (br s, 1H), 7.72 (br s, 1H), 7.65 (br d, J = 8.1 Hz, 1H), 6.76 (s, 1H), 6.02-5.87 (m, 1H), 3.31 (s, 1H), 3.22 (s, 1H), 3.13 (s, 1H), 2.89 (s, 2H), 1.70 (t, J = 6.6 Hz, 3H); five protons are not visible, likely due to overlap with suppressed water peak or low integration. |

| Ex. No. | Structure | LC/MS [M + H]+ | RT (min) | 1H NMR (500 MHz, DMSO-d6) |
|---|---|---|---|---|
| 583 | 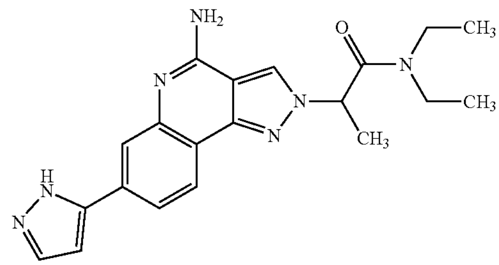 [SMILES: CCN(CC)C(=O)C(C)n1cc2c(N)nc3cc(-c4ccn[nH]4)ccc3c2n1] | 378.1 | 1.39 | δ 8.69 (s, 1H), 8.06 (d, J = 7.9 Hz, 1H), 7.89 (s, 1H), 7.72 (br s, 1H), 7.65 (br d, J = 7.9 Hz, 1H), 6.75 (d, J = 1.8 Hz, 1H), 5.84 (q, J = 6.7 Hz, 1H), 3.41-3.32 (m, 1H), 3.27-3.19 (m, 1H), 1.70 (d, J = 6.7 Hz, 3H), 1.14 (t, J = 7.0 Hz, 3H), 1.03 (t, J = 7.0 Hz, 3H); two protons are not visible, likely due to overlap with suppressed water peak. |
| 584 | 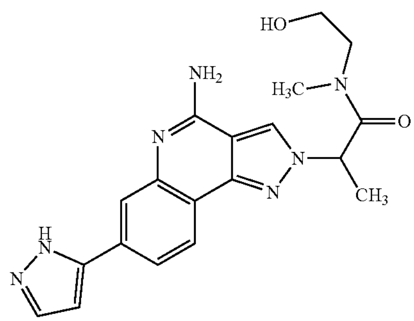 [SMILES: CC(C(=O)N(C)CCO)n1cc2c(N)nc3cc(-c4ccn[nH]4)ccc3c2n1] | 380.3 | 1.06 | δ 9.20-9.06 (m, 1H), 8.27-8.06 (m, 2H), 8.00-7.80 (m, 2H), 6.89-6.74 (m, 1H), 6.12-5.95 (m, 1H), 3.81-3.59 (m, 1H), 3.84-3.38 (m, 4H), 1.82-1.70 (m, 3H); six protons not visible, likely due to overlap with water/water suppression. |
| 585 | 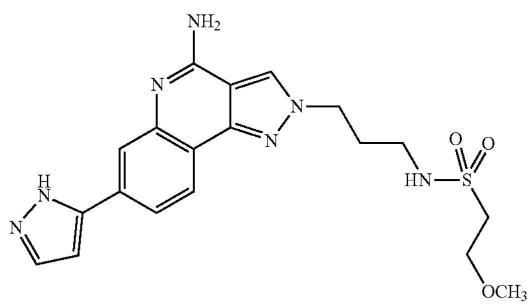 [SMILES: COCCS(=O)(=O)NCCCn1cc2c(N)nc3cc(-c4ccn[nH]4)ccc3c2n1] | 430.3 | 1.12 | δ 8.48 (s, 1H), 8.08 (d, J = 8.2 Hz, 1H), 7.87 (s, 1H), 7.71 (br s, 1H), 7.63 (br d, J = 7.8 Hz, 1H), 6.75 (d, J = 1.9 Hz, 1H), 4.46 (br t, J = 6.7 Hz, 2H), 3.73-3.61 (m, 3H), 3.28 (br t, J = 6.2 Hz, 2H), 3.22 (s, 3H), 2.98 (br d, J = 1.8 Hz, 2H), 2.16-2.08 (m, 2H) |
| 586 | 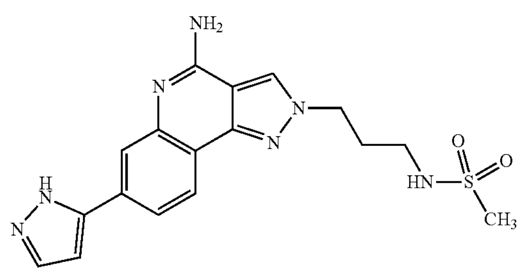 [SMILES: CS(=O)(=O)NCCCn1cc2c(N)nc3cc(-c4ccn[nH]4)ccc3c2n1] | 386.3 | 1.03 | δ 8.47 (s, 1H), 8.07 (d, J = 8.2 Hz, 1H), 7.87 (d, J = 0.9 Hz, 1H), 7.71 (br s, 1H), 7.62 (br d, J = 8.2 Hz, 1H), 6.75 (d, J = 1.8 Hz, 1H), 4.48 (t, J = 6.9 Hz, 2H), 3.00 (br d, J = 5.2 Hz, 2H), 2.91 (s, 3H), 2.13 (quin, J = 6.9 Hz, 2H) |
| 587 | 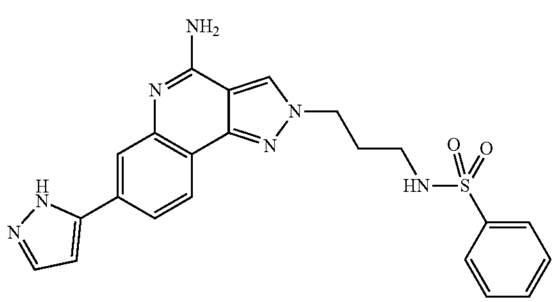 [SMILES: Nc1nc2cc(-c3ccn[nH]3)ccc2c2nn(CCCNS(=O)(=O)c3ccccc3)cc12] | 448.2 | 1.10 | δ 8.42 (s, 1H), 8.04 (d, J = 7.9 Hz, 1H), 7.87 (s, 1H), 7.77 (d, J = 7.3 Hz, 2H), 7.71 (br s, 1H), 7.61 (br t, J = 6.9 Hz, 2H), 7.58-7.51 (m, 2H), 6.75 (d, J = 2.1 Hz, 1H), 4.42 (br t, J = 6.7 Hz, 2H), 2.80 (br t, J = 6.6 Hz, 2H), 2.05 (quin, J = 6.9 Hz, 2H) |

-continued

| Ex. No. | Structure | LC/MS [M + H]+ | RT (min) | ¹H NMR (500 MHz, DMSO-d₆) |
|---|---|---|---|---|
| 588 | 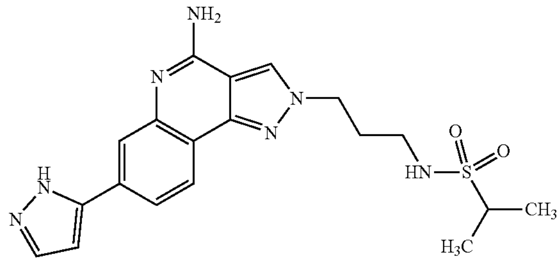 [SMILES: CC(C)S(=O)(=O)NCCCn1cc2c(N)nc3cc(-c4ccn[nH]4)ccc3c2n1] | 414.2 | 1.12 | δ 8.47 (s, 1H), 8.06 (d, J = 8.2 Hz, 1H), 7.87 (d, J = 1.4 Hz, 1H), 7.71 (br s, 1H), 7.62 (br d, J = 8.5 Hz, 1H), 6.75 (d, J = 2.1 Hz, 1H), 4.47 (t, J = 6.9 Hz, 2H), 3.23-3.12 (m, 1H), 3.01 (q, J = 6.3 Hz, 2H), 2.12 (quin, J = 7.0 Hz, 2H), 1.22 (d, J = 6.7 Hz, 6H) |
| 589 | 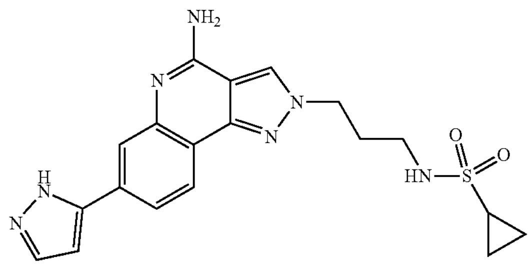 [SMILES: Nc1nc2cc(-c3ccn[nH]3)ccc2c2nn(CCCNS(=O)(=O)C3CC3)cc12] | 412.2 | 1.17 | δ 8.47 (s, 1H), 8.07 (d, J = 8.1 Hz, 1H), 7.87 (s, 1H), 7.71 (br s, 1H), 7.62 (br d, J = 7.8 Hz, 1H), 6.75 (d, J = 1.9 Hz, 1H), 4.49 (br t, J = 6.9 Hz, 2H), 3.04 (br d, J = 5.5 Hz, 2H), 2.15 (quin, J = 6.6 Hz, 2H), 1.89 (s, ~2H), 0.98-0.89 (m, 2H), 0.90-0.81 (m, 2H) (one methine obscured by solvent) |
| 590 | 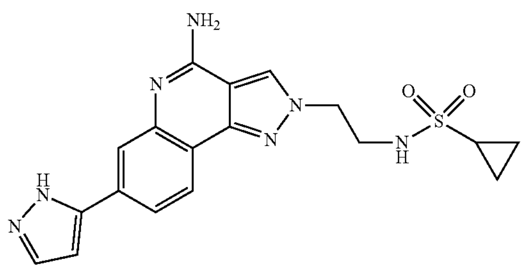 [SMILES: Nc1nc2cc(-c3ccn[nH]3)ccc2c2nn(CCNS(=O)(=O)C3CC3)cc12] | 398.3 | 1.13 | δ 8.50 (s, 1H), 8.08 (d, J = 8.2 Hz, 1H), 7.88 (s, 1H), 7.78-7.67 (m, 1H), 7.63 (br d, J = 7.0 Hz, 1H), 6.75 (d, J = 1.5 Hz, 1H), 4.51 (t, J = 5.6 Hz, 2H), 3.55 (br d, J = 4.3 Hz, 1H (intensity reduced by water suppression), 0.96-0.85 (m, 4H) |
| 591 | 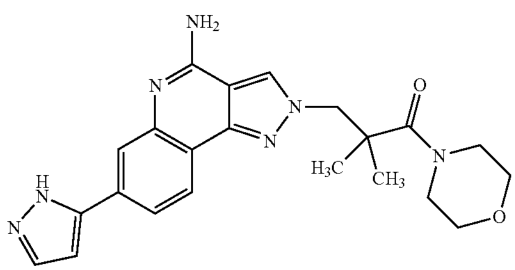 [SMILES: CC(C)(Cn1cc2c(N)nc3cc(-c4ccn[nH]4)ccc3c2n1)C(=O)N1CCOCC1] | 420.3 | 1.21 | δ 8.49 (s, 1H), 8.04 (d, J = 8.2 Hz, 1H), 7.86 (s, 1H), 7.78-7.67 (m, 1H), 7.62 (br d, J = 8.3 Hz, 1H), 6.75 (d, J = 2.0 Hz, 1H), 4.63 (s, 2H), 3.64 (s, 4H), 3.59-3.37 (m, 3H) (intensity reduced by water suppression), 1.29 (s, 6H) |
| 592 | 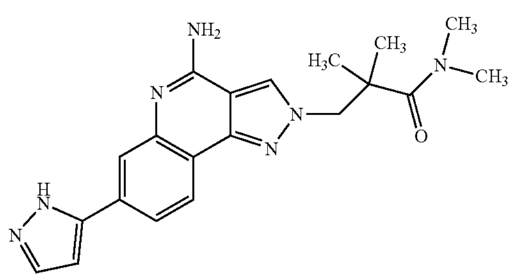 [SMILES: CN(C)C(=O)C(C)(C)Cn1cc2c(N)nc3cc(-c4ccn[nH]4)ccc3c2n1] | 378.3 | 1.24 | δ 8.63 (br s, 1H), 8.08 (d, J = 8.2 Hz, 1H), 7.92 (s, 1H), 7.74 (br s, 1H), 7.69 (br d, J = 8.2 Hz, 1H), 6.76 (s, 1H), 4.64 (s, 2H), 1.30 (s, 6H) (some resonances obscured by water suppression routine) |

| Ex. No. | Structure | LC/MS [M + H]+ | RT (min) | ¹H NMR (500 MHz, DMSO-d₆) |
|---|---|---|---|---|
| 593 | 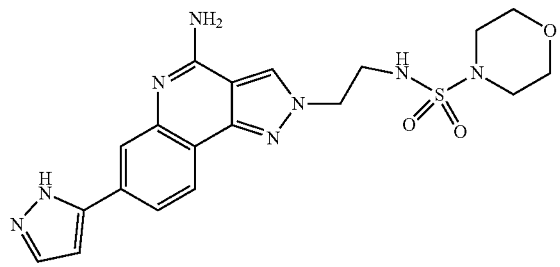 [SMILES: Nc1nc2cc(-c3ccn[nH]3)ccc2c2nn(CCNS(=O)(=O)N3CCOCC3)cc12] | 443.3 | 1.11 | δ 8.51 (s, 1H), 8.08 (d, J = 8.2 Hz, 1H), 7.88 (s, 1H), 7.71 (br s, 1H), 7.64 (br d, J = 8.2 Hz, 1H), 6.76 (s, 1H), 4.49 (br t, J = 5.8 Hz, 2H), 3.53 (br s, 1H) (intensity reduced by water suppression), 2.92 (br s, 4H) (some resonances obscured by water suppression routine) |
| 594 | 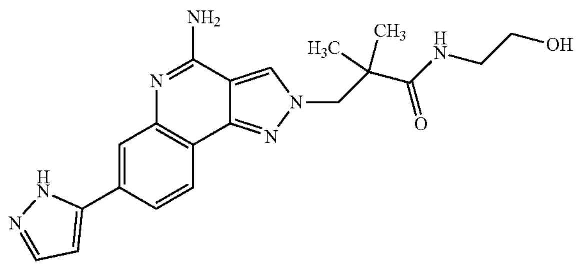 [SMILES: CC(C)(Cn1cc2c(N)nc3cc(-c4ccn[nH]4)ccc3c2n1)C(=O)NCCO] | 394.3 | 1.06 | δ 8.77-8.50 (m, 1H), 8.12 (d, J = 8.2 Hz, 1H), 7.98 (br s, 1H), 7.82-7.73 (m, 1H), 7.65 (br t, J = 5.3 Hz, 1H), 6.78 (s, 1H), 4.56 (s, 2H), 3.51-3.33 (m, 1H) (intensity reduced by water suppression), 3.16 (q, J = 6.3 Hz, 1H) (intensity reduced by water suppression), 1.18 (s, 6H) |
| 595 | 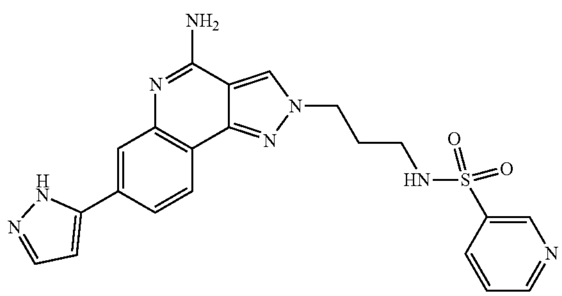 [SMILES: Nc1nc2cc(-c3ccn[nH]3)ccc2c2nn(CCCNS(=O)(=O)c3cccnc3)cc12] | 449.0 | 1.13 | δ 8.94 (d, J = 1.8 Hz, 1H), 8.88 (s, 1H), 8.80 (d, J = 4.0 Hz, 1H), 8.16 (d, J = 8.2 Hz, 2H), 8.10 (br s, 1H), 8.06 (br t, J = 5.0 Hz, 1H), 7.92 (br d, J = 8.2 Hz, 1H), 7.85 (br s, 1H), 7.63 (dd, J = 8.1, 4.7 Hz, 1H), 6.81 (d, J = 1.8 Hz, 1H), 4.51 (br t, J = 6.9 Hz, 2H), 2.89 (q, J = 6.3 Hz, 2H), 2.09 (quin, J = 6.6 Hz, 2H) |
| 596 | 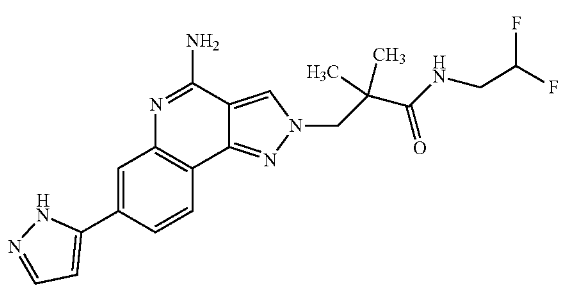 [SMILES: CC(C)(Cn1cc2c(N)nc3cc(-c4ccn[nH]4)ccc3c2n1)C(=O)NCC(F)F] | 414.3 | 1.2 | δ 8.40 (s, 1H), 8.10 (br t, J = 5.6 Hz, 1H), 8.05 (d, J = 8.2 Hz, 1H), 7.87 (s, 1H), 7.71 (br s, 1H), 7.63 (br d, J = 8.0 Hz, 1H), 6.75 (d, J = 1.7 Hz, 1H), 6.20-5.88 (m, 1H), 4.54 (s, 2H), 3.63-3.34 (m, 1H) (intensity reduced by water suppression), 1.18 (s, 6H) |
| 597 | 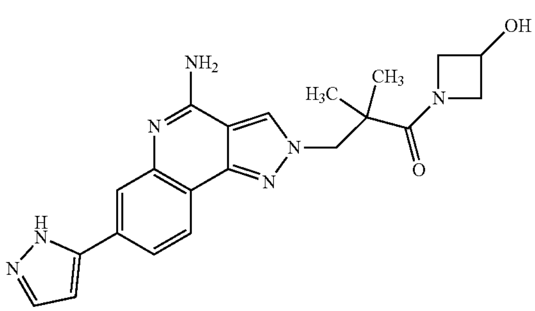 [SMILES: CC(C)(Cn1cc2c(N)nc3cc(-c4ccn[nH]4)ccc3c2n1)C(=O)N1CC(O)C1] | 406.1 | 1.09 | δ 8.49 (s, 1H), 8.11 (d, J = 8.2 Hz, 1H), 7.89 (s, 1H), 7.72 (br s, 1H), 7.67 (br d, J = 8.2 Hz, 1H), 6.76 (d, J = 1.8 Hz, 1H), 4.50 (s, 2H), 4.37-4.28 (m, 1H), 1.16 (s, 6H) (some resonances obscured by water suppression routine) |

-continued

| Ex. No. | Structure | LC/MS [M + H]+ | RT (min) | ¹H NMR (500 MHz, DMSO-d₆) |
|---|---|---|---|---|
| 598 | 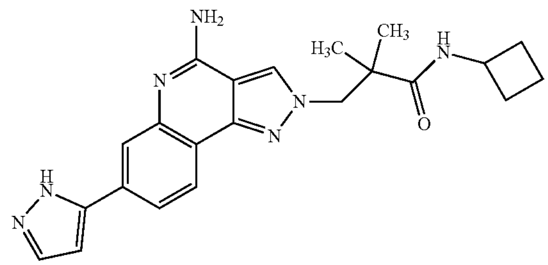 [SMILES: CC(C)(Cn1cc2c(N)nc3cc(-c4ccn[nH]4)ccc3c2n1)C(=O)NC1CCC1] | 404.1 | 1.27 | δ 8.37 (s, 1H), 8.05 (d, J = 8.2 Hz, 1H), 7.86 (s, 1H), 7.75-7.67 (m, 2H), 7.63 (br d, J = 8.2 Hz, 1H), 6.75 (d, J = 2.1 Hz, 1H), 4.48 (s, 2H), 4.27-4.15 (m, 1H), 2.19-2.06 (m, 2H), 1.64-1.51 (m, 2H), 1.14 (s, 6H) |
| 599 | 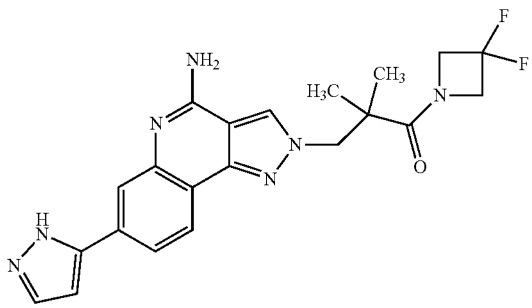 [SMILES: CC(C)(Cn1cc2c(N)nc3cc(-c4ccn[nH]4)ccc3c2n1)C(=O)N1CC(F)(F)C1] | 426.3 | 1.28 | δ 8.88 (s, 1H), 8.15 (d, J = 8.2 Hz, 1H), 8.10 (br s, 1H), 7.91 (br d, J = 8.2 Hz, 1H), 7.85 (br s, 1H), 6.82 (d, J = 2.0 Hz, 1H), 4.62 (s, 2H), 1.22 (s, 6H) (some resonances obscured by water suppression routine) |
| 600 | 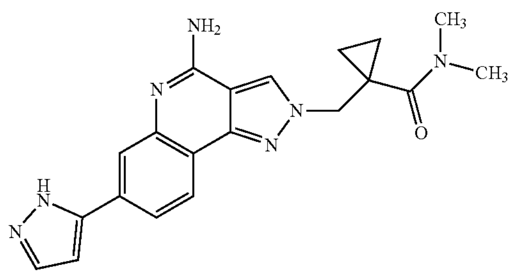 [SMILES: CN(C)C(=O)C1(Cn2cc3c(N)nc4cc(-c5ccn[nH]5)ccc4c3n2)CC1] | 376.1 | 1.11 | δ 8.53 (s, 1H), 8.07 (d, J = 7.9 Hz, 1H), 7.90 (s, 1H), 7.72 (br s, 1H), 7.65 (br d, J = 8.2 Hz, 1H), 6.75 (d, J = 1.8 Hz, 1H), 4.58 (s, 2H), 3.00-2.75 (m, 3H), 1.91 (s, 3H), 1.09-1.01 (m, 2H), 1.01-0.92 (m, 2H) (some resonances obscured by water suppression routine) |
| 601 | 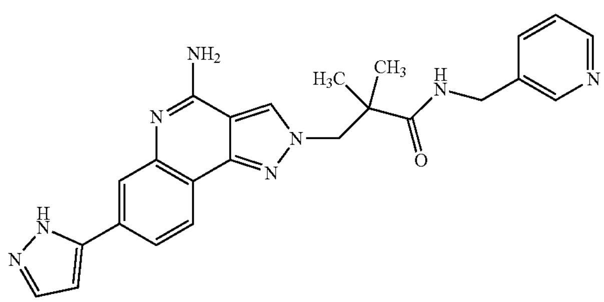 [SMILES: CC(C)(Cn1cc2c(N)nc3cc(-c4ccn[nH]4)ccc3c2n1)C(=O)NCc1cccnc1] | 441.1 | 1.03 | δ 9.79-9.53 (m, 1H), 8.86 (s, 1H), 8.42 (br s, 2H), 8.36 (br t, J = 5.6 Hz, 1H), 8.13 (d, J = 8.2 Hz, 1H), 8.09 (br s, 1H), 7.91 (br d, J = 8.2 Hz, 1H), 7.84 (br s, 1H), 7.58 (br d, J = 7.8 Hz, 1H), 7.26 (dd, J = 7.5, 5.0 Hz, 1H), 6.82 (d, J = 1.4 Hz, 1H), 4.62 (s, 2H), 4.31 (br d, J = 5.9 Hz, 2H), 1.25 (s, 6H) |
| 602 | 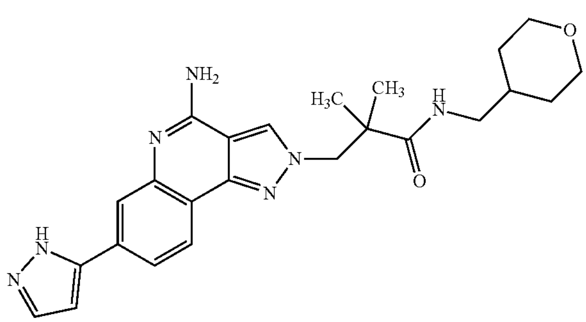 [SMILES: CC(C)(Cn1cc2c(N)nc3cc(-c4ccn[nH]4)ccc3c2n1)C(=O)NCC1CCOCC1] | 448.1 | 1.2 | δ 8.39 (s, 1H), 8.04 (d, J = 8.1 Hz, 1H), 7.86 (s, 1H), 7.71 (br s, 1H), 7.62 (br d, J = 6.6 Hz, 2H), 6.75 (d, J = 1.6 Hz, 1H), 4.50 (s, 2H), 3.67 (br dd, J = 11.1, 2.4 Hz, 2H), 3.10 (br t, J = 11.0 Hz, 2H), 2.93 (br t, J = 6.4 Hz, 2H), 1.69-1.54 (m, 1H), 1.31 (br d, J = 13.0 Hz, 2H), 1.19 (s, 6H), 1.07-0.95 (m, 2H) |

| Ex. No. | Structure | LC/MS [M + H]+ | RT (min) | $^1$H NMR (500 MHz, DMSO-$d_6$) |
|---|---|---|---|---|
| 603 | 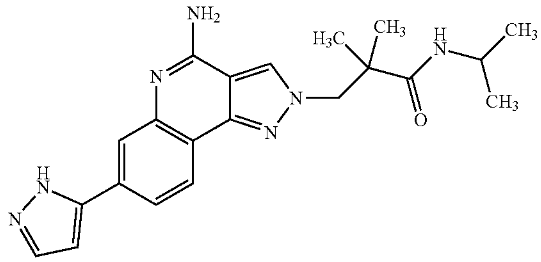 [SMILES: CC(C)NC(=O)C(C)(C)Cn1cc2c(N)nc3cc(-c4ccn[nH]4)ccc3c2n1] | 392.1 | 1.37 | δ 8.50 (br s, 1H), 8.07 (d, J = 8.2 Hz, 1H), 7.91 (s, 1H), 7.73 (br s, 1H), 7.68 (br d, J = 7.9 Hz, 1H), 7.30 (d, J = 7.9 Hz, 1H), 6.76 (d, J = 2.1 Hz, 1H), 4.52 (s, 2H), 4.00-3.86 (m, 1H), 1.16 (s, 6H), 1.03 (d, J = 6.7 Hz, 6H) |
| 604 | 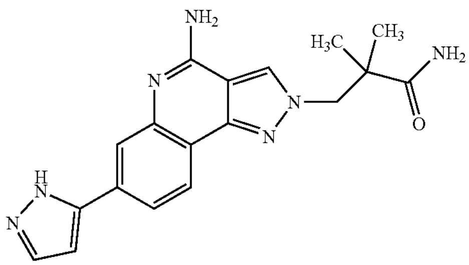 [SMILES: CC(C)(Cn1cc2c(N)nc3cc(-c4ccn[nH]4)ccc3c2n1)C(N)=O] | 350.1 | 1.1 | δ 8.51 (s, 1H), 8.07 (d, J = 8.2 Hz, 1H), 7.90 (s, 1H), 7.73 (br s, 1H), 7.66 (br d, J = 7.2 Hz, 1H), 7.27 (s, 1H), 7.03 (s, 1H), 6.76 (d, J = 2.0 Hz, 1H), 4.52 (s, 2H), 1.17 (s, 6H) |
| 605 | 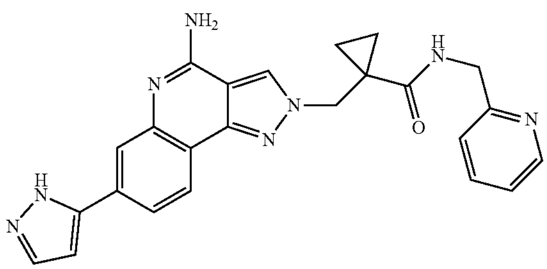 [SMILES: Nc1nc2cc(-c3ccn[nH]3)ccc2c2nn(CC3(C(=O)NCc4ccccn4)CC3)cc12] | 439.1 | 1.01 | δ 8.61 (s, 1H), 8.49 (t, J = 6.0 Hz, 1H), 8.41 (d, J = 4.3 Hz, 1H), 8.02 (d, J = 8.2 Hz, 1H), 7.88 (s, 1H), 7.71 (br s, 1H), 7.62 (br d, J = 7.9 Hz, 1H), 7.50-7.43 (m, 1H), 7.17 (dd, J = 7.0, 5.2 Hz, 1H), 7.01 (d, J = 7.6 Hz, 1H), 6.76 (d, J = 1.8 Hz, 1H), 4.74 (s, 2H), 4.36 (d, J = 5.8 Hz, 2H), 1.32-1.25 (m, 2H), 1.18-1.09 (m, 2H) |
| 606 | 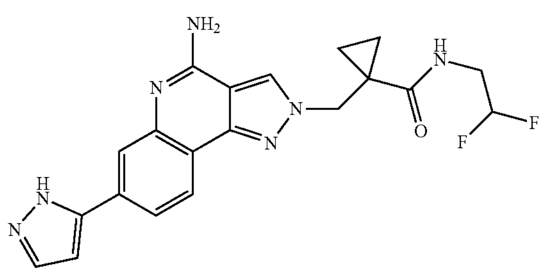 [SMILES: Nc1nc2cc(-c3ccn[nH]3)ccc2c2nn(CC3(C(=O)NCC(F)F)CC3)cc12] | 411.9 | 1.15 | δ 8 9.02 (s, 1H), 8.18 (d, J = 8.2 Hz, 1H), 8.09 (br s, 1H), 8.06 (br t, J = 5.8 Hz, 1H), 7.91 (br d, J = 7.9 Hz, 1H), 7.85 (br s, 1H), 6.81 (d, J = 1.8 Hz, 1H), 6.13-5.81 (m, 1H), 4.73 (s, 2H), 1.36-1.25 (m, 2H), 1.22-1.14 (m, 2H) (some resonances obscured by water suppression routine) |
| 607 | 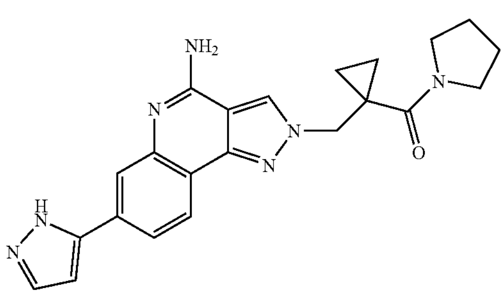 [SMILES: Nc1nc2cc(-c3ccn[nH]3)ccc2c2nn(CC3(C(=O)N4CCCC4)CC3)cc12] | 402.3 | 1.02 | $^1$H NMR (500 MHz, DMSO-$d_6$) δ 8.47 (s, 1H), 8.05 (d, J = 8.2 Hz, 1H), 7.86 (s, 1H), 7.71 (br s, 1H), 7.62 (br d, J = 7.9 Hz, 1H), 6.75 (d, J = 2.1 Hz, 1H), 4.57 (s, 2H), 3.23 (br s, 2H), 1.77-1.49 (m, 4H), 1.05-0.95 (m, 4H) (some resonances obscured by water suppression routine) |

| Ex. No. | Structure | LC/MS [M + H]+ | RT (min) | ¹H NMR (500 MHz, DMSO-d₆) |
|---|---|---|---|---|
| 608 | 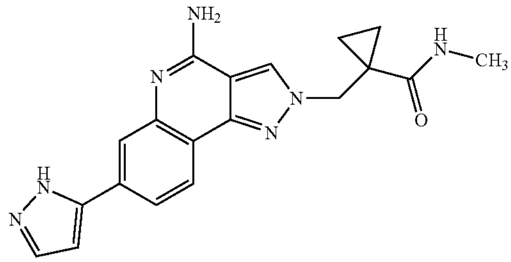 [SMILES: CNC(=O)C1(Cn2cc3c(N)nc4cc(-c5ccn[nH]5)ccc4c3n2)CC1] | 362.1 | 1.08 | δ 8.75 (br s, 1H), 8.11 (d, J = 7.9 Hz, 1H), 7.95 (br s, 1H), 7.74 (br d, J = 7.9 Hz, 2H), 7.65 (br d, J = 4.3 Hz, 1H), 6.77 (d, J = 1.8 Hz, 1H), 4.67 (s, 2H), 2.57 (d, J = 4.3 Hz, 3H), 1.25-1.17 (m, 2H), 1.13-1.06 (m, 2H) |
| 609 | 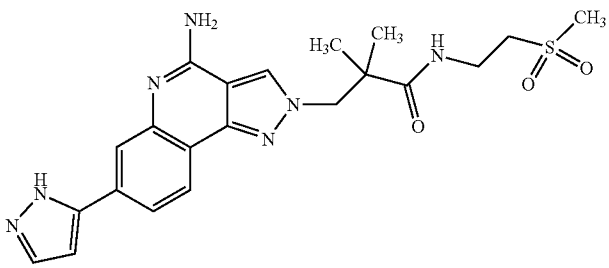 [SMILES: CC(C)(Cn1cc2c(N)nc3cc(-c4ccn[nH]4)ccc3c2n1)C(=O)NCCS(C)(=O)=O] | 456.0 | 1.07 | δ 8.39 (s, 1H), 8.05 (d, J = 8.1 Hz, 1H), 7.92 (br t, J = 5.5 Hz, 1H), 7.86 (d, J = 1.3 Hz, 1H), 7.71 (br s, 1H), 7.61 (br d, J = 8.3 Hz, 1H), 6.74 (d, J = 2.1 Hz, 1H), 4.51 (s, 2H), 3.26 (br t, J = 6.9 Hz, 2H), 2.96 (s, 3H), 1.15 (s, 6H) (some resonances obscured by water suppression routine) |
| 610 | 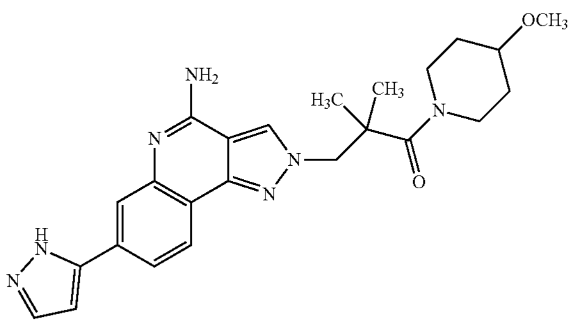 [SMILES: COC1CCN(C(=O)C(C)(C)Cn2cc3c(N)nc4cc(-c5ccn[nH]5)ccc4c3n2)CC1] | 448.2 | 1.46 | δ 8.58 (s, 1H), 8.07 (d, J = 7.9 Hz, 1H), 7.89 (s, 1H), 7.72 (br s, 1H), 7.66 (br d, J = 7.9 Hz, 1H), 6.76 (d, J = 2.1 Hz, 1H), 4.62 (s, 2H), 3.98-3.85 (m, 2H), 3.28 (s, 3H), 1.55-1.43 (m, 2H), 1.28 (s, 6H) (some resonances obscured by water suppression routine) |
| 611 | 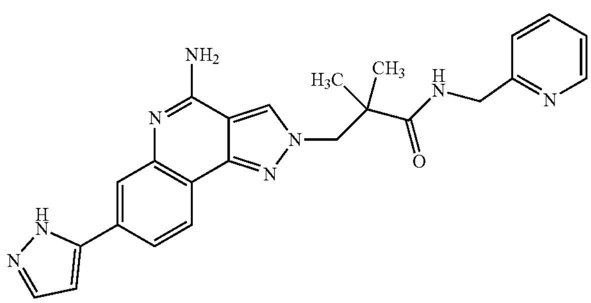 [SMILES: CC(C)(Cn1cc2c(N)nc3cc(-c4ccn[nH]4)ccc3c2n1)C(=O)NCc1ccccn1] | 441.1 | 1.03 | δ 8.49-8.41 (m, 2H), 8.32 (br t, J = 5.7 Hz, 1H), 8.05 (d, J = 8.2 Hz, 1H), 7.90 (s, 1H), 7.72 (br s, 1H), 7.67-7.61 (m, 1H), 7.55 (t, J = 7.7 Hz, 1H), 7.24-7.16 (m, 1H), 7.04 (d, J = 7.9 Hz, 1H), 6.76 (d, J = 2.0 Hz, 1H), 4.59 (s, 2H), 4.40 (d, J = 5.6 Hz, 2H), 1.27 (s, 6H) |
| 612 | 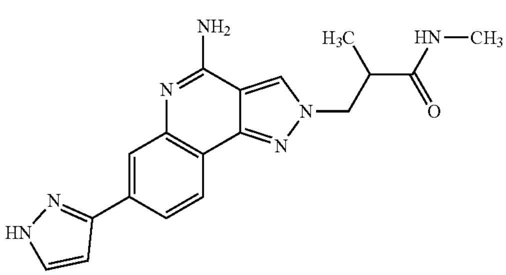 [SMILES: CNC(=O)C(C)Cn1cc2c(N)nc3cc(-c4cc[nH]n4)ccc3c2n1] | 350.1 | 0.52 | (400 MHz, MeOH-d4) δ 8.69 (s, 1H), 8.32 (d, J = 8.5 Hz, 1H), 8.02 (s, 1H), 7.96 (d, J = 7.9 Hz, 1H), 7.79 (s, 1H), 6.84 (s, 1H), 4.46-4.57 (m, 1H), 4.68-4.78 (m, 1H), 3.14-3.25 (m, 1H), 2.65 (s, 3H), 1.28 (d, J = 6.8 Hz, 3H) |

-continued

| Ex. No. | Structure | LC/MS [M + H]+ | RT (min) | 1H NMR (500 MHz, DMSO-d6) |
|---|---|---|---|---|
| 613 | 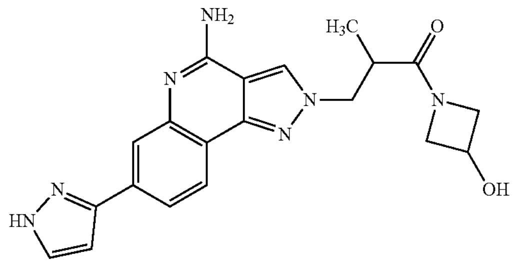 [SMILES: CC(Cn1cc2c(N)nc3cc(-c4cc[nH]n4)ccc3c2n1)C(=O)N1CC(O)C1] | 392.3 | 1.03 | δ 8.42 (d, J = 8.6 Hz, 1H), 8.06-8.13 (m, 1H), 7.88 (s, 1H), 7.72 (s, 1H), 7.61-7.66 (m, 1H), 6.76 (s, 1H), 4.46-4.57 (m, 1H), 4.29-4.43 (m, 3H), 4.11-4.17 (m, 1H), 3.94-4.03 (m, 2H), 3.78-3.90 (m, 1H), 3.07-3.16 (m, 1H), 1.04-1.11 (m, 3H) |
| 614 | 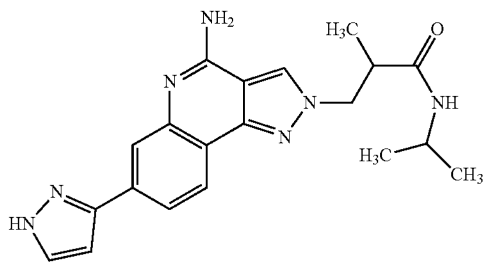 [SMILES: CC(C)NC(=O)C(C)Cn1cc2c(N)nc3cc(-c4cc[nH]n4)ccc3c2n1] | 378.1 | 1.17 | δ 8.55 (br. s, 1H), 8.10 (d, J = 8.2 Hz, 1H), 7.95 (br. s, 1H), 8.79 (d, J = 7.6 Hz, 1H), 7.68-7.83 (m, 1H), 6.78 (s, 1H), 4.48 (ABx, $J_{AB}$ = 13.3 Hz, $J_{AX}$ = 9.0 Hz, $J_{BX}$ = 5.8 Hz, Δν = 91 Hz, 2H), 3.77-3.84 (m, 1H), 2.93-3.01 (m, 1H), 1.09 (d, J = 6.7 Hz, 3H), 1.00 (d, J = 6.4 Hz, 3H), 0.88 (d, J = 6.4 Hz, 3H) |
| 615 | 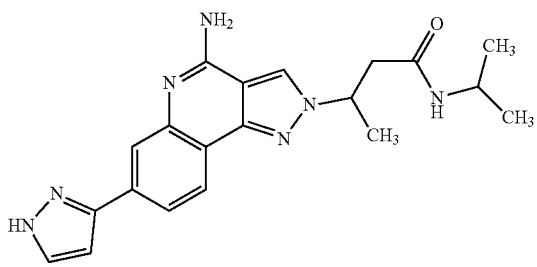 [SMILES: CC(C)NC(=O)CC(C)n1cc2c(N)nc3cc(-c4cc[nH]n4)ccc3c2n1] | 378.1 | 1.19 | δ 8.84 (s, 1H), 8.10 (d, J = 8.2 Hz, 1H), 7.87 (s, 1H), 7.83 (d, J = 7.6 Hz, 1H), 7.68-7.77 (m, 1H), 7.63 (br. d, J = 9.2 Hz, 1H), 6.75 (d, J = 1.8 Hz, 1H), 4.98-5.06 (m, 1H), 3.73-3.81 (m, 1H), 2.73 (ABx, $J_{AB}$ = 15.4 Hz, $J_{AX}$ = 7.8 Hz, $J_{BX}$ = 6.2 Hz, Δν = 64 Hz, 2H), 1.60 (d, J = 6.7 Hz, 3H), 1.00 (d, J = 6.4 Hz, 3H), 0.88 (d, J = 6.7 Hz, 3H). |
| 616 | 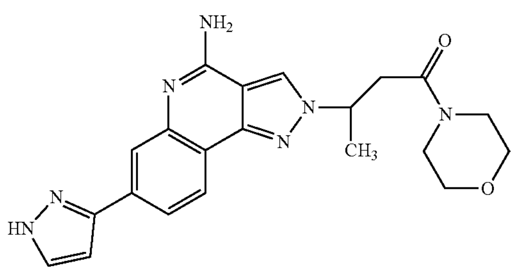 [SMILES: CC(CC(=O)N1CCOCC1)n1cc2c(N)nc3cc(-c4cc[nH]n4)ccc3c2n1] | 406.0 | 1.15 | δ 8.53 (s, 1H), 8.09 (d, J = 8.2 Hz, 1H), 7.88 (d, J = 1.2 Hz, 1H), 7.72 (s, 1H), 7.64 (d, J = 8.3 Hz, 1H), 6.76 (d, J = 2.1 Hz, 1H), 5.05-5.14 (m, 1H), 3.05 (ABx, $J_{AB}$ = 16.2 Hz, $J_{AX}$ = 8.1 Hz, $J_{BX}$ = 5.3 Hz, Δν = 161 Hz, 2H), 1.62 (d, J = 6.7 Hz, 3H); morpholine methylene units not observed. |
| 617 | 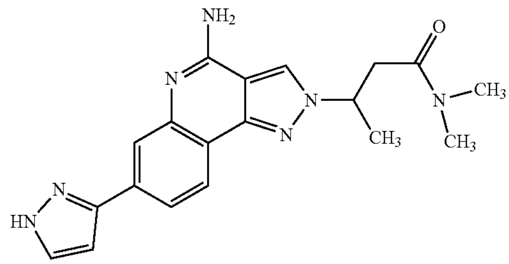 [SMILES: CC(CC(=O)N(C)C)n1cc2c(N)nc3cc(-c4cc[nH]n4)ccc3c2n1] | 364.2 | 0.57 | (400 MHz, MeOH-d4) δ 8.81 (s, 1H), 8.34 (d, J = 8.2 Hz, 1H), 8.02 (d, J = 1.1 Hz, 1H), 7.96 (dd, J = 8.3, 1.5 Hz, 1H), 7.79 (d, J = 2.2 Hz, 1H), 7.85 (d, J = 2.3 Hz, 1H), 5.20-5.29 (m, 1H), 3.22 (ABx, $J_{AB}$ = 16.6 Hz, $J_{AX}$ = 9.0 Hz, $J_{BX}$ = 4.3 Hz, Δν = 174 Hz, 2H), 3.08 (s, 3H), 2.87 (s, 3H), 1.75 (d, J = 6.7 Hz, 3H) |

| Ex. No. | Structure | LC/MS [M + H]+ | RT (min) | ¹H NMR (500 MHz, DMSO-d₆) |
|---|---|---|---|---|
| 618 | 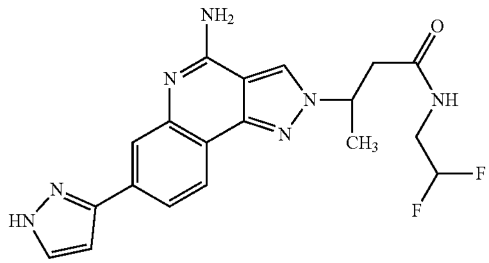 [SMILES: CC(CC(=O)NCC(F)F)n1cc2c(N)nc3cc(-c4cc[nH]n4)ccc3c2n1] | 399.8 | 1.14 | δ 8.54 (s, 1H), 8.42 (t, J = 5.6 Hz, 1H), 8.10 (d, J = 7.9 Hz, 1H), 7.91 (d, J = 0.6 Hz, 1H), 7.74 (br. s, 1H), 7.67 (d, J = 7.9 Hz, 1H), 6.77 (d, J = 2.1 Hz, 1H), 5.92 (tt, J = 56, 3.7 Hz, 1H), 5.03-5.12 (m, 1H), 2.89 (ABx, $J_{AB}$ = 15.0 Hz, $J_{AX}$ = 7.6 Hz, $J_{BX}$ = 6.4 Hz, Δν = 71 Hz, 2H), 1.62 (d, J = 6.7 Hz, 3H); one methylene unit not observed. |
| 619 | 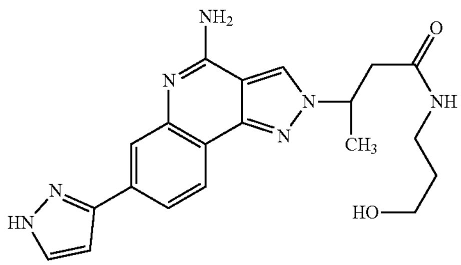 [SMILES: CC(CC(=O)NCCCO)n1cc2c(N)nc3cc(-c4cc[nH]n4)ccc3c2n1] | 394.1 | 1.06 | δ 8.94 (s, 1H), 8.21 (d, J = 8.3 Hz, 1H), 8.11 (br. s, 1H), 7.99 (t, J = 6.0 Hz, 1H), 7.93 (dd, J = 8.2, 2.2 Hz, 1H), 7.86 (br. s, 1H), 6.82 (d, J = 2.0 Hz, 1H), 5.11-5.18 (m, 1H), 3.26 (t, J = 6.3 Hz, 2H), 3.00-3.06 (m, 2H), 2.90-2.97 (m, 1H), 2.81 (ABx, $J_{AB}$ = 15.0 Hz, $J_{AX}$ = 8.3 Hz, $J_{BX}$ = 5.8 Hz, Δν = 52 Hz, 2H), 1.62 (d, J = 6.7 Hz, 3H); one methylene unit not observed. |
| 620 | 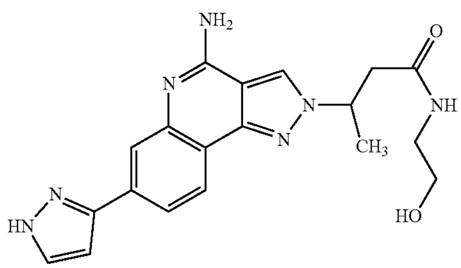 [SMILES: CC(CC(=O)NCCO)n1cc2c(N)nc3cc(-c4cc[nH]n4)ccc3c2n1] | 380.1 | 1.04 | δ 8.93 (s, 1H), 8.22 (d, J = 8.2 Hz, 1H), 8.11 (br. s, 1H), 8.02 (t, J = 5.6 Hz, 1H), 7.94 (br. d, J = 8.9 Hz, 1H), 7.87 (br. s, 1H), 6.83 (d, J = 1.5 Hz, 1H), 5.11-5.18 (m, 1H), 3.25-3.35 (m, 2H), 3.03-3.10 (m, 2H), 2.90-2.97 (m, 1H), 2.83 (ABx, $J_{AB}$ = 15.2 Hz, $J_{AX}$ = 7.9 Hz, $J_{BX}$ = 5.7 Hz, Δν = 56 Hz, 2H), 1.61 (d, J = 6.7 Hz, 3H) |
| 621 | 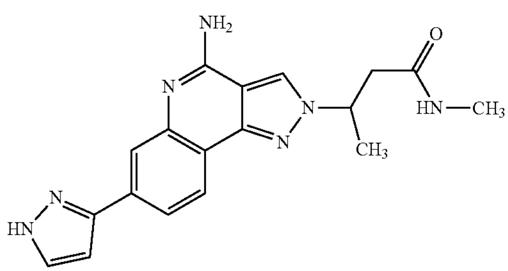 [SMILES: CNC(=O)CC(C)n1cc2c(N)nc3cc(-c4cc[nH]n4)ccc3c2n1] | 350.0 | 1.09 | δ 8.49 (s, 1H), 8.08 (d, J = 8.1 Hz, 1H), 7.91 (q, J = 4.4 Hz, 1H), 7.88 (d, J = 1.1 Hz, 1H), 7.72 (d, J = 0.4 Hz, 1H), 7.63 (d, J = 8.0 Hz, 1H), 6.76 (d, J = 2.0 Hz, 1H), 5.01-5.09 (m, 1H), 2.80 (ABx, $J_{AB}$ = 14.9 Hz, $J_{AX}$ = 7.8 Hz, $J_{BX}$ = 6.2 Hz, Δν = 77 Hz, 2H), 1.58 (d, J = 6.7 Hz, 3H); one methyl group not observed. |
| 622 | 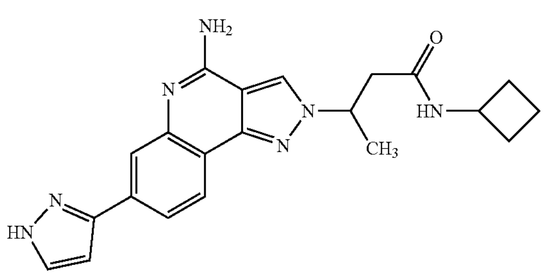 [SMILES: CC(CC(=O)NC1CCC1)n1cc2c(N)nc3cc(-c4cc[nH]n4)ccc3c2n1] | 390.1 | 1.19 | δ 8.92 (s, 1H), 8.23 (d, J = 7.6 Hz, 1H), 8.20 (d, J = 8.2 Hz, 1H), 8.07-8.15 (m, 1H), 7.83-7.97 (m, 2H), 6.82 (d, J = 0.6 Hz, 1H), 5.09-5.17 (m, 1H), 4.06-4.16 (m, 1H), 2.78 (ABx, $J_{AB}$ = 15.3 Hz, $J_{AX}$ = 7.9 Hz, $J_{BX}$ = 5.8 Hz, Δν = 50 Hz, 2H), 1.99-2.07 (m, 1H), 2.07-2.15 (m, 1H), 1.77-1.85 (m, 1H), 1.65-1.73 (m, 1H), 1.61 (d, J = 6.7 Hz, 3H), 1.52-1.59 (m, 2H) |

| Ex. No. | Structure | LC/MS [M + H]+ | RT (min) | 1H NMR (500 MHz, DMSO-d6) |
|---|---|---|---|---|
| 623 | 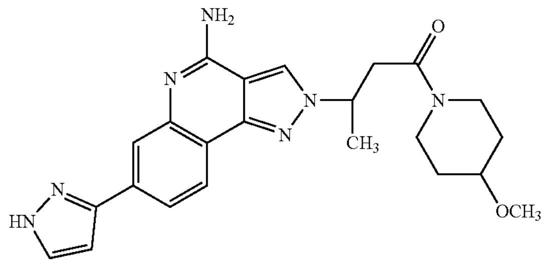 [SMILES: COC1CCN(C(=O)CC(C)n2cc3c(N)nc4cc(-c5cc[nH]n5)ccc4c3n2)CC1] | 434.1 | 1.25 | δ 8.99 (d, J = 3.4 Hz, 1H), 8.21 (d, J = 8.6 Hz, 1H), 8.11 (br. s, 1H), 7.93 (d, J = 8.5 Hz, 1H), 7.87 (br. s, 1H), 6.82 (d, J = 1.2 Hz, 1H), 5.14-5.22 (m, 1H), 3.61-3.81 (m, 2H), 2.90-3.09 (m, 4H), 1.76-1.84 (m, 1H), 1.66-1.73 (m, 1H), 1.64 (d, J = 6.7 Hz, 3H), 1.38-1.47 (m, 1H), 1.22-1.31 (m, 1H); one methoxy, and one methine unit not observed. |
| 624 | 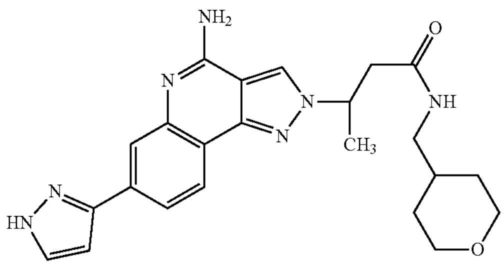 [SMILES: CC(CC(=O)NCC1CCOCC1)n1cc2c(N)nc3cc(-c4cc[nH]n4)ccc3c2n1] | 434.1 | 1.26 | δ 8.56 (s, 1H), 8.42 (t, J = 5.6 Hz, 1H), 8.10 (dd, J = 8.2, 2.1 Hz, 1H), 7.90 (s, 1H), 7.74 (d, J = 0.6 Hz, 1H), 7.66 (d, J = 8.6 Hz, 1H), 6.77 (d, J = 1.8 Hz, 1H), 5.92 (tt, J = 56, 3.7 Hz, 1H), 5.05-5.13 (m, 1H), 2.87-3.77 (m, integration indistinct due to water suppression), 1.67-1.82 (m, 2H), 1.62 (d, J = 6.7 Hz, 3H), 1.13-1.45 (m, 3H) |

Evaluation of Biological Activity

Measurement of IL-1β Production in PMA-Differentiated THP-1 Cells

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 μg/ml), and maintained in log phase prior to experimental setup. Prior to the experiment THP-1 were treated with PMA (Phorbol 12-myristate 13-acetate) (10 μg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of $1\times10^6$ cells/ml, and 100 μl was plated in a 96 well plate. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1 Production in PMA-Differentiated THP-1 Cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 μg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 μg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 μM in assay.

THP-1 cells in RPMI (Gibco, 11875) media with 10% FBS at a density of $1\times10^6$ cell/ml in a T175 flask were treated with a final concentration of phorbol 12-myristate 13-acetate (PMA) (Sigma, P1585) of 50 ng/ml overnight at 37° C. at 5% $CO_2$ for differentiation. Cells were harvested the next day after rinsing well with dPBS using 0.5% trypsin. A cell solution was prepared of $1\times10^6$ cells/ml for 50,000 cells in 50 μl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% $CO_2$ for 2 hours.

After the 2 hour incubation, the cell plates were spun in the centrifuge for 5 minutes at 1200 rpm. Using the Felix (CyBio), 8 μl of the supernatant was transferred to 384 well, low volume, white proxy plates. (Perkin Elmer, 6008230). A human IL1beta hTRF kit was used to analyze the supernatant (CISBIO, 62HIL1BPEG). The kit instructions were followed for preparing the IL1Beta standard curve and then the antibodies from the kit were diluted 1:40 rather than 1:20 as kit instructed. Once combined, the antibodies were added across the plates, 5 μl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100 nl/well using an ECHO 550 acoustic dispenser (Labcyte) to achieve final starting concentration of 10 uM in assay.

Human venous whole blood obtained from healthy donors was pre-treated with LPS (Invivogen, Cat #tlrl-eblps) at 1 ng/ml for four hours at 37° C. in a humidified 95% air/5% $CO_2$ incubator. Primed blood was added to the compound plate and incubated for additional 4 hours at 37° C. IL-1beta in the supernatants was measured using AlphLISA kit (Cat #AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from C57BL/6 mice were obtained from Ericke Latz, University of Bonn/University of Massachusetts Worchester, MA. The cells were harvested using 0.05% Trypsin and washed with PBS. Cell were plated at 30,000 cells per well in 25 ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5 ul/well and cells were incubated for 2 hours at 37° C. at 5% $CO_2$.

Serial dilutions of compounds in DMSO were added to cells in low volume 384 well plates at 60 nl/well using an ECHO 550 acoustic dispenser (Labcyte) to achieve final starting concentration of 50 uM in assay and incubated with compounds for additional 2 hours at 37° C. at 5% $CO_2$.

After the 2 hour incubation, the cell plates were spun in the centrifuge for 5 minutes at 1200 rpm. Using the Felix (CyBio), 8 ul of the supernatant was transferred to 384 well, low volume, white proxy plates. (Perkin Elmer, 6008230). A human IL1beta hTRF kit was used to analyze the supernatant (CISBIO, 62MIL1BPEH). The kit instructions were followed for preparing the IL1Beta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to μg/ml of Il1Beta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, CA) reporter gene are added to individual wells of a 384-well plate (15,000 cells per 20 μL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, CA) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 μM of the reference standard.

Table 1 includes biological data of compounds that were assayed using one or more of the above procedures. Key to activity ranges: A=≤1 μM; B=>1 μM, ≤20 μM; C=> 20 μM, ≤100 μM; D=>100 μM.

TABLE 1

| Ex. No. | NLRP3 hIL1B $EC_{50}$ (μM) | TLR7 Agonist $EC_{50}$ (μM) | TLR8 Agonist $EC_{50}$ (μM) |
| --- | --- | --- | --- |
| 1 | 0.45 | D | D |
| 2 | 0.43 | C | C |
| 3 | 0.56 | D | D |
| 4 | 16.8 | D | D |
| 5 | 0.35 | D | D |
| 6 | 0.56 | D | D |
| 7 | 0.42 | D | D |
| 8 | 0.89 | D | D |
| 9 | 0.57 | D | D |
| 10 | 1.00 | C | B |
| 11 | 2.09 | C | D |
| 12 | 1.52 | C | C |
| 13 | 1.78 | C | D |
| 14 | 1.68 | C | C |
| 15 | 1.81 | C | D |
| 16 | 11.3 | C | D |
| 17 | 2.20 | C | D |
| 18 | 1.13 | C | D |
| 19 | 3.88 | C | C |
| 20 | 1.08 | C | D |
| 21 | 2.08 | C | D |
| 22 | 0.63 | C | D |
| 23 | 1.39 | D | D |
| 24 | 2.90 | D | D |
| 25 | 0.26 | D | D |
| 26 | 0.98 | D | D |
| 27 | 0.43 | D | D |
| 28 | 1.31 | D | D |
| 29 | 6.01 | D | D |
| 30 | 0.77 | D | D |
| 31 | 0.15 | C | B |
| 32 | 14.7 | B | D |
| 33 | 11.8 | D | D |
| 34 | 8.85 | C | D |
| 35 | 20.7 | C | D |
| 36 | 1.38 | C | D |
| 37 | 0.95 | D | D |
| 38 | 4.93 | D | D |
| 39 | 0.25 | D | C |
| 40 | 0.78 | D | D |
| 41 | 0.80 | D | D |
| 42 | 0.67 | D | D |
| 43 | 0.46 | D | D |
| 44 | 0.63 | D | D |
| 45 | 1.41 | D | D |
| 46 | 4.19 | D | D |
| 47 | 23.3 | D | D |
| 48 | 5.20 | D | D |
| 49 | 0.61 | D | C |
| 50 | 1.43 | D | D |
| 51 | 18.8 | D | D |
| 52 | 0.62 | D | D |
| 53 | 0.45 | D | D |
| 54 | 0.19 | C | D |
| 55 | 0.39 | C | C |
| 56 | 0.31 | C | B |
| 57 | 2.21 | D | D |
| 58 | 0.30 | D | B |
| 59 | 0.47 | D | D |
| 60 | 0.27 | D | D |
| 61 | 0.12 | C | D |
| 62 | 0.28 | C | D |
| 63 | 1.61 | D | D |
| 64 | 0.48 | D | D |
| 65 | 0.35 | D | C |
| 66 | 0.80 | D | D |

TABLE 1-continued

| Ex. No. | NLRP3 hILIB EC$_{50}$ (μM) | TLR7 Agonist EC$_{50}$ (μM) | TLR8 Agonist EC$_{50}$ (μM) |
|---|---|---|---|
| 67 | 0.38 | D | D |
| 68 | 0.37 | D | C |
| 69 | 0.70 | D | D |
| 70 | 1.83 | D | D |
| 71 | 0.81 | C | C |
| 72 | 0.14 | C | C |
| 73 | 2.96 | D | D |
| 74 | 0.25 | D | C |
| 75 | 0.64 | D | D |
| 76 | 0.33 | D | D |
| 77 | 1.68 | D | D |
| 78 | 4.71 | D | D |
| 79 | 1.59 | D | D |
| 80 | 2.07 | D | C |
| 81 | 0.68 | D | C |
| 82 | 0.73 | D | C |
| 83 | 0.36 | D | D |
| 84 | 1.79 | D | D |
| 85 | 0.40 | C | C |
| 86 | 2.77 | D | D |
| 87 | 1.03 | D | D |
| 88 | 0.13 | C | C |
| 89 | 0.12 | D | B |
| 90 | 0.08 | C | C |
| 91 | 1.17 | D | C |
| 92 | 1.07 | D | D |
| 93 | 0.63 | D | D |
| 94 | 0.21 | D | C |
| 95 | 0.09 | D | D |
| 96 | 0.31 | D | C |
| 97 | 0.23 | D | D |
| 98 | 1.59 | D | D |
| 99 | 0.46 | C | D |
| 100 | 1.67 | D | D |
| 101 | 2.39 | D | D |
| 102 | 0.41 | C | C |
| 103 | 0.65 | D | D |
| 104 | 0.13 | C | B |
| 105 | 0.98 | C | D |
| 106 | 1.91 | C | C |
| 107 | 2.63 | D | D |
| 108 | 0.91 | C | C |
| 109 | 1.78 | C | C |
| 110 | 13.1 | C | B |
| 111 | 2.09 | C | D |
| 112 | 2.50 | D | D |
| 113 | 3.83 | C | D |
| 114 | 4.84 | D | D |
| 115 | 7.76 | D | D |
| 116 | 7.43 | D | D |
| 117 | 0.57 | D | C |
| 118 | 0.86 | D | D |
| 119 | 9.02 | D | D |
| 120 | 1.87 | D | C |
| 121 | 0.85 | D | D |
| 122 | 5.99 | D | D |
| 123 | 9.02 | D | D |
| 124 | 9.76 | D | D |
| 125 | 8.34 | D | D |
| 126 | 5.34 | D | D |
| 127 | 1.05 | D | D |
| 128 | 0.36 | D | D |
| 129 | 0.70 | D | D |
| 130 | 0.64 | D | D |
| 131 | 0.61 | D | D |
| 132 | 0.34 | D | C |
| 133 | 0.30 | D | D |
| 134 | 0.37 | C | D |
| 135 | 0.98 | D | D |
| 136 | 0.16 | C | D |
| 137 | 1.67 | D | D |
| 138 | 3.92 | D | D |
| 139 | 7.80 | D | D |
| 140 | 1.65 | D | D |
| 141 | 6.28 | D | A |
| 142 | 1.50 | D | C |
| 143 | 0.40 | D | D |
| 144 | 0.66 | D | D |
| 145 | 2.74 | D | D |
| 146 | 7.94 | | |
| 147 | 6.09 | D | D |
| 148 | 2.03 | | |
| 149 | 0.38 | D | D |
| 150 | 0.07 | D | D |
| 151 | 0.06 | D | D |
| 152 | 3.79 | | |
| 153 | 0.70 | D | D |
| 154 | 1.00 | D | D |
| 155 | 0.01 | D | D |
| 156 | 0.31 | D | D |
| 157 | 5.17 | D | D |
| 158 | 0.97 | D | C |
| 159 | 0.68 | D | D |
| 160 | 0.70 | D | D |
| 161 | 5.82 | D | D |
| 162 | 1.22 | D | D |
| 163 | 0.06 | D | D |
| 164 | 0.25 | D | D |
| 165 | 0.14 | D | C |
| 166 | 0.31 | D | D |
| 167 | 0.15 | D | D |
| 168 | 0.20 | D | C |
| 169 | 0.39 | D | C |
| 170 | 1.98 | D | D |
| 171 | 0.60 | D | D |
| 172 | 0.21 | D | D |
| 173 | 0.21 | D | B |
| 174 | 0.23 | B | C |
| 175 | 0.29 | D | D |
| 176 | 0.05 | C | C |
| 177 | 2.23 | D | D |
| 178 | 1.44 | D | D |
| 179 | 25.83 | D | D |
| 180 | 36.67 | D | D |
| 181 | 6.53 | D | D |
| 182 | 1.27 | D | D |
| 183 | 0.11 | D | C |
| 184 | 0.10 | D | |
| 185 | 0.21 | B | D |
| 186 | 0.21 | B | D |
| 187 | 0.22 | D | D |
| 188 | 0.21 | D | D |
| 189 | 0.59 | D | D |
| 190 | 0.22 | D | D |
| 191 | 7.19 | D | D |
| 192 | 0.09 | D | D |
| 193 | 0.24 | C | C |
| 194 | 0.22 | D | D |
| 195 | 2.15 | D | C |
| 196 | 0.18 | D | D |
| 197 | 0.25 | D | D |
| 198 | 0.11 | D | D |
| 199 | 4.44 | D | D |
| 200 | 0.57 | D | D |
| 201 | 0.48 | D | D |
| 202 | 0.66 | D | D |
| 203 | 3.49 | D | D |
| 204 | 2.60 | D | D |
| 205 | 2.04 | D | D |
| 206 | 0.26 | D | D |
| 207 | 0.14 | D | D |
| 208 | 0.49 | D | D |
| 209 | 0.19 | D | D |
| 210 | 0.33 | D | D |
| 211 | 0.63 | D | D |
| 212 | 4.37 | D | D |
| 213 | 3.21 | D | D |
| 214 | 4.55 | D | D |
| 215 | 0.40 | D | D |
| 216 | 3.04 | D | D |
| 217 | 1.17 | D | D |
| 218 | 0.20 | D | D |

TABLE 1-continued

| Ex. No. | NLRP3 hIL1B EC$_{50}$ (μM) | TLR7 Agonist EC$_{50}$ (μM) | TLR8 Agonist EC$_{50}$ (μM) |
|---|---|---|---|
| 219 | 0.30 | D | D |
| 220 | 0.12 | D | D |
| 221 | 0.21 | D | D |
| 222 | 0.27 | D | D |
| 223 | 0.45 | D | D |
| 224 | 0.14 | D | D |
| 225 | 0.20 | D | D |
| 226 | 0.44 | D | D |
| 227 | 1.81 | D | D |
| 228 | 0.30 | D | D |
| 229 | 0.08 | D | D |
| 230 | 0.87 | D | D |
| 231 | 1.21 | D | D |
| 232 | 1.87 | D | D |
| 233 | 1.44 | D | D |
| 234 | 0.56 | D | D |
| 235 | 12.51 | D | D |
| 236 | 0.79 | D | D |
| 237 | 0.09 | D | D |
| 238 | 0.72 | D | D |
| 239 | 0.21 | D | D |
| 240 | 0.62 | D | D |
| 241 | 0.46 | D | D |
| 242 | 0.68 | D | D |
| 243 | 1.39 | D | D |
| 244 | 1.80 | D | D |
| 245 | 0.94 | D | D |
| 246 | 0.58 | D | D |
| 247 | 0.44 | D | D |
| 248 | 0.65 | D | D |
| 249 | 0.64 | D | D |
| 250 | 1.95 | D | D |
| 251 | 0.62 | D | D |
| 252 | 1.13 | D | D |
| 253 | 0.30 | D | D |
| 254 | 20.29 | D | D |
| 255 | 10.92 | D | D |
| 256 | 0.53 | D | D |
| 257 | 0.86 | D | D |
| 258 | 1.78 | D | D |
| 259 | 2.29 | D | D |
| 260 | 5.76 | D | D |
| 261 | 1.29 | D | D |
| 262 | 0.75 | D | D |
| 263 | 1.66 | D | D |
| 264 | 0.99 | D | D |
| 265 | 2.47 | D | D |
| 266 | 2.62 | D | D |
| 267 | 1.07 | D | D |
| 268 | 4.50 | D | D |
| 269 | 4.38 | D | D |
| 270 | 5.18 | D | D |
| 271 | 1.07 | D | D |
| 272 | 5.13 | D | D |
| 273 | 5.16 | D | D |
| 274 | 0.60 | D | D |
| 275 | 1.73 | D | D |
| 276 | 31.66 | D | D |
| 277 | 2.33 | D | D |
| 278 | 0.75 | D | D |
| 279 | 1.13 | D | D |
| 280 | 1.72 | D | D |
| 281 | 0.24 | D | D |
| 282 | 0.10 | D | D |
| 283 | 0.12 | D | D |
| 284 | 0.25 | D | D |
| 285 | 0.63 | D | D |
| 286 | 0.41 | D | D |
| 287 | 0.26 | D | D |
| 288 | 0.45 | D | D |
| 289 | 0.28 | B | D |
| 290 | 0.87 | D | D |
| 291 | 4.65 | D | D |
| 292 | 0.89 | D | D |
| 293 | 0.60 | D | D |
| 294 | 0.43 | D | D |
| 295 | 0.42 | D | D |
| 296 | 1.70 | D | D |
| 297 | 2.83 | D | D |
| 298 | 4.32 | D | D |
| 299 | 2.92 | D | D |
| 300 | 7.36 | D | D |
| 301 | 1.40 | D | D |
| 302 | 3.49 | D | D |
| 303 | 0.21 | D | D |
| 304 | 0.66 | D | D |
| 305 | 0.29 | D | D |
| 306 | 1.26 | D | D |
| 307 | 0.43 | D | D |
| 308 | 0.41 | D | D |
| 309 | 0.75 | D | D |
| 310 | 0.75 | D | D |
| 311 | 0.71 | D | D |
| 312 | 0.22 | D | D |
| 313 | 0.26 | D | D |
| 314 | 0.49 | D | D |
| 315 | 0.89 | D | D |
| 316 | 0.89 | D | D |
| 317 | 2.42 | D | D |
| 318 | 3.09 | D | D |
| 319 | 1.13 | D | D |
| 320 | 6.57 | D | D |
| 321 | 0.19 | D | D |
| 322 | 0.83 | D | D |
| 323 | 0.78 | D | D |
| 324 | 1.57 | D | D |
| 325 | 1.49 | D | D |
| 326 | 0.22 | D | D |
| 327 | 0.70 | D | D |
| 328 | 1.35 | D | D |
| 329 | 0.31 | D | D |
| 330 | 0.17 | D | D |
| 331 | 0.08 | D | D |
| 332 | 0.21 | D | D |
| 333 | 0.24 | D | D |
| 334 | 0.11 | D | D |
| 335 | 0.39 | D | D |
| 336 | 0.47 | D | D |
| 337 | 0.22 | D | D |
| 338 | 0.39 | D | D |
| 339 | 0.21 | D | D |
| 340 | 0.62 | D | D |
| 341 | 0.43 | D | D |
| 342 | 0.34 | D | D |
| 343 | 0.61 | D | D |
| 344 | 1.02 | D | D |
| 345 | 2.03 | D | D |
| 346 | 0.65 | D | D |
| 347 | 0.30 | D | D |
| 348 | 0.62 | D | D |
| 349 | 0.35 | D | D |
| 350 | 0.35 | D | D |
| 351 | 0.64 | D | D |
| 352 | 0.08 | D | D |
| 353 | 0.61 | D | D |
| 354 | 0.30 | D | D |
| 355 | 2.57 | D | D |
| 356 | 0.83 | D | D |
| 357 | 0.19 | D | D |
| 358 | 0.18 | D | D |
| 359 | 1.45 | D | D |
| 360 | 0.11 | D | D |
| 361 | 0.19 | D | D |
| 362 | 0.07 | D | D |
| 363 | 1.84 | D | D |
| 364 | 1.47 | D | D |
| 365 | 1.88 | D | D |
| 366 | 0.42 | D | D |
| 367 | 0.23 | D | D |
| 368 | 0.52 | D | D |
| 369 | 0.19 | D | D |
| 370 | 0.38 | D | D |

TABLE 1-continued

| Ex. No. | NLRP3 hIL1B EC$_{50}$ (μM) | TLR7 Agonist EC$_{50}$ (μM) | TLR8 Agonist EC$_{50}$ (μM) |
|---|---|---|---|
| 371 | 1.94 | D | D |
| 372 | 0.88 | D | D |
| 373 | 1.25 | D | D |
| 374 | 0.65 | D | D |
| 375 | 4.12 | D | D |
| 376 | 0.40 | D | D |
| 377 | 0.45 | D | D |
| 378 | 0.64 | D | D |
| 379 | 0.32 | D | D |
| 380 | 0.77 | D | D |
| 381 | 0.74 | D | D |
| 382 | 5.39 | D | D |
| 383 | 1.38 | D | D |
| 384 | 0.88 | D | D |
| 385 | 2.51 | D | D |
| 386 | 0.21 | D | D |
| 387 | 2.30 | D | D |
| 388 | 0.31 | D | D |
| 389 | 0.91 | D | D |
| 390 | 0.35 | D | D |
| 391 | 0.20 | D | D |
| 392 | 0.08 | D | D |
| 393 | 1.73 | D | D |
| 394 | 0.46 | D | D |
| 395 | 0.07 | D | D |
| 396 | 0.65 | D | D |
| 397 | 0.34 | B | D |
| 398 | 1.55 | D | D |
| 399 | 0.23 | D | D |
| 400 | 1.22 | D | D |
| 401 | 2.66 | D | D |
| 402 | 0.31 | D | D |
| 403 | 3.78 | D | D |
| 404 | 0.74 | D | D |
| 405 | 0.69 | D | D |
| 406 | 0.45 | D | D |
| 407 | 0.50 | D | D |
| 408 | 1.94 | D | D |
| 409 | 1.47 | D | D |
| 410 | 0.33 | D | D |
| 411 | 0.64 | D | D |
| 412 | 1.87 | D | D |
| 413 | 1.92 | D | D |
| 414 | 2.80 | D | D |
| 415 | 1.89 | D | D |
| 416 | 0.15 | D | D |
| 417 | 0.16 | D | D |
| 418 | 3.65 | D | D |
| 419 | 0.35 | D | D |
| 420 | 0.51 | D | D |
| 421 | 0.46 | D | D |
| 422 | 0.14 | D | D |
| 423 | 0.62 | D | D |
| 424 | 3.21 | D | D |
| 425 | 5.73 | D | D |
| 426 | 1.89 | D | D |
| 427 | 2.01 | D | D |
| 428 | 1.81 | D | D |
| 429 | 12.96 | D | D |
| 430 | 1.90 | D | D |
| 431 | 1.23 | D | D |
| 432 | 3.19 | D | D |
| 433 | 4.58 | D | D |
| 434 | 4.35 | D | D |
| 435 | 3.61 | D | D |
| 436 | 2.75 | D | D |
| 437 | 0.56 | D | D |
| 438 | 0.99 | D | D |
| 439 | 0.32 | D | D |
| 440 | 0.13 | D | D |
| 441 | 1.33 | D | D |
| 442 | 0.19 | D | D |
| 443 | 0.23 | D | D |
| 444 | 0.26 | D | D |
| 445 | 0.66 | D | D |
| 446 | 0.20 | D | D |
| 447 | 0.38 | D | D |
| 448 | 1.78 | D | D |
| 449 | 0.70 | D | D |
| 450 | 0.53 | D | D |
| 451 | 1.26 | D | D |
| 452 | 0.40 | D | D |
| 453 | 0.31 | D | D |
| 454 | 0.37 | D | D |
| 455 | 0.22 | D | D |
| 456 | 0.23 | D | D |
| 457 | 0.16 | D | D |
| 458 | 0.16 | D | D |
| 459 | 0.27 | D | D |
| 460 | 0.20 | D | D |
| 461 | 0.25 | D | D |
| 462 | 0.22 | D | D |
| 463 | 0.13 | D | D |
| 464 | 0.24 | D | D |
| 465 | 1.90 | D | D |
| 466 | 0.61 | D | D |
| 467 | 0.94 | D | D |
| 468 | 1.62 | D | D |
| 469 | 0.84 | D | D |
| 470 | 15.35 | D | D |
| 471 | 0.75 | D | D |
| 472 | 0.23 | D | D |
| 473 | 0.49 | D | D |
| 474 | 0.45 | D | D |
| 475 | 1.21 | D | D |
| 476 | 0.51 | D | D |
| 477 | 0.27 | D | D |
| 478 | 0.35 | D | D |
| 479 | 0.08 | D | D |
| 480 | 0.26 | D | D |
| 481 | 0.38 | D | D |
| 482 | 2.21 | D | D |
| 483 | 1.10 | D | D |
| 484 | 1.41 | D | D |
| 485 | 0.08 | D | D |
| 486 | 0.13 | D | D |
| 487 | 0.37 | D | D |
| 488 | 1.15 | D | D |
| 489 | 0.77 | D | D |
| 490 | 0.84 | D | D |
| 491 | 1.17 | D | D |
| 492 | 0.76 | D | D |
| 493 | 0.18 | D | D |
| 494 | 1.89 | D | D |
| 495 | 0.45 | D | D |
| 496 | 0.05 | D | D |
| 497 | 0.05 | D | D |
| 498 | 2.39 | D | D |
| 499 | 1.34 | D | D |
| 500 | 0.37 | D | D |
| 501 | 0.73 | D | D |
| 502 | 1.68 | D | D |
| 503 | 2.58 | D | D |
| 504 | 2.34 | D | D |
| 505 | 29.6 | D | D |
| 506 | 1.40 | D | D |
| 507 | 17.5 | D | D |
| 508 | 7.37 | D | D |
| 509 | 6.95 | D | D |
| 510 | 2.47 | D | D |
| 511 | 4.62 | D | D |
| 512 | 5.82 | D | D |
| 513 | 1.28 | D | D |
| 514 | 1.81 | D | D |
| 515 | 4.09 | D | D |
| 516 | 9.67 | D | D |
| 517 | 1.72 | D | D |
| 518 | 0.53 | D | D |
| 519 | 2.07 | D | D |
| 520 | 0.09 | D | D |
| 521 | 5.67 | D | D |
| 522 | 12.2 | D | D |

TABLE 1-continued

| Ex. No. | NLRP3 hILIB EC$_{50}$ (μM) | TLR7 Agonist EC$_{50}$ (μM) | TLR8 Agonist EC$_{50}$ (μM) |
|---|---|---|---|
| 523 | 7.30 | D | D |
| 524 | 2.03 | D | D |
| 525 | 20.2 | D | D |
| 526 | 0.70 | D | D |
| 527 | 0.40 | D | D |
| 528 | 0.51 | D | D |
| 529 | 0.87 | D | D |
| 530 | 0.68 | D | D |
| 531 | 1.68 | D | D |
| 532 | 0.34 | D | D |
| 533 | 2.28 | D | D |
| 534 | 0.71 | D | D |
| 535 | 0.96 | D | D |
| 536 | 3.58 | D | D |
| 537 | 2.75 | D | D |
| 538 | 0.60 | D | D |
| 539 | 18.5 | D | D |
| 540 | 3.13 | D | D |
| 541 | 0.65 | D | D |
| 542 | 1.58 | D | D |
| 543 | 2.03 | D | D |
| 544 | 4.36 | D | D |
| 545 | 1.79 | D | D |
| 546 | 3.27 | D | D |
| 547 | 5.30 | D | D |
| 548 | 0.78 | D | D |
| 549 | 3.95 | D | D |
| 550 | 5.01 | D | D |
| 551 | 2.24 | D | D |
| 552 | 9.89 | D | D |
| 553 | 2.11 | D | D |
| 554 | 0.46 | D | D |
| 555 | 0.33 | D | D |
| 556 | 1.82 | D | D |
| 557 | 0.42 | D | D |
| 558 | 0.63 | D | D |
| 559 | 0.60 | D | D |
| 560 | 0.36 | D | D |
| 561 | 0.95 | D | D |
| 562 | 0.70 | D | D |
| 563 | 9.21 | D | D |
| 564 | 15.5 | D | D |
| 565 | 4.18 | D | D |
| 566 | 27.6 | D | D |
| 567 | 0.97 | D | D |
| 568 | 2.10 | D | D |
| 569 | 0.94 | D | D |
| 570 | 5.13 | D | D |
| 571 | 2.02 | D | D |
| 572 | 4.41 | D | D |
| 573 | 6.59 | D | D |
| 574 | 14.0 | D | D |
| 575 | 19.7 | D | D |
| 576 | 1.61 | D | D |
| 577 | 2.32 | D | D |
| 578 | 18.6 | D | D |
| 579 | 4.47 | D | D |
| 580 | 20.1 | D | D |
| 581 | 3.17 | D | D |
| 582 | 3.30 | D | D |
| 583 | 1.82 | D | D |
| 584 | 5.03 | D | D |
| 585 | 3.88 | D | D |
| 586 | 2.18 | D | D |
| 587 | 2.39 | D | D |
| 588 | 10.9 | D | D |
| 589 | 2.62 | D | D |
| 590 | 1.20 | D | D |
| 591 | 17.0 | D | D |
| 592 | 0.68 | D | D |
| 593 | 28.1 | D | D |
| 594 | 7.94 | D | D |
| 595 | 12.9 | D | D |
| 596 | 10.1 | D | D |
| 597 | 8.70 | D | D |
| 598 | 1.98 | D | D |
| 599 | 2.18 | D | D |
| 600 | 3.99 | D | D |
| 601 | 32.4 | D | D |
| 602 | 21.2 | D | D |
| 603 | 3.05 | D | D |
| 604 | 0.85 | D | D |
| 605 | 22.4 | D | D |
| 606 | 2.46 | D | D |
| 607 | 13.4 | D | D |
| 608 | 0.70 | D | D |
| 609 | 18.1 | D | D |
| 610 | 4.41 | D | D |
| 611 | 9.94 | D | D |
| 612 | 0.43 | D | D |
| 613 | 23.4 | D | D |
| 614 | 11.6 | D | D |
| 615 | 10.4 | D | D |
| 616 | 9.56 | D | D |
| 617 | 3.88 | D | D |
| 618 | 14.5 | D | D |
| 619 | 19.7 | D | D |
| 620 | 28.6 | D | D |
| 621 | 1.86 | D | D |
| 622 | 7.28 | D | D |
| 623 | 17.3 | D | D |
| 624 | 19.9 | D | D |

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (I):

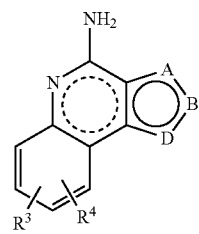

or a stereoisomer, a tautomer or a pharmaceutically acceptable salt thereof, wherein:

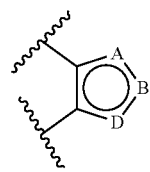

is independently selected from

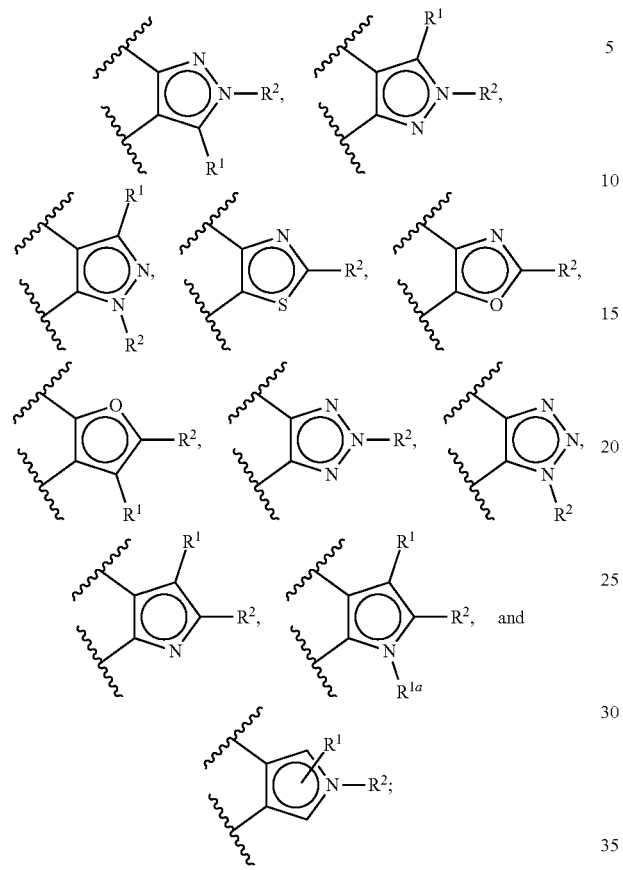

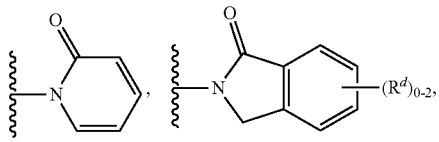

R¹ is, at each occurrence, independently:
(i) H;
(ii) halo;
(iii) X—R⁵, wherein X is $C_{1-6}$ alkylene, and R⁵ is H, OH, cyano, $C_{1-4}$ alkoxy, $C_{1-4}$ haloalkoxy, —C(O)OR$^a$, —NR$^b$R$^c$, or —C(O)NR$^b$R$^k$;
(iv) $C_{1-6}$ alkyl substituted with 1 to 6 F;
(v) $C_{3-6}$ cycloalkyl substituted with 0 to 6 F;
(vi) ($C_{1-3}$ alkylene)-aryl, wherein the aryl is substituted with 0 to 3 R$^d$; or
(vii) ($C_{1-3}$ alkylene)-heteroaryl including from 5 to 6 ring atoms, wherein from 1 to 4 ring atoms are each independently selected from N, N(R$^f$), O, and S, wherein the heteroaryl is substituted with 0 to 3 R$^d$;

R$^{1a}$ is independently H, $C_{1-6}$ alkyl substituted with 0 to 6 F, or $C_{3-6}$ cycloalkyl substituted with 0 to 6 F;

R² is, at each occurrence, independently:
(i) H;
(ii) —Y—R⁶;
(iii) —C(O)—Y—R⁶;
wherein:
Y is independently $C_{1-8}$ alkylene substituted with from 0 to 4 R$^e$; and
R⁶ is, at each occurrence, independently: H, OH, CN, OR$^a$, —C(O)R$^a$, —C(O)OR$^a$, —NR$^b$R$^c$, —C(O)NR$^b$R$^k$, SO$_{1-2}$R$^h$, or heteroaryl including from 5 to 10 ring atoms, wherein from 1-4 ring atoms are each independently selected from N, N(R$^f$), O, and S, wherein the heteroaryl is substituted with from 0 to 3 R$^d$;

(iv) —(Y¹)$_n$—Y²—(Y³)$_p$—R⁷, wherein:
n is independently 0, 1 or 2;
p is independently 0 or 1;
each of Y¹ and Y³ is, independently, $C_{1-3}$ alkylene substituted with from 0 to 2 R$^e$;
Y² is independently $C_{3-6}$ cycloalkylene substituted with from 0 to 4 R$^g$, or heterocycloalkylene including from 3-8 ring atoms, wherein from 1-2 ring atoms are each independently selected from N, N(R$^f$) and O, and wherein the heterocycloalkylene is substituted with from 0 to 4 R$^g$, and
R⁷ is H, OH, —OR$^a$, —C(O)OR$^a$, —NR$^b$R$^c$, —C(O)NR$^b$R$^k$, or heteroaryl including from 5-6 ring atoms, wherein from 1-4 ring atoms are each independently selected from N, N(R$^f$), O, and S, and wherein the heteroaryl is substituted with from 0 to 4 R$^g$;
or
(v) —Z¹—Z²—Z³—R⁸, wherein:
Z¹ is $C_{1-3}$ alkylene substituted with from 0 to 6 F;
Z² is —N(R$^f$)—, —O—, or —S—;
Z³ is $C_{2-5}$ alkylene substituted with from 0 to 6 F; and
R⁸ is OH, OR$^a$, —C(O)R$^a$, —C(O)OR$^a$; —NR$^b$R$^c$, —C(O)NR$^b$R$^k$, or heteroaryl including from 5-6 ring atoms, wherein from 1-4 ring atoms are each independently selected from N, N(R$^f$), O, and S, wherein the heteroaryl is substituted with from 0 to 3 R$^d$;

R³ is independently halo or —($C_{0-3}$ alkylene)-(5-membered heteroaryl) wherein the heteroaryl includes 1 to 4 ring carbon atoms and 1 to 4 ring heteroatoms are each independently selected from: N, N(R$^f$), O, and S, and is substituted with from 0 to 3 R$^g$; provided that when R³ is furanyl, R² is other than $C_{1-4}$ alkyl;

R⁴ is independently selected from: H, halo, cyano, OH, $C_{1-4}$ alkoxy, $C_{1-4}$ haloalkyl, $C_{1-4}$ haloalkoxy, —C(O)OH, —C(O)OR$^a$, —NR$^j$R$^k$, —C(O)NR$^j$R$^k$, —SO$_{1-2}$R$^h$, and $C_{1-4}$ alkyl substituted with from 0 to 2 R$^e$;

R$^a$ is, at each occurrence, independently:
(i) $C_{1-6}$ alkyl substituted with from 0 to 3 R$^e$;
(ii) —($C_{0-3}$ alkylene)-$C_{3-6}$ cycloalkyl, wherein the cycloalkyl is substituted with from 0 to 4 R$^g$;
(iii) —($C_{0-3}$ alkylene)-heterocyclyl including from 3 to 10 ring atoms, wherein from 1 to 3 ring atoms are each independently selected from N(R$^f$), O, and S(O$_{0-2}$, wherein the heterocyclyl is substituted with from 0 to 4 R$^g$;
(iv) —($C_{0-3}$ alkylene)-($C_{6-10}$ aryl), wherein the aryl is substituted with from 0 to 5 R$^d$; or
(v) —($C_{0-3}$ alkylene)-heteroaryl including from 5 to 10 ring atoms, wherein from 1 to 4 ring atoms are each independently selected from N, N(R$^f$), O, and S, wherein the heteroaryl is substituted with from 0 to 3 R$^d$;

R$^b$ is, at each occurrence, independently H or R$^a$;
R$^c$ is, at each occurrence, independently selected from: H, —C(O)R$^a$, —C(O)OR$^a$, —C(O)NR$^j$R$^k$, —S(O)$_{1-2}$R$^h$, C$_{1-6}$ alkyl substituted with from 0 to 2 R$^e$, —(C$_{0-3}$ alkylene)-(phenyl substituted with from 0 to 4 R$^n$), and —(C$_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 R$^n$;

alternatively, R$^b$ and R$^e$, together with the nitrogen atom to which each is attached form heterocyclyl including from 3 to 10 ring atoms, wherein from 1 to 3 ring atoms are each independently selected from N(R$^f$), O, and S, and wherein the heterocyclyl is substituted with from 0 to 4 R$^g$;

R$^d$ is, at each occurrence, independently selected from: halo, OH, cyano, C$_{2-6}$ alkenyl, C$_{2-6}$ alkynyl, C$_{1-4}$ alkoxy, C$_{1-4}$ haloalkyl, C$_{1-4}$ haloalkoxy, —C(O)(C$_{1-4}$ alkyl), —C(O)OH, —C(O)O(C$_{1-4}$ alkyl), —NR$^j$R$^k$, —N(R$^m$)(C(O)(C$_{1-4}$ alkyl), —N(R$^m$)(C(O)O(C$_{1-4}$ alkyl), —C(O)NR$^j$R$^k$, —S(O)$_{1-2}$R$^h$, —S(O)$_{1-2}$NR$^h$R$^j$, C$_{1-6}$ alkyl substituted with from 0 to 2 R$^e$, and —(C$_{0-3}$ alkylene)-R$^p$;

R$^e$ is, at each occurrence, independently selected from: halo, OH, cyano, C$_{1-4}$ alkoxy, C$_{1-4}$ haloalkyl, C$_{1-4}$ haloalkoxy, —C(O)OR$^a$, —OC(O)R$^h$, —NR$^b$R$^c$, and —CONR$^b$R$^k$;

R$^f$ is, at each occurrence, independently selected from: H, OH, C$_{1-4}$ alkyl, C$_{1-4}$ alkoxy, —C(O)(C$_{1-4}$ alkyl), —C(O)(C$_{1-4}$ haloalkyl), —C(O)O(C$_{1-4}$ alkyl), —C(O)NR$^j$R$^k$, —S(O)$_{1-2}$R$^h$, and —(C$_{0-3}$ alkylene)-phenyl;

R$^g$ is, at each occurrence, independently oxo or R$^d$;

R$^h$ is, at each occurrence, independently selected from C$_{1-6}$ alkyl substituted with 0 to 2 R$^n$, C$_{1-4}$ haloalkyl, and —(C$_{0-3}$ alkylene)-R$^p$;

R$^j$ and R$^m$ are, at each occurrence, independently H or C$_{1-4}$ alkyl;

R$^k$ is, at each occurrence, independently selected from H, C$_{1-4}$ alkyl, and —(C$_{0-2}$ alkylene)-phenyl;

R$^n$ is, at each occurrence, independently selected from: halo, OH, C$_{1-6}$ alkyl, C$_{1-4}$ haloalkyl, C$_{1-4}$ alkoxy, C$_{1-4}$ haloalkoxy, cyano, —C(O)OH, —C(O)O(C$_{1-4}$ alkyl), —NR$^j$R$^k$, and —CONR$^j$R$^k$; and R$^p$ is, at each occurrence, independently selected from: C$_{3-6}$ cycloalkyl substituted with from 0 to 4 C$_{1-4}$ alkyl; heterocyclyl including from 3-10 ring atoms, wherein from 1 to 3 ring atoms are each independently selected from NH, N(C$_{1-4}$ alkyl), O, and S, wherein the heterocyclyl is substituted with 0 to 4 independently selected C$_{1-4}$ alkyl; phenyl substituted with 0 to 3 R$^n$; and heteroaryl including from 5 to 10 ring atoms, wherein from 1 to 4 ring atoms are each independently selected from N, NH, N(C$_{1-4}$ alkyl), O, and S, wherein the heteroaryl is substituted with 0 to 3 R$^n$.

2. A compound according to claim 1, wherein:
R$^3$ is independently —(C$_{0-3}$ alkylene)-(5-membered heteroaryl) wherein the heteroaryl includes 2 to 4 ring carbon atoms and 1 to 3 ring heteroatoms are each independently selected from: N, N(R$^f$), and S, and is substituted with 0 to 3 R$^9$; and
R$^6$ is, at each occurrence, independently selected from: OH, OR$^a$, —C(O)R$^a$, —C(O)OR$^a$, —NR$^b$R$^c$, —C(O)NR$^b$R$^k$, —SO$_2$(C$_{1-4}$ alkyl), and heteroaryl including from 5 to 6 ring atoms, wherein from 1 to 4 ring atoms are each independently selected from N, N(R$^f$), O, and S, wherein the heteroaryl is substituted with from 0 to 3 R$^d$.

3. A compound according to claim 2, wherein the compound is of Formula (IIa), (IIb), (IIc), (IId), (IIe), (IIf), (IIg), (IIh) or (IIi):

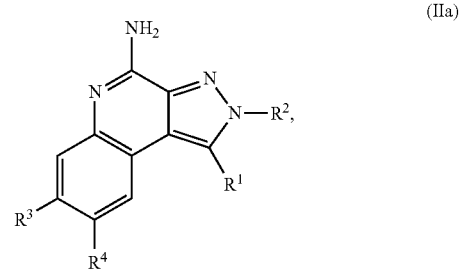

(IIa)

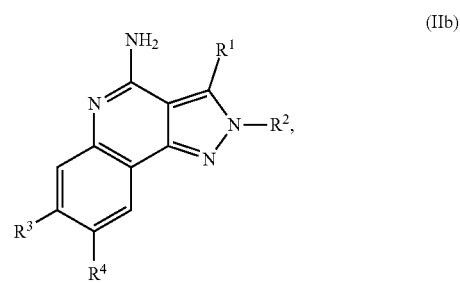

(IIb)

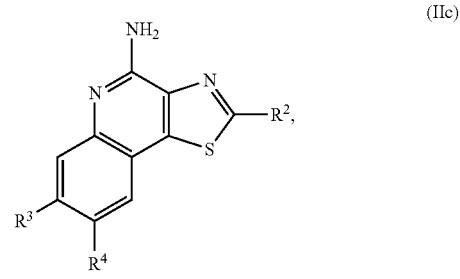

(IIc)

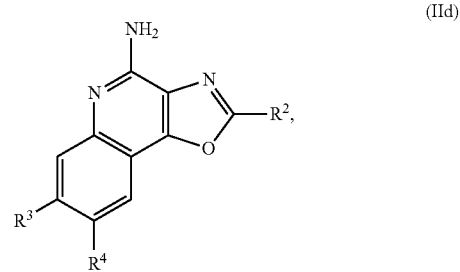

(IId)

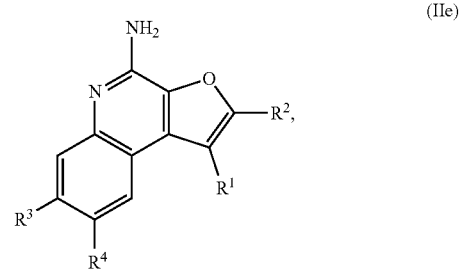

(IIe)

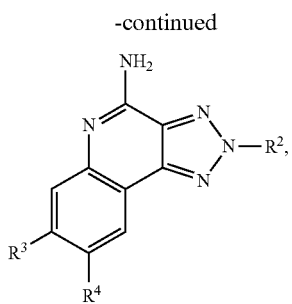

(IIf)

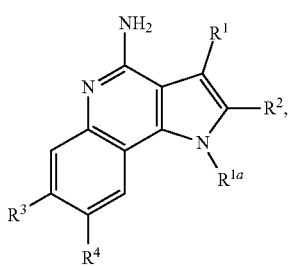

(IIg)

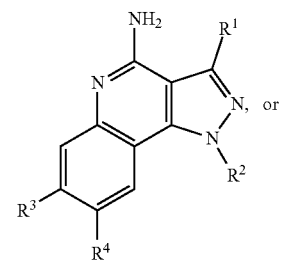

(IIh)

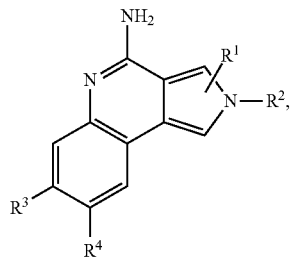

(IIi)

or a stereoisomer, a tautomer or a pharmaceutically acceptable salt thereof.

4. A compound according to claim 3, wherein:

$R^1$ is, at each occurrence, independently selected from H, halo and $C_{1-4}$ alkyl;

$R^2$ is, at each occurrence, independently selected from: H, $C_{1-4}$ alkylalkyl substituted with 0 to 3 F, —Y—$R^6$, —$(CH_2)_{1-3}O(CH_2)_{2-3}OR^a$, —$(CH_2)_{0-2}$—$Y^2$—$R^7$, and

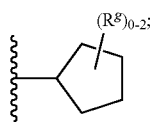

Y is independently $C_{1-6}$ alkylene substituted with from 0 to 3 $R^e$;

$R^3$ is, at each occurrence, independently —$(C_{0-2}$ alkylene)-(5-membered heteroaryl) wherein the heteroaryl includes 2 to 4 ring carbon atoms and 1 to 3 ring heteroatoms are each independently selected from: N, N($R^f$), and S, wherein the heteroaryl is substituted with from 0 to 2 $R^g$; provided that when $R^3$ is furanyl, $R^2$ is other than Ct-4 alkyl;

$R^4$ is, at each occurrence, independently selected from H, halo and $C_{1-4}$ alkyl;

$R^6$ is independently selected from: OH, CN, $OR^a$, —C(O)$R^a$, $NR^bR^c$, —C(O)$NR^bR^k$, —$SO_2(C_{1-4}$ alkyl),

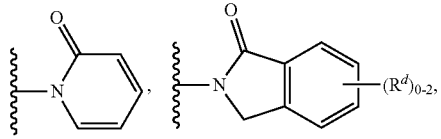

and heteroaryl including from 5 to 10 ring atoms, wherein from 1 to 4 ring atoms are each independently selected from N, N($R^f$), O, and S, wherein the heteroaryl is substituted with from 0 to 3 $R^d$;

—$Y^2$—$R^7$ is independently selected from $C_{3-6}$ cycloalkyl substituted with 0 to 2 $R^d$,

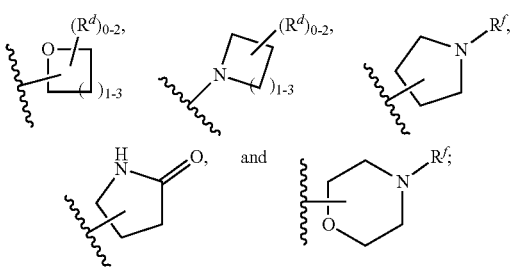

$R^a$ is, at each occurrence, independently:

(i) $C_{1-6}$ alkyl substituted with from 0 to 3 $R^e$;

(ii) $C_{3-6}$ cycloalkyl substituted with from 0 to 2 $R^g$;

(iii) —$(C_{0-2}$ alkylene)-heterocyclyl including from 4 to 10 ring atoms, wherein from 1 to 3 ring atoms are each independently selected from N($R^f$), O, and S, wherein the heterocyclyl is substituted with from 0 to 3 $R^g$;

(iv) —$(C_{0-2}$ alkylene)-($C_{6-10}$ aryl), wherein the aryl is substituted with from 0 to 3 $R^d$; or (v) —$(C_{0-2}$ alkylene)-heteroaryl including from 5 to 10 ring atoms, wherein from 1 to 3 ring atoms are each independently selected from N, N($R^f$), O, and S, wherein the heteroaryl is substituted with from 0 to 3 $R^d$;

$R^b$ is, at each occurrence, independently H or $R^a$;

$R^c$ is, at each occurrence, independently selected from: H, —C(O)$R^a$, —C(O)$OR^a$, —C(O)$NR^jR^k$, —S(O)$_2R^h$, $C_{1-6}$ alkyl substituted with from 0 to 2 $R^e$, —$(C_{0-3}$ alkylene)-(phenyl substituted with from 0 to 4 $R^n$), and —$(C_{0-3}$ alkylene)-heteroaryl including from 5-6 ring atoms, wherein from 1-4 ring atoms are each independently selected from N, N($R^f$), O, and S, wherein the heteroaryl is substituted with from 0 to 3 $R^n$;

alternatively, $R^b$ and $R^c$, together with the nitrogen atom to which each is attached form heterocyclyl including from 3 to 10 ring atoms, wherein from 1 to 3 ring atoms are each independently selected from N($R^f$), O, and S, and wherein the heterocyclyl is substituted with from 0 to 3 $R^g$;

$R^d$ is, at each occurrence, independently selected from: OH, halo, CN, $C_{1-4}$ alkoxy, $C_{1-4}$ haloalkyl, $C_{1-4}$ haloalkoxy, —C(O)O($C_{1-4}$ alkyl), $NH_2$, N($C_{1-4}$ alkyl)$_2$, —CONH$_2$, —CONH(C$_{1-4}$ alkyl), —NHC(O)(C$_{1-4}$ alkyl), —NHC(O)O(C$_{1-4}$ alkyl), —S(O)$_2$(C$_{1-4}$ alkyl), benzoxy, C$_{1-4}$ alkyl substituted with from 0 to 2 R$^e$, phenyl, and heteroaryl including from 5 to 6 ring atoms, wherein from 1 to 4 ring atoms are each independently selected from N, N(R$^f$), O, and S, wherein the heteroaryl is substituted with 0 to 2 R$^n$;

R$^e$ is, at each occurrence, independently selected from: halo, OH, CN, C$_{1-4}$ alkoxy, C$_{1-4}$ haloalkyl, C$_{1-4}$ haloalkoxy, —CONH$_2$, and —CONH(C$_{1-4}$ alkyl);

R$^f$ is, at each occurrence, independently selected from H, C$_{1-4}$ alkyl, —C(O)C$_{1-4}$ alkyl, and —C(O)(C$_{1-4}$ haloalkyl);

R$^g$ is, at each occurrence, independently oxo or R$^d$;

R$^h$ is independently C$_{1-4}$ alkyl substituted with 0 to 2 R$^n$, C$_{3-6}$ cycloalkyl, or phenyl;

R$^j$ is independently H or C$_{1-4}$ alkyl;

R$^k$ is independently selected from H, C$_{1-4}$ alkyl and phenyl; and

R$^n$ is, at each occurrence, independently selected from: halo, C$_{1-4}$ alkyl, and C$_{1-4}$ alkoxy.

5. A compound according to claim 4, wherein the compound is of Formula (IIa):

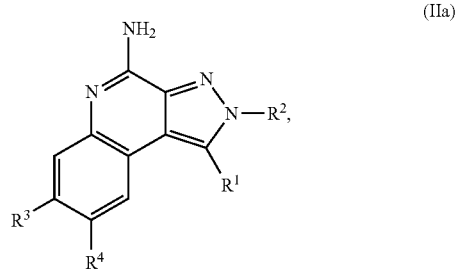

(IIa)

or a stereoisomer, a tautomer or a pharmaceutically acceptable salt thereof, wherein:

R$^1$ is independently selected from H, F and C$_{1-4}$ alkyl;

R$^2$ is independently selected from: H, C$_{1-4}$ alkyl substituted with 0 to 3 F, —(CH$_2$)$_{1-3}$—R$^6$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O(C$_{1-4}$ alkyl), —(CH$_2$)$_{1-3}$O(CH$_2$)$_{2-3}$OR$^a$, —CH$_2$CH(CH$_3$)NHC(O)R$^a$, and —(CH$_2$)$_{1-2}$—Y$^2$—R$^7$;

R$^3$ is independently 5-membered heteroaryl wherein the heteroaryl includes 3 to 4 ring carbon atoms and 1 to 2 ring heteroatoms are each independently selected from: N, NH, and S; provided that when R$^3$ is furanyl, R$^2$ is other than C$_{1-4}$ alkyl;

R$^4$ is independently selected from H, halo and C$_{1-4}$ alkyl;

R$^6$ is independently selected from: OH, OR$^a$, NR$^b$R$^c$, —NR$^b$C(O)R$^a$, —C(O)NR$^b$R$^k$, —NHC(O)OR$^a$, —NHC(O)NR$^j$R$^k$, —NHS(O)$_2$R$^h$, —SO$_2$(C$_{1-4}$ alkyl),

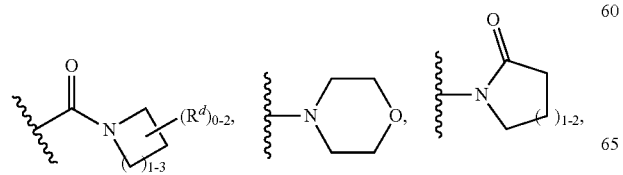

-continued

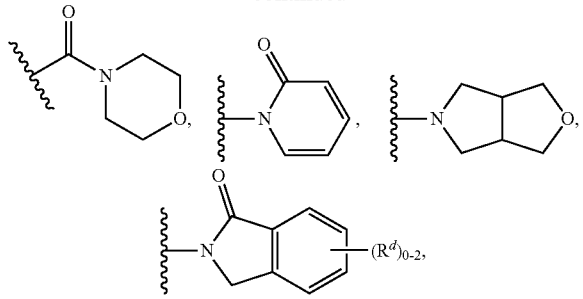

and heteroaryl including from 5 to 6 ring atoms, wherein from 1 to 4 ring atoms are each independently selected from N, N(R$^f$), O, and S, wherein the heteroaryl is substituted with from 0 to 3 R$^d$;

—Y$^2$—R$^7$ is independently selected from C$_{3-6}$ cycloalkyl substituted with 0 to 2 R$^d$,

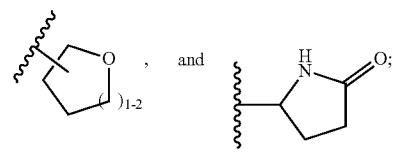

R$^a$ is, at each occurrence, independently selected from: C$_{1-4}$ alkyl substituted with 0 to 2 R$^e$, C$_{3-6}$ cycloalkyl,

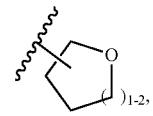

phenyl, benzyl, oxazolyl, isoxazolyl, thiazolyl, N—(C$_{1-4}$ alkyl)-pyrazolyl, pyrazol-1-yl, N—(C$_{1-4}$ alkyl)-imidazolyl, pyridyl, pyridazinyl, pyrimidyl, pyrazinyl, N—(C$_{1-4}$ alkyl)-benzimidazolyl, pyrazolo[1,5-a]pyrimidinyl and

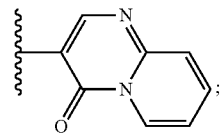 [SMILES: *c1cnc2ccccn2c1=O]

wherein each ring moiety is substituted with 0 to 3 R$^d$;

R$^b$ is, at each occurrence, independently H, C$_{1-4}$ alkyl, or phenyl substituted with 0 to 2 F;

R$^c$ is independently C$_{1-4}$ alkyl, —(C$_{0-3}$ alkylene)-(phenyl substituted with from 0 to 3 R$^n$), or —(C$_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 R$^n$;

R$^d$ is, at each occurrence, independently selected from: halo, CN, —CH$_2$OH, C$_{1-4}$ alkyl, C$_{1-4}$ alkoxy, C$_{1-4}$ haloalkyl, C$_{1-4}$ haloalkoxy, —C(O)O(C$_{1-4}$ alkyl), —CONH$_2$, NH$_2$, N(C$_{1-4}$ alkyl)$_2$, —NHC(O)(C$_{1-4}$ alkyl), —NHC(O)O(C$_{1-4}$ alkyl), —S(O)$_2$(C$_{1-4}$ alkyl), benzoxy, phenyl, and heteroaryl including from 5 to 6 ring atoms, wherein from 1 to 4 ring atoms are each independently selected from N, N(R$^f$), O, and S, wherein the heteroaryl is substituted with 0 to 2 R$^n$;

R$^e$ is, at each occurrence, independently selected from: halo, OH, C$_{1-4}$ alkoxy, C$_{1-4}$ haloalkyl, and C$_{1-4}$ haloalkoxy;

R$^f$ is, at each occurrence, independently H or C$_{1-4}$ alkyl;

R$^h$ is independently C$_{1-4}$ alkyl or phenyl;

R$^j$ is independently H or C$_{1-4}$ alkyl;

R$^k$ is independently selected from H, C$_{1-4}$ alkyl and phenyl; and

R$^n$ is, at each occurrence, independently selected from: halo, C$_{1-4}$ alkyl, and C$_{1-4}$ alkoxy.

6. A compound according to claim 5, wherein:

R$^1$ is H;

R$^2$ is independently selected from: H, C$_{1-4}$ alkyl substituted with 0 to 3 F, —(CH$_2$)$_{1-3}$—R$^6$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O(C$_{1-4}$ alkyl), —(CH$_2$)$_{1-3}$O(CH$_2$)$_{2-3}$OR$^a$, —CH$_2$CH(CH$_3$)NHC(O)R$^a$, and —(CH$_2$)$_{1-2}$—Y$^2$—R$^7$;

R$^3$ is independently selected from

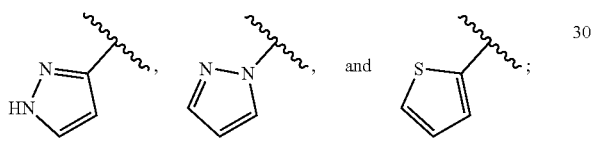

R$^4$ is independently H, F, or Cl;

R$^6$ is independently selected from: OH, OR$^a$, NR$^b$R$^c$, —NR$^b$C(O)R$^a$, —C(O)NR$^b$R$^k$, —NHC(O)O(C$_{1-6}$ alkyl), —NHC(O)OPh, —NHC(O)N(C$_{1-4}$ alkyl)$_2$, —NHC(O)N(C$_{1-4}$ alkyl)Ph, —NHS(O)$_2$(C$_{1-4}$ alkyl), —SO$_2$(C$_{1-4}$ alkyl),

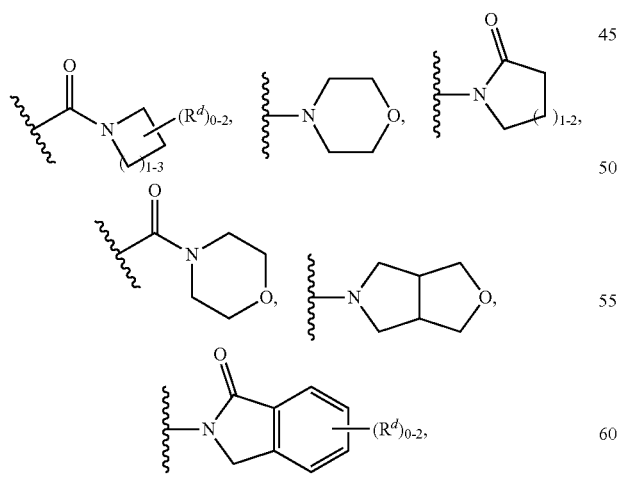

and heteroaryl including from 5 to 6 ring atoms, wherein from 1 to 4 ring atoms are each independently selected from N, N(R$^f$), O, and S, wherein the heteroaryl is substituted with from 0 to 3 R$^d$;

—Y$^2$—R$^7$ is independently selected from: C$_{3-6}$ cycloalkyl substituted with 0 to 2 R$^d$,

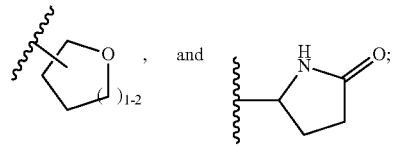

R$^a$ is, at each occurrence, independently selected from: C$_{1-4}$ alkyl substituted with 0 to 2 R$^e$, C$_{3-6}$ cycloalkyl,

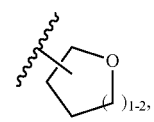

phenyl, benzyl, oxazolyl, isoxazolyl, thiazolyl, N—(C$_{1-4}$ alkyl)-pyrazolyl, pyrazol-1-yl, N—(C$_{1-4}$ alkyl)-imidazolyl, pyridyl, pyridazinyl, pyrimidyl, pyrazinyl, N—(C$_{1-4}$ alkyl)-benzimidazolyl, pyrazolo[1,5-a]pyrimidinyl and

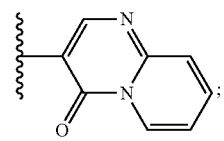 [SMILES: *c1cnc2ccccn2c1=O]

wherein each ring moiety is substituted with 0 to 3 R$^d$;

R$^b$ is, at each occurrence, independently H, C$_{1-4}$ alkyl, or phenyl substituted with 0 to 2 F;

R$^c$ is independently C$_{1-4}$ alkyl, —(C$_{0-3}$ alkylene)-(phenyl substituted with from 0 to 3 R$^n$), or —(C$_{0-3}$ alkylene)-heteroaryl including from 5-6 ring atoms, wherein from 1-4 ring atoms are each independently selected from N, N(R$^f$), O, and S, wherein the heteroaryl is substituted with from 0 to 3 R$^n$;

R$^d$ is, at each occurrence, independently selected from: F, Cl, CN, —CH$_2$OH, C$_{1-4}$ alkyl, C$_{1-4}$ alkoxy, C$_{1-4}$ haloalkyl, C$_{1-4}$ haloalkoxy, —C(O)O(C$_{1-4}$ alkyl), —CONH$_2$, NH$_2$, N(C$_{1-4}$ alkyl)$_2$, —NHC(O)(C$_{1-4}$ alkyl), —NHC(O)O(C$_{1-4}$ alkyl), —S(O)$_2$(C$_{1-4}$ alkyl), benzoxy, phenyl, and heteroaryl including from 5 to 6 ring atoms, wherein from 1 to 4 ring atoms are each independently selected from N, N(R$^f$), O, and S, wherein the heteroaryl is substituted with 0 to 2 R$^n$;

R$^e$ is, at each occurrence, independently selected from: F, Cl, OH, C$_{1-4}$ alkoxy, C$_{1-4}$ haloalkyl, and C$_{1-4}$ haloalkoxy;

R$^f$ is, at each occurrence, independently H or C$_{1-4}$ alkyl;

R$^k$ is independently selected from H, C$_{1-4}$ alkyl and phenyl;

R$^n$ is, at each occurrence, independently selected from: F, Cl, C$_{1-4}$ alkyl, and C$_{1-4}$ alkoxy.

7. A compound according claim 6, wherein:

R$^1$ is H;

R$^2$ is independently selected from: H, C$_{1-4}$ alkyl substituted with 0 to 3 F, —(CH$_2$)$_{1-3}$—R$^6$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O(C$_{1-4}$ alkyl), —CH$_2$CH(CH$_3$)NHC(O)R$^a$, and —(CH$_2$)$_{1-2}$—Y$^2$—R$^7$;

R$^3$ is independently

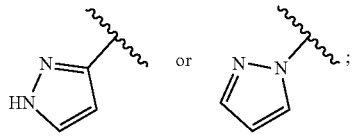 [SMILES: *c1cc[nH]n1 ; *n1cccn1]

R$^4$ is independently H, F, or Cl;
R$^6$ is independently selected from: OH, OR$^a$, N(C$_{1-4}$ alkyl)$_2$, —NH(C$_{1-4}$ alkyl), —NH(CH$_2$)$_{1-2}$(phenyl substituted with 0 to 1 R$^d$), —N(C$_{1-2}$ alkyl)Bn, —NH(pyridyl), —NR$^b$C(O)R$^a$, —NHC(O)O(C$_{1-6}$ alkyl), —NHC(O)OPh, —NHC(O)N(C$_{1-4}$ alkyl)$_2$, —NHC(O)CH$_2$OCH$_2$CF$_3$, —NHC(O)N(C$_{1-4}$ alkyl)Ph, —C(O)NH$_2$, —C(O)NH(C$_{1-4}$ alkyl substituted with 0 to 2 R$^e$), —C(O)N(CH$_3$)(C$_{1-4}$ alkyl substituted with 0 to 2 R$^e$), —C(O)NH(C$_{3-6}$ cycloalkyl), —C(O)NH(phenyl substituted with 0 to 1 F), —C(O)NH(pyridyl), —NHS(O)$_2$(C$_{1-4}$ alkyl), —SO$_2$(C$_{1-4}$ alkyl),

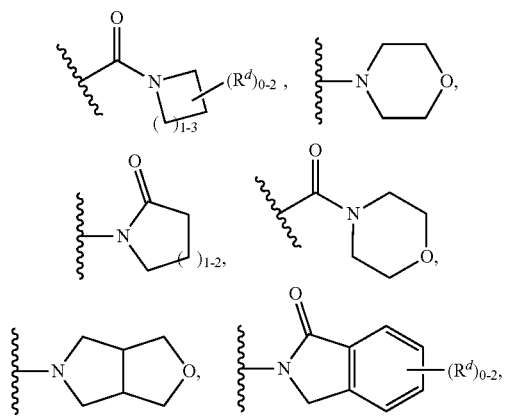

and heteroaryl selected from imidazolyl, pyrazolyl, oxazolyl, isoxazolyl, thiazolyl, oxadiazolyl and pyridyl, wherein the heteroaryl is substituted with 0 to 2 R$^d$;
—Y$^2$—R$^7$ is independently selected from: C$_{3-6}$ cycloalkyl substituted with 0 to 2 R$^d$,

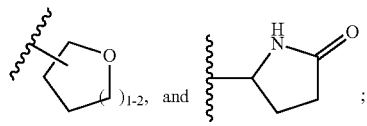

R$^a$ is, at each occurrence, independently selected from: C$_{1-4}$ alkyl substituted with 0 to 2 R$^e$, C$_{3-6}$ cycloalkyl,

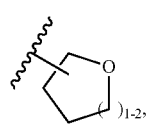

phenyl, oxazolyl, isoxazolyl, thiazolyl, N—(C$_{1-4}$ alkyl)-pyrazolyl, pyrazol-1-yl, N—(C$_{1-4}$ alkyl)-imidazolyl, pyridyl, pyridazinyl, pyrimidyl, pyrazinyl, N—(C$_{1-4}$ alkyl)-benzimidazolyl, and pyrazolo[1,5-a]pyrimidinyl; wherein each ring moiety is substituted with 0 to 3 R$^d$;

R$^b$ is independently H or C$_{1-2}$ alkyl;
R$^d$ is, at each occurrence, independently selected from: F, Cl, CN, —CH$_2$OH, C$_{1-4}$ alkyl, C$_{1-4}$ alkoxy, C$_{1-4}$ haloalkyl, C$_{1-4}$ haloalkoxy, —CONH$_2$, NH$_2$, N(C$_{1-4}$ alkyl)$_2$, —C(O)O(C$_{1-4}$ alkyl), benzoxy, phenyl, and pyridyl; and R$^e$ is independently selected from F, OH and C$_{1-4}$ alkoxy.

8. A compound according to claim 7, wherein the compound is of Formula (IIIa-1):

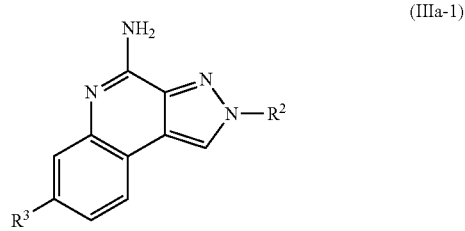

or a stereoisomer, a tautomer or a pharmaceutically acceptable salt thereof, wherein:
R$^2$ is independently selected from: H, C$_{1-4}$ alkyl substituted with 0 to 3 F, —(CH$_2$)$_{1-2}$OCHF$_2$, —(CH$_2$)$_2$O(C$_{1-4}$ alkyl), —(CH$_2$)$_2$O(CH$_2$)$_2$(C$_{1-4}$ alkoxy), —(CH$_2$)$_{2-3}$OH, —(CH$_2$)$_{1-3}$OR$^a$, —(CH$_2$)$_{1-2}$CH(CH$_3$)OH, —(CH$_2$)$_{1-2}$C(CH$_3$)$_2$OH, —(CH$_2$)$_{1-2}$CH(OCH$_3$)CH$_2$OH, —CH(CH$_3$)(CH$_2$)$_{1-2}$OH, —(CH$_2$)$_{1-2}$CH(OH)CH$_2$F, —(CH$_2$)$_{1-2}$CH(CH$_3$)O(C$_{1-4}$ alkyl), —(CH$_2$)$_{2-3}$NHC(O)R$^a$, —CH$_2$CH(CH$_3$)NHC(O)R$^a$, —(CH$_2$)$_{2-3}$NHC(O)CH$_2$OCH$_2$CF$_3$, —(CH$_2$)$_{2-3}$N(CH$_3$)Bn, —(CH$_2$)$_{2-3}$N(CH$_3$)C(O)Ph, —(CH$_2$)$_{2-3}$NHC(O)O(C$_{1-4}$ alkyl), —(CH$_2$)$_{2-3}$NHC(O)OPh, —(CH$_2$)$_2$C(O)NH$_2$, —(CH$_2$)$_{2-3}$SO$_2$(C$_{1-4}$ alkyl), —(CH$_2$)$_{1-2}$NH(C$_{1-4}$ alkyl), —(CH$_2$)$_{1-2}$CONH(C$_{1-4}$ alkyl substituted with 0 to 2 R$^e$), —(CH$_2$)$_{1-2}$CON(CH$_3$)(C$_{1-4}$ alkyl substituted with 0 to 2 R$^e$), —(CH$_2$)$_{1-2}$NH(CH$_2$)$_{1-2}$(phenyl substituted with 0 to 1 R$^d$), —(CH$_2$)$_{2-3}$NH(pyridyl), —(CH$_2$)$_{1-2}$C(O)NH(pyridyl), —(CH$_2$)$_{1-2}$C(O)NH(phenyl substituted with 0 to 1 F), —(CH$_2$)$_{1-2}$CH(CH$_3$)NHSO$_2$(C$_{1-4}$ alkyl),

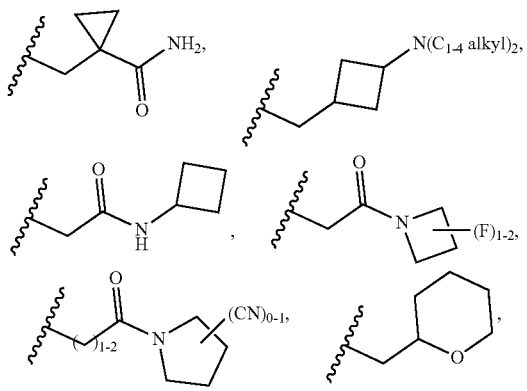

-continued

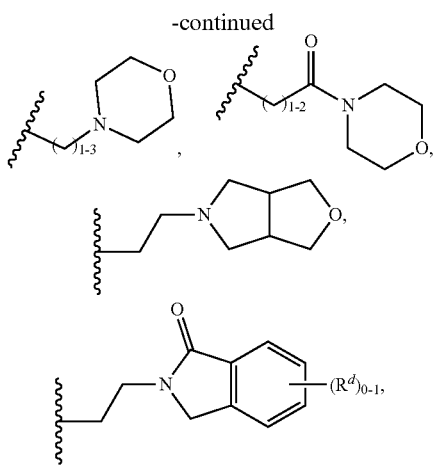

and —(CH$_2$)$_{1-3}$-(heteroaryl), wherein the heteroaryl is selected from imidazolyl, pyrazolyl, oxazolyl, isoxazolyl, thiazolyl, oxadiazolyl and pyridyl, and the heteroaryl is substituted with 0 to 2 R$^d$;

R$^3$ is independently

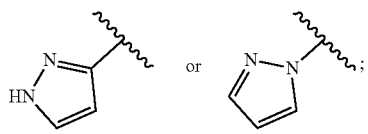 [SMILES: *c1cc[nH]n1 ; *n1cccn1]

R$^a$ is independently selected from: C$_{3-6}$ cycloalkyl,

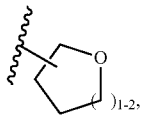

phenyl, oxazolyl, thiazolyl, N—(C$_{1-4}$ alkyl)-pyrazolyl, N—(C$_{1-4}$ alkyl)-imidazolyl, pyridyl, pyrimidyl, pyrazinyl, and N—(C$_{1-4}$ alkyl)-benzimidazolyl; wherein each ring moiety is substituted with 0 to 2 R$^d$;

R$^d$ is, at each occurrence, independently selected from: F, Cl, CN, C$_{1-4}$ alkyl, C$_{1-4}$ alkoxy, C$_{1-4}$ haloalkyl, C$_{1-4}$ haloalkoxy, NH$_2$, —C(O)O(C$_{1-4}$ alkyl), phenyl, and benzoxy; and R$^e$ is independently selected from F, OH and C$_{1-4}$ alkoxy.

9. A compound according to claim 7, wherein the compound is of Formula (IIIa):

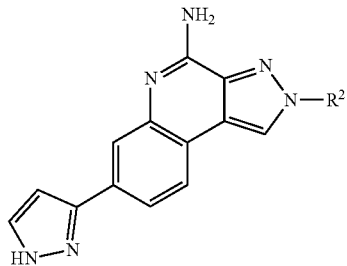

or a stereoisomer, a tautomer or a pharmaceutically acceptable salt thereof, wherein:

R$^2$ is independently C$_{1-4}$ alkyl substituted with 0 to 3 F, —(CH$_2$)$_{2-4}$O(C$_{1-4}$ alkyl), —(CH$_2$)$_{2-3}$NHC(O)R$^a$, —(CH$_2$)$_{2-3}$NHC(O)O(C$_{1-4}$ alkyl), —(CH$_2$)$_2$C(O)NH$_2$, —(CH$_2$)$_{1-2}$C(O)NH(phenyl substituted with 0 to 1 F), —(CH$_2$)$_{1-3}$(heteroaryl), wherein heteroaryl is selected from imidazolyl, pyrazolyl, oxazolyl, isoxazolyl, thiazolyl, oxadiazolyl and pyridyl, and heteroaryl is substituted with 0 to 2 R$^d$;

R$^a$ is independently selected from: oxazolyl, isoxazolyl, thiazolyl, N-methyl-imidazolyl, pyridyl and pyrazinyl; wherein each ring moiety is substituted with 0 to 2 R$^d$; and R$^d$ is, at each occurrence, independently selected from F, Cl, C$_{1-4}$ alkyl, C$_{1-4}$ alkoxy and phenyl.

10. A compound according to claim 9, wherein:
R$^d$ is, at each occurrence, independently selected from F, Cl, CH$_3$, and OCH$_3$.

11. A compound according to claim 3, wherein the compound is of Formula (IIIb-1):

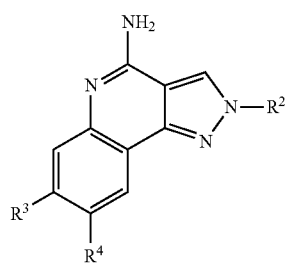

or a stereoisomer, a tautomer or a pharmaceutically acceptable salt thereof, wherein:

R$^2$ is independently selected from H, C$_{1-4}$ alkyl substituted with 0 to 3 F, —(CH$_2$)$_{1-2}$CH(OH)CH$_2$F, —(CH$_2$)$_{1-2}$CH(OH)CF$_3$, —(CH$_2$)$_{1-2}$CH(OH)CH$_2$CF$_3$, —(CH$_2$)$_{1-2}$OCHF$_2$, —(CH$_2$)$_{1-3}$OCF$_3$, —(CH$_2$)$_{1-2}$OCH$_2$CF$_3$, —(CH$_2$)$_{2-5}$OH, —(CH$_2$)$_{2-5}$CN, —(CH$_2$)$_{1-2}$CH(CH$_3$)OH, —(CH$_2$)$_{1-2}$CH(CH$_3$)CH$_2$OH, —(CH$_2$)$_{1-2}$C(CH$_3$)$_2$OH, —C(CH$_3$)$_2$(CH$_2$)$_{1-2}$OH, —(CH$_2$)$_{1-2}$C(CH$_3$)$_2$CH$_2$OH, —CH$_2$CH(OH)CH$_2$OH, —CH$_2$CH(OH)(C$_{1-4}$ alkyl), —CH(CH$_3$)(CH$_2$)$_{1-2}$OH, —CH$_2$CH(C$_{1-2}$ alkyl)(CH$_2$)$_{1-2}$OH, —CH$_2$CH(C$_{1-4}$ alkoxy)(CH$_2$)$_{1-2}$OH, —(CH$_2$)$_{2-4}$O(C$_{1-4}$ alkyl substituted with 0 to 2 R$^e$), —(CH$_2$)$_{1-2}$CH(CH$_3$)O(C$_{1-4}$ alkyl), —(CH$_2$)$_{1-2}$C(CH$_3$)$_2$O(C$_{1-4}$ alkyl), —CH(CH$_3$)(CH$_2$)$_{1-2}$O(C$_{1-4}$ alkyl), —CH$_2$CH(OH)(CH$_2$)$_{1-2}$O(C$_{1-4}$ alkyl), —(CH$_2$)$_{1-2}$CH(CH$_3$)NH$_2$, —CH$_2$C(CH$_3$)$_2$NH$_2$, —(CH$_2$)$_{2-3}$NH(C$_{1-4}$ alkyl), —(CH$_2$)$_{2-3}$N(C$_{1-4}$ alkyl)$_2$, —(CH$_2$)$_{1-3}$C(O)NH$_2$, —(CH$_2$)$_{1-2}$C(CH$_3$)$_2$CONH$_2$, —(CH$_2$)$_{1-2}$C(O)NH(C$_{1-4}$ alkyl substituted with 0 to 2 R$^e$), —(CH$_2$)$_{1-2}$C(O)N(CH$_3$)(C$_{1-4}$ alkyl substituted with 0 to 2 R$^e$), —(CH$_2$)$_{0-1}$CH(CH$_3$)(CH$_2$)$_{0-1}$C(O)NH(C$_{1-4}$ alkyl), —(CH$_2$)$_{1-2}$C(O)N(C$_{1-4}$ alkyl)$_2$, —(CH$_2$)$_{0-1}$CH(CH$_3$)C(O)N(C$_{1-4}$ alkyl)$_2$, —(CH$_2$)$_{1-2}$C(O)N(C$_{1-2}$ alkyl)(CH$_2$)$_2$O(C$_{1-4}$ alkyl), —(CH$_2$)$_{2-3}$NHC(O)R$^a$, —(CH$_2$)$_{1-2}$CH(CH$_3$)NHC(O)R$^a$, —CH$_2$C(CH$_3$)$_2$NHC(O)R$^a$, —(CH$_2$)$_{2-3}$N(CH$_3$)C(O)R$^a$, —(CH$_2$)$_{2-3}$S(O)$_2$(C$_{1-4}$ alkyl), —CH$_2$CH(CH$_3$)S(O)$_2$(C$_{1-4}$ alkyl), —(CH$_2$)$_{2-3}$NHS(O)$_2$(C$_{1-4}$ alkyl), —CH$_2$CH(CH$_3$)NHS(O)$_2$(C$_{1-4}$ alkyl), —(CH$_2$)$_{2-3}$NHS(O)$_2$(C$_{3-6}$ cycloalkyl),

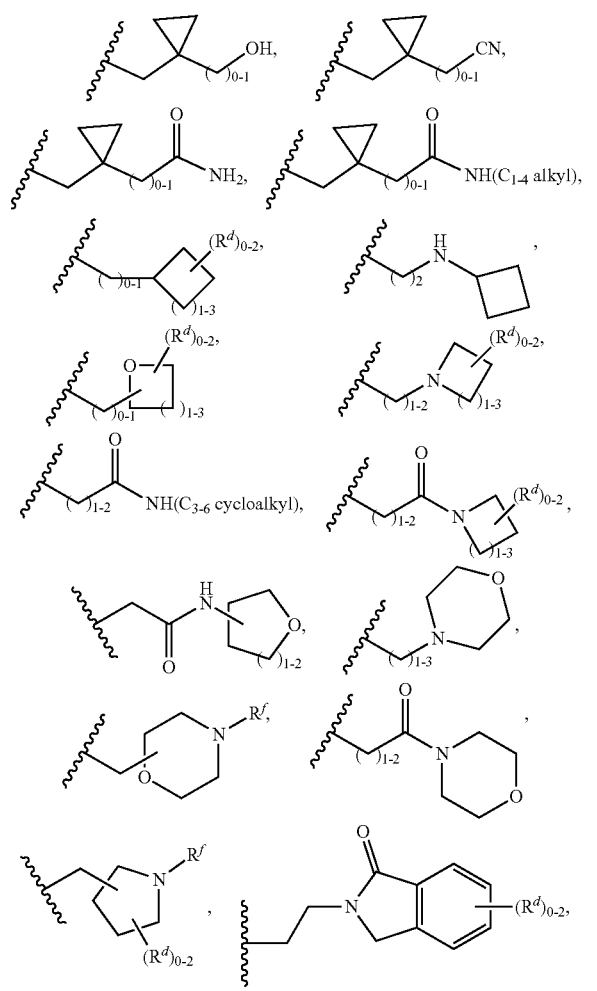

and

—(CH$_2$)$_{1-3}$-(heteroaryl including from 5 to 10 ring atoms, wherein from 1 to 4 ring atoms are each independently selected from N, N(R$^f$), O, and S), and said heteroaryl is substituted with 0 to 2 R$^d$;

R$^3$ is independently

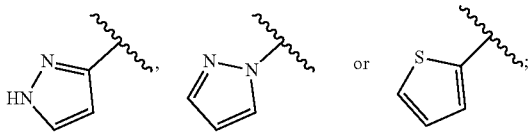 [SMILES: *c1cc[nH]n1 ; *n1cccn1 ; *c1cccs1]

R$^4$ is independently H or F;
R$^a$ is independently C$_{1-4}$ alkyl substituted with 0 to 1 R$^c$, C$_{3-6}$ cycloalkyl substituted with 0 to 2 R$^d$,

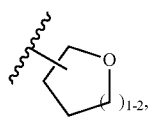

phenyl or heteroaryl selected from oxazolyl, isoxazolyl, thiazolyl, pyridyl and pyrazinyl, wherein said phenyl and heteroaryl are substituted with 0 to 2 R$^d$;

R$^d$ is, at each occurrence, independently selected from: F, Cl, OH, CN, C$_{1-4}$ alkyl, C$_{1-4}$ alkoxy, C$_{1-4}$ haloalkyl, NH$_2$, N(C$_{1-4}$ alkyl)$_2$, —NHC(O)(C$_{1-4}$ alkyl), and phenyl;

R$^e$ is independently selected from F, OH and C$_{1-4}$ alkoxy; and

R$^f$ is, at each occurrence, independently selected from: H, C$_{1-4}$ alkyl, —C(O)(C$_{1-4}$ alkyl), and —C(O)(C$_{1-4}$ haloalkyl).

12. A compound according to claim 11, wherein:
R$^2$ is independently selected from H, C$_{1-4}$ alkyl substituted with 0 to 3 F, —(CH$_2$)$_{1-2}$CH(OH)CH$_2$F, —(CH$_2$)$_{1-2}$CH(OH)CF$_3$, —(CH$_2$)$_{1-2}$CH(OH)CH$_2$CF$_3$, —(CH$_2$)$_{1-2}$CH(OH)CF$_3$, —(CH$_2$)$_{1-2}$CH(OH)CH$_2$CF$_3$, —(CH$_2$)$_{1-2}$OCHF$_2$, —(CH$_2$)$_{1-3}$OCF$_3$, —(CH$_2$)$_{1-2}$OCH$_2$CF$_3$, —(CH$_2$)$_{2-4}$OH, —(CH$_2$)$_{2-4}$CN, —(CH$_2$)$_{1-2}$CH(CH$_3$)OH, —(CH$_2$)$_{1-2}$CH(CH$_3$)CH$_2$OH, —(CH$_2$)$_{1-2}$C(CH$_3$)$_2$OH, —C(CH$_3$)$_2$(CH$_2$)$_{1-2}$OH, —(CH$_2$)$_{1-2}$C(CH$_3$)$_2$CH$_2$OH, —CH$_2$CH(OH)CH$_2$OH, —CH$_2$CH(OH)(C$_{1-4}$ alkyl), —CH(CH$_3$)(CH$_2$)$_{1-2}$OH, —CH$_2$CH(C$_{1-2}$ alkyl)(CH$_2$)$_{1-2}$OH, —CH$_2$CH(C$_{1-4}$ alkoxy)(CH$_2$)$_{1-2}$OH, —(CH$_2$)$_{2-4}$O(C$_{1-4}$ alkyl substituted with 0 to 1 R$^e$), —(CH$_2$)$_{1-2}$CH(CH$_3$)O(C$_{1-4}$ alkyl), —(CH$_2$)$_{1-2}$C(CH$_3$)$_2$O(C$_{1-4}$ alkyl), —CH(CH$_3$)(CH$_2$)$_{1-2}$O(C$_{1-4}$ alkyl), —CH$_2$CH(OH)(CH$_2$)$_{1-2}$O(C$_{1-4}$ alkyl), —(CH$_2$)$_{1-2}$CH(CH$_3$)NH$_2$, —CH$_2$C(CH$_3$)$_2$NH$_2$, —(CH$_2$)$_{2-3}$NH(C$_{1-4}$ alkyl), —(CH$_2$)$_{2-3}$N(C$_{1-4}$ alkyl)$_2$, —(CH$_2$)$_{1-3}$C(O)NH$_2$, —(CH$_2$)$_{1-2}$C(CH$_3$)$_2$CONH$_2$, —(CH$_2$)$_{1-2}$C(O)NH(C$_{1-4}$ alkyl substituted with 0 to 2 R$^e$), —(CH$_2$)$_{1-2}$C(O)N(CH$_3$)(C$_{1-4}$ alkyl substituted with 0 to 2 R$^e$), —(CH$_2$)$_{0-1}$CH(CH$_3$)(CH$_2$)$_{0-1}$C(O)NH(C$_{1-4}$ alkyl), —(CH$_2$)$_{1-2}$C(O)N(C$_{1-4}$ alkyl)$_2$, —(CH$_2$)$_{0-1}$CH(CH$_3$)C(O)N(C$_{1-4}$ alkyl)$_2$, —(CH$_2$)$_{1-2}$C(O)N(C$_{1-2}$ alkyl)(CH$_2$)$_2$O(C$_{1-4}$ alkyl), —(CH$_2$)$_{2-3}$NHC(O)R$^a$, —CH$_2$CH(CH$_3$)NHC(O)R$^a$, —CH$_2$C(CH$_3$)$_2$NHC(O)R$^a$, —(CH$_2$)$_{2-3}$S(O)$_2$(C$_{1-4}$ alkyl), —CH$_2$CH(CH$_3$)S(O)$_2$(C$_{1-4}$ alkyl), —(CH$_2$)$_{2-3}$NHS(O)$_2$(C$_{1-4}$ alkyl), —CH$_2$CH(CH$_3$)NHS(O)$_2$(C$_{1-4}$ alkyl), —(CH$_2$)$_{2-3}$NHS(O)$_2$(C$_{3-6}$ cycloalkyl),

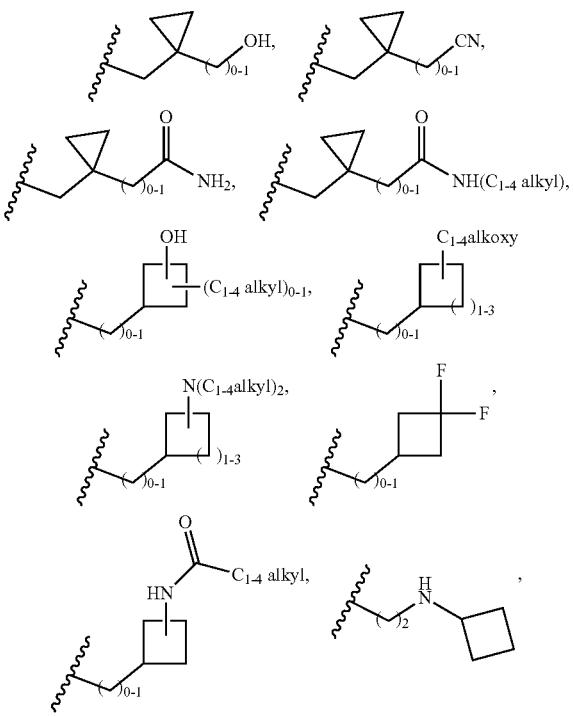

503

-continued

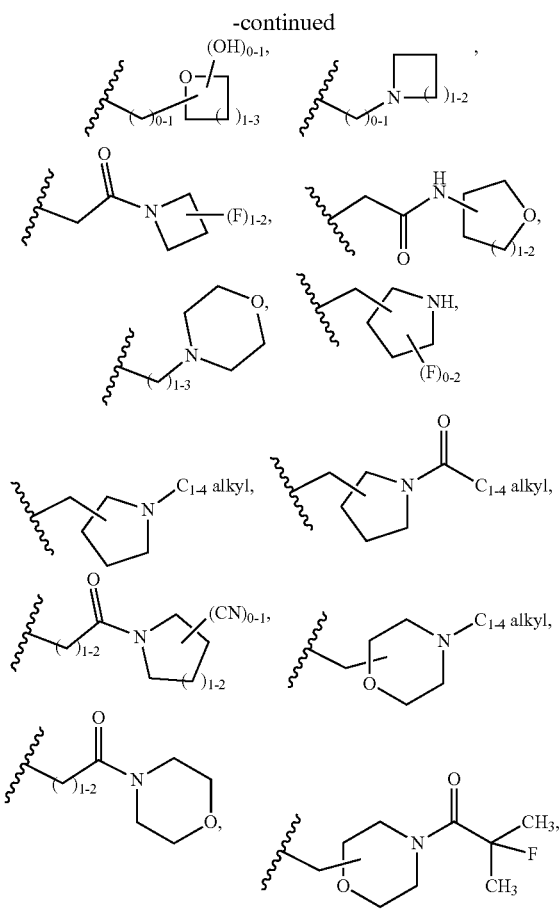

and —(CH$_2$)$_{1-2}$(heteroaryl), wherein the heteroaryl is selected from imidazolyl, pyrazolyl, oxazolyl, isoxazolyl, thiazolyl, oxadiazolyl, pyridyl and pyridazinyl, and the heteroaryl is substituted with 0 to 2 R$^d$;

R$^a$ is independently C$_{1-4}$ alkyl substituted with 0 to 1 R$^e$,

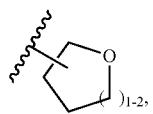

phenyl or heteroaryl selected from oxazolyl, pyridyl and pyrazinyl, wherein said phenyl and heteroaryl are substituted with 0 to 2 R$^d$; and R$^d$ is, at each occurrence, independently selected from: F, Cl, CN, C$_{1-4}$ alkyl, C$_{1-4}$ alkoxy, and C$_{1-4}$ haloalkyl.

13. A compound according to claim 12, wherein:

R$^3$ is independently or

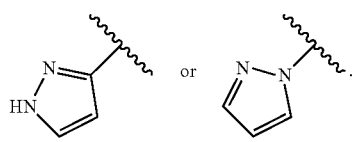 [SMILES: *c1cc[nH]n1 ; *n1cccn1]

504

14. A compound according to claim 13, wherein the compound is of Formula (IIIb-2):

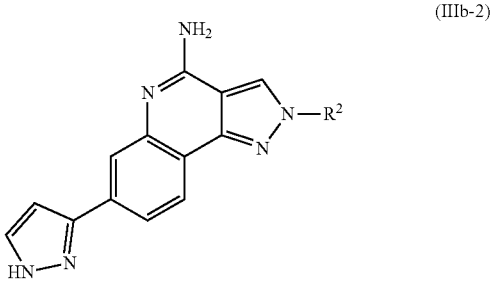

(IIIb-2)

or a stereoisomer, a tautomer or a pharmaceutically acceptable salt thereof, wherein:

R$^2$ is independently selected from H, C$_{1-4}$ alkyl substituted with 0 to 3 F, —(CH$_2$)$_{2-4}$OH, —(CH$_2$)$_{2-4}$CN, —(CH$_2$)$_{1-2}$CH(CH$_3$)OH, —(CH$_2$)$_{1-2}$C(CH$_3$)$_2$OH, —CH$_2$CH(OH)CH$_2$OH, —CH$_2$CH(OH)(C$_{1-4}$ alkyl), —CH(CH$_3$)(CH$_2$)$_{1-2}$OH, —CH$_2$CH(C$_{1-2}$ alkyl)(CH$_2$)$_{1-2}$OH, —CH$_2$CH(C$_{1-2}$ alkoxy)(CH$_2$)$_{1-2}$OH, —(CH$_2$)$_{2-4}$O(C$_{1-4}$ alkyl substituted with 0 to 2 R$^e$), —CH$_2$C(CH$_3$)$_2$NH$_2$, —(CH$_2$)$_{1-3}$C(O)NH$_2$, —(CH$_2$)$_{1-2}$C(CH$_3$)$_2$CONH$_2$, —(CH$_2$)$_{1-2}$C(O)NH(C$_{1-4}$ alkyl), —(CH$_2$)$_{0-1}$CH(CH$_3$)(CH$_2$)$_{0-1}$C(O)NH(C$_{1-4}$ alkyl), —(CH$_2$)$_{1-2}$C(O)N(C$_{1-4}$ alkyl)$_2$, —(CH$_2$)$_{0-1}$CH(CH$_3$)C(O)N(C$_{1-4}$ alkyl)$_2$, —(CH$_2$)$_{1-2}$C(O)NH(C$_{1-4}$ alkyl substituted with 0 to 2 R$^e$), —(CH$_2$)$_{1-2}$C(O)N(CH$_3$)(C$_{1-4}$ alkyl substituted with 0 to 2 R$^e$), —CH$_2$CH(CH$_3$)NHC(O)(C$_{1-4}$ alkyl), —(CH$_2$)$_{2-3}$S(O)$_2$(C$_{1-4}$ alkyl), —CH$_2$CH(CH$_3$)S(O)$_2$(C$_{1-4}$ alkyl), —(CH$_2$)$_{2-3}$NHS(O)$_2$(C$_{1-4}$ alkyl), —CH$_2$CH(CH$_3$)NHS(O)$_2$(C$_{1-4}$ alkyl), —(CH$_2$)$_{2-3}$NHS(O)$_2$(C$_{3-6}$ cycloalkyl),

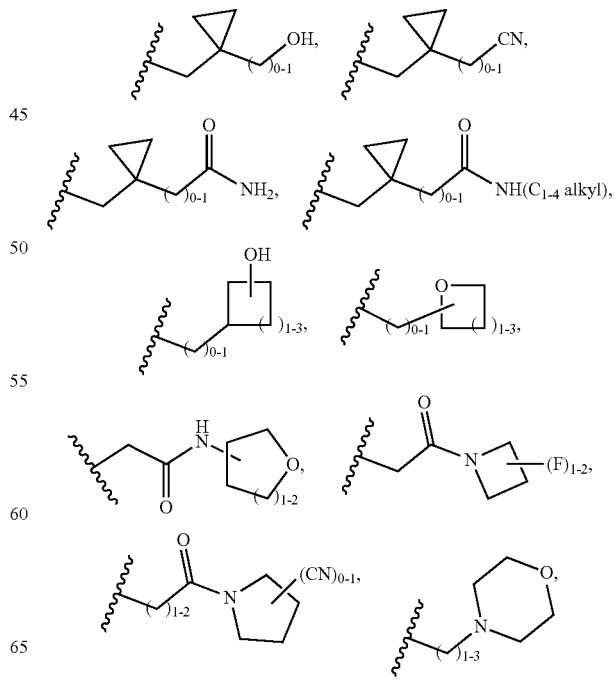

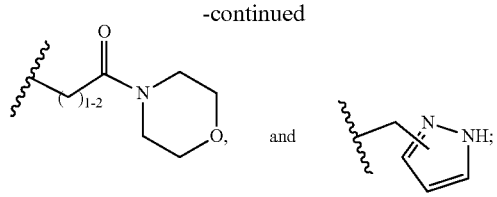 and and
$R^e$ is independently selected from F, OH and $C_{1-4}$ alkoxy.

15. A compound according to claim 14, wherein:
$R^2$ is independently selected from H, —CH$_2$CHF$_2$, —(CH$_2$)$_{2-4}$OH, —(CH$_2$)$_{2-4}$CN, —CH$_2$CH(CH$_3$)OH, —CH$_2$C(CH$_3$)$_2$OH, —CH$_2$CH(OH)CH$_2$OH, —CH$_2$CH(OH)CH$_2$CH$_3$, —CH(CH$_3$)(CH$_2$)$_2$OH, —CH$_2$CH(CH$_3$)CH$_2$OH, —CH$_2$CH(OCH$_3$)CH$_2$OH, —(CH$_2$)$_2$O(CH$_2$)$_2$OH, —(CH$_2$)$_2$O(CH$_2$)$_2$OCH$_3$, —CH$_2$C(CH$_3$)$_2$NH$_2$, —(CH$_2$)$_{1-3}$C(O)NH$_2$, —CH$_2$C(CH$_3$)$_2$CONH$_2$, —(CH$_2$)$_{1-2}$C(O)NH(CH$_3$), —(CH$_2$)$_{1-2}$C(O)NH(CH$_2$CH$_3$), —(CH$_2$)$_{1-2}$C(O)NH(CH(CH$_3$)$_2$), —(CH$_2$)$_{0-1}$CH(CH$_3$)(CH$_2$)$_{0-1}$C(O)NH(CH$_3$), —(CH$_2$)$_{0-1}$CH(CH$_3$)C(O)NH(CH(CH$_3$)$_2$), —(CH$_2$)$_{1-2}$C(O)N(CH$_3$)$_2$, —(CH$_2$)$_{0-1}$CH(CH$_3$)C(O)N(CH$_3$)$_2$, —CH$_2$C(O)NH(CH$_2$CHF$_2$), —CH(CH$_3$)C(O)NH(CH$_2$CHF$_2$), —(CH$_2$)$_{1-2}$C(O)NH(CH$_2$)$_2$OH, —CH(CH$_3$)C(O)NH(CH$_2$)$_{2-3}$OH, —(CH$_2$)$_{1-2}$C(O)NH(C(CH$_3$)$_2$CH$_2$OH), —(CH$_2$)$_{1-2}$C(O)NH(CH$_2$)$_2$OCH$_3$, —(CH$_2$)$_{1-2}$C(O)N(CH$_3$)(CH$_2$)$_2$OCH$_3$, —CH$_2$CH(CH$_3$)NHC(O)(CH$_3$), —(CH$_2$)$_{2-3}$S(O)$_2$CH$_3$, —(CH$_2$)$_{2-3}$S(O)$_2$CH$_2$CH$_3$, —(CH$_2$)$_{2-3}$NHS(O)$_2$CH$_3$, —CH$_2$CH(CH$_3$)NHS(O)$_2$CH$_3$, —(CH$_2$)$_{2-3}$NHS(O)$_2$(cyclopropyl),

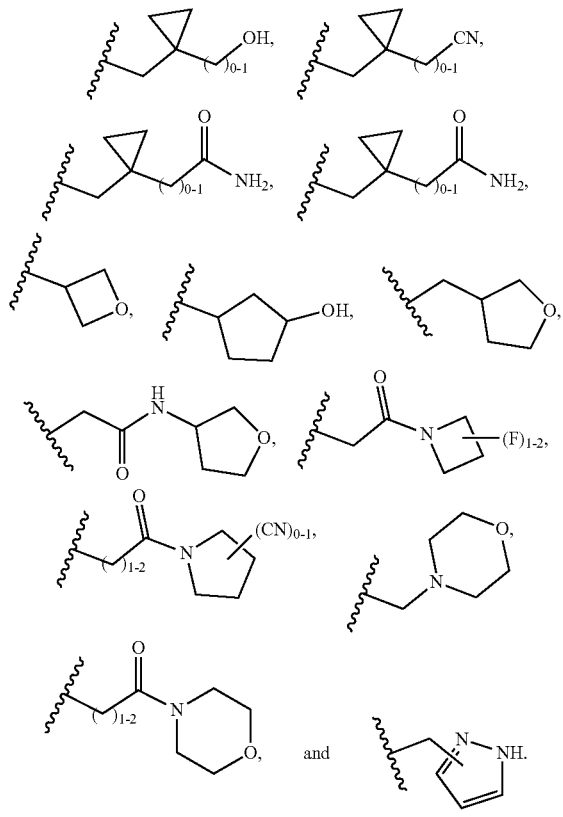

16. A compound according to claim 3, wherein the compound is of Formula (IIIf):

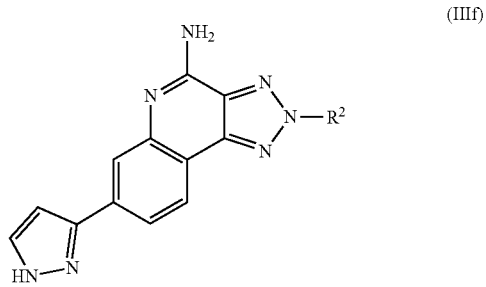

(IIIf)

or a stereoisomer, a tautomer or a pharmaceutically acceptable salt thereof, wherein:
$R^2$ is independently selected from —(CH$_2$)$_2$N(C$_{1-4}$ alkyl)$_2$, —(CH$_2$)$_2$—OR$^a$, —(CH$_2$)$_2$—NHC(O)R$^a$, and

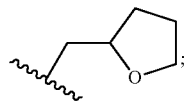 [SMILES: *CC1CCCO1]

$R^a$ is independently selected from: $C_{1-4}$ alkyl substituted with from 0 to 2 F,

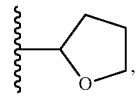

and heteroaryl selected from thiazolyl and pyridyl, wherein said heteroaryl is substituted with 0 to 2 $R^d$; and $R^d$ is, at each occurrence, independently selected from: F, Cl, CN, $C_{1-4}$ alkyl, $C_{1-4}$ alkoxy and $C_{1-4}$ haloalkyl.

17. A compound according to claim 3, wherein the compound is of Formula (IIIg-1):

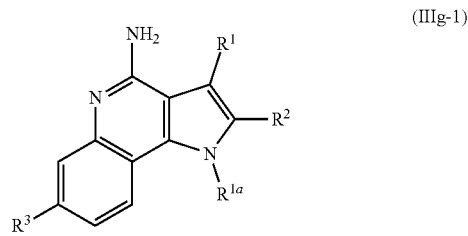

(IIIg-1)

or a stereoisomer, a tautomer or a pharmaceutically acceptable salt thereof, wherein:
$R^1$ is independently H, Cl or $C_{1-4}$ alkyl;
$R^{1a}$ is independently H or $C_{1-4}$ alkyl;
$R^2$ is independently selected from —(CH$_2$)$_{1-4}$—OH, —(CH$_2$)$_{1-2}$—OR$^a$, —(CH$_2$)$_{1-2}$NH$_2$, —(CH$_2$)$_{1-2}$NH(C$_{1-4}$ alkyl substituted with 0 to 1 R$^e$), —(CH$_2$)$_{1-2}$N(C$_{1-4}$ alkyl)$_2$, —(CH$_2$)$_{1-2}$—NHC(O)R$^a$, —(CH$_2$)$_{2-3}$NHS(O)$_2$(C$_{1-4}$ alkyl), —(CH$_2$)$_{2-3}$NHS(O)$_2$Ph,

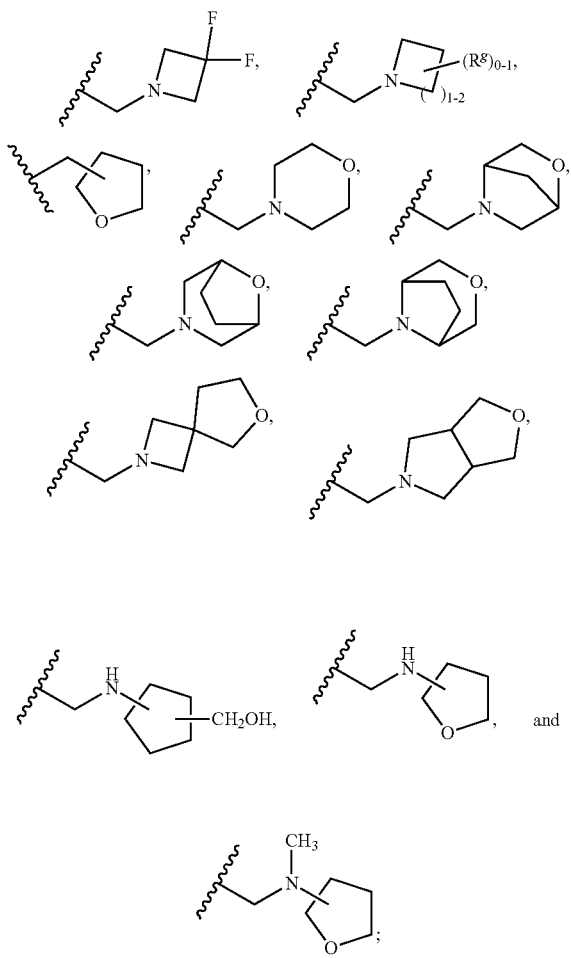

R³ is independently

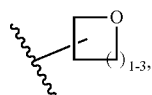 or 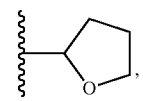;

Rᵃ is independently selected from: $C_{1-4}$ alkyl substituted with from 0 to 2 F, and heteroaryl selected from thiazolyl, oxazolyl, N—$C_{1-4}$ alkyl-imidazolyl, and pyridyl, wherein said heteroaryl is substituted with 0 to 2 $R^d$;

$R^d$ is, at each occurrence, independently selected from: F, Cl, OH, CN, $C_{1-4}$ alkyl, $C_{1-4}$ alkoxy, $C_{1-4}$ haloalkyl, and —NHC(O)($C_{1-4}$ alkyl); and $R^e$ is independently selected from F, OH, $C_{1-4}$ alkoxy and $C_{1-4}$ haloalkyl.

18. A compound according to claim 17, wherein the compound is of Formula (IIIg):

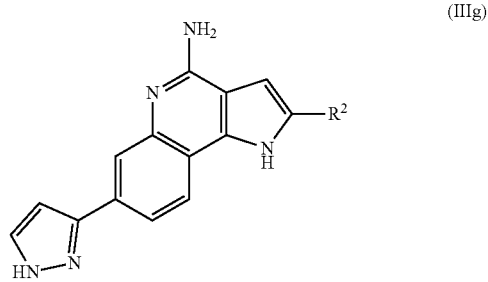

(IIIg)

or a stereoisomer, a tautomer or a pharmaceutically acceptable salt thereof, wherein:

R² is independently selected from —$(CH_2)_{1-2}NH_2$, —$(CH_2)_{1-2}N(C_{1-4}$ alkyl$)_2$, —$(CH_2)_{1-2}NH(C_{1-4}$ alkyl substituted with 0 to 1 $R^e$), —$(CH_2)_{1-2}$—$NHC(O)R^a$;

$R^a$ is independently selected from: $C_{1-4}$ alkyl substituted with from 0 to 2 F,

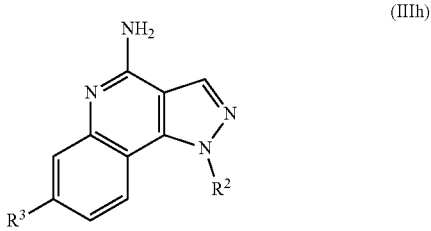

and heteroaryl selected from thiazolyl and pyridyl, wherein said heteroaryl is substituted with 0 to 2 $R^d$; and $R^d$ is, at each occurrence, independently selected from: F, Cl, CN, $C_{1-4}$ alkyl, $C_{1-4}$ alkoxy and $C_{1-4}$ haloalkyl; and $R^e$ is independently selected from F, OH, $OCH_3$, $CHF_2$, and $CF_3$.

19. A compound according to claim 3, wherein the compound is of Formula (IIIh):

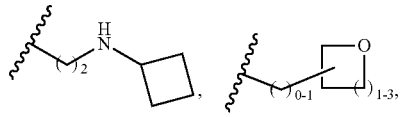

(IIIh)

or a stereoisomer, a tautomer or a pharmaceutically acceptable salt thereof, wherein:

R² is independently selected from $C_{1-4}$ alkyl, —$(CH_2)_{1-2}CHF_2$, —$(CH_2)_{2-4}OH$, —$CH_2CH(CH_3)(CH_2)_{0-2}OH$, —$CH_2CH(OH)CH_2CH_3$, —$(CH_2)_{1-2}C(CH_3)_2OH$, —$(CH_2)_2O(CH_2)_{1-2}OH$, —$(CH_2)_{2-4}O(C_{1-4}$ alkyl), —$CH_2CH(OH)(CH_2)_{1-2}O(C_{1-4}$ alkylalkyl), —$(CH_2)_{2-3}NH(C_{1-4}$ alkyl), —$(CH_2)_{2-3}N(C_{1-4}$ alkyl$)_2$, —$(CH_2)_2$(pyridyl), -continued

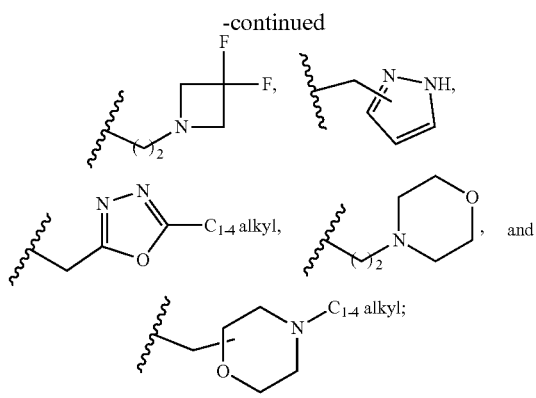

$R^3$ is independently or

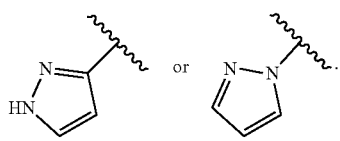 [SMILES: *c1cc[nH]n1 ; *n1cccn1]

20. A compound according to claim 3, wherein the compound is of Formula (IIIi):

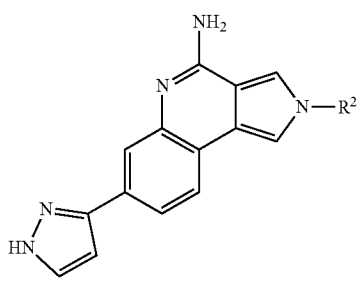
(IIIi)

or a stereoisomer, a tautomer or a pharmaceutically acceptable salt thereof, wherein:
$R^2$ is independently selected from: —$(CH_2)_{2-4}OH$, —$(CH_2)_{2-4}O(C_{1-4}$ alkyl), —$(CH_2)_{2-3}N(C_{1-4}$ alkyl$)_2$, and —$(CH_2)_{2-3}NHC(O)R^a$;
$R^a$ is independently $C_{3-6}$ cycloalkyl,

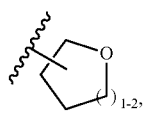

phenyl or heteroaryl selected from oxazolyl, isoxazolyl, thiazolyl, pyridyl and pyrazinyl, wherein said phenyl and heteroaryl are substituted with 0 to 2 $R^d$; and
$R^d$ is, at each occurrence, independently selected from: F, Cl, CN, $C_{1-4}$ alkyl, $C_{1-4}$ alkoxy, and $C_{1-4}$ haloalkyl.

21. A compound according to claim 1, wherein the compound is selected from Examples 1 to 624 or a pharmaceutically acceptable salt thereof.

22. A pharmaceutical composition comprising a compound or a pharmaceutically acceptable salt thereof as claimed claim 1 and one or more pharmaceutically acceptable excipients.

23. A compound according to claim 11, wherein the compound is selected from

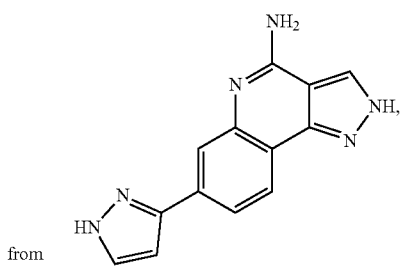

from

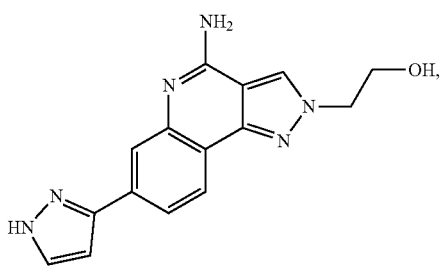

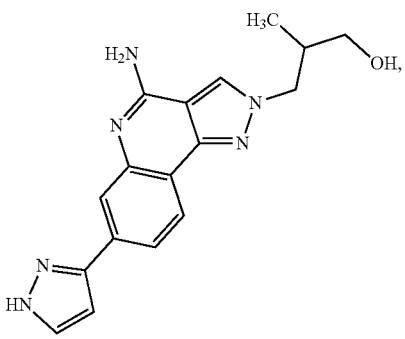

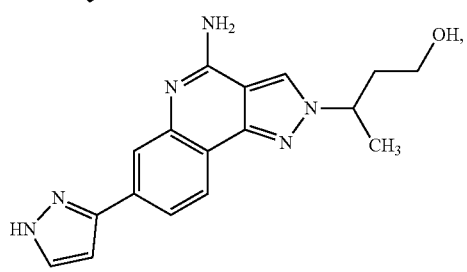

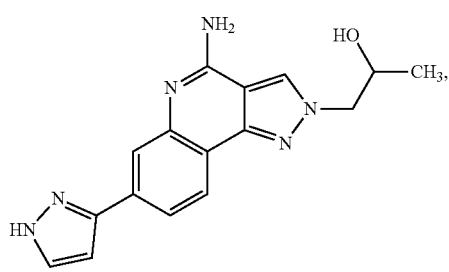

511
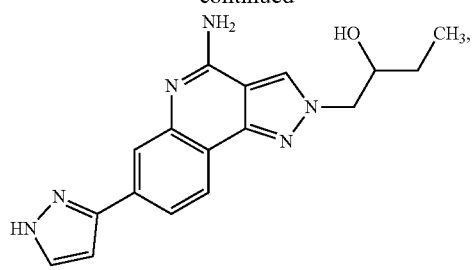
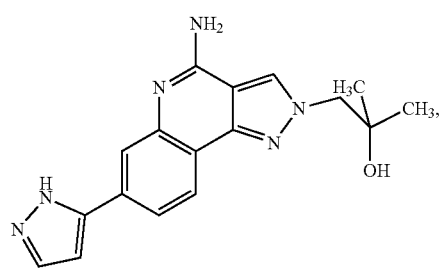
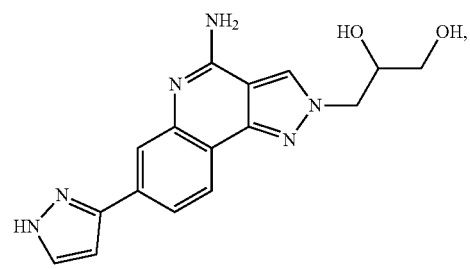
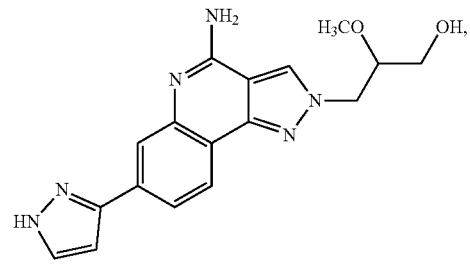
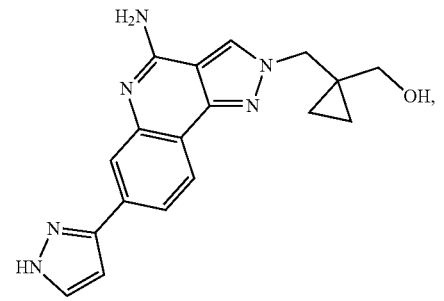
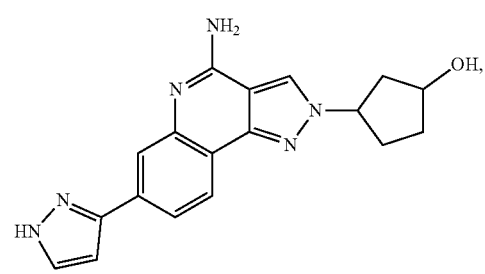
512
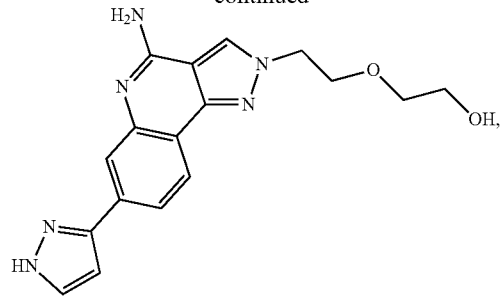
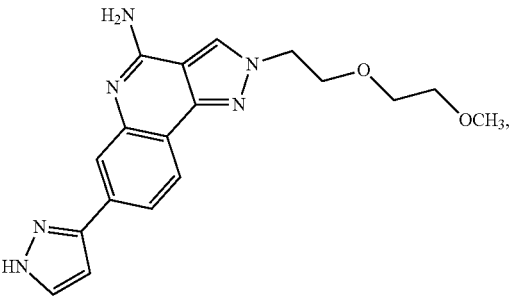
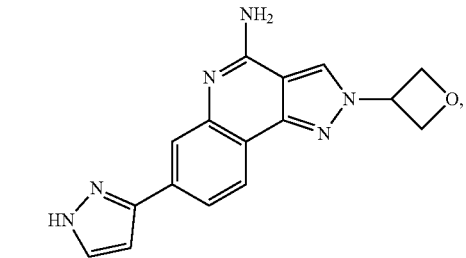
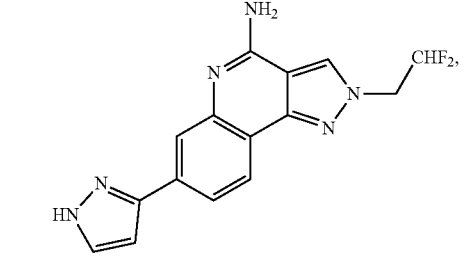
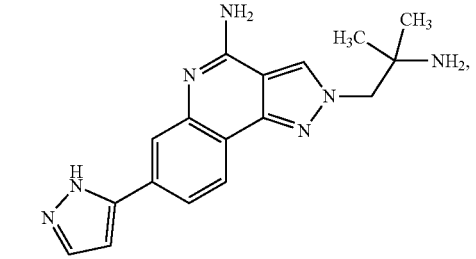
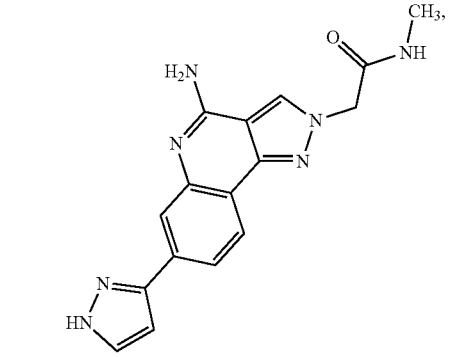

513
-continued
514
-continued
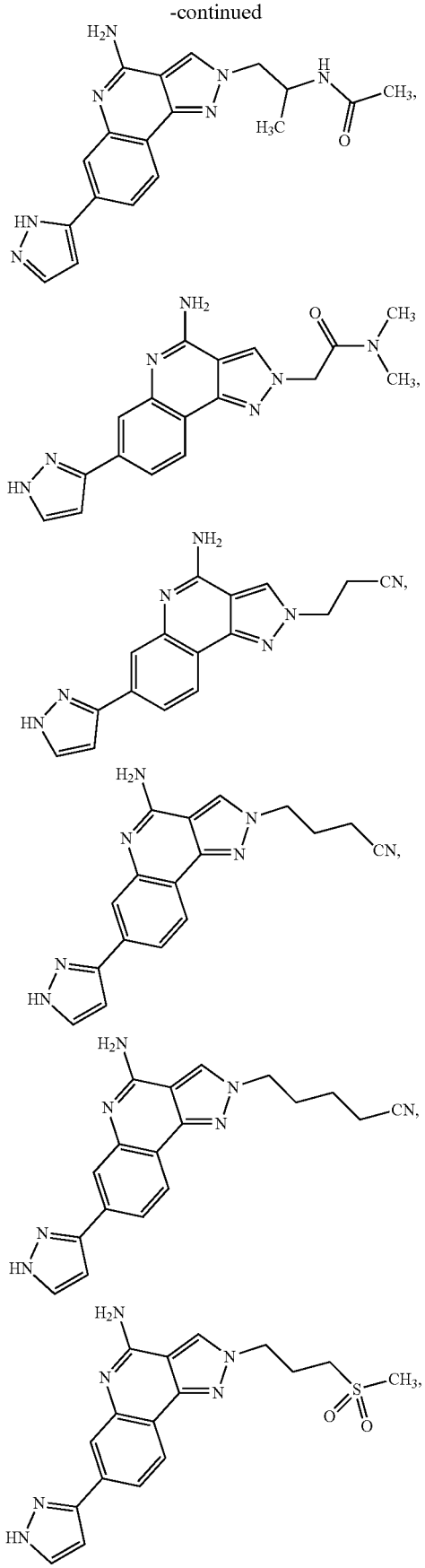
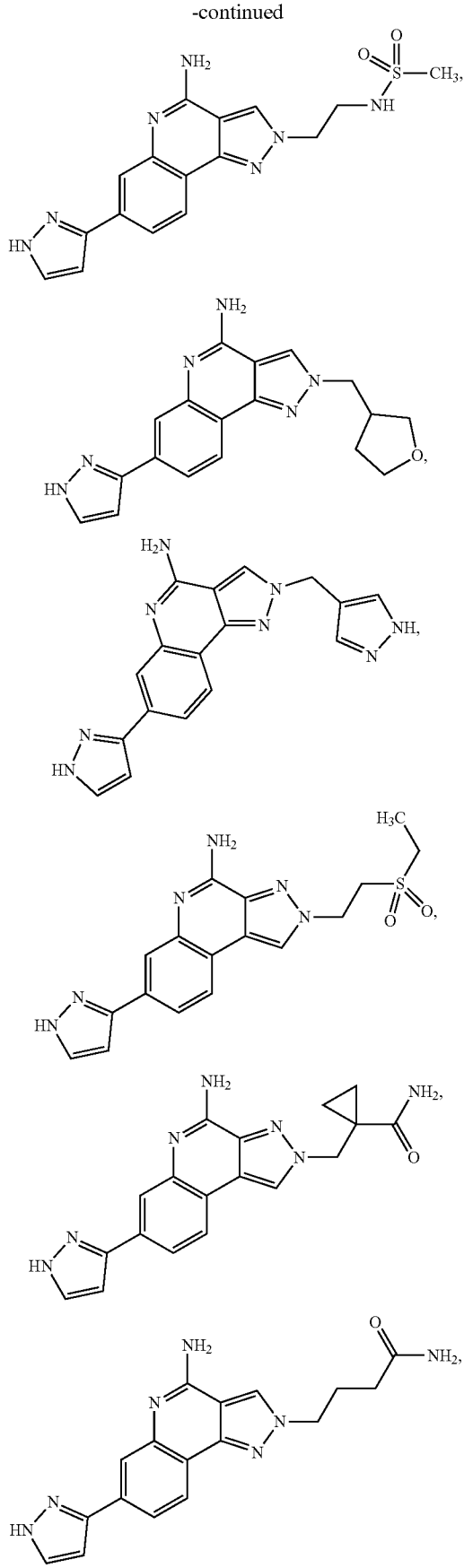

515
-continued
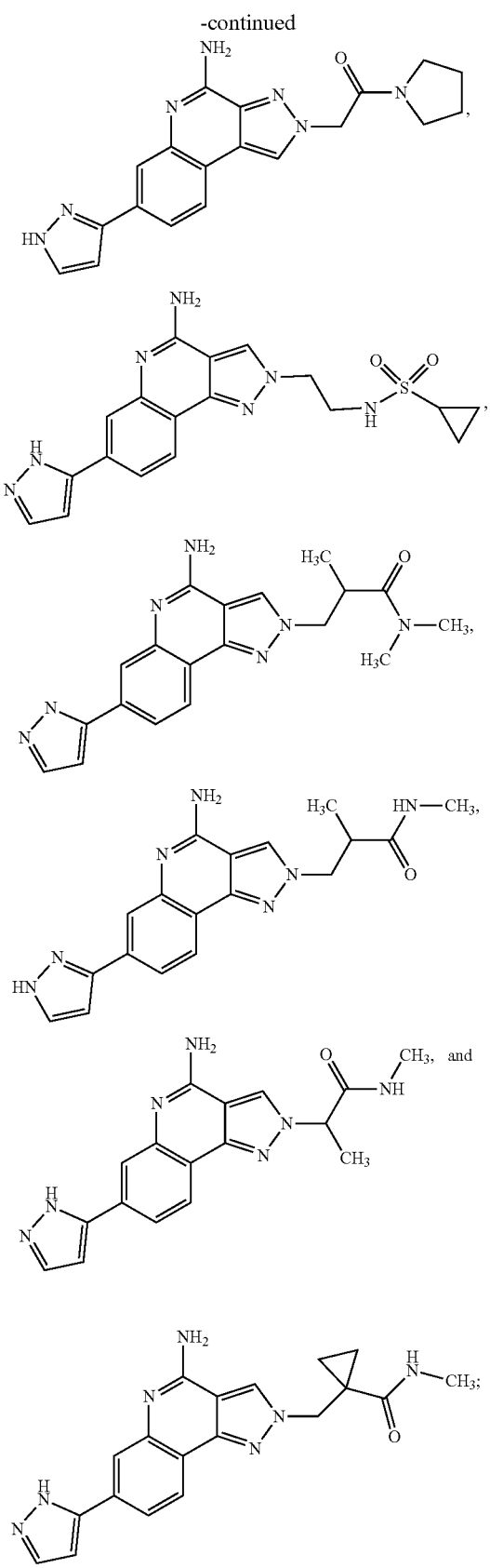
or a stereoisomer, a tautomer or a pharmaceutically acceptable salt thereof.
516
24. A compound according to claim 23, wherein the compound is selected from
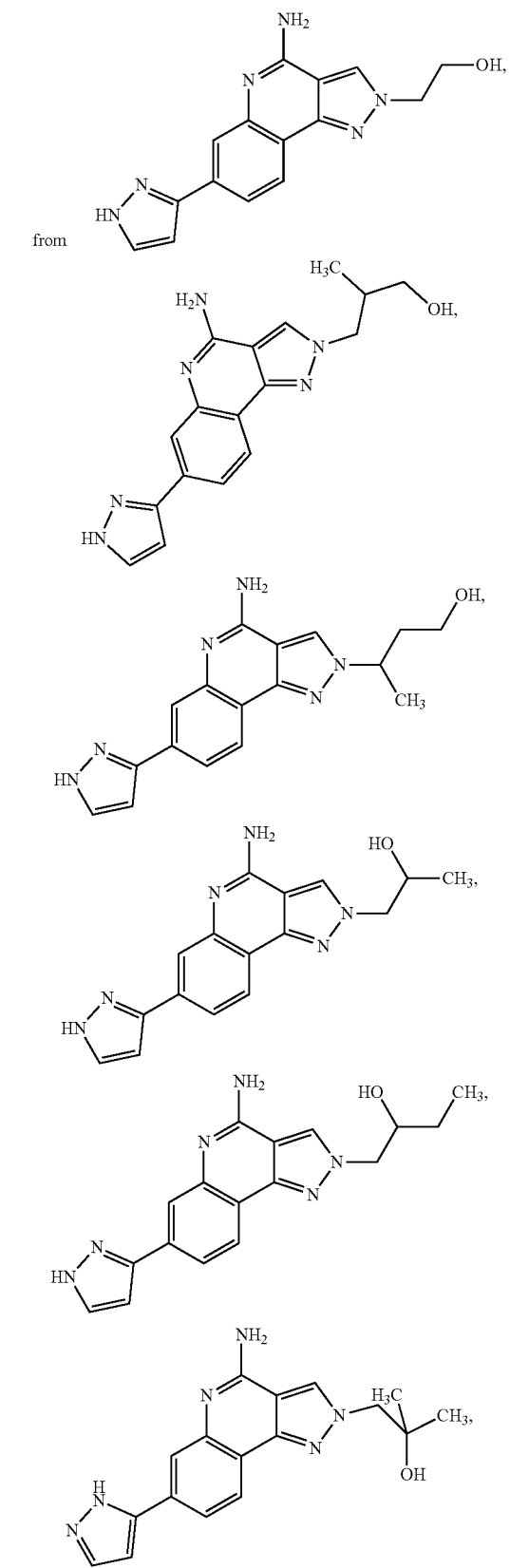
from 517
-continued
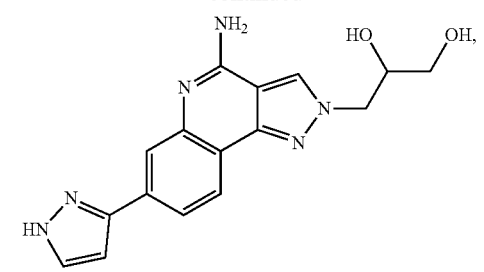
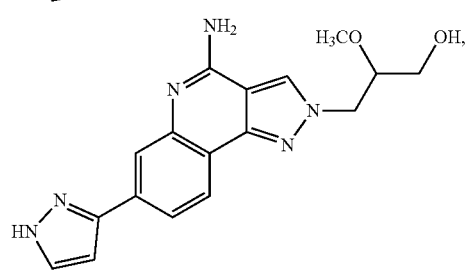
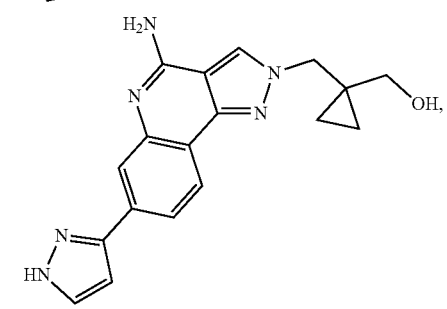
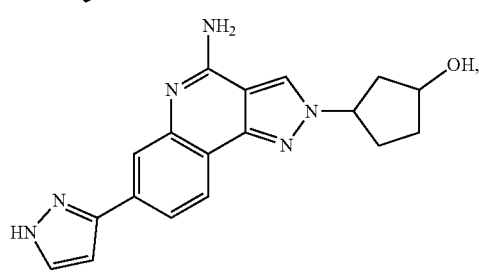
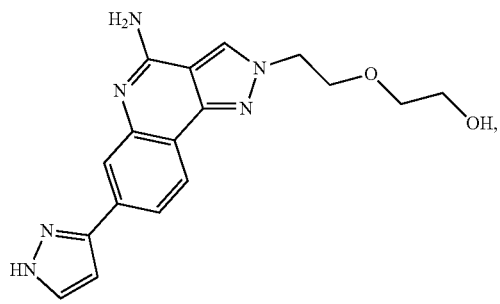
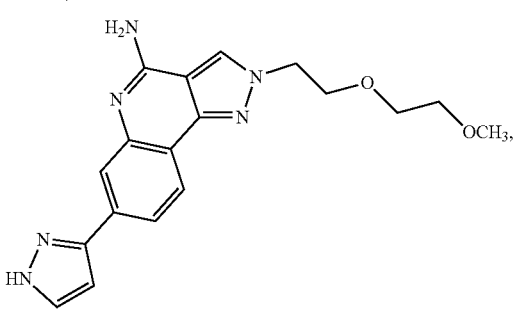
518
-continued
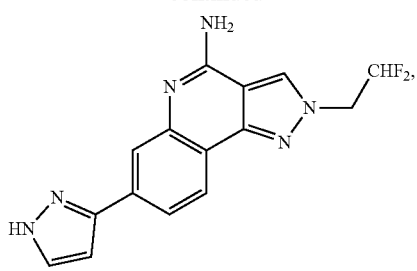
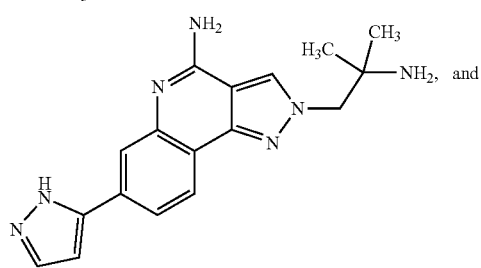
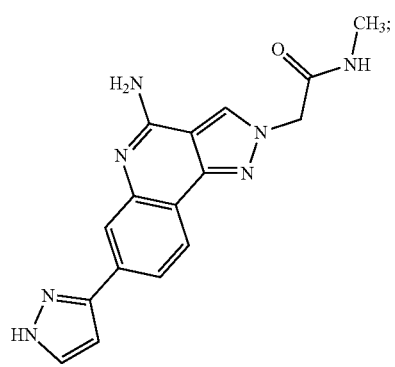
or a stereoisomer, a tautomer or a pharmaceutically acceptable salt thereof.
25. A compound according to claim 24, wherein the compound is selected from
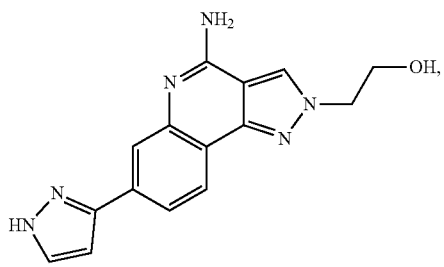
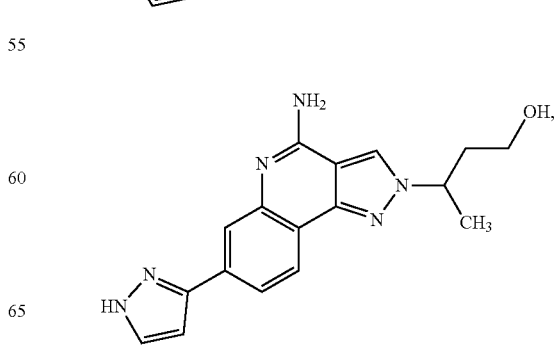

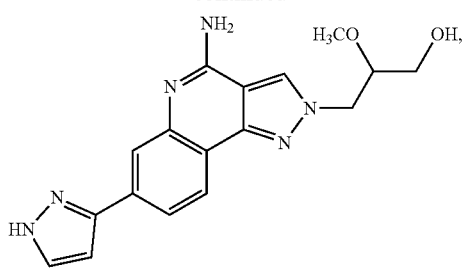
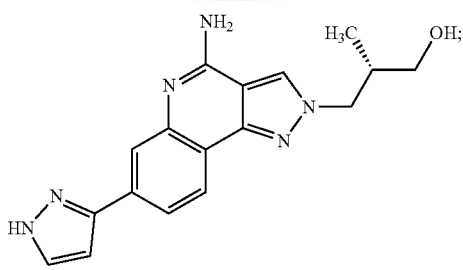
a tautomer or a pharmaceutically acceptable salt thereof.
27. A compound according to claim 17, wherein the compound is selected from
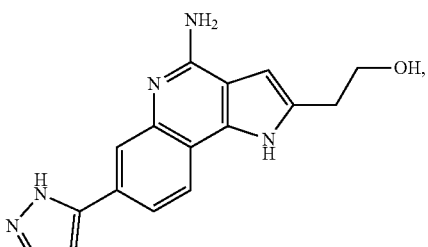
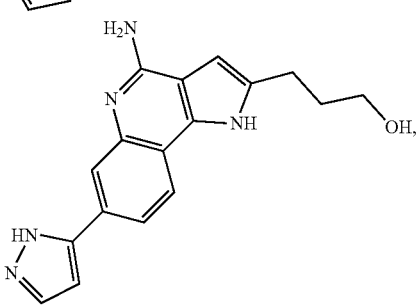
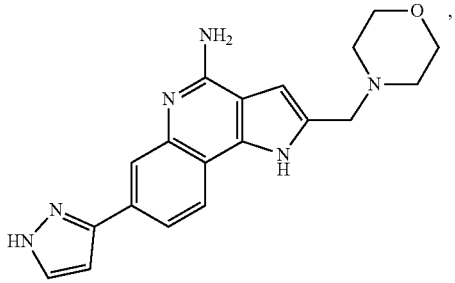
or a stereoisomer, a tautomer or a pharmaceutically acceptable salt thereof.
26. A compound according to claim 25, wherein the compound is selected from
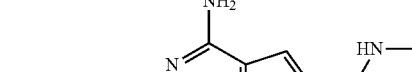

521
-continued

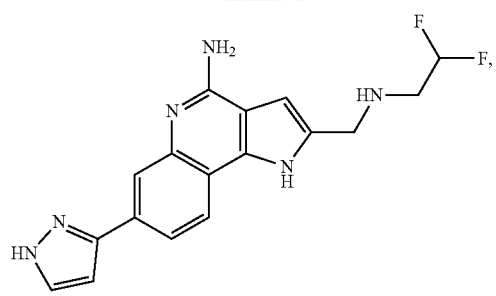

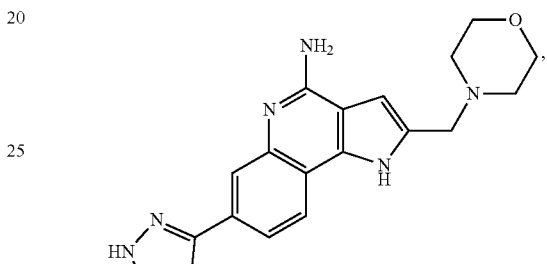

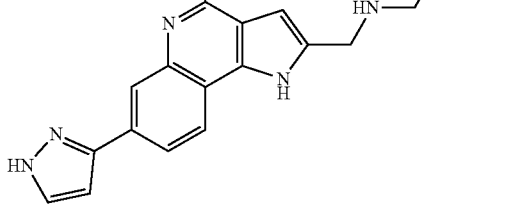

522
-continued

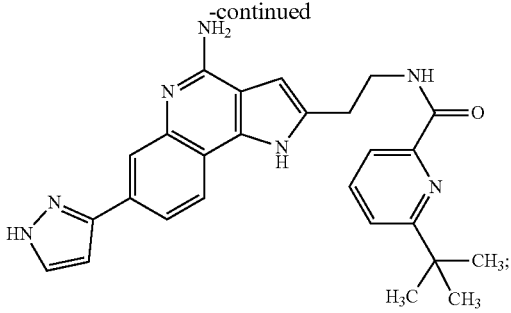

or a tautomer or a pharmaceutically acceptable salt thereof.

28. A compound according to claim 16, wherein the compound is selected from

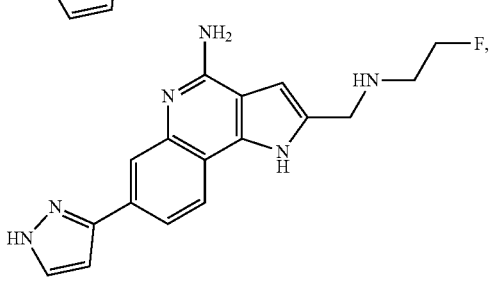

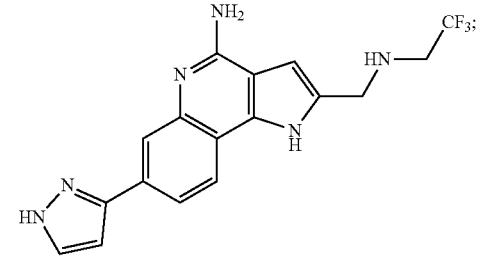

or a tautomer or a pharmaceutically acceptable salt thereof.

29. A pharmaceutical composition comprising a compound or a pharmaceutically acceptable salt thereof as claimed claim 23 and one or more pharmaceutically acceptable excipients.

30. A pharmaceutical composition comprising a compound or a pharmaceutically acceptable salt thereof as claimed claim 24 and one or more pharmaceutically acceptable excipients.

31. A pharmaceutical composition comprising a compound or a pharmaceutically acceptable salt thereof as claimed claim 25 and one or more pharmaceutically acceptable excipients.

32. A pharmaceutical composition comprising a compound or a pharmaceutically acceptable salt thereof as claimed claim 26 and one or more pharmaceutically acceptable excipients.

33. A pharmaceutical composition comprising a compound or a pharmaceutically acceptable salt thereof as claimed claim 27 and one or more pharmaceutically acceptable excipients.

34. A pharmaceutical composition comprising a compound or a pharmaceutically acceptable salt thereof as claimed claim 28 and one or more pharmaceutically acceptable excipients.

* * * * *

UNITED STATES PATENT AND TRADEMARK OFFICE
CERTIFICATE OF CORRECTION

PATENT NO. : 12,037,344 B2
APPLICATION NO. : 17/049612
DATED : July 16, 2024
INVENTOR(S) : Zhang et al.

It is certified that error appears in the above-identified patent and that said Letters Patent is hereby corrected as shown below:

In the Claims

Column 488
Line 55, Claim 1, "S(O$_{0-2}$," should read -- S(O)$_{0-2}$, --.

Column 489
Line 7, Claim 1, "R$^e$," should read -- R$^c$, --;
Line 30, Claim 1, "R$^9$" should read -- R$^g$ --;
Line 60, Claim 2, "R$^9$;" should read -- R$^g$; --.

Column 491
Line 51, Claim 4, "alkylalkyl" should read -- alkyl --.

Column 492
Line 3, Claim 4, "Ct-4" should read -- C$_{1-4}$ --;
Line 18, Claim 4, "N(R$^t$)," should read -- N(R$^f$), --.

Column 493
Line 14, Claim 4, "R$^9$" should read -- R$^g$ --.

Column 494
Line 56, Claim 5, "R$^e$" should read -- R$^c$ --.

Column 496
Line 38, Claim 6, "R$^4$" should read -- R$^c$ --.

Column 498
Line 45, Claim 8, "R$^e$)," should read -- R$^e$), --.

Signed and Sealed this
Seventh Day of January, 2025

Derrick Brent
*Acting Director of the United States Patent and Trademark Office*

CERTIFICATE OF CORRECTION (continued)
U.S. Pat. No. 12,037,344 B2

Column 501
Line 55, Claim 11, "$R^c$," should read -- $R^e$, --.

Column 502
Line 29, Claim 12, "$R^c$)," should read -- $R^e$), --;
Line 48-54, Claim 12,

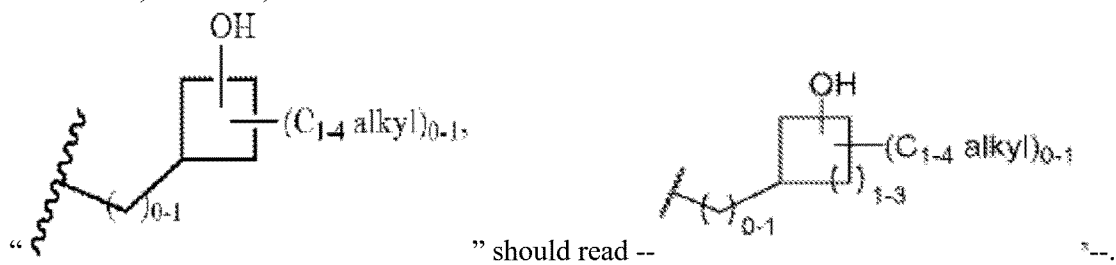

" should read -- --.

Column 503
Line 1-5, Claim 12,

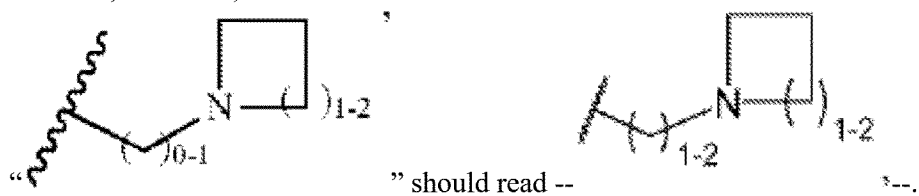

" should read -- --.

Column 505
Line 40-44, Claim 15,

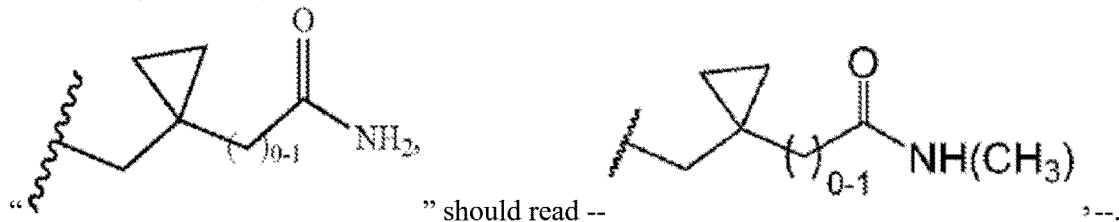

" should read -- --.

Column 508
Line 57, Claim 19, "alkylalkyl)," should read -- alkyl), --.

Column 509
Line 16, Claim 19, after "independently" delete "or".